US012747207B2

(12) United States Patent
Ahlmark et al.

(10) Patent No.: US 12,747,207 B2
(45) Date of Patent: Sep. 29, 2026

(54) TEAD INHIBITORS

(71) Applicant: ORION CORPORATION, Espoo (FI)

(72) Inventors: Marko Ahlmark, Espoo (FI); David Din Belle, Espoo (FI); Dimitris Noutsias, Espoo (FI); Pekka Pietikäinen, Espoo (FI); Petteri Rummakko, Espoo (FI); Julius Sipilä, Espoo (FI); Gerd Wohlfahrt, Berlin (DE)

(73) Assignee: ORION CORPORATION, Espoo (FI)

( * ) Notice: Subject to any disclaimer, the term of this patent is extended or adjusted under 35 U.S.C. 154(b) by 379 days.

(21) Appl. No.: 18/555,291

(22) PCT Filed: Apr. 14, 2022

(86) PCT No.: PCT/FI2022/050249
§ 371 (c)(1),
(2) Date: Oct. 13, 2023

(87) PCT Pub. No.: WO2022/219246
PCT Pub. Date: Oct. 20, 2022

(65) Prior Publication Data

US 2024/0246908 A1 Jul. 25, 2024

(30) Foreign Application Priority Data

Apr. 16, 2021 (FI) ..................................... 20217071

(51) Int. Cl.

| | |
|---|---|
| ***C07D 207/277*** | (2006.01) |
| ***A61K 31/197*** | (2006.01) |
| ***A61K 31/381*** | (2006.01) |
| ***A61K 31/382*** | (2006.01) |
| ***A61K 31/397*** | (2006.01) |

(Continued)

(52) U.S. Cl.
CPC ........ *C07D 207/277* (2013.01); *A61K 31/197* (2013.01); *A61K 31/381* (2013.01); *A61K 31/382* (2013.01); *A61K 31/397* (2013.01); *A61K 31/40* (2013.01); *A61K 31/4015* (2013.01); *A61K 31/4025* (2013.01); *A61K 31/407* (2013.01); *A61K 31/41* (2013.01); *A61K 31/4155* (2013.01); *A61K 31/4166* (2013.01); *A61K 31/421* (2013.01); *A61K 31/4245* (2013.01); *A61K 31/425* (2013.01); *A61K 31/427* (2013.01); *A61K 31/429* (2013.01); *A61K 31/4412* (2013.01); *A61K 31/4439* (2013.01); *A61K 31/45* (2013.01); *A61K 31/4525* (2013.01); *A61K 31/453* (2013.01); *A61K 31/4545* (2013.01); *A61K 31/4709* (2013.01); *A61K 31/495* (2013.01); *A61K 31/496* (2013.01); *C07C 237/04* (2013.01); *C07D 205/04* (2013.01); *C07D 205/08* (2013.01); *C07D 207/16* (2013.01); *C07D 207/24* (2013.01); *C07D 207/263* (2013.01); *C07D 211/78* (2013.01); *C07D 213/81* (2013.01); *C07D 233/32* (2013.01); *C07D 257/04* (2013.01); *C07D 263/24* (2013.01); *C07D 275/03* (2013.01); *C07D 285/00* (2013.01); *C07D 333/48* (2013.01); *C07D 335/02* (2013.01); *C07D 401/12* (2013.01); *C07D 401/14* (2013.01); *C07D 403/04* (2013.01); *C07D 403/06* (2013.01); *C07D 403/12* (2013.01); *C07D 405/04* (2013.01); *C07D 405/12* (2013.01); *C07D 405/14* (2013.01); *C07D 413/12* (2013.01); *C07D 487/04* (2013.01); *C07D 513/04* (2013.01)

(58) Field of Classification Search
CPC ................................................ C07D 207/277
See application file for complete search history.

(56) References Cited

U.S. PATENT DOCUMENTS 4,748,178 A * 5/1988 Burckhardt .......... C07D 401/12 514/270

FOREIGN PATENT DOCUMENTS

| | | | |
|---|---|---|---|
| WO | WO 2010/045580 | A1 | 4/2010 |
| WO | WO 2020/051099 | A1 | 3/2020 |
| WO | WO 2020/081572 | A1 | 4/2020 |

OTHER PUBLICATIONS

Huh "Regulation of TEAD Transcription Factors in Cancer Biology" Cells 2019, 8, 600, 1-22.*

(Continued)

*Primary Examiner* — David K O'Dell
(74) *Attorney, Agent, or Firm* — FINNEGAN, HENDERSON, FARABOW, GARRETT & DUNNER, LLP

(57) ABSTRACT

The present invention relates to a compound of formula (I)

(I)

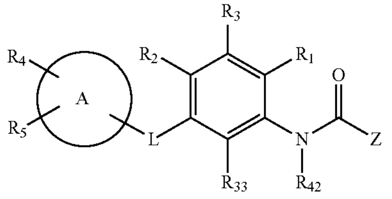

wherein A, Z, L, $R_1$, $R_2$, $R_3$, $R_4$, $R_5$ and $R_{33}$ are as defined in claim 1, or a pharmaceutically acceptable salt thereof. The compounds of formula (I) possess utility as inhibitors of TEAD. The compounds are useful as medicaments in the treatment of diseases or conditions wherein inhibition of TEAD is desired, such as cancer and chronic pain.

47 Claims, No Drawings

(51) Int. Cl.

| | |
|---|---|
| ***A61K 31/40*** | (2006.01) |
| ***A61K 31/4015*** | (2006.01) |
| ***A61K 31/4025*** | (2006.01) |
| ***A61K 31/407*** | (2006.01) |
| ***A61K 31/41*** | (2006.01) |
| ***A61K 31/4155*** | (2006.01) |
| ***A61K 31/4166*** | (2006.01) |
| ***A61K 31/421*** | (2006.01) |
| ***A61K 31/4245*** | (2006.01) |
| ***A61K 31/425*** | (2006.01) |
| ***A61K 31/427*** | (2006.01) |
| ***A61K 31/429*** | (2006.01) |
| ***A61K 31/4412*** | (2006.01) |
| ***A61K 31/4439*** | (2006.01) |
| ***A61K 31/45*** | (2006.01) |
| ***A61K 31/4525*** | (2006.01) |
| ***A61K 31/453*** | (2006.01) |
| ***A61K 31/4545*** | (2006.01) |
| ***A61K 31/4709*** | (2006.01) |
| ***A61K 31/495*** | (2006.01) |
| ***A61K 31/496*** | (2006.01) |
| ***C07C 237/04*** | (2006.01) |
| ***C07D 205/04*** | (2006.01) |
| ***C07D 205/08*** | (2006.01) |
| ***C07D 207/16*** | (2006.01) |
| ***C07D 207/24*** | (2006.01) |
| ***C07D 207/263*** | (2006.01) |
| ***C07D 211/78*** | (2006.01) |
| ***C07D 213/81*** | (2006.01) |
| ***C07D 233/32*** | (2006.01) |
| ***C07D 257/04*** | (2006.01) |
| ***C07D 263/24*** | (2006.01) |
| ***C07D 275/03*** | (2006.01) |
| ***C07D 285/00*** | (2006.01) |
| ***C07D 333/48*** | (2006.01) |
| ***C07D 335/02*** | (2006.01) |
| ***C07D 401/12*** | (2006.01) |
| ***C07D 401/14*** | (2006.01) |
| ***C07D 403/04*** | (2006.01) |
| ***C07D 403/06*** | (2006.01) |
| ***C07D 403/12*** | (2006.01) |
| ***C07D 405/04*** | (2006.01) |
| ***C07D 405/12*** | (2006.01) |
| ***C07D 405/14*** | (2006.01) |
| ***C07D 413/12*** | (2006.01) |
| ***C07D 487/04*** | (2006.01) |
| ***C07D 513/04*** | (2006.01) |

(56) References Cited

OTHER PUBLICATIONS

Tang "The role of non-canonical Hippo pathway in regulating immune homeostasis" European Journal of Medical Research (2023) 28:498.*
Fu The Hippo signaling pathway and its implications in human health and diseases. Sig Transduct Target Ther 7, 376 (2022).*
Benz "The Jeremiah Metzger Lecture Cancer in the Twenty-First Century: An Inside View from an Outsider" Transactions of the American Clinical and Climatological Association, vol. 128, 2017, 275-297.*
Bae, Cancer Targeted Drug Delivery, Springer: New York, 2013, p. v.*
Hayat, M.A. Autophagy Cancer, Other Pathologies, Inflammation, Immunity, Infection, and Aging vol. 5 Academic Press: Sand Diego, 2015, p. xxi.*
Carlo C. Maley and Mel Greaves Frontiers in Cancer Research Springer: 2016, pp. 18-19.*
Costigan "Neuropathic Pain: A Maladaptive Response of the Nervous System to Damage" Annu. Rev. Neurosci. 2009. 32:1-32.*
Damia "Contemporary pre-clinical development of anticancer agents—What are the optimal preclinical models?" European Journal of Cancer 2009, 45, 2768-2781.*
Sharma "Cell line-based platforms to evaluate the therapeutic efficacy of candidate anticancer agents" Nature Reviews Cancer Apr. 2010, vol. 10, 241-253.*
Ocana, A. "Preclinical development of molecular targeted agents for cancer" Nat. Rev. Clin. Oncol. 2011, 8, 200-209.*
Ledford "US cancer institute overhauls cell lines" Nature Feb. 25, 2016 Volume 530 p. 391.*
Cunningham "Pipeline to evaluate YAP-TEAD inhibitors indicates TEAD inhibition represses NF2-mutant mesothelioma" Life Science Alliance Published Online: Jul. 31, 2025 vol 8 | No. 10 | e202503241.*
Le Bars, et al. "Animal Models of Nociception" Pharmacological Reviews 2001, 53, 597-652.*
Johnson, et al. "Relationships between drug activity in NCI preclinical in vitro and in vivo models and early clinical trials." British Journal of Cancer 2001, 84, 1424-1431.*
International Search Report of International Application No. PCT/FI2022/050249, mail date May 27, 2022 (3 pages).
Khuchtumur Bum-Erdene et al., "Small-Molecule Covalent Modification of Conserved Cysteine Leads to Allosteric Inhibition of the TEAD•Yap Protein-Protein Interaction", Cell Chemical Biology, 26, Mar. 21, 2019 (pp. 378-389, 26 pages).

* cited by examiner

TEAD INHIBITORS

This is a National Stage Application under 35 U.S.C. § 371 of International Patent Application No. PCT/FI2022/050249, filed Apr. 14, 2022, which claims the benefit of priority of Finnish Patent Application No. 20217071, filed Apr. 16, 2021, both of which are incorporated herein by reference.

TECHNICAL FIELD

The present invention relates to therapeutically active compounds useful in the inhibition of transcriptional enhancer associate domain (TEAD), and to pharmaceutical compositions containing such compounds. The compounds are useful in the treatment of diseases or disorders associated with increased TEAD activity or TEAD expression, such as various cancers and chronic pain.

BACKGROUND OF THE INVENTION

TEA domain transcription factors (TEAD1-4) is a family of DNA binding transcription factors which regulate the expression of genes involved in cell proliferation, cell fate, cell differentiation, organ overgrowth and organ regeneration. YAP and TAZ are TEAD transcriptional co-activators which can shuttle between the cytoplasm and the nucleus. Altered actin dynamics and the Hippo signalling pathway promote YAP and TAZ phosphorylation, cytoplasmic retention and proteasomal degradation, consequently leading to low YAP and TAZ nuclear levels and TEAD transcriptional activity.

The evolutionarily conserved Hippo signalling pathway is consisting of the large tumor suppressor 1/2 (LATS1/2), the serine/threonine kinases, sterile 20-like kinase 1/2 (MST1/2), and the adaptor proteins Salvador homolog 1 (SAV1) and MOB kinase activator 1A/B (MOB1A/B). The tumor suppressor neurofibromin 2 (NF2) (also known as Merlin) participates upstream of these kinases to inhibit YAP and TAZ activity by promoting the activation of the pathway. The Hippo pathway has been linked to many aspects of tumorigenesis, including cell proliferation, cell differentiation, cancer metastasis and cancer therapy resistance. Therefore, dysregulation in Hippo pathway signalling has been shown to drive oncogenesis across various cancer types. It has also been reported that YAP and TAZ are core mechanisms underlying the pathogenesis of chronic pain, such as chronic neuropathic pain and chronic musculoskeletal pain.

Compounds with TEAD inhibition activity have been disclosed, for example, in WO 2020/081572, WO 2020/070181 and WO 2020051099. Anti-tumor effects of a TEAD inhibitor, K-975, in vivo on malignant pleural mesothelioma has been reported in Am J Cancer Res, 2020; 10(12): 4399-4415.

There is a need for compounds targeting diseases associated with dysregulation in the Hippo pathway components, for example compounds targeting the YAP-TEAD interaction. Such compounds would be useful for the treatment of diseases or conditions wherein inhibition of TEAD is desired, such as chronic pain including neuropathic pain and various cancers including cancers which are resistant to other treatments, such as chemotherapy, immunotherapy and targeted therapies.

SUMMARY OF THE INVENTION

It has been found that compounds of formula (I) are potent inhibitors of YAP-TEAD interaction. The compounds are therefore useful for the treatment of conditions and diseases where inhibition of TEAD is desired. Such conditions and diseases include, but are not limited to, chronic pain, particularly chronic neuropathic pain and chronic musculoskeletal pain, and cancers, particularly cancers associated with dysregulation in the Hippo pathway components including YAP-TEAD. Particular cancers include, but are not restricted to, mesothelioma, squamous cell carcinomas, gynaecological cancers, bladder cancer, gastric cancer, liver cancer, lung cancer and colon cancer.

The present invention relates to a compound of formula (I) or a pharmaceutically acceptable salt thereof (I)

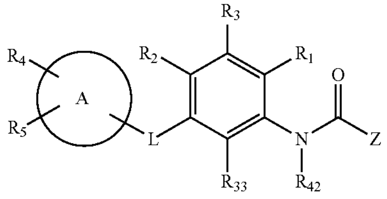

wherein

A is pyridyl, tetrahydropyranyl, a 4-10 membered carbocyclic ring;

L is —O—, —S—, —NH—, —$C_{1-7}$ alkyl-, —$C_{2-7}$ alkenyl-, —$C_{1-7}$ alkyl-O—, —O—$C_{1-7}$ alkyl- or —NH—$C_{1-7}$ alkyl-;

$R_1$ is hydrogen, $C_{1-7}$ alkyl, $C_{1-7}$ alkoxy, halogen, hydroxyl, cyano, —C(O)$NR_{36}R_{37}$, or an optionally substituted 5-6 membered heterocyclic ring having 1-3 heteroatoms as ring atoms independently selected from O, S and N;

$R_2$ is hydrogen, $C_{1-7}$ alkyl, $C_{1-7}$ alkoxy or halogen;

$R_3$ is hydrogen, $C_{1-7}$ alkyl, $C_{1-7}$ alkoxy, halogen, halogen $C_{1-7}$ alkyl or cyano, or $R_1$ and $R_3$ together with the carbon atoms to which they are attached form an optionally substituted 5-6 membered ring having 0-3 heteroatoms as ring atoms independently selected from O, S and N;

$R_4$ is hydrogen, $C_{1-7}$ alkyl, $C_{1-7}$ alkoxy, halogen, halogen $C_{1-7}$ alkyl, halogen $C_{1-7}$ alkoxy, cyano or $C_{1-7}$ alkylcarbonyl;

$R_5$ is hydrogen, $C_{1-7}$ alkyl, $C_{1-7}$ alkoxy, halogen, nitro, amino, hydroxyl, halogen $C_{1-7}$ alkyl, halogen $C_{1-7}$ alkoxy, or $R_4$ and $R_5$ together with the carbon atoms to which they are attached form an optionally substituted 5-6 membered ring having 1-3 heteroatoms as ring atoms independently selected from O, S and N;

Z is —CH($NHR_{25}$)—$(CH_2)_2$—COOH or a group of formula

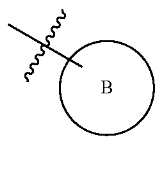

wherein B is any one of the following groups
(1a)
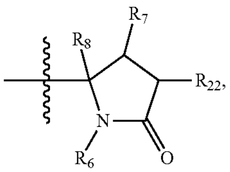
(1b)
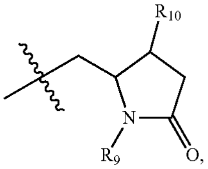
(2)
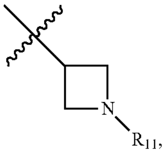
(3)
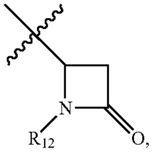
(4)
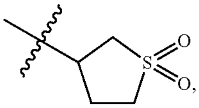
(5)
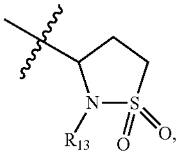
(6)
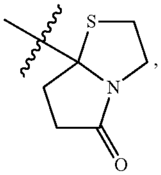
(7)
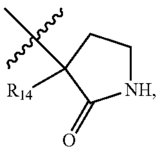
(8)
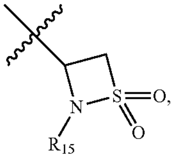
-continued
(9)
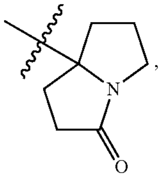
(10)
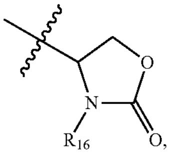
(11)
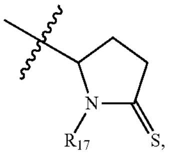
(12)
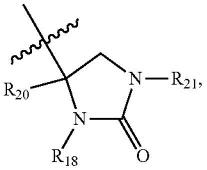
(13)
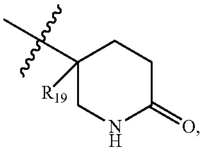
(14)
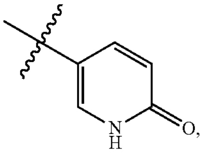
(15)
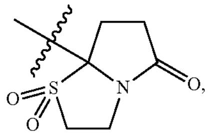
(16)
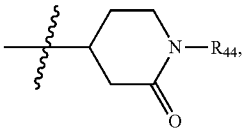
(17)
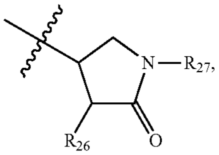

-continued (18)

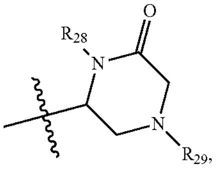

(19)

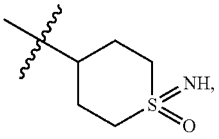

(20)

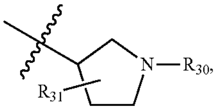

(21)

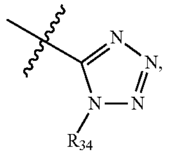

(22)

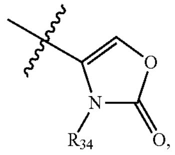

(23)

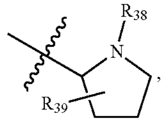

(24)

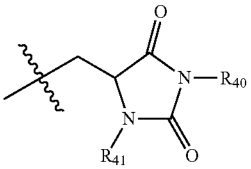

and (25)

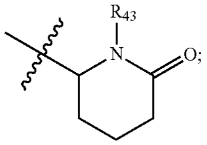

provided that when B is ring (2), then L is —O— or —O—$C_{1-7}$ alkyl-, and $R_1$ is $C_{1-7}$ alkoxy;

when B is ring (3), then L is —O—;

when B is ring (4), then L is —O— and $R_1$ is $C_{1-7}$ alkoxy;

when B is ring (20), (21), (23), (25) or (26), then L is —O— and $R_1$ is $C_{1-7}$ alkoxy;

when L is —$C_{1-7}$ alkyl-O—, then $R_1$ is $C_{1-7}$ alkoxy or $R_1$ and $R_3$ together with the carbon atoms to which they are attached form an optionally substituted 5-6 membered ring having 0-3 heteroatoms as ring atoms independently selected from O, S and N;

when A is a 4-, 5-, 7-, 8-, 9- or 10-membered carbocyclic ring, then $R_1$ is $C_{1-7}$ alkoxy;

$R_6$ and $R_9$ are, independently, hydrogen, $C_{1-7}$ alkyl, $C_{3-7}$ cycloalkyl, $C_{3-7}$ cycloalkyl $C_{1-7}$ alkyl, —C(O)—$R_X$, $C_{1-7}$ alkoxy $C_{1-7}$ alkyl, $C_{1-7}$ alkoxycarbonyl $C_{1-7}$ alkyl, —$SO_2C_{1-7}$ alkyl, —$C_{1-7}$ alkyl-C(O)—$NR_{23}R_{24}$ or an optionally substituted 4-6 membered ring having 0-3 heteroatoms as ring atoms independently selected from O, S and N;

$R_X$ is $C_{1-7}$ alkyl, $C_{3-7}$ cycloalkyl, $C_{1-7}$ alkoxy $C_{1-7}$ alkyl, $C_{1-7}$ alkyl-$NR_{36}R_{37}$, or an optionally substituted 4-6 membered ring having 0-3 heteroatoms as ring atoms independently selected from O, S and N;

$R_7$, $R_8$, $R_{10}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$ and $R_{26}$ are, independently, hydrogen, $C_{1-7}$ alkyl, $C_{3-7}$ cycloalkyl, hydroxyl, $C_{1-7}$ alkoxy or $C_{1-7}$ alkylcarbonyl;

$R_{11}$ is hydrogen, $C_{1-7}$ alkyl, halogen $C_{1-7}$ alkyl or $C_{1-7}$ alkylcarbonyl;

$R_{23}$, $R_{24}$, $R_{27}$, $R_{28}$, $R_{29}$, $R_{31}$, $R_{32}$, $R_{33}$, $R_{34}$, $R_{35}$, $R_{36}$, $R_{37}$, $R_{40}$, $R_{41}$, $R_{42}$, $R_{43}$, $R_{44}$, and $R_{45}$ are, independently, hydrogen, or $C_{1-7}$ alkyl;

$R_{25}$ is $C_{1-7}$ alkyl;

$R_{30}$ is $C_{1-7}$ alkyl, $C_{1-7}$ alkylcarbonyl or —$SO_2C_{1-7}$ alkyl;

$R_{38}$ is hydrogen, $C_{1-7}$ alkyl, $C_{1-7}$ alkylcarbonyl, $C_{1-7}$ alkoxy $C_{1-7}$ alkylcarbonyl or —$C_{1-7}$ alkyl-C(O)—$NR_{23}R_{24}$;

$R_{39}$ is hydrogen, $C_{1-7}$ alkyl or hydroxyl;

wherein optional substitution, in each occurrence, is 1-2 substituents independently selected from $C_{1-7}$ alkyl, halogen, halogen $C_{1-7}$ alkyl, $C_{1-7}$ alkoxy and oxo;

with the proviso that compound of formula (I) is not

N-[2-Methyl-3-(phenoxymethyl)phenyl]-5-oxo-2-pyrrolidinecarboxamide;

N-[5-[(3-Fluorophenoxy)methyl]-2-methoxyphenyl]-1-methyl-5-oxo-2-pyrrolidinecarboxamide;

N-[3-[(4-Chlorophenyl)methyl]phenyl]-5-oxo-2-pyrrolidinecarboxamide;

N-[3-[(Cyclohexyloxy)methyl]phenyl]-1-methyl-5-oxo-2-pyrrolidinecarboxamide;

N-[4-Methyl-3-[(4-methyl-2-pyridinyl)oxy]phenyl]-5-oxo-2-pyrrolidinecarboxamide;

N-[3-(Cyclopentylamino)phenyl]-1-methyl-5-oxo-2-pyrrolidinecarboxamide;

N-[3-[[(3-Methylcyclohexyl)oxy]methyl]phenyl]-6-oxo-3-piperidine-carboxamide;

1-Ethyl-5-oxo-N-(3-phenoxyphenyl)-3-pyrrolidinecarboxamide;

N-[5-[(3-Fluorophenoxy)methyl]-2-methoxyphenyl]-2-pyrrolidinecarboxamide;

1-(1-Ethylpropyl)-N-[5-[(3-fluorophenoxy)methyl]-2-methoxyphenyl]-5-oxo-3-pyrrolidinecarboxamide;

N-[3-[(4-Chlorophenyl)methyl]phenyl]-1,6-dihydro-6-oxo-3-pyridinecarboxamide;

1,6-Dihydro-N-[4-methoxy-3-(phenylmethyl)phenyl]-6-oxo-3-pyridinecarboxamide;

1,6-Dihydro-6-oxo-N-[3-[2-(2-pyridinyl)ethenyl]phenyl]-3-pyridinecarboxamide;

N-[3-[(3-Fluorophenoxy)methyl]phenyl]-2,3-dihydro-2-oxo-1H-imidazole-4-carboxamide;

1-Methyl-N-[2-methyl-3-(phenoxymethyl)phenyl]-5-oxo-3-pyrrolidinecarboxamide;

N-[3-[(1,3-Benzodioxol-5-yloxy)methyl]phenyl]-1-(2-methylpropyl)-5-oxo-3-pyrrolidinecarboxamide;

1,6-Dihydro-N-[3-[[(3-methylcyclohexyl)oxy]methyl]phenyl]-6-oxo-3-pyridinecarboxamide;

N-[3-[(Cyclohexyloxy)methyl]phenyl]-1-ethyl-5-oxo-3-pyrrolidinecarboxamide;

1-Methyl-N-[3-[[(3-methylcyclohexyl)oxy]methyl]phenyl]-5-oxo-3-pyrrolidinecarboxamide;

2,3-Dihydro-3-methyl-N-[3-[[(3-methylcyclohexyl)oxy]methyl]phenyl]-2-oxo-1H-imidazole-4-carboxamide;

2,3-Dihydro-1,3-dimethyl-N-[3-[[(3-methylcyclohexyl)oxy]methyl]phenyl]-2-oxo-1H-imidazole-4-carboxamide;

1-Ethyl-N-[4-methoxy-3-(4-pyridinylmethoxy)phenyl]-5-oxo-3-pyrrolidinecarboxamide;

N-[4-Methoxy-3-(4-methoxyphenoxy)phenyl]-1-(2-methylpropyl)-5-oxo-3-pyrrolidinecarboxamide or 6-Oxo-N-(3-phenoxyphenyl)-2-piperazinecarboxamide.

According to one embodiment, the invention provides a method for the treatment of a disease or condition wherein inhibition of TEAD is desired comprising administering to a subject in need thereof a therapeutically effective amount of a compound of formula (I) or a pharmaceutically acceptable salt thereof (I)

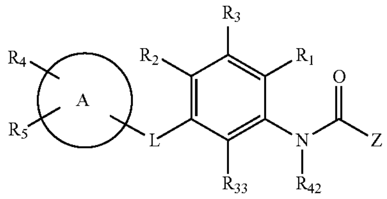

wherein

A is pyridyl, tetrahydropyranyl, a 4-10 membered carbocyclic ring;

L is —O—, —S—, —NH—, —$C_{1-7}$ alkyl-, —$C_{2-7}$ alkenyl-, —$C_{1-7}$ alkyl-O—, —O—$C_{1-7}$ alkyl- or —NH—$C_{1-7}$ alkyl-;

$R_1$ is hydrogen, $C_{1-7}$ alkyl, $C_{1-7}$ alkoxy, halogen, hydroxyl, cyano, —C(O)$NR_{36}R_{37}$, or an optionally substituted 5-6 membered heterocyclic ring having 1-3 heteroatoms as ring atoms independently selected from O, S and N;

$R_2$ is hydrogen, $C_{1-7}$ alkyl, $C_{1-7}$ alkoxy or halogen;

$R_3$ is hydrogen, $C_{1-7}$ alkyl, $C_{1-7}$ alkoxy, halogen, halogen $C_{1-7}$ alkyl or cyano, or $R_1$ and $R_3$ together with the carbon atoms to which they are attached form an optionally substituted 5-6 membered ring having 0-3 heteroatoms as ring atoms independently selected from O, S and N;

$R_4$ is hydrogen, $C_{1-7}$ alkyl, $C_{1-7}$ alkoxy, halogen, halogen $C_{1-7}$ alkyl, halogen $C_{1-7}$ alkoxy, cyano or $C_{1-7}$ alkylcarbonyl;

$R_5$ is hydrogen, $C_{1-7}$ alkyl, $C_{1-7}$ alkoxy, halogen, nitro, amino, hydroxyl, halogen $C_{1-7}$ alkyl, halogen $C_{1-7}$ alkoxy, or $R_4$ and $R_5$ together with the carbon atoms to which they are attached form an optionally substituted 5-6 membered ring having 1-3 heteroatoms as ring atoms independently selected from O, S and N;

Z is —CH($NHR_{25}$)—$(CH_2)_2$—COOH or a group of formula

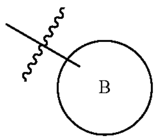

wherein B is any one of the following groups (1a)

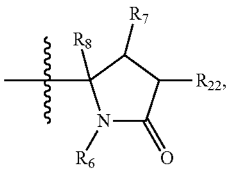

(1b)

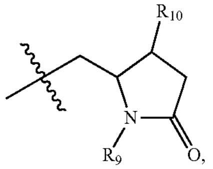

(2)

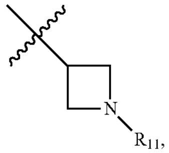

(3)

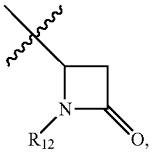

(4)

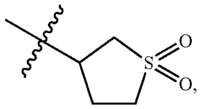

(5)

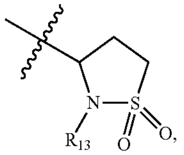

(6)

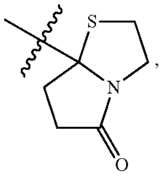

(7)

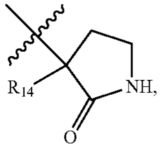

(8)

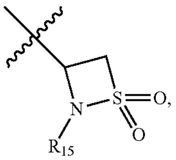

-continued (9)

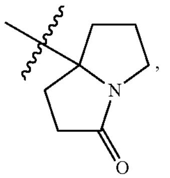

(10)

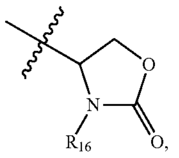

(11)

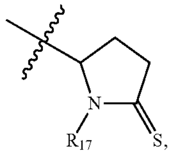

(12)

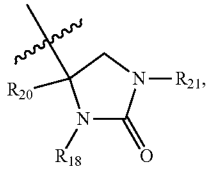

(13)

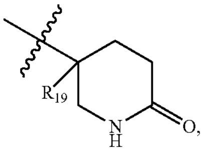

(14)

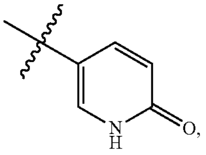

(15)

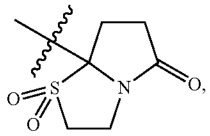

(16)

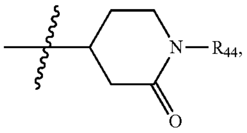

(17)

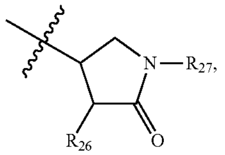

-continued (18)

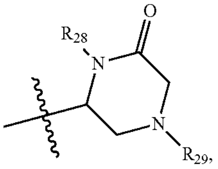

(19)

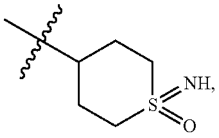

(20)

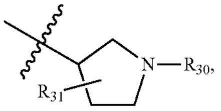

(21)

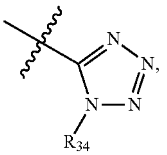

(22)

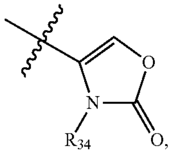

(23)

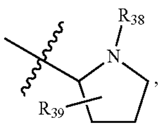

(24)

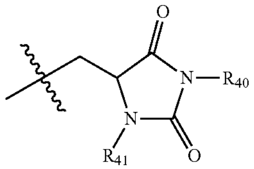

and (25)

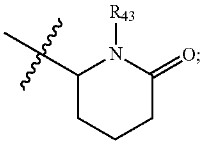

provided that

- when B is ring (2), then L is —O— or —O—$C_{1-7}$ alkyl-, and $R_1$ is $C_{1-7}$ alkoxy;
- when B is ring (3), then L is —O—;
- when B is ring (4), then L is —O— and $R_1$ is $C_{1-7}$ alkoxy;
- when B is ring (20), (21), (23), (25) or (26), then L is —O— and $R_1$ is $C_{1-7}$ alkoxy;
- when L is —$C_{1-7}$ alkyl-O—, then $R_1$ is $C_{1-7}$ alkoxy or $R_1$ and $R_3$ together with the carbon atoms to which they are attached form an optionally substituted 5-6 membered ring having 0-3 heteroatoms as ring atoms independently selected from O, S and N;
- when A is a 4-, 5-, 7-, 8-, 9- or 10-membered carbocyclic ring, then $R_1$ is $C_{1-7}$ alkoxy;

$R_6$ and $R_9$ are, independently, hydrogen, $C_{1-7}$ alkyl, $C_{3-7}$ cycloalkyl, $C_{3-7}$ cycloalkyl $C_{1-7}$ alkyl, —C(O)—$R_X$, $C_{1-7}$ alkoxy $C_{1-7}$ alkyl, $C_{1-7}$ alkoxycarbonyl $C_{1-7}$ alkyl, —$SO_2C_{1-7}$ alkyl, —$C_{1-7}$ alkyl-C(O)—$NR_{23}R_{24}$ or an optionally substituted 4-6 membered ring having 0-3 heteroatoms as ring atoms independently selected from O, S and N;

$R_X$ is $C_{1-7}$ alkyl, $C_{3-7}$ cycloalkyl, $C_{1-7}$ alkoxy $C_{1-7}$ alkyl, $C_{1-7}$ alkyl-$NR_{36}R_{37}$, or an optionally substituted 4-6 membered ring having 0-3 heteroatoms as ring atoms independently selected from O, S and N;

$R_7$, $R_8$, $R_{10}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$ and $R_{26}$ are, independently, hydrogen, $C_{1-7}$ alkyl, $C_{3-7}$ cycloalkyl, hydroxyl, $C_{1-7}$ alkoxy or $C_{1-7}$ alkylcarbonyl;

$R_{11}$ is hydrogen, $C_{1-7}$ alkyl, halogen $C_{1-7}$ alkyl or $C_{1-7}$ alkylcarbonyl;

$R_{23}$, $R_{24}$, $R_{27}$, $R_{28}$, $R_{29}$, $R_{31}$, $R_{32}$, $R_{33}$, $R_{34}$, $R_{35}$, $R_{36}$, $R_{37}$, $R_{40}$, $R_{41}$, $R_{42}$, $R_{43}$, $R_{44}$, and $R_{45}$ are, independently, hydrogen, or $C_{1-7}$ alkyl;

$R_{25}$ is $C_{1-7}$ alkyl;

$R_{30}$ is $C_{1-7}$ alkyl, $C_{1-7}$ alkylcarbonyl or —$SO_2C_{1-7}$ alkyl;

$R_{38}$ is hydrogen, $C_{1-7}$ alkyl, $C_{1-7}$ alkylcarbonyl, $C_{1-7}$ alkoxy $C_{1-7}$ alkylcarbonyl or —$C_{1-7}$ alkyl-C(O)—$NR_{23}R_{24}$;

$R_{39}$ is hydrogen, $C_{1-7}$ alkyl or hydroxyl;

wherein optional substitution, in each occurrence, is 1-2 substituents independently selected from $C_{1-7}$ alkyl, halogen, halogen $C_{1-7}$ alkyl, $C_{1-7}$ alkoxy and oxo.

According to one embodiment, the disease or condition wherein inhibition of TEAD is desired is cancer, for example mesothelioma, squamous cell carcinoma, a gynaecological cancer, bladder cancer, gastric cancer, liver cancer, lung cancer and colon cancer.

According to one embodiment, the disease or condition wherein inhibition of TEAD is desired is chronic pain, for example chronic neuropathic pain and chronic musculoskeletal pain.

According to one embodiment, the invention provides a pharmaceutical composition comprising a compound of formula (I) together with a pharmaceutically acceptable carrier.

DETAILED DESCRIPTION OF THE INVENTION

The present application provides novel compounds of formula (I) or pharmaceutically acceptable salts thereof which are useful as TEAD inhibitors.

One of the embodiments of the present invention provides a compound of formula (I) or a pharmaceutically acceptable salt thereof (I)

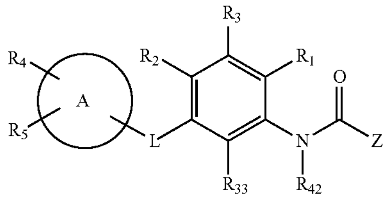

wherein

A is pyridyl, tetrahydropyranyl, a 4-10 membered carbocyclic ring;

L is —O—, —S—, —NH—, —$C_{1-7}$ alkyl-, —$C_{2-7}$ alkenyl-, —$C_{1-7}$ alkyl-O—, —O—$C_{1-7}$ alkyl- or —NH—$C_{1-7}$ alkyl-;

$R_1$ is hydrogen, $C_{1-7}$ alkyl, $C_{1-7}$ alkoxy, halogen, hydroxyl, cyano, —C(O)$NR_{36}R_{37}$, or an optionally substituted 5-6 membered heterocyclic ring having 1-3 heteroatoms as ring atoms independently selected from O, S and N;

$R_2$ is hydrogen, $C_{1-7}$ alkyl, $C_{1-7}$ alkoxy or halogen;

$R_3$ is hydrogen, $C_{1-7}$ alkyl, $C_{1-7}$ alkoxy, halogen, halogen $C_{1-7}$ alkyl or cyano, or $R_1$ and $R_3$ together with the carbon atoms to which they are attached form an optionally substituted 5-6 membered ring having 0-3 heteroatoms as ring atoms independently selected from O, S and N;

$R_4$ is hydrogen, $C_{1-7}$ alkyl, $C_{1-7}$ alkoxy, halogen, halogen $C_{1-7}$ alkyl, halogen $C_{1-7}$ alkoxy, cyano or $C_{1-7}$ alkylcarbonyl;

$R_5$ is hydrogen, $C_{1-7}$ alkyl, $C_{1-7}$ alkoxy, halogen, nitro, amino, hydroxyl, halogen $C_{1-7}$ alkyl, halogen $C_{1-7}$ alkoxy, or $R_4$ and $R_5$ together with the carbon atoms to which they are attached form an optionally substituted 5-6 membered ring having 1-3 heteroatoms as ring atoms independently selected from O, S and N;

Z is —CH($NHR_{25}$)—$(CH_2)_2$—COOH or a group of formula

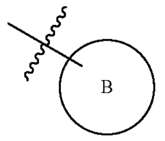

wherein B is any one of the following groups (1a)

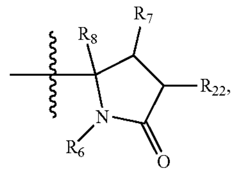

(1b)

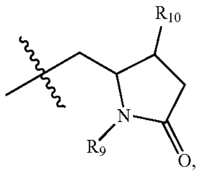

(2)

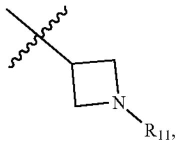

(3)

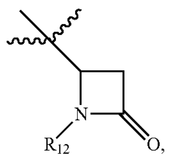

-continued
(4)
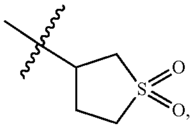
(5)
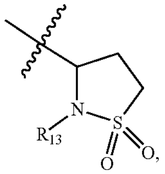
(6)
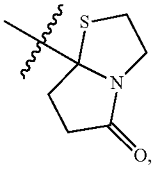
(7)
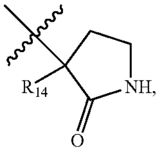
(8)
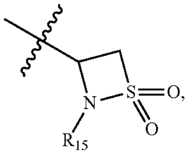
(9)
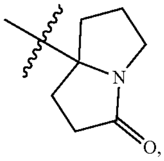
(10)
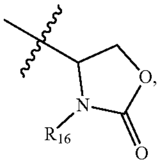
(11)
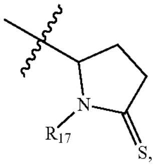
(12)
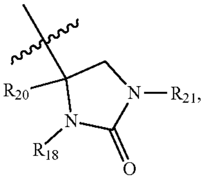
-continued
(13)
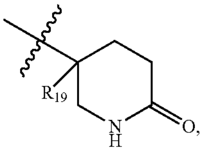
(14)
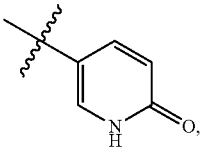
(15)
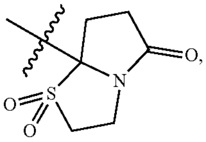
(16)
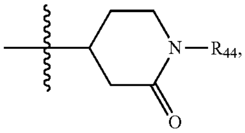
(17)
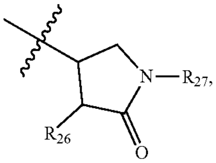
(18)
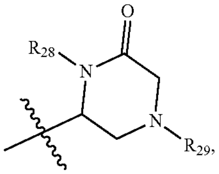
(19)
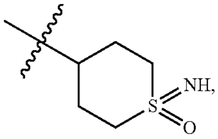
(20)
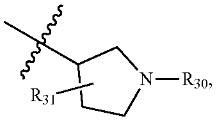
(21)
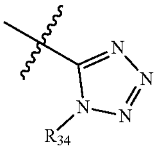
(22)
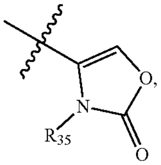

-continued (23)

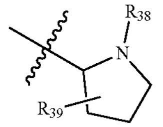

(24)

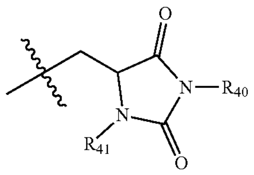

and (25)

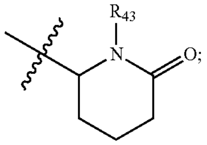

provided that when B is ring (2), then L is —O— or —O—$C_{1-7}$ alkyl-, and $R_1$ is $C_{1-7}$ alkoxy;

when B is ring (3), then L is —O—;

when B is ring (4), then L is —O— and $R_1$ is $C_{1-7}$ alkoxy;

when B is ring (20), (21), (23), (25) or (26), then L is —O— and $R_1$ is $C_{1-7}$ alkoxy;

when L is —$C_{1-7}$ alkyl-O—, then $R_1$ is $C_{1-7}$ alkoxy or $R_1$ and $R_3$ together with the carbon atoms to which they are attached form an optionally substituted 5-6 membered ring having 0-3 heteroatoms as ring atoms independently selected from O, S and N;

when A is a 4-, 5-, 7-, 8-, 9- or 10-membered carbocyclic ring, then $R_1$ is $C_{1-7}$ alkoxy;

$R_6$ and $R_9$ are, independently, hydrogen, $C_{1-7}$ alkyl, $C_{3-7}$ cycloalkyl, $C_{3-7}$ cycloalkyl $C_{1-7}$ alkyl, —C(O)—$R_X$, $C_{1-7}$ alkoxy $C_{1-7}$ alkyl, $C_{1-7}$ alkoxycarbonyl $C_{1-7}$ alkyl, —$SO_2C_{1-7}$ alkyl, —$C_{1-7}$ alkyl-C(O)—$NR_{23}R_{24}$ or an optionally substituted 4-6 membered ring having 0-3 heteroatoms as ring atoms independently selected from O, S and N;

$R_X$ is $C_{1-7}$ alkyl, $C_{3-7}$ cycloalkyl, $C_{1-7}$ alkoxy $C_{1-7}$ alkyl, $C_{1-7}$ alkyl-$NR_{36}R_{37}$, or an optionally substituted 4-6 membered ring having 0-3 heteroatoms as ring atoms independently selected from O, S and N;

$R_7$, $R_8$, $R_{10}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$ and $R_{26}$ are, independently, hydrogen, $C_{1-7}$ alkyl, $C_{3-7}$ cycloalkyl, hydroxyl, $C_{1-7}$ alkoxy or $C_{1-7}$ alkylcarbonyl;

$R_{11}$ is hydrogen, $C_{1-7}$ alkyl, halogen $C_{1-7}$ alkyl or $C_{1-7}$ alkylcarbonyl;

$R_{23}$, $R_{24}$, $R_{27}$, $R_{28}$, $R_{29}$, $R_{31}$, $R_{32}$, $R_{33}$, $R_{34}$, $R_{35}$, $R_{36}$, $R_{37}$, $R_{40}$, $R_{41}$, $R_{42}$, $R_{43}$, $R_{44}$, and $R_{45}$ are, independently, hydrogen, or $C_{1-7}$ alkyl;

$R_{25}$ is $C_{1-7}$ alkyl;

$R_{30}$ is $C_{1-7}$ alkyl, $C_{1-7}$ alkylcarbonyl or —$SO_2C_{1-7}$ alkyl;

$R_{38}$ is hydrogen, $C_{1-7}$ alkyl, $C_{1-7}$ alkylcarbonyl, $C_{1-7}$ alkoxy $C_{1-7}$ alkylcarbonyl or —$C_{1-7}$ alkyl-C(O)—$NR_{23}R_{24}$;

$R_{39}$ is hydrogen, $C_{1-7}$ alkyl or hydroxyl;

wherein optional substitution, in each occurrence, is 1-2 substituents independently selected from $C_{1-7}$ alkyl, halogen, halogen $C_{1-7}$ alkyl, $C_{1-7}$ alkoxy and oxo;

with the proviso that compound of formula (I) is not

N-[2-Methyl-3-(phenoxymethyl)phenyl]-5-oxo-2-pyrrolidinecarboxamide;

N-[5-[(3-Fluorophenoxy)methyl]-2-methoxyphenyl]-1-methyl-5-oxo-2-pyrrolidinecarboxamide;

N-[3-[(4-Chlorophenyl)methyl]phenyl]-5-oxo-2-pyrrolidinecarboxamide;

N-[3-[(Cyclohexyloxy)methyl]phenyl]-1-methyl-5-oxo-2-pyrrolidinecarboxamide;

N-[4-Methyl-3-[(4-methyl-2-pyridinyl)oxy]phenyl]-5-oxo-2-pyrrolidinecarboxamide;

N-[3-(Cyclopentylamino)phenyl]-1-methyl-5-oxo-2-pyrrolidinecarboxamide;

N-[3-[[(3-Methylcyclohexyl)oxy]methyl]phenyl]-6-oxo-3-piperidine-carboxamide;

1-Ethyl-5-oxo-N-(3-phenoxyphenyl)-3-pyrrolidinecarboxamide;

N-[5-[(3-Fluorophenoxy)methyl]-2-methoxyphenyl]-2-pyrrolidinecarboxamide;

1-(1-Ethylpropyl)-N-[5-[(3-fluorophenoxy)methyl]-2-methoxyphenyl]-5-oxo-3-pyrrolidinecarboxamide;

N-[3-[(4-Chlorophenyl)methyl]phenyl]-1,6-dihydro-6-oxo-3-pyridinecarboxamide;

1,6-Dihydro-N-[4-methoxy-3-(phenylmethyl)phenyl]-6-oxo-3-pyridinecarboxamide;

1,6-Dihydro-6-oxo-N-[3-[2-(2-pyridinyl)ethenyl]phenyl]-3-pyridinecarboxamide;

N-[3-[(3-Fluorophenoxy)methyl]phenyl]-2,3-dihydro-2-oxo-1H-imidazole-4-carboxamide;

1-Methyl-N-[2-methyl-3-(phenoxymethyl)phenyl]-5-oxo-3-pyrrolidinecarboxamide;

N-[3-[(1,3-Benzodioxol-5-yloxy)methyl]phenyl]-1-(2-methylpropyl)-5-oxo-3-pyrrolidinecarboxamide;

1,6-Dihydro-N-[3-[[(3-methylcyclohexyl)oxy]methyl]phenyl]-6-oxo-3-pyridinecarboxamide;

N-[3-[(Cyclohexyloxy)methyl]phenyl]-1-ethyl-5-oxo-3-pyrrolidinecarboxamide;

1-Methyl-N-[3-[[(3-methylcyclohexyl)oxy]methyl]phenyl]-5-oxo-3-pyrrolidinecarboxamide;

2,3-Dihydro-3-methyl-N-[3-[[(3-methylcyclohexyl)oxy]methyl]phenyl]-2-oxo-1H-imidazole-4-carboxamide;

2,3-Dihydro-1,3-dimethyl-N-[3-[[(3-methylcyclohexyl)oxy]methyl]phenyl]-2-oxo-1H-imidazole-4-carboxamide;

1-Ethyl-N-[4-methoxy-3-(4-pyridinylmethoxy)phenyl]-5-oxo-3-pyrrolidinecarboxamide;

N-[4-Methoxy-3-(4-methoxyphenoxy)phenyl]-1-(2-methylpropyl)-5-oxo-3-pyrrolidinecarboxamide or 6-Oxo-N-(3-phenoxyphenyl)-2-piperazinecarboxamide.

It is to be understood that the left bond of variants of linker L is attached to the ring A of formula (I) and the right bond to the phenyl group. The wavy line in variants of group B denotes the site of attachment to carboxamide group.

According to one embodiment, specifically provided is a compound according to formula (I) wherein A is phenyl, pyridyl or cyclohexyl. In a subgroup of the preceding embodiment, A is phenyl or cyclohexyl. In still another subgroup A is phenyl or pyridyl. In still another subgroup A is phenyl. In still another subgroup A is cyclohexyl. In still another subgroup A is pyridyl.

According to yet one embodiment, specifically provided are compounds according to any of the above embodiments wherein $R_{42}$ is hydrogen.

According to one embodiment, specifically provided are compounds according to formula (Ia) or a pharmaceutically acceptable salt thereof (Ia)

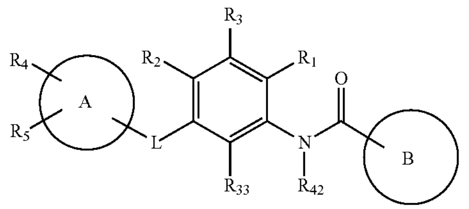

wherein A, L, B, $R_1$, $R_2$, $R_3$, $R_4$, $R_5$, $R_{33}$ and $R_{42}$ are as defined above.

According to yet one embodiment, specifically provided are compounds according to any of the above embodiments wherein B is ring (1a), (3), (4), (6), (8), (9), (10), (11), (12), (13), (16), (17) or (18). In a subgroup of the preceding embodiment, B is ring (1a), (4), (10), (11), (12), (13), (16) or (17). In still another subgroup B is ring (1a), (10), (11) or (12). In still another subgroup B is ring (1a) or (12). In still another subgroup B is ring (1a). In still another subgroup B is ring (12).

In a subgroup of compounds wherein B is ring (1a) are compounds wherein $R_7$ and $R_8$ are hydrogen. In still another subgroup of the preceding embodiment are compounds wherein $R_6$ is hydrogen, $C_{1-7}$ alkyl or $C_{3-7}$ cycloalkyl. According to another subgroup are compounds wherein $R_6$ is —C(O)—$R_X$, wherein $R_X$ is $C_{1-7}$ alkyl or an optionally substituted 4-6 membered ring having 1-3 heteroatoms as ring atoms independently selected from O, S and N. Particular examples of such rings are pyrrolidine and azetidine rings optionally substituted by 1-2 substituents independently selected from $C_{1-7}$ alkyl and oxo.

In a subgroup of compounds wherein B is ring (12) are compounds wherein $R_{20}$ is hydrogen and $R_{18}$ is $C_{1-7}$ alkyl or $C_{3-7}$ cycloalkyl. In still another subgroup of the preceding embodiment are compounds wherein $R_{21}$ is hydrogen or $C_{1-7}$ alkyl.

According to yet one embodiment, specifically provided are compounds according to any of the above embodiments wherein L is —O—, —S—, —NH—, —$C_{1-7}$ alkyl-, —$C_{2-7}$ alkenyl-, —$C_{1-7}$ alkyl-O—, or —O—$C_{1-7}$ alkyl-. In a subgroup of the preceding embodiment are compounds wherein L is —O—, —$C_{2-7}$ alkenyl-, —$C_{1-7}$ alkyl-O—, or —O—$C_{1-7}$ alkyl-. In a subgroup of the preceding embodiment are compounds wherein L is —O—, —$C_{2-7}$ alkenyl- or —O—$C_{1-7}$ alkyl-. In still another subgroup L is —O— or —$C_{2-7}$ alkenyl-. In still another subgroup L is —O—. A particular example of L being $C_{1-7}$ alkyl is —$CH_2$— group. A particular example of L being —$C_{2-7}$ alkenyl- is —CH═CH— group. A particular example of L being —$C_{1-7}$ alkyl-O— is —$CH_2$—O— group. A particular example of L being —O—$C_{1-7}$ alkyl- is —O—$CH_2$— group.

According to one embodiment, specifically provided are compounds according to any of the above embodiments wherein $R_1$ is hydrogen, $C_{1-7}$ alkoxy or halogen. In a subgroup of the preceding embodiment are compounds wherein $R_1$ is $C_{1-7}$ alkoxy or halogen. In a subgroup of the preceding embodiment are compounds wherein $R_1$ is $C_{1-7}$ alkoxy, particularly a methoxy group. According to one embodiment, $R_1$ is an optionally substituted 5-6 membered heterocyclic ring having 1-3 heteroatoms as ring atoms independently selected from O, S and N. Particular examples of such rings include oxadiazolyl and pyrazolyl rings optionally substituted by 1-2 $C_{1-7}$ alkyl or oxo substituents.

According to one embodiment, specifically provided are compounds according to any of the above embodiments wherein $R_2$ is hydrogen, $C_{1-7}$ alkoxy or halogen. In a subgroup of the preceding embodiment are compounds wherein $R_2$ is hydrogen or halogen. In a subgroup of the preceding embodiment are compounds wherein $R_2$ is hydrogen.

According to one embodiment, specifically provided are compounds according to any of the above embodiments wherein $R_3$ is hydrogen, halogen or $C_{1-7}$ alkoxy. In a subgroup are compounds wherein $R_3$ is hydrogen or $C_{1-7}$ alkoxy. In a subgroup are compounds wherein $R_3$ is hydrogen.

According to one embodiment, specifically provided are compounds according to any of the above embodiments wherein $R_1$ and $R_3$ together with the carbon atoms to which they are attached form an optionally substituted 5-6 membered ring having 0-3 heteroatoms as ring atoms independently selected from O, S and N. In a subgroup are compounds wherein $R_1$ and $R_3$ together with the carbon atoms to which they are attached form a 5-6 membered ring having 1-2 heteroatoms as ring atoms independently selected from O and N. In a subgroup are compounds wherein $R_1$ and $R_3$ together with the carbon atoms to which they are attached form a 5-6 membered ring having 1-2 heteroatoms wherein the heteroatom is O. Particular examples of such rings are furanyl, dihydrofuranyl, tetrahydrofuranyl, dioxanyl, dioxolanyl, oxazinyl, pyridinyl, 2,3-dihydro-1,4-dioxinyl, 2,3-dihydro-1,4-oxazinyl rings optionally substituted by 1-2 substituents independently selected from $C_{1-7}$ alkyl and oxo.

According to one embodiment, specifically provided are compounds according to any of the above embodiments wherein $R_1$ and $R_3$ together with the phenyl ring to which they are attached form an optionally substituted fused ring represented by any of the following groups:

(1a)

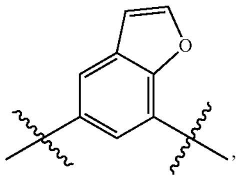

, (2a)

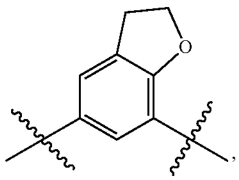

, (3a)

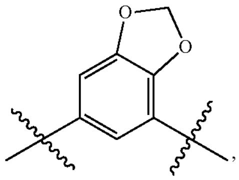

,

-continued (4a)

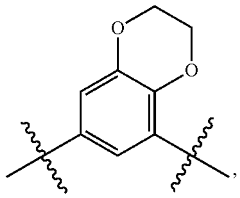

, (5a)

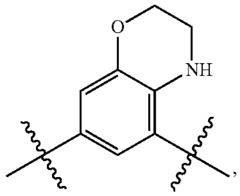

, (6a)

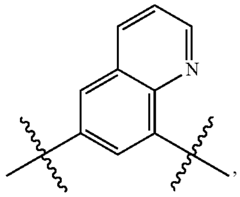

, (7a)

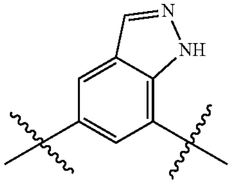

or (8a)

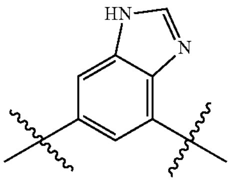

wherein the left wavy line denotes the site of attachment to the L group and the right wavy line denotes the site of attachment to the carboxamide group. The optional substitution may be 1-2 substituents independently selected from $C_{1-7}$ alkyl, halogen, halogen $C_{1-7}$ alkyl, $C_{1-7}$ alkoxy and oxo, in particular $C_{1-7}$ alkyl or oxo.

According to one embodiment, specifically provided are compounds according to any of the above embodiments wherein $R_4$ is hydrogen, halogen, $C_{1-7}$ alkyl, $C_{1-7}$ alkoxy, halogen $C_{1-7}$ alkyl or halogen $C_{1-7}$ alkoxy, and $R_5$ is hydrogen, $C_{1-7}$ alkyl, $C_{1-7}$ alkoxy, cyano, amino or halogen. In a subgroup are compounds wherein $R_4$ is halogen, $C_{1-7}$ alkyl, halogen $C_{1-7}$ alkyl or halogen $C_{1-7}$ alkoxy and $R_5$ is hydrogen, $C_{1-7}$ alkyl, cyano or halogen. In a subgroup are compounds wherein $R_4$ is halogen $C_{1-7}$ alkyl or halogen $C_{1-7}$ alkoxy and $R_5$ is hydrogen or halogen. In a subgroup are compounds wherein $R_4$ is halogen $C_{1-7}$ alkyl or halogen $C_{1-7}$ alkoxy and $R_5$ is hydrogen. In another subgroup are compounds wherein both $R_4$ and $R_5$ are $C_{1-7}$ alkyl, for example methyl. In another subgroup are compounds wherein both $R_4$ and $R_5$ are halogen, for example fluoro. Particular examples of $R_4$ being halogen $C_{1-7}$ alkyl is —$CF_3$ and —$CHF_2$ groups. A particular example of $R_4$ being halogen $C_{1-7}$ alkoxy is —$OCF_3$ group.

According to one embodiment, specifically provided are compounds according to any of the above embodiments wherein ring A together with $R_4$ and $R_5$ represent any of the following groups:

(1′)

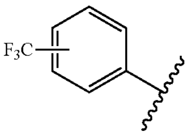

, (2′)

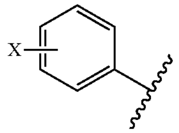

, (3′)

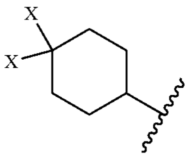

, (4′)

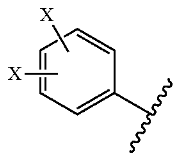

, (5′)

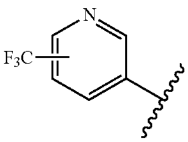

, (6′)

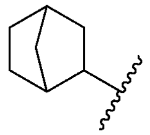

, (7′)

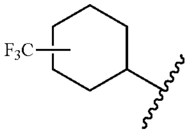

, (8′)

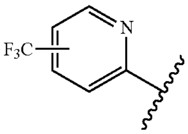

, (9′)

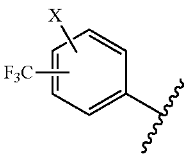

,

-continued (10')

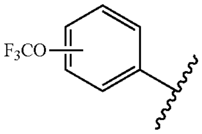

, (11')

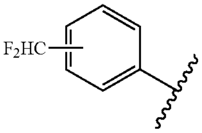

, (12')

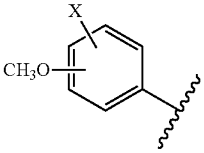

, (13')

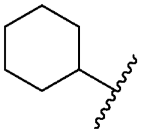

, (14')

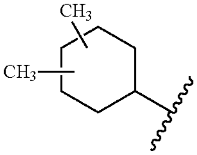

or (15')

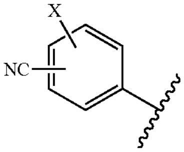

wherein X is halogen and the wavy line denotes the site of attachment to the L group.

According to one embodiment, specifically provided is a compound according to any of the above embodiments wherein A together with $R_4$ and $R_5$ is group (1'), (2'), (3'), (4'), (7'), (8'), (10'), (11') or (13'). In a subgroup are provided a compound according to any of the above embodiments wherein A together with $R_4$ and $R_5$ is group (1'), (4'), (7'), (8'), (10') or (11').

According to one embodiment, specifically provided are compounds according to any of the above embodiments wherein ring A together with $R_4$ and $R_5$ are represented by following groups:

(1")

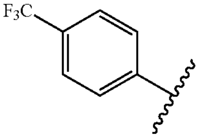

, (2")

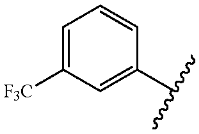

,

-continued (3")

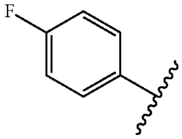

, (4")

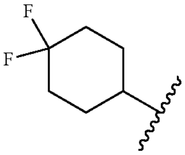

, (5")

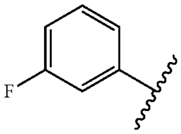

, (6")

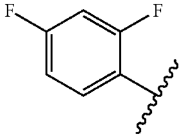

, (7")

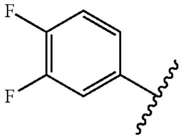

, (8")

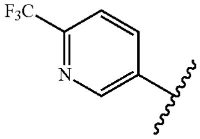

, (9")

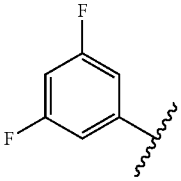

, (10")

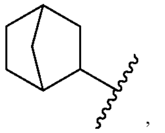

, (11")

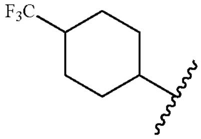

, (12")

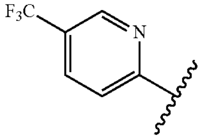

,

-continued (13″)

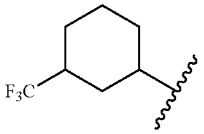

, (14″)

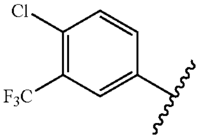

, (15″)

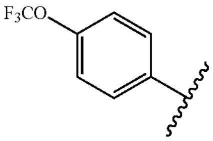

, (16″)

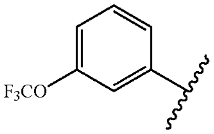

, (17″)

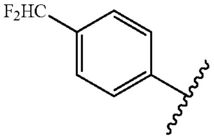

, (18″)

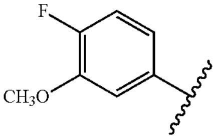

, (19″)

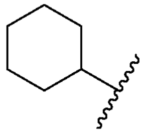

, (20″)

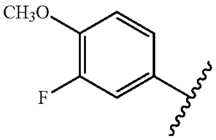

, (21″)

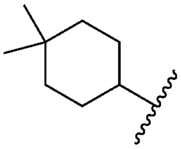

or (22″)

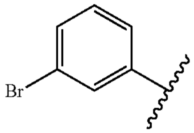

, wherein the wavy line denotes the site of attachment to the L group.

According to one embodiment, specifically provided is a compound according to any of the above embodiments wherein A together with $R_4$ and $R_5$ is group (1"), (2"), (3"), (4"), (7"), (11"), (12"), (13"), (15"), (17"), (19") or (21"). In a subgroup are provided a compound according to any of the above embodiments wherein A together with $R_4$ and $R_5$ is group (1'"), (2"), (4"), (7"), (11"), (12"), (15") or (21").

According to one embodiment, specifically provided is a compound according to any of the above embodiments wherein A is phenyl or pyridyl, L is —O—, $R_1$ is $C_{1-7}$ alkoxy, $R_2$, $R_3$, $R_5$, $R_{33}$ and $R_{42}$ are hydrogen, Z is ring (1a) or (12) and $R_4$ is halogen $C_{1-7}$ alkyl.

According to one embodiment, specifically provided are compounds according to any of the above embodiments wherein Z can also be —CH($NHR_{25}$)—$(CH_2)_2$—COOH.

According to one embodiment, specifically provided are compounds according to formula (Ib) or a pharmaceutically acceptable salt thereof (Ib)

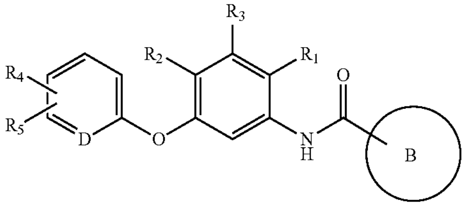

wherein

D is CH or N;

$R_2$ is H or halogen;

$R_4$ is H, halogen or cyano;

$R_5$ is halogen or halogen $C_{1-7}$ alkyl;

B is ring (1a), (10) or (12);

$R_1$ is —$OCH_3$ or halogen, or $R_1$ and $R_3$ together with the phenyl ring to which they are attached form a fused ring represented by any of the following groups:

(1a)

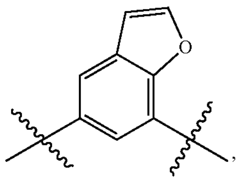

, (2a)

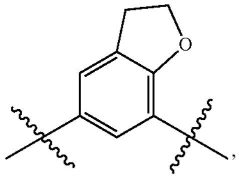

, (3a)

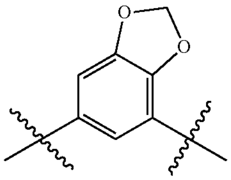

or

-continued (4a)

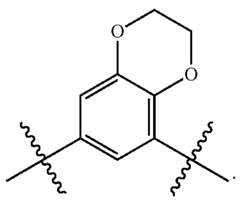

According to one embodiment, specifically provided are compounds according to formula (Ic) or a pharmaceutically acceptable salt thereof (Ic)

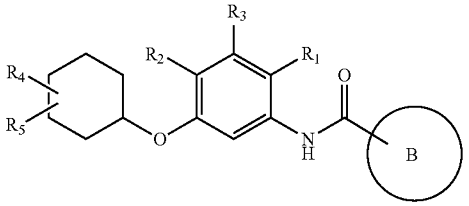

wherein

L is —O— or —CH═CH—;

$R_2$ is H or halogen;

$R_4$ is H, $C_{1-7}$ alkyl or halogen;

$R_5$ is halogen, $C_{1-7}$ alkyl or halogen $C_{1-7}$ alkyl;

B is ring (1a), (10) or (12);

$R_1$ is —$OCH_3$ or halogen, or $R_1$ and $R_3$ together with the phenyl ring to which they are attached form a fused ring represented by any of the following groups:

(1a)

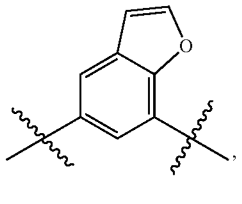

, (2a)

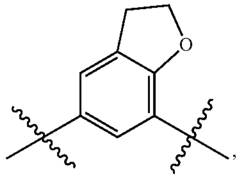

, (3a)

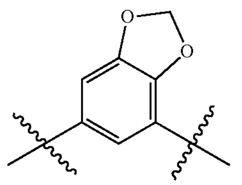

or

-continued (4a)

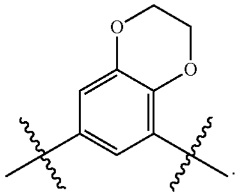

.

According to still one embodiment, the present invention provides a method for the treatment of a disease or condition wherein inhibition of TEAD is desired, such as cancer and chronic pain, comprising administering to a subject in need thereof a therapeutically effective amount of a compound of formula (I) as defined in any of the above embodiments.

The compounds of the invention can be prepared by a variety of synthetic routes analogously to the methods known in the literature using suitable starting materials. The compounds according to formula (I) can be prepared e.g. analogously or according to the following reaction Schemes. Some compounds included in the formula (I) can be obtained by converting the functional groups of the other compounds of formula (I) obtained in accordance with the following Schemes, by well known reaction steps such as oxidation, reduction, hydrolysis, acylation, alkylation, amidation, amination, sulfonation and others. It should be noted that any appropriate leaving groups, e.g. N-protecting groups, such as a t-butoxycarbonyl (t-BOC) group or a phenylsulfonyl group, can be used in well known manner during the syntheses in order to improve the selectivity of the reaction steps.

Compounds of formula (I) can be prepared, for example, according to Scheme 1, wherein A, L, Z, $R_1$, $R_2$, $R_3$, $R_4$, $R_5$, $R_{33}$ and $R_{42}$ are as defined above. In the method of Scheme 1, the aniline compound of formula [1] is coupled with a carboxylic acid derivative of formula [2] in a suitable solvent, such as anhydrous acetonitrile or DMF, in the presence of a suitable coupling reagent such as a combination of N,N,N',N'-tetramethylchloroformamidinium hexafluorophosphate and 1-methyl-1H-imidazole, or hexafluorophosphate azabenzotriazole tetramethyl uranium (HATU) and N,N-diisopropylethylamine (DIPEA) to produce a compound of formula (I).

SCHEME 1.

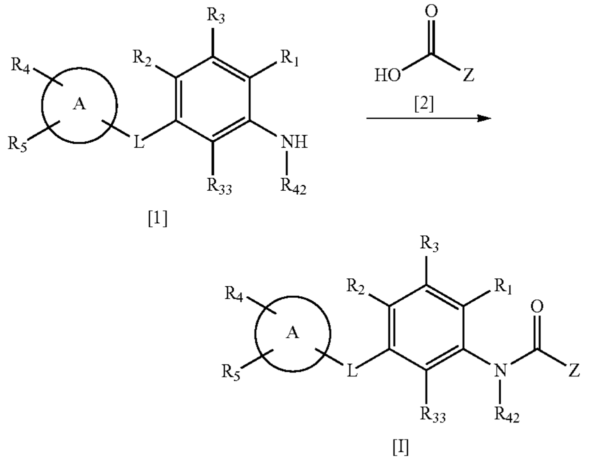

[1] [2] [I]

Alternatively, compounds of formula (I), wherein $R_{42}$ is H, can be prepared according to Scheme 2, wherein A, L, Z, $R_1$, $R_2$, $R_3$, $R_4$, $R_5$ and $R_{33}$ are as defined above and X is a halogen, for example bromo. In the method of Scheme 2, the compound of formula [3] is coupled with a carboxamide compound of formula [4] in a suitable solvent, such as toluene, in the presence a base, such as cesium carbonate, and a suitable catalyst system such as a combination $Pd_2$ (dba) and 4,5-Bis(diphenylphosphino)-9,9-dimethylxanthene (XantPhos), or copper iodide and N1,N2-dimethylcyclohexane-1,2-diamine, to produce a compound of formula (I).

SCHEME 2.

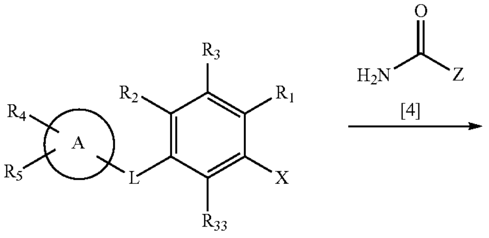

[3]

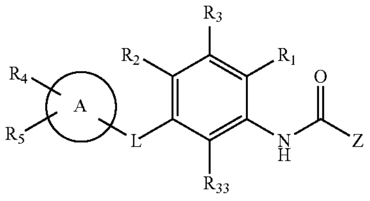

(I')

Compounds of formula (I) wherein L is —O— can also be prepared, for example, according to Scheme 3, wherein A, Z, $R_1$, $R_2$, $R_3$, $R_4$ and $R_5$ are as defined above. In the method of Scheme 3, the compound of formula [3] is condensed with a compound of formula [4] in a suitable solvent, such as tetrahydrofuran, in the presence of Mitsunobu reagents, such as triphenylphosphine (TPP) and diethyl azodicarboxylate (DEAD), to produce a compound of formula (I).

SCHEME 3.

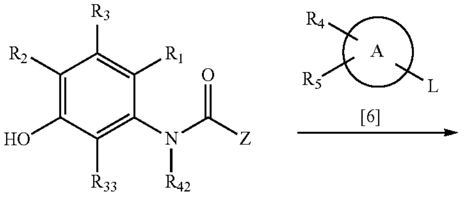

[5]

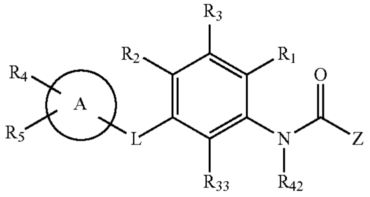

(Ia)

Intermediate compounds can be prepared according to the methods disclosed in the literature or as disclosed in the present disclosure.

For example, intermediate compounds of formula [1a], wherein L is —O—, can be prepared according to Scheme 4, wherein A, $R_1$, $R_2$, $R_3$, $R_4$, $R_5$ and $R_{33}$ are as defined above. In the method of Scheme 4, a compound of formula [7] is coupled with a compound of formula [8] in a suitable solvent such as dichloromethane, in the presence of a base such as pyridine and a catalyst such as diacetoxycopper to produce a compound of formula [8], which can be subsequently reduced, for example, by hydrogenation in the presence of suitable catalyst such as palladium-in-carbon to obtain the intermediate of formula [1a].

SCHEME 4.

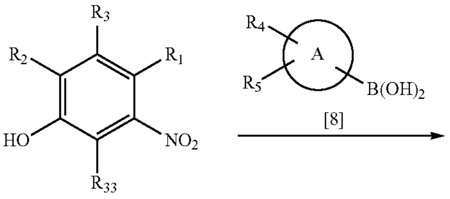

[7]

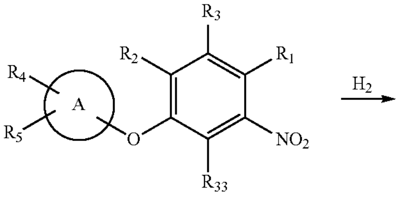

[8]

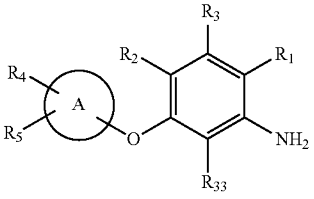

[1a]

Intermediate compounds of formula [3a] wherein L is —O—, can be prepared, for example, according to Scheme 5, wherein A, $R_1$, $R_2$, $R_3$, $R_4$, $R_5$ and $R_{33}$ are as defined above and X is a halogen, for example bromo. In the method of Scheme 5, a compound of formula [9] is coupled with a compound of formula [10] in a suitable solvent such as dichloromethane, in the presence of a base such as pyridine and a catalyst such as diacetoxycopper to produce a compound of formula [3a],

SCHEME 5.

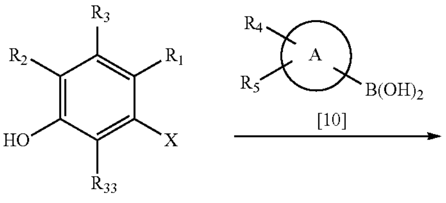

[9]

-continued

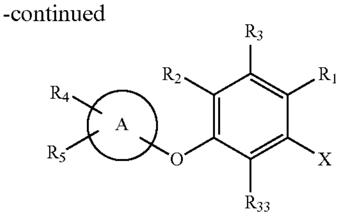

[3a]

Intermediate compounds of formula [5] can be prepared, for example, according to Scheme 6, wherein Z, $R_1$, $R_2$ and $R_3$ are as defined above. In the method of Scheme 6, a compound of formula [11] is coupled with a compound of formula [12] in a suitable solvent such as DMF in the presence of a base such as N,N-diisopropylethylamine (DIPEA) and a coupling agent such as hexafluorophosphate azabenzotriazole tetramethyl uranium (HATU) to produce the intermediate of formula {5].

SCHEME 6.

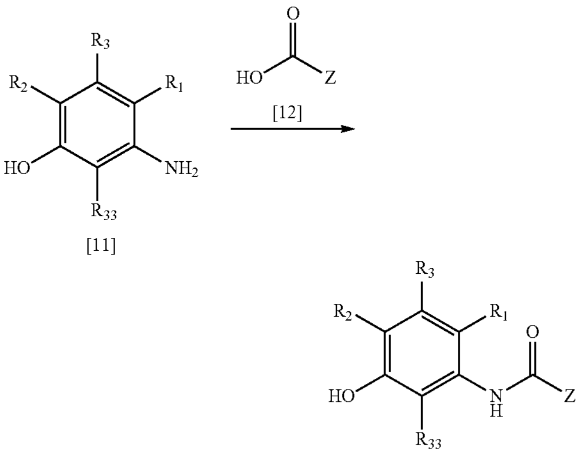

[11] [12] [5]

Alternatively, the compounds of formula (I) can be prepared as disclosed in the specific Examples of the present disclosure.

Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "subject", as employed herein, refers to humans and animals.

The term "halo" or "halogen", as employed herein as such or as part of another group, refers to chlorine, bromine, fluorine or iodine. Preferred halogens are chlorine and fluorine.

The term "$C_{1-7}$ alkyl", as employed herein as such or as part of another group, refers to a straight or branched chain saturated hydrocarbon group having 1, 2, 3, 4, 5, 6 or 7 carbon atom(s). Representative examples of $C_{1-7}$ alkyl include, but are not limited to, methyl, ethyl, n-propyl, iso-propyl, n-butyl, iso-butyl, sec-butyl, tert-butyl, n-pentyl, iso-pentyl and n-hexyl. One preferred embodiment of "$C_{1-7}$ alkyl" is $C_{1-3}$ alkyl. The term "$C_{1-3}$ alkyl" refers to an embodiment of "$C_{1-7}$ alkyl" having 1, 2 or 3 carbon atoms. Examples of "$C_{1-3}$ alkyl" include, but are not limited to, methyl, ethyl, n-propyl and iso-propyl. One preferred "$C_{1-7}$ alkyl" is methyl group.

The term "$C_{2-7}$ alkenyl", as employed herein as such or as part of another group, refers to an aliphatic hydrocarbon group having 2, 3, 4, 5, 6 or 7 carbon atoms and containing one or several double bonds. Representative examples include, but are not limited to, ethenyl, propenyl and hexenyl. One preferred embodiment of "$C_{2-7}$ alkenyl" is $C_{2-4}$ alkenyl. The term "$C_{2-4}$ alkenyl" refers to a embodiment of "$C_{2-7}$ alkenyl" having 2, 3 or 4 carbon atoms. Representative examples include, but are not limited to, ethenyl, propenyl and butenyl. One preferred "$C_{2-7}$ alkenyl" is —CH═CH— group.

The term "$C_{3-7}$ cycloalkyl", as employed herein as such or as part of another group, refers to a saturated cyclic hydrocarbon group containing 3, 4, 5, 6 or 7 carbon atoms. Representative examples of cycloalkyl include, but are not limited to, cyclopropyl, cyclobutyl, cyclopentyl and cyclohexyl. One preferred "$C_{3-7}$ cycloalkyl" is cyclopropyl group.

The term "hydroxy", as employed herein as such or as part of another group, refers to an —OH group.

The term "cyano", as employed herein as such or as part of another group, refers to a —CN group.

The term "carboxy", as employed herein as such or as part of another group, refers to —COOH group.

The term "carbonyl", as employed herein as such or as part of another group, refers to a carbon atom double-bonded to an oxygen atom (C═O).

The term "oxo", as employed herein as such or as part of another group, refers to oxygen atom linked to another atom by a double bond (═O).

The term "$C_{1-7}$ alkoxy", as employed herein as such or as part of another group, refers to $C_{1-7}$ alkyl, as defined herein, appended to the parent molecular moiety through an oxygen atom. Representative examples of $C_{1-7}$ alkoxy include, but are not limited to methoxy, ethoxy, propoxy, butoxy, isobutoxy, sec-butoxy and tert-butoxy. One preferred embodiment of "$C_{1-7}$ alkoxy" is $C_{1-3}$ alkoxy. The term "$C_{1-3}$ alkoxy" refers to an embodiment of "$C_{1-7}$ alkoxy" having 1, 2 or 3 carbon atoms. Representative examples of $C_{1-3}$ alkoxy include, but are not limited to methoxy, ethoxy, propoxy. One preferred "$C_{1-7}$ alkoxy" group is methoxy.

The term "hydroxy $C_{1-7}$ alkyl", as employed herein, refers to at least one hydroxy group, as defined herein, appended to the parent molecular moiety through a $C_{1-7}$ alkyl group, as defined herein. Representative examples of hydroxy $C_{1-7}$ alkyl include, but are not limited to, hydroxymethyl, 2,2-dihydroxyethyl, 1-hydroxyethyl, 3-hydroxypropyl, 1-hydroxypropyl, 1-methyl-1-hydroxyethyl and 1-methyl-1-hydroxypropyl.

The term "halogen $C_{1-7}$ alkyl", as employed herein, refers to at least one halogen, as defined herein, appended to the parent molecular moiety through a $C_{1-7}$ alkyl group, as defined herein. Representative examples of halogen $C_{1-7}$ alkyl include, but are not limited to, fluoromethyl, difluoromethyl, trifluoromethyl, 2-chloroethyl and 3-bromo-propyl. Preferred "halogen $C_{1-7}$ alkyl" groups are trifluoromethyl and difluoromethyl.

The term "halogen $C_{1-7}$ alkoxy", as employed herein, refers to at least one halogen, as defined herein, appended to the parent molecular moiety through a $C_{1-7}$ alkoxy group, as defined herein.

The term "$C_{1-7}$ alkoxy $C_{1-7}$ alkyl", as employed herein as such or as part of another group, refers to at least one $C_{1-7}$ alkoxy group, as defined herein, appended to the parent molecular moiety through a $C_{1-7}$ alkyl group, as defined herein.

The term "4-10 membered carbocyclic ring", as employed herein, refers to a saturated, partially saturated or aromatic ring with 4 to 10 ring atoms consisting of carbon atoms only. One embodiment of a "4-10 membered carbocyclic ring" is a "5-6 membered carbocyclic ring" which refers to a saturated, partially saturated or aromatic ring with 5 to 6 ring atoms consisting of carbon atoms only. Representative examples of a 4-10 membered carbocyclic ring include, but are not limited to, phenyl, cyclohexyl, cyclohexenyl, cyclopentyl, cyclopentenyl and cyclobutyl rings.

The term "substituted" as used herein in connection with various residues refers to, if not otherwise defined, to halogen substituents, such as fluorine, chlorine, bromine, iodine, or $C_{1-7}$ alkyl, $C_{3-7}$ cycloalkyl, hydroxy, amino, nitro, cyano, thiol $C_{1-7}$ alkyl, methylsulfonyl, $C_{1-7}$ alkoxy, halo $C_{1-7}$ alkyl, hydroxy $C_{1-7}$ alkyl or amino $C_{1-7}$ alkyl substituents. Preferred are halogen, $C_{1-7}$ alkyl, hydroxy, amino, halo $C_{1-7}$ alkyl, $C_{1-7}$ alkoxy and methylsulfonyl substituents. In one group of preferred substituents are 1-2 substituents selected from $C_{1-7}$ alkyl or halogen substituents, particularly $C_{1-3}$ alkyl or halogen substituents, particularly methyl, ethyl, chloro, fluoro or bromo substituents.

The "substituted" groups may contain 1 to 3, preferably 1 or 2, of the above mentioned substituents, if not otherwise defined.

Optically active enantiomers or diastereomers of compounds of formula (I) can be prepared e.g. by resolution of the racemic end product by known methods or by using suitable optically active starting materials. Similarly, racemic compounds of formula (I) can be prepared by using racemic starting materials. Resolution of racemic compounds of formula (I) or a racemic starting material thereof can be carried out, for example, by converting the racemic compound into its diastereromeric salt mixture by reaction with an optically active acid and subsequent separation of the diastereomers by crystallization. Representative examples of said optically active acids include, but are not limited to, D-tartaric acid and dibenzoyl-D-tartaric acid. Alternatively, preparative chiral chromatography may be used for resolution of the racemic mixture.

Pharmaceutically acceptable salts are well known in the field of pharmaceuticals. Non-limiting examples of suitable salts include metal salts, ammonium salts, salts with an organic base, salts with an inorganic acid, salts with organic acid, and salts with basic or acidic amino acid. Non-limiting examples of metal salts include alkali metal salts such as sodium salt and potassium salt; alkaline earth metal salts such as calcium salt, and magnesium salt. Non-limiting examples of salts with inorganic or organic acids include chlorides, bromides, sulfates, nitrates, phosphates, sulfonates, methane sulfonates, formates, tartrates, maleates, citrates, benzoates, salicylates, ascorbates, acetates, oxalates, fumarates, hemifumarates, and succinates. Pharmaceutically acceptable esters, when applicable, may be prepared by known methods using pharmaceutically acceptable acids that are conventional in the field of pharmaceuticals and that retain the pharmacological properties of the free form. Non-limiting examples of these esters include esters of aliphatic or aromatic alcohols, e.g. methyl, ethyl, propyl, isopropyl, butyl, isobutyl, sec-butyl, tert-butyl esters. Phosphate esters and carbonate esters, are also within the scope of the invention.

The definition of formula (I) above is inclusive of all the possible isotopes and isomers, such as stereoisomers, of the compounds, including geometric isomers, for example Z and E isomers (cis and trans isomers), and optical isomers, e.g. diastereomers and enantiomers, and prodrug esters, e.g. phosphate esters and carbonate esters.

It will be appreciated by those skilled in the art that the present compounds may contain at least one chiral center. Accordingly, the compounds may exist in optically active or racemic forms. It is to be understood that the formula (I) includes any racemic or optically active form, or mixtures thereof. In one embodiment, the compounds are the pure (R)-isomers. In another embodiment, the compounds are the pure (S)-isomers. In another embodiment, the compounds are a mixture of the (R) and the (S) isomers. In another embodiment, the compounds are a racemic mixture comprising an equal amount of the (R) and the (S) isomers. The compounds may contain two chiral centers. In such case, according to one embodiment, the compounds are a mixture of diasteromers. According to another embodiment, the compounds of the invention are a mixture of enantiomers. According to still another embodiment, the compounds are pure enantiomers. The individual isomers may be obtained using the corresponding isomeric forms of the starting material or they may be separated after the preparation of the end compound according to conventional separation methods. For the separation of optical isomers, e.g. enantiomers or diastereomers, from the mixture thereof the conventional resolution methods, e.g. fractional crystallisation, may be used.

The present compounds may also exist as tautomers or equilibrium mixtures thereof wherein a proton of a compound shifts from one atom to another. Examples of tautomerism include, but are not limited to, amido-imido, keto-enol, phenol-keto, oxime-nitroso, nitro-aci, imine-enamine, annular tautomerism of heterocyclic rings such as pyrozole ring, and the like. Tautomeric forms are intended to be encompassed by compounds of formula (I), even though only one tautomeric form may be depicted.

Examples of preferred compounds of one group of formula (I) include

N-(2-Methoxy-5-(4-(trifluoromethyl)phenoxy)phenyl)-5-oxopyrrolidine-2-carboxamide (Compound 1);

1-Acetyl-N-(5-(3-fluorophenoxy)-2-methoxyphenyl)-5-oxopyrrolidine-2-carboxamide (Compound 2);

1-Acetyl-N-(5-((3-fluorophenoxy)methyl)-2-methoxyphenyl)-5-oxopyrrolidine-2-carboxamide (Compound 3);

N-(5-((3-Fluorophenoxy)methyl)-2,4-dimethoxyphenyl)-5-oxopyrrolidine-2-carboxamide (Compound 4);

1-(2-Fluoroethyl)-N-(5-((3-fluorophenoxy)methyl)-2-methoxyphenyl)azetidine-3-carboxamide (Compound 5);

rac-(trans)-N-(5-((3-Fluorophenoxy)methyl)-2-methoxyphenyl)-3-methyl-5-oxopyrrolidine-2-carboxamide (Compound 6);

4-Oxo-N-(3-(3-(trifluoromethyl)phenoxy)phenyl)azetidine-2-carboxamide (Compound 7);

N-(2-Methoxy-5-(3-(trifluoromethyl)phenoxy)phenyl)-4-oxoazetidine-2-carboxamide (Compound 8);

N-(2-Methoxy-5-(3-(trifluoromethyl)phenoxy)phenyl)-2-(5-oxopyrrolidin-2-yl)acetamide (Compound 9);

N-(2-Methoxy-5-(3-(trifluoromethyl)phenoxy)phenyl)-5-oxopyrrolidine-2-carboxamide (Compound 10);

N-(2-Methoxy-5-(3-(trifluoromethyl)phenoxy)phenyl)-1-methyl-5-oxopyrro-lidine-2-carboxamide (Compound 11);

N-(2-Methoxy-5-(3-(trifluoromethyl)phenoxy)phenyl)tetrahydrothiophene-3-carboxamide 1,1-dioxide (Compound 12);

N-(5-((3-Fluorophenoxy)methyl)-2-methoxyphenyl)-2-methylisothiazolidine-3-carboxamide 1,1-dioxide (Compound 13);

N-(2-Methoxy-5-(3-(trifluoromethyl)phenoxy)phenyl)-2-methyl-5-oxopyrrolidi-ne-2-carboxamide (Compound 14);

N-(5-(3-Fluorophenoxy)-2-methoxyphenyl)-2-methyl-5-oxopyrrolidine-2-carboxamide (Compound 15);

5-Oxo-N-(3-(3-(trifluoromethyl)phenoxy)phenyl) pyrrolidine-2-carboxamide (Compound 16);

N-(5-((3-Fluorophenoxy)methyl)benzofuran-7-yl)-5-oxopyrrolidine-2-carboxamide (Compound 17);

N-(5-(3-Fluorophenoxy)-2-methoxyphenyl)-5-oxotetrahydropyrrolo[2,1-b]-thiazole-7a(5H)-carboxamide (Compound 18);

N-(2-Methoxy-5-(3-(trifluoromethyl)phenoxy)phenyl)-5-oxotetrahydropyrrolo[2,1-b]thiazole-7a(5H)-carboxamide (Compound 19);

rac-(cis)-N-(5-((3-Fluorophenoxy)methyl)-2-methoxyphenyl)-3-methyl-5-oxo-pyrrolidine-2-carboxamide (Compound 20);

(E)-N-(5-(2-(4,4-Difluorocyclohexyl)vinyl)-2-methoxyphenyl)-5-oxopyrroli-dine-2-carboxamide (Compound 21);

(E)-N-(5-(2-(4,4-Difluorocyclohexyl)vinyl)-2-methoxyphenyl)-1-methyl-5-oxo-pyrrolidine-2-carboxamide (Compound 22);

(E)-N-(5-(2-(4,4-Difluorocyclohexyl)vinyl)-2-methoxyphenyl)-5-oxopyrroli-dine-2-carboxamide, enantiomer 1 (Compound 23);

(E)-N-(5-(2-(4,4-Difluorocyclohexyl)vinyl)-2-methoxyphenyl)-5-oxopyrrolidi-ne-2-carboxamide, enantiomer 1 (Compound 24);

(R)—N-(5-(3-Fluorophenoxy)-2-methoxyphenyl)-5-oxopyrrolidine-2-carboxamide (Compound 25);

N-(5-((3-Fluorophenoxy)methyl)-2-methoxyphenyl)-3-methyl-2-oxopyrrolidine-3-carboxamide (Compound 26);

N-(6-((3-Fluorophenoxy)methyl)benzo[d][1,3]dioxol-4-yl)-5-oxopyrrolidine-2-carboxamide (Compound 27);

1-Methyl-5-oxo-N-(5-(3-(trifluoromethyl)phenoxy)benzofuran-7-yl)pyrrolidine-2-carboxamide (Compound 28);

1-Acetyl-N-(2-methoxy-5-(3-(trifluoromethyl)phenoxy)phenyl)-5-oxo-pyrrolidine-2-carboxamide (Compound 29);

1-Acetyl-N-(2-methoxy-5-(3-(trifluoromethyl)phenoxy)phenyl)-5-oxo-pyrrolidine-2-carboxamide, enantiomer 2 (Compound 30);

N-(5-((3-Fluorophenoxy)methyl)-2,3-dihydrobenzofuran-7-yl)-5-oxopyrrolidine-2-carboxamide (Compound 31);

N-(5-((3-Fluorophenoxy)methyl)-2,3-dihydrobenzofuran-7-yl)-1-methyl-5-oxo-pyrrolidine-2-carboxamide (Compound 32);

5-Oxo-N-(6-(3-(trifluoromethyl)phenoxy)benzo[d][1,3]dioxol-4-yl)pyrrolidine-2-carboxamide (Compound 33);

1-Methyl-5-oxo-N-(6-(3-(trifluoromethyl)phenoxy)benzo[d][1,3]dioxol-4-yl)-pyrrolidine-2-carboxamide (Compound 34);

N-(3-Fluoro-5-((3-fluorophenoxy)methyl)-2-methoxyphenyl)-1-methyl-5-oxo-pyrrolidine-2-carboxamide (Compound 35);

N-(3-Fluoro-5-((3-fluorophenoxy)methyl)-2-methoxyphenyl)-5-oxopyrrolidine-2-carboxamide (Compound 36);

1-Ethyl-N-(2-methoxy-5-(3-(trifluoromethyl)phenoxy)phenyl)-5-oxopyrrolidine-2-carboxamide (Compound 37);

1-(Cyclopropanecarbonyl)-N-(2-methoxy-5-(3-(trifluoromethyl)phenoxy)-phenyl)-5-oxopyrrolidine-2-carboxamide (Compound 38);

1-Acetyl-N-(4-fluoro-2-methoxy-5-(3-(trifluoromethyl)phenoxy)phenyl)-5-oxopyrrolidine-2-carboxamide (Compound 39);

1-Acetyl-N-(2-fluoro-5-(3-(trifluoromethyl)phenoxy)phenyl)-5-oxopyrrolidine-2-carboxamide (Compound 40);

N-(2-Fluoro-5-(3-(trifluoromethyl)phenoxy)phenyl)-1-methyl-5-oxopyrrolidine-2-carboxamide (Compound 41);

N-(5-(2,4-Difluorophenoxy)-2-methoxyphenyl)-5-oxopyrrolidine-2-carboxamide (Compound 42);

N-(5-(2,4-Difluorophenoxy)-2-methoxyphenyl)-1-methyl-5-oxopyrrolidine-2-carboxamide (Compound 43);

1-Acetyl-N-(5-(2,4-difluorophenoxy)-2-methoxyphenyl)-5-oxopyrrolidine-2-carboxamide (Compound 44);

N-(2-Methoxy-5-(4-(trifluoromethyl)phenoxy)phenyl)-5-oxopyrrolidine-2-carboxamide (Compound 45);

N-(2-Methoxy-5-(4-(trifluoromethyl)phenoxy)phenyl)-5-oxopyrrolidine-2-carboxamide (Compound 46);

1-Acetyl-N-(2-methoxy-5-(4-(trifluoromethyl)phenoxy)phenyl)-5-oxo-pyrrolidine-2-carboxamide (Compound 47);

N-(2-Methoxy-5-(4-(trifluoromethyl)phenoxy)phenyl)-1-methyl-5-oxopyrrolidi-ne-2-carboxamide (Compound 48);

N-(2-Methoxy-5-((3-(trifluoromethyl)phenoxy)methyl)phenyl)-5-oxopyrrolidine-2-carboxamide (Compound 49);

1-Acetyl-N-(2-methoxy-5-((3-(trifluoromethyl)phenoxy)methyl)phenyl)-5-oxopyrrolidine-2-carboxamide (Compound 50);

1-Acetyl-N-(2-methoxy-5-((3-(trifluoromethyl)benzyl)oxy)phenyl)-5-oxo-pyrrolidine-2-carboxamide (Compound 51);

N-(2-Methoxy-5-((3-(trifluoromethyl)benzyl)oxy)phenyl)-5-oxopyrrolidine-2-carboxamide (Compound 52);

N-(2-Methoxy-5-((3-(trifluoromethyl)benzyl)oxy)phenyl)-1-methyl-5-oxo-pyrrolidine-2-carboxamide (Compound 53);

N-(7-(3-(Trifluoromethyl)phenoxy)-2,3-dihydrobenzo[b][1,4]dioxin-5-yl)-isothiazolidine-3-carboxamide 1,1-dioxide (Compound 54);

5-Oxo-N-(7-(3-(trifluoromethyl)phenoxy)-2,3-dihydrobenzo[b][1,4]dioxin-5-yl)pyrrolidine-2-carboxamide (Compound 55);

1-Acetyl-5-oxo-N-(7-(3-(trifluoromethyl)phenoxy)-2,3-dihydrobenzo[b][1,4]-dioxin-5-yl)pyrrolidine-2-carboxamide (Compound 56);

N-(7-((3-Fluorophenoxy)methyl)-2,3-dihydrobenzo[b][1,4]dioxin-5-yl)-5-oxopyrrolidine-2-carboxamide (Compound 57);

N-(7-((3-Fluorophenoxy)methyl)-2,3-dihydrobenzo[b][1,4]dioxin-5-yl)-1-methyl-5-oxopyrrolidine-2-carboxamide (Compound 58);

N-(5-(3,4-Difluorophenoxy)-2-methoxyphenyl)-5-oxopyrrolidine-2-carboxamide (Compound 59);

N-(5-(3,4-Difluorophenoxy)-2-methoxyphenyl)-1-methyl-5-oxopyrrolidine-2-carboxamide (Compound 60);

N-(8-Methyl-7-(3-(trifluoromethyl)phenoxy)-2,3-dihydrobenzo[b][1,4]dioxin-5-yl)-5-oxopyrrolidine-2-carboxamide (Compound 61);

N-(2-Methoxy-5-((6-(trifluoromethyl)pyridin-3-yl)oxy)phenyl)-5-oxopyrrolidine-2-carboxamide (Compound 62);

N-(2-Methoxy-5-((6-(trifluoromethyl)pyridin-3-yl)oxy)phenyl)-1-methyl-5-oxopyrrolidine-2-carboxamide (Compound 63);

(E)-N-(2-Methoxy-5-(2-(tetrahydro-2H-pyran-4-yl)vinyl)phenyl)-1-methyl-5-oxopyrrolidine-2-carboxamide (Compound 64);
(E)-N-(2-Methoxy-5-(2-(tetrahydro-2H-pyran-4-yl)vinyl)phenyl)-5-oxo-pyrrolidine-2-carboxamide (Compound 65);
5-Oxo-N-(7-(4-(trifluoromethyl)phenoxy)-2,3-dihydrobenzo[b][1,4]dioxin-5-yl)pyrrolidine-2-carboxamide (Compound 66);
1-Methyl-5-oxo-N-(7-(4-(trifluoromethyl)phenoxy)-2,3-dihydrobenzo[b][1,4]-dioxin-5-yl)pyrrolidine-2-carboxamide (Compound 67);
1-Ethyl-N-(2-methoxy-5-(4-(trifluoromethyl)phenoxy)phenyl)-5-oxopyrrolidine-2-carboxamide (Compound 68);
(R)—N-(2-Methoxy-5-(4-(trifluoromethyl)phenoxy)phenyl)-1-methyl-5-oxo-pyrrolidine-2-carboxamide (Compound 69);
(S)—N-(2-Methoxy-5-(4-(trifluoromethyl)phenoxy)phenyl)-1-methyl-5-oxo-pyrrolidine-2-carboxamide (Compound 70);
N-(2-Methoxy-5-(4-(trifluoromethyl)phenoxy)phenyl)-2-methyl-1,2-thiazeti-dine-3-carboxamide 1,1-dioxide (Compound 71);
N-(2-Methoxy-5-(3-(trifluoromethyl)phenoxy)phenyl)-2-methyl-1,2-thiaze-tidine-3-carboxamide 1,1-dioxide (Compound 72);
N-(4-Fluoro-5-((3-fluorophenoxy)methyl)-2-methoxyphenyl)-5-oxopyrrolidine-2-carboxamide (Compound 73);
N-(2-Methoxy-5-((4-(trifluoromethyl)phenyl)amino)phenyl)-1-methyl-5-oxo-pyrrolidine-2-carboxamide (Compound 74);
N-(2-Fluoro-5-(4-(trifluoromethyl)phenoxy)phenyl)-1-methyl-5-oxopyrrolidine-2-carboxamide (Compound 75);
N-(2-Fluoro-5-(4-(trifluoromethyl)phenoxy)phenyl)-5-oxopyrrolidine-2-carboxamide (Compound 76);
1-Acetyl-N-(5-(3,5-difluorophenoxy)-2-methoxyphenyl)-5-oxopyrrolidine-2-carboxamide (Compound 77);
N-(5-(3,5-Difluorophenoxy)-2-methoxyphenyl)-1-methyl-5-oxopyrrolidine-2-carboxamide (Compound 78);
N-(5-(2,5-Difluorophenoxy)-2-methoxyphenyl)-5-oxopyrrolidine-2-carboxamide (Compound 79);
3-Oxo-N-(7-(4-(trifluoromethyl)phenoxy)-2,3-dihydrobenzo[b][1,4]dioxin-5-yl)tetrahydro-1H-pyrrolizine-7a(5H)-carboxamide (Compound 80);
1-Isopropyl-N-(2-methoxy-5-(4-(trifluoromethyl)phenoxy)phenyl)-5-oxo-pyrrolidine-2-carboxamide (Compound 81);
N-(5-(3,4-Difluorophenoxy)-2-methoxyphenyl)-1-isopropyl-5-oxopyrrolidine-2-carboxamide (Compound 82);
N-(2-(1,3,4-Oxadiazol-2-yl)-5-(4-(trifluoromethyl)phenoxy)phenyl)-1-methyl-5-oxopyrrolidine-2-carboxamide (Compound 83);
N-(2-(1,3,4-Oxadiazol-2-yl)-5-(3-(trifluoromethyl)phenoxy)phenyl)-1-methyl-5-oxopyrrolidine-2-carboxamide (Compound 84);
N-(5-(3,4-Difluorophenoxy)-2-(1-methyl-1H-pyrazol-3-yl)phenyl)-1-methyl-5-oxopyrrolidine-2-carboxamide (Compound 85);
N-(5-(3,4-Difluorophenoxy)-2-(1-methyl-1H-pyrazol-5-yl)phenyl)-1-methyl-5-oxopyrrolidine-2-carboxamide (Compound 86);
N-(2-Methoxy-5-(4-(trifluoromethyl)phenoxy)phenyl)-3-methyl-2-oxo-oxazolidine-4-carboxamide (Compound 87);
N-(5-(3,4-Difluorophenoxy)-2-methoxyphenyl)-3-methyl-2-oxooxazolidine-4-carboxamide (Compound 88);
N-(5-((3,4-Difluorophenoxy)methyl)-2-methoxyphenyl)-3-methyl-2-oxo-oxazolidine-4-carboxamide (Compound 89);
N-(5-((3-Fluorophenoxy)methyl)-2-methoxyphenyl)-3-methyl-2-oxo-oxazolidine-4-carboxamide (Compound 90);
N-(2-Methoxy-5-(4-(trifluoromethyl)phenoxy)phenyl)-1-methyl-5-thioxo-pyrrolidine-2-carboxamide (Compound 91);
N-(2-Methoxy-5-(4-(trifluoromethyl)phenoxy)phenyl)-5-thioxopyrrolidine-2-carboxamide (Compound 92);
(R)—N-(5-(3,4-Difluorophenoxy)-2-methoxyphenyl)-1-methyl-5-oxopyrrolidine-2-carboxamide (Compound 93);
(S)—N-(5-(3,4-Difluorophenoxy)-2-methoxyphenyl)-1-methyl-5-oxopyrrolidine-2-carboxamide (Compound 94);
N-(5-((3,4-Difluorophenoxy)methyl)-2-methoxyphenyl)-1-methyl-5-oxo-pyrrolidine-2-carboxamide (Compound 95);
N-(5-(Bicyclo[2.2.1]heptan-2-yloxy)-2-methoxyphenyl)-1-methyl-5-oxo-pyrrolidine-2-carboxamide (Compound 96);
(R)—N-(7-(3,4-Difluorophenoxy)-2,3-dihydrobenzo[b][1,4]dioxin-5-yl)-1-methyl-5-oxopyrrolidine-2-carboxamide (Compound 97);
(S)—N-(7-(3,4-Difluorophenoxy)-2,3-dihydrobenzo[b][1,4]dioxin-5-yl)-1-methyl-5-oxopyrrolidine-2-carboxamide (Compound 98);
(R)-1-Methyl-5-oxo-N-(5-(4-(trifluoromethyl)phenoxy)-2,3-dihydrobenzofuran-7-yl)pyrrolidine-2-carboxamide (Compound 99);
(S)—N-(5-(3,4-Difluorophenoxy)-2,3-dihydrobenzofuran-7-yl)-1-methyl-5-oxopyrrolidine-2-carboxamide (Compound 100);
(R)—N-(2-Methoxy-5-(4-(trifluoromethyl)phenoxy)phenyl)-3-methyl-2-oxooxazolidine-4-carboxamide (Compound 101);
(S)—N-(2-Methoxy-5-(4-(trifluoromethyl)phenoxy)phenyl)-3-methyl-2-oxooxazolidine-4-carboxamide (Compound 102);
(R)—N-(2-Methoxy-5-(((trans)-4-(trifluoromethyl)cyclohexyl)oxy)phenyl)-1-methyl-5-oxopyrrolidine-2-carboxamide (Compound 103);
N-(5-((4,4-Difluorocyclohexyl)oxy)-2-methoxyphenyl)-3-methyl-2-oxo-oxazolidine-4-carboxamide (Compound 104);
(S)—N-(2-Methoxy-5-(((trans)-4-(trifluoromethyl)cyclohexyl)oxy)phenyl)-1-methyl-5-oxopyrrolidine-2-carboxamide (Compound 105);
1-Methyl-5-oxo-N-(3-oxo-7-(3-(trifluoromethyl)phenoxy)-3,4-dihydro-2H-benzo[b][1,4]oxazin-5-yl)pyrrolidine-2-carboxamide (Compound 106);
(S)-1-Methyl-5-oxo-N-(5-(((cis)-4-(trifluoromethyl)cyclohexyl)oxy)-2,3-dihydrobenzofuran-7-yl)pyrrolidine-2-carboxamide (Compound 107);
(R)-1-Methyl-5-oxo-N-(5-(((cis)-4-(trifluoromethyl)cyclohexyl)oxy)-2,3-dihydrobenzofuran-7-yl)pyrrolidine-2-carboxamide (Compound 108);
1-Cyclopropyl-5-oxo-N-(5-(4-(trifluoromethyl)phenoxy)-2,3-dihydro-benzofuran-7-yl)pyrrolidine-2-carboxamide (Compound 109);
1-Cyclopropyl-N-(2-methoxy-5-(4-(trifluoromethyl)phenoxy)phenyl)-5-oxo-pyrrolidine-2-carboxamide (Compound 110);
1-Cyclopropyl-N-(5-(3,4-difluorophenoxy)-2-methoxyphenyl)-5-oxopyrrolidine-2-carboxamide (Compound 111);

N-(2-Methoxy-5-((5-(trifluoromethoxy)pyridin-2-yl)oxy)phenyl)-3-methyl-2-oxooxazolidine-4-carboxamide (Compound 112);

N-(7-(((4,4-Difluorocyclohexyl)oxy)methyl)-2,3-dihydrobenzo[b][1,4]dioxin-5-yl)-1-methyl-5-oxopyrrolidine-2-carboxamide (Compound 113);

1-Cyclopropyl-5-oxo-N-(7-(4-(trifluoromethyl)phenoxy)-2,3-dihydrobenzo[b][1,4]dioxin-5-yl)pyrrolidine-2-carboxamide (Compound 114);

N-(2-Methoxy-5-((5-(trifluoromethoxy)pyridin-2-yl)oxy)phenyl)-1-methyl-5-oxopyrrolidine-2-carboxamide (Compound 115);

N-(2-Methoxy-5-(4-(trifluoromethyl)phenoxy)phenyl)tetrahydrothiophene-3-carboxamide 1,1-dioxide (Compound 116);

N-(2-Methoxy-5-(4-(trifluoromethyl)phenoxy)phenyl)-3-methyl-2-oxo-imidazolidine-4-carboxamide (Compound 117);

N-(2-Methoxy-5-((5-(trifluoromethyl)pyridin-2-yl)oxy)phenyl)-3-methyl-2-oxoimidazolidine-4-carboxamide (Compound 118);

(S)—N-(2-Methoxy-5-(4-(trifluoromethyl)phenoxy)phenyl)-6-oxopiperidine-3-carboxamide (Compound 119);

(R)—N-(2-Methoxy-5-(4-(trifluoromethyl)phenoxy)phenyl)-6-oxopiperidine-3-carboxamide (Compound 120);

N-(2-Methoxy-5-(4-(trifluoromethyl)phenoxy)phenyl)-3-methyl-6-oxo-piperidine-3-carboxamide (Compound 121);

N-(2-Methoxy-5-(4-(trifluoromethyl)phenoxy)phenyl)-6-oxo-1,6-dihydro-pyridine-3-carboxamide (Compound 122);

N-(2-Methoxy-5-((5-(trifluoromethyl)pyridin-2-yl)oxy)phenyl)-3,4-dimethyl-2-oxoimidazolidine-4-carboxamide (Compound 123);

(R)—N-(2-Methoxy-5-((5-(trifluoromethyl)pyridin-2-yl)oxy)phenyl)-3-methyl-2-oxoimidazolidine-4-carboxamide (Compound 124);

(S)—N-(2-Methoxy-5-((5-(trifluoromethyl)pyridin-2-yl)oxy)phenyl)-3-methyl-2-oxooxazolidine-4-carboxamide (Compound 125);

(R)—N-(2-Methoxy-5-((5-(trifluoromethyl)pyridin-2-yl)oxy)phenyl)-3-methyl-2-oxooxazolidine-4-carboxamide (Compound 126);

3-Ethyl-N-(2-methoxy-5-((5-(trifluoromethyl)pyridin-2-yl)oxy)phenyl)-2-oxo-imidazolidine-4-carboxamide (Compound 127);

(R)-1-Cyclopropyl-N-(2-methoxy-5-((5-(trifluoromethyl)pyridin-2-yl)oxy)-phenyl)-5-oxopyrrolidine-2-carboxamide (Compound 128);

(S)-1-Cyclopropyl-N-(2-methoxy-5-((5-(trifluoromethyl)pyridin-2-yl)oxy)-phenyl)-5-oxopyrrolidine-2-carboxamide (Compound 129);

(S)—N-(2-Methoxy-5-((5-(trifluoromethyl)pyridin-2-yl)oxy)phenyl)-3-methyl-2-oxoimidazolidine-4-carboxamide (Compound 130);

3-Cyclopropyl-N-(2-methoxy-5-((5-(trifluoromethyl)pyridin-2-yl)oxy)phenyl)-2-oxoimidazolidine-4-carboxamide (Compound 131);

1-(Cyclopropylmethyl)-N-(2-methoxy-5-((5-(trifluoromethyl)pyridin-2-yl)oxy)-phenyl)-5-oxopyrrolidine-2-carboxamide, enantiomer 1 (Compound 132);

1-(Cyclopropylmethyl)-N-(2-methoxy-5-((5-(trifluoromethyl)pyridin-2-yl)oxy)-phenyl)-5-oxopyrrolidine-2-carboxamide, enantiomer 2 (Compound 133);

(R)—N-(2-methoxy-5-(4-(trifluoromethyl)phenoxy)phenyl)-1,2-dimethyl-5-oxopyrrolidine-2-carboxamide (Compound 134);

(S)—N-(2-Methoxy-5-(4-(trifluoromethyl)phenoxy)phenyl)-1,2-dimethyl-5-oxo-pyrrolidine-2-carboxamide (Compound 135);

1-(2-Amino-2-oxoethyl)-N-(2-methoxy-5-(4-(trifluoromethyl)phenoxy)phenyl)-5-oxopyrrolidine-2-carboxamide (Compound 136);

N-(2-Methoxy-5-(4-(trifluoromethyl)phenoxy)phenyl)-1-(1-methyl-1H-pyrazol-4-yl)-5-oxopyrrolidine-2-carboxamide (Compound 137);

N-(2-Methoxy-5-(4-(trifluoromethyl)phenoxy)phenyl)-5-oxo-1-(tetrahydrofuran-3-yl)pyrrolidine-2-carboxamide (Compound 138);

N-(2-Methoxy-5-(4-(trifluoromethyl)phenoxy)phenyl)-1,3-dimethyl-2-oxo-imidazolidine-4-carboxamide (Compound 139);

(R)—N-(2-Methoxy-5-(4-(trifluoromethyl)phenoxy)phenyl)-3-methyl-2-oxo-imidazolidine-4-carboxamide (Compound 140);

(S)—N-(2-Methoxy-5-(4-(trifluoromethyl)phenoxy)phenyl)-3-methyl-2-oxoimidazolidine-4-carboxamide (Compound 141);

3-Acetyl-N-(2-methoxy-5-(4-(trifluoromethyl)phenoxy)phenyl)-1-methyl-2-oxoimidazolidine-4-carboxamide (Compound 142);

(2S)-4-Methoxy-N-(2-methoxy-5-(4-(trifluoromethyl)phenoxy)phenyl)-1-methyl-5-oxopyrrolidine-2-carboxamide (Compound 143);

N-(2-Methoxy-5-(4-(trifluoromethyl)phenoxy)phenyl)-2-oxoimidazolidine-4-carboxamide (Compound 144);

N-(2-Methoxy-4-(4-(trifluoromethyl)phenoxy)phenyl)-1-(2-(methylamino)-2-oxoethyl)-5-oxopyrrolidine-2-carboxamide (Compound 145);

1-(2-(Dimethylamino)-2-oxoethyl)-N-(2-methoxy-4-(4-(trifluoromethyl)-phenoxy)phenyl)-5-oxopyrrolidine-2-carboxamide (Compound 146);

1-(Cyclopropylmethyl)-N-(2-methoxy-5-(4-(trifluoromethyl)phenoxy)phenyl)-5-oxopyrrolidine-2-carboxamide, enantiomer 1 (Compound 147);

1-(Cyclopropylmethyl)-N-(2-methoxy-5-(4-(trifluoromethyl)phenoxy)phenyl)-5-oxopyrrolidine-2-carboxamide, enantiomer 2 (Compound 148);

N-(5-(4-(Difluoromethyl)phenoxy)-2-methoxyphenyl)-3-methyl-2-oxoimidazoli-dine-4-carboxamide (Compound 149);

(S)-1-Methyl-5-oxo-N-(5-(((trans)-4-(trifluoromethyl)cyclohexyl)oxy)-2,3-dihydrobenzofuran-7-yl)pyrrolidine-2-carboxamide (Compound 150);

(R)-1-Methyl-5-oxo-N-(5-(((trans)-4-(trifluoromethyl)cyclohexyl)oxy)-2,3-dihydrobenzofuran-7-yl)pyrrolidine-2-carboxamide (Compound 151);

N-(4-Fluoro-2-methoxy-5-((5-(trifluoromethyl)pyridin-2-yl)oxy)phenyl)-3-methyl-2-oxooxazolidine-4-carboxamide (Compound 152);

N-(4-Fluoro-2-methoxy-5-((5-(trifluoromethyl)pyridin-2-yl)oxy)phenyl)-3-methyl-2-oxoimidazolidine-4-carboxamide (Compound 153);

(R)—N-(4-Fluoro-2-methoxy-5-((5-(trifluoromethyl)pyridin-2-yl)-oxy)phenyl)-3-methyl-2-oxooxazolidine-4-carboxamide (Compound 154);

(R)—N-(4-Fluoro-2-methoxy-5-((5-(trifluoromethyl)pyridin-2-yl)oxy)phenyl)-3-methyl-2-oxoimidazolidine-4-carboxamide (Compound 155);

(S)—N-(4-Fluoro-2-methoxy-5-((5-(trifluoromethyl)pyridin-2-yl)oxy)phenyl)-3-methyl-2-oxoimidazolidine-4-carboxamide (Compound 156);

(S)—N-(4-Fluoro-2-methoxy-5-((5-(trifluoromethyl)pyridin-2-yl)oxy)phenyl)-3-methyl-2-oxooxazolidine-4-carboxamide (Compound 157);

N-(5-(2-Chloro-4-(trifluoromethyl)phenoxy)-4-fluoro-2-methoxyphenyl)-3-methyl-2-oxoimidazolidine-4-carboxamide (Compound 158);

3-Methyl-2-oxo-N-(5-((5-(trifluoromethyl)pyridin-2-yl)oxy)-2,3-dihydrobenzo-furan-7-yl)imidazolidine-4-carboxamide (Compound 159);

2-Oxo-N-(5-((5-(trifluoromethyl)pyridin-2-yl)oxy)-2,3-dihydrobenzofuran-7-yl)-piperidine-4-carboxamide (Compound 160);

6-Oxo-N-(5-((5-(trifluoromethyl)pyridin-2-yl)oxy)-2,3-dihydrobenzofuran-7-yl)piperidine-3-carboxamide (Compound 161);

(R)-1-Methyl-5-oxo-N-(5-((5-(trifluoromethyl)pyridin-2-yl)oxy)-2,3-dihydro-benzofuran-7-yl)pyrrolidine-2-carboxamide (Compound 162);

(S)-1-Methyl-5-oxo-N-(5-((5-(trifluoromethyl)pyridin-2-yl)oxy)-2,3-dihydro-benzofuran-7-yl)pyrrolidine-2-carboxamide (Compound 163);

3-Cyclopropyl-2-oxo-N-(5-((5-(trifluoromethyl)pyridin-2-yl)oxy)-2,3-dihydro-benzofuran-7-yl)imidazolidine-4-carboxamide (Compound 164);

(S)-1-Cyclopropyl-5-oxo-N-(5-((5-(trifluoromethyl)pyridin-2-yl)oxy)-2,3-dihydrobenzofuran-7-yl)pyrrolidine-2-carboxamide (Compound 165);

(R)-1-Cyclopropyl-5-oxo-N-(5-((5-(trifluoromethyl)pyridin-2-yl)oxy)-2,3-dihydrobenzofuran-7-yl)pyrrolidine-2-carboxamide (Compound 166);

3-Ethyl-2-oxo-N-(5-((5-(trifluoromethyl)pyridin-2-yl)oxy)-2,3-dihydrobenzo-furan-7-yl)imidazolidine-4-carboxamide (Compound 167);

(S)-3-Methyl-2-oxo-N-(5-((5-(trifluoromethyl)pyridin-2-yl)oxy)-2,3-dihydro-benzofuran-7-yl)imidazolidine-4-carboxamide (Compound 168);

(R)-3-Methyl-2-oxo-N-(5-((5-(trifluoromethyl)pyridin-2-yl)oxy)-2,3-dihydro-benzofuran-7-yl)imidazolidine-4-carboxamide (Compound 169);

(R)-1-Ethyl-5-oxo-N-(5-((5-(trifluoromethyl)pyridin-2-yl)oxy)-2,3-dihydro-benzofuran-7-yl)pyrrolidine-2-carboxamide (Compound 170);

(S)-1-Ethyl-5-oxo-N-(5-((5-(trifluoromethyl)pyridin-2-yl)oxy)-2,3-dihydro-benzofuran-7-yl)pyrrolidine-2-carboxamide (Compound 171);

(2R)-1-Methyl-N-(2-methyl-5-((5-(trifluoromethyl)pyridin-2-yl)oxy)-2,3-di-hydrobenzofuran-7-yl)-5-oxopyrrolidine-2-carboxamide, enantiomer 1 (Compound 172);

(2R)-1-Methyl-N-(2-methyl-5-((5-(trifluoromethyl)pyridin-2-yl)oxy)-2,3-di-hydrobenzofuran-7-yl)-5-oxopyrrolidine-2-carboxamide, enantiomer 2 (Compound 173);

(S)-1-Methyl-5-oxo-N-(6-((5-(trifluoromethyl)pyridin-2-yl)oxy)chroman-8-yl)pyrrolidine-2-carboxamide (Compound 174);

(R)-1-Methyl-5-oxo-N-(6-((5-(trifluoromethyl)pyridin-2-yl)oxy)chroman-8-yl)pyrrolidine-2-carboxamide (Compound 175);

3-Methyl-2-oxo-N-(6-((5-(trifluoromethyl)pyridin-2-yl)oxy)chroman-8-yl)-imidazolidine-4-carboxamide (Compound 176);

1-Methyl-5-oxo-N-(6-((5-(trifluoromethyl)pyridin-2-yl)oxy)chroman-8-yl)-pyrrolidine-2-carboxamide (Compound 177);

3-Methyl-2-oxo-N-(6-((5-(trifluoromethyl)pyridin-2-yl)oxy)benzo[d]-[1,3]dioxol-4-yl)imidazolidine-4-carboxamide (Compound 178);

1-Cyclopropyl-5-oxo-N-(6-((5-(trifluoromethyl)pyridin-2-yl)oxy)benzo[d]-[1,3]dioxol-4-yl)pyrrolidine-2-carboxamide (Compound 179);

(S)-3-Methyl-2-oxo-N-(6-((5-(trifluoromethyl)pyridin-2-yl)oxy)benzo-[d][1,3]dioxol-4-yl)imidazolidine-4-carboxamide (Compound 180);

(R)-3-Methyl-2-oxo-N-(6-((5-(trifluoromethyl)pyridin-2-yl)oxy)benzo-[d][1,3]dioxol-4-yl)imidazolidine-4-carboxamide (Compound 181);

3-Methyl-2-oxo-N-(7-((5-(trifluoromethyl)pyridin-2-yl)oxy)-2,3-dihydrobenzo-[b][1,4]dioxin-5-yl)imidazolidine-4-carboxamide (Compound 182);

3-Methyl-2-oxo-N-(7-((5-(trifluoromethyl)pyridin-2-yl)oxy)-2,3-dihydrobenzo-[b][1,4]dioxin-5-yl)imidazolidine-4-carboxamide, enantiomer 1 (Compound 183);

3-Methyl-2-oxo-N-(7-((5-(trifluoromethyl)pyridin-2-yl)oxy)-2,3-dihydrobenzo-[b][1,4]dioxin-5-yl)imidazolidine-4-carboxamide, enantiomer 2 (Compound 184);

1-Methyl-5-oxo-N-(5-(4-(trifluoromethyl)phenoxy)benzofuran-7-yl)pyrrolidine-2-carboxamide (Compound 185);

3-Methyl-2-oxo-N-(6-(4-(trifluoromethyl)phenoxy)benzo[d][1,3]dioxol-4-yl)-imidazolidine-4-carboxamide (Compound 186);

2-Oxo-N-(5-(4-(trifluoromethyl)phenoxy)-2,3-dihydrobenzofuran-7-yl)-piperidine-4-carboxamide (Compound 187);

1-(2-(Methylamino)-2-oxoethyl)-5-oxo-N-(5-(4-(trifluoromethyl)phenoxy)-2,3-dihydrobenzofuran-7-yl)pyrrolidine-2-carboxamide (Compound 188);

1-(2-Amino-2-oxoethyl)-5-oxo-N-(5-(4-(trifluoromethyl)phenoxy)-2,3-dihydro-benzofuran-7-yl)pyrrolidine-2-carboxamide (Compound 189);

N-(5-((4,4-Difluorocyclohexyl)oxy)-2,3-dihydrobenzofuran-7-yl)-6-oxo-piperidine-3-carboxamide (Compound 190);

N-(7-((4,4-Difluorocyclohexyl)oxy)-2,3-dihydrobenzo[b][1,4]dioxin-5-yl)-6-oxopiperidine-3-carboxamide (Compound 191);

3-Methyl-2-oxo-N-(7-(4-(trifluoromethyl)phenoxy)-2,3-dihydrobenzo[b][1,4]-dioxin-5-yl)imidazolidine-4-carboxamide (Compound 192);

3-Methyl-2-oxo-N-(5-((5-(trifluoromethyl)pyridin-2-yl)oxy)-1H-indazol-7-yl)-imidazolidine-4-carboxamide (Compound 193);

1-Methyl-N-(1-methyl-5-((5-(trifluoromethyl)pyridin-4-yl)oxy)-1H-indazol-7-yl)-5-oxopyrrolidine-2-carboxamide (Compound 194);

(S)—N-(2-Fluoro-5-((5-(trifluoromethyl)pyridin-2-yl)oxy)phenyl)-3-methyl-2-oxoimidazolidine-4-carboxamide (Compound 195);

(R)—N-(2-Fluoro-5-((5-(trifluoromethyl)pyridin-2-yl)oxy)phenyl)-3-methyl-2-oxoimidazolidine-4-carboxamide (Compound 196);

N-(2-Fluoro-5-((5-(trifluoromethyl)pyridin-2-yl)oxy)phenyl)-3-methyl-2-oxooxazolidine-4-carboxamide (Compound 197);

(R)—N-(2-Fluoro-5-((5-(trifluoromethyl)pyridin-2-yl)oxy)phenyl)-3-methyl-2-oxooxazolidine-4-carboxamide (Compound 198);

(S)—N-(2-Fluoro-5-((5-(trifluoromethyl)pyridin-2-yl)oxy)phenyl)-3-methyl-2-oxooxazolidine-4-carboxamide (Compound 199);

N-(2-Methoxy-5-((4-(trifluoromethyl)pyridin-2-yl)oxy)phenyl)-3-methyl-2-oxoimidazolidine-4-carboxamide (Compound 200);

N-(2-Methoxy-5-((4-(trifluoromethyl)pyridin-2-yl)oxy)phenyl)-1-methyl-5-oxopyrrolidine-2-carboxamide (Compound 201);

N-(5-((5-Fluoropyridin-2-yl)oxy)-2-methoxyphenyl)-1-methyl-5-oxopyrrolidine-2-carboxamide (Compound 202);

N-(5-((5-Chloropyridin-2-yl)oxy)-2-methoxyphenyl)-1-methyl-5-oxo-pyrrolidine-2-carboxamide (Compound 203);

N-(5-(2-Fluoro-4-nitrophenoxy)-2-methoxyphenyl)-1-methyl-5-oxopyrrolidine-2-carboxamide (Compound 204);

N-(5-(((4,4-Difluorocyclohexyl)oxy)methyl)-2-methoxyphenyl)-1-methyl-5-oxopyrrolidine-2-carboxamide (Compound 205);

N-(5-((4,4-Difluorocyclohexyl)methoxy)-2-methoxyphenyl)-1-methyl-5-oxopyrrolidine-2-carboxamide (Compound 206);

(2S)—N-(5-((4,4-Difluorocycloheptyl)oxy)-2-methoxyphenyl)-1-methyl-5-oxopyrrolidine-2-carboxamide (Compound 207);

(R)—N-(2-Methoxy-5-((4-(trifluoromethyl)cyclohexyl)oxy)phenyl)-3-methyl-2-oxooxazolidine-4-carboxamide (Compound 208);

(R)—N-(2-Methoxy-5-(((cis)-4-(trifluoromethyl)cyclohexyl)oxy)phenyl)-1-methyl-5-oxopyrrolidine-2-carboxamide (Compound 209);

(S)—N-(2-Methoxy-5-(((cis)-4-(trifluoromethyl)cyclohexyl)oxy)phenyl)-1-methyl-5-oxopyrrolidine-2-carboxamide (Compound 210);

N-(5-((5-(Difluoromethyl)pyridin-2-yl)oxy)-2-methoxyphenyl)-1-methyl-5-oxopyrrolidine-2-carboxamide (Compound 211);

N-(5-((5-(Difluoromethyl)pyridin-2-yl)oxy)-2-methoxyphenyl)-3-methyl-2-oxoimidazolidine-4-carboxamide (Compound 212);

N-(5-(4-(Difluoromethyl)phenoxy)-2,3-dihydrobenzofuran-7-yl)-3-methyl-2-oxoimidazolidine-4-carboxamide (Compound 213);

(S)—N-(5-(4-(Difluoromethyl)phenoxy)-2,3-dihydrobenzofuran-7-yl)-1-methyl-5-oxopyrrolidine-2-carboxamide (Compound 214);

(R)—N-(5-(4-(Difluoromethyl)phenoxy)-2,3-dihydrobenzofuran-7-yl)-1-methyl-5-oxopyrrolidine-2-carboxamide (Compound 215);

(S)-3-Methyl-2-oxo-N-(5-((5-(trifluoromethyl)pyridin-2-yl)oxy)benzofuran-7-yl)imidazolidine-4-carboxamide (Compound 216);

(R)-3-Methyl-2-oxo-N-(5-((5-(trifluoromethyl)pyridin-2-yl)oxy)benzofuran-7-yl)imidazoledine-4-carboxamide (Compound 217);

(S)-3-Methyl-N-(1-methyl-6-((5-(trifluoromethyl)pyridin-2-yl)oxy)-1H-benzo-[d]imidazol-4-yl)-2-oxoimidazolidine-4-carboxamide (Compound 218);

(R)-3-Methyl-N-(1-methyl-6-((5-(trifluoromethyl)pyridin-2-yl)oxy)-1H-benzo-[d]imidazol-4-yl)-2-oxoimidazolidine-4-carboxamide (Compound 219);

(S)—N-(4-Fluoro-2-methoxy-5-((5-(trifluoromethyl)pyridin-2-yl)oxy)phenyl)-1-methyl-5-oxopyrrolidine-2-carboxamide (Compound 220);

(R)—N-(4-Fluoro-2-methoxy-5-((5-(trifluoromethyl)pyridin-2-yl)oxy)phenyl)-1-methyl-5-oxopyrrolidine-2-carboxamide (Compound 221);

N-(5-(3,4-Dichlorophenoxy)-2-methoxyphenyl)-1-methyl-5-oxopyrrolidine-2-carboxamide (Compound 222);

N-(5-(3-Chloro-4-fluorophenoxy)-2-methoxyphenyl)-1-methyl-5-oxo-pyrrolidine-2-carboxamide (Compound 223);

N-(5-(3,4-Difluorophenoxy)-2-(1,3,4-oxadiazol-2-yl)phenyl)-1-methyl-5-oxo-pyrrolidine-2-carboxamide (Compound 224);

1-Methyl-5-oxo-N-(5-(4-(trifluoromethyl)phenoxy)-1H-indazol-7-yl)-pyrrolidine-2-carboxamide (Compound 225);

(S)—N-(2-Methoxy-5-(4-(trifluoromethyl)phenoxy)phenyl)-1,3-dimethyl-2-oxoimidazolidine-4-carboxamide (Compound 226);

(R)—N-(2-Methoxy-5-(4-(trifluoromethyl)phenoxy)phenyl)-1,3-dimethyl-2-oxoimidazolidine-4-carboxamide (Compound 227);

4-Hydroxy-N-(2-methoxy-5-(4-(trifluoromethyl)phenoxy)phenyl)-1-methyl-5-oxopyrrolidine-3-carboxamide (Compound 228);

N-(2-Methoxy-5-(4-(trifluoromethyl)phenoxy)phenyl)-5-oxo-1-(5-oxopyrrolidi-ne-2-carbonyl)pyrrolidine-2-carboxamide (Compound 229);

N-(2-Methoxy-5-(4-(trifluoromethyl)phenoxy)phenyl)-1-(1-methyl-5-oxo-pyrrolidine-2-carbonyl)-5-oxopyrrolidine-2-carboxamide (Compound 230);

N-(2-Methoxy-5-(4-(trifluoromethyl)phenoxy)phenyl)-5-oxo-1-(4-oxoazetidine-2-carbonyl)pyrrolidine-2-carboxamide (Compound 231);

N-(5-(3,4-difluorophenoxy)-2-methoxyphenyl)-5-oxo-1-(4-oxoazetidine-2-carbonyl)pyrrolidine-2-carboxamide (Compound 232);

1-Methyl-5-oxo-N-(7-(3-(trifluoromethyl)phenoxy)-2,3-dihydrobenzo[b][1,4]-dioxin-5-yl)pyrrolidine-2-carboxamide (Compound 233);

1-Methyl-5-oxo-N-(7-(3-(trifluoromethyl)phenoxy)-2,3-dihydrobenzo[b][1,4]-dioxin-5-yl)pyrrolidine-2-carboxamide, enantiomer 1 (Compound 234);

1-Methyl-5-oxo-N-(7-(3-(trifluoromethyl)phenoxy)-2,3-dihydrobenzo[b][1,4]-dioxin-5-yl)pyrrolidine-2-carboxamide, enantiomer 2 (Compound 235);

1-Methyl-N-(8-methyl-7-(3-(trifluoromethyl)phenoxy)-2,3-dihydrobenzo[b]-[1,4]dioxin-5-yl)-5-oxopyrrolidine-2-carboxamide (Compound 236);

1-Methyl-5-oxo-N-(5-(4-(trifluoromethyl)phenoxy)-2,3-dihydrobenzofuran-7-yl)pyrrolidine-2-carboxamide (Compound 237);

1-Methyl-5-oxo-N-(5-((3-(trifluoromethyl)benzyl)oxy)-2,3-dihydrobenzofuran-7-yl)pyrrolidine-2-carboxamide (Compound 238);

N-(5-(3,4-Difluorophenoxy)-2,3-dihydrobenzofuran-7-yl)-1-methyl-5-oxopyrro-lidine-2-carboxamide (Compound 239);

N-(7-(3,4-Difluorophenoxy)-2,3-dihydrobenzo[b][1,4]dioxin-5-yl)-1-methyl-5-oxopyrrolidine-2-carboxamide (Compound 240);

N-(7-(4-Fluorophenoxy)-2,3-dihydrobenzo[b][1,4]dioxin-5-yl)-1-methyl-5-oxo-pyrrolidine-2-carboxamide (Compound 241);

N-(5-((3,4-Difluorophenoxy)methyl)-2,3-dihydrobenzofuran-7-yl)-1-methyl-5-oxopyrrolidine-2-carboxamide (Compound 242);

N-(6-((3,4-Difluorophenoxy)methyl)-2,3-dihydrobenzofuran-4-yl)-1-methyl-5-oxopyrrolidine-2-carboxamide (Compound 243);

1-Methyl-N-(1-methyl-6-((5-(trifluoromethyl)pyridin-2-yl)oxy)-1H-benzo-[d]imidazol-4-yl)-5-oxopyrrolidine-2-carboxamide, enantiomer 1 (Compound 244);

1-Methyl-N-(1-methyl-6-((5-(trifluoromethyl)pyridin-2-yl)oxy)-1H-benzo-[d]imidazol-4-yl)-5-oxopyrrolidine-2-carboxamide, enantiomer 2 (Compound 245);

N-(5-(((3-Fluorophenyl)amino)methyl)-2-methoxyphenyl)-5-oxopyrrolidine-2-carboxamide (Compound 246);

N-(5-((4,4-Difluorocyclohexyl)oxy)-2-methoxyphenyl)-1-methyl-5-oxopyrro-lidine-2-carboxamide (Compound 247);

N-(5-((3,4-Difluorobenzyl)oxy)-2,3-dihydrobenzofuran-7-yl)-1-methyl-5-oxo-pyrrolidine-2-carboxamide (Compound 248);

N-(5-((3-Fluorophenoxy)methyl)benzofuran-7-yl)-1-methyl-5-oxopyrrolidine-2-carboxamide (Compound 249);

N-(2-Fluoro-3-methoxy-5-(4-(trifluoromethyl)phenoxy)phenyl)-1-methyl-5-oxo-pyrrolidine-2-carboxamide (Compound 250);

N-(5-(3,4-difluorophenoxy)-2-fluoro-3-methoxyphenyl)-1-methyl-5-oxopyrro-lidine-2-carboxamide (Compound 251);

N-(2-Methoxy-5-(4-(trifluoromethyl)phenoxy)phenyl)-5-oxotetrahydropyrrolo-[2,1-b]thiazole-7a(5H)-carboxamide 1,1-dioxide (Compound 252);

N-(3-Methoxy-5-(4-(trifluoromethyl)phenoxy)phenyl)-5-oxopyrrolidine-2-carboxamide (Compound 253);

(E)-N-(5-(3-Fluorostyryl)-2-methoxyphenyl)-1-methyl-5-oxopyrrolidine-2-carboxamide (Compound 254);

N-(2-Methoxy-5-((4-(trifluoromethyl)cyclohexyl)oxy)phenyl)-1-methyl-5-oxo-pyrrolidine-2-carboxamide (Compound 255);

N-(2-Methoxy-5-(3-(trifluoromethyl)benzyl)phenyl)-1-methyl-5-oxopyrrolidine-2-carboxamide (Compound 256);

N-(2-Methoxy-5-(4-(trifluoromethyl)benzyl)phenyl)-1-methyl-5-oxopyrrolidine-2-carboxamide (Compound 257);

N-(2-Chloro-5-(4-(trifluoromethyl)phenoxy)phenyl)-1-methyl-5-oxopyrrolidine-2-carboxamide (Compound 258);

N-(4-Methoxy-3-(4-(trifluoromethyl)phenoxy)phenyl)-1-methyl-5-oxo-pyrrolidine-2-carboxamide (Compound 259);

N-(5-(4-Fluorophenoxy)-2-methoxyphenyl)-1-methyl-5-oxopyrrolidine-2-carboxamide (Compound 260);

N-(3-Methoxy-5-(3-(trifluoromethyl)phenoxy)phenyl)-5-oxopyrrolidine-2-carboxamide (Compound 261);

N-(5-((6-Fluoro-5-methylpyridin-3-yl)oxy)-2-methoxyphenyl)-5-oxopyrrolidine-2-carboxamide (Compound 262);

(R)—N-(5-((6-fluoro-5-methylpyridin-3-yl)oxy)-2-methoxyphenyl)-1-methyl-5-oxopyrrolidine-2-carboxamide (Compound 263);

N-(2-Methoxy-5-((4-(trifluoromethyl)cyclohexyl)oxy)phenyl)-1-methyl-5-oxo-pyrrolidine-2-carboxamide (Compound 264);

(R)—N-(2-Methoxy-5-((4-(trifluoromethyl)cyclohexyl)oxy)phenyl)-1-methyl-5-oxopyrrolidine-2-carboxamide (Compound 265);

N-(2-Methoxy-5-(((1R,3S)-3-(trifluoromethyl)cyclohexyl)oxy)phenyl)-5-oxo-pyrrolidine-2-carboxamide (Compound 266);

N-(2-Methoxy-5-(((1S,3S)-3-(trifluoromethyl)cyclohexyl)oxy)phenyl)-5-oxo-pyrrolidine-2-carboxamide (Compound 267);

(R)—N-(2-Methoxy-5-(((1R,3S)-3-(trifluoromethyl)cyclohexyl)oxy)phenyl)-1-methyl-5-oxopyrrolidine-2-carboxamide (Compound 268);

(R)—N-(2-Methoxy-5-(((1S,3S)-3-(trifluoromethyl)cyclohexyl)oxy)phenyl)-1-methyl-5-oxopyrrolidine-2-carboxamide (Compound 269);

N-(2-Fluoro-5-((4-(trifluoromethyl)cyclohexyl)oxy)phenyl)-1-methyl-5-oxo-pyrrolidine-2-carboxamide (Compound 270);

(R)—N-(4-methoxy-3-(((1r,4R)-4-(trifluoromethyl)cyclohexyl)oxy)phenyl)-1-methyl-5-oxopyrrolidine-2-carboxamide (Compound 271);

(R)—N-(4-Methoxy-3-(((1s,4S)-4-(trifluoromethyl)cyclohexyl)oxy)phenyl)-1-methyl-5-oxopyrrolidine-2-carboxamide (Compound 272);

N-(3-Methoxy-5-(3-(trifluoromethyl)phenoxy)phenyl)-1-methyl-5-oxo-pyrrolidine-2-carboxamide (Compound 273);

N-(3-(4-Chloro-3-(trifluoromethyl)phenoxy)-5-methoxyphenyl)-1-methyl-5-oxopyrrolidine-2-carboxamide (Compound 274);

(R)—N-(3-((4,4-Difluorocyclohexyl)oxy)-5-methoxyphenyl)-1-methyl-5-oxo-pyrrolidine-2-carboxamide (Compound 275);

N-(2-methoxy-5-((5-(trifluoromethyl)pyridin-2-yl)oxy)phenyl)-1-methyl-5-oxopyrrolidine-2-carboxamide (Compound 276);

N-(3-Methoxy-5-((5-(trifluoromethyl)pyridin-2-yl)oxy)phenyl)-1-methyl-5-oxopyrrolidine-2-carboxamide (Compound 277);

(R)—N-(3-Methoxy-5-(4-(trifluoromethyl)phenoxy)phenyl)-1-methyl-5-oxo-pyrrolidine-2-carboxamide (Compound 278);

N-(3-Methoxy-5-(4-(trifluoromethyl)phenoxy)phenyl)-1-methyl-5-oxo-pyrrolidine-2-carboxamide (Compound 279);

1-Methyl-5-oxo-N-(6-((5-(trifluoromethyl)pyridin-2-yl)oxy)quinolin-8-yl)-pyrrolidine-2-carboxamide (Compound 280);

(R)-1-Methyl-5-oxo-N-(6-((5-(trifluoromethyl)pyridin-2-yl)oxy)quinolin-8-yl)pyrrolidine-2-carboxamide (Compound 281);

(R)—N-(3-Methoxy-5-((4-(trifluoromethyl)cyclohexyl)oxy)phenyl)-1-methyl-5-oxopyrrolidine-2-carboxamide (Compound 282);

(R)—N-(2-Methoxy-5-((5-(trifluoromethyl)pyridin-2-yl)oxy)phenyl)-1-methyl-5-oxopyrrolidine-2-carboxamide (Compound 283);

N-(3-(3,4-Difluorophenoxy)-5-methoxyphenyl)-1-methyl-5-oxopyrrolidine-2-carboxamide (Compound 284);

(R)—N-(3-(3,4-Difluorophenoxy)-5-methoxyphenyl)-1-methyl-5-oxopyrrolidine-2-carboxamide (Compound 285);

N-(5-(Cyclohexyloxy)-2-methoxyphenyl)-1-methyl-5-oxopyrrolidine-2-carboxamide (Compound 286);

N-(5-(Cyclohex-2-en-1-yloxy)-2-methoxyphenyl)-1-methyl-5-oxopyrrolidine-2-carboxamide (Compound 287);

(S)—N-(5-((5-Chloropyridin-2-yl)oxy)-2-methoxyphenyl)-1-methyl-5-oxo-pyrrolidine-2-carboxamide (Compound 288);

1-Acetyl-N-(2-methoxy-5-(3-(trifluoromethyl)phenoxy)phenyl)azetidine-3-carboxamide (Compound 289);

(R)—N-(2-Methoxy-5-(4-(trifluoromethoxy)phenoxy)phenyl)-1-methyl-5-oxo-pyrrolidine-2-carboxamide (Compound 290);

N-(2-methoxy-5-(3-(trifluoromethoxy)phenoxy)phenyl)-1-methyl-5-oxo-pyrrolidine-2-carboxamide (Compound 291);

N-(5-(4-(Difluoromethyl)phenoxy)-2-methoxyphenyl)-1-methyl-5-oxo-pyrrolidine-2-carboxamide (Compound 292);

(R)—N-(5-(4-Fluoro-3-methoxyphenoxy)-2-methoxyphenyl)-1-methyl-5-oxo-pyrrolidine-2-carboxamide (Compound 293);

N-(5-(Cyclohexylmethoxy)-2-methoxyphenyl)-1-methyl-5-oxopyrrolidine-2-carboxamide (Compound 294);

N-(5-(3-Fluoro-4-methoxyphenoxy)-2-methoxyphenyl)-1-methyl-5-oxo-pyrrolidine-2-carboxamide (Compound 295);

N-(5-((4,4-Dimethylcyclohexyl)oxy)-2-methoxyphenyl)-1-methyl-5-oxo-pyrrolidine-2-carboxamide (Compound 296);

N-(5-((3,4-Difluorophenyl)thio)-2-methoxyphenyl)-1-methyl-5-oxopyrrolidine-2-carboxamide (Compound 297);

N-(5-((3,4-Difluorophenyl)thio)-2-methoxyphenyl)-5-oxopyrrolidine-2-carboxamide (Compound 298);

N-(5-(3-Bromophenoxy)-2-methoxyphenyl)-1-methyl-5-oxopyrrolidine-2-carboxamide (Compound 299);

N-(2-Methoxy-5-(4-(trifluoromethoxy)phenoxy)phenyl)-5-oxopyrrolidine-2-carboxamide (Compound 300);

N-(5-(4-Isopropoxyphenoxy)-2-methoxyphenyl)-5-oxopyrrolidine-2-carboxamide (Compound 301);

N-(5-((3,3-Difluorocyclobutyl)methoxy)-2-methoxyphenyl)-1-methyl-5-oxopyrrolidine-2-carboxamide (Compound 302);

N-(3-(4-Fluorophenoxy)-5-(trifluoromethyl)phenyl)-1-methyl-5-oxopyrrolidine-2-carboxamide (Compound 303);

N-(5-(4-Chlorophenoxy)-2-methoxyphenyl)-1-methyl-5-oxopyrrolidine-2-carboxamide (Compound 304);

N-(5-(4-Chloro-3-fluorophenoxy)-2-methoxyphenyl)-1-methyl-5-oxopyrrolidine-2-carboxamide (Compound 305);

N-(3-Cyano-5-(4-(trifluoromethyl)phenoxy)phenyl)-1-methyl-5-oxopyrrolidine-2-carboxamide (Compound 306);

(S)—N-(5-(4-Chlorophenoxy)-2-methoxyphenyl)-1-methyl-5-oxopyrrolidine-2-carboxamide (Compound 307);

(R)—N-(5-(4-Chlorophenoxy)-2-methoxyphenyl)-1-methyl-5-oxopyrrolidine-2-carboxamide (Compound 308);

N-(5-(3-Chloro-4-cyanophenoxy)-2-methoxyphenyl)-1-methyl-5-oxopyrrolidine-2-carboxamide (Compound 309);

(S)—N-(5-(3-Chloro-4-cyanophenoxy)-2-methoxyphenyl)-1-methyl-5-oxo-pyrrolidine-2-carboxamide (Compound 310);

(S)—N-(2-Methoxy-5-(4-(trifluoromethyl)phenoxy)phenyl)-1-(methylsulfonyl)-pyrrolidine-2-carboxamide (Compound 311);

(S)—N-(5-(4-Chloro-3-fluorophenoxy)-2-methoxyphenyl)-1-methyl-5-oxo-pyrrolidine-2-carboxamide (Compound 312);

(S)—N-(5-(4-(Difluoromethyl)phenoxy)-2-methoxyphenyl)-1-methyl-5-oxo-pyrrolidine-2-carboxamide (Compound 313);

N-(2-Methoxy-5-((1-methyl-1H-indol-5-yl)oxy)phenyl)-1-methyl-5-oxo-pyrrolidine-2-carboxamide (Compound 314);

N-(5-((2,3-Dihydrobenzofuran-5-yl)oxy)-2-methoxyphenyl)-1-methyl-5-oxopyrrolidine-2-carboxamide (Compound 315);

N-(5-(3-Chlorophenoxy)-2-methoxyphenyl)-1-methyl-5-oxopyrrolidine-2-carboxamide (Compound 316);

N-(5-(4-Cyano-3-methylphenoxy)-2-methoxyphenyl)-1-methyl-5-oxo-pyrrolidine-2-carboxamide (Compound 317);

N-(2-Methoxy-5-(4-(trifluoromethyl)phenoxy)phenyl)-1-(2-methoxyethyl)-5-oxopyrrolidine-2-carboxamide (Compound 318);

(R)—N-(5-(4-(Difluoromethyl)phenoxy)-2-methoxyphenyl)-1-methyl-5-oxo-pyrrolidine-2-carboxamide (Compound 319);

N-(2-Methoxy-5-(4-(trifluoromethyl)phenoxy)phenyl)-1-methyl-6-oxo-piperidine-2-carboxamide (Compound 320);

N-(5-(3,4-Difluorophenoxy)-2-methoxyphenyl)-1-methyl-6-oxopiperidine-2-carboxamide (Compound 321);

N-(2-Methoxy-5-(4-(trifluoromethyl)phenoxy)phenyl)-2-oxopiperidine-4-carboxamide (Compound 322);

N-(2-Methoxy-5-(4-(trifluoromethyl)phenoxy)phenyl)-1-methyl-2-oxo-piperidine-4-carboxamide (Compound 323);

N-(2-Methoxy-5-((5-(trifluoromethyl)pyridin-2-yl)oxy)phenyl)-2-oxopiperidine-4-carboxamide, enantiomer 1 (Compound 324);

N-(2-Methoxy-5-((5-(trifluoromethyl)pyridin-2-yl)oxy)phenyl)-2-oxopiperidine-4-carboxamide, enantiomer 2 (Compound 325);

N-(2-Methoxy-5-(4-(trifluoromethyl)phenoxy)phenyl)-1-(methylsulfonyl)-pyrrolidine-3-carboxamide (Compound 326);

N-(2-methoxy-5-((4-(trifluoromethyl)pyridin-2-yl)oxy)phenyl)-2-oxopiperidine-4-carboxamide, enantiomer 1 (Compound 327);

N-(2-Fluoro-5-(4-(trifluoromethoxy)phenoxy)phenyl)-1-methyl-5-oxo-pyrrolidine-2-carboxamide (Compound 328);

N-(2-Chloro-5-(4-(trifluoromethoxy)phenoxy)phenyl)-1-methyl-5-oxo-pyrrolidine-2-carboxamide (Compound 329);

N-(2-Carbamoyl-5-(4-(trifluoromethyl)phenoxy)phenyl)-1-methyl-5-oxopyrrolidine-2-carboxamide (Compound 330);

N-(2-Methoxy-5-((4-(trifluoromethyl)-pyridin-2-yl)oxy)phenyl)-1-(2-methoxyacetyl)-5-oxopyrrolidine-2-carboxamide (Compound 331);

(S)—N-(2-Methoxy-5-(4-(trifluoromethyl)phenoxy)phenyl)-1-methyl-2-oxo-imidazolidine-4-carboxamide (Compound 332);

(S)—N-(2-Methoxy-5-(4-(trifluoromethyl)phenoxy)phenyl)-1-(2-methoxyacetyl)-5-oxopyrrolidine-2-carboxamide (Compound 333);

N-(5-((3-Fluoro-5-(trifluoromethyl)pyridin-2-yl)oxy)-2-methoxyphenyl)-1-(2-methoxyacetyl)-5-oxopyrrolidine-2-carboxamide (Compound 334);

N-(2-Methoxy-5-(4-(trifluoromethyl)phenoxy)phenyl)-5-oxopyrrolidine-3-carboxamide (Compound 335);

(S)—N-(2-Methoxy-5-(4-(trifluoromethyl)phenoxy)phenyl)-1-(2-methoxyacetyl)-pyrrolidine-2-carboxamide (Compound 336);

(S)-1-(2-Amino-2-oxoethyl)-N-(2-methoxy-5-(4-(trifluoromethyl)phenoxy)-phenyl)pyrrolidine-2-carboxamide (Compound 337);

(S)—N-(5-(4-Chloro-3-fluorophenoxy)-2-methoxyphenyl)-3-methyl-2-oxo-imidazolidine-4-carboxamide (Compound 338);

(S)—N-(5-((3-Fluoro-5-(trifluoromethyl)pyridin-2-yl)oxy)-2-methoxyphenyl)-3-methyl-2-oxoimidazolidine-4-carboxamide (Compound 339);

(S)—N-(5-(4-(Difluoromethyl)phenoxy)-2-methoxyphenyl)-3-methyl-2-oxo-imidazolidine-4-carboxamide (Compound 340);

2-(1,3-Dimethyl-2,5-dioxoimidazolidin-4-yl)-N-(2-methoxy-5-(4-(trifluoro-methyl)phenoxy)phenyl)acetamide (Compound 341);

(S)-3-Acetyl-N-(2-methoxy-5-(4-(trifluoromethyl)phenoxy)phenyl)-1-methyl-2-oxoimidazolidine-4-carboxamide (Compound 342);

(S)-3-Acetyl-N-(5-((3-fluoro-5-(trifluoromethyl)pyridin-2-yl)oxy)-2-methoxy-phenyl)-1-methyl-2-oxoimidazolidine-4-carboxamide (Compound 343);

N-(2-Methoxy-5-((5-(trifluoromethyl)pyridin-2-yl)oxy)phenyl)-5-oxopyrrolidine-3-carboxamide carboxamide (Compound 344);

(S)—N-(5-((3-Chloro-5-(trifluoromethyl)pyridin-2-yl)oxy)-2-methoxyphenyl)-3-methyl-2-oxoimidazolidine-4-carboxamide (Compound 345);

(S)—N-(2-Methoxy-5-((5-(trifluoromethyl)pyridin-2-yl)oxy)phenyl)-1,3-dimethyl-2-oxoimidazolidine-4-carboxamide (Compound 346);

(R)—N-(2-Methoxy-5-(4-(trifluoromethyl)phenoxy)phenyl)-1-(2-methoxyacetyl)-pyrrolidine-2-carboxamide (Compound 347);

(S)—N-(5-(3-Chlorophenoxy)-2-methoxyphenyl)-3-methyl-2-oxoimidazolidine-4-carboxamide (Compound 348);

N-(2-Methoxy-5-(4-(trifluoromethyl)phenoxy)phenyl)-1-methyl-5-oxo-pyrrolidine-3-carboxamide (Compound 349);

N-(5-(2-Chloro-4-(trifluoromethyl)phenoxy)-2-methoxyphenyl)-5-oxopyrrolidi-ne-2-carboxamide (Compound 350);

(S)—N-(3-Chloro-5-((5-(trifluoromethyl)pyridin-2-yl)oxy)phenyl)-3-methyl-2-oxoimidazolidine-4-carboxamide (Compound 351);

N-(3-Chloro-5-((5-(trifluoromethyl)pyridin-2-yl)oxy)phenyl)-1-methyl-5-oxopyrrolidine-2-carboxamide (Compound 352);

(S)—N-(5-(4-(Fluoromethyl)phenoxy)-2-methoxyphenyl)-3-methyl-2-oxoimidazolidine-4-carboxamide (Compound 353);

Methyl 2-(2-((2-methoxy-5-(4-(trifluoromethyl)phenoxy)phenyl)carbamoyl)-5-oxopyrrolidin-1-yl)acetate (Compound 354);

(S)—N-(2-Methoxy-5-(4-(trifluoromethyl)phenoxy)phenyl)-5-oxopyrrolidine-3-carboxamide (Compound 355);

(S)—N-(5-(4-Chlorophenoxy)-2-methoxyphenyl)-3-methyl-2-oxoimidazolidine-4-carboxamide (Compound 356);

(R)—N-(2-Methoxy-5-(4-(trifluoromethyl)phenoxy)phenyl)-5-oxopyrrolidine-3-carboxamide (Compound 357);

(S)-1-Acetyl-N-(5-((3-fluoro-5-(trifluoromethyl)pyridin-2-yl)oxy)-2-methoxyphenyl)pyrrolidine-2-carboxamide (Compound 358);

(S)—N-(5-((3-Fluoro-5-(trifluoromethyl)pyridin-2-yl)oxy)-2-methoxyphenyl)-1,3-dimethyl-2-oxoimidazolidine-4-carboxamide (Compound 359);

(S)-1,3-Dimethyl-2-oxo-N-(6-((5-(trifluoromethyl)pyridin-2-yl)oxy)benzo[d]-[1,3]dioxol-4-yl)imidazolidine-4-carboxamide (Compound 360);

(S)—N-(2,4-Difluoro-5-((5-(trifluoromethyl)pyridin-2-yl)oxy)phenyl)-3-methyl-2-oxoimidazolidine-4-carboxamide (Compound 361);

(S)—N-(3-Fluoro-5-((5-(trifluoromethyl)pyridin-2-yl)oxy)phenyl)-3-methyl-2-oxoimidazolidine-4-carboxamide (Compound 362);

(S)—N-(2-Fluoro-5-(4-(trifluoromethyl)phenoxy)phenyl)-1-methyl-5-oxo-pyrrolidine-2-carboxamide (Compound 363);

(S)-1,3-Dimethyl-2-oxo-N-(5-((5-(trifluoromethyl)pyridin-2-yl)oxy)-2,3-dihydrobenzofuran-7-yl)imidazolidine-4-carboxamide (Compound 364);

(S)—N-(2-Fluoro-5-(4-(trifluoromethyl)phenoxy)phenyl)-3-methyl-2-oxo-imidazolidine-4-carboxamide (Compound 365);

N-(2-Bromo-5-(3-(trifluoromethyl)phenoxy)phenyl)-1-methyl-5-oxopyrrolidine-2-carboxamide (Compound 366);

N-(2-Cyano-5-(4-(trifluoromethyl)phenoxy)phenyl)-1-methyl-5-oxopyrrolidine-2-carboxamide (Compound 367);

N-(2-Fluoro-5-((5-(trifluoromethyl)pyridin-2-yl)oxy)phenyl)-1-methyl-5-oxopyrrolidine-2-carboxamide (Compound 368);

N-(2-Fluoro-5-((5-(trifluoromethyl)pyridin-2-yl)oxy)phenyl)-1-methyl-5-oxopyrrolidine-2-carboxamide (Compound 369);

(2S,4R)-4-Hydroxy-N-(2-methoxy-5-(4-(trifluoromethyl)phenoxy)-phenyl)pyrrolidine-2-carboxamide (Compound 370);

(S)-1-Acetyl-N-(2-methoxy-5-(4-(trifluoromethyl)phenoxy)phenyl)-5-oxopyrrolidine-2-carboxamide (Compound 371);

N-(2-Hydroxy-5-(4-(trifluoromethyl)phenoxy)phenyl)-1-methyl-5-oxo-pyrrolidine-2-carboxamide (Compound 372);

(S)—N-(2-Hydroxy-5-((5-(trifluoromethyl)pyridin-2-yl)oxy)phenyl)-3-methyl-2-oxoimidazolidine-4-carboxamide (Compound 373);

N-(2-Methoxy-5-(4-(trifluoromethyl)phenoxy)phenyl)-1-methyl-6-oxo-piperazine-2-carboxamide (Compound 374);

4-Amino-5-((2-methoxy-5-(4-(trifluoromethyl)phenoxy)phenyl)amino)-5-oxopentanoic acid (Compound 375);

1-Methyl-6-oxo-N-(5-(4-(trifluoromethyl)phenoxy)-2,3-dihydrobenzofuran-7-yl)piperazine-2-carboxamide (Compound 376);

(R)—N-(2-Methoxy-5-(4-(trifluoromethyl)phenoxy)phenyl)-5-oxo-1-(1H-pyrazol-4-yl)pyrrolidine-2-carboxamide (Compound 377);

(R)—N-(2-Methoxy-5-(4-(trifluoromethyl)phenoxy)phenyl)-5-oxo-1-(1H-pyrazol-4-yl)pyrrolidine-2-carboxamide (Compound 378);

1-(3-Amino-3-oxopropyl)-N-(2-methoxy-5-(4-(trifluoromethyl)phenoxy)-phenyl)-5-oxopyrrolidine-2-carboxamide (Compound 379);

(2S,4S)-4-Hydroxy-N-(2-methoxy-5-(4-(trifluoromethyl)phenoxy)phenyl)-1-methyl-5-oxopyrrolidine-2-carboxamide (Compound 380);

1-Imino-N-(2-methoxy-5-(4-(trifluoromethyl)phenoxy)phenyl)hexahydro-1$\lambda^6$-thiopyran-4-carboxamide 1-oxide (Compound 381);

N-(4-Fluoro-2-methoxy-5-(4-(trifluoromethyl)phenoxy)phenyl)-3-methyl-2-oxoimidazolidine-4-carboxamide (Compound 382);

1,4-Dimethyl-6-oxo-N-(5-(4-(trifluoromethyl)phenoxy)-2,3-dihydrobenzofuran-7-yl)piperazine-2-carboxamide (Compound 383);

N-(5-(4-Amino-2-fluorophenoxy)-2-methoxyphenyl)-1-methyl-5-oxopyrrolidine-2-carboxamide (Compound 384);
N-(5-(4-Chloro-2-fluorophenoxy)-2-methoxyphenyl)-1-methyl-5-oxopyrrolidine-2-carboxamide (Compound 385);
N-(5-(3-Acetylphenoxy)-2-methoxyphenyl)-1-methyl-5-oxopyrrolidine-2-carboxamide (Compound 386);
N-(5-(3-Acetylphenoxy)-2-methoxyphenyl)-1-methyl-5-oxopyrrolidine-2-carboxamide (Compound 387);
N-(2-Methoxy-5-(4-(trifluoromethyl)phenoxy)phenyl)-2-oxo-2,3-dihydro-oxazole-4-carboxamide (Compound 388);
N-(3-(3,4-Difluorophenoxy)-6-methoxy-2-methylphenyl)-1-methyl-5-oxopyrrolidine-2-carboxamide (Compound 389);
N-(5-(3-Cyanophenoxy)-2-methoxyphenyl)-1-methyl-5-oxopyrrolidine-2-carboxamide (Compound 390);
N-(2-Methoxy-5-(3-methoxy-4-(trifluoromethyl)phenoxy)phenyl)-1-methyl-5-oxopyrrolidine-2-carboxamide (Compound 391);
N-(2-Methoxy-5-(4-(trifluoromethyl)phenoxy)phenyl)-1H-tetrazole-5-carboxamide (Compound 392);
(R)—N-(2-Methoxy-5-((4-(trifluoromethyl)pyridin-2-yl)oxy)phenyl)-1-methyl-5-oxopyrrolidine-2-carboxamide (Compound 393);
(S)—N-(2-Methoxy-5-((4-(trifluoromethyl)pyridin-2-yl)oxy)phenyl)-1-methyl-5-oxopyrrolidine-2-carboxamide (Compound 394);
N-(2-Methoxy-5-(3-methoxy-4-(trifluoromethyl)phenoxy)phenyl)-1-methyl-5-oxopyrrolidine-2-carboxamide (Compound 395);
N-(5-(4-Cyano-3-(trifluoromethyl)phenoxy)-2-methoxyphenyl)-1-methyl-5-oxopyrrolidine-2-carboxamide (Compound 396);
N-(5-(3-Cyano-4-fluorophenoxy)-2-methoxyphenyl)-1-methyl-5-oxopyrrolidine-2-carboxamide (Compound 397);
(S)—N-(5-(2-Fluoro-4-(trifluoromethyl)phenoxy)-2-methoxyphenyl)-1-methyl-5-oxopyrrolidine-2-carboxamide (Compound 398);
(N-(5-((5-Fluoro-6-(trifluoromethyl)pyridin-3-yl)oxy)-2-methoxyphenyl)-1-methyl-5-oxopyrrolidine-2-carboxamide (Compound 399);
N-(5-((6-Fluoro-5-(trifluoromethyl)pyridin-2-yl)oxy)-2-methoxyphenyl)-1-methyl-5-oxopyrrolidine-2-carboxamide (Compound 400);
(S)—N-(5-((6-Fluoro-5-(trifluoromethyl)pyridin-2-yl)oxy)-2-methoxyphenyl)-1-methyl-5-oxopyrrolidine-2-carboxamide (Compound 401);
(R)—N-(5-((6-Fluoro-5-(trifluoromethyl)pyridin-2-yl)oxy)-2-methoxyphenyl)-1-methyl-5-oxopyrrolidine-2-carboxamide (Compound 402);
(S)—N-(2-Methoxy-5-((5-(trifluoromethyl)pyridin-2-yl)oxy)phenyl)-1-methyl-5-oxopyrrolidine-2-carboxamide (Compound 403);
(E)-N-(5-(2-(4,4-Difluorocyclohexyl)vinyl)-2-methoxyphenyl)-2-oxo-imidazolidine-4-carboxamide (Compound 404);
(R,E)-N-(5-(2-(4,4-Difluorocyclohexyl)vinyl)-2,3-dihydrobenzofuran-7-yl)-1-methyl-5-oxopyrrolidine-2-carboxamide (Compound 405);
(S,E)-N-(5-(2-(4,4-Difluorocyclohexyl)vinyl)-2,3-dihydrobenzofuran-7-yl)-1-methyl-5-oxopyrrolidine-2-carboxamide (Compound 406);
(S,E)-N-(5-(2-(4,4-Difluorocyclohexyl)vinyl)-2,3-dihydrobenzofuran-7-yl)-3-methyl-2-oxoimidazolidine-4-carboxamide (Compound 407);
(E)-N-(5-(2-(4,4-Difluorocyclohexyl)vinyl)-2-methoxyphenyl)-1,3-dimethyl-2-oxoimidazolidine-4-carboxamide (Compound 408);
((S,E)-N-(6-(2-(4,4-Difluorocyclohexyl)vinyl)benzo[d][1,3]dioxol-4-yl)-3-methyl-2-oxoimidazolidine-4-carboxamide (Compound 409);
N-(2-hydroxy-5-(3-methoxy-4-(trifluoromethyl)phenoxy)phenyl)-1-methyl-5-oxopyrrolidine-2-carboxamide (Compound 410);
N-(5-(2-Hydroxy-4-(trifluoromethyl)phenoxy)-2-methoxyphenyl)-1-methyl-5-oxopyrrolidine-2-carboxamide (Compound 411);
1-Acetyl-N-(2-methoxy-5-(4-(trifluoromethyl)phenoxy)phenyl)pyrrolidine-3-carboxamide (Compound 412);
1-Acetyl-N-(5-(3-fluorophenoxy)-2-methoxyphenyl)pyrrolidine-3-carboxamide (Compound 413);
1-Glycyl-N-(2-methoxy-5-(4-(trifluoromethyl)phenoxy)phenyl)-5-oxopyrrolidi-ne-2-carboxamide, HCl (Compound 414);
(S)—N-(2-Methoxy-5-(4-(trifluoromethyl)phenoxy)phenyl)pyrrolidine-2-carboxamide (Compound 415);
(S)—N-(5-((3-Fluoro-5-(trifluoromethyl)pyridin-2-yl)oxy)-2-methoxyphenyl)-pyrrolidine-2-carboxamide (Compound 416);
(S)—N-(2-Methoxy-5-(4-(trifluoromethyl)phenoxy)phenyl)-N,1-dimethyl-5-oxopyrrolidine-2-carboxamide (Compound 417);
and tautomers and pharmaceutically acceptable salts thereof.

Compounds of the invention may be administered to a patient in therapeutically effective amounts which range usually from about 0.5 to about 2000 mg, more typically form about 1 to about 500 mg, for example from about 2 to about 100 mg, daily depending on the age, sex, weight, ethnic group, condition of the patient, condition to be treated, administration route and the active ingredient used. The compounds of the invention can be formulated into dosage forms using the principles known in the art. The compound can be given to a patient as such or in combination with suitable pharmaceutical excipients in the form of tablets, granules, capsules, suppositories, emulsions, suspensions or solutions. Choosing suitable ingredients for the composition is a routine for those of ordinary skill in the art. Suitable carriers, solvents, gel forming ingredients, dispersion forming ingredients, antioxidants, colours, sweeteners, wetting compounds and other ingredients normally used in this field of technology may also be used. The compositions containing the active compound can be given enterally or parenterally, the oral route being the preferred way. The contents of the active compound in the composition is from about 0.5 to 100%, typically from about 0.5 to about 20%, per weight of the total composition.

The compounds of the invention can be given to the subject as the sole active ingredient or in combination with one of more other active ingredients for treatment of a particular disease.

In the treatment of diseases and conditions wherein inhibition of TEAD is desired, such as various cancers or chronic pain, a combination of therapeutic agents and/or other treatments (e.g., radiation therapy) is often advantageous. The second (or third) agent to be administered may have the same or different mechanism of action than the primary therapeutic agent.

Accordingly, a compound of the invention may be administered in combination with other anti-cancer treatments useful in the treatment of cancers. For example, a compound of the invention can be packaged together with instructions that the compound is to be used in combination with other anti-cancer agents and treatments for the treatment of cancer. Similarly, a compound of the invention may be administered in combination with other pain reliever agents useful in the treatment of chronic pain. For example, a compound of the invention can be packaged together with instructions that the compound is to be used in combination with other anti-cancer agents and treatments for the treatment of cancer, or with other pain reliever agents and treatments for the treatment of chronic pain. The present invention further comprises combinations of a compound of the invention and one or more additional agents in kit form, for example, where they are packaged together or placed in separate packages to be sold together as a kit, or where they are packaged to be formulated together.

According to one embodiment of the invention, the therapeutically effective amount of a compound of formula (I) or a pharmaceutically acceptable salt thereof is co-administered with one or more anti-cancer agents or pain reliever agents.

The optional other anti-cancer agents which can be administered in addition to a compound of formula (I) or a pharmaceutically acceptable salt thereof include, but are not limited to,

- chemotherapeutic agents (e.g. docetaxel and paclitaxel),
- tyrosine kinase inhibitors including EGFR inhibitors (e.g. gefitinib and osimertinib), VEGFR inhibitors (e.g. bevacizumab) and FGFR inhibitors (e.g. erdafitinib);
- immune checkpoint inhibitors (e.g. nivolumab and pembrolizumab),
- epigenetic modulators (e.g. BET inhibitors and HDAC inhibitors),
- mTOR inhibitors (e.g. everolimus);
- AKT inhibitors (e.g. AZ5363);
- radiopharmaceuticals (e.g. alpharadin);
- GnRH/LHRH analogues (such as leuprorelin);
- PI3K inhibitors (e.g. idelalisib); and
- CDK4/6 inhibitors (e.g. ribocyclib)
- steroidogenesis inhibitors (e.g. CYP17A1 inhibitors such as abiraterone acetate and seviteronel); and
- a non-steroidal androgen receptor antagonist (e.g. enzalutamide, apalutamide and darolutamide).

According to still another embodiment, the present invention provides a pharmaceutical combination comprising a compound of formula (I) or a pharmaceutically acceptable salt thereof and at least one additional active ingredient selected from the list consisting of

- chemotherapeutic agents (e.g. docetaxel and paclitaxel),
- tyrosine kinase inhibitors including EGFR inhibitors (e.g. gefitinib and osimertinib), VEGFR inhibitors (e.g. bevacizumab) and FGFR inhibitors (e.g. erdafitinib);
- immune checkpoint inhibitors (e.g. nivolumab and pembrolizumab),
- epigenetic modulators (e.g. BET inhibitors and HDAC inhibitors),
- mTOR inhibitors (e.g. everolimus);
- AKT inhibitors (e.g. AZ5363);
- radiopharmaceuticals (e.g. alpharadin);
- GnRH/LHRH analogues (such as leuprorelin);
- PI3K inhibitors (e.g. idelalisib); and
- CDK4/6 inhibitors (e.g. ribocyclib)
- steroidogenesis inhibitors (e.g. CYP17A1 inhibitors such as abiraterone acetate and seviteronel); and
- a non-steroidal androgen receptor antagonist (e.g. enzalutamide, apalutamide and darolutamide), for simultaneous, separate or sequential administration.

The above other therapeutic agents, when employed in combination with a compound of the invention can be used, for example, in those amounts indicated in the Physicians' Desk Reference (PDR) or as otherwise determined by one of ordinary skill in the art.

The compounds of the invention can be prepared by a variety of synthetic routes analogously to the methods known in the literature using suitable starting materials. The present invention will be explained in more detail by the following experiments and examples. The experiments and examples are meant only for illustrating purposes and do not limit the scope of the invention defined in claims.

EXAMPLES

Purification methods used:

A) Reverse phase HPLC (water/acetonitrile, 2-8 min 0-65%, 30 mL/min, column: SunFire 100*19 mm).

B) Reverse phase HPLC (water/methanol, 2-8 min 0-65%, 30 mL/min, column: SunFire 100*19 mm).

C) Reverse phase HPLC (water/acetonitrile/formic acid, 2-10 min 0-40%, 30 mL/min, column: SunFire 100*19 mm).

D) Reverse phase HPLC (water/acetonitrile/ammonia, 2-8 min 0-65%, 30 mL/min, column: SunFire 100*19 mm).

E) Reverse phase HPLC (water/methanol/ammonia, 2-10 min 40-50%, 30 mL/min, column: SunFire 100*19 mm).

F) Reverse phase HPLC (water/acetonitrile/trifluoroacetic acid, 2-10 min 0-50%, 30 mL/min, column: SunFire 100*19 mm).

G) Reverse phase HPLC (water/methanol/trifluoroacetic acid, 2-10 min 10-50%, 30 mL/min, column: SunFire 100*19 mm).

H) Preparative chiral HPLC (methanol/isopropanol, 50-50, 12 mL/min, column: ChiralpakAD-H (250*20 mm).

I) Preparative chiral HPLC (methanol/IPA/Hexane, 25-25-50, 0.6 mL/min, column: Chiralpak IC (250*4.6 mm).

J) Preparative chiral HPLC (methanol/$CO_2$, 50-50, 2 mL/min, column: ChiralpakAD-H (250*4.6 mm).

Intermediate 1. 5-Bromo-2-fluoro-4-methoxyphenyl formate

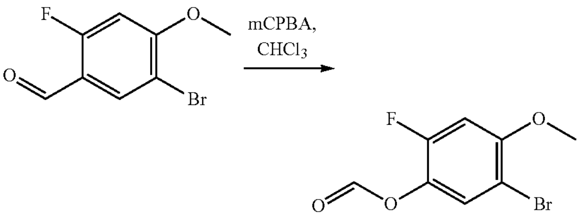

Int-1

To a solution of 5-bromo-2-fluoro-4-methoxybenzaldehyde (1.000 g, 1 eq., 4.291 mmol) in $CHCl_3$ (20 mL) was added 3-chlorobenzoperoxoic acid (1.851 g, 2.5 eq., 10.73 mmol) at 4° C. followed by stirring for 30 min. The mixture was diluted with water (50 ml) and the resulted mixture was extracted with ethyl acetate (3×10 mL). The organic layers were combined, washed with saturated solution of $NaHCO_3$ (2×10 mL) and brine (10 ml), dried over sodium sulfate, filtered and concentrated to give the title compound. $^1H$ NMR (400 MHz, DMSO-d6) δ: 8.57 (s, 1H), 7.69 (dd, 1H), 7.29 (dd, 1H), 3.86 (d, 3H).

The following intermediates were prepared according to the procedure described for Intermediate 1 from the starting materials indicated in the Table. Where LCMS/GCMS data was not informative, the data is not shown.

| No. | Structure | LCMS/ GCMS m/z | Starting material |
|---|---|---|---|
| Int-2 | 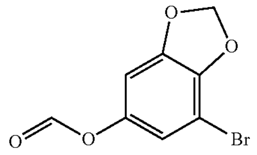 [SMILES: O=COc1cc(Br)c2c(c1)OCO2] | 244 [M]$^+$ | 7-Bromobenzo[d][1,3]dioxole-5-carbaldehyde |
| Int-3 | 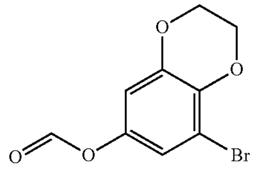 [SMILES: O=COc1cc(Br)c2c(c1)OCCO2] | — | 8-Bromo-2,3-dihydrobenzo[b]-[1,4]dioxine-6-carbaldehyde |
| Int-4 | 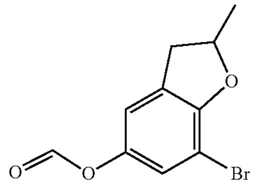 | — | 7-Bromo-2-methyl-2,3-dihydro-benzofuran-5-carbaldehyde |

Intermediate 5. 5-Bromo-2-fluoro-4-methoxyphenol

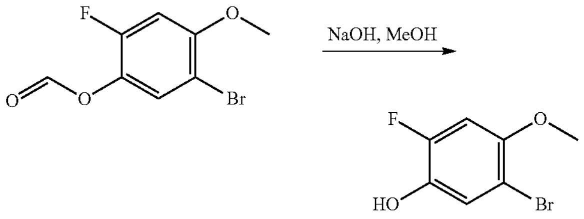

Int-5

Sodium hydroxide (1.606 g, 2.5 eq., 40.15 mmol) was added to a solution of 5-bromo-2-fluoro-4-methoxyphenyl formate (4.0 g, 1 eq., 16.06 mmol) in methanol (100 mL). The mixture was stirred at 25° C. for 12 h. Then the mixture was concentrated, diluted with 50 mL of water, acidified to pH 1 and extracted with ethyl acetate (3×30 mL). The combined organic phases were dried over $Na_2SO_4$ and concentrated. The crude product was purified twice by column chromatography using hexane-MTBE and chloroform-acetonitrile systems to give the title compound (1.4 g, 6.0 mmol, 37%, 95% purity). $^1H$ NMR (500 MHz, DMSO-d6) δ: 9.66 (s, 1H), 7.12 (d, 1H), 7.04 (d, 1H), 3.73 (s, 3H).

The following intermediates were prepared according to the procedure described for Intermediate 4 from the starting materials indicated in the Table. Where LCMS/GCMS data was not informative, the data is not shown.

| No. | Structure | LCMS/ GCMS m/z | Starting material |
|---|---|---|---|
| Int-6 | 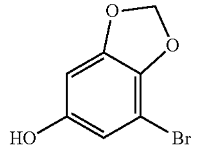 | — | 7-Bromobenzo[d][1,3]dioxol-5-yl formate |
| Int-7 | 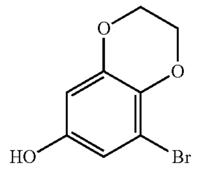 [SMILES: Oc1cc(Br)c2c(c1)OCCO2] | — | 8-Bromo-2,3-dihydrobenzo[b]-[1,4]dioxin-6-yl formate |
| Int-8 | 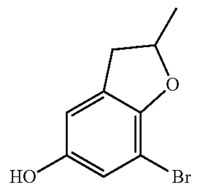 | — | 7-Bromo-2-methyl-2,3-dihydro-benzofuran-5-yl formate |

Intermediate 9. 5-Methoxy-7-nitrobenzofuran

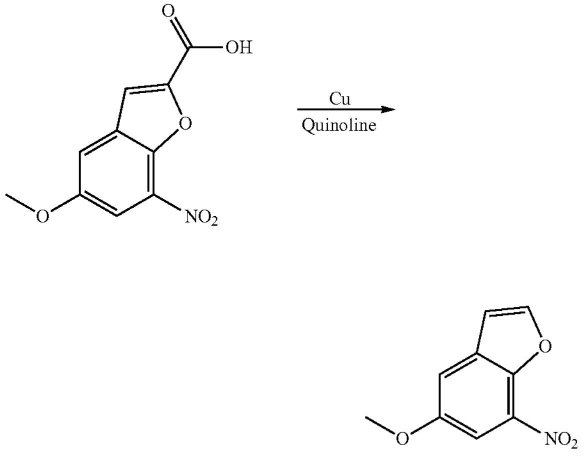

Int-9

5-Methoxy-7-nitrobenzofuran-2-carboxylic acid (1 g, 1 eq., 4.22 mmol) and copper (201 mg, 0.75 eq., 3.16 mmol) were refluxed in quinoline (20 mL) for 30 min. After cooling to RT the mixture was filtered and the filtrate was poured to 2 N hydrochloric acid and filtered. The obtained precipitate was concentrated three times with acetonitrile to give the title compound (710 mg, 3.5 mmol). $^1H$ NMR (500 MHz, DMSO-d6) δ: 8.20 (s, 1H), 7.66 (d, 1H), 7.10 (s, 1H), 3.86 (s, 3H).

Intermediate 10a. 3-(4-Methoxy-2-nitrophenyl)-1-methyl-1H-pyrazole

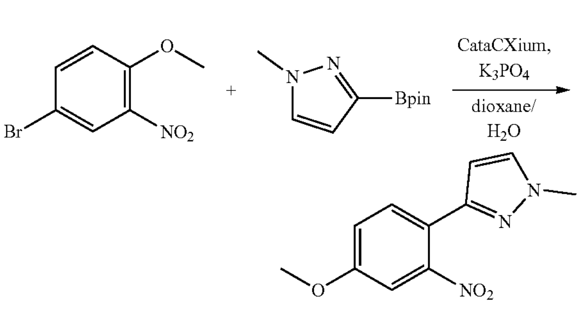

Int-10a

1-Bromo-4-methoxy-2-nitrobenzene (0.272 g, 1.17 mmol), 1-methyl-3-(4,4,5,5-tetramethyl-1,3,2-dioxaborolan-2-yl)-1H-pyrazole (244 mg, 1.17 mmol) and potassium phosphate (746 mg, 3.52 mmol) were mixed in dioxane (4 mL) and water (0.4 mL) under argon atmosphere and the mixture was heated to 100° C. Then di(1-adamantyl)-n-butylphosphine (21.0 mg, 0.05 eq., 58.6 μmol) and (2'-amino-[1,1'-biphenyl]-2-yl)-((methylsulfonyl)oxy)palladium (21.7 mg, 0.05 eq., 58.6 μmol) were added and the mixture was stirred for 14 h at 100° C. After cooling to RT the mixture was concentrated in vacuum. The residue was dissolved in ethyl acetate (5 mL), washed with brine (2×5 mL), dried over sodium sulfate, filtered and concentrated in vacuum to give crude title compound (0.2 g, 0.73 mmol) which was used in the next step without further purification. LCMS: m/z 234.2 $[M+H]^+$.

Intermediate 10b. 4-(1-Methyl-1H-pyrazol-3-yl)-3-nitrophenol

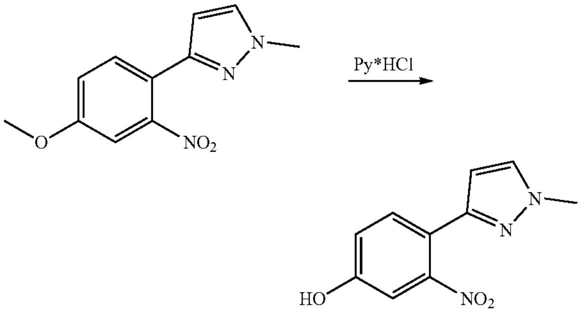

Int-10b 3-(4-Methoxy-2-nitrophenyl)-1-methyl-1H-pyrazole (1.2 g, 1 eq., 5.145 mmol) was mixed with pyridine HCl (2.973 g, 5 eq., 25.73 mmol) followed by stirring at 200° C. for 30 h. After cooling to RT the reaction mass was poured into water (10 mL) and extracted with ethyl acetate (3×20 mL). Combined organic phases were dried over sodium sulfate, filtered and concentrated to give the title compound (0.90 g, 3.7 mmol). $^1H$ NMR (400 MHz, DMSO-$d_6$) δ: 10.42 (s, 1H), 7.70 (d, 1H), 7.54 (d, 1H), 7.10 (d, 1H), 7.05 (dd, 1H), 6.33 (d, 1H), 3.81 (s, 3H).

The following intermediate was prepared according to the procedure described for Intermediate 10b from the starting material indicated in the Table.

| No. | Structure | LCMS/ GCMS m/z | Starting material |
|---|---|---|---|
| Int-11 | 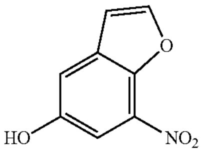 | LCMS: m/z 177.8 $[M - H]^-$. | 5-Methoxy-7-nitrobenzofuran |

Intermediate 12a. (4-Fluoro-3-methoxyphenoxy)triisopropylsilane

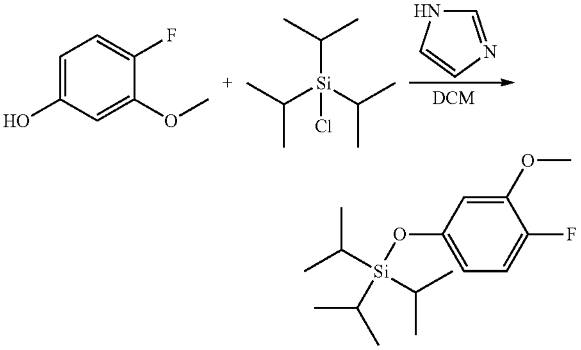

Int-12a

To a stirred solution of 4-fluoro-3-methoxyphenol (6 g, 1 eq., 42.21 mmol) and imidazole (5.748 g, 2 eq., 84.43 mmol) in DCM (60 mL) at RT was added chlorotriiso-propylsilane (8.546 g, 9.487 mL, 1.05 eq., 44.33 mmol). The mixture was stirred for 16 h and then poured into saturated aqueous $NH_4Cl$ (40 mL), followed by extraction with DCM (3×50 mL). The combined extracts were washed with brine (30 mL), dried over $Na_2SO_4$, and concentrated in vacuum to give the title compound (10.00 g, 30 mmol). $^1H$ NMR (400 MHz, Chloroform-d) δ: 6.87 (dd, 1H), 6.48 (dd, 1H), 6.34 (dt, 1H), 3.82 (s, 3H), 1.23 (dh, 3H), 1.08 (d, 21H).

Intermediate 12b. (4-Fluoro-3-iodo-5-methoxyphenoxy)triisopropylsilane

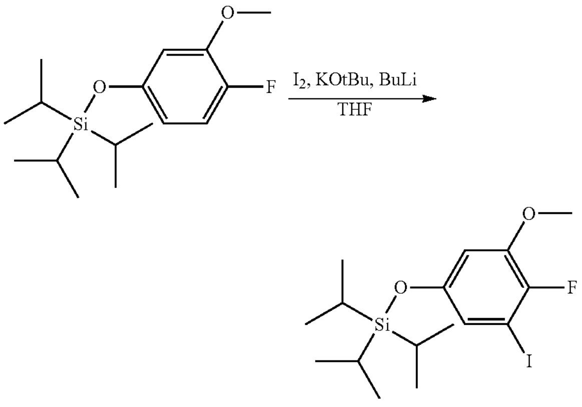

Int-12b (4-Fluoro-3-methoxyphenoxy)triisopropylsilane (6.544 g, 1 eq., 21.93 mmol) and potassium 2-methylpropan-2-olate (2.706 g, 1.1 eq., 24.12 mmol) were mixed in THF (60 mL) under argon atmosphere and cooled to −78° C. Butyl lithium (1.545 g, 9.647 mL, 2.5 molar, 1.1 eq., 24.12 mmol) was added dropwise at −78° C. Then the mixture was stirred for 1 h at the same temperature. The solution of iodine (6.678 g, 1.2 eq., 26.31 mmol) in THF (20 mL) was added dropwise at −78° C. After stirring at RT overnight, the mixture was cooled to −20° C. and aqueous solution of ammonium chloride (20 mL) was added dropwise. Then the solution was warmed to RT. EtOAc (70 mL) was added and the organic layer was washed with brine (2×30 mL), dried over sodium sulfate, filtered and concentrated. The residue was purified by flash chromatography (hexane/MTBE) to give the title compound (2.0 g, 3.3 mmol). GCMS: m/z 424 $[M]^+$.

Intermediate 12c. 4-Fluoro-3-iodo-5-methoxyphenol

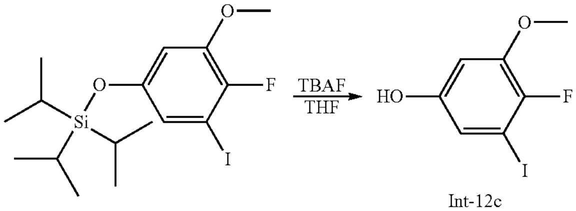

Int-12c (4-Fluoro-3-iodo-5-methoxyphenoxy)triisopropylsilane (2.3 g, 1 eq., 5.420 mmol) was dissolved in THF (10 mL) and tetrabutylammonium fluoride (3.543 g, 13.55 mL, 1 molar, 2.5 eq., 13.55 mmol) was added dropwise. The mixture was stirred at RT for 16 h and then concentrated in vacuum. The residue was dissolved in EtOAc (20 mL), washed with water (2×5 mL), dried under sodium sulfate and concentrated in vacuum. The obtained residue was purified by flash chromatography (hexane/MTBE) to give the title compound (0.575 g, 1.9 mmol). $^1H$ NMR (400 MHz, Chloroform-d) δ: 6.72 (t, 1H), 6.45 (dd, 1H), 4.86 (s, 1H), 3.82 (s, 3H).

Intermediate 13. 1-Methoxy-2-nitro-4-(4-(trifluoromethyl)phenoxy)benzene

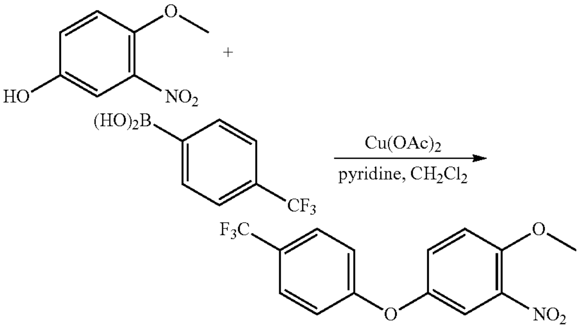

Int-13

4-Methoxy-3-nitrophenol (1 g, 1 Eq., 6 mmol), (4-(trifluoromethyl)phenyl)-boronic acid (2 g, 2 eq., 0.01 mol), pyridine (0.9 g, 1 mL, 2 eq., 0.01 mol), diacetoxycopper (1 g, 1.05 eq., 6 mmol) and powdered molecular sieves 4 Å (1 g) were suspended in dichloromethane (10 mL). The air was bubbled through the resulting solution for 30 min and the mixture was stirred at RT overnight. The mixture was filtered. The filtrate was washed with water (2×30 mL), dried over sodium sulfate, filtered and the solvent was removed under reduced pressure. The residue was purified by method A to afford the title compound. LCMS: m/z 314.0 $[M+H]^+$.

The following intermediates were prepared according to the procedure described for Intermediate 13 from the starting materials indicated in the Table. Where LCMS/GCMS data was not informative, the data is not shown.

| No. | Structure | LCMS/ GCMS m/z | Starting material |
|---|---|---|---|
| Int-14 | 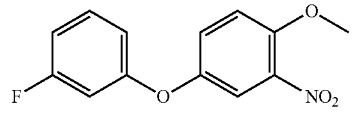 [SMILES: COc1ccc(Oc2cccc(F)c2)cc1[N+](=O)[O-]] | 264.2 $[M + H]^+$ | 4-Methoxy-3-nitrophenol and (3-Fluorophenyl)boronic acid |
| Int-15 | 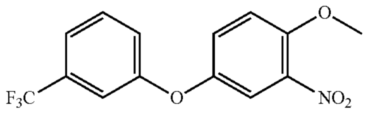 [SMILES: COc1ccc(Oc2cccc(C(F)(F)F)c2)cc1[N+](=O)[O-]] | 314.0 $[M + H]^+$ | 4-Methoxy-3-nitrophenol and (3-(Trifluoromethyl)phenyl)-boronic acid |
| Int-16 | 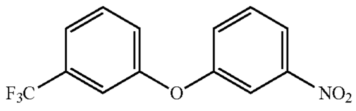 | 284.2 $[M + H]^+$ | 3-Nitrophenol and (3-(Trifluoro-methyl)phenyl)boronic acid |
| Int-17 | 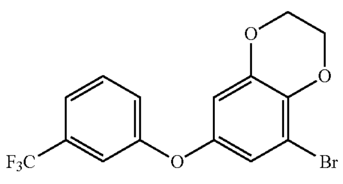 [SMILES: FC(F)(F)c1cccc(Oc2cc(Br)c3c(c2)OCCO3)c1] | 376.2 $[M + H]^+$ | 8-Bromo-2,3-dihydrobenzo[b]-[1,4]dioxin-6-ol and (3-(Trifluroo-methyl)phenyl)boronic acid |

-continued

| No. | Structure | LCMS/ GCMS m/z | Starting material |
|---|---|---|---|
| Int-18 | 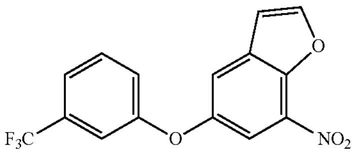 [SMILES: O=[N+]([O-])c1cc(Oc2cccc(C(F)(F)F)c2)cc2ccoc12] | 323.1 $[M]^+$ | 7-Nitrobenzofuran-5-ol and (3-(Trifluoromethyl)phenyl)boronic acid |
| Int-19 | 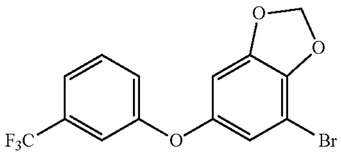 [SMILES: FC(F)(F)c1cccc(Oc2cc(Br)c3c(c2)OCO3)c1] | 359.93 $[M]^+$ | 7-Bromobenzo[d][1,3]dioxol-5-ol and (3-(Trifluoromethyl)phenyl)-boronic acid |
| Int-20 | 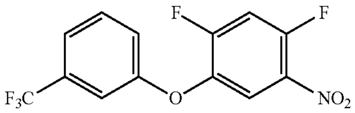 [SMILES: O=[N+]([O-])c1cc(Oc2cccc(C(F)(F)F)c2)c(F)cc1F] | 320.0 $[M + H]^+$ | 2,4-Difluoro-5-nitrophenol and (3-(Trifluoromethyl)phenyl)-boronic acid |
| Int-21 | 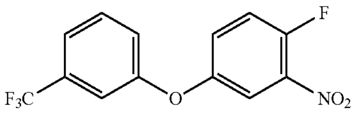 | 301.0 $[M]^+$ | 4-Fluoro-3-nitrophenol and (3-(Trifluoromethyl)phenyl)boronic acid |
| Int-22 | 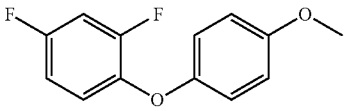 [SMILES: COc1ccc(Oc2ccc(F)cc2F)cc1] | 236.0 $[M]^+$ | (4-Methoxyphenyl)boronic acid and 2,4-Difluorophenol |
| Int-23 | 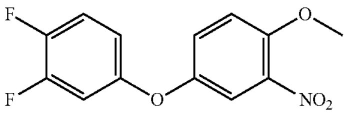 [SMILES: COc1ccc(Oc2ccc(F)c(F)c2)cc1[N+](=O)[O-]] | 282.0 $[M + H]^+$ | 4-Methoxy-3-nitrophenol and (3,4-Difluorophenyl)boronic acid |
| Int-24 | 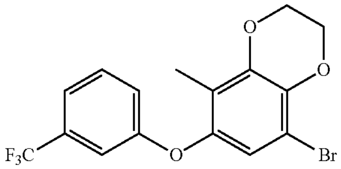 [SMILES: Cc1c(Oc2cccc(C(F)(F)F)c2)cc(Br)c2c1OCCO2] | 390.2 $[M + H]^+$ | 8-Bromo-5-methyl-2,3-dihydro-benzo[b][1,4]dioxin-6-ol and (3-(Trifluoromethyl)phenyl)-boronic acid |
| Int-25 | 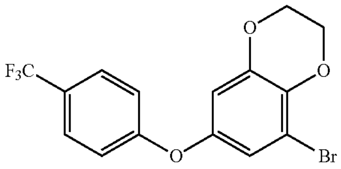 [SMILES: FC(F)(F)c1ccc(Oc2cc(Br)c3c(c2)OCCO3)cc1] | 376.2 $[M + H]^+$ | 8-Bromo-2,3-dihydrobenzo[b]-[1,4]dioxin-6-ol and (4-(Trifluoro-methyl)phenyl)boronic acid |
| Int-26 | 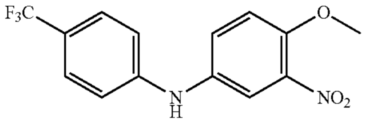 | 313.2 $[M + H]^+$ | 4-Methoxy-3-nitroaniline and (4-(Trifluoromethyl)phenyl)boronic acid |
| Int-27 | 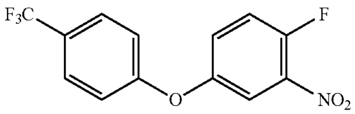 [SMILES: O=[N+]([O-])c1cc(Oc2ccc(C(F)(F)F)cc2)ccc1F] | 302.2 $[M + H]^+$ | 4-Fluoro-3-nitrophenol and (4-(Trifluoromethyl)phenyl)boronic acid |

-continued

| No. | Structure | LCMS/ GCMS m/z | Starting material |
|---|---|---|---|
| Int-28 | 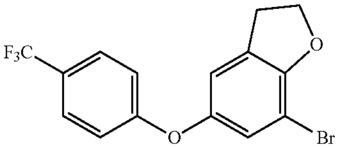 [SMILES: FC(F)(F)c1ccc(Oc2cc(Br)c3c(c2)CCO3)cc1] | 358.0 [M]+ | 7-Bromo-2,3-dihydrobenzofuran-5-ol and (4-(Trifluoromethyl) phenyl)boronic acid |
| Int-29 | 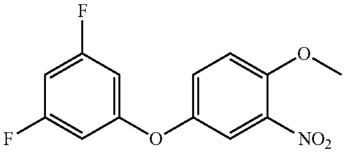 [SMILES: COc1ccc(Oc2cc(F)cc(F)c2)cc1[N+](=O)[O-]] | 282.2 [M + H]+ | 4-Methoxy-3-nitrophenol and (3,5-Difluorophenyl)boronic acid |
| Int-30 | 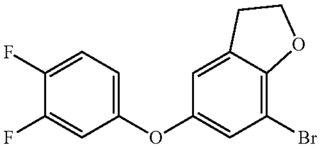 [SMILES: Fc1ccc(Oc2cc(Br)c3c(c2)CCO3)cc1F] | 326.0 [M]+ | 7-Bromo-2,3-dihydrobenzofuran-5-ol and (3,4-Difluorophenyl)-boronic acid |
| Int-31 | 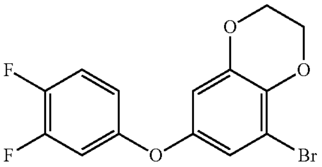 [SMILES: Fc1ccc(Oc2cc(Br)c3c(c2)OCCO3)cc1F] | 344.2 [M + H]+ | 8-Bromo-2,3-dihydrobenzo[b]-[1,4]dioxin-6-ol and (3,4-Difluorophenyl)boronic acid |
| Int-32 | 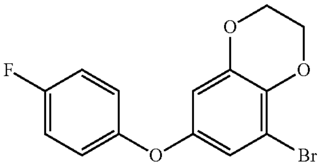 [SMILES: Fc1ccc(Oc2cc(Br)c3c(c2)OCCO3)cc1] | 326.0 [M + H]+ | 8-Bromo-2,3-dihydrobenzo[b]-[1,4]dioxin-6-ol and (4-Fluorophenyl)boronic acid |
| Int-33 | 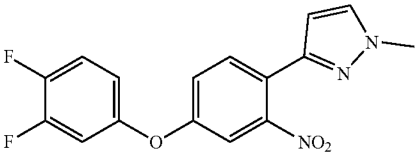 | 332.0 [M + H]+ | 4-(1-Methyl-1H-pyrazol-3-yl)-3-nitrophenol and (3,4-Difluorophenyl)boronic acid |
| Int-34 | 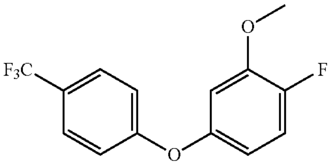 [SMILES: COc1cc(Oc2ccc(C(F)(F)F)cc2)ccc1F] | — | 4-Fluoro-3-methoxyphenol and (4-(Trifluoromethyl)phenyl)-boronic acid |
| Int-35 | 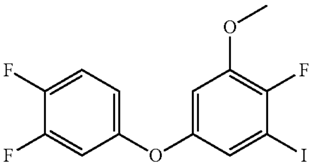 [SMILES: COc1cc(Oc2ccc(F)c(F)c2)cc(I)c1F] | — | 4-Fluoro-3-iodo-5-methoxyphenol and (3,4-Difluorophenyl)boronic acid |
| Int-36 | 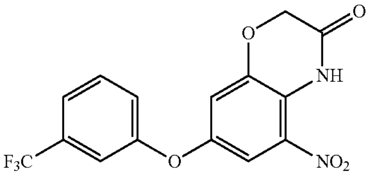 [SMILES: O=C1COc2cc(Oc3cccc(C(F)(F)F)c3)cc([N+](=O)[O-])c2N1] | 355.0 [M + H]+ | 7-Hydroxy-5-nitro-2H-benzo[b]-[1,4]oxazin-3(4H)-one and (3-(Trifluoromethyl)phenyl)boronic acid |

-continued

| No. | Structure | LCMS/ GCMS m/z | Starting material |
|---|---|---|---|
| Int-37 | 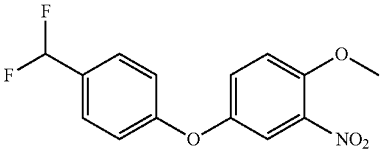 [SMILES: COc1ccc(Oc2ccc(C(F)F)cc2)cc1[N+](=O)[O-]] | 296.0 $[M]^+$ | 4-Methoxy-3-nitrophenol and (4-(Difluoromethyl)phenyl)boronic acid |
| Int-38 | 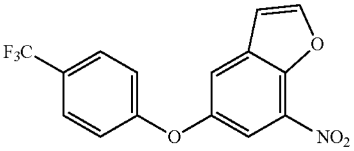 | — | 7-Nitrobenzofuran-5-ol and (4-(Trifluoromethyl)phenyl)boronic acid |
| Int-39 | 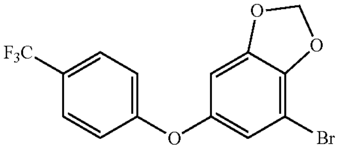 [SMILES: FC(F)(F)c1ccc(Oc2cc(Br)c3c(c2)OCO3)cc1] | — | 7-Bromobenzo[d][1,3]dioxol-5-ol and (4-(Trifluoroemthyl)phenyl)-boronic acid |
| Int-40 | 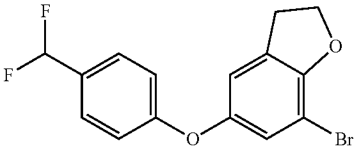 [SMILES: FC(F)c1ccc(Oc2cc(Br)c3c(c2)CCO3)cc1] | — | 7-Bromo-2,3-dihydrobenzofuran-5-ol and (4-(Difluoromethyl)-phenyl)boronic acid |
| Int-41 | 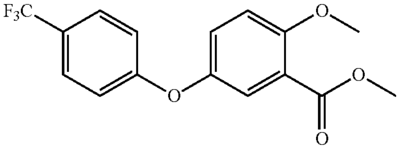 [SMILES: COC(=O)c1cc(Oc2ccc(C(F)(F)F)cc2)ccc1OC] | — | Methyl 5-hydroxy-2-methoxy-benzoate and (4-(Trifluoro-methyl)phenyl)boronic acid |
| Int-42 | 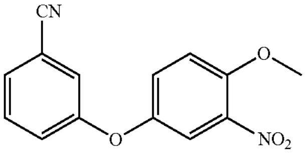 [SMILES: COc1ccc(Oc2cccc(C#N)c2)cc1[N+](=O)[O-]] | 271.2 $[M + H]^+$ | 4-Methoxy-3-nitrophenol and 3-Cyanophenylboronic acid |
| Int-43 | 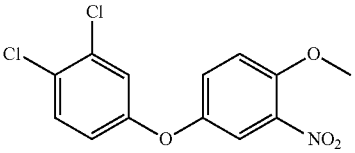 [SMILES: COc1ccc(Oc2ccc(Cl)c(Cl)c2)cc1[N+](=O)[O-]] | 315.9 [M + H]+ | 4-Methoxy-3-nitrophenol and 3,4-Dichlorophenylboronic acid |
| Int-44 | 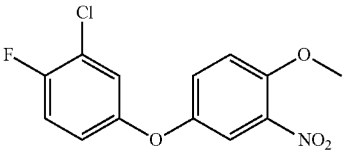 [SMILES: COc1ccc(Oc2ccc(F)c(Cl)c2)cc1[N+](=O)[O-]] | 297.9 [M + H]+ | 4-Methoxy-3-nitrophenol and 3-Chloro-4-fluorophenylboronic acid |

-continued

| No. | Structure | LCMS/ GCMS m/z | Starting material |
|---|---|---|---|
| Int-45 | 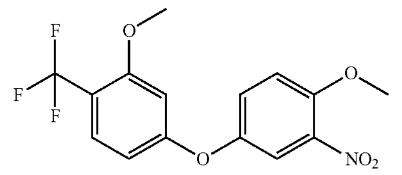 [SMILES: COc1ccc(Oc2ccc(C(F)(F)F)c(OC)c2)cc1[N+](=O)[O-]] | 344.3 [M + H]+ | 4-Methoxy-3-nitrophenol and 3-Methoxy-4-(trifluoromethyl)-phenylboronic acid |
| Int-46 | 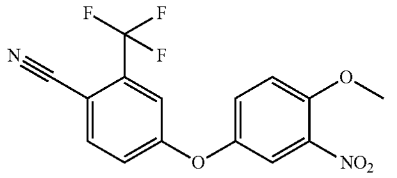 [SMILES: COc1ccc(Oc2ccc(C#N)c(C(F)(F)F)c2)cc1[N+](=O)[O-]] | 338.9 [M + H]+ | 4-Methoxy-3-nitrophenol and (4-Cyano-3-(trifluoromethyl)-phenyl)boronic acid |
| Int-47 | 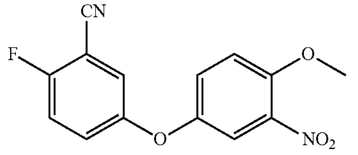 | 288.6 [M + H]+ | 4-Methoxy-3-nitrophenol and 3-Cyano-4-fluorobenzene boronic acid |

Intermediate 48. 2-Fluoro-1-iodo-3-methoxy-5-(4-(trifluoromethyl)phenoxy)-benzene

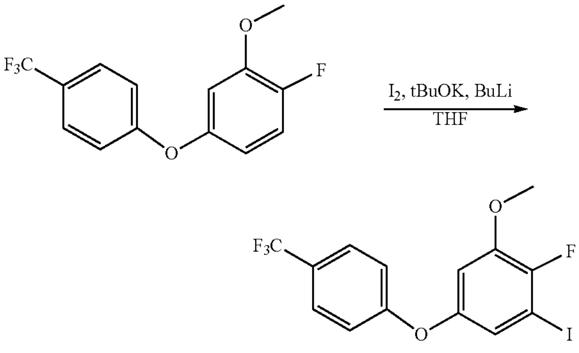

Int-48

1-Fluoro-2-methoxy-4-(4-(trifluoromethyl)phenoxy)benzene (4.000 g, 1 eq., 13.97 mmol) and potassium 2-methylpropan-2-olate (1.725 g, 1.1 eq., 15.37 mmol) were mixed in THF (60 mL) and cooled to −78° C. under argon atmosphere. Butyl lithium (984.7 mg, 6.149 mL, 2.5 molar, 1.1 eq., 15.37 mmol) was added dropwise at −78° C. and the mixture was stirred for 2 h at the same temperature. A solution of iodine (4.256 g, 1.2 eq., 16.77 mmol) in THF (20 mL) was added dropwise at −78° C. After stirring at RT overnight, the mixture was cooled to −20° C. and aqueous solution of ammonium chloride (10 mL) was added dropwise. Then the solution was warmed to RT. EtOAc (100 mL) was added and the organic layer was washed with brine (2×25 mL), dried over sodium sulfate, filtered and concentrated. The residue was purified by flash chromatography (hexane/MTBE) to give the title compound (0.900 g, 2.0 mmol, 14%, 90% purity).

Intermediate 49. 6-Hydroxy-8-nitrochroman-4-one

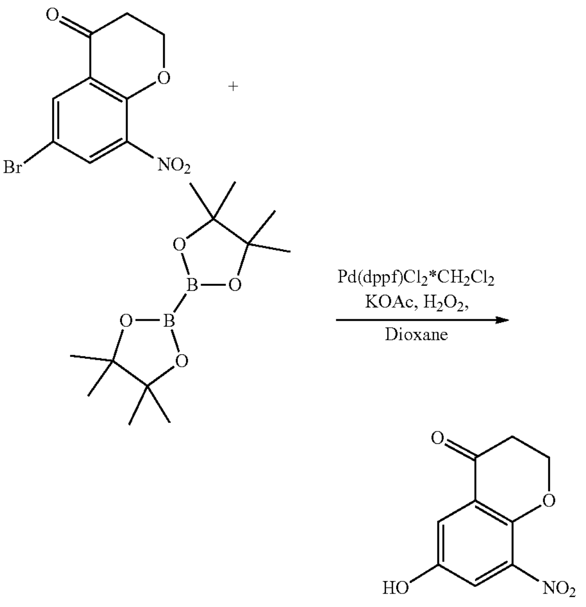

Int-49

6-Bromo-8-nitrochroman-4-one (2.00 g, 1 eq., 7.35 mmol), 4,4,4',4',5,5,5',5'-octamethyl-2,2'-bi(1,3,2-dioxaborolane) (2.24 g, 1.2 eq., 8.82 mmol) and potassium acetate (2.16 g, 3 eq., 22.1 mmol) were mixed in 1,4-dioxane (20 mL). Argon was bubbled into the solution at 25° C. for 1 h to remove any excess oxygen. $PdCl_2(dppf)CH_2Cl_2$ (180 mg, 0.03 eq., 221 μmol) was added to the mixture under argon atmosphere. The mixture was heated to 80° C. and stirred for 3 h until the reaction was completed. The mixture was cooled to 25° C. and then filtered. The precipitate was washed with dioxane (15 mL). The filtered solutions were combined, concentrated and then transferred to a reactor. Hydrogen peroxide (4.29 g, 4.29 mL, 35 w-%, 6 eq., 44.1 mmol) was added and the mixture was heated to 50° C. and stirred for 40 min until the reaction was completed. Water (10 mL) was added to the mixture, and the mixture was extracted with DCM (2×50 mL). The organic phase was collected, washed with 15% brine (2×15 mL) and extracted with 15% $Na_2CO_3$ (2×25 mL). The aqueous phase was collected and the pH value was adjusted to 4-5 with 3 M HCl. The aqueous phase was then extracted with ethyl acetate (2×50 mL). The organic phase was collected, dried over $Na_2SO_4$ and concentrated under reduced pressure to obtain the title compound (810 mg, 3.6 mmol). LCMS: m/z 208.0 $[M+H]^+$ The following intermediate was prepared according to the procedure described for Intermediate 49 from the starting material indicated in the Table.

| No. | Structure | LCMS/ GCMS m/z | Starting material |
|---|---|---|---|
| Int-50 | 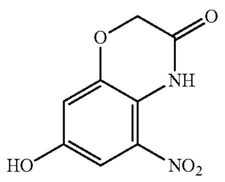 | 210.2 $[M + H]^+$. | 7-Bromo-5-nitro-2H-benzo[b]-[1,4]oxazin-3(4H)-one |

Intermediate 51. (7-Nitrobenzo[d][1,3]dioxol-5-yl) methanol

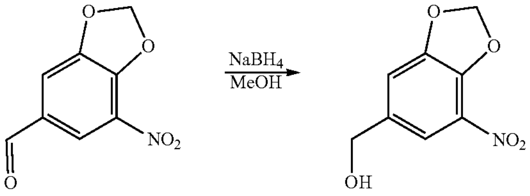

Int-51

7-Nitrobenzo[d][1,3]dioxole-5-carbaldehyde (1000 mg, 1 eq., 5.125 mmol) was dissolved in anhydrous methanol (40 mL). The mixture was cooled to 0° C. and sodium borohydride (232.6 mg, 1.2 eq., 6.150 mmol) was added portion-wise during 10 min. The mixture was stirred at RT for 18 h and then concentrated under reduced pressure. The resulting residue was treated with saturated ammonium chloride solution (30 mL), extracted with ethyl acetate (3×20 mL), dried over anhydrous sodium sulphate, and concentrated under reduced pressure to give the title compound (0.693 g, 3.29 mmol, 64.1%, 93.46% purity). $^1H$ NMR (500 MHz, DMSO-d6) δ: 7.50 (s, 1H), 7.21 (s, 1H), 6.28 (s, 2H), 5.41 (s, 1H), 4.45 (s, 2H).

The following intermediates were prepared according to the procedure described for Intermediate 51 from the starting materials indicated in the table. Where LCMS/GCMS data was not informative, the data is not shown.

| No. | Structure | LCMS/ GCMS m/z | Starting material |
|---|---|---|---|
| Int-52 | 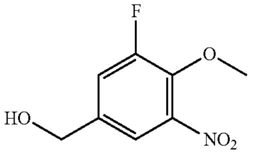 | 201.03 $[M]^+$ | 3-Fluoro-4-methoxy-5-nitro-benzaldehyde |
| Int-53 | 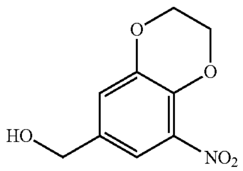 [SMILES: O=[N+]([O-])c1cc(CO)cc2c1OCCO2] | — | 8-Nitro-2,3-dihydrobenzo[b]-[1,4]dioxine-6-carbaldehyde |
| Int-54 | 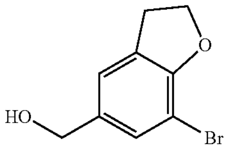 [SMILES: OCc1cc(Br)c2c(c1)CCO2] | — | 7-Bromo-2,3-dihydrobenzofuran-5-carbaldehyde |
| Int-55 | 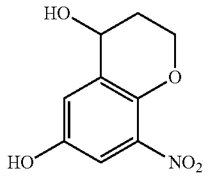 [SMILES: O=[N+]([O-])c1cc(O)cc2c1OCCC2O] | 212.0 $[M + H]^+$ | 6-Hydroxy-8-nitrochroman-4-one |

Intermediate 56. 1-(Chloromethyl)-2,4-dimethoxy-5-nitrobenzene

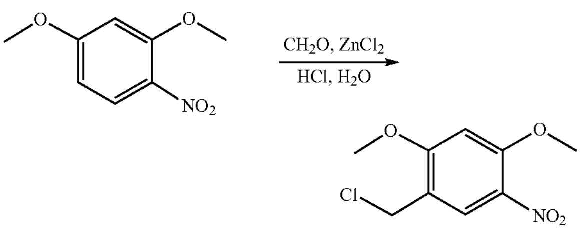

Int-56

2,4-Dimethoxy-1-nitrobenzene (1 g, 1 eq., 5 mmol), formaldehyde (0.3 g, 2 eq., 0.01 mol, aq. 40%) and zinc (II) chloride (0.07 g, 0.1 eq., 0.5 mmol) were dissolved in aqueous (37%) hydrochloric acid (10 mL) followed by stirring at 100° C. for 12 h. After cooling to RT the reaction mixture was extracted with dichloromethane (2×50 mL), organic layers were combined, washed with water (2×100 mL), dried over sodium sulfate, filtered and concentrated in vacuum to give crude title compound (312 mg, 1.46 mmol, 30%, 100% purity), which was purified by method A. $^1H$ NMR (400 MHz, DMSO-$d_6$) δ: 7.97 (s, 1H), 6.81 (d, 1H), 4.43 (d, 2H), 4.01 (d, 1H), 3.96 (dd, 6H).

The following intermediate was prepared according to the procedure described for Intermediate 56 from the starting material indicated in the table.

| No. | Structure | LCMS/ GCMS m/z | Starting material |
|---|---|---|---|
| Int-57 | 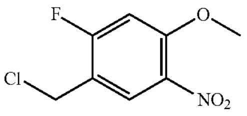 | 218.98 $[M]^+$ | 4-Fluoro-2-methoxy-1-nitrobenzene |

Intermediate 58. 5-(Chloromethyl)-1-fluoro-2-methoxy-3-nitrobenzene

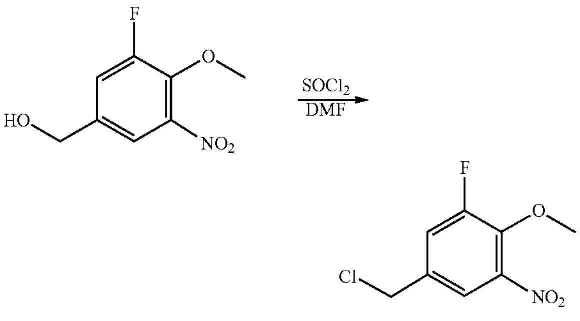

Int-58

(3-Fluoro-4-methoxy-5-nitrophenyl)methanol (610 mg, 1 eq., 3.03 mmol) was dissolved in DCM (7 mL) and DMF (2.22 mg, 2.35 μL, 0.01 eq., 30.3 μmol) was added. The resulting solution was cooled to 0° C. and thionyl chloride (722 mg, 443 μL, 2 eq., 6.07 mmol) was added dropwise to the mixture at the same temperature and the solution was stirred at 0° C. for 10 min followed by warming to RT and stirring at this temperature overnight. The solution was then poured into 10% aqueous sodium bicarbonate solution (10 mL) and stirred for 10 min. Then the aqueous layer was extracted with DCM (10 mL). Combined organic layers were dried over sodium sulfate, filtered and the solvent was evaporated under vacuum to give the title compound (602 mg, 2.4 mmol, 80%, 88% purity), which was used in the next step without further purification. LCMS: m/z 219.8 $[M+H]^+$.

The following intermediates were prepared according to the procedure described for Intermediate 58 from the starting materials indicated in the table. Where LCMS/GCMS data was not informative, the data is not shown.

| No. | Structure | LCMS/ GCMS m/z | Starting material |
|---|---|---|---|
| Int-59 | 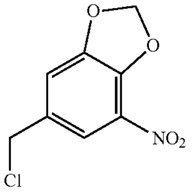 [SMILES: O=[N+]([O-])c1cc(CCl)cc2c1OCO2] | 215.8 $[M + H]^+$ | (7-Nitro-benzo[d][1,3]dioxol-5-yl)methanol |
| Int-60 | 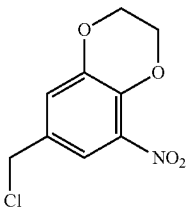 [SMILES: O=[N+]([O-])c1cc(CCl)cc2c1OCCO2] | 230.2 $[M + H]^+$ | (8-Nitro-2,3-dihydrobenzo[b]-[1,4]dioxin-6-yl)methanol |
| Int-61 | 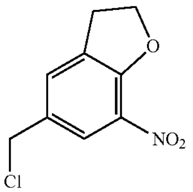 [SMILES: O=[N+]([O-])c1cc(CCl)cc2c1OCC2] | — | (7-Bromo-2,3-dihydro-benzofuran-5-yl)methanol |

Intermediate 62. tert-Butyl (3-fluorophenyl)(4-methoxy-3-nitrobenzyl)-carbamate

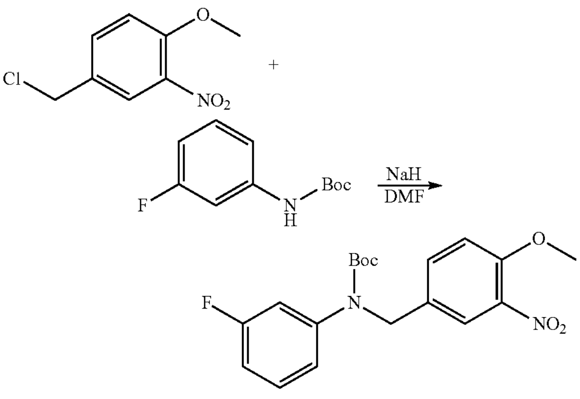

Int-62

To a solution of tert-butyl (3-fluorophenyl)carbamate (1.048 g, 1 eq., 4.960 mmol) in DMF (20 mL) at 0° C. sodium hydride (238.1 mg, 60%, 1.2 eq., 5.952 mmol) was added and the mixture was stirred at RT for 30 min. 4-(Chloromethyl)-1-methoxy-2-nitrobenzene (1.000 g, 1 eq., 4.960 mmol) was added in a single portion and the mixture was stirred at RT for 18 h. The resulting mixture was filtered, and the filtrate was diluted with water (50 mL) and ethyl acetate (50 mL). Layers were separated, the organic phase was washed with brine (4×30 mL), dried over sodium sulfate, filtered and the solvent was removed under reduced pressure, to afford the title compound, which was used in the next step without further purification.

The following intermediates were prepared according to the procedure described for Intermediate 62 from the starting materials indicated in the table.

| No. | Structure | LCMS/ GCMS m/z | Starting materials |
|---|---|---|---|
| Int-63 | 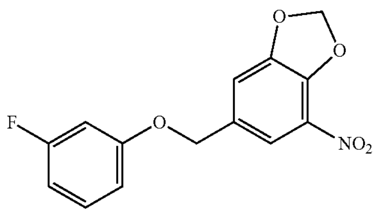 | 293.2 [M + H]$^+$ | 6-(Chloromethyl)-4-nitrobenzo-[d][1,3]dioxole and 3-fluoro-phenol |
| Int-64 | 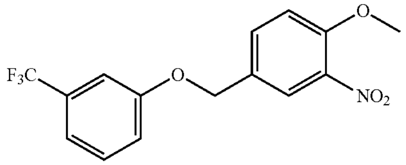 [SMILES: COc1ccc(COc2cccc(C(F)(F)F)c2)cc1[N+](=O)[O-]] | 328.2 [M + H]$^+$ | 4-(Chloromethyl)-1-methoxy-2-nitrobenzene and 3-(Trifluoro-methyl)phenol |
| Int-65 | 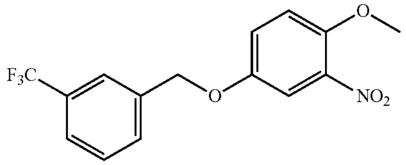 [SMILES: COc1ccc(OCc2cccc(C(F)(F)F)c2)cc1[N+](=O)[O-]] | 328.2 [M + H]$^+$ | 4-Methoxy-3-nitrophenol and 1-(Bromomethyl)-3-(trifluoro-methyl)benzene |
| Int-66 | 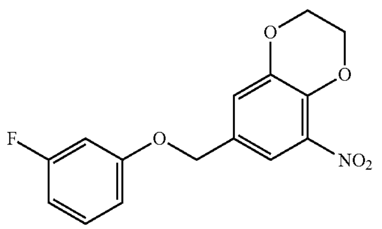 [SMILES: O=[N+]([O-])c1cc(COc2cccc(F)c2)cc2c1OCCO2] | 307.2 [M + H]$^+$ | 7-(Chloromethyl)-5-nitro-2,3-dihydrobenzo[b][1,4]dioxine and 3-Fluorophenol |
| Int-67 | 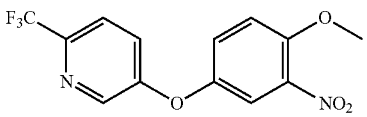 | 315.0 [M + H]$^+$ | 4-Methoxy-3-nitrophenol and 5-Fluoro-2-(trifluoromethyl)-pyridine |
| Int-68 | 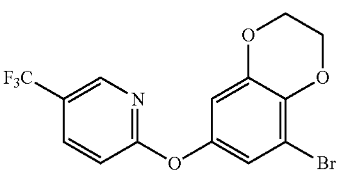 [SMILES: FC(F)(F)c1ccc(Oc2cc(Br)c3c(c2)OCCO3)nc1] | 378.0 [M + H]$^+$ | 8-Bromo-2,3-dihydrobenzo[b]-[1,4]dioxin-6-ol and 2-Fluoro-5-(trifluoromethyl)pyridine |

Intermediate 69. 4-((3,4-Difluorophenoxy)methyl)-1-methoxy-2-nitrobenzene

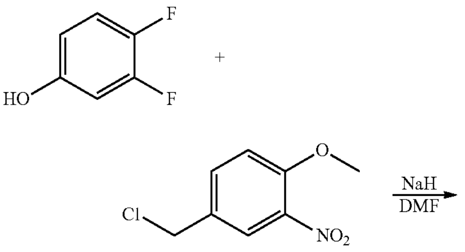

-continued

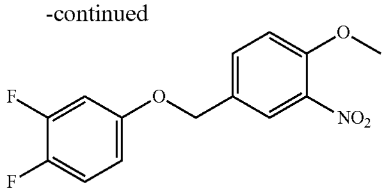

Int-69

3,4-Difluorophenol (2.00 g, 1 eq., 15.4 mmol) was dissolved in DMF (20 mL), sodium hydride (676 mg, 60%, 1.1 eq., 16.9 mmol) was added at RT and the mixture was stirred at this temperature for 30 min 4-(Chloromethyl)-1-methoxy-2-nitrobenzene (3.41 g, 1.1 eq., 16.9 mmol) was added and the mixture was heated at 100° C. for 16 h. The solution was cooled to RT and concentrated. The residue was taken up in ethyl acetate (60 mL). The resulting solution was washed with brine (3×50 mL), dried over sodium sulfate, filtered and evaporated to give the title compound (4.5 g, 14 mmol, 94%, 95% purity). The crude product was used in the next step without further purification.

The following intermediates were prepared according to the procedure described for Intermediate 69 from the starting materials indicated in the table. Where LCMS/GCMS data was not informative, the data is not shown.

Intermediate 75. 4-(2,5-Difluorophenoxy)-1-methoxy-2-nitrobenzene

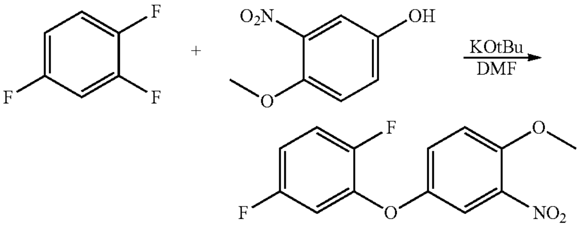

Int-75

1,2,4-Trifluorobenzene (2.4 g, 1 eq., 18 mmol), 4-methoxy-3-nitrophenol (3.1 g, 1 eq., 18 mmol) and potassium 2-methylpropan-2-olate (2.2 g, 1.1 eq., 20 mmol) were dissolved in DMF (50 mL) and the resulting mixture was stirred at 80° C. for 10 h. Then EtOAc (50 mL) was added and the organic layer was washed with brine (5×30 mL), dried and evaporated under reduced pressure to afford title compound, which was used in the next step without further purification. GCMS: m/z 281 $[M]^+$

| No. | Structure | LCMS/ GCMS m/z | Starting materials |
|---|---|---|---|
| Int-70 | 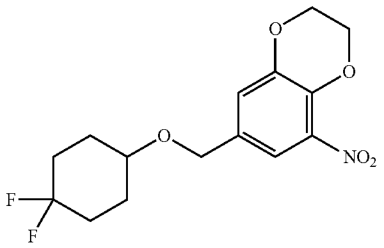 | — | 7-(Chloromethyl)-5-nitro-2,3-dihydrobenzo[b][1,4]dioxine and 4,4-Difluorocyclohexan-1-ol |
| Int-71 | 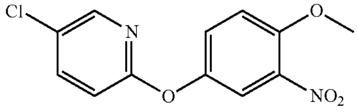 [SMILES: COc1ccc(Oc2ccc(Cl)cn2)cc1[N+](=O)[O-]] | 281.0 $[M + H]^+$ | 4-Methoxy-3-nitrophenol and 5-Chloro-2-fluoropyridine |
| Int-72 | 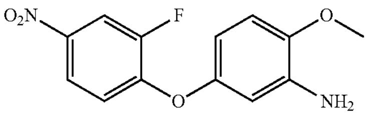 [SMILES: COc1ccc(Oc2ccc([N+](=O)[O-])cc2F)cc1N] | 279.0 $[M + H\ ]^+$ | 5-Hydroxy-2-methoxy-benzenaminium chloride and 1,2-Difluoro-4-nitrobenzene |
| Int-73 | 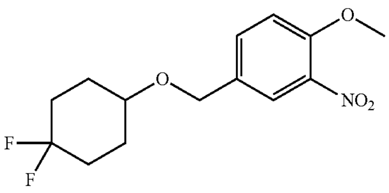 [SMILES: COc1ccc(COC2CCC(F)(F)CC2)cc1[N+](=O)[O-]] | — | 4,4-Difluorocyclohexan-1-ol and 4-(Chloromethyl)-1-methoxy-2-nitrobenzene |
| Int-74 | 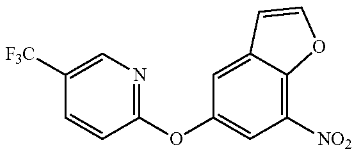 [SMILES: O=[N+]([O-])c1cc(Oc2ccc(C(F)(F)F)cn2)cc2ccoc12] | 325.0 $[M + H]^+$ | 7-Nitrobenzofuran-5-ol and 2-Fluoro-5-(trifluoromethyl)pyridine |

Intermediate 76. (E)-2-Methoxy-5-(2-(tetrahydro-2H-pyran-4-yl)vinyl)aniline

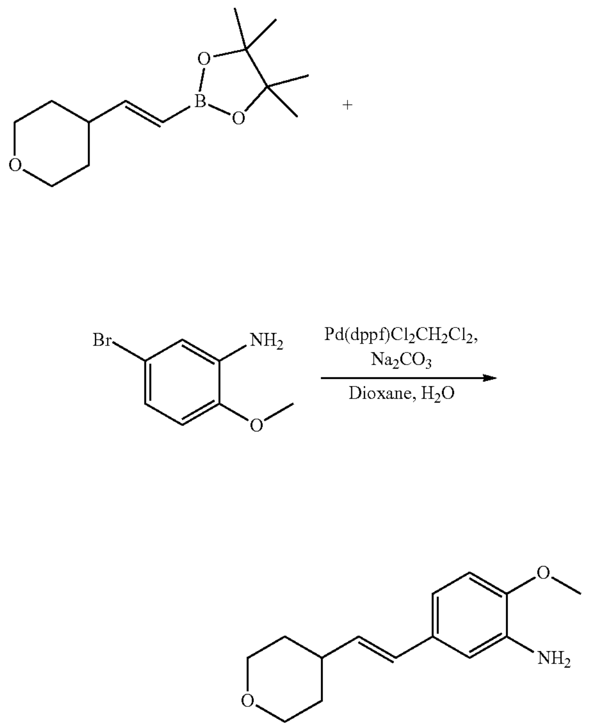

Int-76

5-Bromo-2-methoxyaniline (730 mg, 1 eq., 3.61 mmol), (E)-4,4,5,5-tetramethyl-2-(2-(tetrahydro-2H-pyran-4-yl)vinyl)-1,3,2-dioxaborolane (1.29 g, 1.5 eq., 5.42 mmol), sodium carbonate (383 mg, 1 eq., 3.61 mmol) and $PdCl_2$ (dppf)-$CH_2Cl_2$ adduct (295 mg, 0.1 eq., 361 μmol) were suspended in degassed 1,4-dioxane (12 mL) and water (2.4 mL). The mixture was heated under argon at 90° C. overnight. After cooling to RT the solvent was evaporated in vacuum, the residue was dissolved in ethyl acetate (30 mL), washed with brine (20 mL), dried over sodium sulfate, filtered, concentrated in vacuum and the residue was purified by method A to give the title compound (205 mg, 839 μmol, 23.2%, 95.5% purity). LCMS: m/z 234.2 $[M+H]^+$.

The following intermediates were prepared according to the procedure described for Intermediate 76 from the starting materials indicated in the table.

Intermediate 78. 7-Bromo-5-((3,4-difluorobenzyl)oxy)-2,3-dihydrobenzofuran

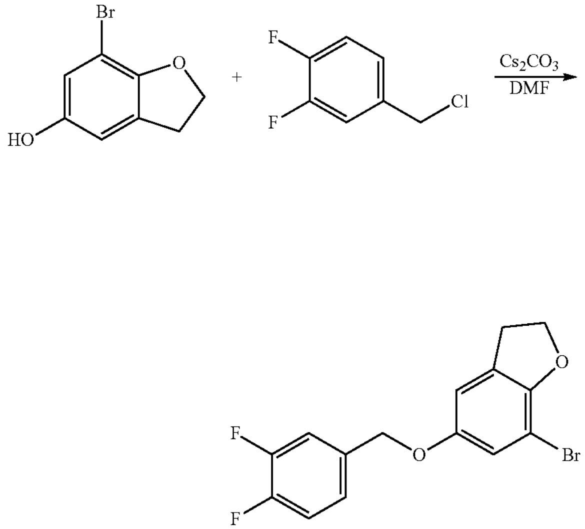

Int-78

7-Bromo-2,3-dihydrobenzofuran-5-ol (0.500 g, 1 eq., 2.33 mmol) was dissolved in N,N-Dimethylformamide (5 mL) and cesium carbonate (1.52 g, 2 eq., 4.65 mmol) was added. The mixture was stirred at RT for 10 min and 4-(chloromethyl)-1,2-difluoro-benzene (378 mg, 1 eq., 2.33 mmol) was added. The mixture was stirred at RT for 12 h. The resulting solution was concentrated under reduced pressure. The residue was taken up in ethyl acetate (20 mL). The obtained solution was washed with brine (20 mL), water (20 mL), dried over sodium sulfate, filtered and evaporated to afford the title compound. The crude product was used in the next step without further purification. $^1H$ NMR (400 MHz, $CDCl_3$) δ: 7.22-7.02 (m, 3H), 6.85 (s, 1H), 6.75 (s, 1H), 4.90 (s, 2H), 4.61 (t, 2H), 3.26 (t, 2H).

The following intermediates were prepared according to the procedure described for Intermediate 78 from the starting materials indicated in the table. Where LCMS/GCMS data was not informative, the data is not shown.

| No. | Structure | LCMS/ GCMS m/z | Starting materials |
|---|---|---|---|
| Int-77 | 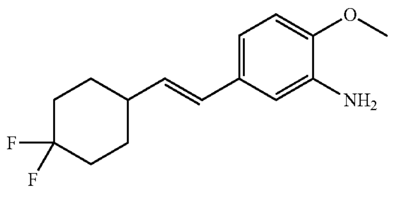 [SMILES: COc1ccc(/C=C/C2CCC(F)(F)CC2)cc1N] | 268.0 $[M + H]^+$ | 5-Bromo-2-methoxyaniline and (E)-2-(2-(4,4-difluorocyclohexyl)-vinyl)-4,4,5,5-tetramethyl-1,3,2-dioxaborolane |

| No. | Structure | LCMS/ GCMS m/z | Starting materials |
|---|---|---|---|
| Int-79 | 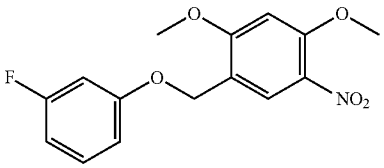 [SMILES: COc1cc(OC)c([N+](=O)[O-])cc1COc1cccc(F)c1] | 308.2 $[M]^+$ | 1-(Chloromethyl)-2,4-dimethoxy-5-nitrobenzene and 3-Fluoro-phenol |
| Int-80 | 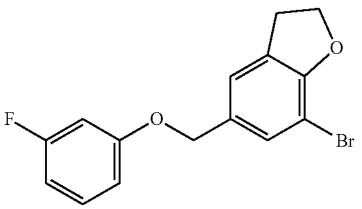 [SMILES: Fc1cccc(OCc2cc(Br)c3c(c2)CCO3)c1] | 322.0 $[M]^+$ | 7-Bromo-5-(chloromethyl)-2,3-dihydrobenzofuran and 3-Fluoro-phenol |
| Int-81 | 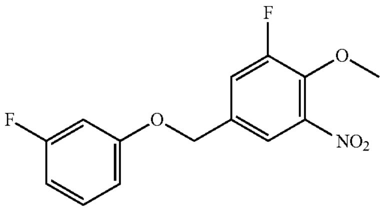 [SMILES: COc1c(F)cc(COc2cccc(F)c2)cc1[N+](=O)[O-]] | 295.04 $[M]^+$ | 5-(Chloromethyl)-1-fluoro-2-methoxy-3-nitrobenzene and 3-Fluorophenol |
| Int-82 | 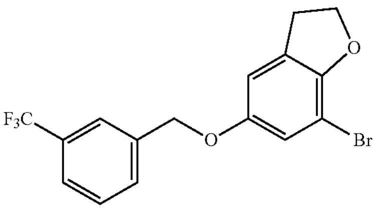 [SMILES: FC(F)(F)c1cccc(COc2cc(Br)c3c(c2)CCO3)c1] | 371.6 $[M-H]^-$ | 7-Bromo-2,3-dihydrobenzofuran-5-ol and 1-(Chloromethyl)-3-(tri-fluromethyl)benzene |
| Int-83 | 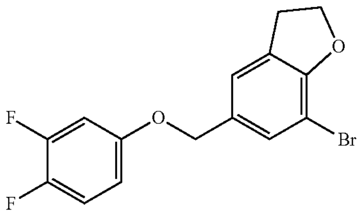 [SMILES: Fc1ccc(OCc2cc(Br)c3c(c2)CCO3)cc1F] | — | 7-Bromo-5-(chloromethyl)-2,3-di-hydrobenzofuran and 3,4-Di-fluorophenol |

Intermediate 84. 1-Fluoro-2-((3-fluorophenoxy) methyl)-5-methoxy-4-nitrobenzene

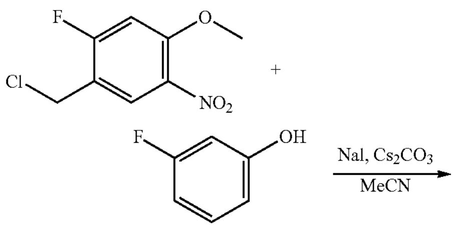

-continued

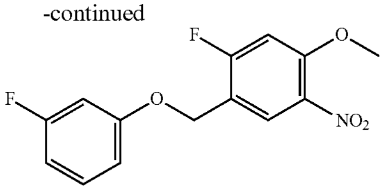

Int-84

1-(Chloromethyl)-2-fluoro-4-methoxy-5-nitrobenzene (0.306 g, 1 eq., 1.39 mmol) was dissolved in acetonitrile (3 mL), cesium carbonate (908 mg, 2 eq., 2.79 mmol) and sodium iodide (209 mg, 1 eq., 1.39 mmol) were added. The mixture was stirred for 10 min and 3-fluorophenol (141 mg, 114 μL, 0.9 eq., 1.25 mmol) was added. The mixture was stirred at RT for 10 h. The resulting solution was filtered and concentrated to give the title compound (0.362 g, 0.61 mmol, 44%, 50% purity), which was used in the next step without further purification. LCMS: m/z 297.2 $[M+H]^+$ Intermediate 85. 1-Fluoro-5-methoxy-4-nitro-2-(3-(trifluoromethyl)phenoxy)-benzene

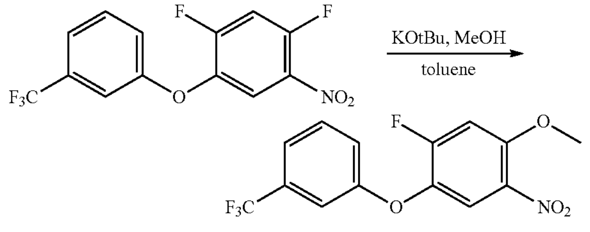

Int-85

1,5-Difluoro-2-nitro-4-(3-(trifluoromethyl)phenoxy)benzene (150 mg, 1 eq., 470 μmol) was dissolved in toluene (2 mL). The solution was cooled to 0° C., then methanol (15.1 mg, 19.0 μL, 1 eq., 470 μmol) was added at 0° C. To the obtained solution potassium tert-butoxide (52.7 mg, 1 eq., 470 μmol) was added at 0° C. The mixture was stirred at 0° C. for 10 minutes, then temperature was raised to RT followed by stirring for 12 h. The reaction mixture was quenched with water (15 mL) followed by stirring for 15 minutes. Toluene (10 mL) was added to the mixture. The layers were separated, and the aqueous layer was extracted with toluene (2×10 mL). Combined organic layers were washed with water (20 mL), brine (20 mL) and dried over sodium sulfate. The solvent was evaporated under reduced pressure to afford the title compound which was used in next step without further purification. GCMS: m/z 331.0 $[M]^+$.

Intermediate 86. 7-Bromo-5-((3-fluorophenoxy)methyl)benzofuran

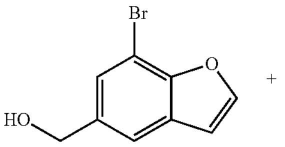

+

-continued

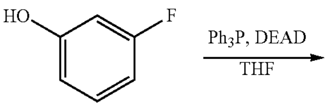

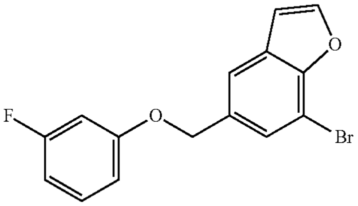

Int-86

A solution of (7-bromobenzofuran-5-yl)methanol (3.110 g, 1 eq., 13.70 mmol) and triphenylphosphine (4.311 g, 1.2 eq., 16.44 mmol) in THF (100 mL) was cooled to 0° C. under inert atmosphere. Diethyl (E)-diazene-1,2-dicarboxylate (2.863 g, 2.58 mL, 1.2 eq., 16.44 mmol) was slowly added and the mixture was stirred for 30 min followed by addition of 3-fluorophenol (1.612 g, 1.302 mL, 1.05 eq., 14.38 mmol). The ice-bath was removed and the mixture was stirred at RT for 17 h. The THF was evaporated, and the mixture was dissolved in MTBE (10 mL), washed with NaOH (3 mL, 10%) and water (3 mL), dried over $Na_2SO_4$ and concentrated in vacuo. The residue was purified by flash-chromatography (MTBE/hexane, flow rate 30 mL/min) to give the title compound (1.42 g, 4.2 mmol, 31%, 95% purity). $^1H$ NMR (400 MHz, DMSO-$d_6$) δ: 8.03 (s, 1H), 7.72 (s, 1H), 7.59 (s, 1H), 7.33-7.23 (m, 1H), 7.03 (d, 1H), 6.83 (d, 2H), 6.75-6.65 (m, 1H), 5.17 (s, 2H).

The following intermediates were prepared according to the procedure described for Intermediate 86 from the starting materials indicated in the table. Where LCMS/GCMS data was not informative, the data is not shown.

| No. | Structure | LCMS/ GCMS m/z | Starting materials |
|---|---|---|---|
| Int-87 | 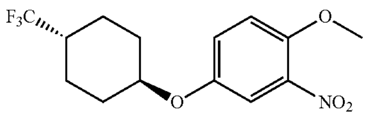 [SMILES: COc1ccc(O[C@H]2CC[C@H](C(F)(F)F)CC2)cc1[N+](=O)[O-]] | 320.0 $[M + H]^+$ | 4-Methoxy-3-nitrophenol and (trans)-4-(Trifluoromethyl)cyclohexan-1-ol |
| Int-88 | 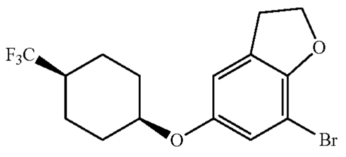 [SMILES: FC(F)(F)[C@H]1CC[C@@H](Oc2cc(Br)c3c(c2)CCO3)CC1] | — | 7-Bromo-2,3-dihydrobenzofuran-5-ol and (cis)-4-(Trifluoromethyl) cyclohexan-1-ol |

-continued

| No. | Structure | LCMS/ GCMS m/z | Starting materials |
|---|---|---|---|
| Int-89 | 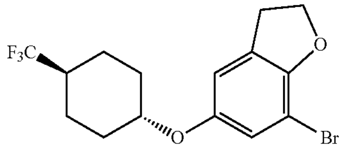 [SMILES: FC(F)(F)[C@H]1CC[C@H](Oc2cc(Br)c3c(c2)CCO3)CC1] | 364 [M]+ | 7-Bromo-2,3-dihydrobenzofuran-5-ol and (trans)-4-(Trifluoromethyl)cyclohexan-1-ol |
| In-90 | 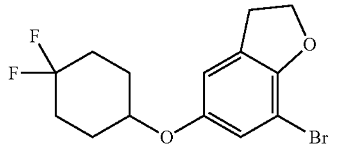 [SMILES: FC1(F)CCC(Oc2cc(Br)c3c(c2)CCO3)CC1] | 333.8 [M + H]+ | 7-Bromo-2,3-dihydrobenzofuran-5-ol and 4,4-Difluorocyclohexan-ol |
| Int-91 | 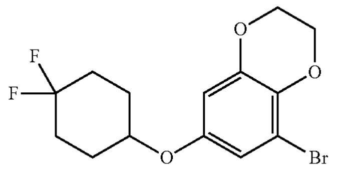 [SMILES: FC1(F)CCC(Oc2cc(Br)c3c(c2)OCCO3)CC1] | 348 [M]+ | 8-Bromo-2,3-dihydrobenzo[b]-[1,4]dioxin-6-ol and 4,4-Difluorocyclohexan-1-ol |
| Int-92 | 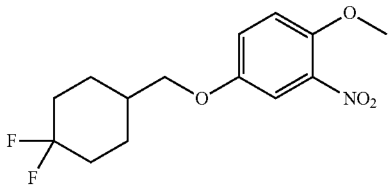 | 302.0 [M + H]+ | (4,4-Difluorocyclohexyl)methanol and 4-Methoxy-3-nitrophenol |
| Int-93 | 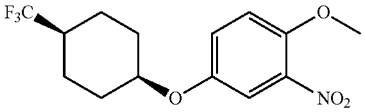 [SMILES: COc1ccc(O[C@H]2CC[C@@H](C(F)(F)F)CC2)cc1[N+](=O)[O-]] | — | (trans)-4-(Trifluoromethyl)cyclohexan-1-ol and 4-Methoxy-3-nitrophenol |
| Int-94 | 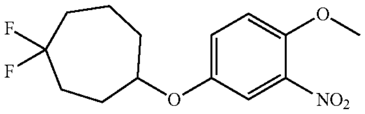 | — | 4-Methoxy-3-nitrophenol and 4,4-Difluorocycloheptan-1-ol |
| Int-95 | 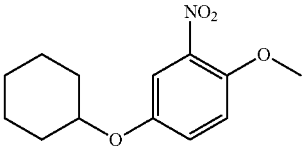 [SMILES: COc1ccc(OC2CCCCC2)cc1[N+](=O)[O-]] | 252.1 [M + H]+ | 4-Methoxy-3-nitrophenol and Cyclohexanol |
| Int-96 | 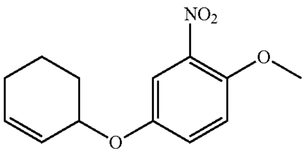 [SMILES: COc1ccc(OC2C=CCCC2)cc1[N+](=O)[O-]] | 250.1 [M + H]+ | 4-Methoxy-3-nitrophenol and Cyclohex-2-en-1-ol |

Intermediate 97. 2-4-Methoxy-3-nitrophenoxy)bicyclo[2.2.1]heptane

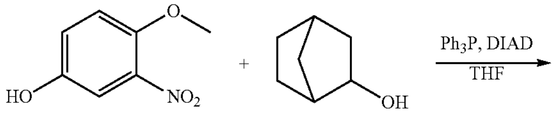

-continued

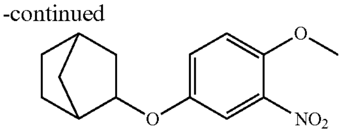

Int-97

4-Methoxy-3-nitrophenol (5.00 g, 1 eq., 29.6 mmol), triphenylphosphine (15.5 g, 2 eq., 59.1 mmol) and bicyclo [2.2.1]heptan-2-ol (3.32 g, 1 eq., 29.6 mmol) were dissolved in THF (50 mL). The mixture was cooled to 4° C. and diisopropyl diazene-1,2-dicarboxylate (12.0 g, 11.5 mL, 2 eq., 59.1 mmol) was added. The mixture was stirred at RT for 16 h, then concentrated and purified by flash-chromatography (MTBE/hexane, flow rate 30 mL/min) to afford the title compound.

The following intermediate was prepared according to the procedure described for Intermediate 97 from the starting materials indicated in the table. Where LCMS/GCMS data was not informative, the data is not shown.

| No. | Structure | LCMS/ GCMS m/z | Starting materials |
|---|---|---|---|
| Int-98 | 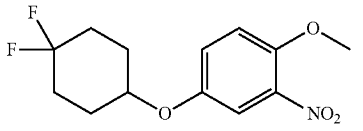 | — | 4-Methoxy-3-nitrophenol and 4,4-Difluorocyclohexan-1-ol |

Intermediate 99._4-(2,4-Difluorophenoxy)-1-methoxy-2-nitrobenzene

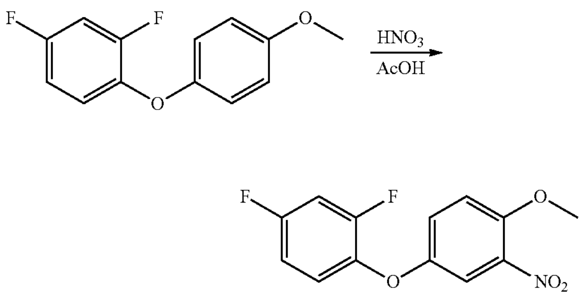

Int-99

2,4-Difluoro-1-(4-methoxyphenoxy)benzene (0.180 g, 1 eq., 762 µmol) was dissolved in acetic acid (1 mL) and the solution was cooled to 0° C. Then nitric acid (144 mg, 102 µL, 3 eq., 2.29 mmol) was added to the mixture dropwise and the resulting solution was stirred at RT for 10 h. Then the mixture was poured into ice-cooled saturated sodium carbonate solution (5 mL) and EtOAc (5 mL) was added. The organic layer was separated, dried over sodium sulfate and concentrated in vacuum to afford the title compound, which was used in the next step without further purification. GCMS: m/z 281 $[M]^+$ Intermediate 100. 8-Nitrochroman-6-ol

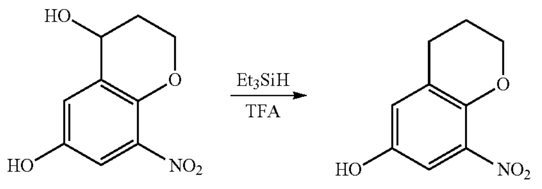

Int-100

8-Nitrochromane-4,6-diol (135 mg, 1 eq., 639 µmol) was dissolved in TFA (2 mL) and triethylsilane (372 mg, 0.511 mL, 5.00 eq., 3.20 mmol) was added. The mixture was stirred at 23° C. for 16 h, than concentrated, mixed with hexane (10 mL) and filtered. Obtained precipitate was dried under reduced pressure to give the title compound (100 mg, 0.49 mmol). The crude product was used in the next step without further purification. LCMS: m/z 196.0 $[M+H]^+$ Intermediate 101 and 102. 4-Bromo-6-methoxy-1-methyl-1H-benzo[d]-imidazole and 7-Bromo-5-methoxy-1-methyl-1H-benzo[d]imidazole

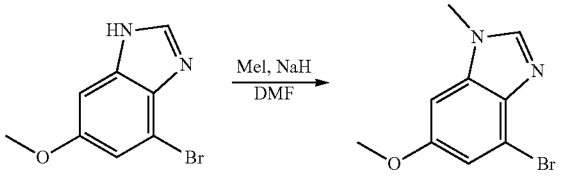

Int-101

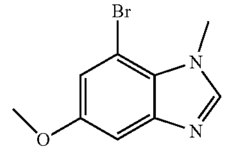

Int-102

7-Bromo-5-methoxy-1H-benzo[d]imidazole (0.3 g, 1 eq., 1.32 mmol) was dissolved in DMF (5 mL). The mixture was cooled to 5° C. and sodium hydride (58.1 mg, 60 w-%, 1.1 eq., 1.45 mmol) was added in portions. The mixture was stirred at 5° C. for 30 min and methyl iodide (206 mg, 90.9 µL, 1.1 eq., 1.45 mmol) was added dropwise at the same temperature. The resulting mixture was heated to 20° C. and stirred for 12 h, poured into ice-cooled water (10 mL) and extracted with EtOAc (2x20 mL). The combined organic layers were washed with brine (4x5 mL), dried and concentrated to give a mixture of crude products, which were separated by HPLC (Method A) to give two regioisomers 7-bromo-5-methoxy-1-methyl-1H-benzo[d]imidazole (0.0467 g, 194 µmol) and 4-bromo-6-methoxy-1-methyl-1H-benzo[d]imidazole (0.0868 g, 360 µmol). LCMS: m/z 243.0 $[M+H]^+$.

Intermediate 103. 4-Bromo-1-methyl-1H-benzo[d]imidazol-6-ol

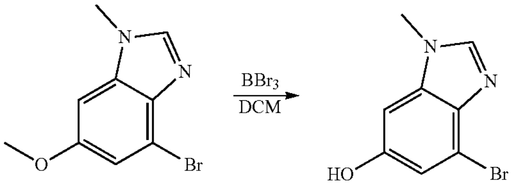

Int-103

4-Bromo-6-methoxy-1-methyl-1H-benzo[d]imidazole (80 mg, 1 eq., 0.33 mmol) was dissolved in DCM (2 mL) and tribromoborane (0.83 g, 0.32 mL, 10 eq., 3.3 mmol) was added to the mixture dropwise at 4° C. The resulting mixture was stirred at 28° C. for 18 h and the MeOH (5 mL) was added to the mixture at 4° C. dropwise. The mixture was concentrated under reduced pressure and the residue was poured into saturated aqueous sodium carbonate solution (10 mL) and extracted with ethyl acetate (3×50 mL). The combined organic layer was dried over sodium sulfate and concentrated to give crude 4-bromo-1-methyl-1H-benzo[d]imidazol-6-ol (80 mg, 0.26 mmol) which was used in the next step without further purification. LCMS: m/z 227.0 $[M+H]^+$ Intermediate 104. 2-(5-Bromo-2-fluoro-4-methoxyphenoxy)-5-(trifluoro-methyl)pyridine

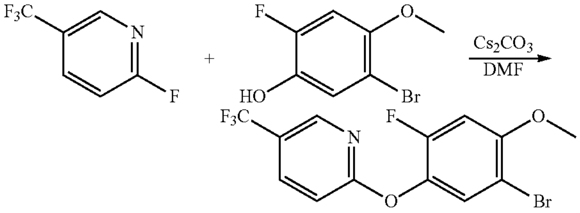

Int-104

The mixture of 5-bromo-2-fluoro-4-methoxyphenol (4.75 g, 1 eq., 21.49 mmol), 2-fluoro-5-(trifluoromethyl)pyridine (3.548 g, 1 eq., 21.49 mmol) and cesium carbonate (14 g, 2 eq., 42.98 mmol) in DMF (100 mL) was stirred at 60° C. for 18 h. Water (100 mL) was added to the residue and the resulted mixture was extracted with ethyl acetate (100×20 mL). Organic layers were combined, washed with brine (4×100 mL), dried over sodium sulfate, filtered and evaporated to give crude title compound (6.35 g, 14.8 mmol) which was used in the next step without further purification. $^1H$ NMR (400 MHz, Chloroform-d) δ: 8.38 (s, 1H), 7.91 (dd, 1H), 7.42 (d, 1H), 7.07 (d, 1H), 6.78 (d, 1H), 3.88 (s, 3H).

Intermediate 105. Methyl 4-(3,4-difluorophenoxy)-2-nitrobenzoate

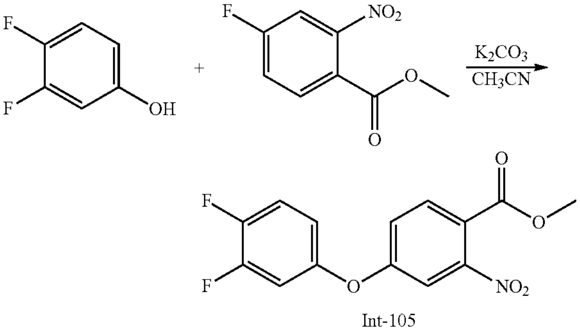

Int-105

Methyl 4-fluoro-2-nitrobenzoate (5.0 g, 1 eq., 25.11 mmol), 3,4-difluorophenol (3.593 g, 1.1 eq., 27.62 mmol) and potassium carbonate (6.940 g, 2 eq., 50.22 mmol) were mixed in acetonitrile (100 mL) followed by heating at reflux temperature for 14 h. After cooling to RT, the mixture was concentrated under reduced pressure, extracted with EtOAc (100 mL) and washed with water (20 mL), $K_2CO_3$ solution (20 mL, 15% in water) and brine (20 mL). The organic phase was dried over $Na_2SO_4$ and concentrated in vacuum to give the title compound (6.68 g, 19 mmol, 77%, 90% purity). $^1H$ NMR (500 MHz, DMSO-d6) δ: 7.89 (d, 1H), 7.63 (d, 1H), 7.59-7.50 (m, 1H), 7.47 (dq, 1H), 7.33 (dd, 1H), 7.12-7.03 (m, 1H), 3.81 (s, 3H).

The following intermediates were prepared according to the procedure described for Intermediate 105 from the starting materials indicated in the table. Where LCMS/GCMS data was not informative, the data is not shown.

| No. | Structure | LCMS/ GCMS m/z | Starting materials |
|---|---|---|---|
| Int-106 | 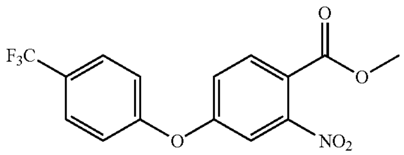 [SMILES: COC(=O)c1ccc(Oc2ccc(C(F)(F)F)cc2)cc1[N+](=O)[O-]] | 341.1 $[M]^+$ | Methyl 4-fluoro-2-nitrobenzoate and 4-(Trifluoromethyl)phenol |
| Int-107 | 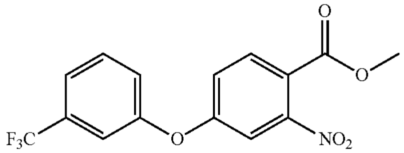 [SMILES: COC(=O)c1ccc(Oc2cccc(C(F)(F)F)c2)cc1[N+](=O)[O-]] | 341.1 $[M]^+$ | Methyl 4-fluoro-2-nitrobenzoate and 3-(Trifluoromethyl)phenol |

-continued

| No. | Structure | LCMS/ GCMS m/z | Starting materials |
|---|---|---|---|
| Int-108 | 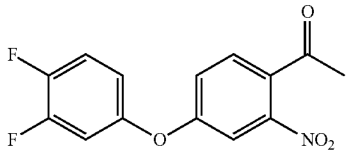 [SMILES: CC(=O)c1ccc(Oc2ccc(F)c(F)c2)cc1[N+](=O)[O-]] | 294.2 [M + H]$^+$ | 1-(4-Fluoro-2-nitrophenyl)ethan-1-one and 3,4-Difluorophenol |
| Int-109 | 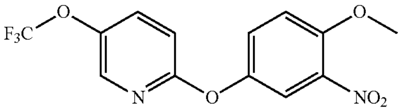 [SMILES: COc1ccc(Oc2ccc(OC(F)(F)F)cn2)cc1[N+](=O)[O-]] | 331.0 [M + H]$^+$ | 2-Fluoro-5-(trifluoromethoxy)-pyridine and 4-Methoxy-3-nitro-phenol |
| Int-110 | 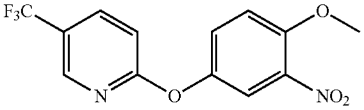 [SMILES: COc1ccc(Oc2ccc(C(F)(F)F)cn2)cc1[N+](=O)[O-]] | 299.0 [M − H]$^-$ | 4-Methoxy-3-nitrophenol and 2-Fluoro-5-(trifluoromethyl)-pyridine |
| Int-111 | 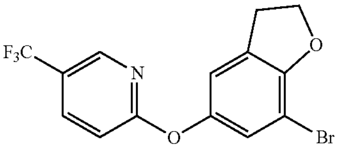 [SMILES: FC(F)(F)c1ccc(Oc2cc(Br)c3c(c2)CCO3)nc1] | — | 2-Chloro-5-(trifluoromethyl)-pyridine and 7-Bromo-2,3-dihydrobenzofuran-5-ol |
| Int-112 | 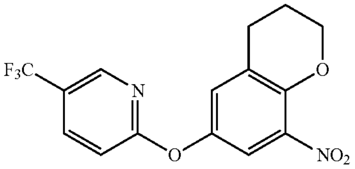 [SMILES: O=[N+]([O-])c1cc(Oc2ccc(C(F)(F)F)cn2)cc2c1OCCC2] | 341.0 [M]$^+$ | 8-Nitrochroman-6-ol and 2-Fluoro-5-(trifluoromethyl)-pyridine |
| Int-113 | 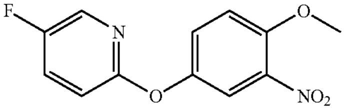 [SMILES: COc1ccc(Oc2ccc(F)cn2)cc1[N+](=O)[O-]] | 265.0 [M]$^+$ | 4-Methoxy-3-nitrophenol and 2,5-Difluoropyridine |
| Int-114 | 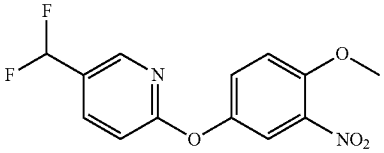 | 297.0 [M + H]$^+$ | 4-Methoxy-3-nitrophenol and 5-(Difluoromethyl)-2-fluoropyridine |
| Int-115 | 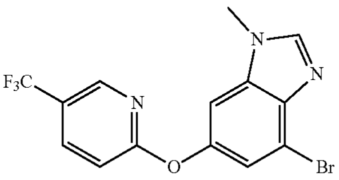 [SMILES: Cn1cnc2c(Br)cc(Oc3ccc(C(F)(F)F)cn3)cc21] | 371.8 [M + H]$^+$ | 4-Bromo-1-methyl-1H-benzo[d]-imidazol-6-ol and 2-Fluoro-5-(trifluoromethyl)pyridine |

Intermediate 116. 4-(3,4-Difluorophenoxy)-2-nitrobenzohydrazide

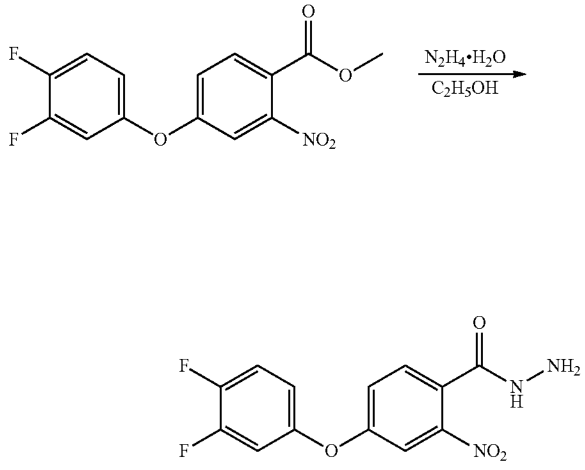

Int-116

To a solution of the methyl 4-(3,4-difluorophenoxy)-2-nitrobenzoate (2.000 g, 1 eq., 6.468 mmol) in ethanol (20 mL) was added hydrazine hydrate (2.266 g, 7 eq., 45.28 mmol). The mixture was heated under reflux overnight. Then the solvent was evaporated under reduced pressure, and water (20 mL) was added to the residue. The obtained solid was filtered, washed with water, hexane and dried in vacuum to give the title compound (1.900 g, 5.5 mmol, 85%, 90% purity). $^1$H NMR (500 MHz, DMSO-d6) δ: 9.77 (s, 1H), 7.59 (d, 1H), 7.59-7.49 (m, 2H), 7.47-7.42 (m, 1H), 7.33 (dd, 1H), 7.07-6.99 (m, 1H), 4.32 (s, 1H).

The following intermediates were prepared according to the procedure described for Intermediate 116 from the starting materials indicated in the table.

Intermediate 119. 2-(4-(3,4-Difluorophenoxy)-2-nitrophenyl)-1,3,4-oxadiazole

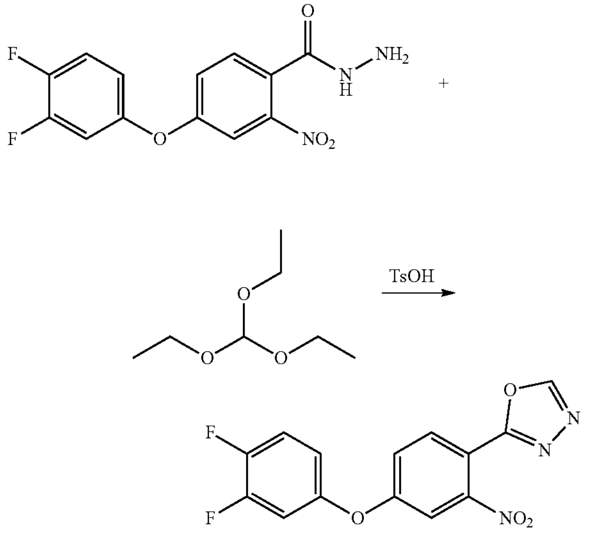

Int-119

4-(3,4-Difluorophenoxy)-2-nitrobenzohydrazide (1.000 g, 1 eq., 3.234 mmol), 4-methylbenzenesulfonic acid (111.4 mg, 0.2 eq., 646.8 μmol) and triethoxymethane (20 mL) were heated at reflux temperature for 14 h. The mixture was then concentrated in vacuum to give the title compound (1.00 g, 2.2 mmol, 69%, 71% purity) LCMS: m/z 320.0 [M+H]$^+$.

The following intermediates were prepared according to the procedure described for Intermediate 119 from the starting materials indicated in the table.

| No. | Structure | LCMS/ GCMS m/z | Starting materials |
|---|---|---|---|
| Int-117 | 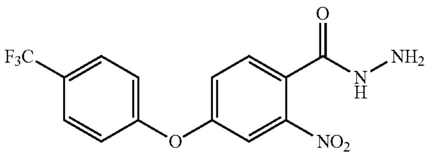 [SMILES: NNC(=O)c1ccc(Oc2ccc(C(F)(F)F)cc2)cc1[N+](=O)[O-]] | 342.2 [M + H]$^+$ | Methyl 2-nitro-4-(4-(trifluoromethyl)phenoxy)benzoate and Hydrazine hydrate |
| Int-118 | 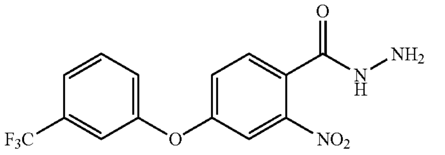 [SMILES: NNC(=O)c1ccc(Oc2cccc(C(F)(F)F)c2)cc1[N+](=O)[O-]] | 342.4 [M + H]$^+$ | Methyl 2-nitro-4-(3-(trifluoromethyl)phenoxy)benzoate and Hydrazine hydrate |

| No. | Structure | LCMS/ GCMS m/z | Starting materials |
|---|---|---|---|
| Int-120 | 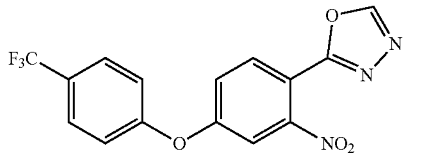 | 352.0 [M + H]$^+$ | 2-Nitro-4-(4-(trifluoromethyl)-phenoxy)benzohydrazide and Triethoxymethane |
| Int-121 | 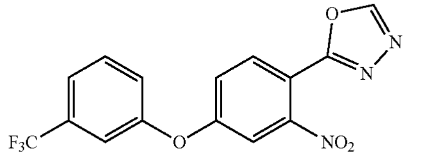 | 352.2 [M + H]$^+$ | 2-Nitro-4-(3-(trifluoromethyl)-phenoxy)benzohydrazide and Triethoxymethane |

Intermediate 122. (E)-1-(4-(3,4-Difluorophenoxy)-2-nitrophenyl)-3-(dimethyl-amino)prop-2-en-1-one

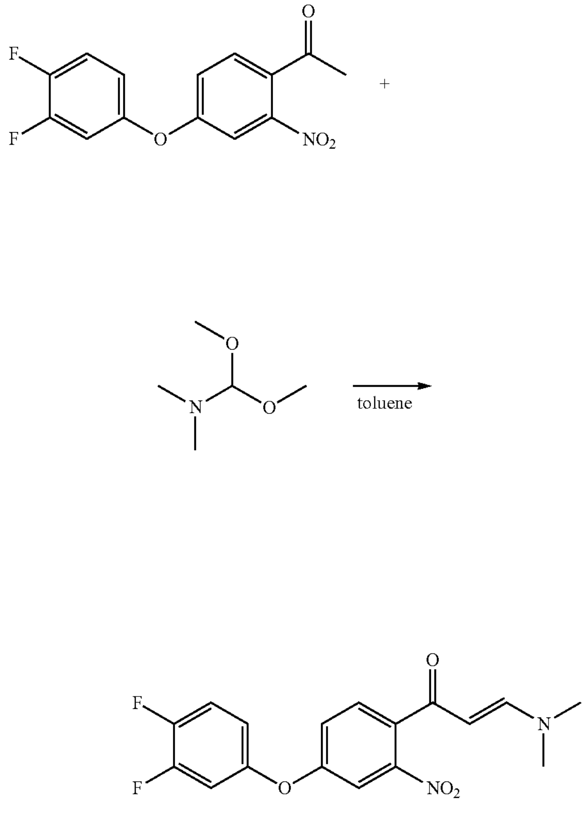

Int-122

A solution of 1-(4-(3,4-difluorophenoxy)-2-nitrophenyl) ethan-1-one (0.300 g, 1 eq., 1.02 mmol), DMF-DMA (244 mg, 272 μL, 2 Eq, 2.05 mmol) and toluene (3 mL) was stirred and heated at reflux temperature for 16 h followed by cooling to RT. The resulting solid was filtered, washed with toluene, hexane and dried in vacuum to afford the title compound (0.246 g, 706 μmol, 69.0%) as a yellow solid. LCMS: m/z 349.2 [M+H]$^+$.

Intermediate 123. 5-(4-(3,4-Difluorophenoxy)-2-nitrophenyl)-1-methyl-1H-pyrazole

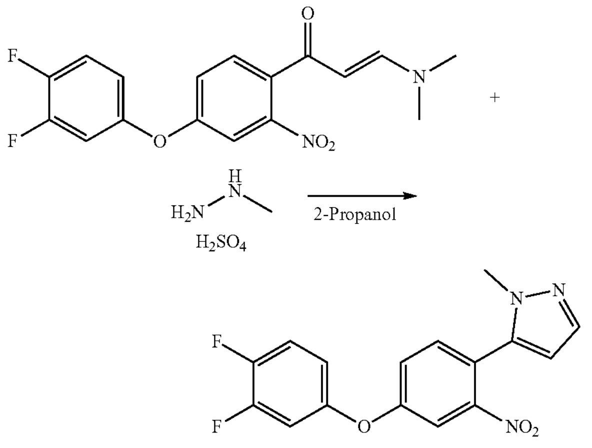

Int-123

(E)-1-(4-(3,4-Difluorophenoxy)-2-nitrophenyl)-3-(dimethylamino)prop-2-en-1-one (0.246 g, 1 eq., 706 μmol) and methylhydrazine sulfate (112 mg, 1.1 eq., 777 μmol) were mixed in 2-propanol (4 mL) and heated at reflux temperature for 18 h. The mixture was cooled to RT, concentrated in vacuum and purified by method C to give the title compound (0.109 g, 329 μmol, 46.6%, 100% purity). LCMS: m/z 332.0 [M+H]$^+$.

Intermediate 124. 7-Nitro-5-((5-(trifluoromethyl) pyridin-2-yl)oxy)-1H-indazole

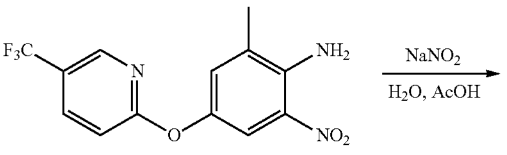

-continued

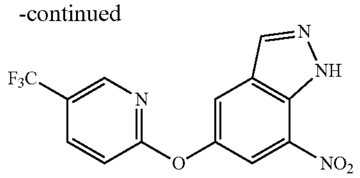

Int-124

To a stirred solution of 2-methyl-6-nitro-4-((5-(trifluoromethyl)pyridin-2-yl)-oxy)aniline (1.524 g, 1 eq., 4.865 mmol) in acetic acid (70.5 mL), a solution of sodium nitrite (369.2 mg, 1.1 eq., 5.352 mmol) in water (2.4 mL) was added and the mixture was stirred for 1 h. After completion of the reaction, acetic acid was distilled off and the obtained residue was mixed with ice water (200 mL) and extracted with MTBE (3×30 mL). The combined organic phase was washed with water (2×10 mL), dried under sodium sulfate and concentrated under reduced pressure to yield the title compound (1.5 g, 3.9 mmol, 80%, 84% purity). LCMS: m/z 325.0 $[M+H]^+$.

The following intermediate was prepared according to the procedure described for Intermediate 124 from the starting material indicated in the table.

| No. | Structure | LCMS/ GCMS m/z | Starting materials |
|---|---|---|---|
| Int-125 | 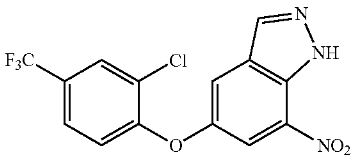 [SMILES: O=[N+]([O-])c1cc(Oc2ccc(C(F)(F)F)cc2Cl)cc2cn[nH]c12] | 358.0 $[M + H]^+$ | 4-(2-Chloro-4-(trifluoromethyl)phenoxy)-2-methyl-6-nitroaniline |

Intermediate 126. 5-(4-(Trifluoromethyl)phenoxy)-1H-indazol-7-amine

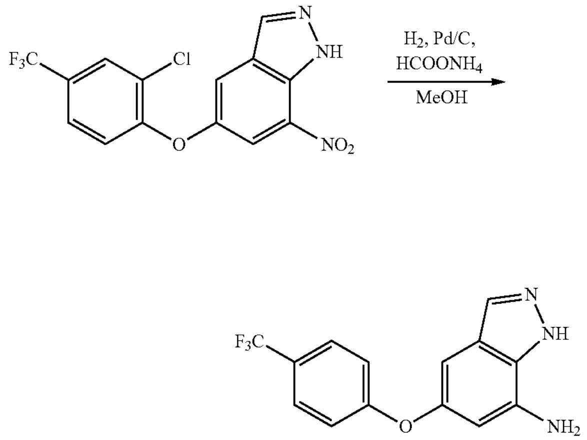

Int-126

5-(2-Chloro-4-(trifluoromethyl)phenoxy)-7-nitro-1H-indazole (0.093 g, 1 eq., 0.26 mmol) was dissolved in methanol (15 mL). Formic acid, ammonia salt (0.33 g, 20 eq., 5.2 mmol) and palladium (0.22 g, 10 w-%, 0.8 eq., 0.21 mmol) were added. The resulting mixture was stirred at 65° C. for 16 h, cooled to RT and filtered. The filtrate was concentrated under reduced pressure and treated with EtOAc (10 mL). The precipitate was filtered and dried under reduced pressure to give the title compound (0.044 g, 0.15 mmol, 58%, 100% purity) which was used in the next step without further purification. $^1H$ NMR (500 MHz, DMSO-d6) δ: 7.87 (s, 1H), 7.65 (d, 2H), 7.06 (d, 2H), 6.62 (s, 1H), 6.18 (s, 1H), 5.69 (s, 2H).

Intermediate 127. 1-Methyl-7-nitro-5-((5-(trifluoromethyl)pyridin-2-yl)oxy)-1H-indazole

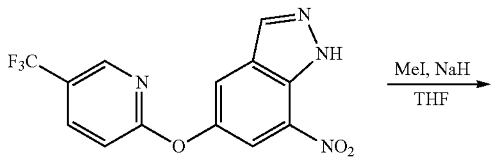

-continued

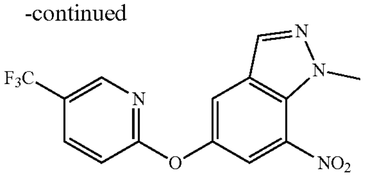

Int-127

To a solution of 7-nitro-5-((5-(trifluoromethyl)pyridin-2-yl)oxy)-1H-indazole (0.1 g, 1 eq., 308 μmol) in THF (4 mL) cooled to 0° C. sodium hydride (14.8 mg, 60 w-%, 1.2 eq., 370 μmol) was added. After stirring for 1 h at 23° C., methyl iodide (46.0 mg, 20.3 μL, 1.05 eq., 324 μmol) was added dropwise at 0° C. The mixture was stirred for 16 h at 23° C. Water (1 mL) was added and the resulting mixture was concentrated under reduced pressure. The crude material was dissolved in EtOAc (10 mL), washed with water and brine, dried over $MgSO_s$ and the solvent removed under reduced pressure to give the title compound (0.129 g, 310 μmol, 100%, 81.2% purity), which was used in the next step without further purification. LCMS: m/z 339.2 $[M+H]^+$.

Intermediate 128. 1-(3,4-Difluorophenoxy)-4-methoxy-2-methyl-3-nitrobenzene

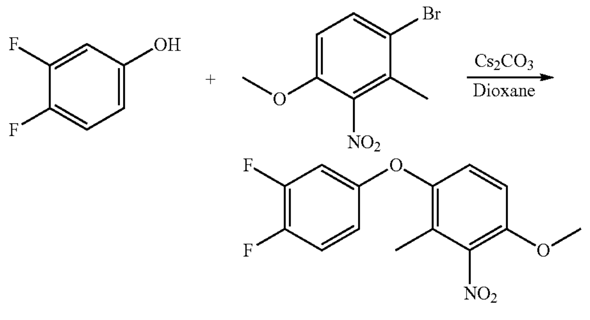

Int-128

A mixture of 1-Bromo-4-methoxy-2-methyl-3-nitrobenzene (0.384 g, 1.5 mmol), 3,4-difluorophenol (0.13 g, 1.0 mmol), $Cs_2CO_3$ (0.652 g, 2.0 mmol), CuI (0.057 g, 0.3 mmol) and N,N-dimethylglycine (0.031 g, 0.3 mmol) in dioxane (5 ml) was heated at 130° C. for 24 hours. The mixture was evaporated and the residue was purified by normal phase chromatography to yield 0.175 g of the title compound. $^1H$ NMR (400 MHz, DMSO-$d_6$) δ: 2.07 (3H, s), 3.87 (3H, s), 6.71-6.79 (1H, m), 7.12-7.19 (1H, m), 7.19-7.27 (2H, m), 7.38-7.49 (1H, m).

Intermediate 129. 2-Methoxy-5-(4-(trifluoromethyl)phenoxy)aniline

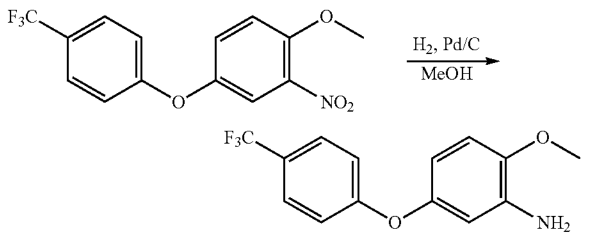

Int-129

1-Methoxy-2-nitro-4-(4-(trifluoromethyl)phenoxy)benzene (558 mg, 1 eq., 1.78 mmol) was dissolved in methanol (20 mL) and treated with Pd/C (37.9 mg, 0.2 eq., 356 μmol). The resulting mixture was hydrogenated at 1 atm pressure at RT overnight. The catalyst was filtered off and the solvent was evaporated under reduced pressure to afford the crude title product which was used in the next step without further purification. LCMS: m/z 284.2 $[M+H]^+$.

The following intermediates were prepared according to the procedure described for Intermediate 129 from the starting material indicated in the table.

| No. | Structure | LCMS/ GCMS m/z | Starting materials |
|---|---|---|---|
| Int-130 | 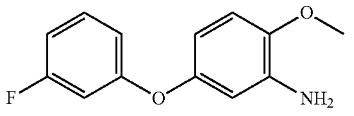 | 234.2 $[M + H]^+$ | 4-(3-Fluorophenoxy)-1-methoxy-2-nitrobenzene |
| Int-131 | 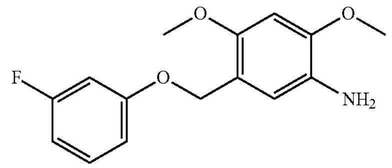 [SMILES: COc1cc(OC)c(COc2cccc(F)c2)cc1N] | 279.2 $[M + H]^+$ | 1-((3-Fluorophenoxy)methyl)-2,4-dimethoxy-5-nitrobenzene |
| Int-132 | 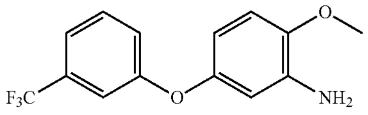 | 284.2 $[M + H]^+$ | 1-Methoxy-2-nitro-4-(3-(trifluoromethyl)phenoxy)benzene |
| Int-133 | 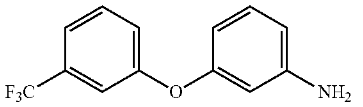 | 254.2 $[M + H]^+$ | 1-Nitro-3-(3-(trifluoromethyl)-phenoxy)benzene |
| Int-134 | 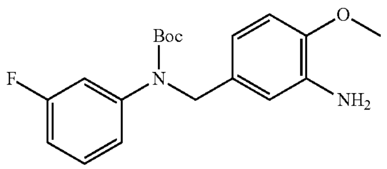 [SMILES: COc1ccc(CN(C(=O)OC(C)(C)C)c2cccc(F)c2)cc1N] | 347.2 $[M + H]^+$ | tert-Butyl (3-fluorophenyl)(4-methoxy-3-nitrobenzyl)-carbamate |

-continued

| No. | Structure | LCMS/ GCMS m/z | Starting materials |
|---|---|---|---|
| Int-135 | 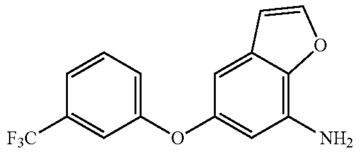 | 294.0 [M + H]+ | 7-Nitro-5-(3-(trifluoromethyl)-phenoxy)benzofuran |
| Int-136 | 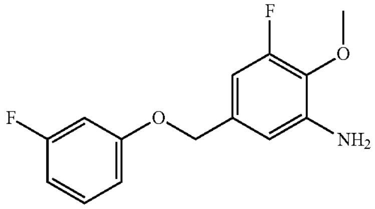 [SMILES: COc1c(N)cc(COc2cccc(F)c2)cc1F] | 266.0 [M + H]+ | 1-Fluoro-5-((3-fluorophenoxy)methyl)-2-methoxy-3-nitrobenzene |
| Int-137 | 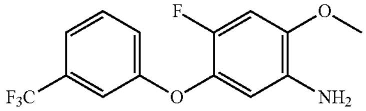 | 302.0 [M + H]+ | 1-Fluoro-5-methoxy-4-nitro-2-(3-(trifluoromethyl)phenoxy)-benzene |
| Int-138 | 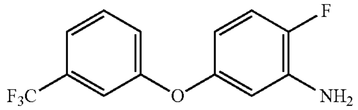 | 272.0 [M + H]+ | 1-Fluoro-2-nitro-4-(3-(tri-fluoromethyl)phenoxy)benzene |
| Int-139 | 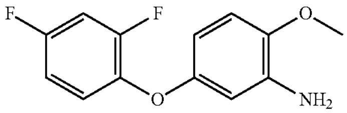 [SMILES: COc1ccc(Oc2ccc(F)cc2F)cc1N] | 252.0 [M + H]+ | 4-(2,4-Difluorophenoxy)-1-methoxy-2-nitrobenzene |
| Int-140 | 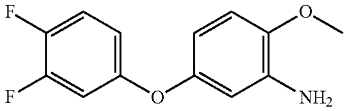 | 251.0 [M + H]+ | 4-(3,4-Difluorophenoxy)-1-methoxy-2-nitrobenzene |
| Int-141 | 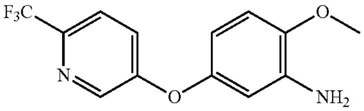 [SMILES: COc1ccc(Oc2ccc(C(F)(F)F)nc2)cc1N] | 286.0 [M + H]+ | 5-(4-Methoxy-3-nitro-phenoxy)-2-(trifluoromethyl)-pyridine |
| Int-142 | 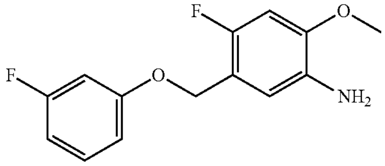 [SMILES: COc1cc(F)c(COc2cccc(F)c2)cc1N] | 266.2 [M + H]+ | 1-Fluoro-2-((3-fluoro-phenoxy)methyl)-5-methoxy-4-nitrobenzene |
| Int-143 | 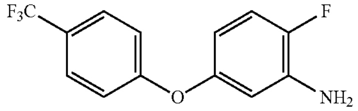 | 271.07 [M]+ | 1-Fluoro-2-nitro-4-(4-(tri-fluoromethyl)phenoxy)benzene |
| Int-144 | 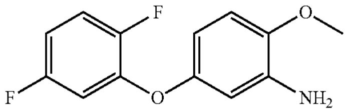 [SMILES: COc1ccc(Oc2cc(F)ccc2F)cc1N] | 252.2 [M + H]+ | 4-(2,5-Difluorophenoxy)-1-methoxy-2-nitrobenzene |

-continued

| No. | Structure | LCMS/ GCMS m/z | Starting materials |
|---|---|---|---|
| Int-145 | 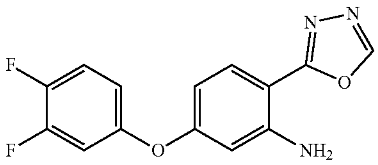 [SMILES: Nc1cc(Oc2ccc(F)c(F)c2)ccc1-c1nnco1] | 290.2 [M + H]+ | 2-(4-(3,4-Difluorophenoxy)-2-nitrophenyl)-1,3,4-oxadiazole |
| Int-146 | 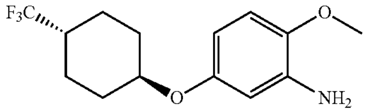 | 290.2 [M + H]+ | 1-Methoxy-2-nitro-4-(((trans)-4-(trifluoromethyl)cyclohexyl)-oxy)benzene |
| Int-147 | 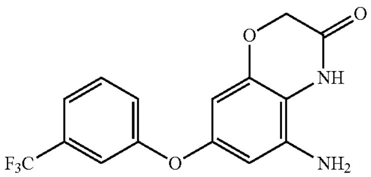 | 325.0 [M + H]+ | 5-Nitro-7-(3-(trifluoromethyl)-phenoxy)-2H-benzo[b][1,4]-oxazin-3(4H)-one |
| Int-148 | 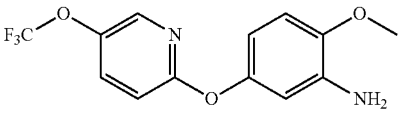 [SMILES: COc1ccc(Oc2ccc(OC(F)(F)F)cn2)cc1N] | 301.0 [M + H]+ | 2-(4-Methoxy-3-nitro-phenoxy)-5-(trifluoro-methoxy)pyridine |
| Int-149 | 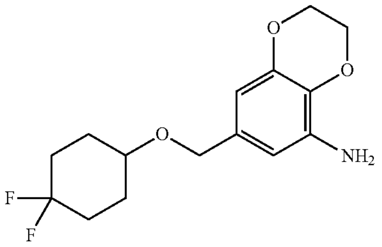 | 300.2 [M + H]+ | 7-(((4,4-Difluorocyclohexyl)-oxy)methyl)-5-nitro-2,3-dihydrobenzo[b][1,4]dioxine |
| Int-150 | 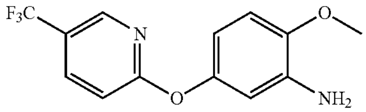 [SMILES: COc1ccc(Oc2ccc(C(F)(F)F)cn2)cc1N] | 285.0 [M + H]+ | 2-(4-Methoxy-3-nitro-phenoxy)-5-(trifluoromethyl)-pyridine |
| Int-151 | 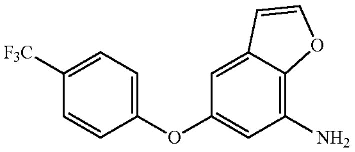 | 294.2 [M + H]+ | 7-Nitro-5-(4-(trifluoromethyl)-phenoxy)benzofuran |
| Int-152 | 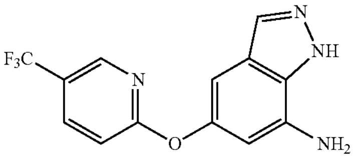 [SMILES: Nc1cc(Oc2ccc(C(F)(F)F)cn2)cc2cn[nH]c12] | 295.0 [M + H]+ | 7-Nitro-5-((5-(trifluoromethyl)pyridin-2-yl)oxy)-1H-indazole |
| Int-153 | 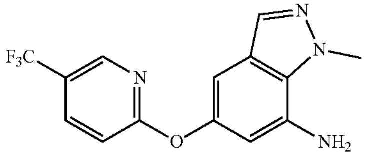 [SMILES: Cn1ncc2cc(Oc3ccc(C(F)(F)F)cn3)cc(N)c21] | 309.0 [M + H]+ | 1-Methyl-7-nitro-5-((5-(tri-fluoromethyl)pyridin-2-yl)-oxy)-1H-indazole |

-continued

| No. | Structure | LCMS/ GCMS m/z | Starting materials |
|---|---|---|---|
| Int-154 | 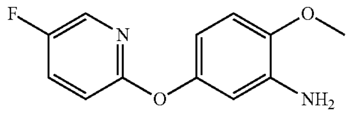 [SMILES: COc1ccc(Oc2ccc(F)cn2)cc1N] | 235.2 $[M + H]^+$ | 5-Fluoro-2-(4-methoxy-3-nitrophenoxy)pyridine |
| Int-155 | 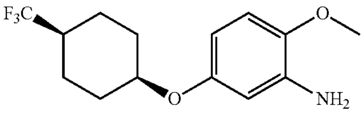 | 290.2 $[M + H]^+$ | 1-Methoxy-2-nitro-4-(((cis)-4-(trifluoromethyl)cyclohexyl)-oxy)benzene |
| Int-156 | 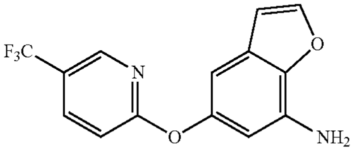 | 295.0 $[M + H]^+$ | 2-((7-Nitrobenzofuran-5-yl)-oxy)-5-(trifluoromethyl)-pyridine |
| Int-157 | 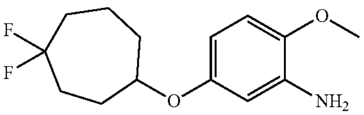 | 272.2 $[M + H]^+$ | 1,1-Difluoro-4-(4-methoxy-3-nitrophenoxy)cycloheptane |

Intermediate 158. 2-(4-Methoxy-3-nitrophenoxy)-4-(trifluoromethyl)pyridine

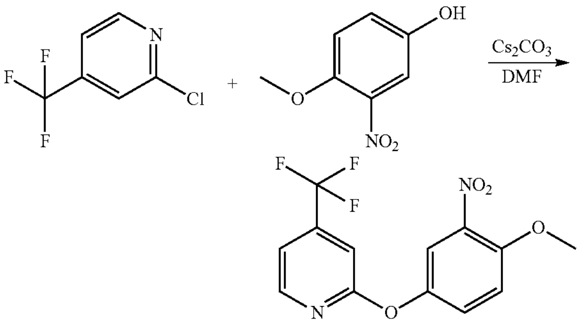

Int-158

A mixture of 2-chloro-4-(trifluoromethyl)pyridine (2.72 g, 15.0 mmol), 4-methoxy-3-nitrophenol (2.80 g, 15.8 mmol) and $Cs_2CO_3$ (5.68 g, 17.3 mmol) in DMF (20 ml) was heated at 100° C. for 7 h. Water was added (50 ml) and the mixture was extracted with EtOAc (3×50 ml). The organic layers were combined and evaporated to yield 4.71 g of the crude title compound which was used in the next reaction without further purification. $^1H$ NMR (400 MHz, DMSO-$d_6$) δ: 3.96 (3H, s), 7.44 (1H, d), 7.50-7.59 (3H, m), 7.84 (1H, d), 8.41 (1H, d). LCMS: m/z 315.4 $[M+H]^+$ The following intermediates were prepared according to the procedure described for Intermediate 158 from the starting material indicated in the table.

| No. | Structure | LCMS/ GCMS m/z | Starting materials |
|---|---|---|---|
| Int-159 | 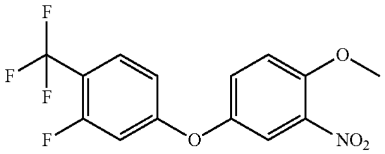 [SMILES: COc1ccc(Oc2ccc(C(F)(F)F)c(F)c2)cc1[N+](=O)[O-]] | 332.0 $[M + H]^+$ | 4-Methoxy-3-nitrophenol and 2,4-Difluoro-1-(trifluoromethyl)-benzene |
| Int-160 | 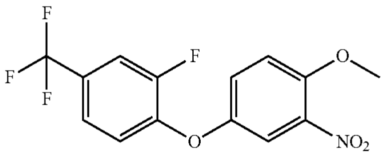 [SMILES: COc1ccc(Oc2ccc(C(F)(F)F)cc2F)cc1[N+](=O)[O-]] | 332.0 [M + H]+ | 4-Methoxy-3-nitrophenol and 3,4-difluorobenzotrifluoride (DMSO solvent, 120° C. for 4 h) |

-continued

| No. | Structure | LCMS/ GCMS m/z | Starting materials |
|---|---|---|---|
| Int-161 | 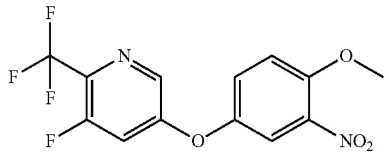 [SMILES: COc1ccc(Oc2cnc(C(F)(F)F)c(F)c2)cc1[N+](=O)[O-]] | 333.2 [M + H]+ | 4-Methoxy-3-nitrophenol and 3,5-Difluoro-2-(trifluoromethyl)-pyridine |
| Int-162 | 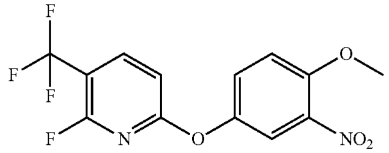 | 332.9 [M + H]+ | 4-Methoxy-3-nitrophenol and 2,6-Difluoro-3-trifluoromethyl-pyridine |

Intermediate 163. 2-Methoxy-5-((3-(trifluoromethyl)benzyl)oxy)aniline hydrochloride

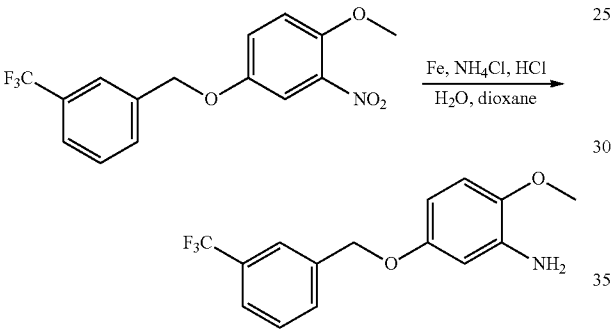

Int-163

1-Methoxy-2-nitro-4-((3-(trifluoromethyl)benzyl)oxy)benzene (8.70 g, 1 eq., 26.6 mmol), water (7.43 g, 7.4 mL, 15.5 eq., 412 mmol), ammonia hydrochloride (142 mg, 0.1 eq., 2.66 mmol) and hydrogen chloride (266 mg, 226 μL, 36.5% aqueous, 0.1 eq., 2.66 mmol) were mixed in 1,4-dioxane (200 mL) followed by addition of iron (7.42 g, 5 eq., 133 mmol). The mixture was stirred at 110° C. for 5 h and at RT for 16 h. The mixture was filtered through thin layer of silica, concentrated and the residue was added to dioxane saturated with hydrochloric acid (30 mL). The solution was evaporated under reduced pressure. The obtained residue was washed with ethyl acetate and dried to give the title compound. LCMS: m/z 334.2 $[M+H]^+$.

The following intermediates were prepared according to the procedure described for Intermediate 163 from the starting material indicated in the table.

| No. | Structure | LCMS/ GCMS m/z | Starting materials |
|---|---|---|---|
| Int-164 | 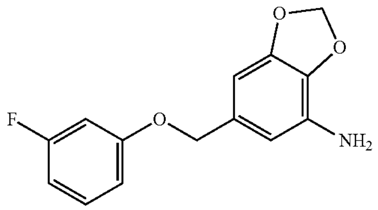 | 262.0 $[M + H]^+$ | 6-((3-Fluorophenoxy)methyl)-4-nitrobenzo[d][1,3]dioxole |
| Int-165 | 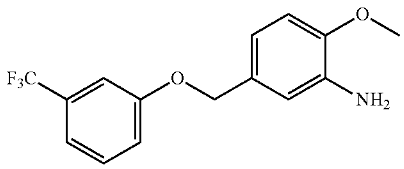 [SMILES: COc1ccc(COc2cccc(C(F)(F)F)c2)cc1N] | 298.2 $[M + H]^+$ | 1-Methoxy-2-nitro-4-((3-(trifluoromethyl)phenoxy)methyl)-benzene |

-continued

| No. | Structure | LCMS/ GCMS m/z | Starting materials |
|---|---|---|---|
| Int-166 | 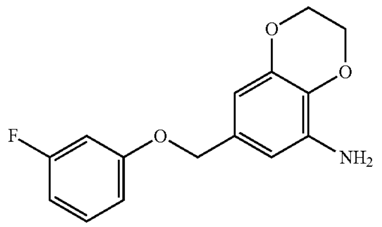 | 276.0 [M + H]+ | 7-((3-Fluorophenoxy)methyl)-5-nitro-2,3-dihydrobenzo[b][1,4]-dioxine |
| Int-167 | 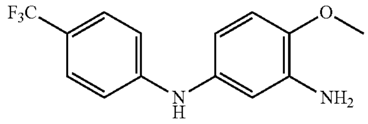 | 283.2 [M + H]+ | 4-Methoxy-3-nitro-N-(4-(tri-fluoromethyl)phenyl)aniline |
| Int-168 | 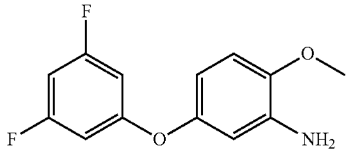 [SMILES: COc1ccc(Oc2cc(F)cc(F)c2)cc1N] | 252.2 [M + H]+ | 4-(3,5-Difluorophenoxy)-1-methoxy-2-nitrobenzene |
| Int-169 | 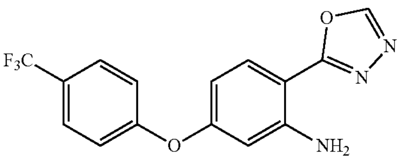 [SMILES: Nc1cc(Oc2ccc(C(F)(F)F)cc2)ccc1-c1nnco1] | 322.0 [M + H]+ | 2-(2-Nitro-4-(4-(trifluoro-methyl)phenoxy)phenyl)-1,3,4-oxadiazole |
| Int-170 | 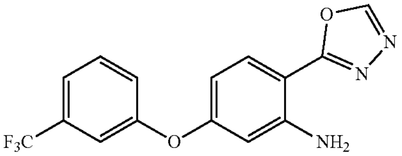 [SMILES: Nc1cc(Oc2cccc(C(F)(F)F)c2)ccc1-c1nnco1] | 322.2 [M + H]+ | 2-(2-Nitro-4-(3-(trifluoro-methyl)phenoxy)phenyl)-1,3,4-oxadiazole |
| Int-171 | 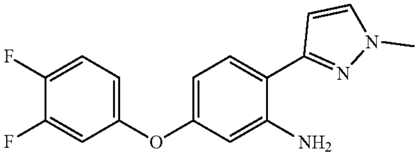 [SMILES: Cn1ccc(-c2ccc(Oc3ccc(F)c(F)c3)cc2N)n1] | 302.0 [M + H]+ | 3-(4-(3,4-Difluorophenoxy)-2-nitrophenyl)-1-methyl-1H-pyrazole |
| Int-172 | 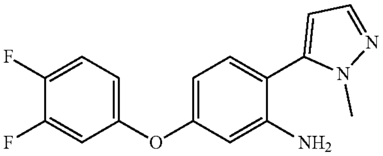 [SMILES: Cn1nccc1-c1ccc(Oc2ccc(F)c(F)c2)cc1N] | 302.2 [M + H]+ | 5-(4-(3,4-Difluorophenoxy)-2-nitrophenyl)-1-methyl-1H-pyrazole |
| Int-173 | 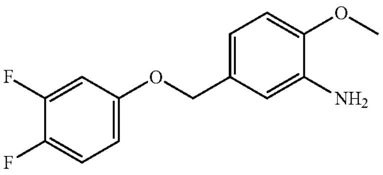 | 302.2 [M + H]+ | 4-((3,4-Difluorophenoxy)-methyl)-1-methoxy-2-nitro-benzene |
| Int-174 | 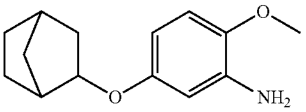 | 334.0 [M + H]+ | 2-(4-Methoxy-3-nitrophenoxy)-bicyclo[2.2.1]heptane |

-continued

| No. | Structure | LCMS/ GCMS m/z | Starting materials |
|---|---|---|---|
| Int-175 | 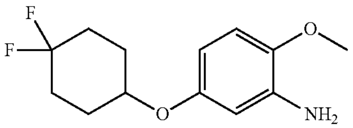 [SMILES: COc1ccc(OC2CCC(F)(F)CC2)cc1N] | 258.2 [M + H]$^+$ | 4-((4,4-Difluorocyclohexyl)-oxy)-1-methoxy-2-nitrobenzene |
| Int-176 | 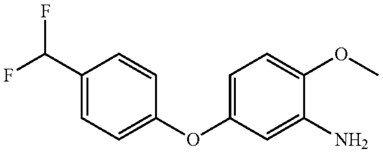 | 266.2 [M + H]$^+$ | 4-(4-(Difluoromethyl)phenoxy)-1-methoxy-2-nitrobenzene |
| Int-177 | 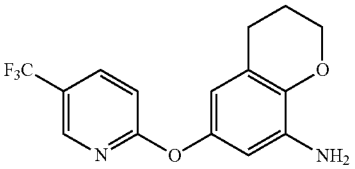 [SMILES: Nc1cc(Oc2ccc(C(F)(F)F)cn2)cc2c1OCCC2] | 311.2 [M + H]$^+$ | 2-((8-Nitrochroman-6-yl)oxy)-5-(trifluoromethyl)pyridine |
| Int-178 | 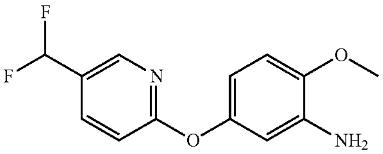 | 267.0 [M + H]$^+$ | 5-(Difluoromethyl)-2-(4-methoxy-3-nitrophenoxy)-pyridine |
| Int-179 | 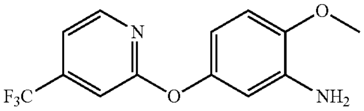 [SMILES: COc1ccc(Oc2cc(C(F)(F)F)ccn2)cc1N] | 285.0 [M + H]$^+$ | 2-(4-Methoxy-3-nitrophenoxy)-4-(trifluoromethyl)pyridine |
| Int-180 | 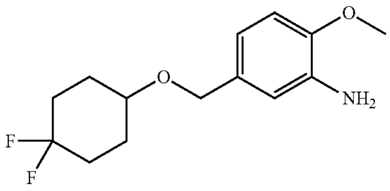 [SMILES: COc1ccc(COC2CCC(F)(F)CC2)cc1N] | 272.0 [M + H]$^+$ | 4-(((4,4-Difluorocyclohexyl)-oxy)methyl)-1-methoxy-2-nitro-benzene |
| Int-181 | 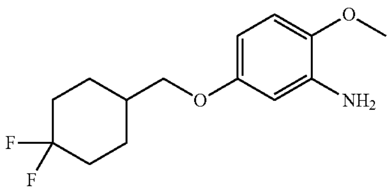 [SMILES: COc1ccc(OCC2CCC(F)(F)CC2)cc1N] | 272.2 [M + H]$^+$ | 4-((4,4-Difluorocyclohexyl)-methoxy)-1-methoxy-2-nitro-benzene |

Intermediate 182. 5-((5-Chloropyridin-2-yl)oxy)-2-methoxyaniline

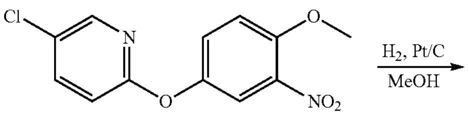

-continued

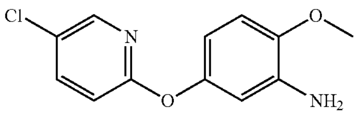

Int-182

5-Chloro-2-(4-methoxy-3-nitrophenoxy)pyridine (197 mg, 1 eq., 702 μmol) was dissolved in methanol (5 mL) and platinum (20.5 mg, 0.15 eq., 105 μmol) was added. The mixture was degassed and stirred in atmosphere of hydrogen for 12 h, then filtered and the solvent was evaporated to give the title compound (175 mg, 0.66 mmol, 94%, 95% purity) which was used in next step without further purification. LCMS: m/z 251.0 $[M+H]^+$.

Intermediate 183. 1,1-Diphenyl-N-(6-(3-(trifluoromethyl)phenoxy)benzo[d]-[1,3]dioxol-4-yl) methanimine

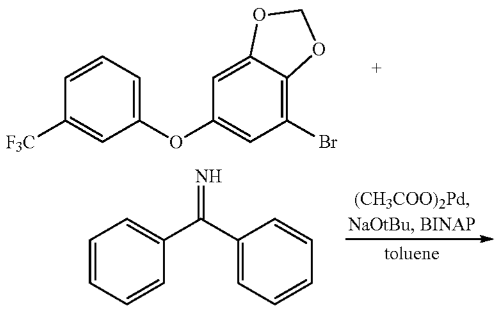

-continued

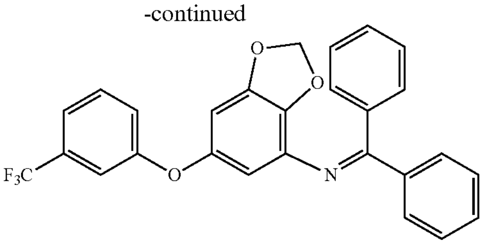

Int-183

4-Bromo-6-(3-(trifluoromethyl)phenoxy)benzo[d][1,3]dioxole (1.20 g, 1 eq., 3.32 mmol), diphenylmethanimine (663 mg, 1.1 eq., 3.66 mmol), sodium 2-methyl-propan-2-olate (335 mg, 1.05 eq., 3.49 mmol) and 2,2'-bis(diphenylphosphino)-1,1'-binaphthyl (207 mg, 0.1 eq., 332 μmol) were dissolved in toluene (20 mL). The solution was bubbled with argon for 1 min, then diacetoxy palladium (37.3 mg, 0.05 eq., 166 μmol) was added and the mixture was stirred at 110° C. for 12 h in argon atmosphere. The mixture was filtered and the solid was washed with ethyl acetate (2×20 mL). Then ethyl acetate solution was washed with brine (2×50 mL). The organic phase was dried over sodium sulfate and filtered. Solvent was evaporated under reduced pressure to give title compound which was used in the next step without further purification. LCMS: m/z 462.0 $[M+H]^+$.

The following intermediates were prepared according to the procedure described for Intermediate 183 from the starting material indicated in the table.

| No. | Structure | LCMS/ GCMS m/z | Starting materials |
|---|---|---|---|
| Int-184 | 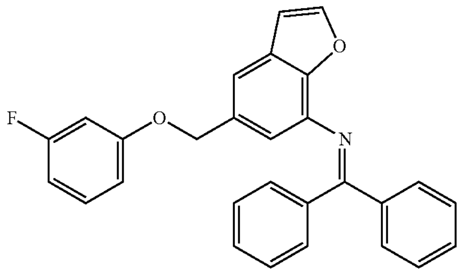 [SMILES: Fc1cccc(OCc2cc(N=C(c3ccccc3)c3ccccc3)c3occc3c2)c1] | 422.2 $[M + H]^+$ | 7-Bromo-5-((3-fluorophenoxy)-methyl)benzofuran and Diphenylmethanimine |
| Int-185 | 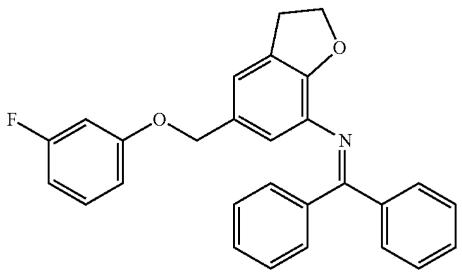 [SMILES: Fc1cccc(OCc2cc3c(c(N=C(c4ccccc4)c4ccccc4)c2)OCC3)c1] | 425.2 $[M + H]^+$ | 7-Bromo-5-((3-fluorophenoxy)-methyl)-2,3-dihydrobenzofuran and Diphenylmethanimine |

-continued

| No. | Structure | LCMS/ GCMS m/z | Starting materials |
|---|---|---|---|
| Int-186 | 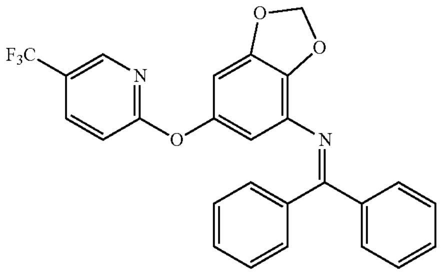 [SMILES: FC(F)(F)c1ccc(Oc2cc(N=C(c3ccccc3)c3ccccc3)c3c(c2)OCO3)nc1] | 463.0 [M + H]+ | 2-((7-Bromobenzo[d][1,3]dioxol-5-yl)oxy)-5-(trifluoromethyl)pyridine and Diphenylmethanimine |
| Int-187 | 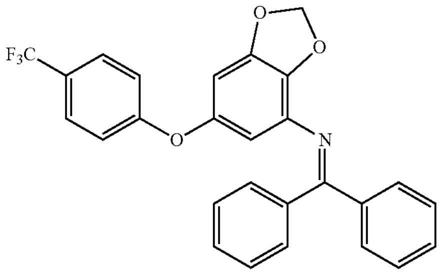 [SMILES: FC(F)(F)c1ccc(Oc2cc(N=C(c3ccccc3)c3ccccc3)c3c(c2)OCO3)cc1] | 462.2 [M + H]+ | 4-Bromo-6-(4-(trifluoromethyl)-phenoxy)benzo[d][1,3]dioxole and Diphenylmethanimine |
| Int-188 | 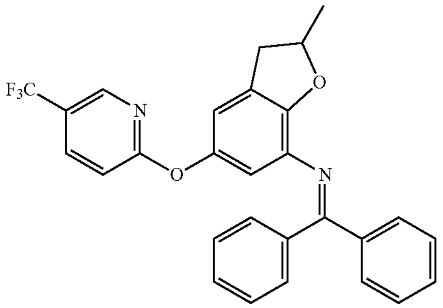 [SMILES: CC1Cc2cc(Oc3ccc(C(F)(F)F)cn3)cc(N=C(c3ccccc3)c3ccccc3)c2O1] | 475.2 [M + H]+ | 2-((7-Bromo-2-methyl-2,3-dihydrobenzofuran-5-yl)oxy)-5-(trifluoromethyl)pyridine and Diphenylmethanimine |

Intermediate 189. tert-Butyl (7-(4-(trifluoromethyl)phenoxy)-2,3-dihydrobenzo[b][1,4]dioxin-5-yl)carbamate

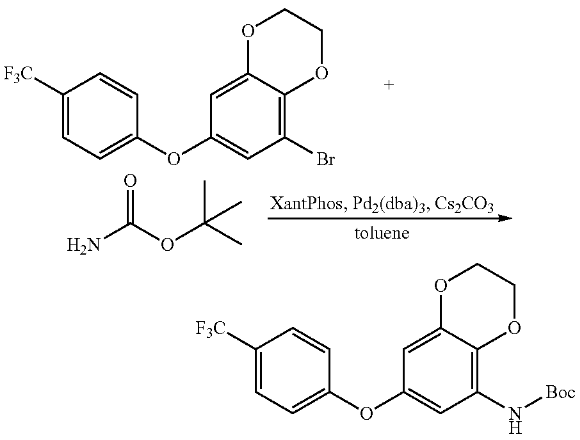

Int-189

To a mixture of 5-bromo-7-(4-(trifluoromethyl)phenoxy)-2,3-dihydrobenzo[b]-[1,4]dioxine (1.410 g, 1 eq., 3.759 mmol), tert-butyl carbamate (660.5 mg, 1.5 eq., 5.638 mmol) and cesium carbonate (3.674 g, 3 eq., 11.28 mmol) in toluene (40 mL) under argon XantPhos (326.2 mg, 0.15 eq., 563.8 μmol) and tris(dibenzylideneacetone)-dipalladium (172.1 mg, 0.05 eq., 187.9 μmol) were added and the mixture was heated at 110° C. for 18 h. After cooling to RT the mixture was filtered and concentrated. The residue was diluted with ethyl acetate (10 mL) and washed with brine (2×50 mL). The organic phase was dried over $Na_2SO_4$, filtered and concentrated in vacuum. The residue was recrystallized from acetonitrile to give the title compound. LCMS: m/z 412.2 $[M+H]^+$.

The following intermediates were prepared according to the procedure described for Intermediate 189 from the starting materials indicated in the table. Where LCMS/GCMS data was not informative, the data is not shown.

| No. | Structure | LCMS/ GCMS m/z | Starting materials |
|---|---|---|---|
| Int-190 | 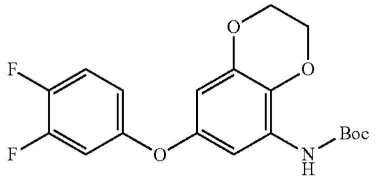 [SMILES: CC(C)(C)OC(=O)Nc1cc(Oc2ccc(F)c(F)c2)cc2c1OCCO2] | 380.0 [M + H]+ | 5-Bromo-7-(3,4-difluoro-phenoxy)-2,3-dihydrobenzo[b]-[1,4]dioxine and tert-Butyl carbamate |
| Int-191 | 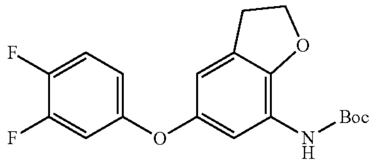 [SMILES: CC(C)(C)OC(=O)Nc1cc(Oc2ccc(F)c(F)c2)cc2c1OCC2] | 364.2 [M + H]+ | 7-Bromo-5-(3,4-difluoro-phenoxy)-2,3-dihydrobenzo-furan and tert-Butyl carbamate |
| Int-192 | 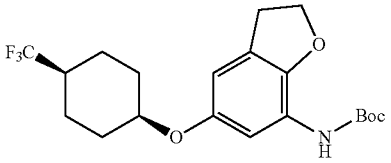 [SMILES: CC(C)(C)OC(=O)Nc1cc(O[C@H]2CC[C@@H](C(F)(F)F)CC2)cc2c1OCC2] | 402.0 [M + H]+ | 7-Bromo-5-(((cis)-4-(trifluoro-methyl)cyclohexyl)oxy)-2,3-di-hydrobenzofuran and tert-Butyl carbamate |
| Int-193 | 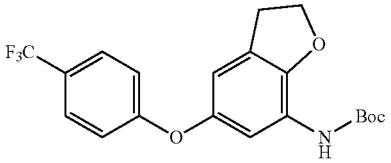 | 396.0 [M + H]+ | 7-Bromo-5-(4-(trifluoromethyl)-phenoxy)-2,3-dihydrobenzo-furan and tert-Butyl carbamate |
| Int-194 | 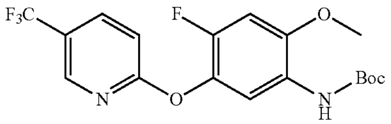 [SMILES: COc1cc(F)c(Oc2ccc(C(F)(F)F)cn2)cc1NC(=O)OC(C)(C)C] | 303.0 [M + H]+ | 2-(5-Bromo-2-fluoro-4-methoxyphenoxy)-5-(trifluoro-methyl)pyridine and tert-Butyl carbamate |
| Int-195 | 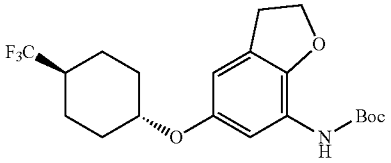 [SMILES: CC(C)(C)OC(=O)Nc1cc(O[C@H]2CC[C@H](C(F)(F)F)CC2)cc2c1OCC2] | — | 7-Bromo-5-(((trans)-4-(trifluoro-methyl)cyclohexyl)oxy)-2,3-di-hydrobenzofuran and tert-Butyl carbamate |
| Int-196 | 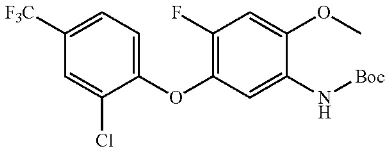 [SMILES: COc1cc(F)c(Oc2ccc(C(F)(F)F)cc2Cl)cc1NC(=O)OC(C)(C)C] | 336.0 [M + H]+ | 1-Bromo-5-(2-chloro-4-(tri-fluoromethyl)phenoxy)-4-fluoro-2-methoxybenzene and tert-Butyl carbamate |
| Int-197 | 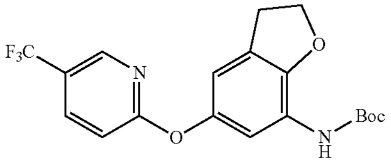 [SMILES: CC(C)(C)OC(=O)Nc1cc(Oc2ccc(C(F)(F)F)cn2)cc2c1OCC2] | — | 2-((7-Bromo-2,3-dihydrobenzo-furan-5-yl)oxy)-5-(trifluoro-methyl)pyridine and tert-Butyl carbamate |
| Int-198 | 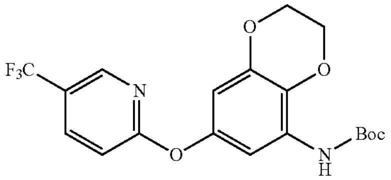 [SMILES: CC(C)(C)OC(=O)Nc1cc(Oc2ccc(C(F)(F)F)cn2)cc2c1OCCO2] | 411.0 [M + H]+ | 2-((8-Bromo-2,3-dihydrobenzo-[b][1,4]dioxin-6-yl)oxy)-5-(trifluoromethyl)pyridine and tert-Butyl carbamate |

-continued

| No. | Structure | LCMS/ GCMS m/z | Starting materials |
|---|---|---|---|
| Int-199 | 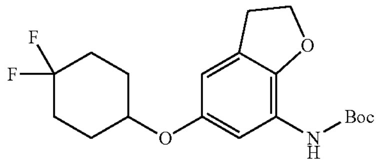 [SMILES: CC(C)(C)OC(=O)Nc1cc(OC2CCC(F)(F)CC2)cc2c1OCC2] | 268.8 [M − H]⁻ | 7-Bromo-5-((4,4-difluorocyclo-hexyl)oxy)-2,3-dihydrobenzo-furan and tert-Butyl carbamate |
| Int-200 | 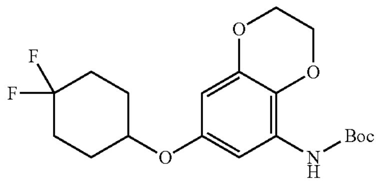 [SMILES: CC(C)(C)OC(=O)Nc1cc(OC2CCC(F)(F)CC2)cc2c1OCCO2] | 387.2 [M + H]⁺ | 5-Bromo-7-((4,4-difluorocyclo-hexyl)oxy)-2,3-dihydrobenzo-[b][1,4]dioxine and tert-Butyl carbamate |
| Int-201 | 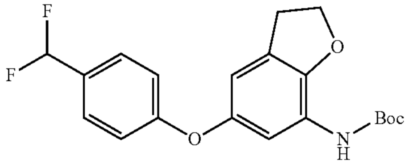 [SMILES: CC(C)(C)OC(=O)Nc1cc(Oc2ccc(C(F)F)cc2)cc2c1OCC2] | 278.0 [M + H]⁺ | 7-Bromo-5-(4-(difluoromethyl)-phenoxy)-2,3-dihydrobenzofuran and tert-Butyl carbamate |

Intermediate 202. 7-(4-(Trifluoromethyl)phenoxy)-2,3-dihydrobenzo[b][1,4]dioxin-5-amine hydrochloride

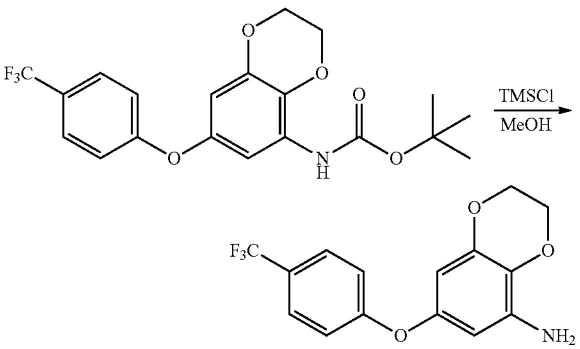

Int-202

Chlorotrimethylsilane (1.320 g, 1.54 mL, 5 eq., 12.15 mmol) was added to methanol (25 mL) at 0° C. dropwise. The mixture was stirred for 30 min and tert-butyl (7-(4-(trifluoromethyl)phenoxy)-2,3-dihydrobenzo[b][1,4]dioxin-5-yl)carbamate (1 g, 1 eq., 2.431 mmol) was added and this solution was stirred at RT for 48 h. The mixture was concentrated in vacuum to give crude title compound (808 mg, 2.11 mmol, 86.9%, 90.93% purity). LCMS: m/z 312.2 $[M+H]^+$.

The following intermediates were prepared according to the procedure described for Intermediate 202 from the starting material indicated in the table.

| No. | Structure | LCMS/ GCMS m/z | Starting materials |
|---|---|---|---|
| Int-203 | 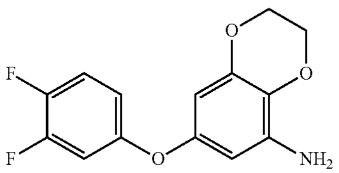 [SMILES: Nc1cc(Oc2ccc(F)c(F)c2)cc2c1OCCO2] | 280.0 [M + H]⁺ | tert-Butyl (7-(3,4-difluoro-phenoxy)-2,3-dihydrobenzo[b]-[1,4]dioxin-5-yl)carbamate |
| Int-204 | 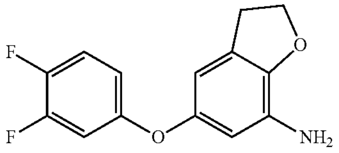 [SMILES: Nc1cc(Oc2ccc(F)c(F)c2)cc2c1OCC2] | 264.2 [M + H]⁺ | tert-Butyl (5-(3,4-difluoro-phenoxy)-2,3-dihydrobenzo-furan-7-yl)carbamate |

-continued

| No. | Structure | LCMS/ GCMS m/z | Starting materials |
|---|---|---|---|
| Int-205 | 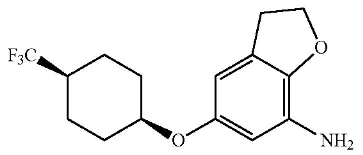 [SMILES: Nc1cc(O[C@H]2CC[C@@H](C(F)(F)F)CC2)cc2c1OCC2] | 302.2 [M + H]+ | tert-Butyl (5-(((cis)-4-(trifluoro-methyl)cyclohexyl)oxy)-2,3-di-hydrobenzofuran-7-yl)carbamate |
| Int-206 | 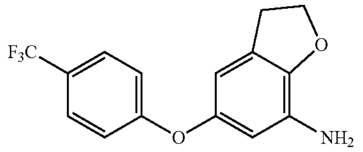 [SMILES: Nc1cc(Oc2ccc(C(F)(F)F)cc2)cc2c1OCC2] | 296.0 [M + H]+ | tert-Butyl (5-(4-(trifluoro-methyl)phenoxy)-2,3-dihydro-benzofuran-7-yl)carbamate |
| Int-207 | 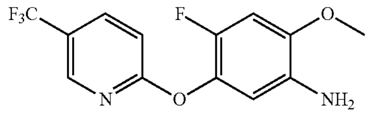 [SMILES: COc1cc(F)c(Oc2ccc(C(F)(F)F)cn2)cc1N] | 303.0 [M + H]+ | tert-Butyl (4-fluoro-2-methoxy-5-((5-(trifluoromethyl)pyridin-2-yl)oxy)phenyl)carbamate |
| Int-208 | 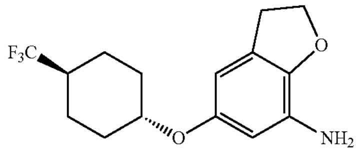 [SMILES: Nc1cc(O[C@H]2CC[C@H](C(F)(F)F)CC2)cc2c1OCC2] | 302.0 [M + H]+ | tert-Butyl (5-(((trans)-4-(tri-fluoromethyl)cyclohexyl)oxy)-2,3-dihydrobenzofuran-7-yl)-carbamate |
| Int-209 | 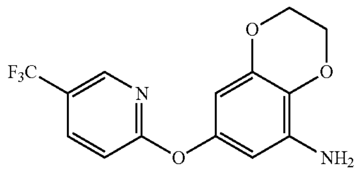 [SMILES: Nc1cc(Oc2ccc(C(F)(F)F)cn2)cc2c1OCCO2] | 313.0 [M + H]+ | tert-Butyl (7-((5-(trifluoro-methyl)pyridin-2-yl)oxy)-2,3-dihydrobenzo[b][1,4]dioxin-5-yl)carbamate |
| Int-210 | 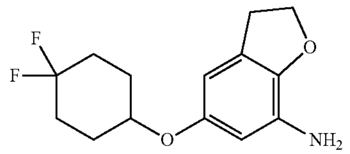 [SMILES: Nc1cc(OC2CCC(F)(F)CC2)cc2c1OCC2] | 270.2 [M + H]+ | tert-Butyl (5-((4,4-difluorocyclo-hexyl)oxy)-2,3-dihydrobenzo-furan-7-yl)carbamate |
| Int-211 | 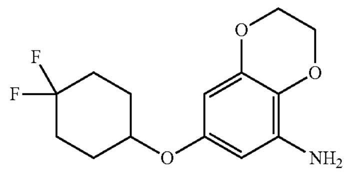 [SMILES: Nc1cc(OC2CCC(F)(F)CC2)cc2c1OCCO2] | 286.2 [M + H]+ | tert-Butyl (7-((4,4-difluorocyclo-hexyl)oxy)-2,3-dihydrobenzo[b][1,4]dioxin-5-yl)carbamate |
| Int-212 | 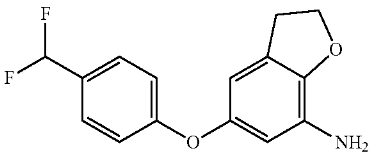 [SMILES: Nc1cc(Oc2ccc(C(F)F)cc2)cc2c1OCC2] | 278.2 [M + H]+ | tert-Butyl (5-(4-(difluoro-methyl)phenoxy)-2,3-dihydro-benzofuran-7-yl)carbamate |
| Int-213 | 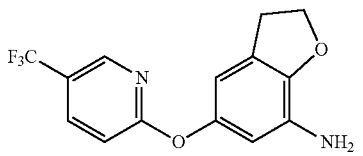 | 297.0 [M + H]+ | tert-Butyl (5-((5-(trifluoro-methyl)pyridin-2-yl)oxy)-2,3-dihydrobenzofuran-7-yl)-carbamate |

Intermediate 214. 6-(3-(Trifluoromethyl)phenoxy)benzo[d][1,3]dioxol-4-amine

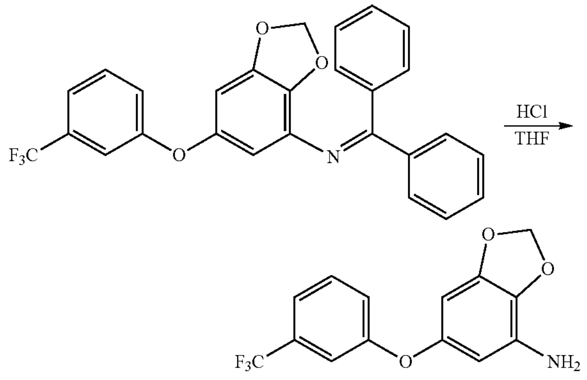

Int-214

1,1-Diphenyl-N-(6-(3-(trifluoromethyl)phenoxy)benzo[d][1,3]dioxol-4-yl)-methanimine (0.800 g, 1 eq., 1.73 mmol) was dissolved in THF (10 mL) and HCl solution (253 mg, 6.93 mL, 1 molar, 4 eq., 6.93 mmol) was added at RT. A mixture was stirred at RT for 10 mi and then evaporated in vacuum to give the title compound (640 mg, 1.1 mmol, 62%, 50% purity) which was used in the next step without further purification. LCMS: m/z 298.0 $[M+H]^+$.

The following intermediates were prepared according to the procedure described for Intermediate 214 from the starting material indicated in the table.

| No. | Structure | LCMS/ GCMS m/z | Starting materials |
|---|---|---|---|
| Int-215 | 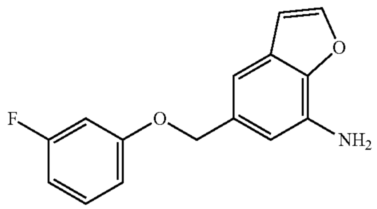 [SMILES: Nc1cc(COc2cccc(F)c2)cc2ccoc12] | 258.2 $[M + H]^+$ | N-(5-((3-Fluorophenoxy)-methyl)benzofuran-7-yl)-1,1-di-phenylmethanimine |
| Int-216 | 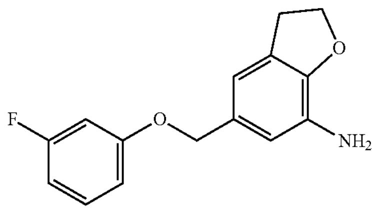 [SMILES: Nc1cc(COc2cccc(F)c2)cc2c1OCC2] | 260.2 $[M + H]^+$ | N-(5-((3-Fluorophenoxy)-methyl)-2,3-dihydrobenzofuran-7-yl)-1,1-diphenylmethanimine |
| Int-217 | 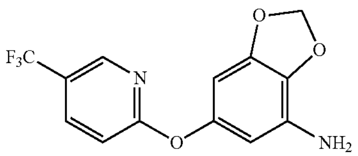 [SMILES: Nc1cc(Oc2ccc(C(F)(F)F)cn2)cc2c1OCO2] | 299.1 $[M + H]^+$ | 1,1-Diphenyl-N-(6-((5-(tri-fluoromethyl)pyridin-2-yl)oxy)-benzo[d][1,3]dioxol-4-yl)-methanimine |
| Int-218 | 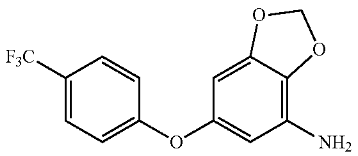 [SMILES: Nc1cc(Oc2ccc(C(F)(F)F)cc2)cc2c1OCO2] | 298.0 $[M + H]^+$ | 1,1-Diphenyl-N-(6-(4-(trifluoro-methyl)phenoxy)benzo[d][1,3]-dioxol-4-yl)methanimine |
| Int-219 | 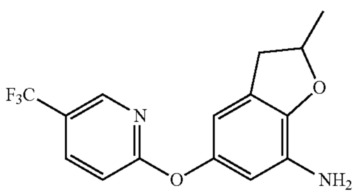 [SMILES: CC1Cc2cc(Oc3ccc(C(F)(F)F)cn3)cc(N)c2O1] | 311.1 $[M + H]^+$ | N-(2-Methyl-5-((5-(trifluoro-methyl)pyridin-2-yl)oxy)-2,3-dihydrobenzofuran-7-yl)-1,1-diphenylmethanimine |

Intermediate 220. 5-(2-Chloro-4-(trifluoromethyl)phenoxy)-4-fluoro-2-methoxyaniline hydrochloride

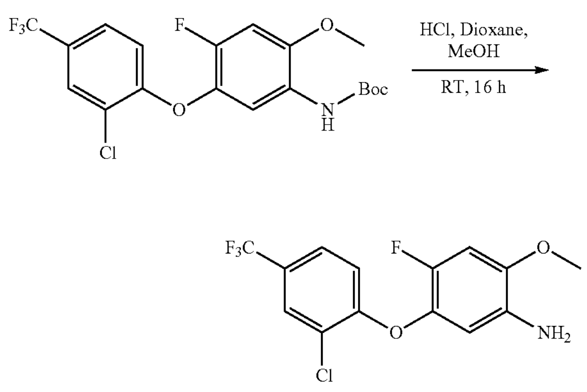

Int-220 tert-Butyl (5-(2-chloro-4-(trifluoromethyl)phenoxy)-4-fluoro-2-methoxy-phenyl)carbamate (0.185 g, 1 eq., 425 μmol) was dissolved in methanol (5 mL) and the solution of HCl (155 mg, 104 μL, 10 w-%, 1 eq., 425 μmol) in dioxane was added dropwise at 25° C. The mixture was stirred at 25° C. for 56 h and then concentrated under reduced pressure to give the title compound (0.150 g, 0.32 mmol, 76%, 80% purity) which was used in the next step without further purification. $^1$H NMR (500 MHz, DMSO-d6) δ: 8.00 (s, 1H), 7.66 (d, 1H), 7.21 (d, 1H), 6.97 (m, 2H), 3.85 (s, 3H). LCMS: m/z 336.0 $[M+H]^+$.

Intermediate 221a. Methyl N-methylalaninate 1,1-dioxide

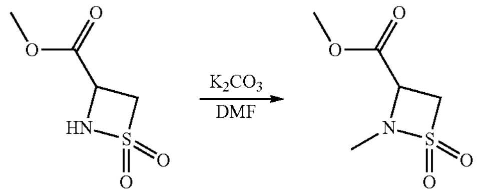

Int-221a

Methyl alaninate 1,1-dioxide (350 mg, 1 eq., 2.12 mmol) and potassium carbonate (879 mg, 3 eq., 6.36 mmol) were mixed in anhydrous DMF (5 mL) followed by adding iodomethane (1.50 g, 660 μL, 5 eq., 10.6 mmol) in a single portion. The mixture was stirred at 27° C. for 18 h. The mixture was concentrated in vacuum, the residue was treated with water (5 mL) and the obtained suspension was extracted with ethyl acetate (2×20 mL). Combined organic phases were washed with brine (2×15 mL), dried over sodium sulfate, filtered and concentrated in vacuum to give the title compound (116 mg, 0.39 mmol, 18%, 60% purity) which was used in the next step without further purification. $^1$H NMR (500 MHz, DMSO-d6) δ: 4.56-4.46 (m, 1H), 4.38 (m, 1H), 3.95 (m, 1H), 3.71 (s, 3H), 2.67 (s, 3H).

Intermediate 221b. Lithium N-methylalaninate 1,1-dioxide

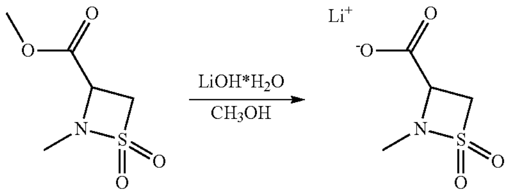

Int-221b

Methyl N-methylalaninate 1,1-dioxide (100 mg, 1 eq., 558 μmol) and lithium hydroxide hydrate (23.4 mg, 1 eq., 558 μmol) were dissolved in methanol (2 mL) and stirred at RT for 16 h. The mixture was concentrated and the residue was concentrated three times with acetonitrile to give the title compound (77 mg, 0.43 mmol, 77%, 95% purity) which was used in the next step without further purification. $^1$H NMR (400 MHz, DMSO-d6) δ: 4.10-3.96 (m, 2H), 3.13 (t, 1H), 2.61 (s, 3H).

Intermediate 222a. tert-Butyl 1-methyl-5-thioxopyrrolidine-2-carboxylate

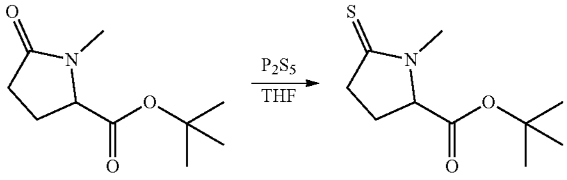

Int-222a

To a solution of tert-butyl 1-methyl-5-oxopyrrolidine-2-carboxylate (470 mg, 1 eq., 2.36 mmol) in THF (3 mL) phosphorus (V) sulfide (262 mg, 0.5 eq., 1.18 mmol) was added. The mixture was refluxed with stirring for 24 h. The solution was cooled and filtered. Chloroform (20 mL) was added, and the organic phase was washed with saturated sodium hydrocarbonate, (20 mL). The aqueous phase was extracted with chloroform (20 mL). The combined organic phases were dried and concentrated under vacuum to give the title compound (500 mg, 1.8 mmol, 76%, 77% purity) which was used in next step without further purification. GCMS: m/z 216.1 $[M]^+$.

Intermediate 222b. 1-Methyl-5-thioxopyrrolidine-2-carboxylic acid

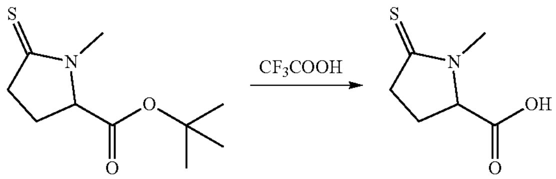

Int-222b tert-Butyl 1-methyl-5-thioxopyrrolidine-2-carboxylate (500 mg, 1 eq., 2.32 mmol) was dissolved in trifluoroacetic acid (2.65 g, 1.79 mL, 10 eq., 23.2 mmol) and the solution was stirred at RT for 12 h. Then the solvent was evaporated and the residue was dissolved in toluene (5 mL) and concentrated to remove excess of TFA to give the title compound (370 mg, 1.2 mmol, 50%, 50% purity) which was used in the next step without further purification.

Intermediate 223. N-(5-Hydroxy-2-methoxyphenyl)-1-methyl-5-oxo-pyrrolidine-2-carboxamide

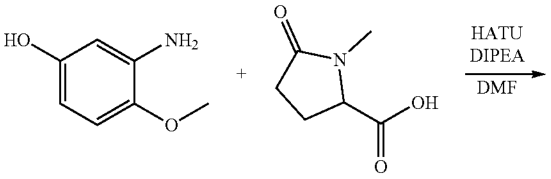

-continued

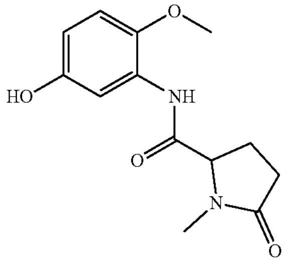

Int-223

1-Methyl-5-oxopyrrolidine-2-carboxylic acid (0.5 g, 1.2 eq., 3.49 mmol) was dissolved in N,N-dimethylformamide (5 mL) and HATU (1.33 g, 1.2 eq., 3.49 mmol) was added. The solution was stirred for 5 min at RT. To this solution, 3-amino-4-methoxyphenol hydrochloride (511 mg, 1 eq., 2.91 mmol) was added, followed by the addition of DIPEA (1.05 g, 1.42 mL, 2.8 eq., 8.15 mmol). The mixture was then stirred at RT for 2 h. The solvent was removed in vacuum. The crude material was dissolved in ethyl acetate (10 mL), washed with brine (50 mL) and water (50 mL), dried and the solvent was evaporated. The residue was purified using method B to give the title compound (0.0667 g). $^{1}H$ NMR (400 MHz, DMSO-d6) δ: 9.34 (s, 1H), 8.96 (s, 1H), 7.54 (s, 1H), 6.85 (d, 1H), 6.45 (d, 1H), 4.42 (d, 1H), 3.32 (s, 2H), 2.66 (s, 3H), 2.37-2.11 (m, 3H), 1.87 (s, 1H). LCMS: m/z 265.2 $[M+H]^{+}$.

The following intermediate was prepared according to the procedure described for Intermediate 223 from the starting material indicated in the table.

| No. | Structure | LCMS/ GCMS m/z | Starting materials |
|---|---|---|---|
| Int-224 | 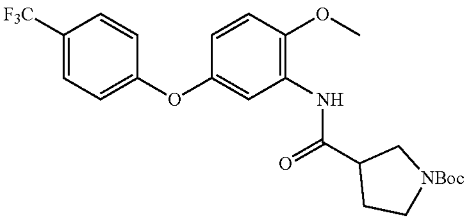 [SMILES: COc1ccc(Oc2ccc(C(F)(F)F)cc2)cc1NC(=O)C1CCN(C(=O)OC(C)(C)C)C1] | 479.5 $[M-H]^{-}$ | 2-Methoxy-5-(4-(trifluoromethyl)phenoxy)aniline and 1-(tert-Butoxycarbonyl)-pyrrolidine-3-carboxylic acid |
| Int-225 | 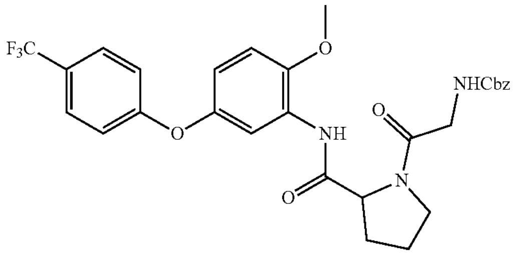 | 586.192 $(M+H)^{+}$ | 2-Methoxy-5-(4-(trifluoromethyl)phenoxy)aniline and 1-(((Benzyloxy)carbonyl)-glycyl)-5-oxopyrrolidine-2-carboxylic acid |

Intermediate 226. tert-Butyl (3-fluorophenyl)(4-methoxy-3-(5-oxopyrrolidine-2-carboxamido)benzyl)carbamate

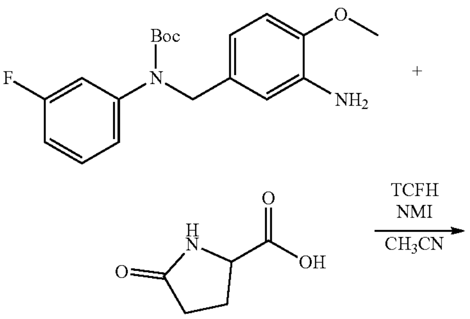

-continued

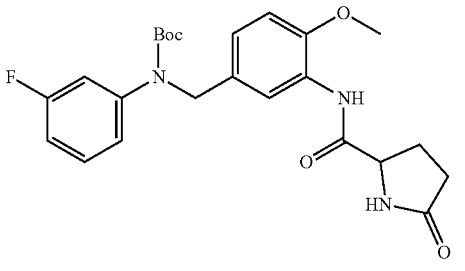

Int-226

To a mixture of tert-butyl (3-amino-4-methoxybenzyl)(3-fluorophenyl)carbamate (200 mg, 1 eq., 577 μmol), 5-oxopyrrolidine-2-carboxylic acid (74.5 mg, 1 eq., 577 μmol) and 1-methyl-1H-imidazole (237 mg, 5 eq., 2.89 mmol) in acetonitrile (4 mL) was added N-(chloro(dimethylamino)methylene)-N-methylmethanaminium hexafluorophosphate(V) (243 mg, 1.5 eq., 866 μmol). The mixture was stirred at RT for 18 h and then concentrated in vacuum. Water (20 mL) was added to the residue and the resulted mixture was extracted with ethyl acetate (2×20 mL). Organic layers were combined, washed with brine (20 mL), dried over sodium sulfate, filtered and evaporated to give the title compound (0.3 g) which was used in the next step without further purification. LCMS: m/z 358.0 $[M+H]^+$.

Intermediate 227a. Methyl 4-(methoxymethoxy)-2,3-dihydrobenzofuran-6-carboxylate

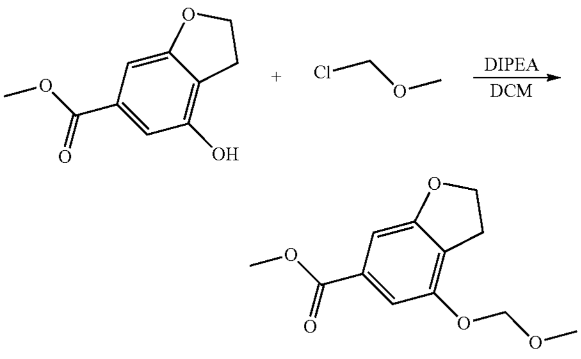

Int-227a

To the solution of methyl 4-hydroxy-2,3-dihydrobenzofuran-6-carboxylate (2 g, 1 eq., 10.30 mmol) and N-ethyl-N-isopropylpropan-2-amine (3.994 g, 5.38 mL, 3 eq., 30.90 mmol) in DCM (80 mL) chloro(methoxy)methane (1.309 g, 1.24 mL, 95 w-%, 1.5 eq., 15.45 mmol) was added at 0° C. followed by stirring the mixture at 20° C. for 18 h. The mixture was washed with brine (3×10 mL), dried over sodium sulfate, filtered and evaporated to afford the title compound (2.3 g, 8.834 mmol, 85.78%, 90.75% purity) which was used in the next step without further purification. $^1$H NMR (500 MHz, Chloroform-d) δ: 7.29 (s, 1H), 7.13 (s, 1H), 5.23 (s, 2H), 4.63 (t, 2H), 3.87 (s, 3H), 3.49 (s, 3H), 3.20 (t, 2H).

Intermediate 227b. (4-(Methoxymethoxy)-2,3-dihydrobenzofuran-6-yl)-methanol

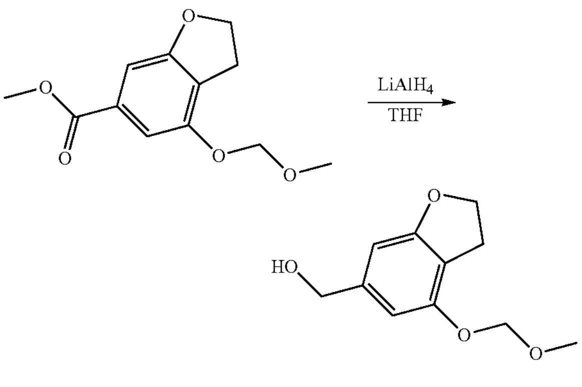

Int-227b

The solution of $LiAlH_4$ (127 mg, 2 eq., 3.36 mmol) in THF (5 mL) was cooled to 0° C. and the solution of methyl 4-(methoxymethoxy)-2,3-dihydrobenzofuran-6-carboxylate (400 mg, 1 eq., 1.68 mmol) in THF (5 mL) was added dropwise. The cooling bath was removed and the mixture was stirred at 20° C. for 18 h. The mixture was cooled to 0° C. and water (130 μL) and 30% solution of $K_2CO_3$ (4×130 μL) were added dropwise. The mixture was filtered and the residue was washed by THF (5 mL). The organic layer was separated and concentrated to afford the crude title compound (340 mg, 1.48 mmol, 88.0%, 91.31% purity) as yellow oil, which was used in the next step without further purification. $^1$H NMR (400 MHz, Chloroform-d) δ: 6.59 (s, 1H), 6.48 (s, 1H), 5.17 (s, 2H), 4.66-4.48 (m, 4H), 3.47 (s, 3H), 3.14 (t, 2H).

Intermediate 227c. 5-((3,4-Difluorophenoxy)methyl)-4-(methoxymethoxy)-2,3-dihydrobenzofuran

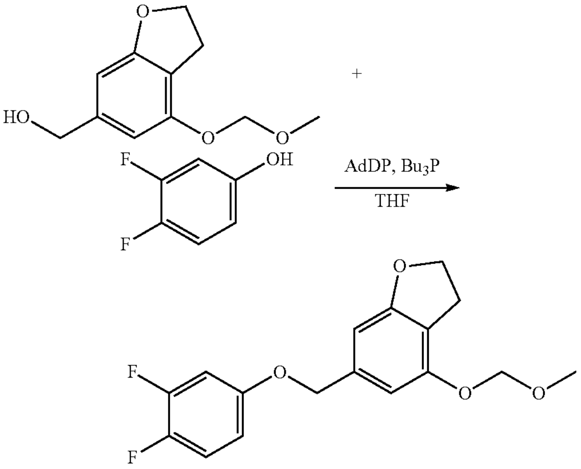

Int-227c

To the mixture of (7-(methoxymethoxy)-2,3-dihydrobenzofuran-5-yl)methanol (200 mg, 1 eq., 951 μmol) and 3,4-difluorophenol (124 mg, 1 eq., 951 μmol) in THF (40 mL) at 0° C. under Ar atmosphere were added tributylphosphane (385 mg, 0.48 mL, 2 eq., 1.90 mmol) and then (E)-diazene-1,2-diylbis(piperidin-1-ylmethanone) (480 mg, 2 eq., 1.90 mmol). The mixture was stirred at 20° C. for 18 h. The solvent of the mixture was evaporated under reduced pressure. The residue was purified by reverse phase HPLC (water-acetonitrile) to afford the title compound (178 mg, 552 μmol, 58.1%). $^1$H NMR (500 MHz, Chloroform-d) δ: 7.04 (q, 1H), 6.83-6.71 (m, 1H), 6.64 (s, 2H), 6.54 (s, 1H), 5.19 (s, 2H), 4.92 (s, 2H), 4.60 (t, 2H), 3.49 (s, 3H), 3.17 (t, 2H).

Intermediate 227d. 5-((3,4-Difluorophenoxy)methyl)-2,3-dihydrobenzofuran-4-ol

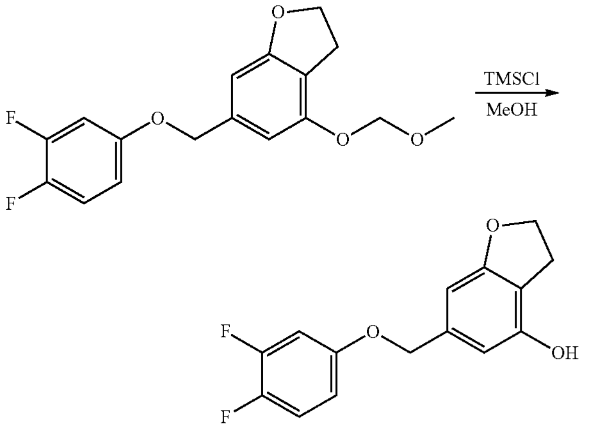

Int-227d

Chlorotrimethylsilane (146 mg, 170 μL, 2 eq., 1.34 mmol) was added to MeOH (4 mL) at 0° C. dropwise. The mixture was stirred for 30 min and 5-((3,4-difluoro-phenoxy)methyl)-4-(methoxymethoxy)-2,3-dihydrobenzofuran (216 mg, 1 eq., 670 μmol) in MeOH (1 mL) was added followed by stirring at 20° C. for 18 h. The mixture was concentrated under reduced pressure to give crude title compound (178 mg, 623 μmol, 92.9%, 97.37% purity) as a beige solid. $^1$H NMR (500 MHz, DMSO-d6) δ: 9.50 (s, 1H), 7.34-7.27 (m, 1H), 7.14-7.01 (m, 1H), 6.83-6.73 (m, 1H), 6.34 (s, 1H), 6.28 (s, 1H), 4.92 (s, 2H), 4.47 (t, 2H), 2.99 (t, 2H).

Intermediate 227e. 6-((3,4-Difluorophenoxy)methyl)-2,3-dihydrobenzofuran-4-yl trifluoromethanesulfonate

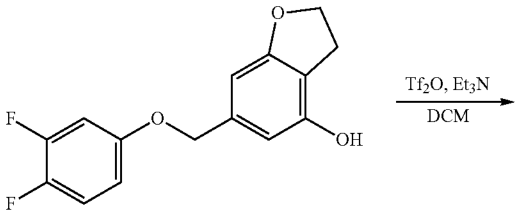

-continued

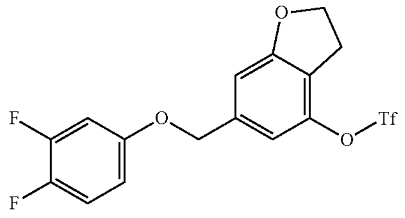

Int-227e

To a solution of 5-((3,4-difluorophenoxy)methyl)-2,3-dihydrobenzofuran-4-ol (178 mg, 1 eq., 640 μmol) and triethylamine (84.2 mg, 116 μL, 1.3 eq., 832 μmol) in DCM (5 mL) trifluoromethanesulfonic anhydride (199 mg, 118 μL, 1.1 eq., 704 μmol) was added dropwise at 0° C. followed by stirring the mixture at 20° C. for 18 h. DCM (10 mL) was added to mixture and the solution was washed with $NaHSO_4$ solution (2×5 mL), dried over sodium sulfate, filtered and evaporated to give the title compound (238 mg, 0.52 mmol, 82%, 90% purity) as a brown oil, which was used in the next step without further purification. $^1$H NMR (500 MHz, Chloroform-d) δ: 7.06 (q, 1H), 6.84 (s, 1H), 6.80 (s, 1H), 6.79-6.72 (m, 1H), 6.66-6.60 (m, 1H), 4.96 (s, 2H), 4.68 (t, 2H), 3.34 (t, 2H).

Intermediate 228. 2-Methoxy-5-(4-(trifluoromethyl)phenoxy)benzoic acid

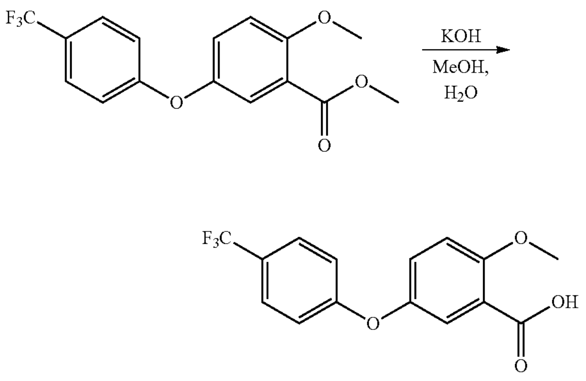

Int-228

Solution of potassium hydroxide (51.6 mg, 1.5 eq., 919 μmol) in water (0.6 mL) was added to a solution of methyl 2-methoxy-5-(4-(trifluoromethyl)phenoxy)-benzoate (0.200 g, 1 eq., 613 μmol) in methanol (5 mL). The mixture was stirred for 16 h at 25° C. and then concentrated under reduced pressure. The residue was dissolved in water (5 mL) and washed with EtOAc (2×2 mL). The aqueous mixture was acidified with $NaHSO_4$ (5 mL, 15% in water). The resulting mixture was extracted with EtOAc (2×8 mL). The combined organic layers were dried under sodium sulfate and concentrated under reduced pressure to give the title compound (0.08 g, 0.26 mmol, 42%). LCMS: m/z 311.0 $[M-H]^-$.

Intermediate 229. 1-Methoxy-3-nitro-5-(4-(trifluoromethyl)phenoxy)benzene

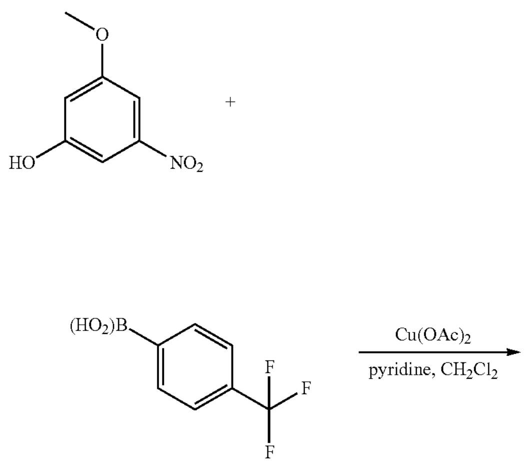

-continued

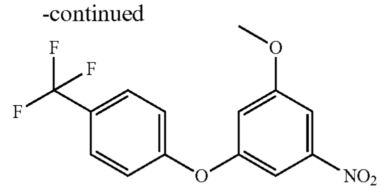

Int-229

3-Methoxy-5-nitrophenol (0.5 g, 1 eq., 2.96 mmol), 4-trifluorophenylboronic acid (0.7 g, 1.5 eq., 4.43 mol), pyridine (1.2 g, 1.2 mL, 5 eq., 14.8 mol), diacetoxycopper (0.54 g, 1 eq., 2.96 mmol) and powdered molecular sieves 4 Å (1 g) were suspended in DCM (15 ml). The air was bubbled through the resulting solution for 30 min and the mixture was stirred at RT overnight. The mixture was filtered, the filtrate was washed with water (2×30 mL), dried over sodium sulfate, filtered and the solvent was removed under reduced pressure. The residue was purified by method A to afford the title compound. LCMS: m/z 314.2 $[M+H]^+$.

The following intermediates were prepared according to the procedure described for Intermediate 229 from the starting material indicated in the table.

| No. | Structure | LCMS/ GCMS m/z | Starting materials |
|---|---|---|---|
| Int-230 | 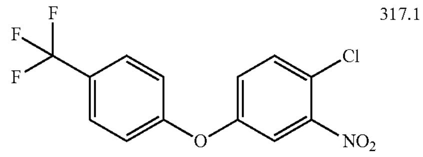 | 317.1 $[M]^+$ | 4-(Trifluoromethyl)phenylboronic acid and 4-Chloro-3-nitrophenol |
| Int-231 | 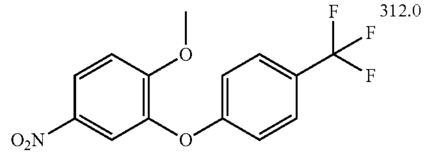 | 312.0 $[M + H]^+$ | 4-(Trifluoromethyl)phenylboronic acid and (2-Methoxy-5-nitrophenol |
| Int-232 | 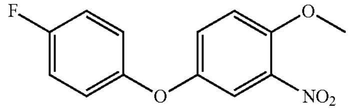 | 264.0 $[M + H]^+$ | 4-Methoxy-3-nitrophenol and 4-Fluorobenzeneboronic acid |
| Int-233 | 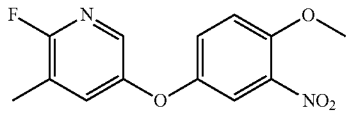 | 279.1 $[M + H]^+$ | 4-Methoxy-3-nitrophenol and (6-Fluoro-5-methylpyridin-3-yl)-boronic acid |
| Int-234 | 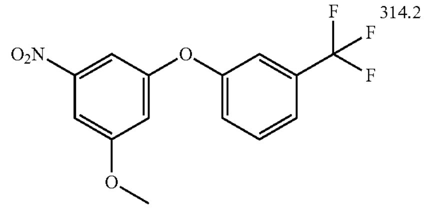 | 314.2 $[M + H]^+$ | 3-Bromo-5-nitro anisole and 3-(Trifluoromethyl)phenol |

-continued

| No. | Structure | LCMS/ GCMS m/z | Starting materials |
|---|---|---|---|
| Int-235 | 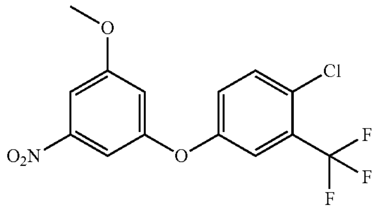 [SMILES: COc1cc(Oc2ccc(Cl)c(C(F)(F)F)c2)cc([N+](=O)[O-])c1] | 346.3 [M + H]$^+$ | 3-Bromo-5-nitro anisole and 4-Chloro-3-(trifluoromethyl)-phenol |
| Int-236 | 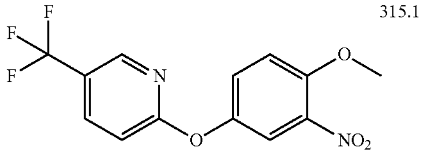 | 315.1 [M + H]$^+$ | 4-Methoxy-3-nitrophenol and 2-Chloro-5-(trifluoromethyl)-pyridine |
| Int-237 | 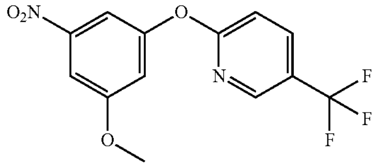 [SMILES: COc1cc(Oc2ccc(C(F)(F)F)cn2)cc([N+](=O)[O-])c1] | 316.1 [M + H]$^+$ | 3-Methoxy-5-nitrophenol and 2-Chloro-5-(trifluoromethyl)-pyridine |
| Int-238 | 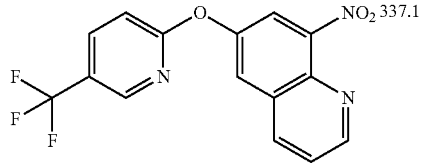 | 337.1 [M + H]$^+$ | 8-Nitroquinolin-6-ol and 2-Chloro-5-(trifluoromethyl)-pyridine |
| Int-239 | 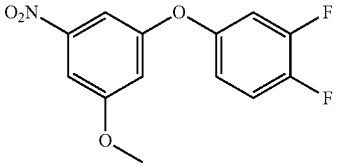 [SMILES: COc1cc(Oc2ccc(F)c(F)c2)cc([N+](=O)[O-])c1] | 283.1 [M + H]$^+$ | 3,4-Difluorophenylboronic acid and 3-Methoxy-5-nitrophenol |

Intermediate 240. 1-Methoxy-2-nitro-4-((4-(trifluoromethyl)cyclohexyl)oxy)-benzene

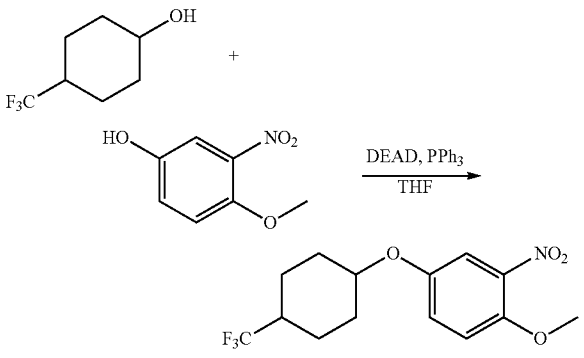

Int-240

To a mixture of 4-methoxy-3-nitrophenol (0.25 g, 1.47 mmol), 4-trifluoro-methyl-1-hydroxycyclohexane (0.20 ml, 1.47 mmol) and triphenylphosphine (465 mg, 1.77 mmol) in anhydrous THF (10 mL) under nitrogen was added DEAD (0.28 ml, 1.77 mmol) dropwise at RT and the mixture was left stirring for 24 h. The mixture was diluted with $Et_2O$ (30 ml) and washed with NaOH (2×10 ml), water (10 ml) and brine (10 ml). The organic phase was dried over sodium sulfate, filtered and concentrated. The crude residue was purified further with the purification method A to give 0.1 g of the title compound. LCMS: m/z 320.28 [M+H]$^+$ The following intermediates were prepared according to the procedure described for Intermediate 240 from the starting material indicated in the table.

| No. | Structure | LCMS/ GCMS m/z | Starting materials |
|---|---|---|---|
| Int-241 | 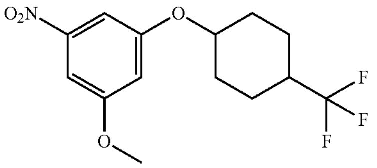 [SMILES: COc1cc(OC2CCC(C(F)(F)F)CC2)cc([N+](=O)[O-])c1] | 320.1 [M + H]$^+$ | 3-Methoxy-5-nitrophenol and 4-Trifluoromethyl-1-hydroxy-cyclohexane |
| Int-242 | 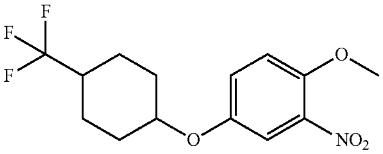 [SMILES: COc1ccc(OC2CCC(C(F)(F)F)CC2)cc1[N+](=O)[O-]] | 320.1 [M + H]$^+$ | 4-Methoxy-3-nitrophenol and 4-Trifluoromethyl-1-hydroxy-cyclohexane |
| Int-243 | 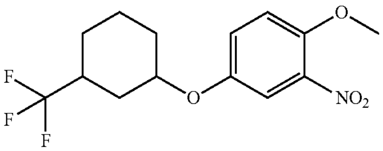 [SMILES: COc1ccc(OC2CCCC(C(F)(F)F)C2)cc1[N+](=O)[O-]] | 320.2 [M + H]$^+$ | 4-Methoxy-3-nitrophenol and 3-(Trifluoromethyl)cyclohexanol, mixture of cis/trans isomers |
| Int-244 | 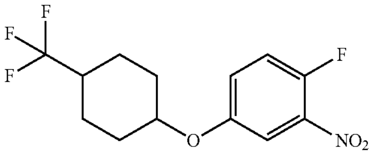 [SMILES: O=[N+]([O-])c1cc(OC2CCC(C(F)(F)F)CC2)ccc1F] | 320.2 [M + H]$^+$ | 4-Fluoro-3-nitrophenol and 4-Trifluoromethyl-1-hydroxy-cyclohexane |
| Int-245 | 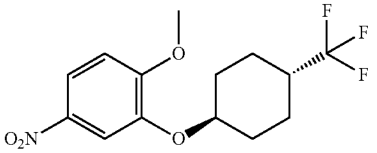 | 320.3 [M + H]$^+$ | 2-Methoxy-5-nitrophenol and 4-Trifluoromethyl-1-hydroxy-cyclohexane |
| Int-246 | 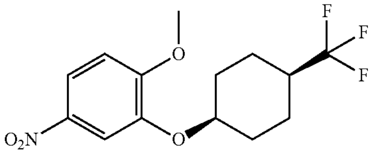 [SMILES: COc1ccc([N+](=O)[O-])cc1O[C@H]1CC[C@@H](C(F)(F)F)CC1] | 320.3 [M + H]$^+$ | 2-Methoxy-5-nitrophenol and 4-Trifluoromethyl-1-hydroxy-cyclohexane |
| Int-247 | 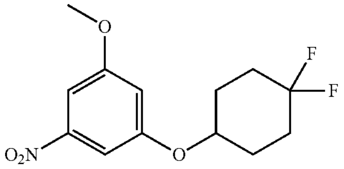 | 288.1 [M + H]$^+$ | 3-Methoxy-5-nitrophenol and 1,1-Difluoro-4-hydroxycyclo-hexane |

Intermediate 248. (E)-4-(3-Fluorostyryl)-1-methoxy-2-nitrobenzene

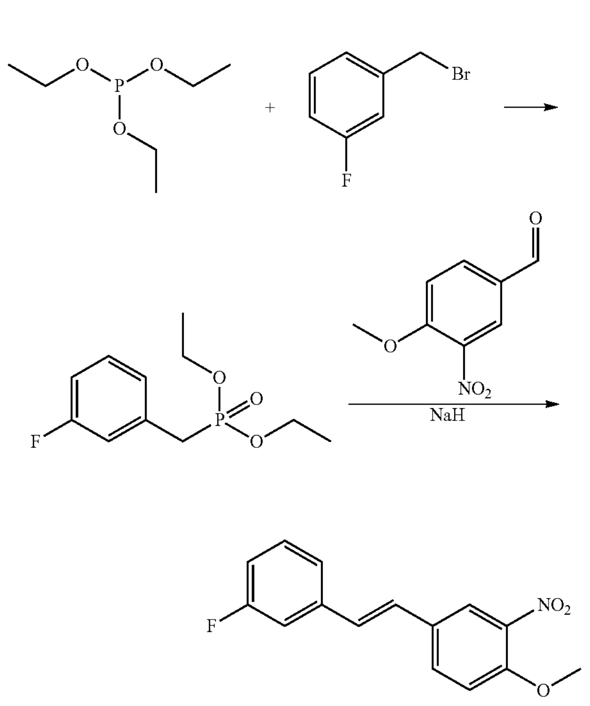

Int-248

Triethyl phosphine (5.6 ml, 32.6 mmol) was added to 3-fluorobenzyl bromide (2.0 ml, 16.3 mmol) at RT under $N_2$. The resulting mixture was heated at 150° C. for 2 h. The mixture was cooled and purified by flash chromatography to yield diethyl (3-fluorobenzyl)phosphonate. To the mixture of diethyl (3-fluorobenzyl)phosphonate (0.82 g, 3.3 mmol) in dry THF (10 ml) at 0-5° C. was added NaH (0.27 g, 11.0 mmol). After 30 min 4-methoxy-3-nitro benzaldehyde (0.5 g, 2.8 mmol) in dry THF (10 ml) was added dropwise to the mixture followed by stirred at RT for 3 h. The mixture was cooled, quenched with ice water (20 ml), made acidic with 2 M HCl and then extracted with ethyl acetate (2×10 ml). The combined organic layers were washed with water, dried, evaporated and then purified by flash chromatography to yield the title compound.

LCMS m/z 274.2 $[M+H]^+$. $^1H$ NMR (Chloroform-d, 400 MHz) δ: 8.0-8.0 (m, 1H), 7.6-7.7 (m, 1H), 7.2-7.4 (m, 4H), 6.9-7.1 (m, 3H), 3.99 (s, 3H).

Intermediate 249. 1-Methoxy-2-nitro-4-(3-(trifluoromethyl)benzyl)benzene

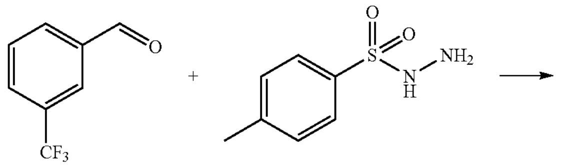

-continued

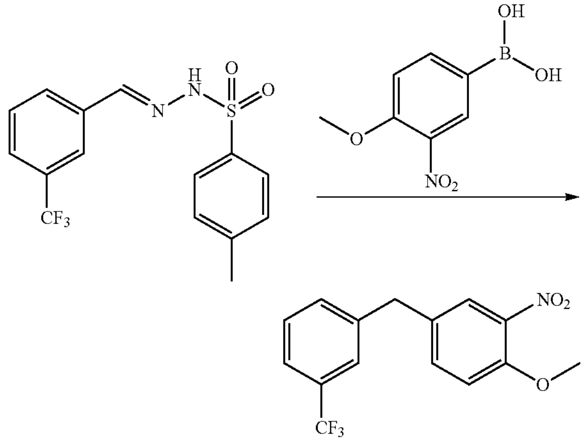

Int-249

A mixture of 3-(trifluoromethyl)benzaldehyde (0.20 ml, 1.4 mmol) and toluene sulfonhydrazide (0.27 g, 1.4 mmol) in 1,4-dioxane (10 ml) was heated at 60° C. for 90 min. To the obtained crude product of (E)-4-methyl-N'-(3-(trifluoromethyl)benzylide-ne)benzenesulfonohydrazide (0.4 g, 1.168 mmol) was added $K_2CO_3$ (0.24 g, 1.8 mmol) and 4-methoxy-3-nitrophenylboronic acid (0.23 g, 1.2 mmol). The mixture was heated under nitrogen atmosphere at 110° C. for 4 h followed by cooling to RT. The mixture was quenched with 2 M $NaHCO_3$ (5 ml) and then extracted with ethyl acetate (2×10 ml). The combined organic layers were washed with water, dried, evaporated and purified by flash chromatography to yield the title compound. LCMS m/z 312.3 $[M+H]^+$. $^1H$ NMR (400 MHz, Chloroform-d) δ: 3.89-4.00 (m, 3H), 4.02 (s, 2H), 7.03 (d, 1H), 7.27-7.35 (m, 3H), 7.49-7.62 (m, 2H), 7.65-7.70 (m, 1H).

Intermediate 250. 1-Methoxy-2-nitro-4-(4-(trifluoromethyl)benzyl)benzene

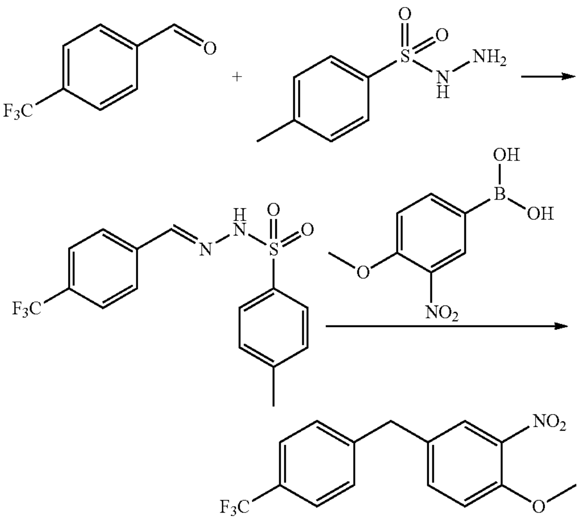

Int-250

1-Methoxy-2-nitro-4-(4-(trifluoromethyl)benzyl)benzene was prepared using the procedure described for Intermediate 234 using 4-(trifluoromethyl)benzaldehyde as starting material. LCMS m/z 312.3 $[M+H]^+$. $^1H$ NMR (400 MHz, Chloroform-d) δ: 3.90-4.04 (m, 5H), 6.99-7.26 (m, 1H), 7.32-7.34 (m, 1H), 7.39-7.63 (m, 4H), 7.69 (d, 1H).

Intermediate 251. 1-Methoxy-2-nitro-4-(4-(trifluoromethyl)benzyl)benzene

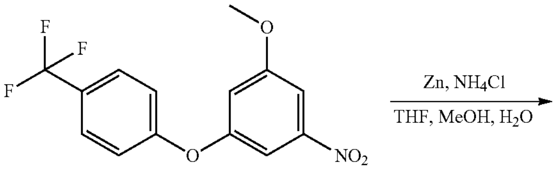

-continued

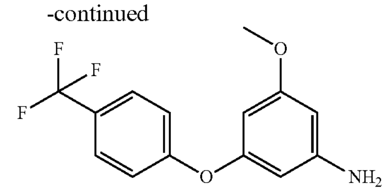

Int-251

A mixture of 1-methoxy-3-nitro-5-(4-(trifluoromethyl)phenoxy)benzene (0.1 g, 1 eq., 0.32 mmol), zinc (0.21 g, 10 eq., 3.2 mmol), ammonium chloride (0.17 g, 10 eq., 3.2 mmol) in THF (5 ml), MeOH (2.5 ml) and water (2.5 ml) was stirred at RT for 4 h. The mixture was filtered through celite. The filtrate was washed with water (2>30 mL), dried over sodium sulfate, filtered and the solvent was removed under reduced pressure. The residue was purified by flash chromatography to afford the title compound. LCMS m/z 284.1 $[M]^+$ The following intermediates were prepared according to the procedure described for Intermediate 251 from the starting material indicated in the table.

| No. | Structure | LCMS/ GCMS m/z | Starting materials |
|---|---|---|---|
| Int-252 | 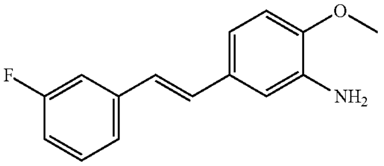 [SMILES: COc1ccc(/C=C/c2cccc(F)c2)cc1N] | 244.2 $[M + H]^+$ | (E)-4-(3-fluorostyryl)-1-methoxy-2-nitrobenzene |
| Int-253 | 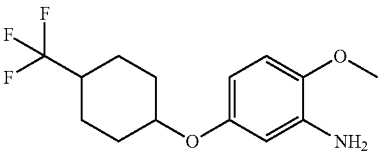 | 290.6 $[M + H]^+$ | 1-Methoxy-2-nitro-4-((4-(trifluoromethyl)cyclohexyl)oxy)-benzene |
| Int-254 | 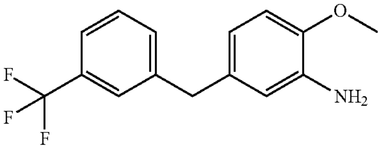 [SMILES: COc1ccc(Cc2cccc(C(F)(F)F)c2)cc1N] | 282.2 $[M + H]^+$ | 1-Methoxy-2-nitro-4-(3-(trifluoromethyl)benzyl)benzene |
| Int-255 | 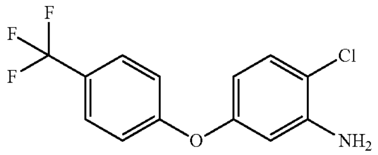 | 286.1 $[M]^+$ | 1-Chloro-2-nitro-4-(4-(trifluoromethyl)phenoxy)benzene |
| Int-256 | 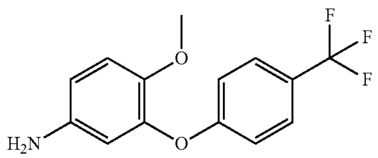 [SMILES: COc1ccc(N)cc1Oc1ccc(C(F)(F)F)cc1] | 284.1 $[M + H]^+$ | 1-Methoxy-4-nitro-2-(4-(trifluoromethyl)phenoxy)benzene |
| Int-257 | 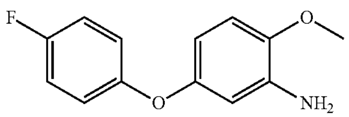 [SMILES: COc1ccc(Oc2ccc(F)cc2)cc1N] | 234.1 $[M + H]^+$ | 4-(4-Fluorophenoxy)-1-methoxy-2-nitrobenzene |

-continued

| No. | Structure | LCMS/ GCMS m/z | Starting materials |
| --- | --- | --- | --- |
| Int-258 | 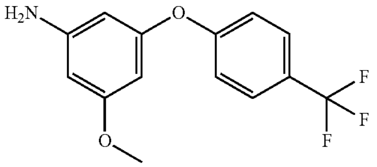 | 284.1 [M + H]$^+$ | 1-Methoxy-3-nitro-5-(4-(trifluoromethyl)phenoxy)benzene |
| Int-259 | 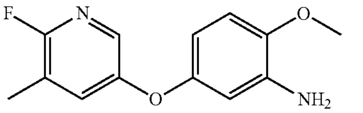 | 249.3 [M + H]$^+$ | 2-Fluoro-5-(4-methoxy-3-nitrophenoxy)-3-methylpyridine |
| Int-260 | 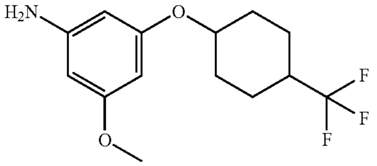 | 291.1 [M + H]$^+$ | 1-Methoxy-3-nitro-5-((4-(trifluoromethyl)cyclohexyl)oxy)benzene |
| Int-261 | 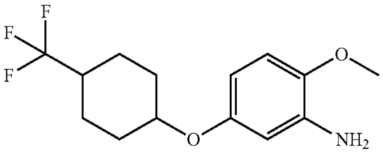 | 291.1 [M + H]$^+$ | 1-Methoxy-2-nitro-4-((4-(trifluoromethyl)cyclohexyl)oxy)benzene |
| Int-262 | 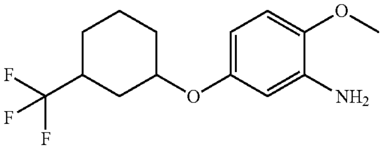 [SMILES: COc1ccc(OC2CCCC(C(F)(F)F)C2)cc1N] | 291.2 [M + H]$^+$ | 1-Methoxy-2-nitro-4-((3-(trifluoromethyl)cyclohexyl)oxy)benzene |
| Int-263 | 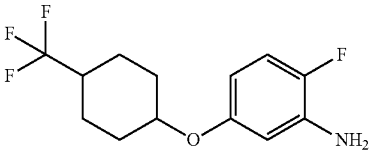 | 278.1 [M + H]$^+$ | 1-Fluoro-2-nitro-4-((4-(trifluoromethyl)cyclohexyl)oxy)benzene |
| Int-264 | 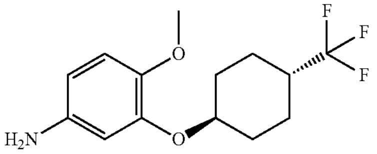 | 290.1 [M + H]$^+$ | 1-Methoxy-4-nitro-2-(((1r,4r)-4-(trifluoromethyl)cyclohexyl)oxy)benzene |
| Int-265 | 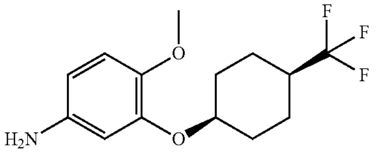 | 290.1 [M + H]$^+$ | 1-Methoxy-4-nitro-2-(((1s,4s)-4-(trifluoromethyl)cyclohexyl)oxy)benzene |
| Int-266 | 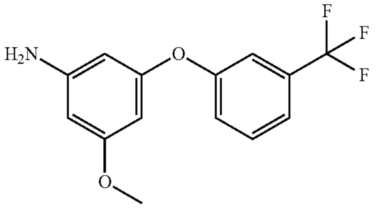 | 284.3 [M + H]$^+$ | 1-Methoxy-3-nitro-5-(3-(trifluoromethyl)phenoxy)benzene |

-continued

| No. | Structure | LCMS/ GCMS m/z | Starting materials |
|---|---|---|---|
| Int-267 | 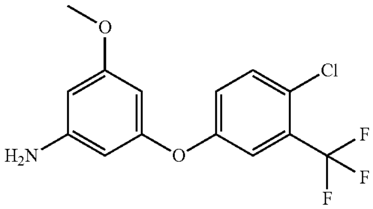 | 318.2 [M + H]+ | 1-Chloro-4-(3-methoxy-5-nitro-phenoxy)-2-(trifluoromethyl)-benzene |
| Int-268 | 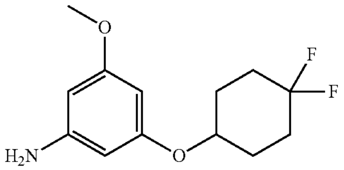 | 259.1 [M + H]+ | 1-((4,4-Difluorocyclohexyl)-oxy)-3-methoxy-5-nitrobenzene |
| Int-269 | 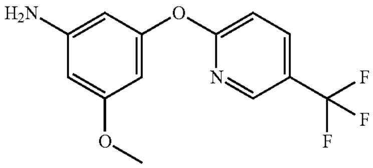 | 286.1 [M + H]+ | 2-(3-Methoxy-5-nitrophenoxy)-5-(trifluoromethyl)pyridine |
| Int-270 | 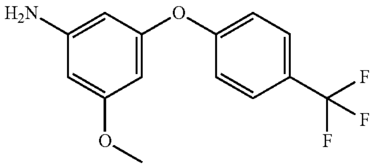 | 284.1 [M + H]+ | 1-Methoxy-3-nitro-5-(4-(tri-fluoromethyl)phenoxy)benzene |
| Int-271 | 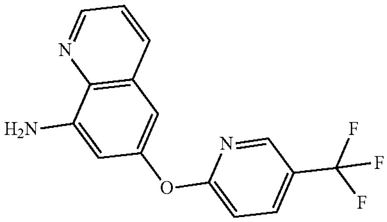 [SMILES: Nc1cc(Oc2ccc(C(F)(F)F)cn2)cc2cccnc12] | 306.0 [M + H]+ | 8-Nitro-6-((5-(trifluoromethyl)-pyridin-2-yl)oxy)quinolone |
| Int-272 | 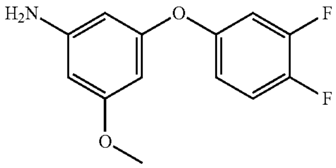 | 254.0 [M + H]+ | 1,2-Difluoro-4-(3-methoxy-5-nitrophenoxy)benzene |
| Int-273 | 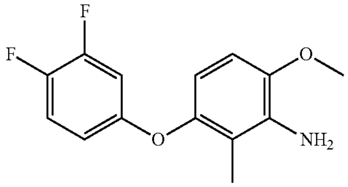 [SMILES: COc1ccc(Oc2ccc(F)c(F)c2)c(C)c1N] | 265.6 [M + H]+ | 1-(3,4-Difluorophenoxy)-4-methoxy-2-methyl-3-nitro-benzene |
| Int-274 | 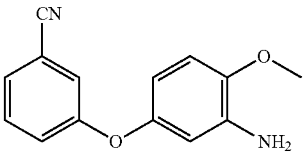 [SMILES: COc1ccc(Oc2cccc(C#N)c2)cc1N] | 241.5 [M + H]+ | 3-(4-Methoxy-3-nitrophenoxy)-benzonitrile |

-continued

| No. | Structure | LCMS/ GCMS m/z | Starting materials |
|---|---|---|---|
| Int-275 | 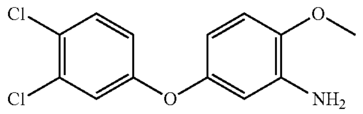 [SMILES: COc1ccc(Oc2ccc(Cl)c(Cl)c2)cc1N] | 285.1 [M + H]$^+$ | 1,2-Dichloro-4-(4-methoxy-3-nitrophenoxy)benzene |
| Int-276 | 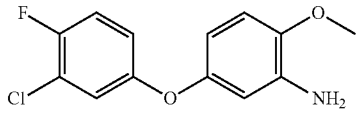 | 267.1 [M + H]$^+$ | 2-Chloro-1-fluoro-4-(4-methoxy-3-nitrophenoxy)-benzene |
| Int-277 | 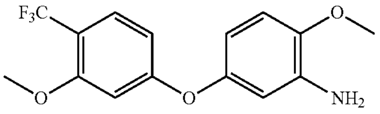 | 314.5 [M + H]$^+$ | 2-Methoxy-4-(4-methoxy-3-nitrophenoxy)-1-(trifluoro-methyl)benzene |
| Int-278 | 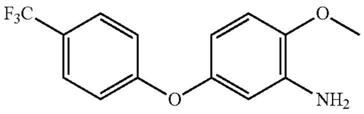 | 284.4 [M + H]$^+$ | 1-Methoxy-2-nitro-4-(4-(tri-fluoromethyl)phenoxy)benzene |
| Int-279 | 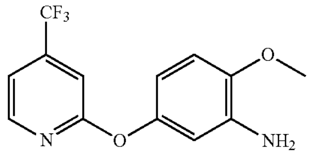 | 285.5 [M + H]$^+$ | 2-(4-Methoxy-3-nitrophenoxy)-4-(trifluoromethyl)pyridine |
| Int-280 | 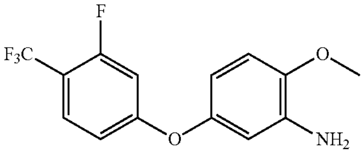 [SMILES: COc1ccc(Oc2ccc(C(F)(F)F)c(F)c2)cc1N] | 302.5 [M + H]$^+$ | 2-Fluoro-4-(4-methoxy-3-nitro-phenoxy)-1-(trifluoromethyl)-benzene |
| Int-281 | 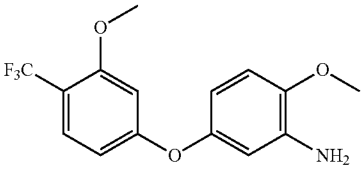 [SMILES: COc1ccc(Oc2ccc(C(F)(F)F)c(OC)c2)cc1N] | 314.5 [M + H]$^+$ | 2-Methoxy-4-(4-methoxy-3-nitrophenoxy)-1-(trifluoro-methyl)benzene |
| Int-282 | 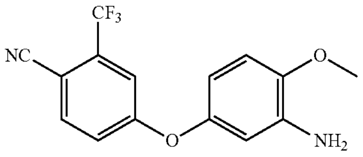 [SMILES: COc1ccc(Oc2ccc(C#N)c(C(F)(F)F)c2)cc1N] | 309.5 [M + H]$^+$ | 4-(4-Methoxy-3-nitrophenoxy)-2-(trifluoromethyl)benzonitrile |
| Int-283 | 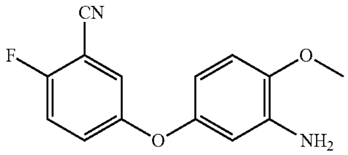 [SMILES: COc1ccc(Oc2ccc(F)c(C#N)c2)cc1N] | 259.5 [M + H]$^+$ | 2-Fluoro-5-(4-methoxy-3-nitro-phenoxy)benzonitrile |
| Int-284 | 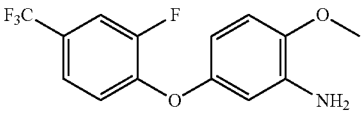 [SMILES: COc1ccc(Oc2ccc(C(F)(F)F)cc2F)cc1N] | 302.4 [M + H]$^+$ | 2-Fluoro-1-(4-methoxy-3-nitro-phenoxy)-4-(trifluoromethyl)-benzene |

-continued

| No. | Structure | LCMS/ GCMS m/z | Starting materials |
|---|---|---|---|
| Int-285 | 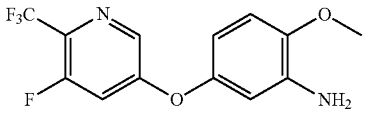 | 303.3 [M + H]$^+$ | 3-Fluoro-5-(4-methoxy-3-nitro-phenoxy)-2-(trifluoromethyl)-pyridine |
| Int-286 | 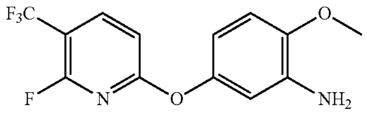 [SMILES: COc1ccc(Oc2ccc(C(F)(F)F)c(F)n2)cc1N] | 303.3 [M + H]$^+$ | 2-Fluoro-6-(4-methoxy-3-nitro-phenoxy)-3-(trifluoromethyl)-pyridine |
| Int-287 | 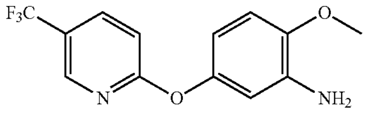 [SMILES: COc1ccc(Oc2ccc(C(F)(F)F)cn2)cc1N] | 285.4 [M + H]$^+$ | 2-(4-Methoxy-3-nitrophenoxy)-5-(trifluoromethyl)pyridine |
| Int-288 | 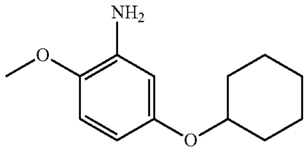 [SMILES: COc1ccc(OC2CCCCC2)cc1N] | 222.2 [M + H]$^+$ | 4-(Cyclohexyloxy)-1-methoxy-2-nitrobenzene |
| Int-289 | 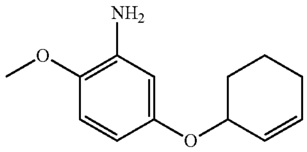 [SMILES: COc1ccc(OC2C=CCCC2)cc1N] | 220.2 [M + H]$^+$ | 4-(Cyclohex-2-en-1-yloxy)-1-methoxy-2-nitrobenzene |

Intermediate 290. 2-Methoxy-5-(3-(trifluoromethoxy)phenoxy)aniline

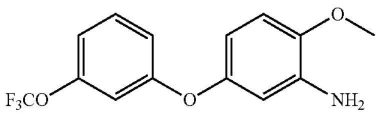 [SMILES: COc1ccc(Oc2cccc(OC(F)(F)F)c2)cc1N]

A mixture of 1-methoxy-2-nitro-4-(3-(trifluoromethoxy) phenoxy)benzene 5 (0.050 g, 0.152 mol), zinc powder (0.050 g, 0.759 mmol), $NH_4Cl$ (0.041 g, 0.759 mmol), ethanol (1.5 ml) and water (0.5 ml) was stirred at 50° C. until the reaction was completed. The mixture was filtered through a pad of Celite. Celite layer was further washed with ethanol and the filtrate was evaporated to afford 0.040 g of the title compound. LCMS: m/z 299.8 [M+H]$^+$.

Intermediate 291. 5-(4-Isopropoxyphenoxy)-2-methoxyaniline

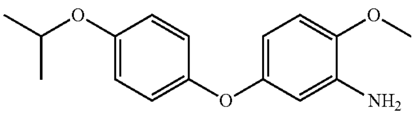 [SMILES: COc1ccc(Oc2ccc(OC(C)C)cc2)cc1N]

The compound was prepared according to the procedure of Intermediate 257 starting from 4-(4-isopropoxyphenoxy)-1-methoxy-2-nitrobenzene (0.22 g, 0.725 mmol) using 4 eq. of zinc powder and 4 eq. of $NH_4Cl$. Raw product was purified by reverse phase flash chromatography to afford the title compound. Yield: 0.044 g. LCMS: m/z 273.9 [M+H]$^+$.

Intermediate 292. 2-Methoxy-5-(4-(trifluoromethoxy)phenoxy)aniline

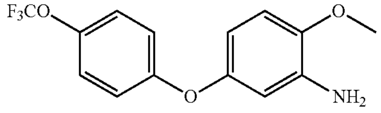 [SMILES: COc1ccc(Oc2ccc(OC(F)(F)F)cc2)cc1N]

A mixture of 1-methoxy-2-nitro-4-(4-(trifluoromethoxy) phenoxy)benzene (0.12 g, 0.364 mol), iron powder (0.061 g, 1.093 mmol), anhydrous $CaCl_2$) (0.040 g, 0.364 mmol), ethanol (1.0 ml) and water (0.25 ml) was stirred at 60° C. until the reaction was completed. The mixture was filtered through a pad of Celite. Celite layer was washed with EtOAc. The filtrate was washed with water (2×), dried and evaporated to afford 0.090 g of the title compound. LCMS: m/z 299.7 [M]$^+$ The following intermediates were prepared according to the procedure described for Intermediate 292 from the starting material indicated in the table.

| No. | Structure | LCMS m/z | Starting materials |
|---|---|---|---|
| Int-293 | 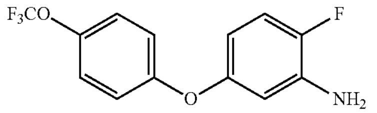 | 287.9 $[M]^+$ | 1-Fluoro-2-nitro-4-(4-(trifluoro-methoxy)phenoxy)benzene |
| Int-294 | 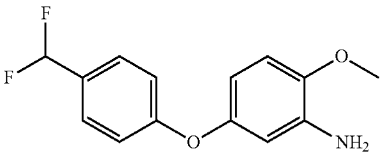 | 265.6 $[M]^+$ | 4-(4-(Difluoromethyl)phenoxy)-1-methoxy-2-nitrobenzene |
| Int-295 | 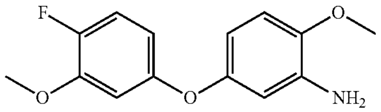 | 263.6 $[M]^+$ | 1-Fluoro-2-methoxy-4-(4-methoxy-3-nitrophenoxy)-benzene |
| Int-296 | 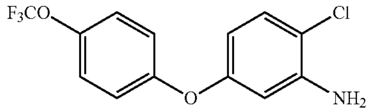 | 304.5 $[M + H]^+$ | 1-Chloro-2-nitro-4-(4-(trifluoro-methoxy)phenoxy)benzene |

Intermediate 297. 2-Amino-4-(4-(trifluoromethyl)phenoxy)benzamide

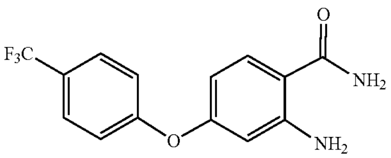 [SMILES: NC(=O)c1ccc(Oc2ccc(C(F)(F)F)cc2)cc1N]

The compound was prepared according to the procedure of Intermediate 292 starting from 2-nitro-4-(4-(trifluoromethyl)phenoxy)benzonitrile (0.36 g, 1.168 mmol). Raw product was purified by flash chromatography to afford the title compound. Yield: 0.21 g. LCMS: m/z 296.8 $[M]^+$.

Intermediate 298. 5-(Cyclohexylmethoxy)-2-methoxyaniline

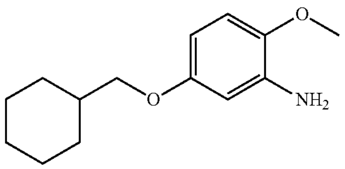

A mixture of 4-(cyclohexylmethoxy)-1-methoxy-2-nitrobenzene (0.26 g, 0.98 mol), zinc powder (0.32 g, 4.90 mmol, 5.0 eq.), $NH_4Cl$ (0.262 g, 4.90 mmol, 5.0 eq.), THF (3.0 ml), methanol (0.75 ml) and water (0.75 ml) was stirred at RT until the reaction was completed. The mixture was filtered through a pad of Celite. Celite layer was washed with EtOAc. The filtrate was washed with water (2×), dried and evaporated. Crude was purified by flash chromatography to afford 0.15 g of the title compound. LCMS: m/z 235.4 $[M]^+$ The following intermediates were prepared according to the procedure described for Intermediate 298 from the starting material indicated in the table.

| No. | Structure | Purification; LCMS m/z | Starting materials |
|---|---|---|---|
| Int-299 | 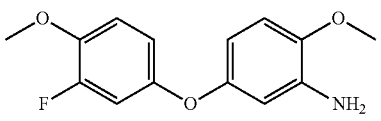 | Crude; 263.6 $[M]^+$ | 2-Fluoro-1-methoxy-4-(4-methoxy-3-nitrophenoxy)-benzene |
| Int-300 | 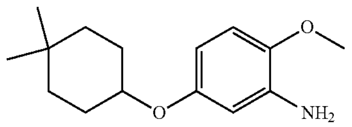 | Crude; 249.4 $[M]^+$ | 4-((4,4-Dimethylcyclohexyl)-oxy)-1-methoxy-2-nitro-benzene |

-continued

| No. | Structure | Purification; LCMS m/z | Starting materials |
|---|---|---|---|
| Int-301 | 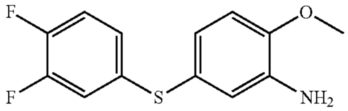 | Flash chromatography; 267.7 $[M]^+$ | (3,4-Difluorophenyl)(4-methoxy-3-nitrophenyl)sulfane |
| Int-302 | 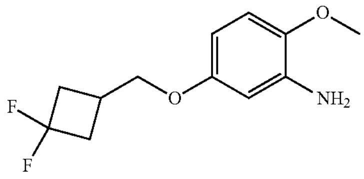 [SMILES: COc1ccc(OCC2CC(F)(F)C2)cc1N] | Crude; 244.6 $[M + H]^+$ | 4-((3,3-Difluorocyclobutyl)-methoxy)-1-methoxy-2-nitro-benzene |
| Int-303 | 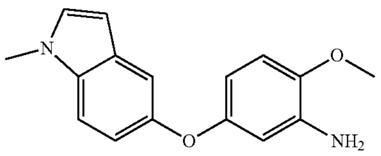 | Flash chromatography; 269.5 $[M + H]^+$ | 5-(4-Methoxy-3-nitro-phenoxy)-1-methyl-1H-indole |
| Int-304 | 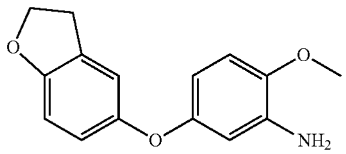 | Flash chromatography; 258.5 $[M + H]^+$ | 5-(4-Methoxy-3-nitro-phenoxy)-2,3-dihydrobenzo-furan |
| Int-305 | 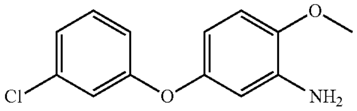 | Crude; 251.1 $[M + H]^+$ | 4-(3-Chlorophenoxy)-1-methoxy-2-nitrobenzene |

Intermediate 306. 5-(3-Bromophenoxy)-2-methoxyaniline

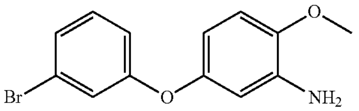

The compound was prepared using the procedure as described for Intermediate 298 starting from 4-(3-bromophenoxy)-1-methoxy-2-nitrobenzene (0.46 g, 1.419 mmol) using 7.5 eq. of zinc powder and 7.5 eq. of $NH_4Cl$. Yield: 0.34 g. LCMS: m/z 294.2 $[M]^+$.

The following intermediates were prepared according to the procedure described for Intermediate 306 from the starting material indicated in the table.

| No. | Structure | Purification; LCMS m/z | Starting materials |
|---|---|---|---|
| Int-307 | 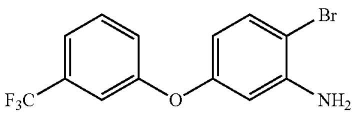 | Flash chromatography; 332.2 $[M]^+$ | 1-Bromo-2-nitro-4-(3-(tri-fluoromethyl)phenoxy)benzene |
| Int-308 | 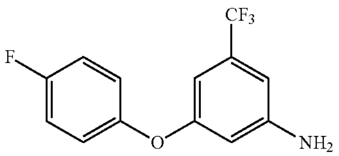 [SMILES: Nc1cc(Oc2ccc(F)cc2)cc(C(F)(F)F)c1] | Crude; 272.4 $[M + H]^+$ | 1-(4-Fluorophenoxy)-3-nitro-5-(trifluoromethyl)benzene |

-continued

| No. | Structure | Purification; LCMS m/z | Starting materials |
| --- | --- | --- | --- |
| Int-309 | 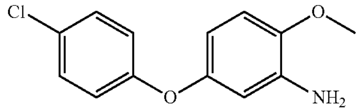 [SMILES: COc1ccc(Oc2ccc(Cl)cc2)cc1N] | Crude; 251.2 [M + H]$^+$ | 4-(4-Chlorophenoxy)-1-methoxy-2-nitrobenzene |
| Int-310 | 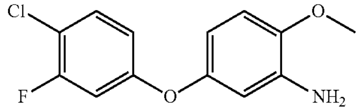 [SMILES: COc1ccc(Oc2ccc(Cl)c(F)c2)cc1N] | Crude; 269.2 [M + H]$^+$ | 1-Chloro-2-fluoro-4-(4-methoxy-3-nitrophenoxy)-benzene |
| Int-311 | 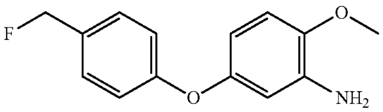 [SMILES: COc1ccc(Oc2ccc(CF)cc2)cc1N] | Crude; 248.6 [M + H]$^+$ | 4-(4-(Fluoromethyl)phenoxy)-1-methoxy-2-nitrobenzene |

Intermediate 312. 5-((3-Fluoro-5-(trifluoromethyl) pyridin-2-yl)oxy)-2-methoxyaniline

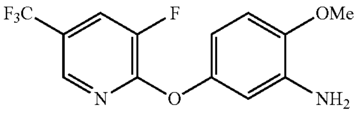

The compound was prepared according to the procedure of Intermediate 298 starting from 3-fluoro-2-(4-methoxy-3-nitrophenoxy)-5-(trifluoromethyl)pyridine (0.50 g, 1.505 mmol) using 10 eq. of zinc powder and 10 eq. of $NH_4Cl$. Yield: 0.43 g. LCMS: m/z 303.5 [M+H]$^+$.

The following intermediates were prepared according to the procedure described for Intermediate 312 from the starting material indicated in the table.

| No. | Structure | Purification; LCMS m/z | Starting materials |
| --- | --- | --- | --- |
| Int-313 | 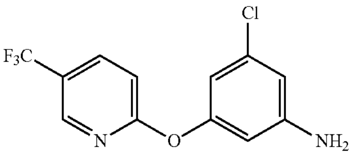 [SMILES: Nc1cc(Cl)cc(Oc2ccc(C(F)(F)F)cn2)c1] | Crude; 289.5 [M + H]$^+$ | 2-(3-Chloro-5-nitrophenoxy)-5-(trifluoromethyl)pyridine |
| Int-314 | 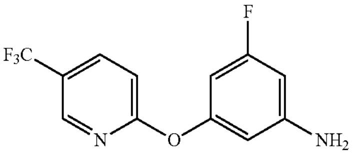 | Flash chromatography; 273.6 [M + H]$^+$ | 2-(3-Fluoro-5-nitrophenoxy)-5-(trifluoromethyl)pyridine |

Intermediate 315. 3-Amino-5-(4-(trifluoromethyl)phenoxy)benzonitrile

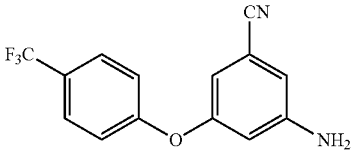 [SMILES: N#Cc1cc(N)cc(Oc2ccc(C(F)(F)F)cc2)c1]

To a mixture of 3-nitro-5-(4-(trifluoromethyl)phenoxy) benzonitrile (0.22 g, 0.714 mmol) in 1,4-dioxane (3.5 ml) was added tin(II) chloride dihydrate (0.805 g, 3.57 mmol) dissolved in 37% aqueous HCl (1.0 ml). The mixture was stirred at RT until the reaction was completed. The mixture was made basic with 6 M NaOH solution. DCM was added and the mixture was filtered through a short plug of Celite.

Celite was washed with DCM. Filtrate was dried and solvent evaporated to afford the title compound. Yield: 0.14 g. LCMS: m/z 279.3 $[M+H]^+$.

The following intermediates were prepared according to the procedure described for Intermediate 315 from the starting material indicated in the table.

| No. | Structure | Purification; LCMS m/z | Starting materials |
|---|---|---|---|
| Int-316 | 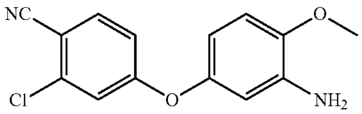 [SMILES: COc1ccc(Oc2ccc(C#N)c(Cl)c2)cc1N] | Crude; 276.2 $[M + H]^+$ | 2-Chloro-4-(4-methoxy-3-nitrophenoxy)benzonitrile |
| Int-317 | 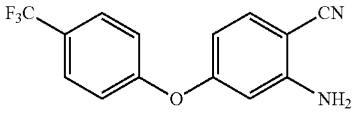 | Flash chromatography; 279.2 $[M + H]^+$ | 2-Nitro-4-(4-(trifluoromethyl)-phenoxy)benzonitrile |
| Int-318 | 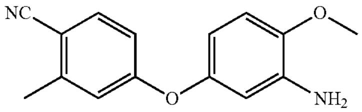 | Crude; 255.5 $[M + H]^+$ | 4-(4-Methoxy-3-nitro-phenoxy)-2-methylbenzonitrile |

Intermediate 319. 1-Methoxy-2-nitro-4-(3-(trifluoromethoxy)phenoxy)benzene

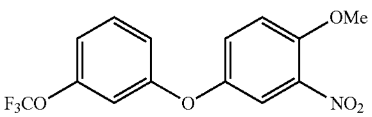 [SMILES: COc1ccc(Oc2cccc(OC(F)(F)F)c2)cc1[N+](=O)[O-]]

To a mixture of 4-methoxy-3-nitrophenol (0.169 g, 1.00 mmol), 3-(trifluoro-methoxy)phenylboronic acid (0.448 g, 2.18 mmol), anhydrous $Cu(OAc)_2$ (0.182 g, 1.00 mmol) and powdered 4 Å molecular sieves (0.25 g) in dry DCM (7.5 ml) was added DIPEA (0.871 ml, 5.00 mmol). The mixture was stirred at RT until maximal conversion was obtained (48 h). The mixture was filtered through a plug of Celite and the Celite layer was washed with EtOAc. Filtrate was washed with 5% aqueous $NH_4OH$ solution, dried and evaporated. Crude was purified by reverse phase flash chromatography to afford 0.050 g of the title compound. LCMS: m/z 330.2 $[M+H]^+$.

Intermediate 320. 1-Methoxy-2-nitro-4-(4-(trifluoromethoxy)phenoxy)benzene

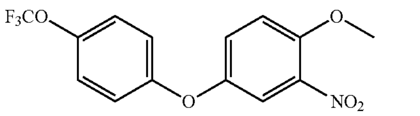

To a mixture of 4-methoxy-3-nitrophenol (0.338 g, 2.00 mmol), 4-(trifluoro-methoxy)phenylboronic acid (0.618 g, 3.00 mmol), anhydrous $Cu(OAc)_2$ (0.363 g, 2.00 mmol) and powdered 4 Å molecular sieves (0.25 g) in dry DCM (15 ml) was added pyridine (0.809 ml, 10.0 mmol). The mixture was stirred at RT until maximal conversion was obtained (24-48 h). The mixture was filtered through a plug of Celite and the Celite layer was washed with DCM. Filtrate was washed with 5% aqueous $NH_4OH$ solution, dried and evaporated. Crude was purified by flash chromatography to afford 0.33 g of the title compound. LCMS: m/z 330.2 $[M+H]^+$.

The following intermediates were prepared according to the procedure described for Intermediate 320 from the starting material indicated in the table.

| No. | Structure | LCMS m/z/$^1$H NMR (400 MHz, $CDCl_3$) | Starting materials |
|---|---|---|---|
| Int-321 | 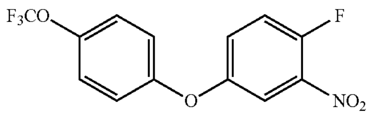 [SMILES: O=[N+]([O-])c1cc(Oc2ccc(OC(F)(F)F)cc2)ccc1F] | δ: 7.63-7.69 (m,1H), 7.23-7.32 (m, 4H), 7.01-7.08 (m, 2H) | 4-Fluoro-3-nitrophenol and 4-(Trifluoromethoxy)-phenylboronic acid (2.2 eq.) |
| Int-322 | 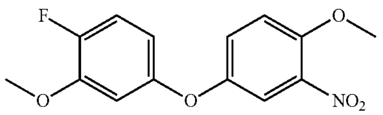 | 294.0 $[M + H]^+$ | 4-Methoxy-3-nitrophenol and 4-Fluoro-3-methoxy-phenylboronic acid (2.2 eq.) |

-continued

| No. | Structure | LCMS m/z/$^1$H NMR (400 MHz, $CDCl_3$) | Starting materials |
|---|---|---|---|
| Int-323 | 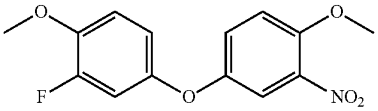 | 294.1 $[M + H]^+$ | 4-Methoxy-3-nitrophenol and 3-Fluoro-4-methoxy-phenylboronic acid (1.8 eq.) |
| Int-324 | 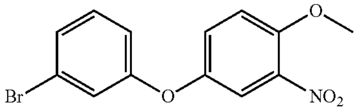 [SMILES: COc1ccc(Oc2cccc(Br)c2)cc1[N+](=O)[O-]] | δ: 7.55 (d, 1H), 7.19-7.29 (m, 3H), 7.07-7.14 (m, 2H), 6.92 (ddd, 1H), 3.97 (s,3H) | 4-Methoxy-3-nitrophenol and 3-Bromophenylboronic acid (2.2 eq.) |
| Int-325 | 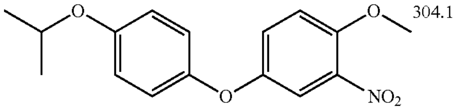 | 304.1 $[M + H]^+$ | 4-Methoxy-3-nitrophenol and (4-Isopropoxyphenyl)-boronic acid (1.5 eq.) |
| Int-326 | 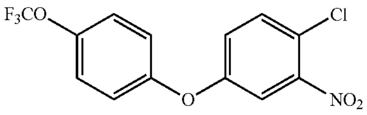 [SMILES: O=[N+]([O-])c1cc(Oc2ccc(OC(F)(F)F)cc2)ccc1Cl] | δ: 7.51 (d, 1H), 7.47 (d, 1H), 7.24-7.30 (m, 2H), 7.16 (dd, 1H), 7.05-7.11 (m, 2H) | 4-Chloro-3-nitrophenol and (4-(Trifluoromethoxy)-phenyl)boronic acid (1.5 eq) |
| Int-327 | 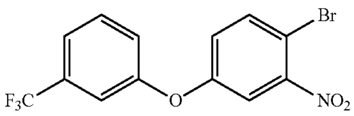 [SMILES: O=[N+]([O-])c1cc(Oc2cccc(C(F)(F)F)c2)ccc1Br] | δ: 7.70 (d, 1H), 7.47-7.57 (m, 2H), 7.47 (d, 1H), 7.30-7.33 (m, 1H), 7.21-7.25 (m, 1H), 7.09 (dd, 1H) | 4-Bromo-3-nitrophenol and (3-(Trifluoromethyl)-phenyl)boronic acid (2.2 eq) |
| Int-328 | 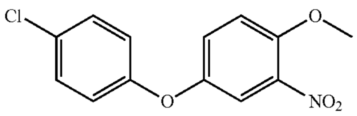 | 279.9 $[M]^+$ | 4-Methoxy-3-nitrophenol and (4-Chlorophenyl)-boronic acid (1.5 eq.) |
| Int-329 | 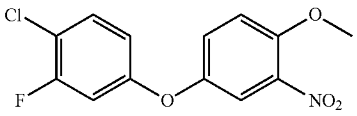 | δ: 7.55 (d, 1H), 7.35 (t, 1H), 7.25 (dd, 1H), 7.11 (d, 1H), 6.79 (dd, 1H), 6.72 (ddd, 1H), 3.97 (s, 3H) | 4-Methoxy-3-nitrophenol and (4-Chloro-3-fluoro-phenyl)boronic acid (1.5 eq.) |
| Int-330 | 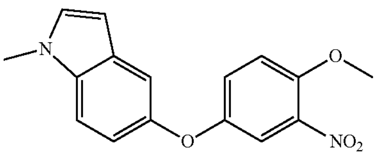 | 299.1 $[M + H]^+$ | 4-Methoxy-3-nitrophenol and (1-Methyl-1H-indol-5-yl)-boronic acid (1.5 eq.) |
| Int-331 | 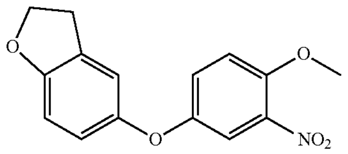 [SMILES: COc1ccc(Oc2ccc3c(c2)CCO3)cc1[N+](=O)[O-]] | 287.8 $[M]^+$ | 4-Methoxy-3-nitrophenol and (2,3-Dihydrobenzo-furan-5-yl)boronic acid (1.5 eq.) |
| Int-332 | 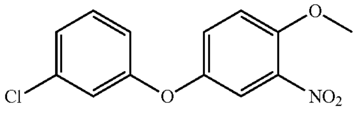 [SMILES: COc1ccc(Oc2cccc(Cl)c2)cc1[N+](=O)[O-]] | 279.9 $[M]^+$ | 4-Methoxy-3-nitrophenol and (3-Chlorophenyl)-boronic acid |

Intermediate 333. 4-(Cyclohexylmethoxy)-1-methoxy-2-nitrobenzene

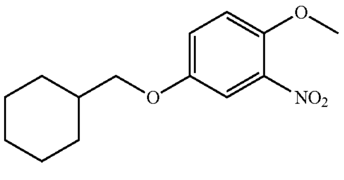 [SMILES: COc1ccc(OCC2CCCCC2)cc1[N+](=O)[O-]]

To a cooled (0-5° C.) mixture of cyclohexylmethanol (0.285 g, 2.50 mmol), 4-methoxy-3-nitrophenol (0.423 g, 2.50 mmol) and triphenylphosphine (0.984 g, 3.75 mmol) in dry THF (17 ml) was added diisopropyl azodicarboxylate (0.738 ml, 3.75 mmol). The mixture was stirred over night at RT. THF was evaporated and the residue was dissolved in DCM. Organic phase was washed with water and brine, dried and evaporated. Crude product was purified by flash chromatography to afford 0.26 g of the title compound. LCMS: m/z 266.2 $[M+H]^+$ The following intermediates were prepared according to the procedure described for Intermediate 333 from the starting material indicated in the table.

b) 4-(4-(Difluoromethyl)phenoxy)-1-methoxy-2-nitrobenzene

Int-336

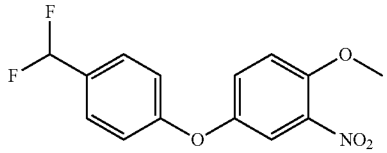

4-(4-Methoxy-3-nitrophenoxy)benzaldehyde (0.49 g, 1.793 mmol) was dissolved in dry DCM (5.5 ml) and cooled to 0-5° C. Diethylaminosulfur trifluoride (0.521 ml, 3.95 mmol) was added in small portions and the mixture was stirred at RT for 24 h. The mixture was diluted with DCM and saturated $NaHCO_3$ solution was added in small portions. Phases were separated and aqueous phase was extracted with DCM. Combined organic phases were washed with water and brine, dried and evaporated. Crude was purified by flash chromatography to afford 0.37 g of the title compound. LCMS: m/z 296.0 $[M+H]^+$.

| No. | Structure | LCMS m/z | Starting materials |
|---|---|---|---|
| Int-334 | 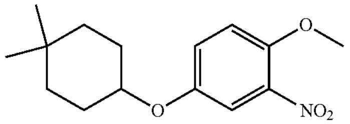 | 280.0 $[M + H]^+$ | 4-Fluoro-3-nitrophenol and 4,4-Dimethylcyclohexan-1-ol |
| Int-335 | 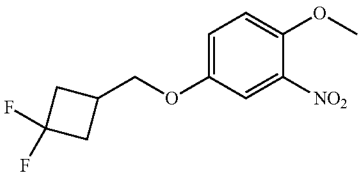 [SMILES: COc1ccc(OCC2CC(F)(F)C2)cc1[N+](=O)[O-]] | 273.8 $[M]^+$ | 4-Methoxy-3-nitrophenol and (3,3-Difluorocyclobutyl)-methanol |

Intermediate 336. 4-(4-(Difluoromethyl)phenoxy)-1-methoxy-2-nitrobenzene a) 4-(4-Methoxy-3-nitrophenoxy)benzaldehyde

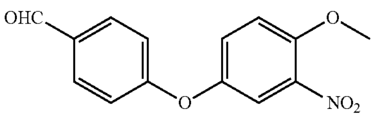 [SMILES: COc1ccc(Oc2ccc(C=O)cc2)cc1[N+](=O)[O-]]

A mixture of 4-fluorobenzaldehyde (0.215 ml, 2.00 mmol), 4-methoxy-3-nitrophenol (0.338 g, 2.00 mmol) and potassium carbonate (0.553 g, 4.00 mmol) in dry DMA (4.0 ml) was stirred at 120° C. until the reaction was completed. Water was added to the cooled mixture and the mixture was extracted with EtOAc. Organic phase was washed with water, dried and evaporated to afford 0.49 g of the title compound. LCMS: m/z 274.1 $[M+H]^+$.

Intermediate 337. (3,4-Difluorophenyl)(4-methoxy-3-nitrophenyl)sulfane

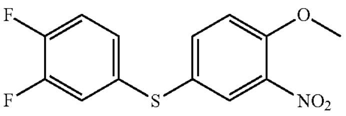 [SMILES: COc1ccc(Sc2ccc(F)c(F)c2)cc1[N+](=O)[O-]]

To a mixture of 3,4-difluorothiophenol (0.155 ml, 1.40 mmol), 4-methoxy-3-nitrophenylboronic acid (0.197 g, 1.00 mmol), copper(II) sulfate (8.0 mg, 0.05 mmol) and 1,10-phenanthroline (9.0 mg, 0.05 mmol) in ethanol (1.0 ml) (bubbled with oxygen before use) was added 40% aqueous tetrabutylammoniumhydroxide (1.0 ml, 3.82 mmol). The mixture was stirred over night at RT. Then mixture was diluted with EtOAc and filtered through a pad of Celite. Celite layer was further washed with EtOAc. Filtrate was evaporated and crude was purified by flash chromatography to afford 0.17 g of the title compound. $^1H$ NMR (400 MHz, $CDCl_3$): δ 7.88 (d, 1H), 7.56 (dd, 1H), 7.00-7.16 (m, 4H), 3.98 (s, 3H).

Intermediate 338. 2-Methoxy-5-(4-(trifluoromethyl)phenoxy)aniline a) 2-Chloro-1-(4-methoxy-3-nitrophenoxy)-4-(trifluoromethyl)benzene

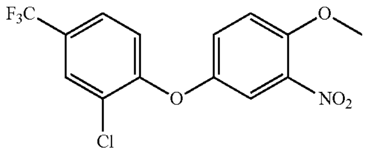 [SMILES: COc1ccc(Oc2ccc(C(F)(F)F)cc2Cl)cc1[N+](=O)[O-]]

A mixture of 2-chloro-1-fluoro-4-(trifluoromethyl)benzene (0.397 g, 2.00 mmol), 4-methoxy-3-nitrophenol (0.372 g, 2.20 mmol) and potassium carbonate (0.608 g, 4.40 mmol) in dry DMF (4.0 ml) was stirred at 120° C. until the reaction was completed. Water was added to the cooled mixture followed by stirring at RT for 1 h. The formed precipitate was filtered, washed with water and dried under reduced pressure to afford 0.62 g of the title compound. LCMS: m/z 348.1 $[M+H]^+$.

b) 2-Methoxy-5-(4-(trifluoromethyl)phenoxy)aniline

Int-338

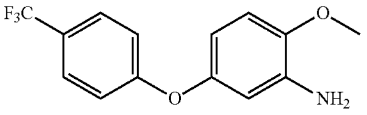

To a mixture of 2-chloro-1-(4-methoxy-3-nitrophenoxy)-4-(trifluoromethyl)-benzene (0.66 g, 1.898 mmol) and ammonium formate (1.197 g, 18.98 mmol) in dry methanol (35 ml) was added 10 wt-% palladium on carbon (0.253 g, 0.237 mmol). The mixture was vigorously stirred at RT until the reaction was completed. The mixture was filtered through a plug of Celite and the Celite layer was washed with methanol. Filtrate was evaporated and the residue was dissolved in EtOAc. Organic phase was washed with water, dried and evaporated to afford 0.52 g of the title compound. LCMS: m/z 284.5 $[M+H]^+$.

Intermediate 339. 2-Chloro-4-(4-methoxy-3-nitrophenoxy)benzonitrile

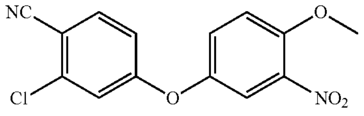

A mixture of 4-methoxy-3-nitrophenol (0.677 g, 4.00 mmol, 1.0 eq.), 2-chloro-4-fluorobenzonitrile (0.622 g, 4.00 mmol, 1.0 eq.) and potassium carbonate (1.216 g, 8.80 mmol, 2.2 eq.) in dry DMF (5.5 ml) was stirred at 100-120° C. until reaction was completed. Cooled mixture was treated with water and the formed precipitate was filtered and dried to afford the title compound. Yield: 1.06 g. LCMS: m/z 304.5 $[M+H]^+$. If the product did not precipitate from water, it was extracted with EtOAc. Organic phase was washed with water, dried and evaporated to afford the title compound which was used as such or purified by flash chromatography.

The following intermediates were prepared according to the procedure described for Intermediate 339 from the starting material indicated in the table.

| No. | Structure | Purification/ LCMS m/z | Starting materials (eq.), base (eq.) |
|---|---|---|---|
| Int-340 | 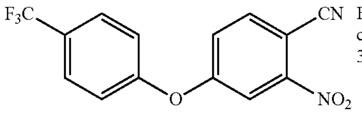 | Flash chromatography; 309.0 $[M + H]^+$ | 4-(Trifluoromethyl)phenol (1.1) and 4-Fluoro-2-nitrobenzonitrile (1.0); $K_2CO_3$ (2.2) |
| Int-341 | 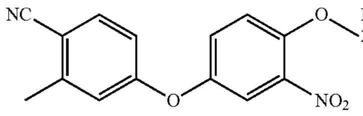 | Precipitation; 285.0 $[M + H]^+$ | 4-Methoxy-3-nitrophenol (1.0) and 4-Fluoro-2-methylbenzonitrile (1.0); $K_2CO_3$ (2.2) |
| Int-342 | 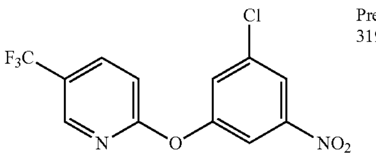 | Precipitation; 319.2 $[M + H]^+$ | 3-Chloro-5-nitrophenol (1.1) and 2-Chloro-5-(trifluoromethyl)-pyridine (1.0); $K_2CO_3$ (1.5) |
| Int-343 | 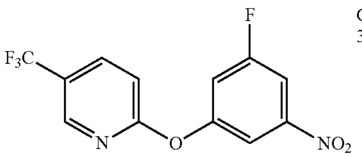 | Crude; 303.2 $[M + H]^+$ | 3-Fluoro-5-nitrophenol (1.0) and 2-Chloro-5-(trifluoromethyl)-pyridine (1.0); $K_2CO_3$ (1.5) |

-continued

| No. | Structure | Purification/ LCMS m/z | Starting materials (eq.), base (eq.) |
|---|---|---|---|
| Int-344 | 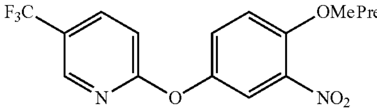 | Precipitation; | 4-Methoxy-3-nitrophenol (1.1) and 2-Chloro-5-(trifluoromethyl)-pyridine (1.0); $K_2CO_3$ (1.5) |
| Int-345 | 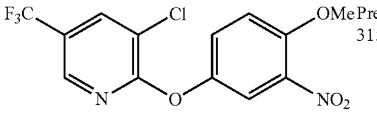 | Precipitation; 315.3 $[M + H]^+$ | 4-Methoxy-3-nitrophenol (1.1) and 2,3-Dichloro-5-(trifluoro-methyl)pyridine (1.0); $K_2CO_3$ (1.5) |
| Int-346 | 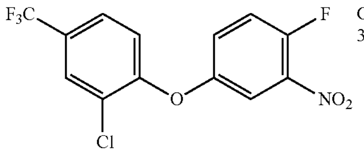 | Crude; 306.5 $[M + H]^+$ | 4-Fluoro-3-nitrophenol (1.1) and 2-Chloro-1-fluoro-4-(trifluoro-methyl)benzene (1.0);$K_2CO_3$ (1.5) |
| Int-347 | 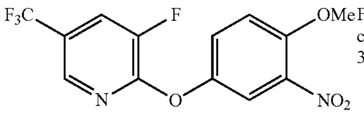 | Flash chromatography; 333.0 $[M + H]^+$ | 4-Methoxy-3-nitrophenol (1.0) and 2,3-Difluoro-5-(trifluoro-methyl)pyridine (1.0); $Cs_2CO_3$ (1.25) |

Intermediate 348. 2-Nitro-4-(4-(trifluoromethyl)phenoxy)benzonitrile

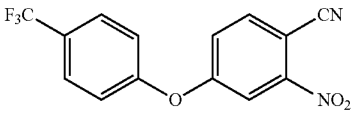 [SMILES: N#Cc1ccc(Oc2ccc(C(F)(F)F)cc2)cc1[N+](=O)[O-]]

A mixture of 4-(trifluoromethyl)phenol (0.40 g, 2.467 mmol), 4-fluoro-2-nitro-benzonitrile (0.40 g, 2.408 mmol) and potassium carbonate (0.666 g, 4.82 mmol) in dry DMA (5.0 ml) was stirred at 100° C. until the reaction was completed. Cooled mixture was diluted with water and extracted with EtOAc. Organic phase was dried and evaporated. Crude was purified by flash chromatography to afford the title compound. Yield: 0.40 g. $^1H$ NMR (400 MHz, $CDCl_3$) δ: 7.89 (d, 1H), 7.87 (d, 1H), 7.74-7.79 (m, 2H), 7.36 (dd, 1H), 7.20-7.25 (m, 2H).

Intermediate 349. 3-Nitro-5-(4-(trifluoromethyl)phenoxy)benzonitrile

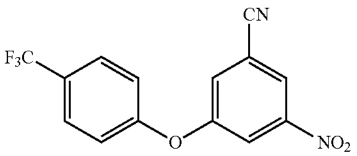

A mixture of 4-(trifluoromethyl)phenol (0.324 g, 2.00 mmol), 3,5-dinitrobenzo-nitrile (0.463 g, 2.40 mmol) and potassium phosphate (0.849 g, 4.00 mmol) in dry DMA (3.0 ml) was stirred at 100° C. until the reaction was completed. Cooled mixture was diluted with water and extracted with EtOAc. Organic phase was dried and evaporated. Crude was purified by flash chromatography to afford the title compound. Yield: 0.42 g. LCMS: m/z 309.2 $[M+H]^+$.

Intermediate 350. 4-(4-(Fluoromethyl)phenoxy)-1-methoxy-2-nitrobenzene a) (4-(4-Methoxy-3-nitrophenoxy)phenyl)methanol

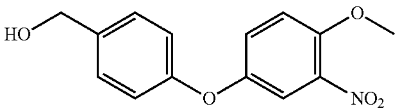 [SMILES: COc1ccc(Oc2ccc(CO)cc2)cc1[N+](=O)[O-]]

To a mixture of 4-(4-methoxy-3-nitrophenoxy)benzaldehyde (0.98 g, 3.59 mmol) in MeOH (15 ml) was added $NaBH_4$ (0.204 g, 5.38 mmol) in small portions and stirred at RT until the reaction was completed. Solvent was evaporated and the residue was treated with water and EtOAc. Phases were separated and the aqueous phase was extracted with EtOAc. Combined organic phases were washed with water and brine, dried and evaporated to afford the title compound. Yield 0.97 g. LCMS: m/z 258.3 $[M-H_2O+H]^+$.

b) 4-(4-(Fluoromethyl)phenoxy)-1-methoxy-2-nitrobenzene

Int-350

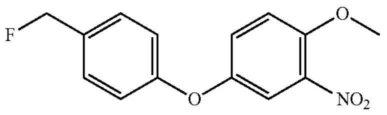

To a cooled (−78° C.) solution of (4-(4-methoxy-3-nitrophenoxy)phenyl)methanol (0.48 g, 1.744 mmol) in dry DCM (5.0 ml) was added diethylaminosulfur trifluoride (DAST) (0.25 ml, 1.892 mmol). Cooling bath was removed and the mixture was allowed to warm to RT and stirred until the reaction was completed. The mixture was diluted with DCM (15 ml) and cooled to 0-5° C. Saturated $NaHCO_3$ solution (5 ml) was added to adjust pH to 7-8. Phases were separated and aqueous phase was extracted with DCM. Combined organic phases were washed with water and brine, dried and evaporated. Crude product was purified by flash chromatography to afford the title compound. Yield: 0.26 g. $^1H$ NMR (400 MHz, $CDCl_3$) δ: 7.53 (d, 1H), 7.36-7.41 (m, 2H), 7.25 (dd, 1H), 7.08 (d, 1H), 6.98-7.03 (m, 2H), 5.35 (d, 2H), 3.96 (s, 3H).

Intermediate 351. 2,4-Difluoro-5-((5-(trifluoromethyl)pyridin-2-yl)oxy)aniline

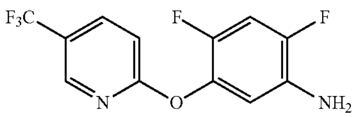 [SMILES: Nc1cc(Oc2ccc(C(F)(F)F)cn2)c(F)cc1F]

A mixture of 5-amino-2,4-difluorophenol (0.218 g, 1.50 mmol) and potassium tert-butoxide (0.185 g, 1.65 mmol) in dry DMSO (3.0 ml) was stirred at RT for 1 h. 2-Chloro-5-(trifluoromethyl)pyridine (0.272 g, 1.50 mmol) and $K_2CO_3$ (0.104 g, 0.75 mmol) were added and stirring was continued at 120° C. until the reaction was completed. Cooled mixture was diluted with water and extracted with EtOAc. Organic phase was washed with 1 M NaOH and water, dried and evaporated. Crude product was purified by filtration through a short plug of silica gel eluting with EtOAc-heptane (4:1). Filtrate was evaporated and the residue dried under vacuum to afford the title compound. Yield: 0.25 g. LCMS: m/z 291.5 [M+H]$^+$.

Intermediate 352. Benzyl (2S,4R)-4-hydroxy-2-((2-methoxy-5-(4-(trifluoro-methyl)phenoxy)phenyl) carbamoyl)pyrrolidine-1-carboxylate

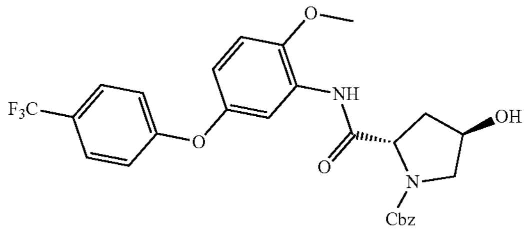 [SMILES: COc1ccc(Oc2ccc(C(F)(F)F)cc2)cc1NC(=O)[C@@H]1C[C@@H](O)CN1C(=O)OCc1ccccc1]

To a mixture of 2-methoxy-5-(4-(trifluoromethyl)phenoxy)aniline (0.085 g, 0.30 mmol), (2S,4R)-1-((benzyloxy)-carbonyl)-4-hydroxypyrrolidine-2-carboxylic acid (0.080 g, 0.30 mmol) in EtOAc (0.40 ml) and pyridine (0.20 ml) was added 1-propanephosphonic acid cyclic anhydride, 50 wt-% in EtOAc (0.30 ml, 0.509 mmol). The mixture was stirred at RT overnight. The reaction was quenched with 0.5% HCl-solution and diluted with water and EtOAc. Phases were separated and organic phase was washed with 0.5% HCl-solution, water and brine, dried and evaporated to afford the title compound. Yield: 0.111 g. LC-MS: m/z=531.3 [M+H]$^+$. Crude product was used as such or purified by reverse phase flash chromatography to afford the pure compound.

The following intermediates were prepared according to the procedure described for Intermediate 352 from the starting material indicated in the table.

| No. | Structure | Purification/ LCMS m/z | Starting materials |
|---|---|---|---|
| Int-353 | 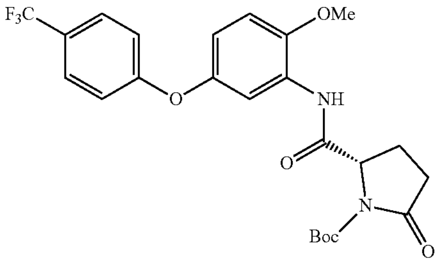 [SMILES: COc1ccc(Oc2ccc(C(F)(F)F)cc2)cc1NC(=O)[C@@H]1CCC(=O)N1C(=O)OC(C)(C)C] | Crude; 481.4 [M + H]$^+$ | 2-Methoxy-5-(4-(trifluoro-methyl)phenoxy)aniline and (S)-1-(tert-butoxycarbonyl)-5-oxopyrrolidine-2-carboxylic acid |
| Int-354 | 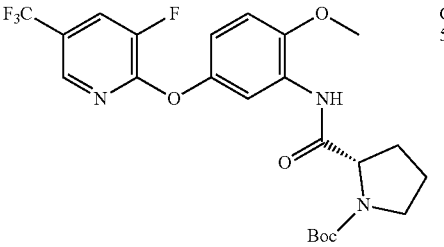 | Crude; 500.4 [M + H]$^+$ | 5-((3-Fluoro-5-(trifluoro-methyl)pyridin-2-yl)oxy)-2-methoxyaniline and (tert-Butoxycarbonyl)-L-proline |

-continued

| No. | Structure | Purification/ LCMS m/z | Starting materials |
| --- | --- | --- | --- |
| Int-355 | 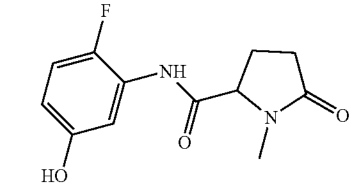 [SMILES: CN1C(=O)CCC1C(=O)Nc1cc(O)ccc1F] | Reverse phase flash chromatography; 253.3 [M + H]+ | 3-Amino-4-fluorophenol and 1-Methyl-5-oxopyrrolidine-2-carboxylic acid |
| Int-356 | 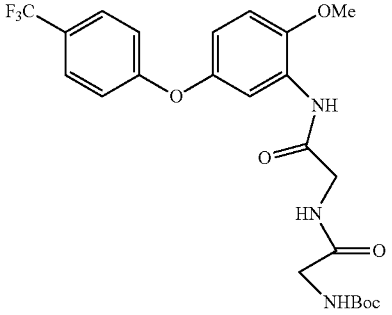 [SMILES: COc1ccc(Oc2ccc(C(F)(F)F)cc2)cc1NC(=O)CNC(=O)CNC(=O)OC(C)(C)C] | Crude; 498.4 [M + H]+ | 2-Methoxy-5-(4-(trifluoromethyl)phenoxy)aniline and (tert-Butoxycarbonyl)glycylglycine |

Intermediate 357. tert-Butyl 1-(2-methoxyacetyl)-5-oxopyrrolidine-2-carboxylate

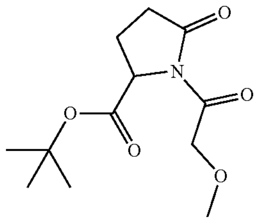 [SMILES: COCC(=O)N1C(=O)CCC1C(=O)OC(C)(C)C]

To a cooled (0-5° C.) mixture of tert-butyl 5-oxopyrrolidine-2-carboxylate (0.37 g, 2.00 mmol) in dry THF (5.0 ml) was added 60 wt-% NaH in oil (0.10 g, 2.50 mmol) followed by stirring at 0-5° C. for 30 min. 2-Methoxyacetyl chloride (0.26 g, 2.40 mmol) dissolved in dry THF (2.5 ml) was added and stirring continued at RT overnight. Solvent was evaporated and the residue treated with DCM and water. Phases were separated and the organic phase was washed with water and brine. Organic phase was dried and evaporated to afford the title compound. Yield: 0.51 g. LCMS: m/z 258.0 $[M+H]^+$. Crude product was used as such or purified by reverse phase flash chromatography to afford the pure compound.

The following intermediates were prepared according to the procedure described for Intermediate 357 from the starting material indicated in the table.

| No. | Structure | Purification/ LCMS m/z | Starting materials (eq.), base (eq.) |
| --- | --- | --- | --- |
| Int-358 | 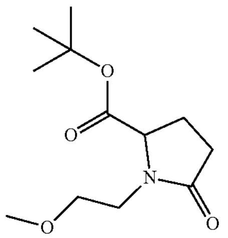 [SMILES: COCCN1C(=O)CCC1C(=O)OC(C)(C)C] | Reverse phase flash chromatography; 244.2 [M + H]+ | tert-Butyl 5-oxopyrrolidine-2-carboxylate (1.0) and 1-Iodo-2-methoxyethane (1.38); NaH (1.75) |
| Int-359 | 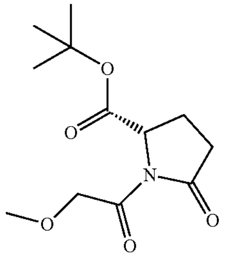 | Crude; 257.1 [M]+ | tert-Butyl (S)-5-oxopyrrolidine-2-carboxylate (1.0) and 2-Methoxyacetyl chloride (1.25); NaH (1.35) |

-continued

| No. | Structure | Purification/ LCMS m/z | Starting materials (eq.), base (eq.) |
|---|---|---|---|
| Int-360 | 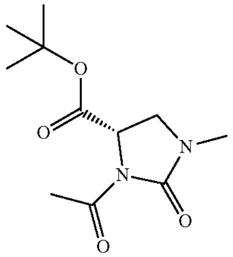 [SMILES: CC(=O)N1C(=O)N(C)C[C@H]1C(=O)OC(C)(C)C] | Crude; 243.3 $[M+H]^+$ | tert-Butyl (S)-1-methyl-2-oxoimidazolidine-4-carboxylate (1.0) and Acetyl chloride (2.0); NaH (1.75) |
| Int-361 | 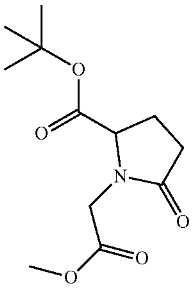 [SMILES: COC(=O)CN1C(=O)CCC1C(=O)OC(C)(C)C] | Reverse phase flash chromatography; 258.2 $[M+H]^+$ | tert-butyl 1-(2-Methoxy-2-oxoethyl)-5-oxopyrrolidine-2-carboxylate (1.0) and Methyl 2-bromoacetate (2.5); NaH (2.0) |

Intermediate 362. tert-Butyl (2-methoxyacetyl)-L-prolinate

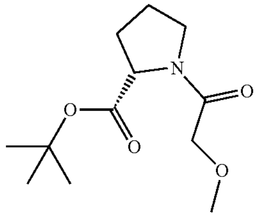

To a cooled (0-5° C.) solution of tert-butyl L-prolinate (0.342 g, 2.00 mmol) and triethylamine (0.558 ml, 4.00 mmol) in dry DCM (10 ml) was added 2-methoxyacetyl chloride (0.239 g, 2.20 mmol). The mixture was stirred overnight at RT. The mixture was filtered and the filtrate was washed with saturated $NH_4Cl$ solution, saturated $NaHCO_3$ solution, and brine, dried and evaporated to afford the title compound. Yield: 0.34 g. LCMS: m/z 244.2 $[M+H]^+$.

Intermediate 363. tert-Butyl (2-methoxyacetyl)-L-prolinate

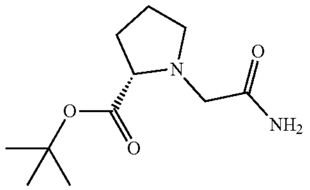 [SMILES: CC(C)(C)OC(=O)[C@@H]1CCCN1CC(N)=O]

A mixture of tert-butyl L-prolinate (0.342 g, 2.00 mmol), 2-bromoacetamide (0.331 g, 2.40 mmol) and potassium hydrogencarbonate (0.30 g, 3.00 mmol) in dry acetonitrile (10 ml) was stirred at 80° C. until the reaction was completed. Cooled mixture was filtered and the filtrate evaporated. Residue was treated with water and DCM. Phases were separated and the aqueous phase was extracted with DCM. Combined organic phases were dried and evaporated to afford the title compound. Yield: 0.34 g. LCMS: m/z 229.4 $[M+H]^+$.

Intermediate 364. (S)-1-(2-Methoxyacetyl)-5-oxopyrrolidine-2-carboxylic acid

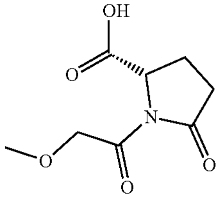

To a mixture of tert-butyl (S)-1-(2-methoxyacetyl)-5-oxopyrrolidine-2-carboxylate (0.77 g, 2.99 mmol) in dry DCM (15 ml) was added trifluoroacetic acid (2.50 ml, 32.4 mmol, 10.8 eq) followed by stirring overnight at RT. Solvent was evaporated and the residue was treated with toluene and evaporated again. This procedure was repeated and residue was dried under vacuum to afford the title compound. The crude product was either: (a) used in the next step as such or (b) extracted with DCM after basification with saturated $Na_2CO_3$ solution followed by drying and evaporating the organic phase. LCMS: m/z 201.9 $[M+H]^+$ The following intermediates were prepared according to the procedure described for Intermediate 364 from the starting material indicated in the table.

| No. | Structure | Purification/ LCMS m/z | Starting materials (eq.); TFA (eq.) |
|---|---|---|---|
| Int-365 | 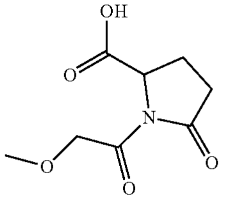 | A/202.0 [M + H]+ | tert-Butyl 1-(2-methoxyacetyl)-5-oxopyrrolidine-2-carboxylate; TFA (10.5) |
| Int-366 | 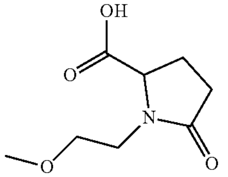 | A/188.0 [M + H]+ | tert-Butyl 1-(2-methoxyethyl)-5-oxopyrrolidine-2-carboxylate; TFA (12.5) |
| Int-367 | 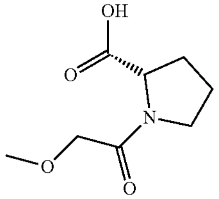 | A/187.9 [M + H]+ | tert-Butyl (2-methoxyacetyl)-L-prolinate; TFA (11.2) |
| Int-368 | 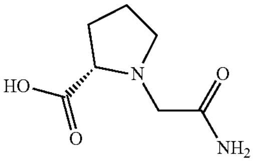 [SMILES: NC(=O)CN1CCC[C@H]1C(=O)O] | A/173.0 [M + H]+ | tert-Butyl (2-amino-2-oxoethyl)-L-prolinate; TFA (10.5) |
| Int-369 | 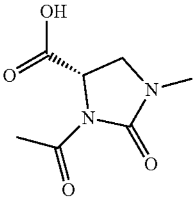 | A/187.0 [M + H]+ | tert-Butyl (S)-3-acetyl-1-methyl-2-oxoimidazolidine-4-carboxylate; TFA (10.3) |
| Int-370 | 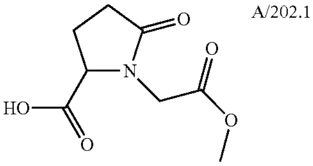 | A/202.1 [M + H]+ | tert-Butyl 1-(2-methoxy-2-oxo-ethyl)-5-oxopyrrolidine-2-carboxylate; TFA (10.4) |

Intermediate 371. (E)-5-(2-(4,4-Difluorocyclohexyl) vinyl)-2,3-dihydrobenzo-furan-7-amine

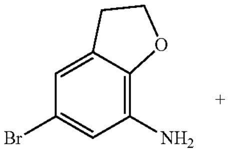

-continued

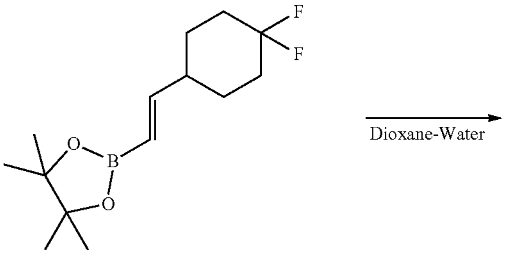

-continued

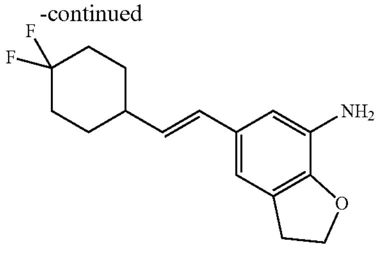

Int-371

A mixture of 5-bromo-2,3-dihydrobenzofuran-7-amine (0.158 g, 0.738 mmol), 2-[(E)-2-(4,4-difluorocyclohexyl) ethenyl]-4,4,5,5-tetramethyl-1,3,2-dioxaborolane (0.243 g, 1.15 mmol), $K_3PO_4$ (0.313 g, 2.0 mmol) and SPhos Pd G2 (0.040 g, 0.075 mmol) in dioxane (1 ml) and water (1 ml) was heated under nitrogen atmosphere at 85° C. for 8 h. The mixture was extracted with ethyl acetate (2×4 ml). The combined organic layers were evaporated and then purified by normal phase chromatography to yield 0.144 g of the title compound. $^1$H NMR (400 MHz, DMSO-$d_6$) δ: 1.34-1.46 (2H, m), 1.76-1.95 (4H, m), 1.97-2.09 (2H, m), 2.20-2.29 (1H, m), 3.08 (2H, t), 4.47 (2H, t), 4.57 (2H, s), 5.88-5.95 (1H, m), 6.21 (1H, d), 6.50 (1H, d), 6.53 (1H, br s). LCMS: m/z 280.7 $[M+H]^+$ The following intermediate was prepared according to the procedure described for Intermediate 371 from the starting material indicated in the table.

| No. | Structure | LCMS/ GCMS m/z | Starting materials |
|---|---|---|---|
| Int-372 | 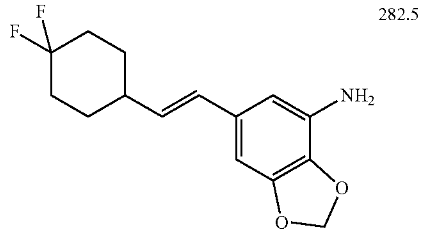 | 282.5 $[M + H]^+$ | 6-Bromo-1,3-dioxaindan-4-amine and 2-[(E)-2-(4,4-difluorocyclohexyl)ethenyl]-4,4,5,5-tetramethyl-1,3,2-dioxaborolane |

Intermediate 373. 1-(((Benzyloxy)carbonyl)glycyl)-5-oxopyrrolidine-2-carboxylic acid a) 4-Nitrophenyl ((benzyloxy)carbonyl)glycinate

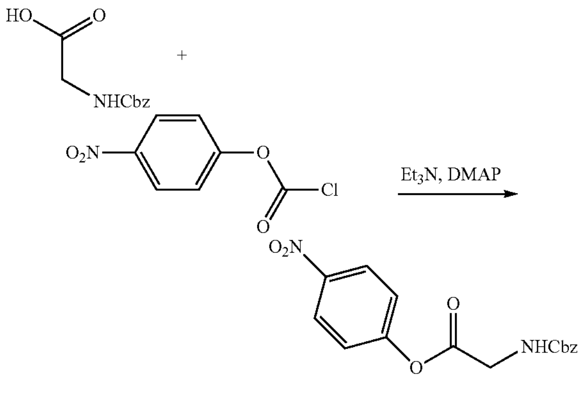

Triethylamine (290 mg, 2.87 mmol, 1.2 eq.) was added to a suspension of the N-carbobenzyloxyglycine (1 eq.) in anhydrous $CH_2Cl_2$ (12 mL). The stirred mixture was cooled to 0° C. and 4-nitrophenyl chloroformate (578 mg, 2.87 mmol, 1.2 eq.) was added. After 10 min, DMAP (29.2 mg, 0.239 mmol, 0.1 eq.) was added and the mixture was stirred at 0° C. for 1 h. The mixture was further diluted with $CH_2Cl_2$ (20 mL) and washed with saturated $NaHCO_3$ solution (10 mL), 0.1 M HCl solution (10 mL), brine (10 mL), and then dried ($Na_2SO_4$), filtered and evaporated in vacuum to give the crude product. The crude residue was purified further with reversed phase chromatography to obtain the title compound. LCMS: m/z 331.068 $(M+H)^+$.

b) tert-Butyl 1-(((benzyloxy)carbonyl)glycyl)-5-oxopyrrolidine-2-carboxylate

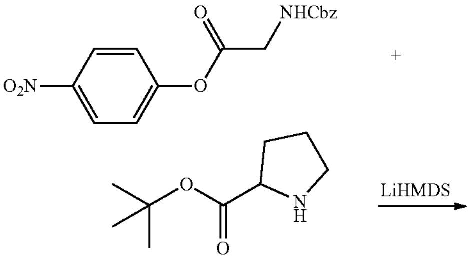

-continued

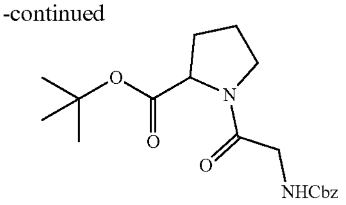

LiHMDS (896 μL, 0.896 mmol, 1.06 eq.) was added dropwise to a solution of 5-oxo-2-pyrrolidinecarboxylic acid tert-butyl ester (157 mg, 0.845 mmol, 1 eq.) in anhydrous THF (3 ml) at −78° C. under nitrogen. The mixture stirred at RT for 15 min followed by the addition of a solution of 4-nitrophenyl ((benzyloxy)carbonyl)glycinate in anhydrous THF (4 ml) at −78° C. The mixture was stirred for 1 h at this temperature. The mixture was diluted with ethyl acetate (20 ml) and washed with $NH_4Cl$ (10 ml), brine (10 ml) and then dried ($Na_2SO_4$), filtered and solvent evaporated in vacuum to give the crude product. The crude residue was purified further with reverse phase chromatography to obtain the title compound. LCMS: m/z 377.155 $(M+H)^+$.

c) 1-(((Benzyloxy)carbonyl)glycyl)-5-oxopyrrolidine-2-carboxylic acid (intermediate 373)

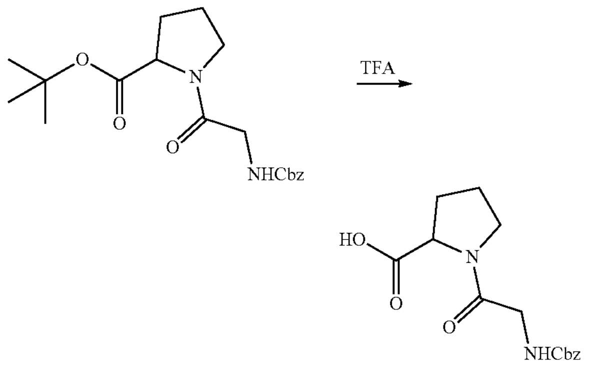

Int-373

Trifluoroacetic acid was added dropwise to a solution of tert-butyl 1-(((benzyloxy)carbonyl)glycyl)-5-oxopyrrolidine-2-carboxylate (285 mg, 0.76 mmol, 1 eq.) in anhydrous DCM under nitrogen at 0° C. The mixture was stirred at 0° C. for 2 h. DCM and trifluoroacetic acid residue were removed in vacuum to give the crude product. The crude residue was purified further with reverse phase chromatography to obtain the title compound. LCMS: m/z 321.031 $(M+H)^+$.

Example 1. N-(2-Methoxy-5-(4-(trifluoromethyl)phenoxy)phenyl)-5-oxo-pyrrolidine-2-carboxamide (Compound 1)

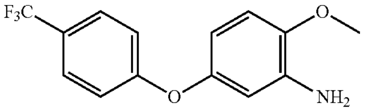

+

-continued

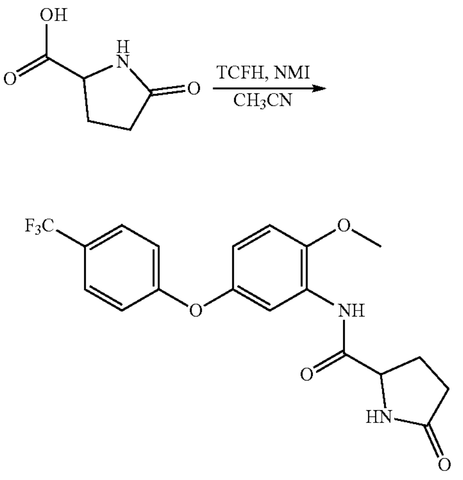

Compound 1

To a solution of 2-methoxy-5-(4-(trifluoromethyl)phenoxy)aniline (215 mg, 1 eq., 759 μmol) in anhydrous acetonitrile (5 mL) were added 5-oxopyrrolidine-2-carboxylic acid (98.0 mg, 1 eq., 759 μmol) and 1-methyl-1H-imidazole (312 mg, 5 eq., 3.80 mmol). The mixture was stirred at RT for 10 min and N,N,N',N'-tetramethylchloroformamidinium hexafluorophosphate (319 mg, 1.5 eq., 1.14 mmol) was added in a single portion. The resulting solution was stirred at RT overnight and the mixture was directly purified by method A to afford the title compound (0.194 g). $^1$H NMR (400 MHz, DMSO-$d_6$) δ: 9.35 (s, 1H), 7.91 (d, 2H), 7.71 (d, 2H), 7.14 (d, 1H), 7.08 (d, 2H), 6.91 (dd, 1H), 4.38 (dd, 1H), 3.88 (s, 3H), 2.38-2.27 (m, 1H), 2.26-2.07 (m, 2H), 2.02-1.90 (m, 1H). LCMS: m/z 395.0 $[M+H]^+$.

The following compounds were prepared according to the procedure described for Compound 1. The compound code, structure, starting materials, purification method and characterization data are indicated in the table.

| No. | Structure and starting material | Purification method and characterization data |
| --- | --- | --- |
| 2 | 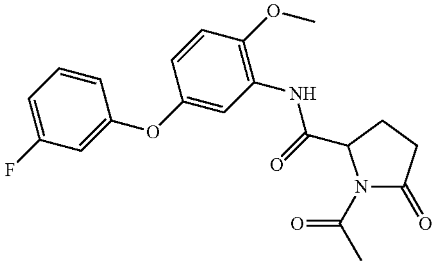 [SMILES: COc1ccc(Oc2cccc(F)c2)cc1NC(=O)C1CCC(=O)N1C(C)=O] Starting materials: 5-(3-Fluorophenoxy)-2-methoxyaniline and 1-Acetyl-5-oxopyrrolidine-2-carboxylic acid | Purification method A. $^1$H NMR (400 MHz, DMSO-$d_6$) δ: 9.73 (s, 1H), 7.84 (d, 1H), 7.41-7.29 (m, 1H), 7.10 (d, 1H), 6.94-6.80 (m, 2H), 6.80-6.69 (m, 2H), 5.07 (d, 1H), 2.65-2.51 (m, 2H), 2.37 (s, 3H), 2.34-2.19 (m, 1H), 1.97-1.83 (m, 1H). LCMS: m/z 387.2 $[M + H]^+$ |

-continued

| No. | Structure and starting material | Purification method and characterization data |
|---|---|---|
| 3 | 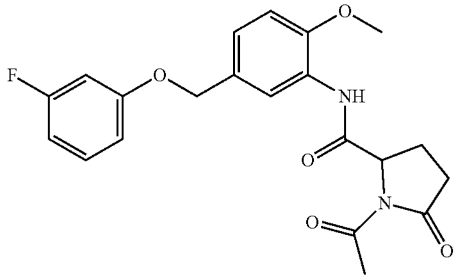 [SMILES: COc1ccc(COc2cccc(F)c2)cc1NC(=O)C1CCC(=O)N1C(C)=O]<br>Starting materials: 5-((3-Fluoro-phenoxy)methyl)-2-methoxyaniline and 1-Acetyl-5-oxopyrrolidine-2-carboxylic acid | Purification method A. $^1H$ NMR (400 MHz, DMSO-$d_6$) δ: 9.62 (s, 1H), 8.09 (d, 1H), 7.36-7.25 (m, 1H), 7.18 (d, 1H), 7.11-6.99 (m, 1H), 6.91-6.79 (m, 2H), 6.79-6.68 (m, 1H), 5.05 (dd, 1H), 4.99 (s, 2H), 3.86 (s, 3H), 2.71-2.53 (m, 2H), 2.34-2.23 (m, 1H), 1.99-1.84 (m, 1H). LCMS: m/z 401.4 $[M + H]^+$ |
| 4 | 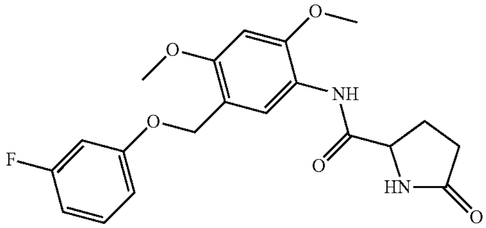 [SMILES: COc1cc(OC)c(NC(=O)C2CCC(=O)N2)cc1COc1cccc(F)c1]<br>Starting materials: 5-((3-Fluoro-phenoxy)methyl)-2,4-dimethoxy-aniline and 5-Oxopyrrolidine-2-carboxylic acid | Purification method A. $^1H$ NMR (400 MHz, DMSO-$d_6$) δ: 9.11 (s, 1H), 7.90 (s, 1H), 7.83 (s, 1H), 7.37-7.22 (m, 1H), 6.89-6.71 (m, 4H), 4.96 (s, 2H), 4.34-4.19 (m, 1H), 3.87 (d, 6H), 2.31-2.04 (m, 3H), 2.01-1.90 (m, 1H). LCMS: m/z 389.2 $[M + H]^+$ |
| 5 | 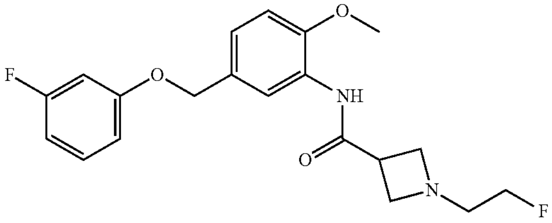 [SMILES: COc1ccc(COc2cccc(F)c2)cc1NC(=O)C1CN(CCF)C1]<br>Starting materials: 5-((3-Fluoro-phenoxy)methyl)-2-methoxyaniline HCl and Lithium 1-(2-fluoroethyl)-azetidine-3-carboxylate | Purification method B. $^1H$ NMR (400 MHz, DMSO-$d_6$) δ: 9.26 (s, 1H), 8.11 (s, 1H), 7.35-7.26 (m, 1H), 7.16 (d, 1H), 7.04 (d, 1H), 6.94-6.81 (m, 2H), 6.79-6.71 (m, 1H), 5.01 (s, 2H), 4.45 (t, 1H), 4.33 (t, 1H), 3.83 (s, 3H), 3.56-3.41 (m, 3H), 3.28-3.21 (m, 2H), 2.70 (t, 1H), 2.62 (t, 1H). LCMS: m/z 377.2 $[M + H]^+$ |
| 6 | 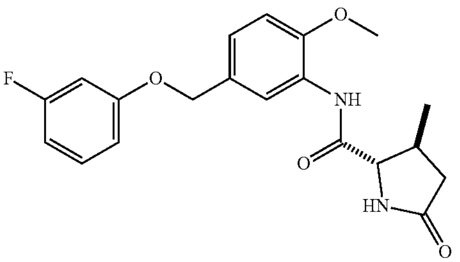<br>Starting materials: 5-((3-Fluoro-phenoxy)methyl)-2-methoxyaniline HCl and rac-(trans)-3-Methyl-5-oxo-pyrrolidine-2-carboxylic acid | Purification method B. $^1H$ NMR (400 MHz, DMSO-$d_6$) δ: 9.28 (d, 1H), 8.09 – 8.00 (m, 1H), 7.86 (d, 1H), 7.34-7.25 (m, 1H), 7.19 (d, 1H), 7.07 (d, 1H), 6.91-6.80 (m, 2H), 6.80-6.69 (m, 1H), 5.02 (s, 2H), 4.36 (d, 1H), 3.85 (s, 3H), 2.24-1.84 (m, 1H), 1.07 (dd, 3H). LCMS: m/z 373.2 $[M + H]^+$ |

-continued

| No. | Structure and starting material | Purification method and characterization data |
|---|---|---|
| 7 | 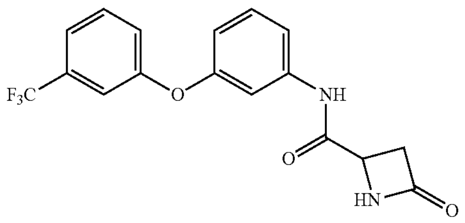 [SMILES: O=C1CC(C(=O)Nc2cccc(Oc3cccc(C(F)(F)F)c3)c2)N1] Starting materials: 3-(3-(Trifluoro-methyl)phenoxy)aniline and 4-Oxo-azetidine-2-carboxylic acid | Purification method A. $^1$H NMR (400 MHz, DMSO-$d_6$) δ: 10.31 (s, 1H), 8.23 (s, 1H), 7.68-7.61 (m, 1H), 7.51 (d, 1H), 7.47-7.30 (m, 5H), 6.82 (d, 1H), 4.12 (d, 1H), 3.16 (dd, 1H), 2.91-2.78 (m, 1H). LCMS: m/z 351.2 [M + H]$^+$ |
| 8 | 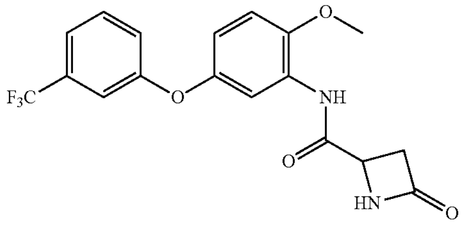 [SMILES: COc1ccc(Oc2cccc(C(F)(F)F)c2)cc1NC(=O)C1CC(=O)N1] Starting materials: 2-Methoxy-5-(3-(trifluoromethyl)phenoxy)aniline and 4-Oxoazetidine-2-carboxylic acid | Purification method A. $^1$H NMR (500 MHz, DMSO-$d_6$) δ: 9.48 (s, 1H), 8.25 (s, 1H), 7.89 (s, 1H), 7.61-7.55 (m, 1H), 7.42 (d, 1H), 7.25-7.18 (m, 2H), 7.11 (d, 1H), 6.88 (dd, 1H), 4.37-4.31 (m, 1H), 3.86 (s, 3H), 3.15 (dd, 1H), 2.83 (d, 1H). LCMS: m/z 281.0 [M + H]$^+$ |
| 9 | 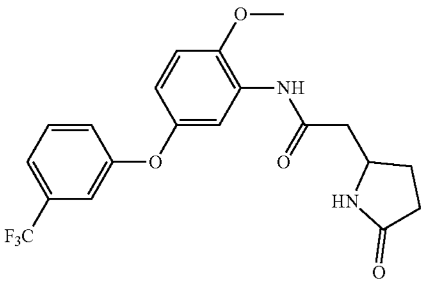 [SMILES: COc1ccc(Oc2cccc(C(F)(F)F)c2)cc1NC(=O)CC1CCC(=O)N1] Starting materials: 2-Methoxy-5-(3-(trifluoromethyl)phenoxy)aniline and 2-(5-Oxopyrrolidin-2-yl)acetic acid | Purification method A. $^1$H NMR (400 MHz, DMSO-$d_6$) δ: 9.32 (s, 1H), 7.88 (s, 1H), 7.63-7.53 (m, 2H), 7.42 (d, 1H), 7.25-7.18 (m, 2H), 7.09 (d, 1H), 6.85 (dd, 1H), 3.88 (d, 1H), 3.86 (s, 3H), 2.69-2.57 (m, 2H), 2.22-2.02 (m, 3H), 1.74-1.60 (m, 1H). LCMS: m/z 409.2 [M + H]$^+$ |
| 10 | 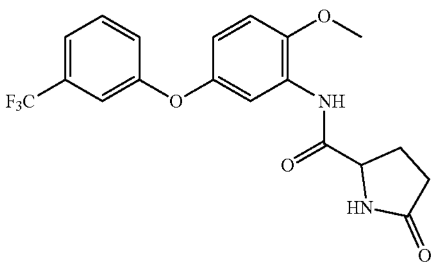 [SMILES: COc1ccc(Oc2cccc(C(F)(F)F)c2)cc1NC(=O)C1CCC(=O)N1] Starting materials: 2-Methoxy-5-(3-(trifluoromethyl)phenoxy)aniline and 5-Oxopyrrolidine-2-carboxylic acid | Purification method A. $^1$H NMR (400 MHz, DMSO-$d_6$) δ: 9.34 (s, 1H), 7.95-7.87 (m, 2H), 7.58 (dd, 1H), 7.43 (d, 1H), 7.26-7.19 (m, 2H), 7.12 (d, 1H), 6.88 (dd, 1H), 4.38 (dd, 1H), 3.87 (s, 3H), 2.39-2.27 (m, 1H), 2.27-2.03 (m, 2H), 2.02-1.88 (m, 1H). LCMS: m/z 395.0 [M + H]$^+$ |

-continued

| No. | Structure and starting material | Purification method and characterization data |
|---|---|---|
| 11 | 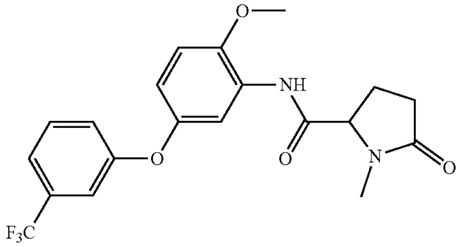 [SMILES: COc1ccc(Oc2cccc(C(F)(F)F)c2)cc1NC(=O)C1CCC(=O)N1C] Starting materials: 2-Methoxy-5-(3-(trifluoromethyl)phenoxy)aniline and 1-Methyl-5-oxopyrrolidine-2-carboxylic acid | Purification method A. $^1H$ NMR (400 MHz, DMSO-$d_6$) δ: 9.63 (s, 1H), 7.85 (d, 1H), 7.63-7.55 (m, 1H), 7.43 (d, 1H), 7.25-7.19 (m, 2H), 7.13 (d, 1H), 6.90 (dd, 1H), 4.52-4.41 (m, 1H), 3.88 (s, 3H), 2.64 (s, 3H), 2.33-2.15 (m, 3H), 1.93-1.85 (m, 1H). LCMS: m/z 409.2 $[M + H]^+$ |
| 12 | 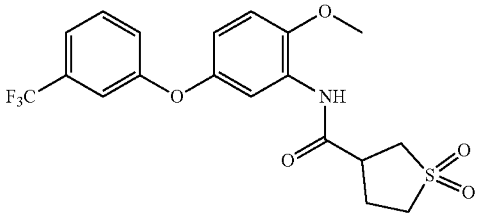 [SMILES: COc1ccc(Oc2cccc(C(F)(F)F)c2)cc1NC(=O)C1CCS(=O)(=O)C1] Starting materials: 2-Methoxy-5-(3-(trifluoromethyl)phenoxy)aniline and Tetrahydrothiophene-3-carboxylic acid 1,1-dioxide | Purification method A. $^1H$ NMR (400 MHz, DMSO-$d_6$) δ: 9.61 (s, 1H), 7.85 (d, 1H), 7.63-7.54 (m, 1H), 7.43 (d, 1H), 7.21 (s, 2H), 7.12 (d, 1H), 6.89 (dd, 3.0 Hz, 1H), 3.69-3.59 (m, 1H), 3.40-3.33 (m, 1H), 3.29-3.20 (m, 1H), 3.17-3.01 (m, 2H), 2.45-2.37 (m, 1H), 2.21-2.07 (m, 1H). LCMS: m/z 430.0 $[M + H]^+$ |
| 13 | 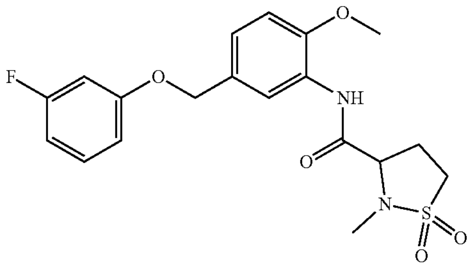 [SMILES: COc1ccc(COc2cccc(F)c2)cc1NC(=O)C1CCS(=O)(=O)N1C] Starting materials: 5-((3-Fluorophenoxy)methyl)-2-methoxyaniline HCl and 2-Methylisothiazolidine-3-carboxylic acid 1,1-dioxide | Purification method A. $^1H$ NMR (400 MHz, DMSO-$d_6$) δ: 9.36 (s, 1H), 8.11 (s, 1H), 7.37-7.26 (m, 1H), 7.22 (d, 1H), 7.08 (d, 1H), 6.93-6.80 (m, 2H), 6.80-6.72 (m, 1H), 5.03 (s, 2H), 4.02 (t, 1H), 3.86 (s, 3H), 3.41-3.33 (m, 1H), 3.29-3.20 (m, 1H), 2.64 (s, 3H), 2.63-2.58 (m, 1H), 2.32-2.20 (m, 1H). LCMS: m/z 409.2 $[M + H]^+$ |
| 14 | 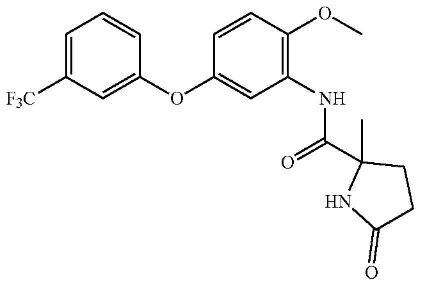 [SMILES: COc1ccc(Oc2cccc(C(F)(F)F)c2)cc1NC(=O)C1(C)CCC(=O)N1] Starting materials: 2-Methoxy-5-(3-(trifluoromethyl)phenoxy)aniline and 2-Methyl-5-oxopyrrolidine-2-carboxylic acid | Purification method A. $^1H$ NMR (500 MHz, DMSO-$d_6$) δ: 8.85 (s, 1H), 8.36 (s, 1H), 7.90 (d, 1H), 7.62-7.54 (m, 1H), 7.43 (d, 1H), 7.25-7.18 (m, 2H), 7.13 (d, 1H), 6.88 (dd, 1H), 3.86 (s, 3H), 2.31-2.26 (m, 1H), 2.22 (t, 2H), 2.00-1.89 (m, 1H), 1.40 (s, 3H). LCMS: m/z 409.2 $[M + H]^+$ |

-continued

| No. | Structure and starting material | Purification method and characterization data |
|---|---|---|
| 15 | 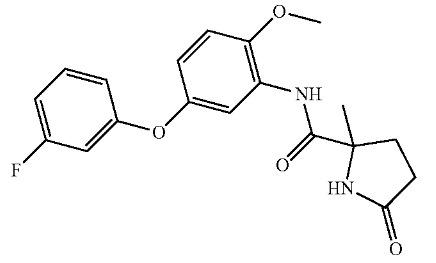 [SMILES: COc1ccc(Oc2cccc(F)c2)cc1NC(=O)C1(C)CCC(=O)N1] Starting materials: 5-(3-Fluoro-phenoxy)-2-methoxyaniline and 2-Methyl-5-oxopyrrolidine-2-carboxylic acid | Purification method A. $^1$H NMR (500 MHz, DMSO-$d_6$) δ: 8.83 (s, 1H), 8.36 (s, 1H), 7.89 (d, 1H), 7.40-7.33 (m, 1H), 7.11 (d, 1H), 6.94-6.88 (m, 1H), 6.85 (dd, 1H), 6.80-6.70 (m, 2H), 3.86 (s, 3H), 2.32-2.25 (m, 1H), 2.25-2.20 (m, 2H), 2.00-1.91 (m, 1H), 1.40 (s, 3H). LCMS: m/z 359.2 [M + H]$^+$ |
| 16 | 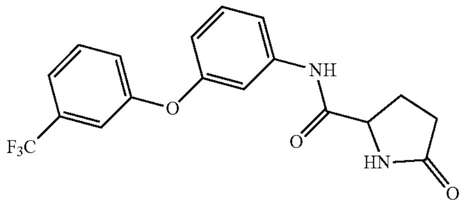 [SMILES: O=C1CCC(C(=O)Nc2cccc(Oc3cccc(C(F)(F)F)c3)c2)N1] Starting materials: 3-(3-(Trifluoro-methyl)phenoxy)aniline and 5-Oxo-pyrrolidine-2-carboxylic acid | Purification method A. $^1$H NMR (400 MHz, DMSO-$d_6$) δ: 10.15 (s, 1H), 7.84 (s, 1H), 7.68 – 7.59 (m, 1H), 7.51 (d, 1H), 7.45-7.28 (m, 5H), 6.81 (d, 1H), 4.15 (dd, 1H), 2.36-2.27 (m, 1H), 2.22-2.04 (m, 2H), 2.03-1.90 (m, 1H). LCMS: m/z 364.2 [M + H]$^+$ |
| 17 | 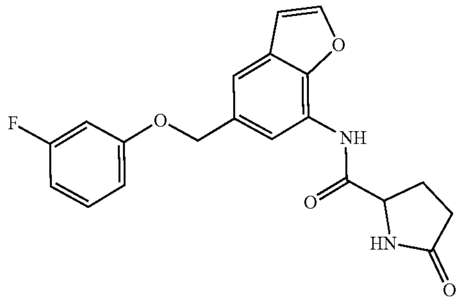 [SMILES: O=C1CCC(C(=O)Nc2cc(COc3cccc(F)c3)cc3ccoc23)N1] Starting materials: 5-((3-Fluoro-phenoxy)methyl)benzofuran-7-amine and 5-Oxopyrrolidine-2-carboxylic acid | Purification method C. $^1$H NMR (400 MHz, DMSO-$d_6$) δ: 10.20 (s, 1H), 8.07 (s, 1H), 7.90 (d, 2H), 7.53 (s, 1H), 7.35-7.27 (m, 1H), 7.04-7.00 (m, 1H), 6.95-6.85 (m, 2H), 6.82-6.73 (m, 1H), 5.18 (d, 2H), 4.41 (dd, 1H), 2.38 (q, 1H), 2.29-2.12 (m, 2H), 2.11-1.99 (m, 1H). LCMS: m/z 369.0 [M + H]$^+$ |
| 18 | 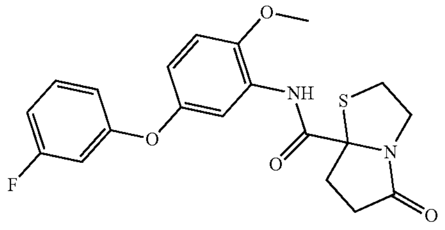 [SMILES: COc1ccc(Oc2cccc(F)c2)cc1NC(=O)C12CCC(=O)N1CCS2] Starting materials: 5-(3-Fluoro-phenoxy)-2-methoxyaniline and 5-Oxotetrahydropyrrolo[2,1-b]thiazole-7a(5H)-carboxylic acid | Purification method A. $^1$H NMR (400 MHz, Methanol-$d_4$) δ: 7.83 (d, 1H), 7.36-7.26 (m, 1H), 7.09 (d, 1H), 6.87 (dd, 1H), 6.84-6.72 (m, 2H), 6.71-6.60 (m, 1H), 4.59 (s, 1H), 4.47-4.38 (m, 1H), 3.94 (s, 3H), 3.26-3.19 (m, 3H), 2.89-2.70 (m, 2H), 2.67-2.52 (m, 2H). LCMS: m/z 403.2 [M + H]$^+$ |

-continued

| No. | Structure and starting material | Purification method and characterization data |
|---|---|---|
| 19 | 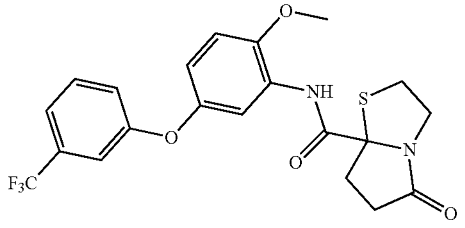 [SMILES: COc1ccc(Oc2cccc(C(F)(F)F)c2)cc1NC(=O)C12CCC(=O)N1CCS2] Starting materials: 2-Methoxy-5-(3-(trifluoromethyl)phenoxy)aniline and 5-Oxotetrahydropyrrolo[2,1-b]-thiazole-7a(5H)-carboxylic acid | Purification method B. $^1$H NMR (400 MHz, DMSO-$d_6$) δ: 9.19 (s, 1H), 7.70 (d, 1H), 7.63-7.55 (m, 1H), 7.44 (d, 1H), 7.23 (d, 2H), 7.15 (d, 1H), 6.94 (dd, 1H), 4.38-4.23 (m, 1H), 3.87 (s, 3H), 3.18-3.00 (m, 3H), 2.75-2.56 (m, 3H), 2.47-2.38 (m, 1H). LCMS: m/z 453.0 [M + H]$^+$ |
| 20 | 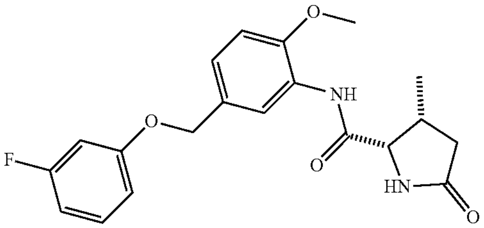 [SMILES: COc1ccc(COc2cccc(F)c2)cc1NC(=O)[C@H]1NC(=O)C[C@H]1C] Starting materials: 5-((3-Fluoro-phenoxy)methyl)-2-methoxyaniline HCl and rac-(cis)-3-methyl-5-oxo-pyrrolidine-2-carboxylic acid | Purification method B. $^1$H NMR (400 MHz, DMSO-$d_6$) δ: 9.32 (s, 1H), 8.04 (d, 1H), 7.81 (s, 1H), 7.37-7.26 (m, 1H), 7.19 (dd, 1H), 7.07 (d, 1H), 6.92-6.80 (m, 2H), 6.80-6.69 (m, 1H), 5.02 (s, 2H), 4.36 (d, 1H), 3.85 (s, 3H), 2.70-2.62 (m, 1H), 2.20 (dd, 1H), 1.91 (dd, 1H), 0.99 (d, 3H). LCMS: m/z 373.2 [M + H]$^+$ |
| 21 | 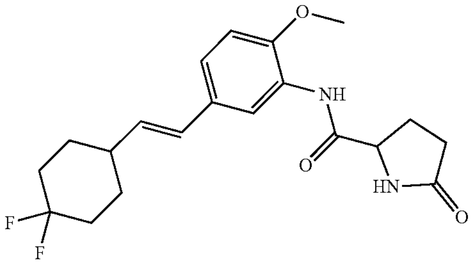 [SMILES: COc1ccc(/C=C/C2CCC(F)(F)CC2)cc1NC(=O)C1CCC(=O)N1] Starting materials: (E)-5-(2-(4,4-Di-fluorocyclohexyl)vinyl)-2-methoxy-aniline and 5-Oxopyrrolidine-2-carboxylic acid | Purification method B. $^1$H NMR (400 MHz, DMSO-$d_6$) δ: 9.19 (s, 1H), 8.05 (s, 1H), 7.94 (s, 1H), 7.12 (d, 1H), 7.00 (d, 1H), 6.35 (d, 1H), 6.05 (dd, 1H), 4.35 (d, 1H), 3.83 (s, 3H), 2.35-1.79 (m, 11H), 1.43 (q, 2H). LCMS: m/z 379.2 [M + H]$^+$ |
| 22 | 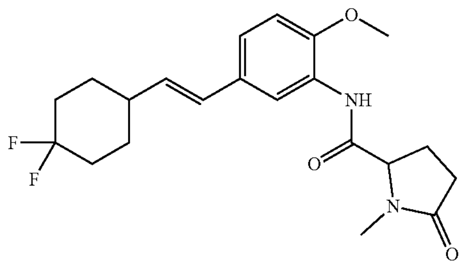 [SMILES: COc1ccc(/C=C/C2CCC(F)(F)CC2)cc1NC(=O)C1CCC(=O)N1C] Starting materials: (E)-5-(2-(4,4-di-fluorocyclohexyl)vinyl)-2-methoxy-aniline and 1-Methyl-5-oxopyrroli-dine-2-carboxylic acid | Purification method A. $^1$H NMR (400 MHz, DMSO-$d_6$) δ: 9.47 (s, 1H), 8.01 (s, 1H), 7.13 (d, 1H), 7.00 (d, 1H), 6.35 (d, 1H), 6.06 (dd, 1H), 4.48-4.39 (m, 1H), 3.83 (s, 3H), 2.67 (s, 3H), 2.39-2.15 (m, 4H), 2.09-1.97 (m, 2H), 1.97-1.74 (m, 5H), 1.43 (q, 2H). LCMS: m/z 393.2 [M + H]$^+$ |

-continued

| No. | Structure and starting material | Purification method and characterization data |
| --- | --- | --- |
| 23 | 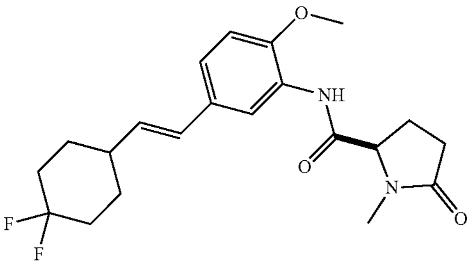 [SMILES: COc1ccc(/C=C/C2CCC(F)(F)CC2)cc1NC(=O)[C@H]1CCC(=O)N1C] Starting materials: rac-(E)-N-(5-(2-(4,4-difluorocyclohexyl)vinyl)-2-methoxyphenyl)-1-methyl-5-oxo-pyrrolidine-2-carboxamide | Purification method A followed by method H. Retention time = 17.42 min; ee 98%. $^1$H NMR (400 MHz, DMSO-$d_6$) δ: 9.49 (s, 1H), 8.02 (d, 1H), 7.13 (dd, 1H), 7.00 (d, 1H), 6.34 (d, 1H), 6.06 (dd, 1H), 4.51-4.35 (m, 1H), 3.83 (s, 3H), 2.67 (s, 3H), 2.28-2.20 (m, 4H), 2.14-1.75 (m, 7H), 1.50-1.32 (m, 2H). LCMS: m/z 393.2 $[M + H]^+$ |
| 24 | 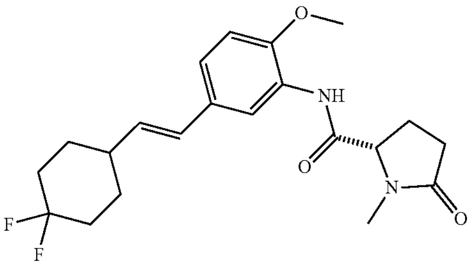 [SMILES: COc1ccc(/C=C/C2CCC(F)(F)CC2)cc1NC(=O)[C@@H]1CCC(=O)N1C] Starting materials: rac-(E)-N-(5-(2-(4,4-difluorocyclohexyl)vinyl)-2-methoxyphenyl)-1-methyl-5-oxo-pyrrolidine-2-carboxamide | Purification method A followed by method H. Retention time = 20.55 min; ee 100%. $^1$H NMR (400 MHz, DMSO-$d_6$) δ: 9.49 (s, 1H), 8.02 (d, 1H), 7.13 (dd, 1H), 7.00 (d, 1H), 6.34 (d, 1H), 6.06 (dd, 1H), 4.51-4.36 (m, 1H), 3.83 (s, 3H), 2.67 (s, 3H), 2.34-2.17 (m, 4H), 2.11-1.98 (m, 2H), 1.98-1.76 (m, 5H), 1.51-1.32 (m, 2H). LCMS: m/z 393.2 $[M + H]^+$ |
| 25 | 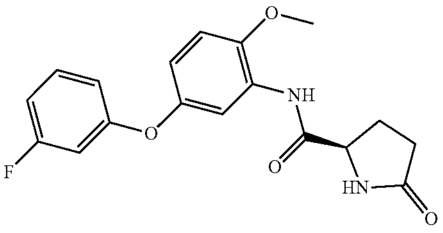 Starting materials: 5-(3-Fluoro-phenoxy)-2-methoxyaniline and (R)-5-Oxopyrrolidine-2-carboxylic acid | Purification method B. $^1$H NMR (400 MHz, DMSO-$d_6$) δ: 9.33 (s, 1H), 7.91 (s, 1H), 7.87 (d, 1H), 7.44-7.34 (m, 1H), 7.10 (d, 1H), 6.93-6.88 (m, 1H), 6.85 (dd, 1H), 6.80-6.72 (m, 2H), 4.38 (dd, 1H), 3.86 (s, 3H), 2.35-2.25 (m, 1H), 2.24-2.03 (m, 2H), 2.03-1.82 (m, 1H). LCMS: m/z 354.2 $[M + H]^+$ |
| 26 | 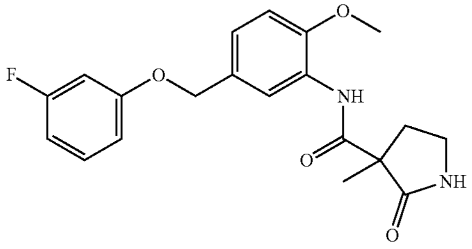 [SMILES: COc1ccc(COc2cccc(F)c2)cc1NC(=O)C1(C)CCNC1=O] Starting materials: 5-((3-Fluoro-phenoxy)methyl)-2-methoxyaniline HCl and 3-Methyl-2-oxopyrrolidine-3-carboxylic acid | Purification method B. $^1$H NMR (400 MHz, DMSO-$d_6$) δ: 10.11 (s, 1H), 8.35 (s, 1H), 8.19 (s, 1H), 7.37-7.24 (m, 1H), 7.14 (d, 1H), 7.05 (d, 1H), 6.95-6.80 (m, 2H), 6.80-6.71 (m, 1H), 5.02 (s, 2H), 3.29-3.12 (m, 2H), 2.58-2.52 (m, 1H), 2.05-1.89 (m, 1H), 1.41 (s, 3H). LCMS: m/z 373.0 $[M + H]^+$ |

-continued

| No. | Structure and starting material | Purification method and characterization data |
| --- | --- | --- |
| 27 | 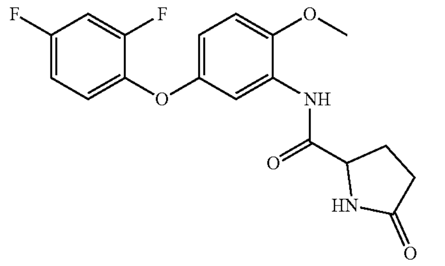 Starting materials: 6-((3-Fluoro-phenoxy)methyl) benzo[d][1,3]-dioxol-4-amine and 5-Oxopyrrolidine-2-carboxylic acid | Purification method B. $^1$H NMR (400 MHz, DMSO-$d_6$) δ: 9.84 (s, 1H), 7.88 (s, 1H), 7.36 (d, 1H), 7.35-7.25 (m, 1H), 6.91-6.80 (m, 3H), 6.80-6.73 (m, 1H), 6.07 (d, 2H), 4.99 (s, 2H), 4.28 (dd, 1H), 2.38-2.27 (m, 1H), 2.27-2.05 (m, 2H), 2.05-1.89 (m, 1H). LCMS: m/z 374.2 $[M + H]^+$ |
| 28 | 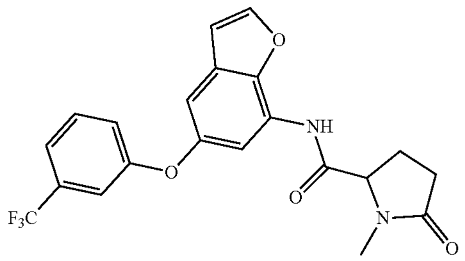 [SMILES: CN1C(=O)CCC1C(=O)Nc1cc(Oc2cccc(C(F)(F)F)c2)cc2ccoc12] Starting materials: 5-(3-(Trifluoro-methyl)phenoxy)benzofuran-7-amine and 1-Methyl-5-oxopyrrolidine-2-carboxylic acid | Purification method C. $^1$H NMR (400 MHz, DMSO-$d_6$) δ: 10.61 (s, 1H), 8.14 (d, 1H), 7.70 (d, 1H), 7.63-7.57 (m, 1H), 7.46 (d, 1H), 7.31-7.24 (m, 2H), 7.19 (d, 1H), 7.01 (d, 1H), 4.51-4.43 (m, 1H), 2.68 (s, 3H), 2.34-2.22 (m, 3H), 2.00-1.92 (m, 1H). LCMS: m/z 419.0 $[M + H]^+$ |
| 29 | 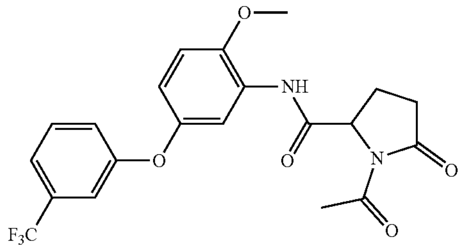 [SMILES: COc1ccc(Oc2cccc(C(F)(F)F)c2)cc1NC(=O)C1CCC(=O)N1C(C)=O] Starting materials: 2-Methoxy-5-(3-(trifluoromethyl)phenoxy)aniline and 1-Acetyl-5-oxopyrrolidine-2-carboxylic acid | Purification method A. $^1$H NMR (400 MHz, DMSO-$d_6$) δ: 9.74 (s, 1H), 7.85 (d, 1H), 7.61-7.53 (m, 1H), 7.42 (d, 1H), 7.20 (d, 2H), 7.12 (d, 1H), 6.88 (dd, 1H), 5.07 (d, 1H), 3.89 (s, 3H), 3.37-3.32 (m, 1H), 2.47-2.40 (m, 1H), 2.37 (s, 3H), 2.35-2.22 (m, 1H), 1.99-1.87 (m, 1H). LCMS: m/z 437.0 $[M + H]^+$ |
| 30 | 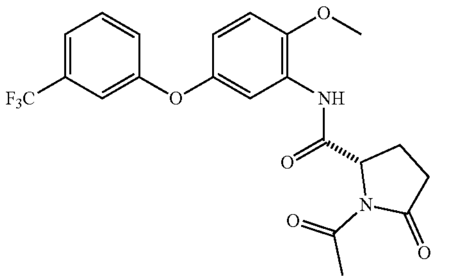 [SMILES: COc1ccc(Oc2cccc(C(F)(F)F)c2)cc1NC(=O)[C@@H]1CCC(=O)N1C(C)=O] Starting materials: 2-Methoxy-5-(3-(trifluoromethyl)phenoxy)aniline and 1-Acetyl-5-oxopyrrolidine-2-carboxylic acid | Purification method A followed by method I. Retention time 23.52 min; ee 100%. $^1$H NMR (400 MHz, DMSO-$d_6$) δ: 9.74 (s, 1H), 7.85 (d, 1H), 7.61-7.53 (m, 1H), 7.42 (d, 1H), 7.20 (d, 2H), 7.12 (d, 1H), 6.88 (dd, 1H), 5.07 (d, 1H), 3.89 (s, 3H), 3.37-3.32 (m, 1H), 2.47-2.40 (m, 1H), 2.37 (s, 3H), 2.35-2.22 (m, 1H), 1.99-1.87 (m, 1H). LCMS: m/z 437.0 $[M + H]^+$ |

-continued

| No. | Structure and starting material | Purification method and characterization data |
|---|---|---|
| 31 | 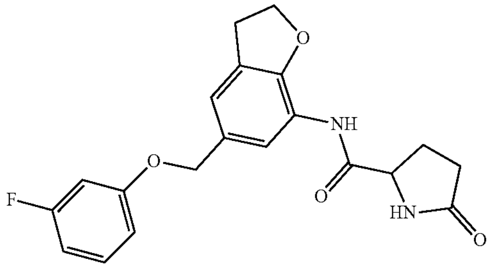 [SMILES: O=C1CCC(C(=O)Nc2cc(COc3cccc(F)c3)cc3c2OCC3)N1] Starting materials: 5-((3-Fluoro-phenoxy)methyl)-2,3-dihydrobenzo-furan-7-amine and 5-Oxopyrrolidine-2-carboxylic acid | Purification method A. $^1H$ NMR (400 MHz, DMSO-$d_6$) δ: 9.49 (s, 1H), 7.88 (s, 1H), 7.75 (s, 1H), 7.36-7.25 (m, 1H), 7.11 (s, 1H), 6.91-6.80 (m, 2H), 6.80-6.69 (m, 1H), 4.98 (s, 2H), 4.61 (t, 2H), 4.32 (dd, 1H), 3.23 (t, 2H), 2.35-2.25 (m, 1H), 2.25-2.06 (m, 2H), 2.06-1.89 (m, 1H). LCMS: m/z 371.2 $[M + H]^+$ |
| 32 | 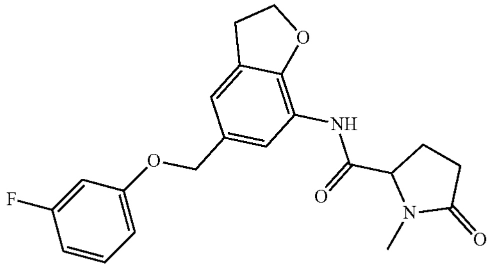 [SMILES: CN1C(=O)CCC1C(=O)Nc1cc(COc2cccc(F)c2)cc2c1OCC2] Starting materials: 5-((3-Fluoro-phenoxy)methyl)-2,3-dihydrobenzo-furan-7-amine and 1-Methyl-5-oxo-pyrrolidine-2-carboxylic acid | Purification method A. $^1H$ NMR (600 MHz, DMSO-$d_6$) δ: 9.77 (s, 1H), 7.73 (s, 1H), 7.32-7.24 (m, 1H), 7.10 (s, 1H), 6.89-6.79 (m, 2H), 6.74 (dd, 1H), 4.96 (s, 2H), 4.60 (t, 2H), 4.39-4.31 (m, 1H), 3.22 (t, 2H), 2.64 (s, 3H), 2.31-2.17 (m, 3H), 1.94-1.84 (m, 1H). LCMS: m/z 385.2 $[M + H]^+$ |
| 33 | 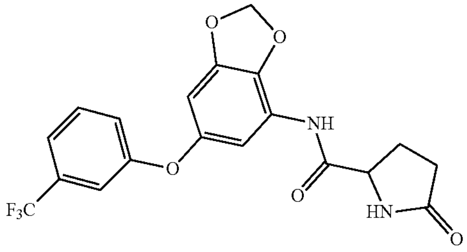 [SMILES: O=C1CCC(C(=O)Nc2cc(Oc3cccc(C(F)(F)F)c3)cc3c2OCO3)N1] Starting materials: 6-(3-(Trifluoro-methyl)phenoxy) benzo[d][1,3]-dioxol-4-amine and 5-Oxopyrrolidine-2-carboxylic acid | Purification method A. $^1H$ NMR (400 MHz, DMSO-$d_6$) δ: 9.95 (s, 1H), 7.83 (s, 1H), 7.64-7.54 (m, 1H), 7.45 (d, 1H), 7.25 (d, 2H), 7.13 (d, 1H), 6.68 (d, 1H), 6.12 (s, 2H), 4.29 (dd, 1H), 2.35-2.25 (m, 1H), 2.22-2.06 (m, 2H), 2.00-1.86 (m, 1H). LCMS: m/z 409.2 $[M + H]^+$ |
| 34 | 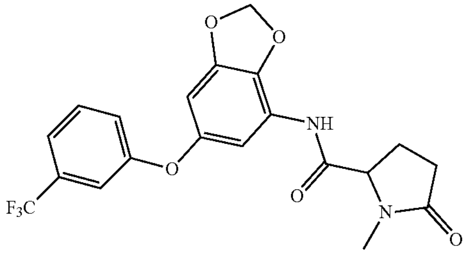 [SMILES: CN1C(=O)CCC1C(=O)Nc1cc(Oc2cccc(C(F)(F)F)c2)cc2c1OCO2] Starting materials: 6-(3-(Trifluoro-methyl)phenoxy) benzo[d][1,3]-dioxol-4-amine and 1-Methyl-5-oxopyrrolidine-2-carboxylic acid | Purification method A. $^1H$ NMR (400 MHz, DMSO-$d_6$) δ: 10.19 (s, 1H), 7.63-7.54 (m, 1H), 7.44 (d, 1H), 7.24 (d, 2H), 7.15 (d, 1H), 6.73-6.66 (m, 1H), 6.13 (d, 2H), 4.34 (dd, 1H), 2.69-2.60 (m, 3H), 2.31-2.14 (m, 3H), 1.94-1.83 (m, 1H). LCMS: m/z 423.0 $[M + H]^+$ |

-continued

| No. | Structure and starting material | Purification method and characterization data |
|---|---|---|
| 35 | 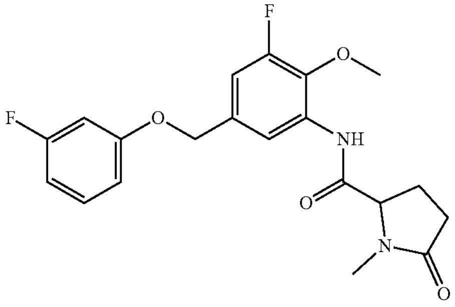 [SMILES: COc1c(F)cc(COc2cccc(F)c2)cc1NC(=O)C1CCC(=O)N1C] Starting materials: 3-Fluoro-5-((3-fluorophenoxy)methyl)-2-methoxy-aniline and 1-Methyl-5-oxopyrrolidine-2-carboxylic acid | Purification method A. $^1$H NMR (600 MHz, DMSO-$d_6$) δ: 9.80 (s, 1H), 7.88 (s, 1H), 7.35-7.26 (m, 1H), 7.15 (dd, 1H), 6.90-6.86 (m, 1H), 6.85-6.80 (m, 1H), 6.80-6.74 (m, 1H), 5.03 (s, 2H), 4.48-4.43 (m, 1H), 3.85 (s, 3H), 2.66 (s, 3H), 2.32-2.17 (m, 3H), 1.95-1.89 (m, 1H). LCMS: m/z 391.2 [M + H]$^+$ |
| 36 | 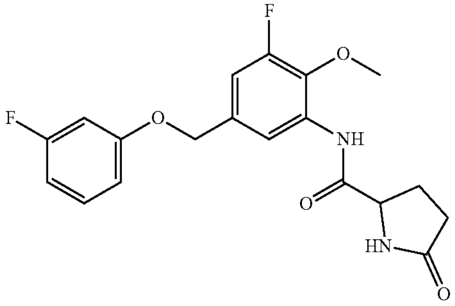 [SMILES: COc1c(F)cc(COc2cccc(F)c2)cc1NC(=O)C1CCC(=O)N1] Starting materials: 3-Fluoro-5-((3-fluorophenoxy)methyl)-2-methoxy-aniline and 5-Oxopyrrolidine-2-carboxylic acid | Purification method A. $^1$H NMR (600 MHz, DMSO-$d_6$) δ: 9.52 (s, 1H), 7.91 (s, 2H), 7.36-7.25 (m, 1H), 7.13 (dd, 1H), 6.89-6.85 (m, 1H), 6.83 (dd, 1H), 6.79-6.72 (m, 1H), 5.04 (s, 2H), 4.39 (dd, 1H), 3.84 (s, 3H), 2.38-2.30 (m, 1H), 2.25-2.16 (m, 1H), 2.16-2.06 (m, 1H), 2.03-1.94 (m, 1H). LCMS: m/z 377.1 [M + H]$^+$ |
| 37 | 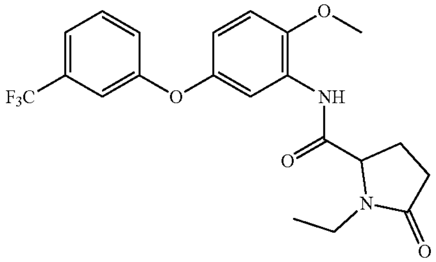 [SMILES: CCN1C(=O)CCC1C(=O)Nc1cc(Oc2cccc(C(F)(F)F)c2)ccc1OC] Starting materials: 2-Methoxy-5-(3-(trifluoromethyl)phenoxy)aniline and 1-Ethyl-5-oxopyrrolidine-2-carboxylic acid | Purification method A. $^1$H NMR (400 MHz, DMSO-$d_6$) δ: 9.66 (s, 1H), 7.85 (d, 1H), 7.63-7.55 (m, 1H), 7.43 (d, 1H), 7.24-7.18 (m, 2H), 7.13 (d, 1H), 6.90 (dd, 1H), 4.63-4.56 (m, 1H), 3.88 (s, 3H), 3.53-3.43 (m, 1H), 2.88-2.77 (m, 1H), 2.33-2.15 (m, 3H), 1.96-1.87 (m, 1H), 1.00 (t, 3H). LCMS: m/z 423.0 [M + H]$^+$ |
| 38 | 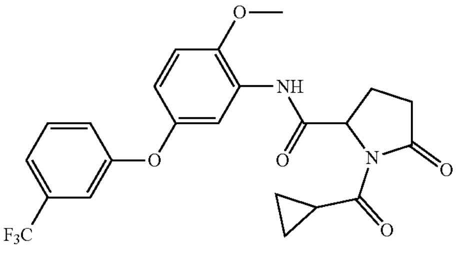 Starting materials: 2-Methoxy-5-(3-(trifluoromethyl)phenoxy)aniline and 1-(Cyclopropanecarbonyl)-5-oxo-pyrrolidine-2-carboxylic acid | Purification method A. $^1$H NMR (400 MHz, DMSO-$d_6$) δ: 9.70 (s, 1H), 7.85 (d, 1H), 7.61-7.54 (m, 1H), 7.42 (d, 1H), 7.23-7.15 (m, 2H), 7.12 (d, 1H), 6.87 (dd, 1H), 5.06 (dd, 1H), 3.88 (s, 3H), 3.18-3.07 (m, 1H), 2.70-2.54 (m, 2H), 2.36-2.24 (m, 1H), 1.98-1.86 (m, 1H), 0.99-0.76 (m, 4H). LCMS: m/z 463.0 [M + H]$^+$ |

-continued

| No. | Structure and starting material | Purification method and characterization data |
| --- | --- | --- |
| 39 | 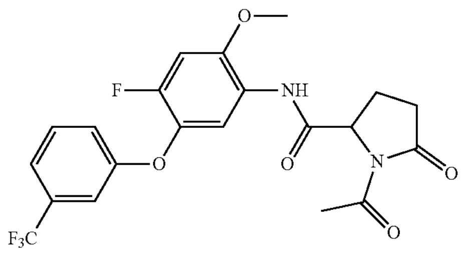 [SMILES: COc1cc(F)c(Oc2cccc(C(F)(F)F)c2)cc1NC(=O)C1CCC(=O)N1C(C)=O] Starting materials: 4-Fluoro-2-methoxy-5-(3-(trifluoromethyl)-phenoxy)aniline and 1-Acetyl-5-oxopyrrolidine-2-carboxylic acid | Purification method A. $^{1}H$ NMR (400 MHz, DMSO-$d_6$) : 9.77 (s, 1H), 7.93 (d, 1H), 7.62-7.54 (m, 1H), 7.44 (d, 1H), 7.28-7.15 (m, 4H), 5.03 (d, 1H), 3.92 (s, 3H), 2.65-2.57 (m, 2H), 2.37 (s, 3H), 2.31-2.22 (m, 1H), 1.99-1.88 (m, 1H). LCMS: m/z 455.1 $[M + H]^+$ |
| 40 | 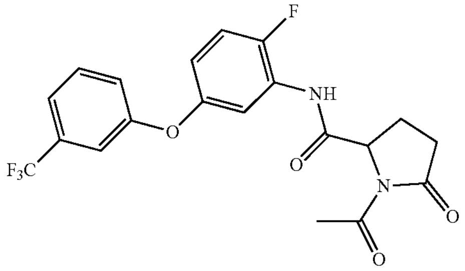 Starting materials: 2-Fluoro-5-(3-(trifluoromethyl)phenoxy)aniline and 1-Acetyl-5-oxopyrrolidine-2-carboxylic acid | Purification method C. $^{1}H$ NMR (400 MHz, DMSO-$d_6$) δ: 10.29 (s, 1H), 7.80 (dd, 1H), 7.64-7.56 (m, 1H), 7.48 (d, 1H), 7.41-7.22 (m, 3H), 6.96-6.87 (m, 1H), 4.98 (dd, 1H), 2.68-2.52 (m, 2H), 2.38 (s, 3H), 2.35-2.25 (m, 1H), 2.01-1.93 (m, 1H). LCMS: m/z 383.2 $[M + H]^+$ |
| 41 | 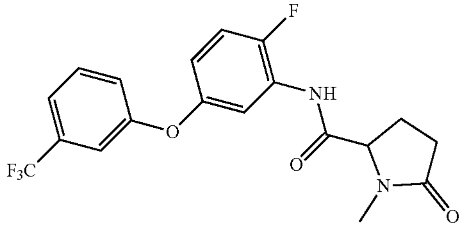 [SMILES: CN1C(=O)CCC1C(=O)Nc1cc(Oc2cccc(C(F)(F)F)c2)ccc1F] Starting materials: 2-Fluoro-5-(3-(trifluoromethyl)phenoxy)aniline and 1-Methyl-5-oxopyrrolidine-2-carboxylic acid | Purification method A. $^{1}H$ NMR (400 MHz, Methanol-$d_4$) δ: 7.81 (dd, 1H), 7.59-7.52 (m, 1H), 7.41 (d, 1H), 7.30-7.19 (m, 3H), 6.93-6.84 (m, 1H), 4.42 (dd, 1H), 2.83 (s, 3H), 2.57-2.32 (m, 3H), 2.13-2.05 (m, 1H). LCMS: m/z 397.0 $[M + H]^+$ |
| 42 | 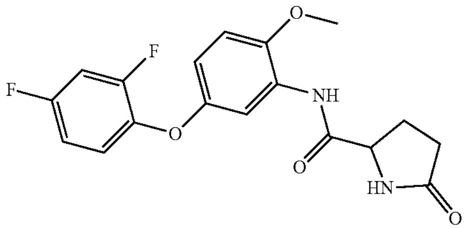 [SMILES: COc1ccc(Oc2ccc(F)cc2F)cc1NC(=O)C1CCC(=O)N1] Starting materials: 5-(2,4-Difluorophenoxy)-2-methoxyaniline and 5-Oxopyrrolidine-2-carboxylic acid | Purification method A. $^{1}H$ NMR (600 MHz, DMSO-$d_6$) δ: 9.27 (s, 1H), 7.89 (s, 1H), 7.81 (d, 1H), 7.47-7.39 (m, 1H), 7.19-7.12 (m, 1H), 7.09-7.05 (m, 1H), 7.03 (d, 1H), 6.71 (dd, 1H), 4.35 (dd, 1H), 3.82 (s, 3H), 2.33-2.25 (m, 1H), 2.20-2.13 (m, 1H), 2.12-2.05 (m, 1H), 1.95-1.89 (m, 1H). LCMS: m/z 363.2 $[M + H]^+$ |

-continued

| No. | Structure and starting material | Purification method and characterization data |
|---|---|---|
| 43 | 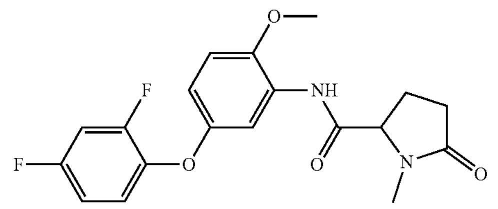 [SMILES: COc1ccc(Oc2ccc(F)cc2F)cc1NC(=O)C1CCC(=O)N1C] Starting materials: 5-(2,4-Difluoro-phenoxy)-2-methoxyaniline and 1-Methyl-5-oxopyrrolidine-2-carboxylic acid | Purification method A. $^1H$ NMR (400 MHz, DMSO-$d_6$) δ: 9.57 (s, 1H), 7.80 (d, 1H), 7.50-7.42 (m, 1H), 7.21-7.11 (m, 1H), 7.07 (dd, 2H), 6.74 (dd, 1H), 4.50-4.40 (m, 1H), 3.84 (s, 3H), 2.64 (s, 3H), 2.29-2.11 (m, 3H), 1.92-1.83 (m, 1H). LCMS: m/z 377.2 $[M + H]^+$ |
| 44 | 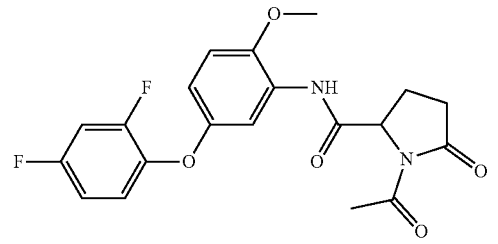 [SMILES: COc1ccc(Oc2ccc(F)cc2F)cc1NC(=O)C1CCC(=O)N1C(C)=O] Starting materials: 5-(2,4-Difluoro-phenoxy)-2-methoxyaniline and 1-Acetyl-5-oxopyrrolidine-2-carboxylic acid | Purification method A. $^1H$ NMR (400 MHz, DMSO-$d_6$) δ: 9.67 (s, 1H), 7.81 (d, 1H), 7.50-7.39 (m, 1H), 7.17-7.10 (m, 1H), 7.10-7.02 (m, 2H), 6.72 (dd, 1H), 5.06 (dd, 1H), 3.85 (s, 3H), 2.66-2.54 (m, 2H), 2.38 (s, 3H), 2.33-2.20 (m, 1H), 1.97-1.85 (m, 1H). LCMS: m/z 405.0 $[M + H]^+$ |
| 45 | 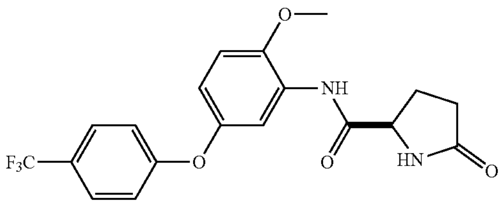 [SMILES: COc1ccc(Oc2ccc(C(F)(F)F)cc2)cc1NC(=O)[C@H]1CCC(=O)N1] Starting materials: 2-Methoxy-5-(4-(trifluoromethyl)phenoxy)aniline and 5-Oxopyrrolidine-2-carboxylic acid | Purification method A followed by method I. Retention time 4.29 min; ee 100%. $^1H$ NMR (400 MHz, DMSO-$d_6$) δ: 9.35 (s, 1H), 7.91 (d, 2H), 7.71 (d, 2H), 7.14 (d, 1H), 7.08 (d, 2H), 6.91 (dd, 1H), 4.38 (dd, 1H), 3.88 (s, 3H), 2.38-2.27 (m, 1H), 2.26-2.07 (m, 2H), 2.02-1.90 (m, 1H). LCMS: m/z 395.2 $[M + H]^+$. |
| 46 | 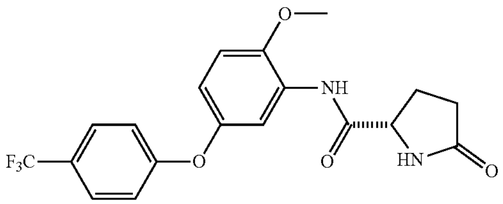 [SMILES: COc1ccc(Oc2ccc(C(F)(F)F)cc2)cc1NC(=O)[C@@H]1CCC(=O)N1] Starting materials: 2-Methoxy-5-(4-(trifluoromethyl)phenoxy)aniline and 5-Oxopyrrolidine-2-carboxylic acid | Purification method A followed by method I. Retention time 7.87 min; ee 99%. $^1H$ NMR (400 MHz, DMSO-$d_6$) δ: 9.35 (s, 1H), 7.91 (d, 2H), 7.71 (d, 2H), 7.14 (d, 1H), 7.08 (d, 2H), 6.91 (dd, 1H), 4.38 (dd, 1H), 3.88 (s, 3H), 2.38-2.27 (m, 1H), 2.26-2.07 (m, 2H), 2.02-1.90 (m, 1H). LCMS: m/z 395.0 $[M + H]^+$. |

-continued

| No. | Structure and starting material | Purification method and characterization data |
|---|---|---|
| 47 | 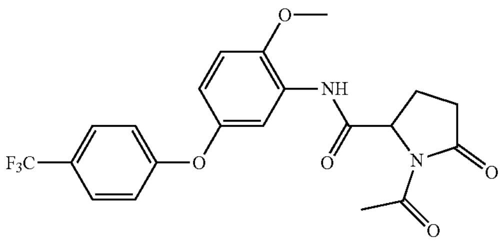 [SMILES: COc1ccc(Oc2ccc(C(F)(F)F)cc2)cc1NC(=O)C1CCC(=O)N1C(C)=O] Starting materials: 2-Methoxy-5-(4-(trifluoromethyl)phenoxy)aniline and 1-Acetyl-5-oxopyrrolidine-2-carboxylic acid | Purification method A. $^{1}$H NMR (600 MHz, DMSO-$d_6$) δ: 9.73 (s, 1H), 7.85 (d, 1H), 7.68 (d, 2H), 7.12 (d, 1H), 7.04 (d, 2H), 6.88 (dd, 1H), 5.05 (dd, 1H), 2.64-2.53 (m, 2H), 2.35 (s, 3H), 2.33-2.20 (m, 1H), 1.95-1.86 (m, 1H). LCMS: m/z 437.0 $[M + H]^+$ |
| 48 | 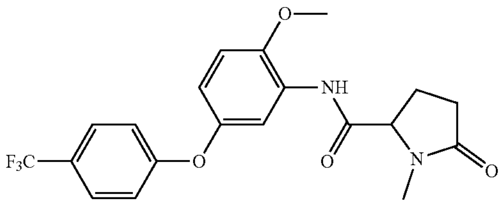 [SMILES: COc1ccc(Oc2ccc(C(F)(F)F)cc2)cc1NC(=O)C1CCC(=O)N1C] Starting materials: 2-Methoxy-5-(4-(trifluoromethyl)phenoxy)aniline and 1-Methyl-5-oxopyrrolidine-2-carboxylic acid | Purification method B. $^{1}$H NMR (400 MHz, DMSO-$_{d6}$) δ: 9.64 (s, 1H), 7.87 (d, 1H), 7.71 (d, 2H), 7.14 (d, 1H), 7.08 (d, 2H), 6.92 (dd, 1H), 4.47 (d, 1H), 3.89 (s, 3H), 2.64 (s, 3H), 2.31-2.16 (m, 3H), 1.94-1.80 (m, 1H). GCMS m/z 409.13 $[M]^+$ |
| 49 | 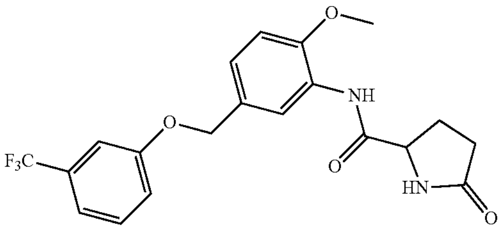 [SMILES: COc1ccc(COc2cccc(C(F)(F)F)c2)cc1NC(=O)C1CCC(=O)N1] Starting materials: 2-Methoxy-5-((3-(trifluoromethyl)phenoxy)methyl)-aniline HCl and 5-Oxopyrrolidine-2-carboxylic acid | Purification method A. $^{1}$H NMR (400 MHz, DMSO-$d_6$) δ: 9.23 (s, 1H), 8.12 (s, 1H), 7.94 (s, 1H), 7.57-7.47 (m, 1H), 7.32-7.24 (m, 3H), 7.21 (d, 1H), 7.08 (d, 1H), 5.10 (s, 2H), 4.36 (d, 1H), 3.85 (s, 3H), 2.34-1.96 (m, 4H). LCMS: m/z 409.2 $[M + H]^+$ |
| 50 | 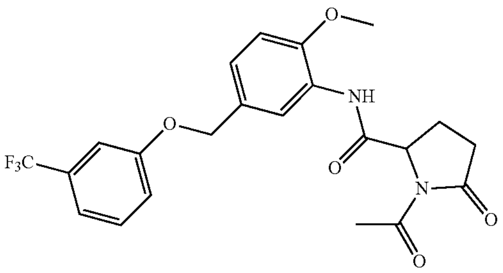 [SMILES: COc1ccc(COc2cccc(C(F)(F)F)c2)cc1NC(=O)C1CCC(=O)N1C(C)=O] Starting materials: 2-Methoxy-5-((3-(trifluoromethyl)phenoxy)methyl)-aniline HCl and 1-Acetyl-5-oxo-pyrrolidine-2-carboxylic acid | Purification method A. $^{1}$H NMR (600 MHz, DMSO-$d_6$) δ: 9.60 (s, 1H), 8.10 (d, 1H), 7.52-7.45 (m, 1H), 7.31-7.24 (m, 3H), 7.18 (dd, 1H), 7.05 (d, 1H), 5.06 (s, 2H), 5.04 (dd, 1H), 3.85 (s, 3H), 2.64-2.50 (m, 2H), 2.38 (s, 3H), 2.32-2.23 (m, 1H), 1.95-1.89 (m, 1H). LCMS: m/z 452.1 $[M + H]^+$ |

-continued

| No. | Structure and starting material | Purification method and characterization data |
|---|---|---|
| 51 | 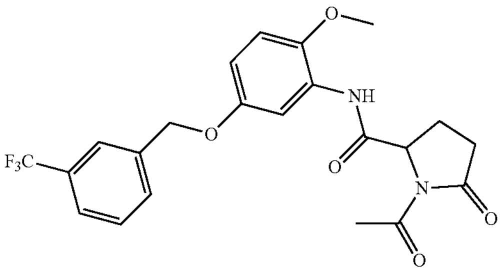 [SMILES: COc1ccc(OCc2cccc(C(F)(F)F)c2)cc1NC(=O)C1CCC(=O)N1C(C)=O]<br>Starting materials: 2-Methoxy-5-((3-(trifluoromethyl)benzyl)oxy)aniline HCl and 1-Acetyl-5-oxopyrrolidine-2-carboxylic acid | Purification method A. $^1H$ NMR (400 MHz, DMSO-$d_6$) δ: 9.58 (s, 1H), 7.86-7.56 (m, 5H), 6.98 (d, 1H), 6.74 (dd, 1H), 5.12 (s, 2H), 5.10-5.03 (m, 1H), 3.81 (s, 3H), 2.72-2.56 (m, 1H), 2.40 (s, 3H), 2.36-2.18 (m, 1H), 1.98-1.86 (m, 1H). LCMS: m/z 451.0 $[M + H]^+$ |
| 52 | 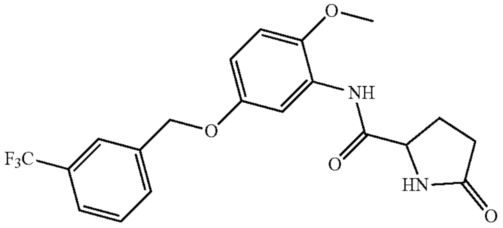 [SMILES: COc1ccc(OCc2cccc(C(F)(F)F)c2)cc1NC(=O)C1CCC(=O)N1]<br>Starting materials: 2-Methoxy-5-((3-(trifluoromethyl)benzyl)oxy)aniline HCl and 5-Oxopyrrolidine-2-carboxylic acid | Purification method A. $^1H$ NMR (500 MHz, DMSO-$d_6$) δ: 9.17 (s, 1H), 7.93 (s, 1H), 7.87-7.57 (m, 5H), 6.96 (d, 1H), 6.73 (dd, 1H), 5.12 (s, 2H), 4.35 (dd, 1H), 3.78 (s, 3H), 2.37-2.26 (m, 1H), 2.24-2.02 (m, 2H), 2.01-1.86 (m, 1H). LCMS: m/z 409.2 $[M + H]^+$ |
| 53 | 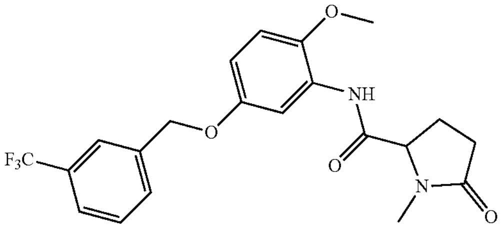 [SMILES: COc1ccc(OCc2cccc(C(F)(F)F)c2)cc1NC(=O)C1CCC(=O)N1C]<br>Starting materials: 2-Methoxy-5-((3-(trifluoromethyl)benzyl)oxy)aniline HCl and 1-Methyl-5-oxopyrrolidine-2-carboxylic acid | Purification method A. $^1H$ NMR (400 MHz, DMSO-$d_6$) δ: 9.49 (s, 1H), 7.84-7.60 (m, 5H), 6.99 (d, 1H), 6.77 (d, 1H), 5.14 (s, 2H), 4.49-4.43 (m, 1H), 3.80 (s, 3H), 2.66 (s, 3H), 2.28-2.16 (m, 3H), 1.93-1.88 (m, 1H). LCMS: m/z 423.0 $[M + H]^+$ |
| 54 | 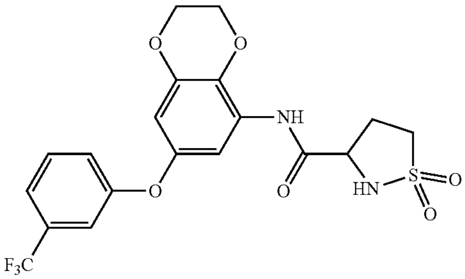 [SMILES: O=C(Nc1cc(Oc2cccc(C(F)(F)F)c2)cc2c1OCCO2)C1CCS(=O)(=O)N1]<br>Starting materials: 7-(3-(Trifluoromethyl)phenoxy)-2,3-dihydrobenzo-[b][1,4]dioxin-5-amine HCl and Isothiazolidine-3-carboxylic acid 1,1-dioxide | Purification method D. $^1H$ NMR (600 MHz, Acetonitrile-$d_3$) δ: 9.03 (s, 1H), 7.65 (d, 1H), 7.57-7.51 (m, 1H), 7.42 (d, 1H), 7.27 (d, 1H), 7.23 (dd, 1H), 6.45 (d, 1H), 4.39-4.30 (m, 4H), 4.25 (dd, 1H), 3.30-3.21 (m, 1H), 3.08-2.99 (m, 1H), 2.91-2.80 (m, 1H), 2.46-2.37 (m, 1H). LCMS: m/z 458.9 $[M + H]^+$ |

-continued

| No. | Structure and starting material | Purification method and characterization data |
|---|---|---|
| 55 | 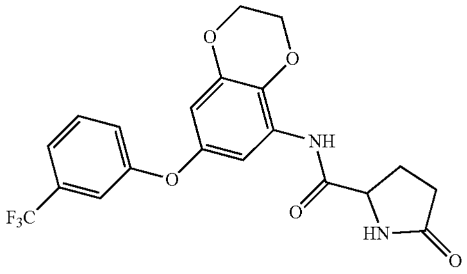 [SMILES: O=C1CCC(C(=O)Nc2cc(Oc3cccc(C(F)(F)F)c3)cc3c2OCCO3)N1] Starting materials: 7-(3-(Trifluoro-methyl)phenoxy)-2,3-dihydrobenzo-[b][1,4]dioxin-5-amine HCl and 5-Oxopyrrolidine-2-carboxylic acid | Purification method A. $^{1}$H NMR (400 MHz, DMSO-$d_6$) δ: 9.38 (s, 1H), 7.89 (s, 1H), 7.63-7.55 (m, 1H), 7.47-7.38 (m, 2H), 7.27-7.16 (m, 2H), 6.48 (d, 1H), 4.39-4.25 (m, 5H), 2.35-2.26 (m, 1H), 2.23-2.07 (m, 2H), 2.01-1.89 (m, 1H). LCMS: m/z 423.2 $[M + H]^+$ |
| 56 | 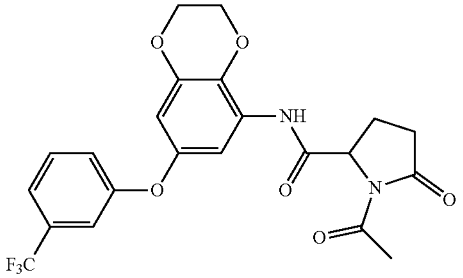 [SMILES: CC(=O)N1C(=O)CCC1C(=O)Nc1cc(Oc2cccc(C(F)(F)F)c2)cc2c1OCCO2] Starting materials: 7-(3-(Trifluoro-methyl)phenoxy)-2,3-dihydrobenzo-[b][1,4]dioxin-5-amine HCl and 1-Acetyl-5-oxopyrrolidine-2-carboxylic acid | Purification method A. $^{1}$H NMR (400 MHz, DMSO-$d_6$) δ: 9.79 (s, 1H), 7.64-7.55 (m, 1H), 7.50-7.38 (m, 2H), 7.28-7.14 (m, 2H), 6.47 (d, 1H), 5.06 (dd, 1H), 4.41-4.27 (m, 4H), 2.64-2.52 (m, 2H), 2.37 (s, 3H), 2.32-2.20 (m, 1H), 1.95 - 1.86 (m, 1H). LCMS: m/z 465.0 $[M + H]^+$ |
| 57 | 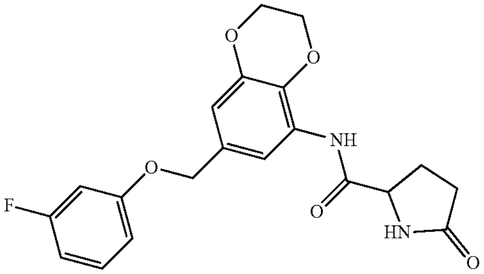 [SMILES: O=C1CCC(C(=O)Nc2cc(COc3cccc(F)c3)cc3c2OCCO3)N1] Starting materials: 7-((3-Fluoro-phenoxy)methyl)-2,3-dihydrobenzo-[b][1,4]dioxin-5-amine and 5-Oxo-pyrrolidine-2-carboxylic acid | Purification method B. $^{1}$H NMR (400 MHz, DMSO-$d_6$) δ: 9.26 (s, 1H), 7.93 (s, 1H), 7.64 (s, 1H), 7.35-7.27 (m, 1H), 6.91-6.80 (m, 2H), 6.80-6.73 (m, 2H), 4.97 (s, 2H), 4.41-4.21 (m, 5H), 2.38-2.27 (m, 1H), 2.27-2.04 (m, 2H), 2.01-1.90 (m, 1H). LCMS: m/z 388.0 $[M + H]^+$ |
| 58 | 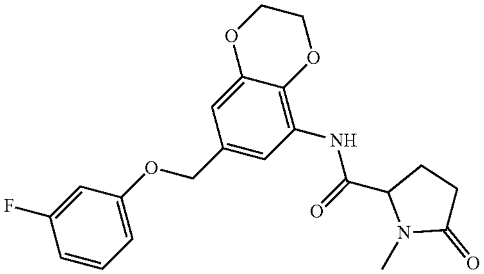 [SMILES: CN1C(=O)CCC1C(=O)Nc1cc(COc2cccc(F)c2)cc2c1OCCO2] Starting materials: 7-((3-Fluoro-phenoxy)methyl)-2,3-dihydrobenzo-[b][1,4]dioxin-5-amine and 1-Methyl-5-oxopyrrolidine-2-carboxylic acid | Purification method B. $^{1}$H NMR (400 MHz, DMSO-$d_6$) δ: 9.57 (s, 1H), 7.61 (s, 1H), 7.34-7.25 (m, 1H), 6.88-6.81 (m, 2H), 6.81-6.67 (m, 2H), 4.97 (s, 2H), 4.43 (s, 1H), 4.30 (dd, 4H), 2.66 (s, 3H), 2.36-2.17 (m, 3H), 1.95-1.84 (m, 1H). LCMS: m/z 401.0 $[M + H]^+$ |

-continued

| No. | Structure and starting material | Purification method and characterization data |
|---|---|---|
| 59 | 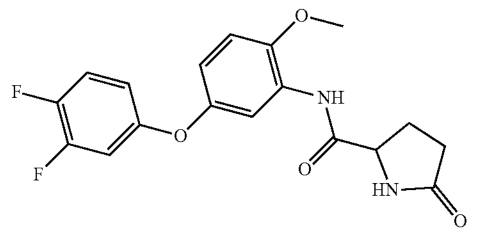 [SMILES: COc1ccc(Oc2ccc(F)c(F)c2)cc1NC(=O)C1CCC(=O)N1] Starting materials: 5-(3,4-Difluoro-phenoxy)-2-methoxyaniline and 5-Oxopyrrolidine-2-carboxylic acid | Purification method A. $^{1}H$ NMR (400 MHz, DMSO-$d_6$) δ: 9.32 (s, 1H), 7.95-7.83 (m, 2H), 7.47-7.36 (m, 1H), 7.09 (d, 2H), 6.83 (dd, 1H), 6.76 (d, 1H), 4.38 (dd, 1H), 3.86 (s, 3H), 2.39-2.05 (m, 3H), 2.01-1.92 (m, 1H). LCMS: m/z 363.2 $[M + H]^+$ |
| 60 | 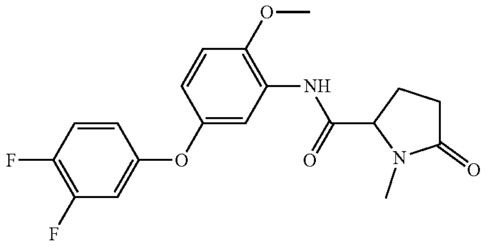 [SMILES: COc1ccc(Oc2ccc(F)c(F)c2)cc1NC(=O)C1CCC(=O)N1C] Starting materials: 5-(3,4-Difluoro-phenoxy)-2-methoxyaniline and 1-Methyl-5-oxopyrrolidine-2-carboxylic acid | Purification method A. $^{1}H$ NMR (600 MHz, DMSO-$d_6$) δ: 9.58 (s, 1H), 7.81 (d, 1H), 7.45-7.36 (m, 1H), 7.11-7.03 (m, 2H), 6.82 (dd, 1H), 6.79-6.65 (m, 1H), 4.45 (dd, 1H), 3.85 (s, 3H), 2.62 (s, 3H), 2.29-2.12 (m, 3H), 1.92-1.81 (m, 1H). LCMS: m/z 377.2 $[M + H]^+$ |
| 61 | 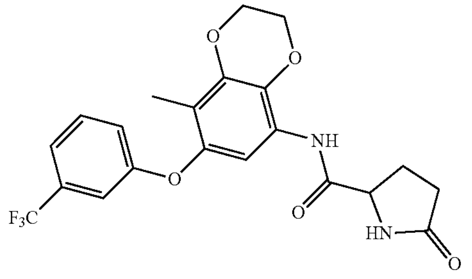 [SMILES: Cc1c(Oc2cccc(C(F)(F)F)c2)cc(NC(=O)C2CCC(=O)N2)c2c1OCCO2] Starting materials: 8-Methyl-7-(3-(trifluoromethyl)phenoxy)-2,3-dihydrobenzo[b][1,4]dioxin-5-amine hydrochloride and 5-Oxopyrrolidine-2-carboxylic acid | Purification method A. $^{1}H$ NMR (400 MHz, DMSO-$d_6$) δ: 9.32 (s, 1H), 7.87 (s, 1H), 7.62-7.51 (m, 2H), 7.45-7.35 (m, 2H), 7.16 (d, 1H), 7.13-7.06 (m, 1H), 4.40-4.28 (m, 5H), 2.34-2.26 (m, 1H), 2.23-2.02 (m, 2H), 1.93 (s, 3H), 1.92-1.87 (m, 1H). LCMS: m/z 437.0 $[M + H]^+$ |
| 62 | 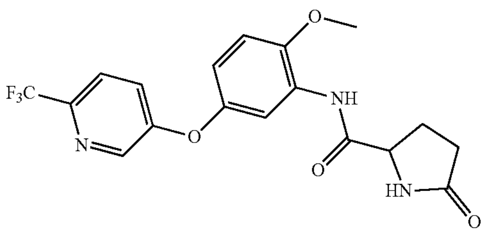 [SMILES: COc1ccc(Oc2ccc(C(F)(F)F)nc2)cc1NC(=O)C1CCC(=O)N1] Starting materials: 2-Methoxy-5-((6-(trifluoromethyl)pyridin-3-yl)oxy)-aniline and 5-Oxopyrrolidine-2-carboxylic acid | Purification method A. $^{1}H$ NMR (400 MHz, DMSO-$d_6$) δ: 9.40 (s, 1H), 8.51 (d, 1H), 7.97-7.89 (m, 2H), 7.87 (d, 1H), 7.46 (dd, 1H), 7.16 (d, 1H), 6.98 (dd, 1H), 4.39 (dd, 1H), 3.89 (s, 3H), 2.38-2.26 (m, 1H), 2.26-2.05 (m, 2H), 2.05-1.87 (m, 1H). LCMS: m/z 396.2 $[M + H]^+$ |

-continued

| No. | Structure and starting material | Purification method and characterization data |
| --- | --- | --- |
| 63 | 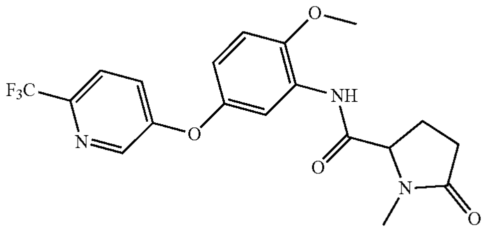 [SMILES: COc1ccc(Oc2ccc(C(F)(F)F)nc2)cc1NC(=O)C1CCC(=O)N1C] Starting materials: 2-Methoxy-5-((6-(trifluoromethyl)pyridin-3-yl)oxy)-aniline and 1-Methyl-5-oxopyrrolidine-2-carboxylic acid | Purification method A. $^1H$ NMR (400 MHz, DMSO-$d_6$) δ: 9.68 (s, 1H), 8.50 (d, 1H), 7.92 (d, 1H), 7.87 (d, 1H), 7.46 (dd, 1H), 7.16 (d, 1H), 6.99 (dd, 1H), 4.53-4.39 (m, 1H), 3.89 (s, 3H), 2.36-2.14 (m, 3H), 1.97-1.83 (m, 1H). LCMS: m/z 410.2 $[M + H]^+$ |
| 64 | 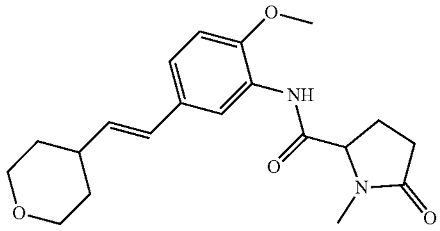 [SMILES: COc1ccc(/C=C/C2CCOCC2)cc1NC(=O)C1CCC(=O)N1C] Starting materials: (E)-2-Methoxy-5-(2-(tetrahydro-2H-pyran-4-yl)-vinyl)aniline and 1-Methyl-5-oxo-pyrrolidine-2-carboxylic acid | Purification method A. $^1H$ NMR (400 MHz, DMSO-$d_6$) δ: 9.47 (s, 1H), 8.02 (d, 1H), 7.12 (dd, 1H), 7.00 (d, 1H), 6.31 (d, 1H), 6.04 (dd, 1H), 4.47-4.42 (m, 1H), 3.90-3.85 (m, 2H), 3.83 (s, 3H), 2.67 (s, 3H), 2.37-2.21 (m, 3H), 1.97-1.87 (m, 1H), 1.64 (d, 2H), 1.49-1.34 (m, 2H). LCMS: m/z 359.2 $[M + H]^+$ |
| 65 | 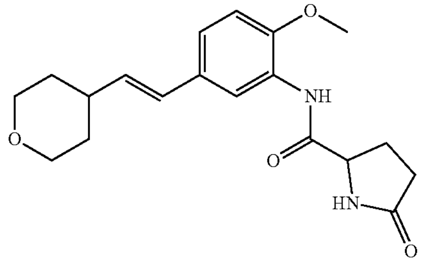 [SMILES: COc1ccc(/C=C/C2CCOCC2)cc1NC(=O)C1CCC(=O)N1] Starting materials: (E)-2-Methoxy-5-(2-(tetrahydro-2H-pyran-4-yl)-vinyl)aniline and 5-Oxopyrrolidine-2-carboxylic acid | Purification method A. $^1H$ NMR (400 MHz, DMSO-$d_6$) δ: 9.19 (s, 1H), 8.06 (d, 1H), 7.94 (s, 1H), 7.11 (dd, 1H), 6.99 (d, 1H), 6.31 (d, 1H), 6.03 (dd, 1H), 3.91-3.84 (m, 2H), 3.83 (s, 3H), 2.40-2.30 (m, 2H), 2.30-2.04 (m, 2H), 2.04-1.93 (m, 1H), 1.64 (d, 2H), 1.49-1.32 (m, 2H). LCMS: m/z 345.2 $[M + H]^+$ |
| 66 | 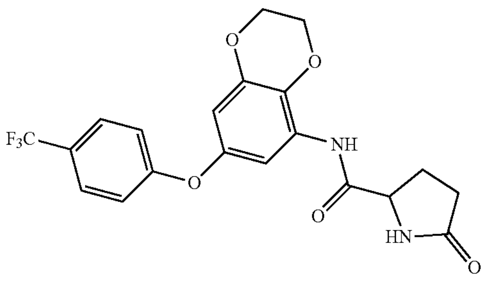 [SMILES: O=C1CCC(C(=O)Nc2cc(Oc3ccc(C(F)(F)F)cc3)cc3c2OCCO3)N1] Starting materials: 7-(4-(Trifluoro-methyl)phenoxy)-2,3-dihydrobenzo-[b][1,4]dioxin-5-amine HCl and 5-Oxopyrrolidine-2-carboxylic acid | Purification method B. $^1H$ NMR (400 MHz, DMSO-$d_6$) δ: 9.38 (s, 1H), 7.89 (s, 1H), 7.71 (d, 2H), 7.44 (d, 1H), 7.09 (d, 2H), 6.51 (d, 1H), 4.39-4.30 (m, 5H), 2.25-1.85 (m, 4H). LCMS: m/z 423.1 $[M + H]^+$ |

-continued

| No. | Structure and starting material | Purification method and characterization data |
| --- | --- | --- |
| 67 | 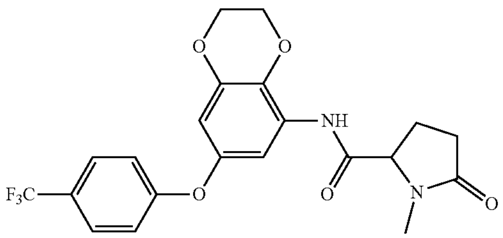 [SMILES: CN1C(=O)CCC1C(=O)Nc1cc(Oc2ccc(C(F)(F)F)cc2)cc2c1OCCO2] Starting materials: 7-(4-(Trifluoromethyl)phenoxy)-2,3-dihydrobenzo-[b][1,4]dioxin-5-amine HCl and 1-Methyl-5-oxopyrrolidine-2-carboxylic acid | Purification method B. $^1$H NMR (400 MHz, DMSO-$d_6$) δ: 9.70 (s, 1H), 7.71 (d, 2H), 7.42 (s, 1H), 7.09 (d, 2H), 6.52 (d, 1H), 4.48-4.43 (m, 1H), 4.37-4.29 (m, 4H), 2.63 (s, 3H), 2.28-2.15 (m, 3H), 1.93-1.82 (m, 1H). LCMS: m/z 437.2 [M + H]$^+$ |
| 68 | 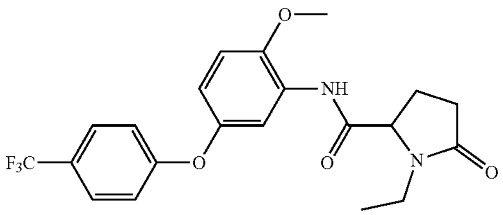 [SMILES: CCN1C(=O)CCC1C(=O)Nc1cc(Oc2ccc(C(F)(F)F)cc2)ccc1OC] Starting materials: 2-Methoxy-5-(4-(trifluoromethyl)phenoxy)aniline and 1-Ethyl-5-oxopyrrolidine-2-carboxylic acid | Purification method A. $^1$H NMR (400 MHz, DMSO-$d_6$) δ: 9.67 (s, 1H), 7.86 (d, 1H), 7.71 (d, 2H), 7.14 (d, 1H), 7.08 (d, 2H), 6.92 (dd, 1H), 4.67-4.58 (m, 1H), 3.89 (s, 3H), 3.53-3.44 (m, 1H), 2.86-2.76 (m, 1H), 2.35-2.13 (m, 3H), 1.98-1.84 (m, 1H), 1.00 (t, 3H). LCMS: m/z 423.1 [M + H]$^+$ |
| 69 | 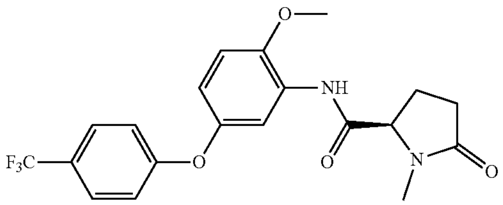 Starting materials: 2-Methoxy-5-(4-(trifluoromethyl)phenoxy)aniline and (R)-1-Methyl-5-oxopyrrolidine-2-carboxylic acid | Purification method A. $^1$H NMR (400 MHz, DMSO-$d_6$) δ: 9.66 (s, 1H), 7.87 (d, 1H), 7.71 (d, 2H), 7.14 (d, 1H), 7.07 (d, 2H), 6.92 (dd, 1H), 4.52-4.43 (m, 1H), 3.88 (s, 3H), 2.64 (s, 3H), 2.30-2.13 (m, 3H), 1.93-1.82 (m, 1H). LCMS: m/z 409.2 [M + H]$^+$ |
| 70 | 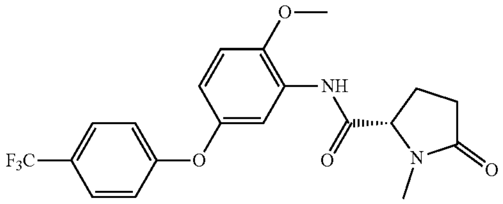 Starting materials: 2-Methoxy-5-(4-(trifluoromethyl)phenoxy)aniline and (S)-1-Methyl-5-oxopyrrolidine-2-carboxylic acid | Purification method A. $^1$H NMR (400 MHz, DMSO-$d_6$) δ: 9.65 (s, 1H), 7.87 (d, 1H), 7.70 (d, 2H), 7.14 (d, 1H), 7.08 (d, 2H), 6.92 (dd, 1H), 4.51-4.41 (m, 1H), 3.89 (s, 3H), 2.64 (s, 3H), 2.31-2.15 (m, 3H), 1.95-1.82 (m, 1H). LCMS: m/z 409.2 [M + H]$^+$ |

-continued

| No. | Structure and starting material | Purification method and characterization data |
|---|---|---|
| 71 | 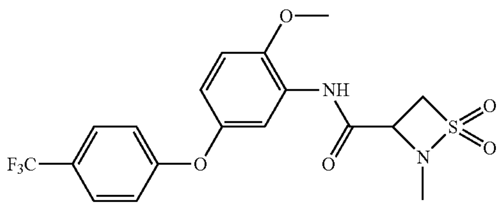 [SMILES: COc1ccc(Oc2ccc(C(F)(F)F)cc2)cc1NC(=O)C1CS(=O)(=O)N1C] Starting materials: 2-Methoxy-5-(4-(trifluoromethyl)phenoxy)aniline and Lithium N-methylalaninate 1,1-dioxide | Purification method A. $^{1}$H NMR (400 MHz, DMSO-$d_6$) δ: 9.68 (s, 1H), 7.91 (d, 1H), 7.71 (d, 2H), 7.17 (d, 1H), 7.09 (d, 2H), 6.95 (dd, 1H), 4.51 (dd, 1H), 4.37 (dd, 1H), 4.07 (dd, 1H), 2.70 (s, 3H). LCMS: m/z 431.2 $[M + H]^+$ Purification method C. |
| 72 | 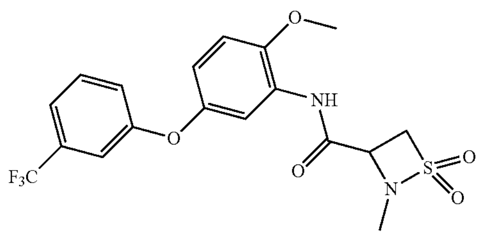 [SMILES: COc1ccc(Oc2cccc(C(F)(F)F)c2)cc1NC(=O)C1CS(=O)(=O)N1C] Starting materials: 2-Methoxy-5-(3-(trifluoromethyl)phenoxy)aniline and Lithium N-methylalaninate 1,1-dioxide | $^{1}$H NMR (400 MHz, DMSO-$d_6$) δ: 9.68 (s, 1H), 7.91 (d, 1H), 7.71 (d, 2H), 7.17 (d, 1H), 7.09 (d, 2H), 6.95 (dd, 1H), 4.51 (dd, 1H), 4.37 (dd, 1H), 4.07 (dd, 1H), 2.70 (s, 3H). LCMS: m/z 431.0 $[M + H]^+$ |
| 73 | 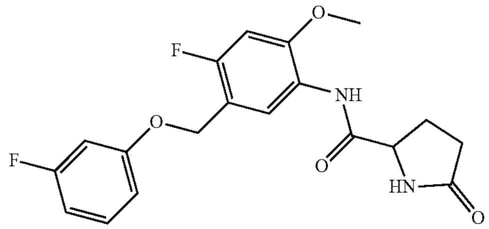 [SMILES: COc1cc(F)c(COc2cccc(F)c2)cc1NC(=O)C1CCC(=O)N1] Starting materials: 4-Fluoro-5-((3-fluorophenoxy)methyl)-2-methoxy-aniline and 5-Oxopyrrolidine-2-carboxylic acid | Purification method A. $^{1}$H NMR (400 MHz, DMSO-$d_6$) δ: 9.16 (s, 1H), 7.87 (s, 1H), 7.72 (d, 1H), 7.01-6.91 (m, 2H), 6.56-6.46 (m, 2H), 4.28 (dd, 1H), 3.81 (s, 3H), 3.76 (s, 2H), 2.31-2.04 (m, 3H), 2.00-1.88 (m, 1H). LCMS: m/z 375.0 $[M - H]^-$ |
| 74 | 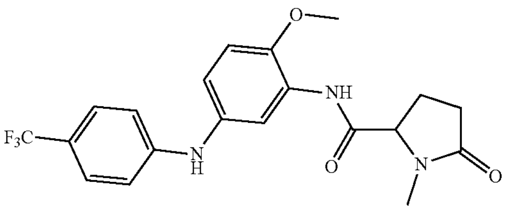 [SMILES: COc1ccc(Nc2ccc(C(F)(F)F)cc2)cc1NC(=O)C1CCC(=O)N1C] Starting materials: 4-Methoxy-N1-(4-(trifluoromethyl)phenyl)benzene-1,3-diamine and 1-Methyl-5-oxopyrrolidine-2-carboxylic acid | Purification method A. $^{1}$H NMR (400 MHz, DMSO-$d_6$) δ: 9.52 (s, 1H), 8.48 (s, 1H), 7.90 (d, 1H), 7.46 (d, 2H), 7.02 (dd, 3H), 6.94 (dd, 1H), 4.51-4.41 (m, 1H), 3.84 (s, 3H), 2.65 (s, 3H), 2.34-2.15 (m, 3H), 1.98-1.82 (m, 1H). LCMS: m/z 408.2 $[M + H]^+$ |

-continued

| No. | Structure and starting material | Purification method and characterization data |
|---|---|---|
| 75 | 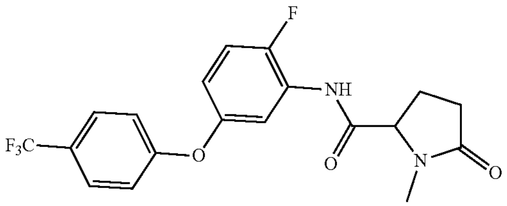 [SMILES: CN1C(=O)CCC1C(=O)Nc1cc(Oc2ccc(C(F)(F)F)cc2)ccc1F] Starting materials: 2-Fluoro-5-(4-(trifluoromethyl)phenoxy)aniline and 1-Methyl-5-oxopyrrolidine-2-carboxylic acid | Purification method A. $^1$H NMR (400 MHz, Chloroform-d) δ: 8.12 (dd, 1H), 7.72 (s, 1H), 7.59 (d, 2H), 7.19-7.12 (m, 1H), 7.05 (d, 2H), 6.82 (dd, 1H), 4.14 (dd, 1H), 2.95 (s, 3H), 2.64-2.40 (m, 3H), 2.22-2.13 (m, 1H). LCMS: m/z 397.2 $[M + H]^+$ |
| 76 | 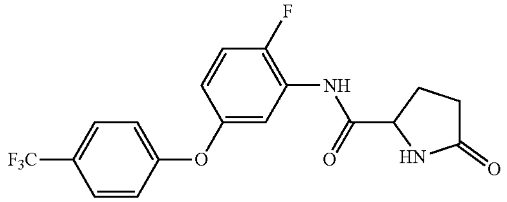 [SMILES: O=C1CCC(C(=O)Nc2cc(Oc3ccc(C(F)(F)F)cc3)ccc2F)N1] Starting materials: 2-Fluoro-5-(4-(trifluoromethyl)phenoxy)aniline and 5-Oxopyrrolidine-2-carboxylic acid | Purification method A. $^1$H NMR (400 MHz, Chloroform-d) δ: 8.12 (dd, 1H), 7.72 (s, 1H), 7.59 (dd, 2H), 7.20-7.12 (m, 1H), 7.05 (d, 2H), 6.82 (dd, 1H), 4.14 (dd, 1H), 2.65-2.39 (m, 3H), 2.22-2.12 (m, 1H). LCMS: m/z 383.2 $[M + H]^+$ |
| 77 | 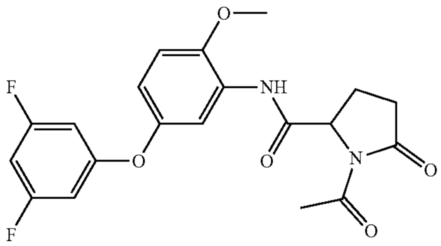 [SMILES: COc1ccc(Oc2cc(F)cc(F)c2)cc1NC(=O)C1CCC(=O)N1C(C)=O] Starting materials: 5-(3,5-Difluorophenoxy)-2-methoxyaniline HCl and 1-Acetyl-5-oxopyrrolidine-2-carboxylic acid | Purification method A. $^1$H NMR (400 MHz, DMSO-$d_6$) δ: 9.76 (s, 1H), 7.85 (d, 1H), 7.12 (d, 1H), 6.98-6.85 (m, 2H), 6.67-6.58 (m, 2H), 5.07 (d, 1H), 3.89 (s, 3H), 2.61-2.55 (m, 1H), 2.38 (s, 3H), 2.34-1.82 (m, 3H). LCMS: m/z 405.2 $[M + H]^+$ |
| 78 | 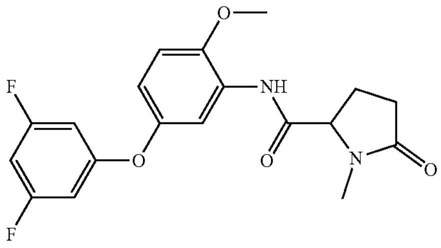 [SMILES: COc1ccc(Oc2cc(F)cc(F)c2)cc1NC(=O)C1CCC(=O)N1C] Starting materials: 5-(3,5-Difluorophenoxy)-2-methoxyaniline HCl and 1-Methyl-5-oxopyrrolidine-2-carboxylic acid | Purification method A. $^1$H NMR (400 MHz, DMSO-$d_6$) δ: 9.67 (s, 1H), 7.86 (d, 1H), 7.13 (d, 1H), 6.98-6.88 (m, 2H), 6.64 (dd, 2H), 4.47 (d, 1H), 3.88 (s, 3H), 2.64 (s, 3H), 2.32-2.17 (m, 3H), 1.93-1.79 (m, 1H). LCMS: m/z 377.0 $[M + H]^+$ |

-continued

| No. | Structure and starting material | Purification method and characterization data |
|---|---|---|
| 79 | 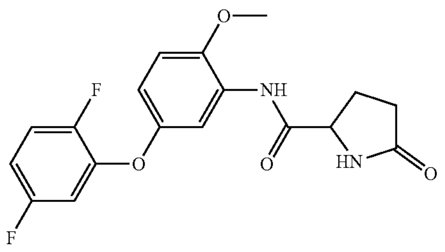 [SMILES: COc1ccc(Oc2cc(F)ccc2F)cc1NC(=O)C1CCC(=O)N1] Starting materials: 5-(2,5-Difluorophenoxy)-2-methoxyaniline and 5-Oxopyrrolidine-2-carboxylic acid | Purification method A. $^1$H NMR (400 MHz, DMSO-$d_6$) δ: 9.32 (s, 1H), 7.97-7.82 (m, 2H), 7.53-7.35 (m, 1H), 7.09 (d, 1H), 7.06-6.97 (m, 1H), 6.96-6.88 (m, 1H), 6.83 (dd, 1H), 4.38 (dd, 1H), 3.86 (s, 3H), 2.35-2.25 (m, 1H), 2.25-2.03 (m, 2H), 2.02-1.87 (m, 1H). LCMS: m/z 363.0 $[M + H]^+$ |
| 80 | 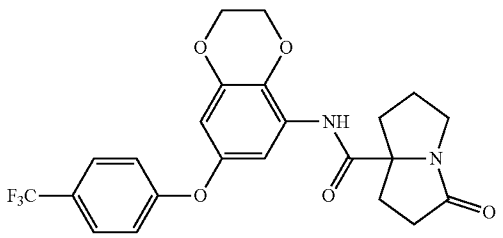 [SMILES: O=C1CCC2(C(=O)Nc3cc(Oc4ccc(C(F)(F)F)cc4)cc4c3OCCO4)CCCN12] Starting materials: 7-(4-(Trifluoromethyl) phenoxy)-2,3-dihydrobenzo-[b][1,4]dioxin-5-amine HCl and Lithium 3-oxotetrahydro-1H-pyrrolizine-7a(5H)-carboxylate | Purification method A. $^1$H NMR (600 MHz, DMSO-$d_6$) δ: 8.90 (s, 1H), 7.70 (d, 2H), 7.32 (d, 1H), 7.08 (d, 2H), 6.53 (d, 1H), 4.35-4.24 (m, 4H), 3.60-3.50 (m, 1H), 3.10-3.01 (m, 1H), 2.71-2.63 (m, 1H), 2.35-2.24 (m, 3H), 2.21-2.14 (m, 1H), 1.97-1.87 (m, 1H), 1.86-1.77 (m, 1H), 1.73-1.65 (m, 1H). LCMS: m/z 463.2 $[M + H]^+$ |
| 81 | 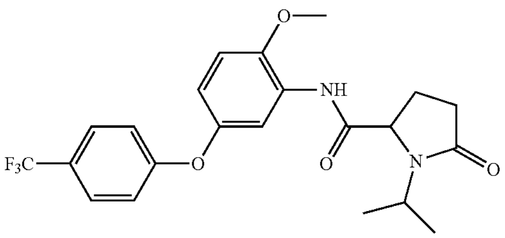 [SMILES: COc1ccc(Oc2ccc(C(F)(F)F)cc2)cc1NC(=O)C1CCC(=O)N1C(C)C] Starting materials: 2-Methoxy-5-(4-(trifluoromethyl)phenoxy)aniline and 1-Isopropyl-5-oxopyrrolidine-2-carboxylic acid | Purification method A. $^1$H NMR (400 MHz, Acetonitrile-$d_3$) δ: 8.51 (s, 1H), 8.06 (d, 1H), 7.68 (d, 2H), 7.09 (dd, 3H), 6.88 (dd, 1H), 4.38 (dd, 1H), 4.22-4.12 (m, 1H), 2.58-2.44 (m, 1H), 2.36-2.20 (m, 3H), 1.22 (d, 3H), 1.10 (d, 3H). LCMS: m/z 437.2 $[M + H]^+$ |
| 82 | 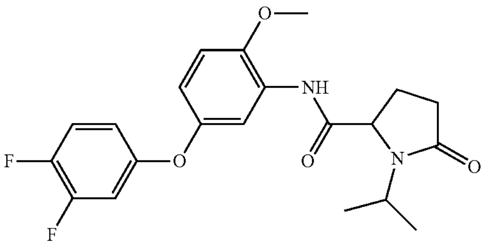 [SMILES: COc1ccc(Oc2ccc(F)c(F)c2)cc1NC(=O)C1CCC(=O)N1C(C)C] Starting materials: 5-(3,4-Difluorophenoxy)-2-methoxyaniline and 1-Isopropyl-5-oxopyrrolidine-2-carboxylic acid | Purification method A. $^1$H NMR (400 MHz, Acetonitrile-$d_3$) δ: 8.49 (s, 1H), 8.02 (dd, 1H), 7.31-7.18 (m, 1H), 7.04 (dd, 1H), 6.99-6.88 (m, 1H), 6.85-6.73 (m, 2H), 4.42-4.34 (m, 1H), 4.24-4.10 (m, 1H), 3.92 (d, 3H), 2.54-2.43 (m, 1H), 2.40 -. 24 (m, 1H), 1.25-1.18 (m, 3H), 1.13-1.04 (m, 3H). LCMS: m/z 405.2 $[M + H]^+$ |

-continued

| No. | Structure and starting material | Purification method and characterization data |
|---|---|---|
| 83 | 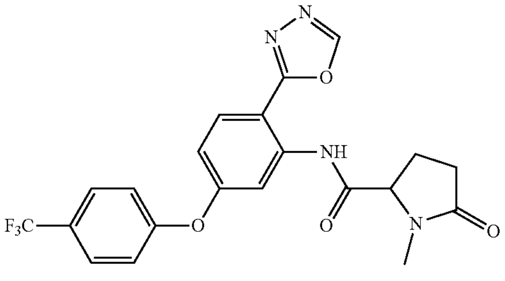 [SMILES: CN1C(=O)CCC1C(=O)Nc1cc(Oc2ccc(C(F)(F)F)cc2)ccc1-c1nnco1] Starting materials: 2-(1,3,4-Oxadiazol-2-yl)-5-(4-(trifluoromethyl)-phenoxy)aniline and 1-Methyl-5-oxopyrrolidine-2-carboxylic acid | Purification method A. $^1$H NMR (400 MHz, DMSO-$d_6$) δ: 10.91 (s, 1H), 9.42 (s, 1H), 8.07 (s, 1H), 8.01 (d, 1H), 7.83 (d, 2H), 7.34 (d, 2H), 7.07 (dd, 1H), 4.29 (dd, 1H), 2.72 (s, 3H), 2.45-2.20 (m, 3H), 2.07-1.95 (m, 1H). LCMS: m/z 447.0 [M + H]$^+$ |
| 84 | 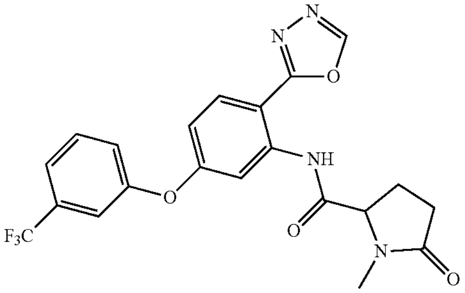 [SMILES: CN1C(=O)CCC1C(=O)Nc1cc(Oc2cccc(C(F)(F)F)c2)ccc1-c1nnco1] Starting materials: 2-(1,3,4-Oxadiazol-2-yl)-5-(3-(trifluoromethyl)-phenoxy)aniline and 1-Methyl-5-oxopyrrolidine-2-carboxylic acid | Purification method A. $^1$H NMR (400 MHz, DMSO-$d_6$) δ: 10.91 (s, 1H), 9.41 (s, 1H), 8.08-7.97 (m, 2H), 7.76-7.67 (m, 1H), 7.63 (d, 1H), 7.54 (s, 1H), 7.48 (d, 1H), 7.01 (dd, 1H), 4.28 (d, 1H), 2.72 (s, 3H), 2.39-2.21 (m, 3H), 2.05-1.94 (m, 1H). LCMS: m/z 447.0 [M + H]$^+$ |
| 85 | 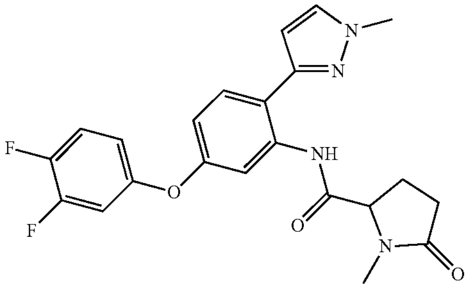 [SMILES: CN1C(=O)CCC1C(=O)Nc1cc(Oc2ccc(F)c(F)c2)ccc1-c1ccn(C)n1] Starting materials: 5-(3,4-Difluoro-phenoxy)-2-(1-methyl-1H-pyrazol-3-yl)aniline and 1-Methyl-5-oxopyrrolidine-2-carboxylic acid | Purification method C. $^1$H NMR (400 MHz, DMSO-$d_6$) δ: 11.79 (s, 1H), 8.34 (d, 1H), 7.90-7.79 (m, 2H), 7.55-7.44 (m, 1H), 7.35-7.25 (m, 1H), 6.98-6.90 (m, 1H), 6.87-6.77 (m, 2H), 4.20 (dd, 1H), 3.94 (s, 3H), 2.79 (s, 3H), 2.44-2.24 (m, 3H), 2.02-1.89 (m, 1H). LCMS: m/z 427.0 [M + H]$^+$ |
| 86 | 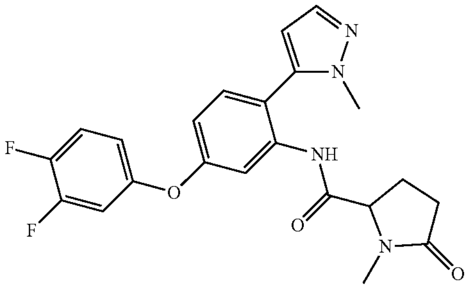 [SMILES: CN1C(=O)CCC1C(=O)Nc1cc(Oc2ccc(F)c(F)c2)ccc1-c1ccnn1C] Starting materials: 5-(3,4-Difluoro-phenoxy)-2-(1-methyl-1H-pyrazol-5-yl)aniline and 1-Methyl-5-oxo-pyrrolidine-2-carboxylic acid | Purification method C. $^1$H NMR (600 MHz, DMSO-$d_6$) δ: 9.61 (s, 1H), 7.55-7.46 (m, 1H), 7.44 (d, 1H), 7.37 (d, 1H), 7.35-7.31 (m, 1H), 7.28 (d, 1H), 7.01-6.92 (m, 2H), 6.21 (d, 1H), 4.10-4.03 (m, 1H), 3.63 (s, 3H), 2.17-2.09 (m, 3H), 1.75-1.66 (m, 1H). LCMS: m/z 427.0 [M + H]$^+$ |

-continued

| No. | Structure and starting material | Purification method and characterization data |
|---|---|---|
| 87 | 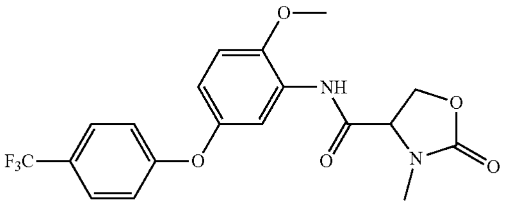 [SMILES: COc1ccc(Oc2ccc(C(F)(F)F)cc2)cc1NC(=O)C1COC(=O)N1C] Starting materials: 2-Methoxy-5-(4-(trifluoromethyl)phenoxy)aniline and 3-Methyl-2-oxooxazolidine-4-carboxylic acid | Purification method A. $^1$H NMR (400 MHz, DMSO-$d_6$) δ: 9.83 (s, 1H), 7.91 (d, 1H), 7.71 (d, 2H), 7.15 (d, 1H), 7.08 (d, 2H), 6.97-6.89 (m, 1H), 4.68 (dd, 1H), 4.42 (t, 1H), 4.18 (dd, 1H), 3.89 (s, 3H), 2.73 (s, 3H). LCMS: m/z 411.0 [M + H]$^+$ |
| 88 | 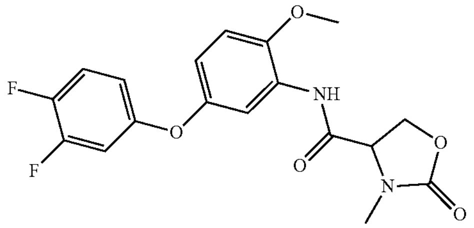 [SMILES: COc1ccc(Oc2ccc(F)c(F)c2)cc1NC(=O)C1COC(=O)N1C] Starting materials: 5-(3,4-Difluoro-phenoxy)-2-methoxyaniline and 3-Methyl-2-oxooxazolidine-4-carboxylic acid | Purification method A. $^1$H NMR (400 MHz, DMSO-$d_6$) δ: 9.79 (s, 1H), 7.86 (d, 1H), 7.47-7.35 (m, 1H), 7.15-7.05 (m, 2H), 6.86 (dd, 1H), 6.80-6.72 (m, 1H), 4.68 (dd, 1H), 4.42 (t, 1H), 4.18 (dd, 1H), 3.87 (s, 3H), 2.73 (s, 3H). LCMS: m/z 379.0 [M + H]$^+$ |
| 89 | 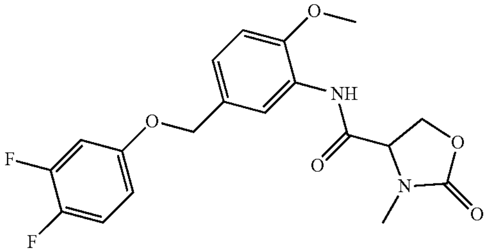 [SMILES: COc1ccc(COc2ccc(F)c(F)c2)cc1NC(=O)C1COC(=O)N1C] Starting materials: 5-((3,4-Difluoro-phenoxy)methyl)-2-methoxyaniline HCl and 3-Methyl-2-oxooxazolidine-4-carboxylic acid | Purification method A. $^1$H NMR (400 MHz, DMSO-$d_6$) δ: 9.71 (s, 1H), 8.09 (d, 1H), 7.41-7.30 (m, 1H), 7.29-7.17 (m, 1H), 7.17-7.11 (m, 1H), 7.08 (d, 1H), 6.87-6.78 (m, 1H), 5.00 (s, 2H), 4.66 (dd, 1H), 4.44 (t, 1H), 4.18 (dd, 1H), 3.86 (s, 3H), 2.75 (s, 3H). LCMS: m/z 391.0 [M−H]- |
| 90 | 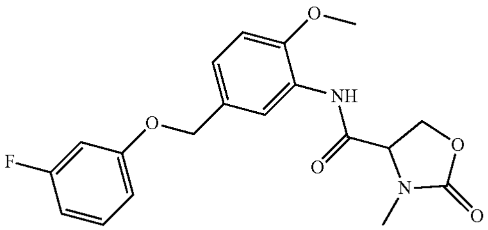 [SMILES: COc1ccc(COc2cccc(F)c2)cc1NC(=O)C1COC(=O)N1C] Starting materials: 5-((3-Fluoro-phenoxy)methyl)-2-methoxyaniline HCl and 3-Methyl-2-oxooxazolidine-4-carboxylic acid | Purification method C. $^1$H NMR (400 MHz, DMSO-$d_6$) δ: 9.71 (s, 1H), 8.10 (s, 1H), 7.31 (d, 1H), 7.25-7.20 (m, 1H), 7.08 (d, 1H), 6.91-6.82 (m, 2H), 6.80-6.72 (m, 1H), 5.02 (s, 2H), 4.69-4.63 (m, 1H), 4.49-4.41 (m, 1H), 4.23-4.15 (m, 1H), 3.86 (s, 3H), 2.75 (s, 3H). LCMS: m/z 375.2 [M + H]$^+$ |

-continued

| No. | Structure and starting material | Purification method and characterization data |
| --- | --- | --- |
| 91 | 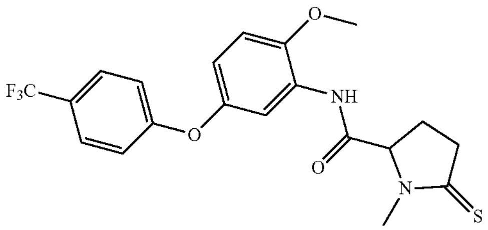 [SMILES: COc1ccc(Oc2ccc(C(F)(F)F)cc2)cc1NC(=O)C1CCC(=S)N1C]<br>Starting materials: 2-Methoxy-5-(4-(trifluoromethyl)phenoxy)aniline and 1-Methyl-5-thioxopyrrolidine-2-carboxylic acid | Purification method C.<br>$^1$H NMR (400 MHz, DMSO-$d_6$) δ: 9.84 (s, 1H), 7.90-7.82 (m, 1H), 7.71 (d, 2H), 7.15 (d, 1H), 7.07 (d, 2H), 6.94 (dd, 1H), 5.00-4.92 (m, 1H), 3.89 (s, 3H), 3.07 (s, 3H), 2.94-2.83 (m, 2H), 2.36-2.29 (m, 1H), 2.06-1.91 (m, 1H). LCMS: m/z 425.0 [M + H]$^+$ |
| 92 | 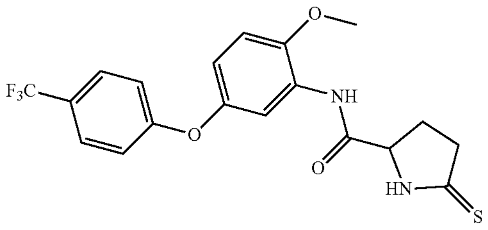 [SMILES: COc1ccc(Oc2ccc(C(F)(F)F)cc2)cc1NC(=O)C1CCC(=S)N1]<br>Starting materials: 2-Methoxy-5-(4-(trifluoromethyl)phenoxy)aniline and Lithium 5-thioxopyrrolidine-2-carboxylate | Purification method A.<br>$^1$H NMR (400 MHz, DMSO-$d_6$) δ: 10.30 (s, 1H), 9.61 (s, 1H), 7.91-7.85 (m, 1H), 7.71 (d, 2H), 7.13 (s, 1H), 7.08 (d, 2H), 6.92 (dd, 1H), 4.84-4.72 (m, 1H), 3.88 (s, 3H), 2.75 (q, 2H), 2.44-2.31 (m, 1H), 2.13-2.01 (m, 1H). LCMS: m/z 411.1 [M + H]$^+$ |
| 93 | 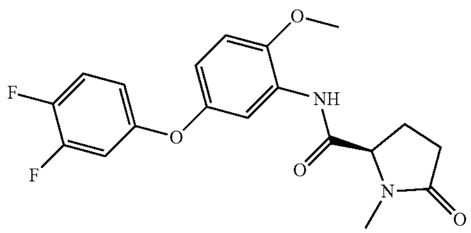 [SMILES: COc1ccc(Oc2ccc(F)c(F)c2)cc1NC(=O)[C@H]1CCC(=O)N1C]<br>Starting materials: 5-(3,4-Difluoro-phenoxy)-2-methoxyaniline and (R)-1-Methyl-5-oxopyrrolidine-2-carboxylic acid | Purification method A.<br>$^1$H NMR (400 MHz, DMSO-$d_6$) δ: 9.62 (s, 1H), 7.83 (d, 1H), 7.48-7.36 (m, 1H), 7.14-7.05 (m, 2H), 6.84 (dd, 1H), 6.76 (d, 1H), 4.50-4.41 (m, 1H), 3.86 (s, 3H), 2.64 (s, 3H), 2.35-2.13 (m, 3H), 1.94-1.81 (m, 1H). LCMS: m/z 377.2 [M + H]$^+$ |
| 94 | 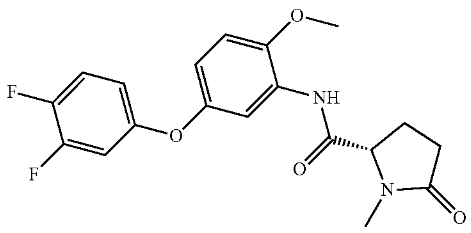 [SMILES: COc1ccc(Oc2ccc(F)c(F)c2)cc1NC(=O)[C@@H]1CCC(=O)N1C]<br>Starting materials: 5-(3,4-Difluoro-phenoxy)-2-methoxyaniline and (S)-1-Methyl-5-oxopyrrolidine-2-carboxylic acid | Purification method A.<br>$^1$H NMR (400 MHz, DMSO-$d_6$) δ: 9.62 (s, 1H), 7.83 (d, 1H), 7.47-7.38 (m, 1H), 7.12-7.04 (m, 2H), 6.84 (dd, 1H), 6.76 (d, 1H), 4.50-4.41 (m, 1H), 3.86 (s, 3H), 2.64 (s, 3H), 2.30-2.14 (m, 3H), 1.92-1.77 (m, 1H). LCMS: m/z 377.2 [M + H]$^+$ |

-continued

| No. | Structure and starting material | Purification method and characterization data |
|---|---|---|
| 95 | 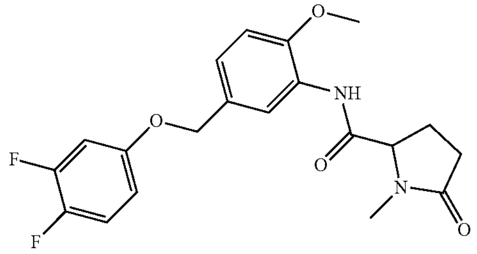 [SMILES: COc1ccc(COc2ccc(F)c(F)c2)cc1NC(=O)C1CCC(=O)N1C]<br>Starting materials: 5-((3,4-Difluoro-phenoxy)methyl)-2-methoxyaniline HCl and 5-Oxopyrrolidine-2-carboxylic acid | Purification method A.<br>$^1H$ NMR (500 MHz, DMSO-$d_6$) δ: 9.50 (s, 1H), 8.03 (d, 1H), 7.38-7.25 (m, 1H), 7.18 (dd, 1H), 7.15-7.09 (m, 1H), 7.05 (d, 1H), 6.82-6.75 (m, 1H), 4.98 (s, 2H), 4.46-4.38 (m, 1H), 3.84 (s, 3H), 2.65 (s, 3H), 2.33-2.12 (m, 3H), 1.93-1.82 (m, 1H). LCMS: m/z 391.2 $[M + H]^+$ |
| 96 | 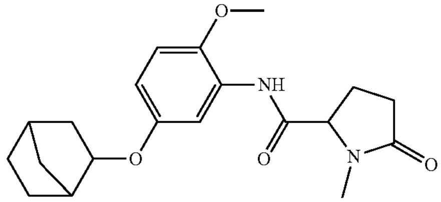 [SMILES: COc1ccc(OC2CC3CCC2C3)cc1NC(=O)C1CCC(=O)N1C]<br>Starting materials: 5-(Bicyclo[2.2.1]-heptan-2-yloxy)-2-methoxyaniline HCl and 1-Methyl-5-oxopyrrolidine-2-carboxylic acid | Purification method A.<br>$^1H$ NMR (400 MHz, DMSO-$d_6$) δ: 9.45 (s, 1H), 7.68-7.61 (m, 1H), 6.94 (d, 1H), 6.60 (dd, 1H), 4.50-4.38 (m, 1H), 4.11 (d, 1H), 3.78 (s, 3H), 2.66 (s, 3H), 2.36-2.15 (m, 5H), 1.96-1.84 (m, 1H), 1.80-1.67 (m, 1H), 1.61-1.33 (m, 4H), 1.24-1.02 (m, 3H). LCMS: m/z 359.2 $[M + H]^+$ |
| 97 | 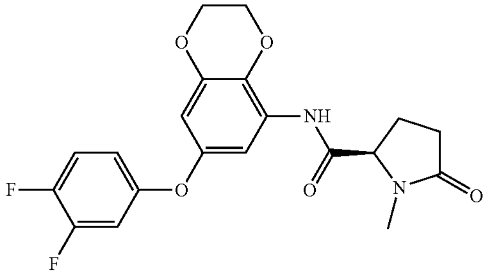 [SMILES: CN1C(=O)CC[C@@H]1C(=O)Nc1cc(Oc2ccc(F)c(F)c2)cc2c1OCCO2]<br>Starting materials: 7-(3,4-Difluoro-phenoxy)-2,3-dihydrobenzo[b][1,4]-dioxin-5-amine HCl and (R)-1-Methyl-5-oxopyrrolidine-2-carboxylic acid | Purification method A.<br>$^1H$ NMR (400 MHz, DMSO-$d_6$) δ: 9.52 (s, 1H), 7.46-7.28 (m, 2H), 7.12-7.01 (m, 1H), 6.79 (d, 1H), 6.41 (d, 1H), 4.44 (dd, 1H), 4.35-4.24 (m, 4H), 2.65 (s, 3H), 2.34-2.13 (m, 3H), 1.96-1.85 (m, 1H). LCMS: m/z 405.0 $[M + H]^+$ |
| 98 | 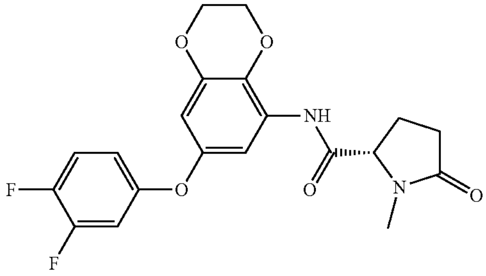 [SMILES: CN1C(=O)CC[C@H]1C(=O)Nc1cc(Oc2ccc(F)c(F)c2)cc2c1OCCO2]<br>Starting materials: 7-(3,4-Difluoro-phenoxy)-2,3-dihydrobenzo[b][1,4]-dioxin-5-amine HCl and (S)-1-Methyl-5-oxopyrrolidine-2-carboxylic acid | Purification method A.<br>$^1H$ NMR (600 MHz, DMSO-$d_6$) δ: 9.64 (s, 1H), 7.44-7.37 (m, 1H), 7.35 (d, 1H), 7.14-6.99 (m, 1H), 6.77 (dd, 1H), 6.41 (d, 1H), 4.43 (dd, 1H), 4.36-4.22 (m, 4H), 2.61 (s, 3H), 2.28-2.14 (m, 3H), 1.90-1.81 (m, 1H). LCMS: m/z 405.0 $[M + H]^+$ |

-continued

| No. | Structure and starting material | Purification method and characterization data |
|---|---|---|
| 99 | 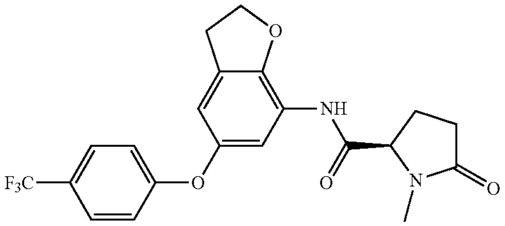 [SMILES: CN1C(=O)CC[C@@H]1C(=O)Nc1cc(Oc2ccc(C(F)(F)F)cc2)cc2c1OCC2] Starting materials: 5-(4-(Trifluoro-methyl)phenoxy)-2,3-dihydrobenzo-furan-7-amine HCl and (R)-1-Methyl-5-oxopyrrolidine-2-carboxylic acid | Purification method A. $^1$H NMR (400 MHz, DMSO-$d_6$) δ: 9.95 (s, 1H), 7.70 (d, 2H), 7.57 (d, 1H), 7.07 (d, 2H), 6.88 (s, 1H), 4.65 (t, 2H), 4.40 (d, 1H), 3.25 (t, 2H), 2.63 (s, 3H), 2.24-2.17 (m, 3H), 1.90-1.80 (m, 1H). LCMS: m/z 421.2 [M + H]$^+$ |
| 100 | 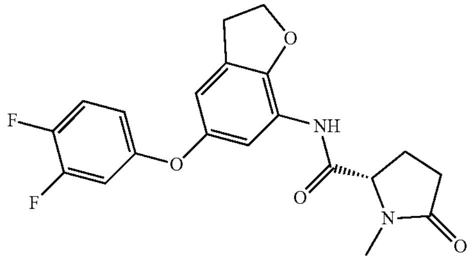 [SMILES: CN1C(=O)CC[C@H]1C(=O)Nc1cc(Oc2ccc(F)c(F)c2)cc2c1OCC2] Starting materials: 5-(3,4-Difluoro-phenoxy)-2,3-dihydrobenzofuran-7-amine HCl and (S)-1-Methyl-5-oxo-pyrrolidine-2-carboxylic acid | Purification method F. $^1$H NMR (400 MHz, DMSO-$d_6$) δ: 9.91 (s, 1H), 7.52 (d, 1H), 7.40 (q, 1H), 7.14-6.97 (m, 1H), 6.81 (d, 1H), 6.78-6.70 (m, 1H), 4.63 (t, 2H), 4.43-4.36 (m, 1H), 3.28-3.19 (m, 2H), 2.63 (s, 3H), 2.29-2.13 (m, 3H), 1.93-1.81 (m, 1H). LCMS: m/z 389.0 [M + H]$^+$ |
| 101 | 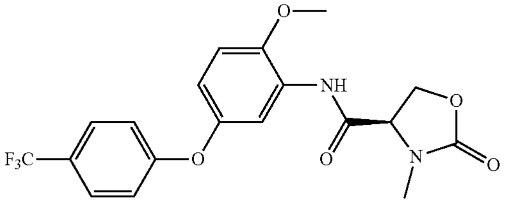 [SMILES: COc1ccc(Oc2ccc(C(F)(F)F)cc2)cc1NC(=O)[C@H]1COC(=O)N1C] Starting materials: 2-Methoxy-5-(4-(trifluoromethyl)phenoxy)aniline and Lithium (R)-3-methyl-2-oxo-oxazolidine-4-carboxylate | Purification method A. $^1$H NMR (400 MHz, DMSO-$d_6$) δ: 9.83 (s, 1H), 7.94-7.88 (m, 1H), 7.71 (d, 2H), 7.15 (d, 1H), 7.08 (d, 2H), 6.94 (dd, 1H), 4.73-4.65 (m, 1H), 4.42 (t, 1H), 4.18 (dd, 1H), 2.73 (s, 3H). LCMS: m/z 411.0 [M + H]$^+$ |
| 102 | 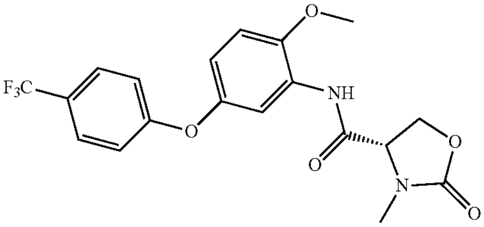 [SMILES: COc1ccc(Oc2ccc(C(F)(F)F)cc2)cc1NC(=O)[C@@H]1COC(=O)N1C] Starting materials: 2-Methoxy-5-(4-(trifluoromethyl)phenoxy)aniline and Lithium (S)-3-methyl-2-oxo-oxazolidine-4-carboxylate | Purification method A. $^1$H NMR (400 MHz, DMSO-$d_6$) δ: 9.83 (s, 1H), 7.96-7.86 (m, 1H), 7.71 (d, 2H), 7.15 (d, 1H), 7.08 (d, 2H), 6.94 (dd, 1H), 4.68 (dd, 1H), 4.42 (t, 1H), 4.18 (dd, 1H), 3.89 (s, 3H), 2.73 (s, 3H). LCMS: m/z 411.0 [M + H]$^+$ |

-continued

| No. | Structure and starting material | Purification method and characterization data |
|---|---|---|
| 103 | 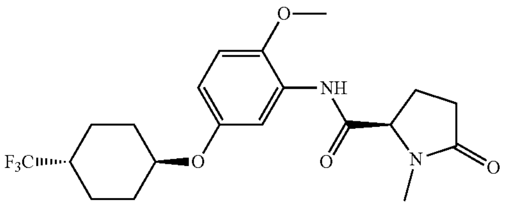 [SMILES: COc1ccc(O[C@H]2CC[C@H](C(F)(F)F)CC2)cc1NC(=O)[C@H]1CCC(=O)N1C] Starting materials: 2-Methoxy-5-(((trans)-4-(trifluoromethyl)cyclohexyl)oxy)aniline and (R)-1-Methyl-5-oxopyrrolidine-2-carboxylic acid | Purification method C. $^1$H NMR (400 MHz, DMSO-$d_6$) δ: 9.46 (s, 1H), 7.65 (d, 1H), 6.95 (d, 1H), 6.71 (dd, 1H), 4.50-4.41 (m, 1H), 4.19-4.08 (m, 1H), 2.66 (s, 3H), 2.37-2.15 (m, 4H), 2.10 (d, 2H), 1.97-1.84 (m, 3H), 1.49-1.31 (m, 4H). LCMS: m/z 415.0 [M + H]$^+$ |
| 104 | 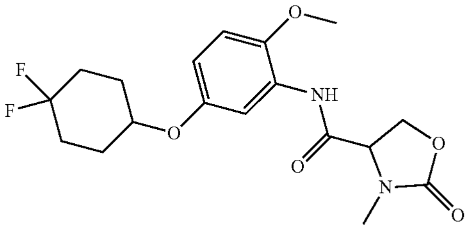 [SMILES: COc1ccc(OC2CCC(F)(F)CC2)cc1NC(=O)C1COC(=O)N1C] Starting materials: 5-((4,4-Difluoro-cyclohexyl)oxy)-2-methoxyaniline HCl and 3-Methyl-2-oxooxazolidine-4-carboxylic acid | Purification method C. $^1$H NMR (400 MHz, DMSO-$d_6$) δ: 9.68 (s, 1H), 7.74 (s, 1H), 6.98 (d, 1H), 6.77 (d, 1H), 4.74-4.62 (m, 1H), 4.49-4.37 (m, 2H), 4.19 (dd, 1H), 3.80 (s, 3H), 2.74 (s, 3H), 2.06-1.76 (m, 8H). LCMS: m/z 385.2 [M + H]$^+$ |
| 105 | 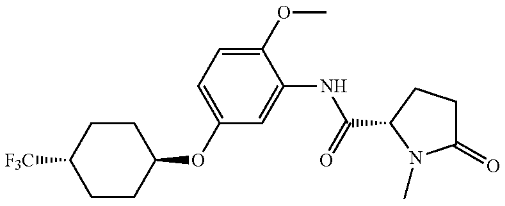 [SMILES: COc1ccc(O[C@H]2CC[C@H](C(F)(F)F)CC2)cc1NC(=O)[C@@H]1CCC(=O)N1C] Starting materials: 2-Methoxy-5-(((trans)-4-(trifluoromethyl)cyclohexyl)oxy)aniline and (S)-1-Methyl-5-oxopyrrolidine-2-carboxylic acid | Purification method C. $^1$H NMR (400 MHz, DMSO-$d_6$) δ: 9.46 (s, 1H), 7.65 (d, 1H), 6.95 (d, 1H), 6.71 (dd, 1H), 4.49-4.41 (m, 1H), 4.22-4.09 (m, 1H), 3.78 (s, 3H), 2.66 (s, 3H), 2.35-2.16 (m, 4H), 2.10 (d, 2H), 1.95-1.84 (m, 3H), 1.39 (q, 4H). LCMS: m/z 415.0 [M + H]$^+$ |
| 106 | 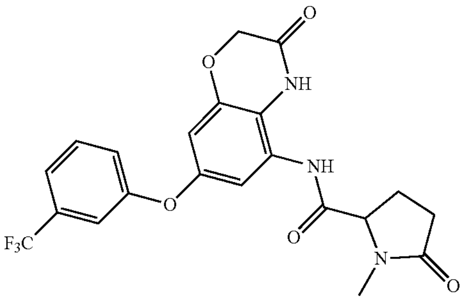 [SMILES: CN1C(=O)CCC1C(=O)Nc1cc(Oc2cccc(C(F)(F)F)c2)cc2c1NC(=O)CO2] Starting materials: 5-Amino-7-(3-(trifluoromethyl)phenoxy)-2H-benzo[b][1,4]oxazin-3(4H)-one and 1-Methyl-5-oxopyrrolidine-2-carboxylic acid | Purification method A. $^1$H NMR (400 MHz, DMSO-$d_6$) δ: 10.40 (s, 1H), 9.65 (s, 1H), 7.65-7.58 (m, 2H), 7.47 (d, 2H), 7.28 (d, 3H), 7.11 (d, 1H), 6.68 (d, 1H), 4.61 (s, 3H), 4.32-4.26 (m, 1H), 2.67 (s, 3H), 2.33-2.11 (m, 5H), 2.07-1.94 (m, 1H). LCMS: m/z 450.0 [M + H]$^+$ |

-continued

| No. | Structure and starting material | Purification method and characterization data |
|---|---|---|
| 107 | 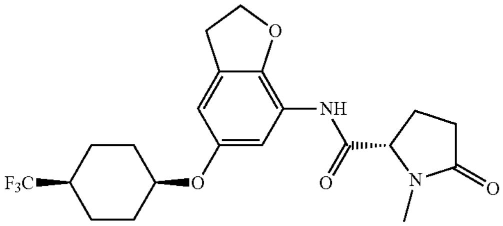 [SMILES: CN1C(=O)CC[C@H]1C(=O)Nc1cc(O[C@H]2CC[C@@H](C(F)(F)F)CC2)cc2c1OCC2] Starting materials: 5-(((cis)-4-(Trifluoromethyl)cyclohexyl)oxy)-2,3-dihydrobenzofuran-7-amine HCl and (S)-1-Methyl-5-oxopyrrolidine-2-carboxylic acid | Purification method A. $^1$H NMR (400 MHz, DMSO-$d_6$) δ: 9.75 (s, 1H), 7.37 (d, 1H), 6.70 (d, 1H), 4.55 (t, 2H), 4.46-4.34 (m, 2H), 3.18 (t, 2H), 2.65 (s, 3H), 2.40-2.16 (m, 4H), 2.03-1.83 (m, 3H), 1.69-1.49 (m, 6H). LCMS: m/z 427.2 $[M + H]^+$ |
| 108 | 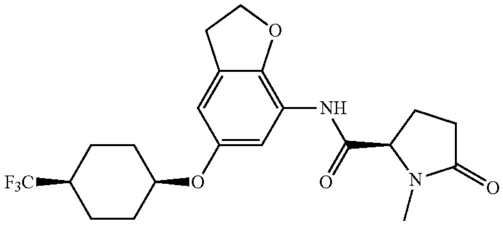 [SMILES: CN1C(=O)CC[C@@H]1C(=O)Nc1cc(O[C@H]2CC[C@@H](C(F)(F)F)CC2)cc2c1OCC2] Starting materials: 5-(((cis)-4-(Trifluoromethyl)cyclohexyl)oxy)-2,3-dihydrobenzofuran-7-amine HCl and (R)-1-Methyl-5-oxopyrrolidine-2-carboxylic acid | Purification method A. $^1$H NMR (400 MHz, DMSO-$d_6$) δ: 9.75 (s, 1H), 7.37 (d, 1H), 6.70 (d, 1H), 4.55 (t, 2H), 4.48-4.32 (m, 2H), 3.18 (t, 2H), 2.65 (s, 3H), 2.39-2.17 (m, 5H), 1.97 (d, 2H), 1.89 (d, 1H), 1.68-1.54 (m, 6H). LCMS: m/z 427.2 $[M + H]^+$ |
| 109 | 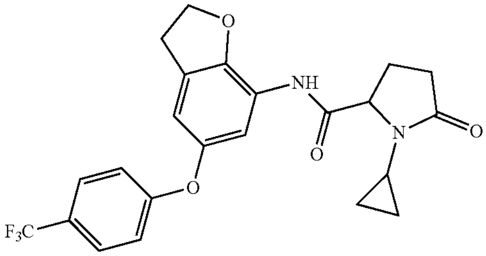 [SMILES: O=C(Nc1cc(Oc2ccc(C(F)(F)F)cc2)cc2c1OCC2)C1CCC(=O)N1C1CC1] Starting materials: 5-(4-(Trifluoromethyl)phenoxy)-2,3-dihydrobenzofuran-7-amine HCl and 1-Cyclopropyl-5-oxopyrrolidine-2-carboxylic acid | Purification method A. $^1$H NMR (400 MHz, DMSO-$d_6$) δ: 9.93 (s, 1H), 7.70 (d, 2H), 7.60 (d, 1H), 7.07 (d, 2H), 6.87 (s, 1H), 4.66 (t, 2H), 4.40 (d, 1H), 3.29-3.20 (m, 2H), 2.36-2.05 (m, 2H), 1.92-1.76 (m, 1H), 0.77-0.40 (m, 4H). LCMS: m/z 447.0 $[M + H]^+$ |
| 110 | 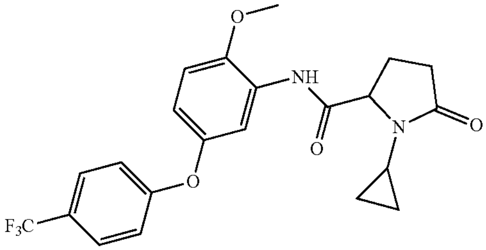 [SMILES: COc1ccc(Oc2ccc(C(F)(F)F)cc2)cc1NC(=O)C1CCC(=O)N1C1CC1] Starting materials: 2-Methoxy-5-(4-(trifluoromethyl)phenoxy)aniline and 1-Cyclopropyl-5-oxopyrrolidine-2-carboxylic acid | Purification method A. $^1$H NMR (400 MHz, DMSO-$d_6$) δ: 9.65 (s, 1H), 7.95-7.84 (m, 1H), 7.71 (d, 2H), 7.14 (d, 1H), 7.08 (d, 2H), 6.92 (dd, 1H), 4.54-4.42 (m, 1H), 3.89 (s, 3H), 2.44-2.37 (m, 1H), 2.32-2.24 (m, 1H), 2.24-2.10 (m, 2H), 1.94-1.78 (m, 1H), 0.74-0.46 (m, 4H). LCMS: m/z 435.2 $[M + H]^+$ |

-continued

| No. | Structure and starting material | Purification method and characterization data |
|---|---|---|
| 111 | 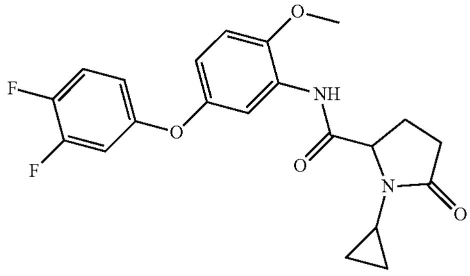 [SMILES: COc1ccc(Oc2ccc(F)c(F)c2)cc1NC(=O)C1CCC(=O)N1C1CC1] Starting materials: 5-(3,4-Difluoro-phenoxy)-2-methoxyaniline and 1-Cyclopropyl-5-oxopyrrolidine-2-carboxylic acid | Purification method E. $^1$H NMR (400 MHz, DMSO-$d_6$) δ: 9.61 (s, 1H), 7.87-7.82 (m, 1H), 7.47-7.35 (m, 1H), 7.13-7.04 (m, 2H), 6.84 (dd, 1H), 6.81-6.70 (m, 1H), 4.51-4.42 (m, 1H), 3.87 (s, 3H), 2.44-2.37 (m, 1H), 2.37-2.22 (m, 1H), 2.22-2.09 (m, 2H), 1.92-1.80 (m, 1H), 0.75-0.48 (m, 4H). LCMS: m/z 403.2 [M + H]$^+$ |
| 112 | 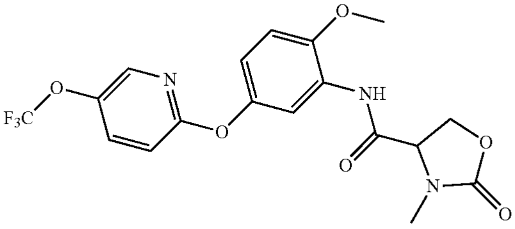 Starting materials: 2-Methoxy-5-((5-(trifluoromethoxy)pyridin-2-yl)oxy)-aniline and 3-Methyl-2-oxooxazolidine-4-carboxylic acid | Purification method A. $^1$H NMR (400 MHz, DMSO-$d_6$) δ: 9.79 (s, 1H), 8.23 (d, 1H), 7.99-7.93 (m, 1H), 7.89 (d, 1H), 7.19-7.08 (m, 2H), 6.95 (dd, 1H), 4.68 (dd, 1H), 4.43 (t, 1H), 4.18 (dd, 1H), 3.87 (s, 3H), 2.73 (s, 3H). LCMS: m/z 428.2 [M + H]$^+$ |
| 113 | 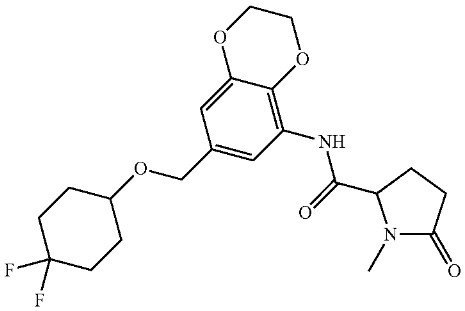 [SMILES: CN1C(=O)CCC1C(=O)Nc1cc(COC2CCC(F)(F)CC2)cc2c1OCCO2] Starting materials: 7-(((4,4-Difluoro-cyclohexyl)oxy)methyl)-2,3-dihydro-benzo[b][1,4]dioxin-5-amine and 1-Methyl-5-oxopyrrolidine-2-carboxylic acid | Purification method A. $^1$H NMR (400 MHz, DMSO-$d_6$) δ: 9.54 (s, 1H), 7.49 (s, 1H), 6.64 (s, 1H), 4.47-4.39 (m, 1H), 4.35 (s, 2H), 4.32-4.23 (m, 4H), 3.58-3.52 (m, 1H), 2.66 (s, 3H), 2.33-2.14 (m, 3H), 1.98-1.64 (m, 9H). LCMS: m/z 425.0 [M + H]$^+$ |
| 114 | 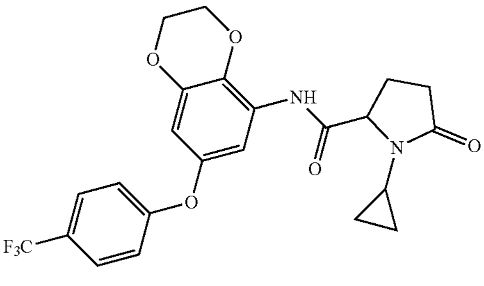 [SMILES: O=C(Nc1cc(Oc2ccc(C(F)(F)F)cc2)cc2c1OCCO2)C1CCC(=O)N1C1CC1] Starting materials: 7-(4-(Trifluoro-methyl)phenoxy)-2,3-dihydro-benzo[b][1,4]dioxin-5-amine HCl and 1-Cyclopropyl-5-oxopyrrolidine-2-carboxylic acid | Purification method C. $^1$H NMR (400 MHz, DMSO-$d_6$) δ: 9.70 (s, 1H), 7.71 (d, 2H), 7.45 (d, 1H), 7.09 (d, 2H), 6.52 (d, 1H), 4.47 (d, 1H), 4.41-4.27 (m, 4H), 2.41-2.11 (m, 4H), 1.90-1.75 (m, 1H), 0.78-0.43 (m, 4H). LCMS: m/z 463.2 [M + H]$^+$ |

-continued

| No. | Structure and starting material | Purification method and characterization data |
|---|---|---|
| 115 | 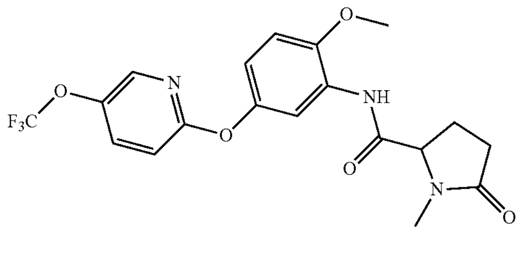 [SMILES: COc1ccc(Oc2ccc(OC(F)(F)F)cn2)cc1NC(=O)C1CCC(=O)N1C] Starting materials: 2-Methoxy-5-((5-(trifluoromethoxy)pyridin-2-yl)oxy)-aniline and 1-Methyl-5-oxopyrrolidine-2-carboxylic acid | Purification method E. $^1$H NMR (400 MHz, DMSO-$d_6$) δ: 9.62 (s, 1H), 8.23 (d, 1H), 7.98-7.90 (m, 1H), 7.85 (d, 1H), 7.11 (dd, 2H), 6.93 (dd, 1H), 4.53-4.41 (m, 1H), 3.88 (s, 3H), 2.65 (s, 3H), 2.31-2.16 (m, 3H), 1.95-1.81 (m, 1H). LCMS: m/z 426.2 [M + H]$^+$ |
| 116 | 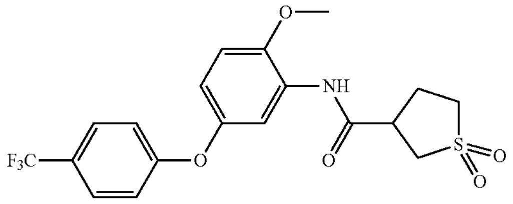 [SMILES: COc1ccc(Oc2ccc(C(F)(F)F)cc2)cc1NC(=O)C1CCS(=O)(=O)C1] Starting materials: 2-Methoxy-5-(4-(trifluoromethyl)phenoxy)aniline and Tetrahydrothiophene-3-carboxylic acid 1,1-dioxide | Purification method A. $^1$H NMR (400 MHz, DMSO-$d_6$) δ: 9.62 (s, 1H), 8.23 (d, 1H), 7.98-7.90 (m, 1H), 7.85 (d, 1H), 7.11 (dd, 2H), 6.93 (dd, 1H), 4.53-4.41 (m, 1H), 3.88 (s, 3H), 2.65 (s, 3H), 2.31-2.16 (m, 3H), 1.95-1.81 (m, 1H).LCMS: m/z 430.2 [M + H]$^+$ |
| 117 | 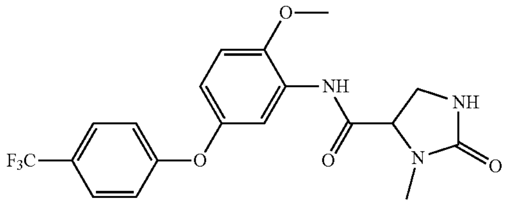 [SMILES: COc1ccc(Oc2ccc(C(F)(F)F)cc2)cc1NC(=O)C1CNC(=O)N1C] Starting materials: 2-Methoxy-5-(4-(trifluoromethyl)phenoxy)aniline and 3-Methyl-2-oxoimi-dazolidine-4-carboxylic acid | Purification method A. $^1$H NMR (400 MHz, DMSO-$d_6$) δ: 9.51 (s, 1H), 7.89 (s, 1H), 7.71 (d, 2H), 7.14 (d, 1H), 7.08 (d, 2H), 6.49-6.44 (m, 1H), 4.41-4.35 (m, 1H), 3.88 (s, 3H), 3.19-3.09 (m, 1H), 2.62 (s, 3H). LCMS: m/z 410.2 [M + H]$^+$ |
| 118 | 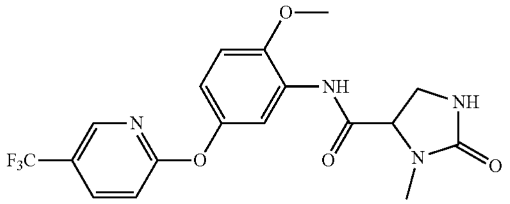 [SMILES: COc1ccc(Oc2ccc(C(F)(F)F)cn2)cc1NC(=O)C1CNC(=O)N1C] Starting materials: 2-Methoxy-5-((5-(trifluoromethyl)pyridin-2-yl)oxy)-aniline and 3-Methyl-2-oxoimi-dazolidine-4-carboxylic acid | Purification method A. $^1$H NMR (400 MHz, DMSO-$d_6$) δ: 9.49 (s, 1H), 8.55 (s, 1H), 8.21 (d, 1H), 7.90 (s, 1H), 7.20 (d, 1H), 7.13 (d, 1H), 6.96 (d, 1H), 6.47 (s, 1H), 4.43-4.33 (m, 1H), 3.88 (s, 3H), 3.58-3.48 (m, 1H), 3.20-3.10 (m, 1H), 2.62 (s, 3H). LCMS: m/z 411.0 [M + H]$^+$ |

-continued

| No. | Structure and starting material | Purification method and characterization data |
|---|---|---|
| 119 | 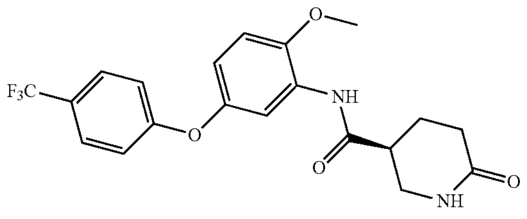 [SMILES: COc1ccc(Oc2ccc(C(F)(F)F)cc2)cc1NC(=O)[C@H]1CCC(=O)NC1] Starting materials: 2-Methoxy-5-(4-(trifluoromethyl)phenoxy)aniline and (S)-6-Oxopiperidine-3-carboxylic acid | Purification method A. $^1$H NMR (400 MHz, DMSO-$d_6$) δ: 9.44 (s, 1H), 7.89-7.84 (m, 1H), 7.70 (d, 2H), 7.48 (d, 1H), 7.09 (dd, 3H), 6.89 (dd, 1H), 3.87 (s, 3H), 3.30-3.18 (m, 2H), 3.09-2.94 (m, 1H), 2.24-2.16 (m, 2H), 1.97-1.90 (m, 1H), 1.86-1.77 (m, 1H). LCMS: m/z 409.2 $[M + H]^+$ |
| 120 | 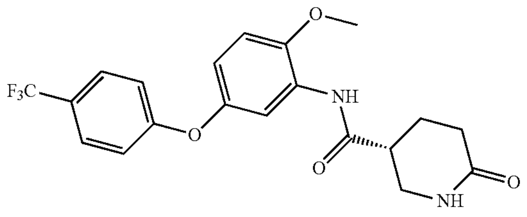 [SMILES: COc1ccc(Oc2ccc(C(F)(F)F)cc2)cc1NC(=O)[C@@H]1CCC(=O)NC1] Starting materials: 2-Methoxy-5-(4-(trifluoromethyl)phenoxy)aniline and (R)-6-Oxopiperidine-3-carboxylic acid | Purification method A. $^1$H NMR (400 MHz, DMSO-$d_6$) δ: 9.45 (s, 1H), 7.91-7.84 (m, 1H), 7.70 (d, 2H), 7.48 (d, 1H), 7.09 (dd, 3H), 6.89 (dd, 1H), 3.87 (s, 3H), 3.31-3.17 (m, 2H), 3.05-2.92 (m, 1H), 2.25-2.15 (m, 2H), 2.00-1.87 (m, 1H), 1.87 - 1.69 (m, 1H). LCMS: m/z 409.2 $[M + H]^+$ |
| 121 | 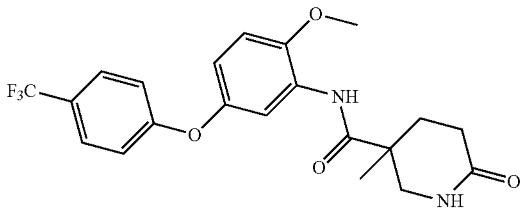 [SMILES: COc1ccc(Oc2ccc(C(F)(F)F)cc2)cc1NC(=O)C1(C)CCC(=O)NC1] Starting materials: 2-Methoxy-5-(4-(trifluoromethyl)phenoxy)aniline and 3-Methyl-6-oxopiperidine-3-carboxylic acid | Purification method A. $^1$H NMR (400 MHz, DMSO-$d_6$) δ: 8.85 (s, 1H), 7.71 (d, 2H), 7.60 (dd, 1H), 7.52 (s, 1H), 7.13 (d, 1H), 7.08 (d, 2H), 6.95 (dd, 1H), 3.85 (s, 3H), 3.55 (d, 1H), 3.04 (d, 1H), 2.24-2.14 (m, 3H), 1.86-1.75 (m, 1H), 1.26 (s, 3H). LCMS: m/z 423.0 $[M + H]^+$ |
| 122 | 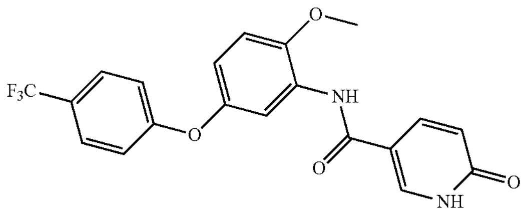 Starting materials: 2-Methoxy-5-(4-(trifluoromethyl)phenoxy)aniline and 6-Oxo-1,6-dihydropyridine-3-carboxylic acid | Purification method A. $^1$H NMR (400 MHz, DMSO-$d_6$) δ: 12.06 (s, 1H), 9.39 (s, 1H), 8.14 (d, 1H), 7.90 (dd, 1H), 7.72 (d, 2H), 7.62 (dd, 1H), 7.15 (d, 1H), 7.10 (d, 2H), 6.97 (dd, 1H), 6.38 (d, 1H), 3.86 (s, 3H). LCMS: m/z 423.0 $[M + H]^+$ |

-continued

| No. | Structure and starting material | Purification method and characterization data |
|---|---|---|
| 123 | 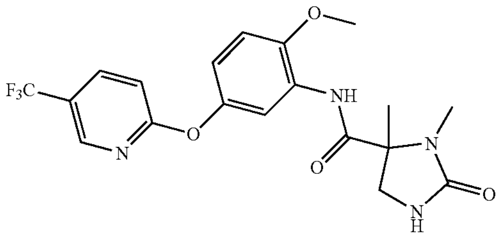 [SMILES: COc1ccc(Oc2ccc(C(F)(F)F)cn2)cc1NC(=O)C1(C)CNC(=O)N1C] Starting materials: 2-Methoxy-5-((5-(trifluoromethyl)pyridin-2-yl)oxy)-aniline and 3,4-Dimethyl-2-oxo-imidazolidine-4-carboxylic acid | Purification method A. $^1$H NMR (400 MHz, DMSO-d6) δ: 8.90 (s, 1H), 8.55 (s, 1H), 8.22 (dd, 1H), 7.83 (d, 1H), 7.17 (dd, 2H), 6.97 (dd, 1H), 3.88 (s, 3H), 3.43 (d, 1H), 3.20 (d, 1H), 2.67 (s, 3H), 1.43 (s, 3H). LCMS: m/z 425.2 [M + H]$^+$ |
| 124 | 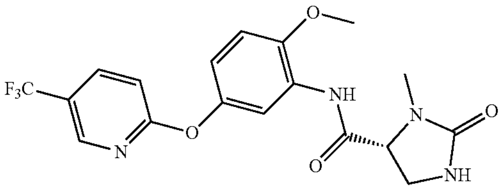 [SMILES: COc1ccc(Oc2ccc(C(F)(F)F)cn2)cc1NC(=O)[C@H]1CNC(=O)N1C] Starting materials: 2-Methoxy-5-((5-(trifluoromethyl)pyridin-2-yl)oxy)-aniline and (R)-3-Methyl-2-oxo-imidazolidine-4-carboxylic acid | Purification method A. $^1$H NMR (400 MHz, DMSO-d6) δ: 9.47 (s, 1H), 8.55 (s, 1H), 8.23-8.17 (m, 1H), 7.89 (d, 1H), 7.20 (d, 1H), 7.12 (d, 1H), 7.02-6.86 (m, 1H), 6.46 (s, 1H), 4.45-4.25 (m, 1H), 3.88 (s, 3H), 3.54 (t, 1H), 3.18-3.09 (m, 1H), 2.62 (d, 3H). LCMS: m/z 411.0 [M + H]$^+$ |
| 125 | 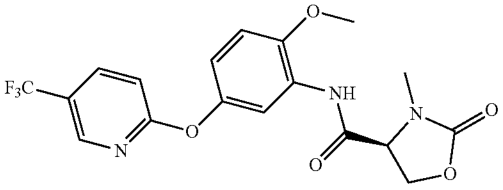 [SMILES: COc1ccc(Oc2ccc(C(F)(F)F)cn2)cc1NC(=O)[C@@H]1COC(=O)N1C] Starting materials: 2-Methoxy-5-((5-(trifluoromethyl)pyridin-2-yl)oxy)-aniline and Lithium (S)-3-methyl-2-oxooxazolidine-4-carboxylate | Purification method A $^1$H NMR (400 MHz, Acetonitrile-d3) δ: 8.59 (s, 1H), 8.33 (d, 1H), 8.12 (d, 1H), 7.35 (d, 1H), 7.28 (s, 1H), 7.10 (d, 1H), 6.95 (dd, 1H), 4.54-4.44 (m, 2H), 4.31-4.21 (m, 1H). LCMS: m/z 412.0 [M + H]$^+$ |
| 126 | 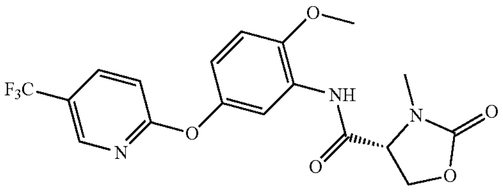 [SMILES: COc1ccc(Oc2ccc(C(F)(F)F)cn2)cc1NC(=O)[C@H]1COC(=O)N1C] Starting materials: 2-Methoxy-5-((5-(trifluoromethyl)pyridin-2-yl)oxy)-aniline and Lithium (R)-3-methyl-2-oxooxazolidine-4-carboxylate | Purification method A. $^1$H NMR (400 MHz, DMSO-d6) δ: 9.79 (s, 1H), 8.38 (d, 1H), 7.90 (d, 1H), 7.46 (d, 1H), 7.42 (s, 1H), 7.12 (d, 1H), 6.96 (dd, 1H), 4.68 (dd, 1H), 4.43 (t, 1H), 4.18 (dd, 1H), 3.89 (s, 3H), 2.73 (s, 3H). LCMS: m/z 412.0 [M + H]$^+$ |

-continued

| No. | Structure and starting material | Purification method and characterization data |
|---|---|---|
| 127 | 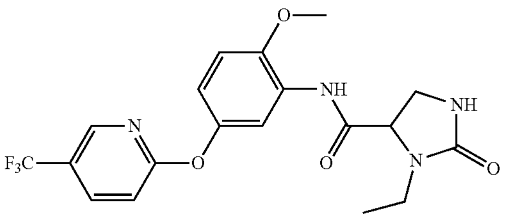 [SMILES: CCN1C(=O)NCC1C(=O)Nc1cc(Oc2ccc(C(F)(F)F)cn2)ccc1OC] Starting materials: 2-Methoxy-5-((5-(trifluoromethyl)pyridin-2-yl)oxy)-aniline and 3-ethyl-2-oxoimidazolidine-4-carboxylic acid | Purification method A. $^{1}$H NMR (500 MHz, DMSO-d6) δ: 9.46 (s, 1H), 8.36 (d, 1H), 7.87 (d, 1H), 7.44 (d, 1H), 7.39 (s, 1H), 7.10 (d, 1H), 6.93 (dd, 1H), 6.43 (s, 1H), 4.49 (dd, 1H), 3.86 (s, 3H), 3.51 (t, 1H), 3.18-3.13 (m, 1H), 2.87 (dq, 1H), 0.98 (t, 3H). LCMS: m/z 425.0 $[M + H]^+$ |
| 128 | 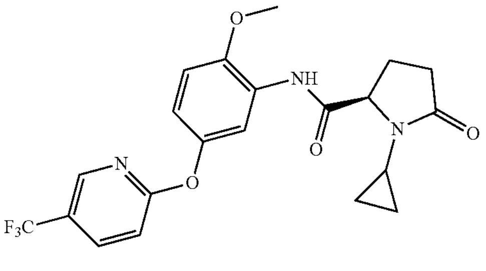 [SMILES: COc1ccc(Oc2ccc(C(F)(F)F)cn2)cc1NC(=O)[C@H]1CCC(=O)N1C1CC1] Starting materials: 2-Methoxy-5-((5-(trifluoromethyl)pyridin-2-yl)oxy)-aniline and (R)-1-Cyclopropyl-5-oxopyrrolidine-2-carboxylic acid | Purification method F. $^{1}$H NMR (400 MHz, Acetonitrile-$d_3$) δ: 8.51-8.41 (m, 2H), 8.13 (d, 1H), 8.09-8.03 (m, 1H), 7.13 (d, 1H), 7.09 (s, 1H), 6.96-6.89 (m, 1H), 4.30-4.20 (m, 1H), 3.96 (s, 3H), 2.60-2.45 (m, 1H), 2.45-2.35 (m, 1H), 2.35-2.20 (m, 2H), 2.07-2.03 (m, 1H), 0.86 – 0.68 (m, 2H), 0.67 – 0.48 (m, 2H). LCMS: m/z 436.1 $[M + H]^+$ |
| 129 | 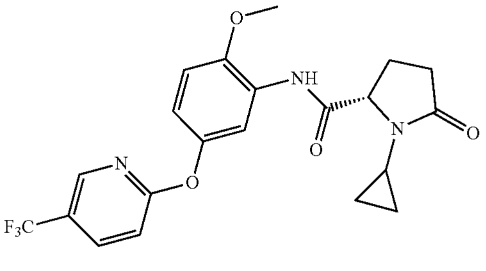 [SMILES: COc1ccc(Oc2ccc(C(F)(F)F)cn2)cc1NC(=O)[C@@H]1CCC(=O)N1C1CC1] Starting materials: 2-Methoxy-5-((5-(trifluoromethyl)pyridin-2-yl)oxy)-aniline and (S)-1-Cyclopropyl-5-oxopyrrolidine-2-carboxylic acid | Purification method A. $^{1}$H NMR (400 MHz, DMSO-d6) δ: 9.62 (s, 1H), 8.55 (s, 1H), 8.27-8.15 (m, 1H), 7.90 (d, 1H), 7.20 (d, 1H), 7.12 (d, 1H), 7.00-6.91 (m, 1H), 4.52-4.42 (m, 1H), 3.89 (s, 3H), 2.45-2.38 (m, 2H), 2.36-2.26 (m, 1H), 2.22-2.10 (m, 2H), 1.95-1.75 (m, 1H), 0.79-0.67 (m, 1H), 0.67-0.47 (m, 3H). LCMS: m/z 436.2 $[M + H]^+$ |
| 130 | 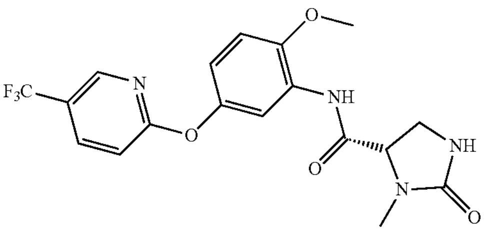 Starting materials: 2-Methoxy-5-((5-(trifluoromethyl)pyridin-2-yl)oxy)-aniline and (S)-3-Methyl-2-oxo-imidazolidine-4-carboxylic acid | Purification method A. $^{1}$H NMR (400 MHz, DMSO-d6) δ: 9.47 (s, 1H), 8.55 (s, 1H), 8.23-8.17 (m, 1H), 7.89 (d, 1H), 7.20 (d, 1H), 7.12 (d, 1H), 7.02-6.86 (m, 1H), 6.46 (s, 1H), 4.45-4.25 (m, 1H), 3.88 (s, 3H), 3.54 (t, 1H), 3.18-3.09 (m, 1H), 2.62 (d, 3H). LCMS: m/z 411.0 $[M + H]^+$ |

-continued

| No. | Structure and starting material | Purification method and characterization data |
|---|---|---|
| 131 | 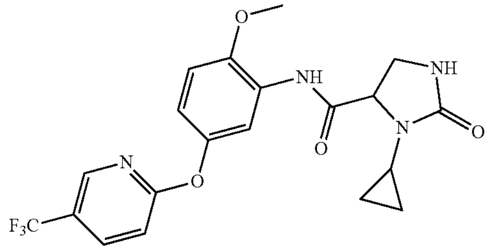 [SMILES: COc1ccc(Oc2ccc(C(F)(F)F)cn2)cc1NC(=O)C1CNC(=O)N1C1CC1] Starting materials: 2-Methoxy-5-((5-(trifluoromethyl)pyridin-2-yl)oxy)-aniline and 3-cyclopropyl-2-oxo-imidazolidine-4-carboxylic acid | Purification method A $^1$H NMR (400 MHz, DMSO-d6) δ: 9.49 (s, 1H), 8.55 (d, 1H), 8.21 (dd, 1H), 7.92 (d, 1H), 7.16 (dd, 2H), 6.95 (dd, 1H), 6.45 (s, 1H), 4.44 (dd, 1H), 3.89 (s, 3H), 3.46 (t, 1H), 3.14 (dd, 1H), 2.43-2.30 (m, 1H), 0.66-0.44 (m, 4H). LCMS: m/z 437.2 $[M + H]^+$ |
| 132 | 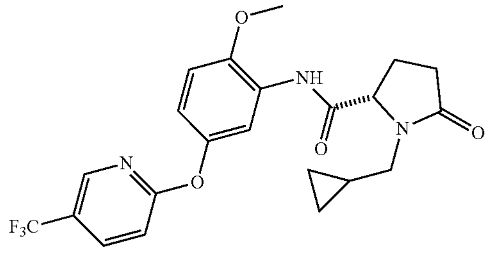 Starting materials: 2-Methoxy-5-((5-(trifluoromethyl)pyridin-2-yl)oxy)-aniline and 1-(Cyclopropylmethyl)-5-oxopyrrolidine-2-carboxylic acid (racemic) | Purification method A followed by method I. Retention time 14.3 min. $^1$H NMR (600 MHz, DMSO-d6) δ: 9.65 (s, 1H), 8.52 (d, 1H), 8.26-8.13 (m, 1H), 7.82 (d, 1H), 7.17 (d, 1H), 7.10 (d, 1H), 6.98-6.92 (m, 1H), 4.77-4.55 (m, 1H), 2.62 (d, 1H), 2.33-2.13 (m, 2H), 1.94-1.74 (m, 1H), 0.81 (dq, 1H), 0.49-0.43 (m, 1H), 0.39-0.27 (m, 1H), 0.19-0.12 (m, 1H), 0.12-0.04 (m, 1H). LCMS: m/z 450.2 $[M + H]^+$ |
| 133 | 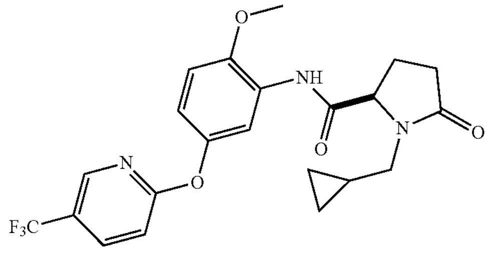 Starting materials: 2-Methoxy-5-((5-(trifluoromethyl)pyridin-2-yl)oxy)-aniline and 1-(Cyclopropylmethyl)-5-oxopyrrolidine-2-carboxylic acid (racemic) | Purification A method followed by method I. Retention time 16.9 min. $^1$H NMR (600 MHz, DMSO-d6) δ: 9.65 (s, 1H), 8.52 (d, 1H), 8.26-8.13 (m, 1H), 7.82 (d, 1H), 7.17 (d, 1H), 7.10 (d, 1H), 6.98-6.92 (m, 1H), 4.77-4.55 (m, 1H), 2.62 (d, 1H), 2.33-2.13 (m, 2H), 1.94-1.74 (m, 1H), 0.81 (dq, 1H), 0.49-0.43 (m, 1H), 0.39-0.27 (m, 1H), 0.19-0.12 (m, 1H), 0.12-0.04 (m, 1H). LCMS: m/z 450.2 $[M + H]^+$ |
| Int-279 | 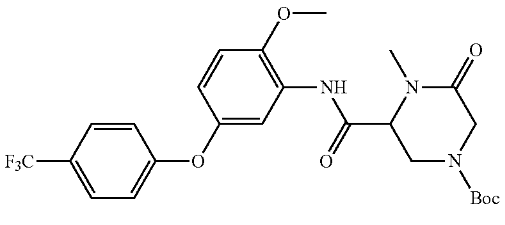 [SMILES: COc1ccc(Oc2ccc(C(F)(F)F)cc2)cc1NC(=O)C1CN(C(=O)OC(C)(C)C)CC(=O)N1C] (Intermediate) Starting materials: 2-Methoxy-5-(4-(trifluoromethyl)phenoxy)aniline and Lithium 4-(tert-butoxycarbonyl)-1-methyl-6-oxopiperazine-2-carboxylate | LCMS: m/z 523.5 $[M + H]^+$ |

-continued

| No. | Structure and starting material | Purification method and characterization data |
|---|---|---|
| 134 | 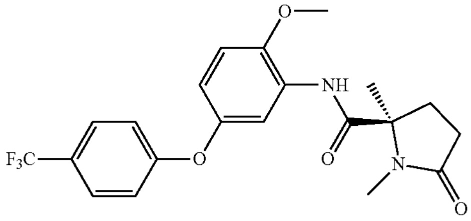 [SMILES: COc1ccc(Oc2ccc(C(F)(F)F)cc2)cc1NC(=O)[C@@]1(C)CCC(=O)N1C] Starting materials: 2-Methoxy-5-(4-(trifluoromethyl)phenoxy)aniline and Lithium (R)-1,2-dimethyl-5-oxo-pyrrolidine-2-carboxylate | Purification method A. $^1$H NMR (400 MHz, DMSO-d6) δ: 8.83 (s, 1H), 7.72 (d, 2H), 7.62 (dd, 1H), 7.15 (d, 1H), 7.08 (d, 2H), 6.97 (dd, 1H), 3.85 (s, 3H), 2.69 (s, 3H), 2.30 (d, 2H), 2.00-1.87 (m, 1H), 1.48 (s, 3H). LCMS: m/z 423.2 [M + H]$^+$ |
| Int-280 | 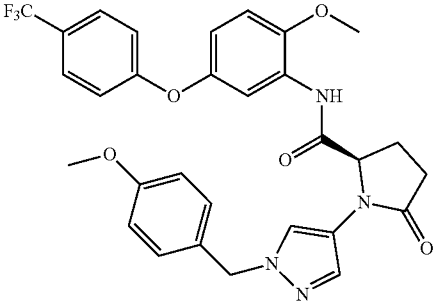 (intermediate) Starting materials: (R)-1-(1-(4-Methoxybenzyl)-1H-pyrazol-4-yl)-5-oxopyrrolidine-2-carboxylic acid and 2-Methoxy-5-(4-(trifluoromethyl)-phenoxy)aniline | LCMS: m/z 479.0 [M − H]$^-$ |
| 135 | 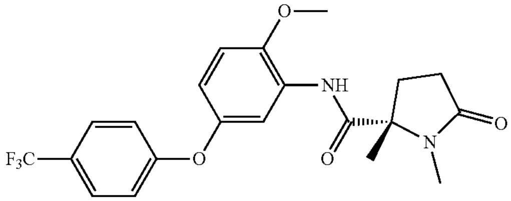 [SMILES: COc1ccc(Oc2ccc(C(F)(F)F)cc2)cc1NC(=O)[C@]1(C)CCC(=O)N1C] Starting materials: 2-Methoxy-5-(4-(trifluoromethyl)phenoxy)aniline and (S)-1,2-Dimethyl-5-oxopyrrolidine-2-carboxylic acid | Purification method A. $^1$H NMR (400 MHz, DMSO-d6) δ: 8.82 (s, 1H), 7.71 (d, 2H), 7.61 (d, 1H), 7.14 (d, 1H), 7.08 (d, 2H), 7.01-6.90 (m, 1H), 3.85 (s, 3H), 2.69 (s, 3H), 2.33-2.17 (m, 3H), 2.02-1.85 (m, 1H), 1.48 (s, 3H). LCMS: m/z 423.2 [M + H] |
| Int-281 | 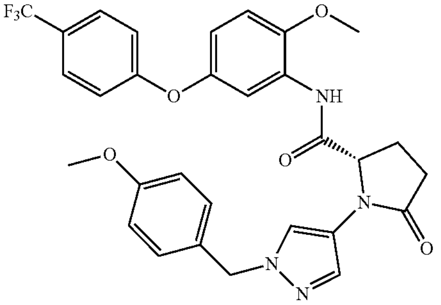 [SMILES: COc1ccc(Cn2cc(N3C(=O)CC[C@H]3C(=O)Nc3cc(Oc4ccc(C(F)(F)F)cc4)ccc3OC)cn2)cc1] (intermediate) Starting materials: (S)-1-(1-(4-Methoxybenzyl)-1H-pyrazol-4-yl)-5-oxopyrrolidine-2-carboxylic acid and 2-Methoxy-5-(4-(trifluoromethyl)-phenoxy)aniline | LCMS: m/z 579.2 [M − H]$^-$ |

-continued

| No. | Structure and starting material | Purification method and characterization data |
| --- | --- | --- |
| Int-282 | 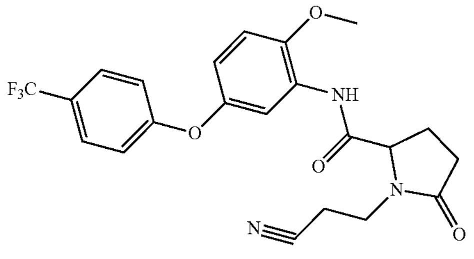 [SMILES: COc1ccc(Oc2ccc(C(F)(F)F)cc2)cc1NC(=O)C1CCC(=O)N1CCC#N] (intermediate) Starting materials: 2-Methoxy-5-(4-(trifluoromethyl)phenoxy)aniline and 1-(2-Cyanoethyl)-5-oxopyrrolidine-2-carboxylic acid | LCMS: m/z 446.0 [M − H]$^-$ |
| 136 | 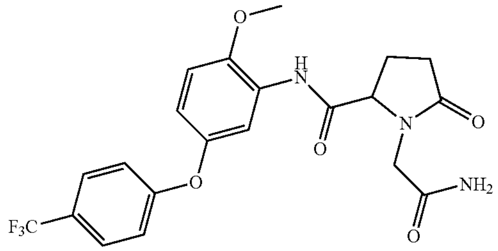 Starting materials: 2-Methoxy-5-(4-(trifluoromethyl)phenoxy)aniline and 1-(2-Amino-2-oxoethyl)-5-oxo-pyrrolidine-2-carboxylic acid | Purification method A. $^1$H NMR (400 MHz, DMSO-d6) δ: 9.75 (s, 1H), 7.82 (s, 1H), 7.71 (d, 2H), 7.43 (s, 1H), 7.23-7.03 (m, 4H), 6.93 (d, 1H), 4.68-4.58 (m, 1H), 4.15 (d, 1H), 3.86 (s, 3H), 3.24 (d, 1H), 2.42-2.21 (m, 3H), 1.96-1.85 (m, 1H). LCMS: m/z 552.0 [M + H]$^+$ |
| 137 | 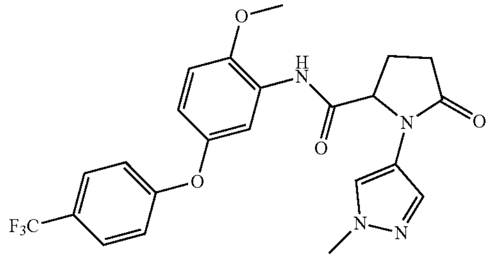 [SMILES: COc1ccc(Oc2ccc(C(F)(F)F)cc2)cc1NC(=O)C1CCC(=O)N1c1cnn(C)c1] Starting materials: 2-Methoxy-5-(4-(trifluoromethyl)phenoxy)aniline and 1-(1-Methyl-1H-pyrazol-4-yl)-5-oxopyrrolidine-2-carboxylic acid | Purification method A. $^1$H NMR (400 MHz, DMSO-d6) δ: 9.82 (s, 1H), 7.93 (d, 1H), 7.81 (d, 1H), 7.69 (d, 2H), 7.45 (s, 1H), 7.15 (d, 1H), 7.06 (d, 2H), 6.92 (dd, 1H), 4.98 (d, 1H), 3.91 (s, 3H), 3.78 (s, 3H), 2.49-2.30 (m, 3H), 2.06 (q, 1H). LCMS: m/z 475.0 [M + H]$^+$ |
| 138 | 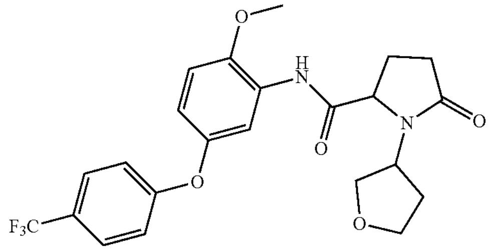 [SMILES: COc1ccc(Oc2ccc(C(F)(F)F)cc2)cc1NC(=O)C1CCC(=O)N1C1CCOC1] Starting materials: 2-Methoxy-5-(4-(trifluoromethyl)phenoxy)aniline and 5-Oxo-1-(tetrahydrofuran-3-yl)-pyrrolidine-2-carboxylic acid | Purification method A. $^1$H NMR (400 MHz, DMSO-d6) δ: 9.65 (d, 1H), 7.84 (t, 1H), 7.71 (d, 2H), 7.19-7.10 (m, 1H), 7.07 (d, 2H), 6.96-6.87 (m, 1H), 4.76-4.59 (m, 1H), 4.38 (m, 1H), 3.78-3.44 (m, 4H), 2.41-2.04 (m, 4H), 2.01-1.76 (m, 2H). LCMS: m/z 465.0 [M + H]$^+$ |

-continued

| No. | Structure and starting material | Purification method and characterization data |
|---|---|---|
| 139 | 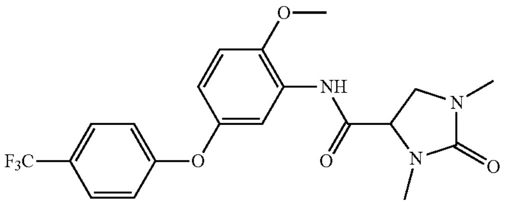 [SMILES: COc1ccc(Oc2ccc(C(F)(F)F)cc2)cc1NC(=O)C1CN(C)C(=O)N1C] Starting materials: 2-Methoxy-5-(4-(trifluoromethyl)phenoxy)aniline and Lithium 1,3-dimethyl-2-oxo-imidazolidine-4-carboxylate | Purification method D. $^{1}H$ NMR (400 MHz, DMSO-d6) δ: 9.57 (s, 1H), 7.88 (d, 1H), 7.71 (d, 2H), 7.11 (dd, 3H), 6.93 (dd, 1H), 4.33 (dd, 1H), 3.88 (s, 3H), 3.54 (t, 1H), 3.19 (dd, 1H), 2.64 (d, 6H). LCMS: m/z 424.0 $[M + H]^+$ |
| 140 | 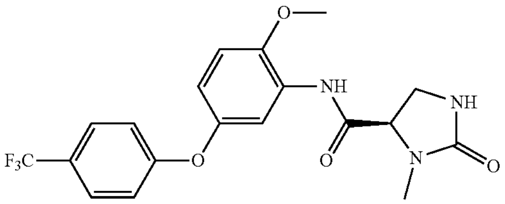 [SMILES: COc1ccc(Oc2ccc(C(F)(F)F)cc2)cc1NC(=O)[C@H]1CNC(=O)N1C] Starting materials: 2-Methoxy-5-(4-(trifluoromethyl)phenoxy)aniline and (R)-3-Methyl-2-oxoimidazolidine-4-carboxylic acid | Purification method A. $^{1}H$ NMR (400 MHz, DMSO-d6) δ: 9.52 (s, 1H), 7.93-7.83 (m, 1H), 7.71 (d, 2H), 7.14 (d, 1H), 7.08 (d, 2H), 6.93 (dd, 1H), 6.47 (s, 1H), 4.46-4.28 (m, 1H), 3.88 (s, 3H), 3.53 (t, 1H), 3.22-3.09 (m, 2H), 2.62 (s, 3H). LCMS: m/z 410.0 $[M + H]^+$ |
| 141 | 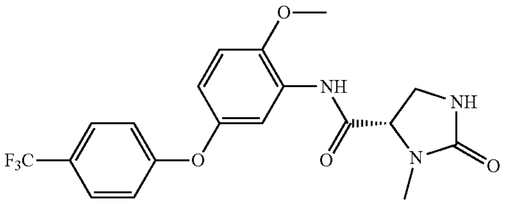 [SMILES: COc1ccc(Oc2ccc(C(F)(F)F)cc2)cc1NC(=O)[C@@H]1CNC(=O)N1C] Starting materials: 2-Methoxy-5-(4-(trifluoromethyl)phenoxy)aniline and 3-Methyl-2-oxoimidazolidine-4-carboxylic acid | Purification method A. $^{1}H$ NMR (400 MHz, DMSO-d6) δ: 9.52 (s, 1H), 7.89 (t, 1H), 7.71 (d, 2H), 7.11 (dd, 3H), 6.93 (dd, 1H), 6.47 (s, 1H), 4.47-4.29 (m, 1H), 3.88 (s, 3H), 3.53 (t, 1H), 3.17 (d, 2H), 2.62 (s, 3H). LCMS: m/z 410.1 $[M + H]^+$ |
| 142 | 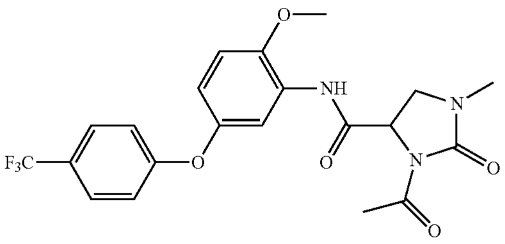 Starting materials: 2-Methoxy-5-(4-(trifluoromethyl)phenoxy)aniline and 3-Acetyl-1-methyl-2-oxoimidazolidine-4-carboxylic acid | Purification method A. $^{1}H$ NMR (400 MHz, DMSO-d6) δ: 9.79 (s, 1H), 7.89 (d, 1H), 7.70 (d, 2H), 7.14 (d, 1H), 7.06 (d, 2H), 6.91 (dd, 1H), 5.03 (dd, 1H), 3.90 (s, 3H), 3.64 (t, 1H), 3.30 (dd, 1H), 2.74 (s, 3H), 2.35 (s, 3H). LCMS: m/z 452.0 $[M + H]^+$ |

-continued

| No. | Structure and starting material | Purification method and characterization data |
| --- | --- | --- |
| Int-283 | 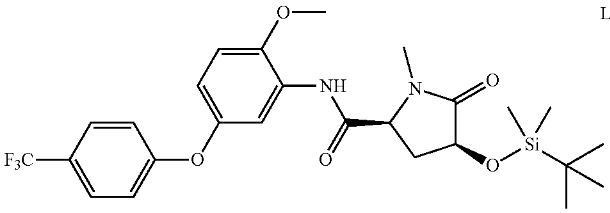 (intermediate) Starting materials: 2-Methoxy-5-(4-(trifluoromethyl)phenoxy)aniline and (2S,4S)-4-((tert-Butyldimethylsilyl)-oxy)-1-methyl-5-oxopyrrolidine-2-carboxylic acid | LCMS: m/z 539.2 [M + H]+ |
| Int-284 | 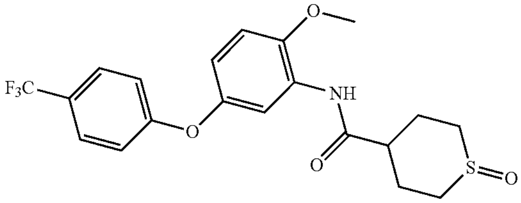 [SMILES: COc1ccc(Oc2ccc(C(F)(F)F)cc2)cc1NC(=O)C1CCS(=O)CC1] (intermediate) Starting materials: 2-Methoxy-5-(4-(trifluoromethyl)phenoxy)aniline and Tetrahydro-2H-thiopyran-4-carboxylic acid 1-oxide | LCMS: m/z 428.2 [M + H]+ |
| 143 | 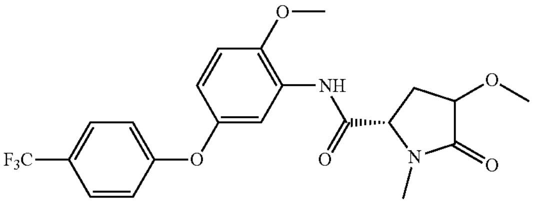 [SMILES: COc1ccc(Oc2ccc(C(F)(F)F)cc2)cc1NC(=O)[C@@H]1CC(OC)C(=O)N1C] Starting materials: 2-Methoxy-5-(4-(trifluoromethyl)phenoxy)aniline and (2S)-4-Methoxy-1-methyl-5-oxo-pyrrolidine-2-carboxylic acid | Purification method A. $^1$H NMR (400 MHz, Acetonitrile-d$_3$) δ: 8.72-8.48 (m, 1H), 8.13-8.01 (m, 1H), 7.68 (d, 2H), 7.18-7.03 (m, 2H), 6.95-6.80 (m, 1H), 4.37-4.26 (m, 1H), 4.19-4.06 (m, 1H), 3.94 (s, 3H), 3.50 (s, 2H), 2.84-2.75 (m, 3H), 2.75-2.67 (m, 1H), 2.52-2.36 (m, 1H). LCMS: m/z 439.2 [M + H]+ |
| 144 | 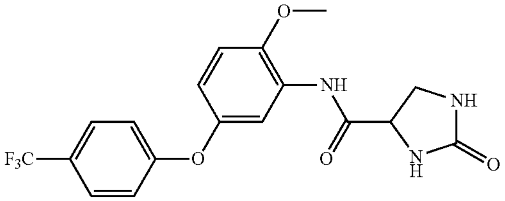 [SMILES: COc1ccc(Oc2ccc(C(F)(F)F)cc2)cc1NC(=O)C1CNC(=O)N1] Starting materials: 2-Methoxy-5-(4-(trifluoromethyl)phenoxy)aniline and 2-Oxoimidazolidine-4-carboxylic acid | Purification method A. H NMR (400 MHz, DMSO-d6) δ: 9.27 (s, 1H), 7.98 (d, 1H), 7.71 (d, 2H), 7.15 (d, 1H), 7.08 (d, 2H), 6.95-6.84 (m, 1H), 6.80 (s, 1H), 6.49 (s, 1H), 4.38-4.28 (m, 1H), 3.63 (t, 1H), 3.30-3.24 (m, 1H). LCMS: m/z 396.0 [M + H]+ |

-continued

| No. | Structure and starting material | Purification method and characterization data |
|---|---|---|
| 145 | 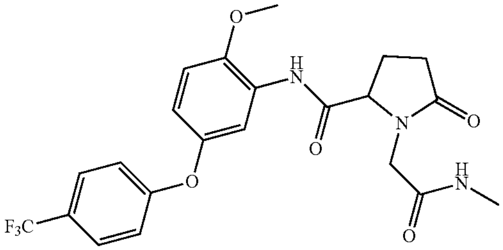 [SMILES: CNC(=O)CN1C(=O)CCC1C(=O)Nc1cc(Oc2ccc(C(F)(F)F)cc2)ccc1OC] Starting materials: 2-Methoxy-4-(4-(trifluoromethyl)phenoxy)aniline and 1-(2-(Methylamino)-2-oxoethyl)-5-oxopyrrolidine-2-carboxylic acid | Purification method A. $^1$H NMR (400 MHz, DMSO-d6) δ: 9.73 (s, 1H), 7.88 (d, 1H), 7.83 (s, 1H), 7.70 (d, 2H), 7.13 (d, 1H), 7.07 (d, 2H), 6.92 (dd, 1H), 4.67-4.58 (m, 1H), 4.16 (d, 1H), 3.86 (s, 3H), 3.26 (d, 1H), 2.60-2.55 (m, 3H), 2.41-2.22 (m, 3H), 1.95-1.84 (m, 1H). LCMS: m/z 466.2 [M + H]$^+$ |
| 146 | 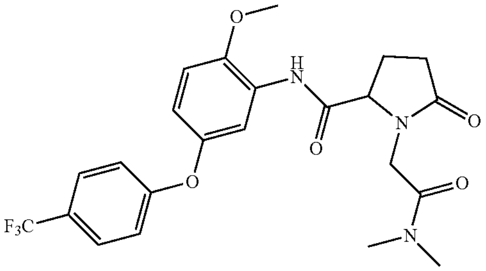 [SMILES: COc1ccc(Oc2ccc(C(F)(F)F)cc2)cc1NC(=O)C1CCC(=O)N1CC(=O)N(C)C] Starting materials: 2-Methoxy-4-(4-(trifluoromethyl)phenoxy)aniline and 1-(2-(Dimethylamino)-2-oxoethyl)-5-oxopyrrolidine-2-carboxylic acid | Purification method F. $^1$H NMR (400 MHz, DMSO-d6) δ: 9.67 (s, 1H), 7.84 (s, 1H), 7.71 (d, 2H), 7.12 (d, 1H), 7.07 (d, 2H), 6.91 (dd, 1H), 4.71-4.58 (m, 1H), 4.42 (d, 1H), 3.86 (s, 3H), 3.57 (d, 1H), 2.92 (s, 3H), 2.80 (s, 3H), 2.41-2.20 (m, 3H), 1.99-1.82 (m, 1H). LCMS: m/z 480.2 [M + H]$^+$ |
| 147 | 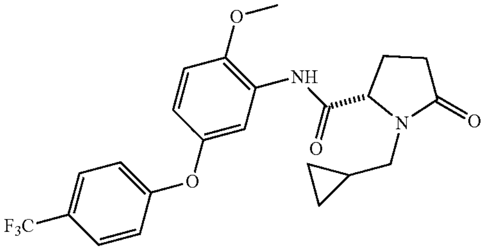 Starting materials: 2-methoxy-5-(4-(trifluoromethyl)phenoxy)aniline and 1-(cyclopropylmethyl)-5-oxo-pyrrolidine-2-carboxylic acid | Purification method A followed by method I. Retention time 16.48 min. $^1$H NMR (600 MHz, DMSO-d6) δ: 9.67 (s, 1H), 7.81 (d, 1H), 7.69 (d, 2H), 7.12 (d, 1H), 7.06 (d, 2H), 6.94-6.84 (m, 1H), 4.72-4.66 (m, 1H), 2.65-2.60 (m, 1H), 2.32-2.15 (m, 2H), 1.96-1.74 (m, 1H), 0.87-0.77 (m, OH), 0.48-0.41 (m, 1H), 0.40-0.33 (m, 1H), 0.18-0.12 (m, 1H), 0.11-0.05 (m, 1H). LCMS: m/z 449.2 [M + H]$^+$ |
| 148 | 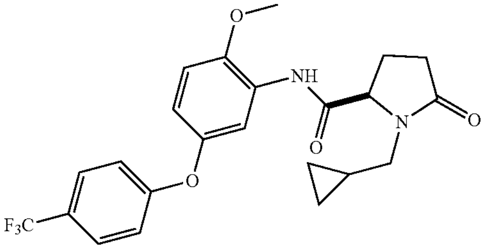 Starting materials: 2-Methoxy-5-(4-(trifluoromethyl)phenoxy)aniline and 1-(Cyclopropylmethyl)-5-oxo-pyrrolidine-2-carboxylic acid | Purification method A followed by method I. Retention time 26.11 min. $^1$H NMR (600 MHz, DMSO-d6) δ: 9.67 (s, 1H), 7.81 (d, 1H), 7.69 (d, 2H), 7.12 (d, 1H), 7.06 (d, 2H), 6.94 6.84 (m, 1H), 4.72-4.66 (m, 1H), 2.65-2.60 (m, 1H), 2.32-2.15 (m, 2H), 1.96-1.74 (m, 1H), 0.87-0.77 (m, OH), 0.48-0.41 (m, 1H), 0.40-0.33 (m, 1H), 0.18-0.12 (m, 1H), 0.11-0.05 (m, 1H). LCMS: m/z 449.2 [M + H]$^+$ |

-continued

| No. | Structure and starting material | Purification method and characterization data |
|---|---|---|
| 149 | 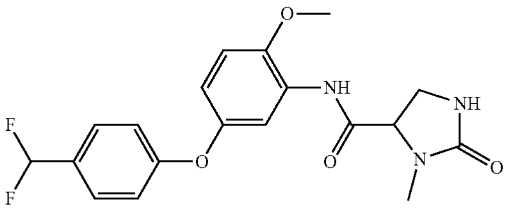 [SMILES: COc1ccc(Oc2ccc(C(F)F)cc2)cc1NC(=O)C1CNC(=O)N1C] Starting materials: 5-(4-(Difluoromethyl)phenoxy)-2-methoxyaniline and 3-Methyl-2-oxoimidazolidine-4-carboxylic acid | Purification method A. $^1$H NMR (400 MHz, Acetonitrile-d3) δ: 8.60 (s, 1H), 8.06 (d, 1H), 7.56 (d, 2H), 7.07 (d, 3H), 6.87 (dd, 1H), 6.79 (t, 1H), 5.01 (s, 1H), 4.19 (dd, 1H), 3.68 (t, 1H), 3.32 (t, 1H), 2.78 (s, 3H). LCMS: m/z 390.1 $[M - H]^-$ |
| 150 | 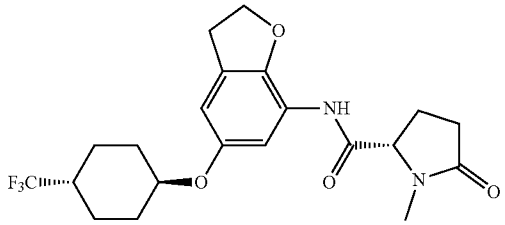 [SMILES: CN1C(=O)CC[C@H]1C(=O)Nc1cc(O[C@H]2CC[C@H](C(F)(F)F)CC2)cc2c1OCC2] Starting materials: 5-(((trans)-4-(Trifluoromethyl)cyclohexyl)oxy)-2,3-dihydrobenzofuran-7-amine HCl and (S)-1-Methyl-5-oxopyrrolidine-2-carboxylic acid | Purification method A. $^1$H NMR (400 MHz, DMSO-d6) δ: 9.74 (s, 1H), 7.33 (s, 1H), 6.70 (s, 1H), 4.55 (t, 2H), 4.37 (m, 1H), 4.17-3.89 (m, 1H), 3.18 (t, 2H), 2.31 (s, 3H), 2.09 (m, 4H), 1.89 (m, 2H), 1.55-1.20 (m, 4H). LCMS: m/z 427.2 $[M + H]^+$ |
| 151 | 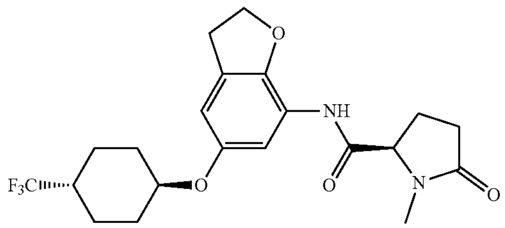 [SMILES: CN1C(=O)CC[C@@H]1C(=O)Nc1cc(O[C@H]2CC[C@H](C(F)(F)F)CC2)cc2c1OCC2] Starting materials: 5-(((trans)-4-(Trifluoromethyl)cyclohexyl)oxy)-2,3-dihydrobenzofuran-7-amine HCl and (R)-1-Methyl-5-oxopyrrolidine-2-carboxylic acid | Purification method A. $^1$H NMR (400 MHz, DMSO-d6) δ: 9.74 (s, 1H), 7.33 (s, 1H), 6.70 (s, 1H), 4.54 (t, 2H), 4.37 (m, 1H), 4.16-4.01 (m, 1H), 3.18 (t, 2H), 2.63 (s, 3H), 2.36-2.13 (m, 4H), 2.10 (m, 2H), 1.89 (s, 3H), 1.51-1.20 (m, 4H). LCMS: m/z 427.2 $[M + H]^+$ |
| 152 | 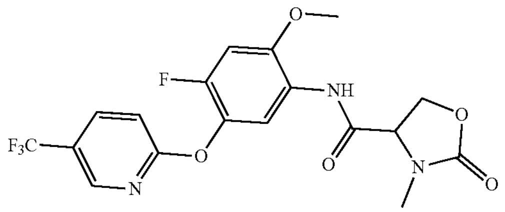 [SMILES: COc1cc(F)c(Oc2ccc(C(F)(F)F)cn2)cc1NC(=O)C1COC(=O)N1C] Starting materials: 4-Fluoro-2-methoxy-5-((5-(trifluoromethyl)-pyridin-2-yl)oxy)aniline HCl and 3-Methyl-2-oxooxazolidine-4-carboxylic acid | Purification method A. $^1$H NMR (500 MHz, DMSO-d6) δ: 9.80 (s, 1H), 8.53 (s, 1H), 8.24 (d, 1H), 7.95 (d, 1H), 7.32 (d, 1H), 7.22 (d, 1H), 4.69-4.59 (m, 1H), 4.41 (t, 1H), 4.21-4.10 (m, 1H), 3.88 (s, 3H), 2.71 (s, 3H). LCMS: m/z 430.0 $[M + H]^+$ |

-continued

| No. | Structure and starting material | Purification method and characterization data |
|---|---|---|
| 153 | 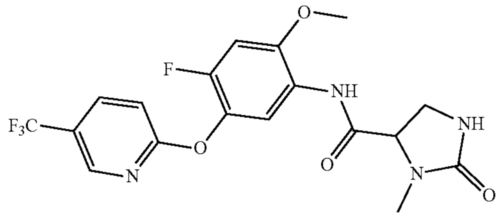 [SMILES: COc1cc(F)c(Oc2ccc(C(F)(F)F)cn2)cc1NC(=O)C1CNC(=O)N1C] Starting materials: 4-Fluoro-2-methoxy-5-((5-(trifluoromethyl)-pyridin-2-yl)oxy)aniline HCl and 3-Methyl-2-oxoimidazolidine-4-carboxylic acid | Purification method A. $^1$H NMR (400 MHz, DMSO-d6) δ: 9.53 (s, 1H), 8.55 (s, 1H), 8.26 (dd, 1H), 7.95 (dd, 1H), 7.34 (d, 1H), 7.23 (d, 1H), 6.45 (s, 1H), 4.43-4.26 (m, 1H), 3.89 (s, 3H), 3.53 (t, 1H), 3.16 (t, 1H), 2.62 (s, 3H). LCMS: m/z 429.2 $[M + H]^+$ |
| 154 | 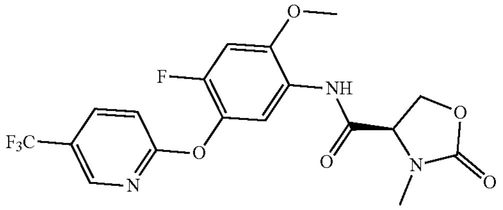 [SMILES: COc1cc(F)c(Oc2ccc(C(F)(F)F)cn2)cc1NC(=O)[C@H]1COC(=O)N1C] Starting materials: 4-Fluoro-2-methoxy-5-((5-(trifluoromethyl)-pyridin-2-yl)oxy)aniline HCl and Lithium (R)-3-methyl-2-oxooxa-zolidine-4-carboxylate | Purification method A. $^1$H NMR (400 MHz, DMSO-d6) δ: 9.82 (s, 1H), 8.57-8.50 (m, 1H), 8.26 (dd, 1H), 7.97 (d, 1H), 7.34 (d, 1H), 7.24 (d, 1H), 4.66-4.61 (m, 1H), 4.43 (t, 1H), 4.21-4.15 (m, 1H), 3.90 (s, 3H), 2.73 (s, 3H). LCMS: m/z 430.0 $[M + H]^+$ |
| 155 | 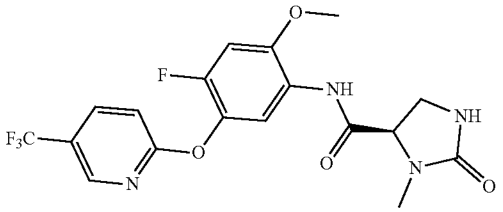 [SMILES: COc1cc(F)c(Oc2ccc(C(F)(F)F)cn2)cc1NC(=O)[C@H]1CNC(=O)N1C] Starting materials: 4-Fluoro-2-methoxy-5-((5-(trifluoromethyl)-pyridin-2-yl)oxy)aniline HCl and (R)-3-Methyl-2-oxoimidazolidine-4-carboxylic acid | Purification method A. $^1$H NMR (600 MHz, DMSO-d6) δ: 9.50 (s, 1H), 8.53 (d, 1H), 8.24 (dd, 1H), 7.92 (d, 1H), 7.32 (d, 1H), 7.21 (d, 1H), 6.42 (s, 1H), 4.33 (dd, 1H), 3.87 (s, 3H), 3.51 (t, 1H), 3.15 (t, 1H), 2.60 (s, 3H). LCMS: m/z 429.2 $[M + H]^+$ |
| 156 | 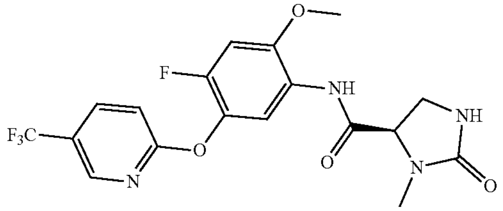 [SMILES: COc1cc(F)c(Oc2ccc(C(F)(F)F)cn2)cc1NC(=O)[C@H]1CNC(=O)N1C] Starting materials: 4-Fluoro-2-methoxy-5-((5-(trifluoromethyl)-pyridin-2-yl)oxy)aniline HCl and (S)-3-Methyl-2-oxoimidazolidine-4-carboxylic acid | Purification method A. $^1$H NMR (400 MHz, DMSO-d6) δ: 9.50 (s, 1H), 8.55 (s, 1H), 8.26 (dd, 1H), 7.94 (d, 1H), 7.34 (d, 1H), 7.23 (d, 1H), 6.44 (s, 1H), 4.39-4.31 (m, 1H), 3.89 (s, 3H), 3.53 (t, 1H), 3.21-3.13 (m, 1H), 2.62 (s, 3H). LCMS: m/z 429.0 $[M + H]^+$ |

-continued

| No. | Structure and starting material | Purification method and characterization data |
|---|---|---|
| 157 | 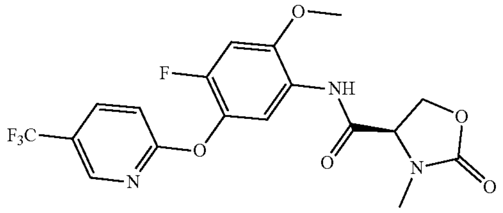 [SMILES: COc1cc(F)c(Oc2ccc(C(F)(F)F)cn2)cc1NC(=O)[C@H]1COC(=O)N1C]<br>Starting materials: 4-Fluoro-2-methoxy-5-((5-(trifluoromethyl)-pyridin-2-yl)oxy)aniline HCl and Lithium (S)-3-methyl-2-oxooxazolidine-4-carboxylate | Purification method A.<br>$^1$H NMR (400 MHz, DMSO-d6) δ: 9.82 (s, 1H), 8.58 – 8.49 (m, 1H), 8.26 (d, 1H), 7.97 (d, 1H), 7.34 (d, 1H), 7.23 (d, 1H), 4.69-4.61 (m, 1H), 4.43 (t, 1H), 4.22-4.13 (m, 1H), 3.90 (s, 3H), 2.73 (s, 3H). LCMS: m/z 430.0 $[M + H]^+$ |
| 158 | 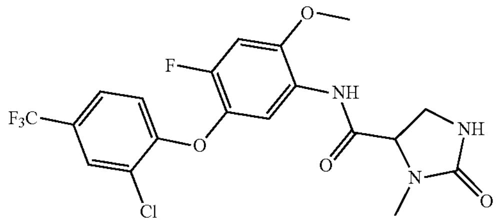 [SMILES: COc1cc(F)c(Oc2ccc(C(F)(F)F)cc2Cl)cc1NC(=O)C1CNC(=O)N1C]<br>Starting materials: 5-(2-Chloro-4-(trifluoromethyl)phenoxy)-4-fluoro-2-methoxyaniline HCl and 3-Methyl-2-oxoimidazolidine-4-carboxylic acid | Purification method A.<br>$^1$H NMR (400 MHz, DMSO-d6) δ: 9.58 (s, 1H), 8.02 (s, 1H), 7.96 (d, 1H), 7.67 (d, 1H), 7.32 (d, 1H), 6.97 (d, 1H), 6.44 (s, 1H), 4.36 (dd, 1H), 3.90 (s, 3H), 3.52 (t, 1H), 3.21-3.10 (m, 1H), 2.61 (s, 3H). LCMS: m/z 462.0 $[M + H]^+$ |
| 159 | 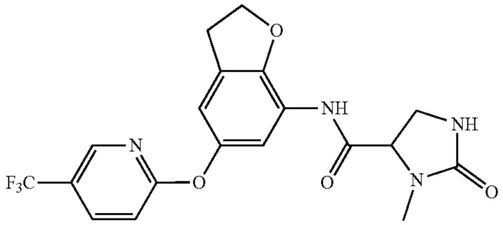 [SMILES: CN1C(=O)NCC1C(=O)Nc1cc(Oc2ccc(C(F)(F)F)cn2)cc2c1OCC2]<br>Starting materials: 5-((5-(Trifluoromethyl)pyridin-2-yl)oxy)-2,3-dihydrobenzofuran-7-amine HCl and 3-Methyl-2-oxoimidazolidine-4-carboxylic acid | Purification method A.<br>$^1$H NMR (400 MHz, DMSO-d6) δ: 9.76 (s, 1H), 8.55 (s, 1H), 8.20 (d, 1H), 7.56 (s, 1H), 7.18 (d, 1H), 6.90 (s, 1H), 6.39 (s, 1H), 4.65 (t, 2H), 4.35 (dd, 1H), 3.51 (t, 1H), 3.25 (t, 2H), 3.18-3.10 (m, 1H), 2.60 (s, 3H). LCMS: m/z 423.0 $[M + H]^+$ |
| 160 | 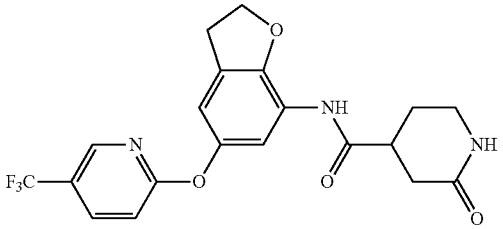<br>Starting materials: 5-((5-(Trifluoromethyl)pyridin-2-yl)oxy)-2,3-dihydrobenzofuran-7-amine HCl and 2-Oxopiperidine-4-carboxylic acid | Purification method A.<br>$^1$H NMR (400 MHz, DMSO-d6) δ: 9.62 (s, 1H), 8.55 (s, 1H), 8.19 (d, 1H), 7.57 (s, 1H), 7.48 (s, 1H), 7.16 (d, 1H), 6.85 (s, 1H), 4.63 (t, 2H), 3.24 (t, 2H), 3.19-2.89 (m, 3H), 2.24 (d, 2H), 2.02-1.57 (m, 2H). LCMS: m/z 422.2 $[M + H]^+$ |

-continued

| No. | Structure and starting material | Purification method and characterization data |
|---|---|---|
| 161 | 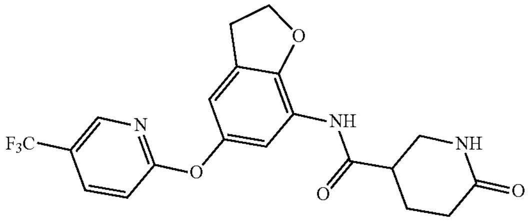 [SMILES: O=C1CCC(C(=O)Nc2cc(Oc3ccc(C(F)(F)F)cn3)cc3c2OCC3)CN1] Starting materials: 5-((5-(Trifluoromethyl)pyridin-2-yl)oxy)-2,3-dihydrobenzofuran-7-amine HCl and 6-Oxopiperidine-3-carboxylic acid | Purification method A. $^1$H NMR (400 MHz, DMSO-d6) δ: 9.65 (s, 1H), 8.53 (s, 1H), 8.17 (d, 1H), 7.53 (s, 1H), 7.44 (s, 1H), 7.14 (d, 1H), 6.84 (s, 1H), 4.62 (t, 2H), 3.22 (m, 4H), 2.96-2.85 (m, 1H), 2.23-2.07 (m, 2H), 1.97-1.70 (m, 2H). LCMS: m/z 422.2 $[M + H]^+$ |
| 162 | 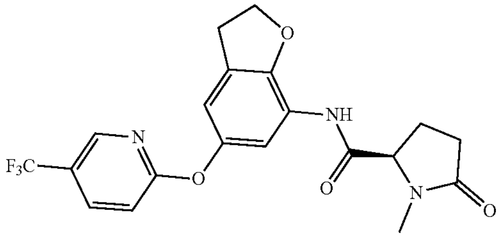 [SMILES: CN1C(=O)CC[C@@H]1C(=O)Nc1cc(Oc2ccc(C(F)(F)F)cn2)cc2c1OCC2] Starting materials: 5-((5-(Trifluoromethyl)pyridin-2-yl)oxy)-2,3-dihydrobenzofuran-7-amine HCl and (R)-1-Methyl-5-oxopyrrolidine-2-carboxylic acid | Purification method A. $^1$H NMR (400 MHz, DMSO-d6) δ: 9.91 (s, 1H), 8.55 (s, 1H), 8.19 (d, 1H), 7.57 (s, 1H), 7.17 (d, 1H), 6.89 (s, 1H), 4.65 (t, 2H), 4.40 (s, 1H), 3.25 (t, 2H), 2.63 (s, 3H), 2.36-2.10 (m, 3H), 1.99-1.73 (m, 1H). LCMS: m/z 422.0 $[M + H]^+$ |
| 163 | 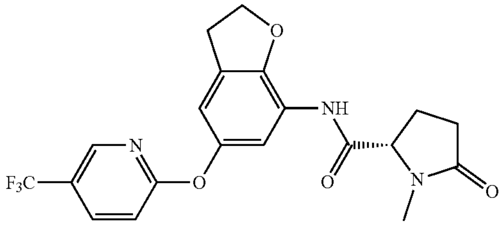 Starting materials: 5-((5-(Trifluoromethyl)pyridin-2-yl)oxy)-2,3-dihydrobenzofuran-7-amine HCl and (S)-1-Methyl-5-oxopyrrolidine-2-carboxylic acid | Purification method A. $^1$H NMR (400 MHz, DMSO-d6) δ: 9.91 (s, 1H), 8.55 (s, 1H), 8.19 (d, 1H), 7.57 (s, 1H), 7.17 (d, 1H), 6.89 (s, 1H), 4.65 (t, 1H), 4.40 (s, 1H), 3.24 (d, 1H), 2.63 (s, 3H), 2.33-2.14 (m, 3H), 1.86 (m, 1H). LCMS: m/z 422.0 $[M + H]^+$ |
| 164 | 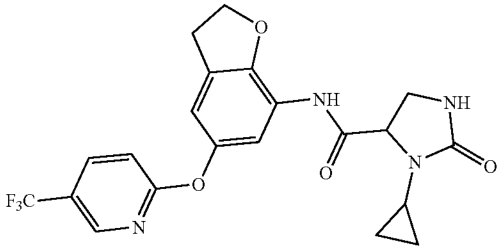 [SMILES: O=C(Nc1cc(Oc2ccc(C(F)(F)F)cn2)cc2c1OCC2)C1CNC(=O)N1C1CC1] Starting materials: 5-((5-(Trifluoromethyl)pyridin-2-yl)oxy)-2,3-dihydrobenzofuran-7-amine HCl and 3-Cyclopropyl-2-oxoimidazolidine-4-carboxylic acid | Purification method A. $^1$H NMR (400 MHz, DMSO-d6) δ: 9.79 (s, 1H), 8.55 (d, 1H), 8.20 (dd, 1H), 7.60 (t, 1H), 7.18 (d, 1H), 6.89 (d, 1H), 6.40 (s, 1H), 4.65 (t, 2H), 4.44-4.35 (m, 1H), 3.43 (t, 1H), 3.25 (t, 2H), 3.16-3.09 (m, 1H), 2.34 (s, 1H), 0.62-0.52 (m, 2H), 0.49 (m, 2H). LCMS: m/z 449.0 $[M + H]^+$ |

-continued

| No. | Structure and starting material | Purification method and characterization data |
|---|---|---|
| 165 | 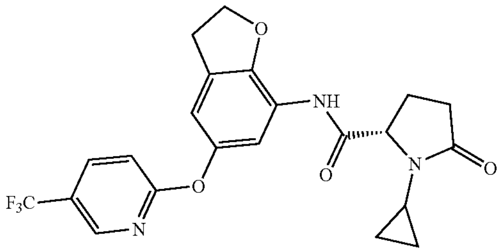 [SMILES: O=C(Nc1cc(Oc2ccc(C(F)(F)F)cn2)cc2c1OCC2)[C@@H]1CCC(=O)N1C1CC1] Starting materials: 5-((5-(Trifluoro-methyl)pyridin-2-yl)oxy)-2,3-dihydrobenzofuran-7-amine and Lithium (S)-1-cyclopropyl-5-oxo-pyrrolidine-2-carboxylate | Purification method A. $^1$H NMR (400 MHz, Acetonitrile-$d_3$) δ: 8.47 (s, 1H), 8.16 (s, 1H), 8.06 (d, 1H), 7.72 (s, 1H), 7.11 (d, 1H), 6.87 (s, 1H), 4.70 (t, 2H), 4.22 (d, 1H), 3.31 (t, 2H), 2.60-2.22 (m, 4H), 0.89-0.66 (m, 2H), 0.60 (m, 2H). LCMS: m/z 448.0 $[M + H]^+$ |
| 166 | 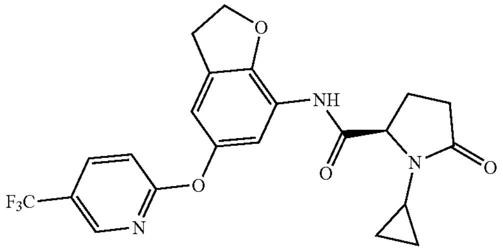 [SMILES: O=C(Nc1cc(Oc2ccc(C(F)(F)F)cn2)cc2c1OCC2)[C@H]1CCC(=O)N1C1CC1] Starting materials: 5-((5-(Trifluoro-methyl)pyridin-2-yl)oxy)-2,3-di-hydrobenzofuran-7-amine and Lithium (R)-1-cyclopropyl-5-oxo-pyrrolidine-2-carboxylate | Purification method A. $^1$H NMR (400 MHz, Acetonitrile-$d_3$) δ: 8.47 (s, 1H), 8.16 (s, 1H), 8.06 (d, 1H), 7.72 (s, 1H), 7.11 (d, 1H), 6.87 (s, 1H), 4.70 (t, 2H), 4.22 (d, 1H), 3.31 (t, 2H), 2.60-2.22 (m, 4H), 0.89-0.66 (m, 2H), 0.60 (m, 2H). LCMS: m/z 448.2 $[M + H]^+$ |
| 167 | 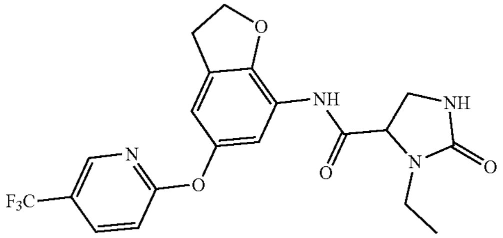 [SMILES: CCN1C(=O)NCC1C(=O)Nc1cc(Oc2ccc(C(F)(F)F)cn2)cc2c1OCC2] Starting materials: 5-((5-(Trifluoro-methyl)pyridin-2-yl)oxy)-2,3-dihydrobenzofuran-7-amine HCl and 3-Ethyl-2-oxoimidazolidine-4-carboxylic acid | Purification method A. $^1$H NMR (400 MHz, DMSO-d6) δ: 9.80 (s, 1H), 8.55 (s, 1H), 8.20 (d, 1H), 7.56 (s, 1H), 7.18 (d, 1H), 6.90 (s, 1H), 6.39 (s, 1H), 4.65 (t, 2H), 4.49 (dd, 1H), 3.49 (t, 1H), 3.38-3.20 (m, 3H), 3.20-3.11 (m, 1H), 2.84 (dq, 1H), 0.98 (t, 3H). LCMS: m/z 437.2 $[M + H]^+$ |
| 168 | 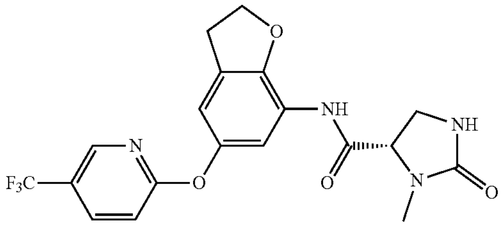 [SMILES: CN1C(=O)NC[C@H]1C(=O)Nc1cc(Oc2ccc(C(F)(F)F)cn2)cc2c1OCC2] Starting materials: (S)-3-Methyl-2-oxoimidazolidine-4-carboxylic acid and 5-((5-(Trifluoromethyl)pyridin-2-yl)oxy)-2,3-dihydrobenzofuran-7-amine | Purification method A. $^1$H NMR (600 MHz, DMSO-d6) δ: 9.75 (s, 1H), 8.53 (d, 1H), 8.18 (dd, 1H), 7.54 (d, 1H), 7.16 (d, 1H), 6.92-6.82 (m, 1H), 6.38 (s, 1H), 4.63 (t, 2H), 4.33 (dd, 1H), 3.49 (t, 1H), 3.23 (t, 2H), 3.17-3.08 (m, 1H), 2.59 (s, 4H). LCMS: m/z 423.0 $[M + H]^+$ |

-continued

| No. | Structure and starting material | Purification method and characterization data |
|---|---|---|
| 169 | 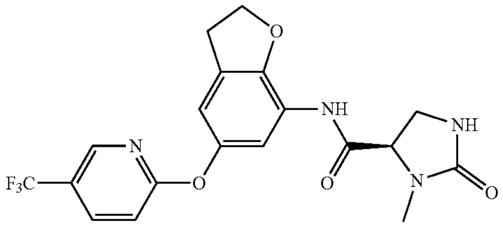 [SMILES: CN1C(=O)NC[C@@H]1C(=O)Nc1cc(Oc2ccc(C(F)(F)F)cn2)cc2c1OCC2] Starting materials: (R)-3-Methyl-2-oxoimidazolidine-4-carboxylic acid and 5-((5-(Trifluoromethyl)pyridin-2-yl)oxy)-2,3-dihydrobenzofuran-7-amine | Purification method A. $^{1}H$ NMR (600 MHz, DMSO-d6) δ: 9.75 (s, 1H), 8.53 (d, 1H), 8.18 (dd, 1H), 7.54 (d, 1H), 7.16 (d, 1H), 6.92-6.83 (m, 1H), 6.38 (s, 1H), 4.63 (t, 2H), 4.33 (dd, 1H), 3.49 (t, 1H), 3.23 (t, 3H), 3.13 (dd, 1H), 2.58 (s, 3H). LCMS: m/z 423.0 $[M + H]^+$ |
| 170 | 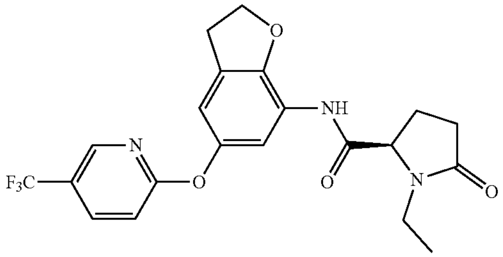 [SMILES: CCN1C(=O)CC[C@@H]1C(=O)Nc1cc(Oc2ccc(C(F)(F)F)cn2)cc2c1OCC2] Starting materials: 5-((5-(Trifluoro-methyl)pyridin-2-yl)oxy)-2,3-dihydrobenzofuran-7-amine and (R)-1-Ethyl-5-oxopyrrolidine-2-carboxylic acid | Purification method A. $^{1}H$ NMR (600 MHz, DMSO-d6) δ: 9.91 (s, 1H), 8.67-8.48 (m, 1H), 8.18 (dd, 1H), 7.55 (d, 1H), 7.15 (d, 1H), 6.88 (d, 1H), 4.64 (t, 1H), 4.53-4.39 (m, 1H), 3.45 (m, 1H), 3.23 (t, 2H), 2.78 (m, 1H), 2.33-2.05 (m, 3H), 1.97-1.75 (m, 1H), 0.98 (t, 3H). LCMS: m/z 436.2 $[M + H]^+$ |
| 171 | 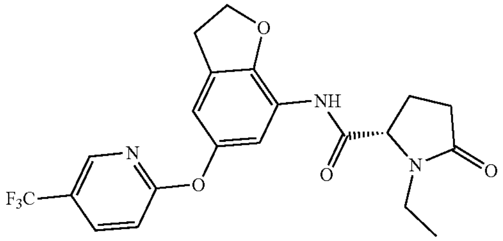 [SMILES: CCN1C(=O)CC[C@H]1C(=O)Nc1cc(Oc2ccc(C(F)(F)F)cn2)cc2c1OCC2] Starting materials: 5-((5-(Trifluoro-methyl)pyridin-2-yl)oxy)-2,3-dihydrobenzofuran-7-amine and 1-(S)-1-Ethyl-5-oxopyrrolidine-2-carboxylic acid | Purification method A. $^{1}H$ NMR (600 MHz, DMSO-d6) δ: 9.91 (s, 1H), 8.53 (t, 1H), 8.18 (dd, 1H), 7.55 (d, 1H), 7.15 (d, 1H), 6.88 (s, 1H), 4.64 (t, 2H), 4.51 (m, 1H), 3.46 (m, 1H), 3.23 (t, 2H), 2.78 (m, 1H), 2.32-2.05 (m, 3H), 1.86 (m, 1H), 0.98 (t, 3H). LCMS: m/z 436.2 $[M + H]^+$ |
| 172 | 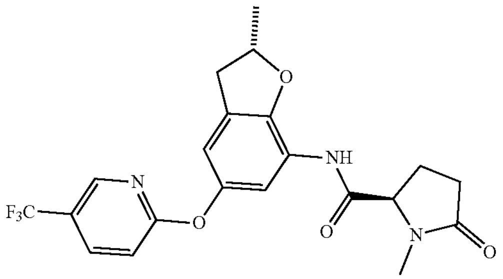 [SMILES: C[C@H]1Cc2cc(Oc3ccc(C(F)(F)F)cn3)cc(NC(=O)[C@H]3CCC(=O)N3C)c2O1] Starting materials: 2-Methyl-5-((5-(trifluoromethyl)pyridin-2-yl)oxy)-2,3-dihydrobenzofuran-7-amine and (R)-1-methyl-5-oxopyrrolidine-2-carboxylic acid | Purification method A followed by method I. Retention time 7.23 min. $^{1}H$ NMR (600 MHz, DMSO-d6) δ: 9.85 (s, 1H), 8.53 (s, 1H), 8.17 (d, 1H), 7.56 (s, 1H), 7.15 (d, 1H), 6.84 (s, 1H), 5.02 (q, 1H), 4.40 (d, 1H), 3.39-3.33 (m, 1H), 2.88-2.80 (m, 1H), 2.61 (s, 3H), 2.29-2.12 (m, 3H), 1.91-1.82 (m, 1H), 1.46 (d, 3H). LCMS: m/z 436.2 $[M + H]^+$ |

-continued

| No. | Structure and starting material | Purification method and characterization data |
|---|---|---|
| 173 | 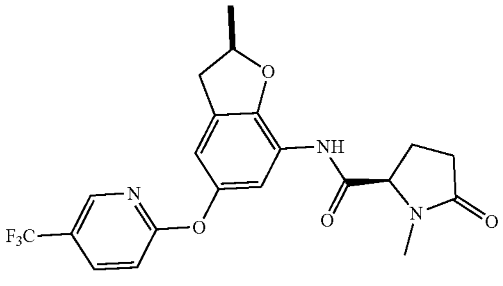 [SMILES: C[C@@H]1Cc2cc(Oc3ccc(C(F)(F)F)cn3)cc(NC(=O)[C@H]3CCC(=O)N3C)c2O1] Starting materials: 2-Methyl-5-((5-(trifluoromethyl)pyridin-2-yl)oxy)-2,3-dihydrobenzofuran-7-amine and (R)-1-Methyl-5-oxopyrrolidine-2-carboxylic acid | Purification method A followed by method I. Retention time 11.33 min. $^1$H NMR (600 MHz, DMSO-d6) δ: 9.84 (s, 1H), 8.53 (s, 1H), 8.17 (d, 1H), 7.56 (s, 1H), 7.15 (d, 1H), 6.83 (s, 1H), 5.02 (q, 1H), 4.40 (d, 1H), 3.39-3.33 (m, 1H), 2.85 (dd, 1H), 2.62 (s, 3H), 2.28-2.15 (m, 3H), 1.90-1.81 (m, 1H), 1.45 (d, 3H). LCMS: m/z 436.2 [M + H]$^+$ |
| 174 | 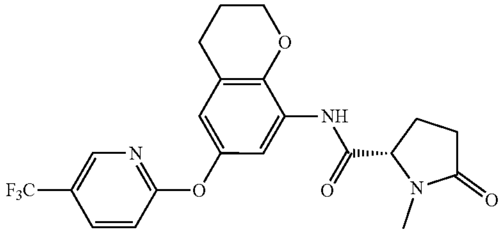 [SMILES: CN1C(=O)CC[C@H]1C(=O)Nc1cc(Oc2ccc(C(F)(F)F)cn2)cc2c1OCCC2] Starting materials: 6-((5-(Trifluoro-methyl)pyridin-2-yl)oxy)chroman-8-amine and (S)-1-Methyl-5-oxopyrrolidine-2-carboxylic acid | Purification method A. $^1$H NMR (400 MHz, Methanol-d4) δ: 8.42 (s, 1H), 8.07 (dd, 1H), 7.76 (d, 1H), 7.09 (d, 1H), 6.71 (d, 1H), 4.45 (dd, 1H), 4.32 (t, 2H), 2.85 (m, 5H), 2.55-2.34 (m, 3H), 2.13-2.00 (m, 3H). LCMS: m/z 436.0 [M + H]$^+$ |
| 175 | 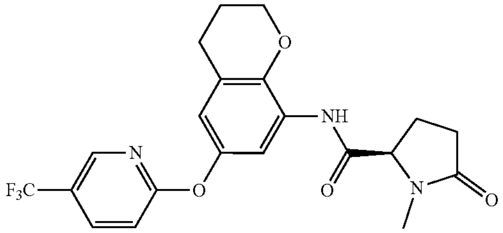 [SMILES: CN1C(=O)CC[C@@H]1C(=O)Nc1cc(Oc2ccc(C(F)(F)F)cn2)cc2c1OCCC2] Starting materials: 6-((5-(Trifluoro-methyl)pyridin-2-yl)oxy)chroman-8-amine and (R)-1-Methyl-5-oxopyrrolidine-2-carboxylic acid | Purification method A. $^1$H NMR (400 MHz, Methanol-d4) δ: 8.42 (s, 1H), 8.07 (dd, 1H), 7.76 (d, 1H), 7.09 (d, 1H), 6.71 (d, 1H), 4.45 (dd, 1H), 4.32 (t, 2H), 2.85 (m, 5H), 2.55-2.34 (m, 3H), 2.13-2.00 (m, 3H). LCMS: m/z 436.0 [M + H]$^+$ |
| 176 | 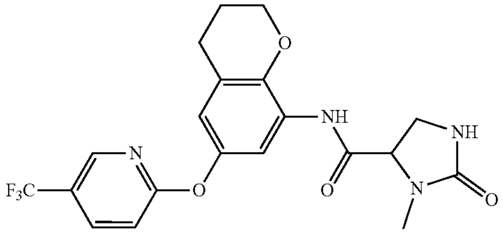 [SMILES: CN1C(=O)NCC1C(=O)Nc1cc(Oc2ccc(C(F)(F)F)cn2)cc2c1OCCC2] Starting materials: 6-((5-(Trifluoro-methyl)pyridin-2-yl)oxy)chroman-8-amine and 3-Methyl-2-oxoimidazolidine-4-carboxylic acid | Purification method A. $^1$H NMR (400 MHz, DMSO-d6) δ: 9.37 (s, 1H), 8.55 (s, 1H), 8.20 (dd, 1H), 7.72 (d, 1H), 7.18 (d, 1H), 6.72 (d, 1H), 6.46 (s, 1H), 4.37 (dd, 1H), 4.26 (t, 2H), 3.53 (t, 1H), 3.14 (t, 1H), 2.76 (t, 2H), 2.61 (s, 3H), 1.96 (t, 2H). LCMS: m/z 437.2 [M + H]$^+$ |

-continued

| No. | Structure and starting material | Purification method and characterization data |
|---|---|---|
| 177 | 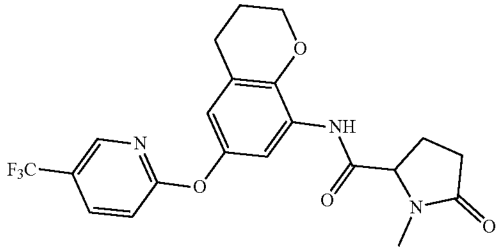 [SMILES: CN1C(=O)CCC1C(=O)Nc1cc(Oc2ccc(C(F)(F)F)cn2)cc2c1OCCC2]<br>Starting materials: 6-((5-(Trifluoro-methyl)pyridin-2-yl)oxy)chroman-8-amine and 1-Methyl-5-oxopyrrolidine-2-carboxylic acid | Purification method A.<br>$^1$H NMR (400 MHz, Methanol-d4) δ: 8.42 (s, 1H), 8.06 (dd, 1H), 7.76 (d, 1H), 7.08 (d, 1H), 6.71 (d, 1H), 4.45 (dd, 1H), 4.35-4.28 (m, 2H), 2.83 (m, 5H), 2.55-2.33 (m, 3H), 2.11-2.00 (m, 3H). LCMS: m/z 436.4 $[M + H]^+$ |
| 178 | 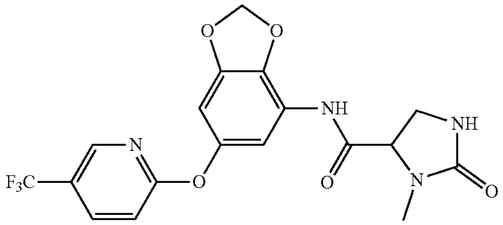<br>Starting materials: 6-((5-(Trifluoro-methyl)pyridin-2-yl)oxy)benzo[d]-[1,3]dioxol-4-amine and 3-Methyl-2-oxoimidazolidine-4-carboxylic acid | Purification method A.<br>$^1$H NMR (400 MHz, DMSO-d6) δ: 10.10 (s, 1H), 8.57 (d, 1H), 8.25-8.16 (m, 1H), 7.26-7.11 (m, 2H), 6.74 (d, 1H), 6.43 (s, 1H), 6.12 (s, 2H), 4.35-4.24 (m, 1H), 3.57-3.47 (m, 1H), 3.22-3.11 (m, 1H), 2.61 (s, 3H). LCMS: m/z 425.0 $[M + H]^+$ |
| 179 | 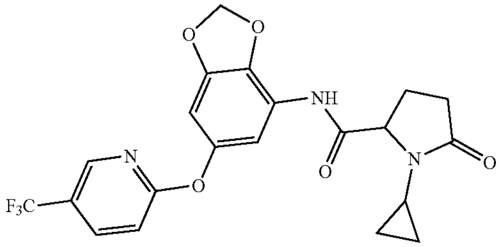 [SMILES: O=C(Nc1cc(Oc2ccc(C(F)(F)F)cn2)cc2c1OCO2)C1CCC(=O)N1C1CC1]<br>Starting materials: 6-((5-(Trifluoro-methyl)pyridin-2-yl)oxy)benzo[d]-[1,3]dioxol-4-amine and 1-Cyclo-propyl-5-oxopyrrolidine-2-carboxylic acid | Purification method A.<br>$^1$H NMR (400 MHz, DMSO-d6) δ: 10.17 (s, 1H), 8.57 (d, 1H), 8.27-8.14 (m, 1H), 7.27-7.14 (m, 2H), 6.74 (d, 1H), 6.14 (d, 2H), 4.47-4.17 (m, 1H), 2.46-2.36 (m, 1H), 2.35-2.23 (m, 1H), 2.23-2.12 (m, 2H), 1.93-1.82 (m, 1H), 0.77-0.67 (m, 1H), 0.66-0.58 (m, 1H), 0.57-0.46 (m, 2H). LCMS: m/z 450.2 $[M + H]^+$ |
| 180 | 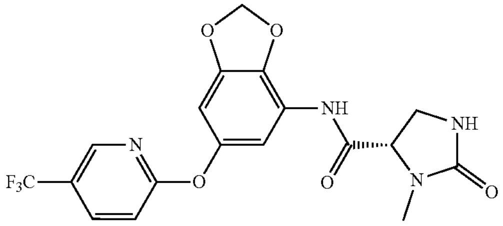 [SMILES: CN1C(=O)NC[C@H]1C(=O)Nc1cc(Oc2ccc(C(F)(F)F)cn2)cc2c1OCO2]<br>Starting materials: 6-((5-(Trifluoro-methyl)pyridin-2-yl)oxy)benzo[d]-[1,3]dioxol-4-amine and (S)-3-Methyl-2-oxoimidazolidine-4-carboxylic acid | Purification method A.<br>$^1$H NMR (400 MHz, DMSO-d6) δ: 10.06 (s, 1H), 8.64-8.53 (m, 1H), 8.25-8.08 (m, 1H), 7.28-7.11 (m, 2H), 6.74 (d, 1H), 6.41 (s, 1H), 6.12 (s, 2H), 4.47-4.14 (m, 1H), 3.69-3.47 (m, 1H), 3.21-3.11 (m, 1H), 2.61 (s, 3H). LCMS: m/z 425.0 $[M + H]^+$ |

-continued

| No. | Structure and starting material | Purification method and characterization data |
|---|---|---|
| 181 | 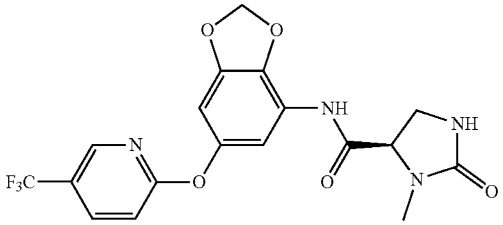 [SMILES: CN1C(=O)NC[C@@H]1C(=O)Nc1cc(Oc2ccc(C(F)(F)F)cn2)cc2c1OCO2] Starting materials: 6-((5-(Trifluoromethyl)pyridin-2-yl)oxy)benzo[d]-[1,3]dioxol-4-amine and (R)-3-Methyl-2-oxoimidazolidine-4-carboxylic acid | Purification method A. $^1$H NMR (400 MHz, DMSO-d6) δ: 10.08 (s, 1H), 8.57 (d, 1H), 8.29-8.10 (m, 1H), 7.28-7.07 (m, 2H), 6.74 (d, 1H), 6.42 (s, 1H), 6.12 (s, 2H), 4.35-4.21 (m, 1H), 3.51 (d, 1H), 3.16 (t, 1H), 2.61 (s, 3H). LCMS: m/z 425.5 $[M + H]^+$ |
| 182 | 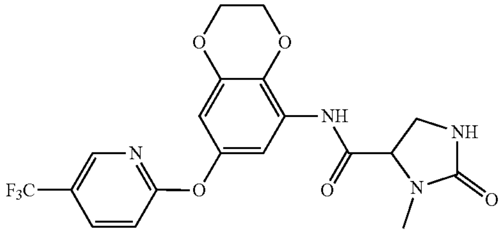 Starting materials: 7-((5-(Trifluoromethyl)pyridin-2-yl)oxy)-2,3-dihydrobenzo[b][1,4]dioxin-5-amine HCl and 3-Methyl-2-oxoimidazolidine-4-carboxylic acid | Purification method B. $^1$H NMR (400 MHz, DMSO-d6) δ: 9.53 (s, 1H), 8.56 (s, 1H), 8.21 (d, 1H), 7.45 (s, 1H), 7.18 (d, 1H), 6.58 (s, 1H), 6.46 (s, 1H), 4.43-4.26 (m, 5H), 3.59-3.45 (m, 1H), 3.20-3.08 (m, 1H), 2.61 (s, 3H). LCMS: m/z 439.0 $[M + H]^+$ |
| 183 | 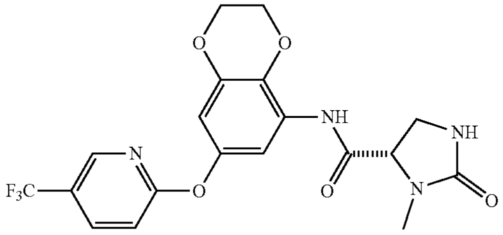 [SMILES: CN1C(=O)NCC1C(=O)Nc1cc(Oc2ccc(C(F)(F)F)cn2)cc2c1OCCO2] Starting materials: 7-((5-(Trifluoromethyl)pyridin-2-yl)oxy)-2,3-dihydrobenzo[b][1,4]dioxin-5-amine HCl and 3-Methyl-2-oxoimidazolidine-4-carboxylic acid | Purification method B followed by method H. Retention time 8.02 min. LCMS: m/z 439.0 $[M + H]^+$ |
| 184 | 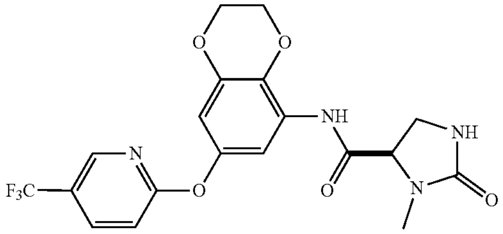 Starting materials: 7-((5-(Trifluoromethyl)pyridin-2-yl)oxy)-2,3-dihydrobenzo[b][1,4]dioxin-5-amine HCl and 3-Methyl-2-oxoimidazolidine-4-carboxylic acid | Purification method B followed by method H. Retention time 12.86 min. LCMS: m/z 439.0 $[M + H]^+$ |

-continued

| No. | Structure and starting material | Purification method and characterization data |
|---|---|---|
| 185 | 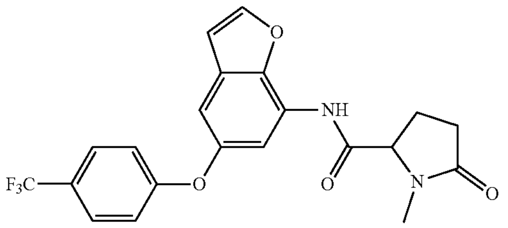<br>Starting materials: 5-(4-(Trifluoro-methyl)phenoxy)benzofuran-7-amine and 1-Methyl-5-oxopyrrolidine-2-carboxylic acid | Purification method A.<br>$^1H$ NMR (400 MHz, DMSO-d6) δ: 10.62 (s, 1H), 8.15 (d, 1H), 7.77-7.65 (m, 3H), 7.23 (d, 1H), 7.12 (d, 2H), 7.02 (d, 1H), 4.52-4.44 (m, 1H), 2.68 (s, 3H), 2.35-2.19 (m, 3H), 2.01-1.90 (m, 1H). LCMS: m/z 419.2 $[M + H]^+$ |
| 186 | 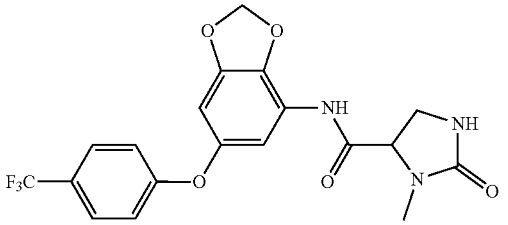 [SMILES: CN1C(=O)NCC1C(=O)Nc1cc(Oc2ccc(C(F)(F)F)cc2)cc2c1OCO2]<br>Starting materials: 6-(4-(Trifluoro-methyl)phenoxy)benzo[d][1,3]-dioxol-4-amine and 3-Methyl-2-oxo-imidazolidine-4-carboxylic acid | Purification method A.<br>$^1H$ NMR (400 MHz, DMSO-d6) δ: 10.10 (s, 1H), 7.71 (d, 2H), 7.15 (s, 1H), 7.11 (d, 2H), 6.71 (d, 1H), 6.42 (s, 1H), 6.13 (s, 2H), 4.36-4.20 (m, 1H), 3.51 (t, 1H), 3.16 (t, 1H), 2.60 (s, 3H). LCMS: LCMS: m/z 424.0 $[M + H]^+$ |
| Int-285 | 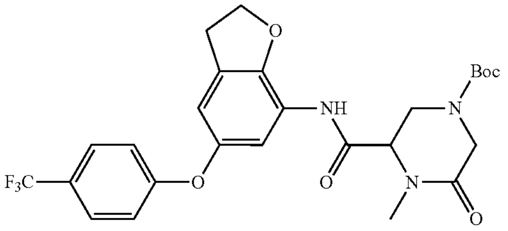 [SMILES: CN1C(=O)CN(C(=O)OC(C)(C)C)CC1C(=O)Nc1cc(Oc2ccc(C(F)(F)F)cc2)cc2c1OCC2]<br>(intermediate)<br>Starting materials: 5-(4-(Trifluoro-methyl)phenoxy)-2,3-dihydrobenzo-furan-7-amine HCl and Lithium 4-(tert-butoxycarbonyl)-1-methyl-6-oxopiperazine-2-carboxylate | LCMS: m/z 534.2 $[M - H]^-$ |
| 187 | 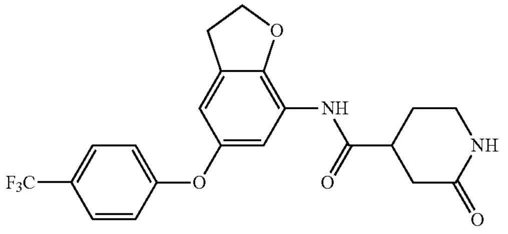 [SMILES: O=C1CC(C(=O)Nc2cc(Oc3ccc(C(F)(F)F)cc3)cc3c2OCC3)CCN1]<br>Starting materials: 5-(4-(Trifluoro-methyl)phenoxy)-2,3-dihydrobenzo-furan-7-amine HCl and 2-Oxopiperidine-4-carboxylic acid | Purification method A.<br>$^1H$ NMR (400 MHz, DMSO-d6) δ: 9.65 (s, 1H), 7.69 (d, 2H), 7.57 (s, 1H), 7.48 (s, 1H), 7.06 (d, 2H), 6.84 (s, 1H), 4.64 (t, 2H), 3.24 (t, 2H), 3.16-2.92 (m, 3H), 2.25 (d, 2H), 2.03-1.80 (m, 1H), 1.74-1.55 (m, 1H). LCMS: m/z 421.2 $[M + H]^+$ |

-continued

| No. | Structure and starting material | Purification method and characterization data |
|---|---|---|
| 188 | 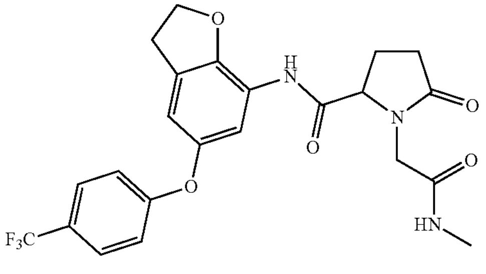 [SMILES: CNC(=O)CN1C(=O)CCC1C(=O)Nc1cc(Oc2ccc(C(F)(F)F)cc2)cc2c1OCC2] Starting materials: 5-(4-(Trifluoromethyl)phenoxy)-2,3-dihydrobenzofuran-7-amine HCl and 1-(2-(Methylamino)-2-oxoethyl)-5-oxopyrrolidine-2-carboxylic acid | Purification method A. $^1$H NMR (400 MHz, DMSO-d6) δ: 9.99 (s, 1H), 7.94-7.81 (m, 1H), 7.70 (d, 2H), 7.52 (s, 1H), 7.07 (d, 2H), 6.87 (s, 1H), 4.64 (t, 2H), 4.59-4.51 (m, 1H), 4.15 (d, 1H), 3.28-3.20 (m, 3H), 2.57 (d, 3H), 2.36-2.22 (m, 3H), 1.95-1.83 (m, 1H). LCMS: m/z 478.0 $[M + H]^+$ |
| 189 | 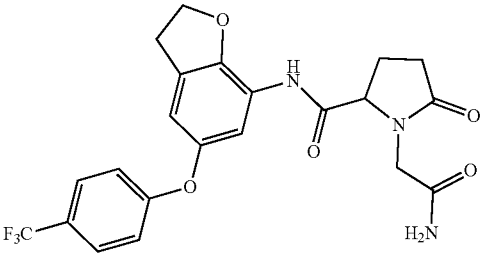 [SMILES: NC(=O)CN1C(=O)CCC1C(=O)Nc1cc(Oc2ccc(C(F)(F)F)cc2)cc2c1OCC2] Starting materials: 5-(4-(Trifluoromethyl)phenoxy)-2,3-dihydrobenzofuran-7-amine HCl and 1-(2-Amino-2-oxoethyl)-5-oxopyrrolidine-2-carboxylic acid | Purification method A. $^1$H NMR (600 MHz, DMSO-d6) δ: 9.99 (s, 1H), 7.68 (d, 2H), 7.50 (s, 1H), 7.40 (s, 1H), 7.12-7.02 (m, 3H), 6.85 (s, 1H), 4.62 (t, 2H), 4.58-4.51 (m, 1H), 4.12 (d, 1H), 3.27-3.15 (m, 3H), 2.34-2.17 (m, 3H), 1.93-1.80 (m, 1H). LCMS: m/z 464.0 $[M + H]^+$ |
| 190 | 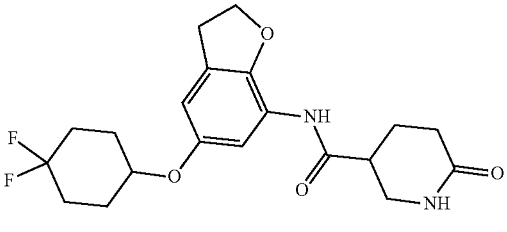 [SMILES: O=C1CCC(C(=O)Nc2cc(OC3CCC(F)(F)CC3)cc3c2OCC3)CN1] Starting materials: 5-((4,4-Difluorocyclohexyl)oxy)-2,3-dihydrobenzofuran-7-amine HCl and 6-Oxopiperidine-3-carboxylic acid | Purification method A. $^1$H NMR (400 MHz, DMSO-d6) δ: 9.52 (s, 1H), 7.47 (s, 1H), 7.36 (s, 1H), 6.70 (s, 1H), 4.54 (t, 2H), 4.36 (s, 1H), 3.25 (s, 2H), 3.17 (t, 2H), 2.91 (m, 1H), 2.27-1.62 (m, 12H). LCMS: m/z 395.2 $[M + H]^+$ |
| 191 | 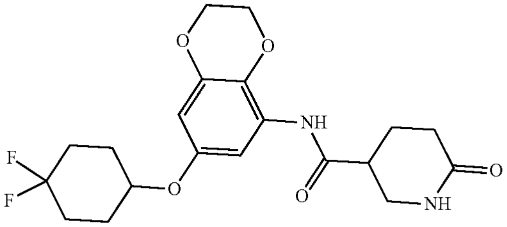 [SMILES: O=C1CCC(C(=O)Nc2cc(OC3CCC(F)(F)CC3)cc3c2OCCO3)CN1] Starting materials: 7-((4,4-Difluorocyclohexyl)oxy)-2,3-dihydrobenzo[b][1,4]dioxin-5-amine HCl and 6-Oxopiperidine-3-carboxylic acid | Purification method A. $^1$H NMR (400 MHz, DMSO-d6) δ: 9.30 (s, 1H), 7.48 (s, 1H), 7.23 (s, 1H), 6.33 (s, 1H), 4.39 (s, 1H), 4.24 (s, 4H), 3.28-3.17 (m, 2H), 2.95 (m, 1H), 2.20 (m, 2H), 2.08-1.67 (m, 8H). LCMS: m/z 411.2 $[M + H]^+$ |

-continued

| No. | Structure and starting material | Purification method and characterization data |
|---|---|---|
| 192 | 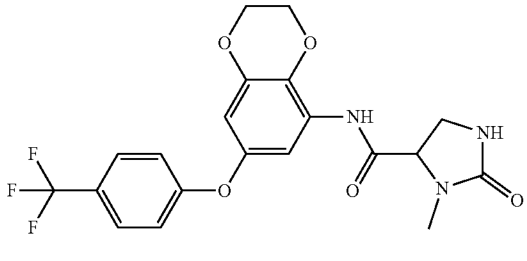 [SMILES: CN1C(=O)NCC1C(=O)Nc1cc(Oc2ccc(C(F)(F)F)cc2)cc2c1OCCO2] Starting materials: 7-(4-(Trifluoro-methyl)phenoxy)-2,3-dihydrobenzo-[b][1,4]dioxin-5-amine HCl and 3-Methyl-2-oxoimidazolidine-4-carboxylic acid | Purification method A. $^{1}H$ NMR (400 MHz, DMSO-d6) δ: 9.57 (s, 1H), 7.71 (d, 2H), 7.43 (s, 1H), 7.09 (d, 2H), 6.53 (s, 1H), 6.46 (s, 1H), 4.43-4.26 (m, 5H), 3.57-3.48 (m, 1H), 3.19-3.09 (m, 1H), 2.60 (s, 3H). LCMS: m/z 438.0 $[M + H]^+$ |
| 193 | 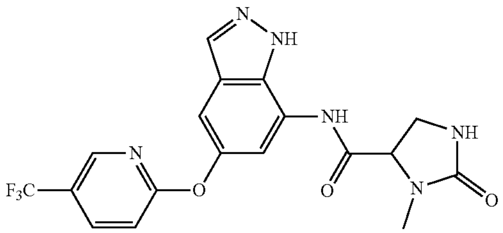 [SMILES: CN1C(=O)NCC1C(=O)Nc1cc(Oc2ccc(C(F)(F)F)cn2)cc2cn[nH]c12] Starting materials: 5-((5-(Trifluoro-methyl)pyridin-2-yl)oxy)-1H-indazol-7-amine and 3-Methyl-2-oxo-imidazolidine-4-carboxylic acid | Purification method A. $^{1}H$ NMR (400 MHz, Methanol-d4) δ: 8.43 (s, 1H), 8.15-8.07 (m, 2H), 7.46 (s, 1H), 7.41 (s, 1H), 7.17 (d, 1H), 4.47-4.37 (m, 1H), 3.80 (t, 1H), 3.56 (t, 1H), 2.87 (s, 3H). LCMS: m/z 421.0 $[M + H]^+$ |
| 194 | 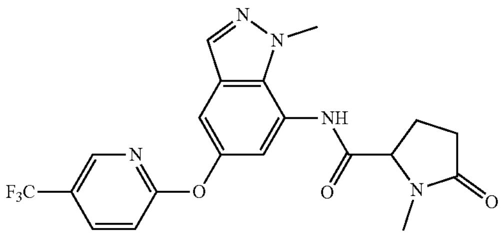 [SMILES: CN1C(=O)CCC1C(=O)Nc1cc(Oc2ccc(C(F)(F)F)cn2)cc2cnn(C)c12] Starting materials: 1-Methyl-5-((5-(trifluoromethyl)pyridin-2-yl)oxy)-1H-indazol-7-amine and 1-Methyl-5-oxopyrrolidine-2-carboxylic acid | Purification method A. $^{1}H$ NMR (400 MHz, Methanol-$d_4$) δ: 8.43 (s, 1H), 8.22 (s, 1H), 8.14-8.06 (m, 1H), 7.90 (d, 1H), 7.25 (d, 1H), 7.14 (d, 1H), 4.56-4.47 (m, 1H), 4.27 (s, 3H), 2.86 (s, 3H), 2.63-2.35 (m, 3H), 2.26-2.05 (m, 2H). LCMS: m/z 434.0 $[M + H]^+$ |
| 195 | 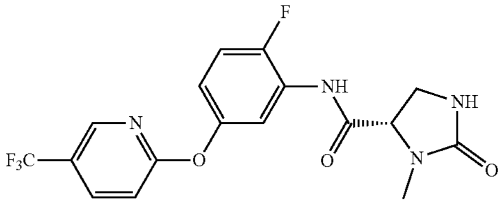 [SMILES: CN1C(=O)NC[C@H]1C(=O)Nc1cc(Oc2ccc(C(F)(F)F)cn2)ccc1F] Starting materials: 2-Fluoro-5-((5-(trifluoromethyl)pyridin-2-yl)oxy)-aniline and (S)-3-Methyl-2-oxoimi-dazolidine-4-carboxylic acid | Purification method A. $^{1}H$ NMR (600 MHz, DMSO-d6) δ: 10.10 (s, 1H), 8.55 (s, 1H), 8.22 (dd, 1H), 7.84-7.75 (m, 1H), 7.39-7.31 (m, 1H), 7.25 (d, 1H), 7.09-6.96 (m, 1H), 6.42 (s, 1H), 4.34 (dd, 1H), 3.53 (t, 1H), 3.18 (t, 1H), 2.61 (s, 3H). LCMS: m/z 399.0 $[M + H]^+$ |

-continued

| No. | Structure and starting material | Purification method and characterization data |
|---|---|---|
| 196 | 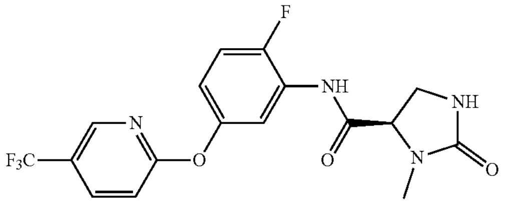 [SMILES: CN1C(=O)NC[C@@H]1C(=O)Nc1cc(Oc2ccc(C(F)(F)F)cn2)ccc1F] Starting materials: 2-Fluoro-5-((5-(trifluoromethyl)pyridin-2-yl)oxy)-aniline and (R)-3-Methyl-2-oxoimi-dazolidine-4-carboxylic acid | Purification method A. $^1H$ NMR (600 MHz, DMSO-d6) δ: 10.10 (s, 1H), 8.55 (s, 1H), 8.22 (dd, 1H), 7.84-7.72 (m, 1H), 7.43-7.31 (m, 1H), 7.25 (d, 1H), 7.08-6.98 (m, 1H), 6.42 (s, 1H), 4.34 (dd, 1H), 3.53 (t, 1H), 3.18 (t, 1H), 2.65 − 2.56 (m, 3H). LCMS: m/z 399.1 $[M + H]^+$ |
| 197 | 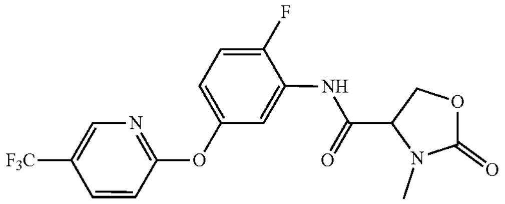 [SMILES: CN1C(=O)OCC1C(=O)Nc1cc(Oc2ccc(C(F)(F)F)cn2)ccc1F] Starting materials: 2-Fluoro-5-((5-(trifluoromethyl)pyridin-2-yl)oxy)-aniline HCl and 3-Methyl-2-oxooxa-zolidine-4-carboxylic acid | Purification method A. $^1H$ NMR (400 MHz, DMSO-d6) δ: 10.32 (s, 1H), 8.56 (s, 1H), 8.28-8.21 (m, 1H), 7.92-7.85 (m, 1H), 7.38 (t, 1H), 7.27 (d, 1H), 7.05 (m, 1H), 4.63 (dd, 1H), 4.45 (t, 1H), 4.23 (dd, 1H), 2.75 (s, 3H). LCMS: m/z 400.0 $[M + H]^+$ |
| 198 | 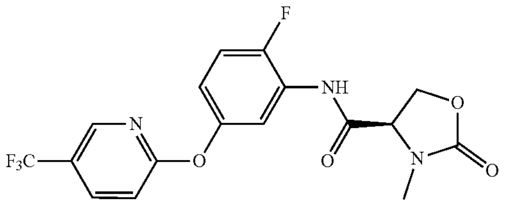 [SMILES: CN1C(=O)OC[C@@H]1C(=O)Nc1cc(Oc2ccc(C(F)(F)F)cn2)ccc1F] Starting materials: 2-Fluoro-5-((5-(trifluoromethyl)pyridin-2-yl)oxy)-aniline HCl and (R)-3-methyl-2-oxooxazolidine-4-carboxylic acid | Purification method A. $^1H$ NMR (400 MHz, DMSO-d6) δ: 10.32 (s, 1H), 8.56 (s, 1H), 8.25 (d, 1H), 7.93-7.81 (m, 1H), 7.43-7.32 (m, 1H), 7.27 (d, 1H), 7.11-6.99 (m, 1H), 4.63 (dd, 1H), 4.45 (t, 1H), 4.23 (dd, 1H), 2.75 (s, 3H). LCMS: m/z 400.0 $[M + H]^+$ |
| 199 | 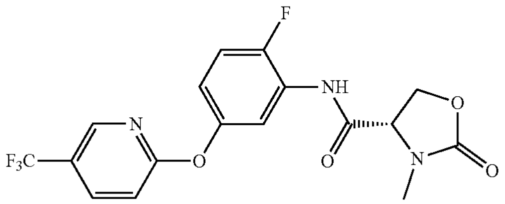 [SMILES: CN1C(=O)OC[C@H]1C(=O)Nc1cc(Oc2ccc(C(F)(F)F)cn2)ccc1F] Starting materials: 2-Fluoro-5-((5-(trifluoromethyl)pyridin-2-yl)oxy)-aniline HCl and (S)-3-Methyl-2-oxooxazolidine-4-carboxylic acid | Purification method A. $^1H$ NMR (400 MHz, DMSO-d6) δ: 10.32 (s, 1H), 8.56 (s, 1H), 8.28-8.21 (m, 1H), 7.92-7.85 (m, 1H), 7.38 (t, 1H), 7.27 (d, 1H), 7.05 (m, 1H), 4.63 (dd, 1H), 4.45 (t, 1H), 4.23 (dd, 1H), 2.75 (s, 3H). LCMS: m/z 400.0 $[M + H]^+$ |

-continued

| No. | Structure and starting material | Purification method and characterization data |
|---|---|---|
| 200 | 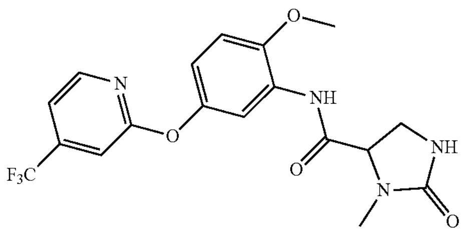 [SMILES: COc1ccc(Oc2cc(C(F)(F)F)ccn2)cc1NC(=O)C1CNC(=O)N1C] Starting materials: 2-Methoxy-5-((4-(trifluoromethyl)pyridin-2-yl)-oxy)aniline and 3-methyl-2-oxo-imidazolidine-4-carboxylic acid | Purification method B. $^1$H NMR (400 MHz, DMSO-d6) δ: 9.47 (s, 1H), 8.38 (d, 1H), 7.89 (d, 1H), 7.46 (d, 1H), 7.41 (s, 1H), 7.12 (d, 1H), 6.95 (dd, 1H), 6.46 (s, 1H), 4.38 (dd, 1H), 3.88 (s, 3H), 3.54 (t, 1H), 3.16 (t, 1H), 2.62 (s, 3H). LCMS: m/z 411.0 $[M + H]^+$ |
| 201 | 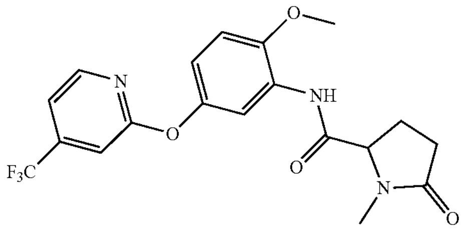 [SMILES: COc1ccc(Oc2cc(C(F)(F)F)ccn2)cc1NC(=O)C1CCC(=O)N1C] Starting materials: 2-Methoxy-5-((4-(trifluoromethyl)pyridin-2-yl)-oxy)aniline and 1-Methyl-5-oxo-pyrrolidine-2-carboxylic acid | Purification method A. $^1$H NMR (400 MHz, DMSO-d6) δ: 9.62 (s, 1H), 8.38 (d, 1H), 7.87 (d, 1H), 7.46 (d, 1H), 7.41 (s, 1H), 7.11 (d, 1H), 6.95 (dd, 1H), 4.46 (d, 1H), 3.88 (s, 3H), 2.65 (s, 3H), 2.30-2.15 (m, 3H), 1.92-1.85 (m, 1H). LCMS: m/z 410.0 $[M + H]^+$ |
| 202 | 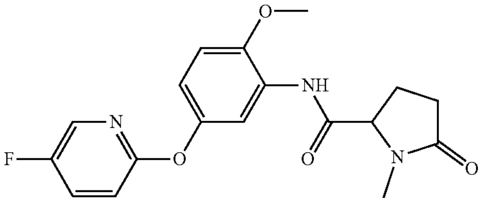 [SMILES: COc1ccc(Oc2ccc(F)cn2)cc1NC(=O)C1CCC(=O)N1C] Starting materials: 5-((5-Fluoro-pyridin-2-yl)oxy)-2-methoxyaniline and 1-Methyl-5-oxopyrrolidine-2-carboxylic acid | Purification method A. $^1$H NMR (400 MHz, DMSO-d6) δ: 9.59 (s, 1H), 8.12 (d, 1H), 7.87-7.77 (m, 2H), 7.11-7.03 (m, 2H), 6.88 (dd, 1H), 4.51-4.42 (m, 1H), 3.87 (s, 3H), 2.64 (s, 3H), 2.31-2.13 (m, 3H), 1.96-1.83 (m, 1H). LCMS: m/z 358.0 $[M - H]^-$ |
| 203 | 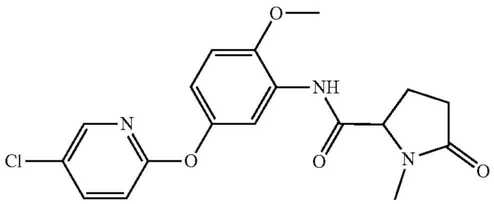 [SMILES: COc1ccc(Oc2ccc(Cl)cn2)cc1NC(=O)C1CCC(=O)N1C] Starting materials: 5-((5-Chloro-pyridin-2-yl)oxy)-2-methoxyaniline and 1-Methyl-5-oxopyrrolidine-2-carboxylic acid | Purification method A. $^1$H NMR (400 MHz, DMSO-d6) δ: 9.61 (s, 1H), 8.17 (d, 1H), 7.93 (dd, 1H), 7.84 (dd, 1H), 7.07 (dd, 2H), 6.90 (dd, 1H), 4.54-4.38 (m, 1H), 3.87 (s, 3H), 2.64 (s, 3H), 2.36-2.11 (m, 3H), 1.99-1.78 (m, 1H). LCMS: m/z 376.0 $[M + H]^+$ |

-continued

| No. | Structure and starting material | Purification method and characterization data |
|---|---|---|
| 204 | 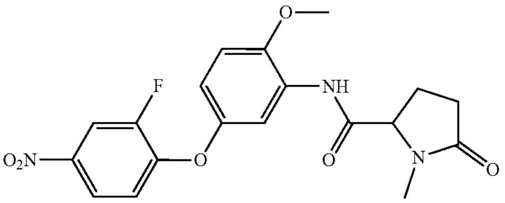 [SMILES: COc1ccc(Oc2ccc([N+](=O)[O-])cc2F)cc1NC(=O)C1CCC(=O)N1C] Starting materials: 5-(2-Fluoro-4-nitrophenoxy)-2-methoxyaniline and 1-Methyl-5-oxopyrrolidine-2-carboxylic acid | Purification method A. LCMS: m/z 404.0 $[M + H]^+$ |
| 205 | 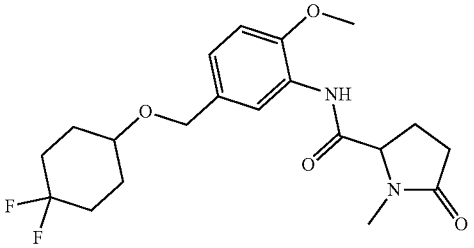 [SMILES: COc1ccc(COC2CCC(F)(F)CC2)cc1NC(=O)C1CCC(=O)N1C] Starting materials: 5-(((4,4-Difluoro-cyclohexyl)oxy)methyl)-2-methoxyaniline HCl and 1-Methyl-5-oxopyrrolidine-2-carboxylic acid | Purification method F. $^1H$ NMR (600 MHz, DMSO-d6) δ: 9.45 (s, 1H), 7.91 (s, 1H), 7.06 (d, 1H), 7.01 (d, 1H), 4.43-4.40 (m, 1H), 4.39 (s, 2H), 3.82 (s, 3H), 3.56 (m, 1H), 2.65 (s, 3H), 2.31-2.15 (m, 3H), 2.01-1.64 (m, 9H). LCMS: m/z 397.2 $[M + H]^+$ |
| 206 | 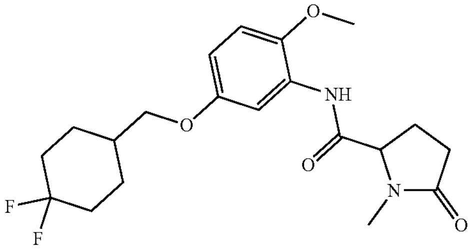 [SMILES: COc1ccc(OCC2CCC(F)(F)CC2)cc1NC(=O)C1CCC(=O)N1C] Starting materials: 5-((4,4-Difluoro-cyclohexyl)methoxy)-2-methoxy-aniline HCl and 1-Methyl-5-oxo-pyrrolidine-2-carboxylic acid | Purification method A. $^1H$ NMR (400 MHz, DMSO-d6) δ: 9.46 (s, 1H), 7.68 (d, 1H), 6.96 (d, 1H), 6.67 (dd, 1H), 4.49-4.40 (m, 1H), 3.79 (s, 4H), 3.76 (d, 4H), 2.66 (s, 3H), 2.34-2.15 (m, 3H), 2.09-1.98 (m, 2H), 1.94-1.73 (m, 6H), 1.31 (q, 2H). LCMS: m/z 397.2 $[M + H]^+$ |
| 207 | 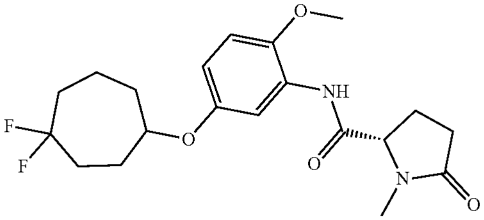 [SMILES: COc1ccc(OC2CCCC(F)(F)CC2)cc1NC(=O)[C@@H]1CCC(=O)N1C] Starting materials: 5-((4,4-Di-fluorocycloheptyl)oxy)-2-methoxy-aniline and (S)-1-Methyl-5-oxo-pyrrolidine-2-carboxylic acid | Purification method A. $^1H$ NMR (400 MHz, Acetonitrile-$d_3$) δ: 8.35 (s, 1H), 7.93 (d, 1H), 6.95 (d, 1H), 6.68 (dd, 1H), 4.56-4.41 (m, 1H), 4.31-4.19 (m, 1H), 3.87 (s, 3H), 2.79 (s, 3H), 2.46-2.03 (m, 11H), 1.92-1.72 (m, 2H), 1.61-1.49 (m, 1H). LCMS: m/z 397.2 $[M + H]^+$ |

-continued

| No. | Structure and starting material | Purification method and characterization data |
| --- | --- | --- |
| 208 | 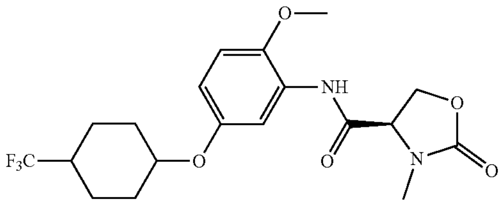 [SMILES: COc1ccc(OC2CCC(C(F)(F)F)CC2)cc1NC(=O)[C@H]1COC(=O)N1C] Starting materials: 2-Methoxy-5-((4-(trifluoromethyl)cyclohexyl)oxy)-aniline and Lithium (R)-3-methyl-2-oxooxazolidine-4-carboxylate | Purification method A. $^1$H NMR (400 MHz, DMSO-d6) δ: 9.54 (s, 1H), 7.69 (d, 1H), 7.03-6.92 (m, 1H), 6.73 (dd, 1H), 4.69-4.61 (m, 1H), 4.50-4.09 (m, 3H), 3.80 (s, 3H), 2.76 (s, 3H), 2.15-2.04 (m, 1H), 2.04-1.87 (m, 2H), 1.73-1.53 (m, 3H), 1.41 (q, 2H). LCMS: m/z 417.2 [M + H]$^+$ |
| 209 | 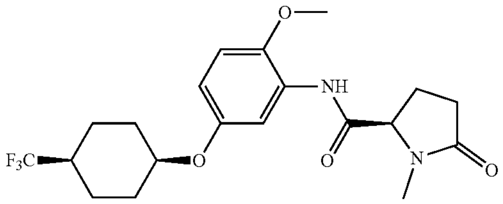 [SMILES: COc1ccc(O[C@H]2CC[C@@H](C(F)(F)F)CC2)cc1NC(=O)[C@H]1CCC(=O)N1C] Starting materials: 2-Methoxy-5-(((cis)-4-(trifluoromethyl)cyclo-hexyl)oxy)aniline and (R)-1-Methyl-5-oxopyrrolidine-2-carboxylic acid | Purification method A. $^1$H NMR (400 MHz, DMSO-d6) δ: 9.46 (s, 1H), 7.76-7.63 (m, 1H), 6.96 (d, 1H), 6.71 (dd, 1H), 4.52-4.39 (m, 2H), 3.80 (s, 3H), 2.66 (s, 3H), 2.42-2.15 (m, 4H), 2.01-1.94 (m, 2H), 1.94-1.86 (m, 1H), 1.72-1.51 (m, 6H). LCMS: m/z 415.0 [M + H]$^+$ |
| 210 | 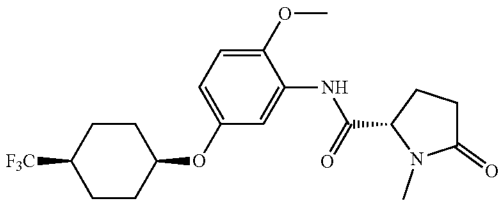 [SMILES: COc1ccc(O[C@H]2CC[C@@H](C(F)(F)F)CC2)cc1NC(=O)[C@@H]1CCC(=O)N1C] Starting materials: 2-Methoxy-5-(((cis)-4-(trifluoromethyl)cyclo-hexyl)oxy)aniline and (S)-1-Methyl-5-oxopyrrolidine-2-carboxylic acid | Purification method A. $^1$H NMR (400 MHz, DMSO-d6) δ: 9.43 (s, 1H), 7.69 (d, 1H), 6.96 (d, 1H), 6.71 (dd, 1H), 4.48 (s, 1H), 4.44 (q, 1H), 3.80 (s, 3H), 2.67 (s, 3H), 2.44-2.14 (m, 4H), 2.02-1.84 (m, 3H), 1.72-1.51 (m, 6H). LCMS: m/z 413.1 [M − H]$^-$ |
| 211 | 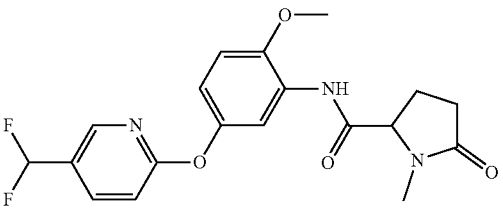 Starting materials: 5-((5-(Difluoro-methyl)pyridin-2-yl)oxy)-2-methoxyaniline and 1-Methyl-5-oxopyrrolidine-2-carboxylic acid | Purification method A. $^1$H NMR (400 MHz, DMSO-d6) δ: 9.63 (s, 1H), 8.34 (s, 1H), 8.04 (d, 1H), 7.87 (s, 1H), 7.27-6.88 (m, 4H), 4.56-4.40 (m, 1H), 3.88 (s, 3H), 2.65 (s, 3H), 2.37-2.11 (m, 3H), 1.98-1.77 (m, 1H). LCMS: m/z 392.0 [M + H]$^+$ |

-continued

| No. | Structure and starting material | Purification method and characterization data |
|---|---|---|
| 212 | 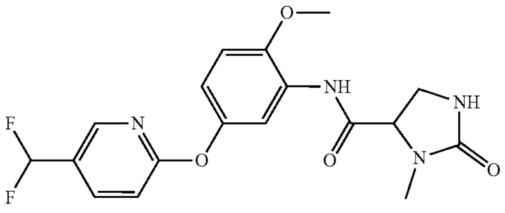 Starting materials: 5-((5-(Difluoro-methyl)pyridin-2-yl)oxy)-2-methoxyaniline and 1-Methyl-5-oxopyrrolidine-2-carboxylic acid | Purification method A. $^1$H NMR (400 MHz, DMSO-d6) δ: 9.48 (s, 1H), 8.35 (s, 1H), 8.10-7.99 (m, 1H), 7.88 (s, 1H), 7.26-6.89 (m, 4H), 6.47 (s, 1H), 4.45-4.32 (m, 1H), 3.88 (s, 3H), 3.53 (t, 1H), 3.23-3.11 (m, 1H), 2.62 (s, 3H). LCMS: m/z 393.1 $[M + H]^+$ |
| 213 | 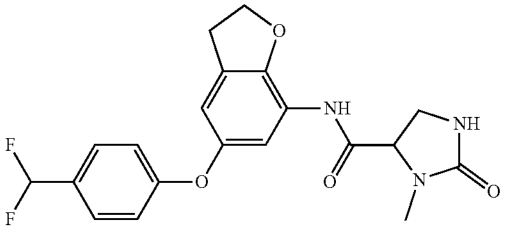 [SMILES: CN1C(=O)NCC1C(=O)Nc1cc(Oc2ccc(C(F)F)cc2)cc2c1OCC2] Starting materials: 5-(4-(Difluoro-methyl)phenoxy)-2,3-dihydrobenzo-furan-7-amine HCl and 3-Methyl-2-oxoimidazolidine-4-carboxylic acid | Purification method A. $^1$H NMR (400 MHz, DMSO-d6) δ: 9.77 (s, 1H), 7.54 (m, 3H), 7.18-6.77 (m, 4H), 6.40 (s, 1H), 4.64 (t, 2H), 4.44-4.25 (m, 1H), 3.62-3.39 (m, 1H), 3.24 (t, 2H), 3.14 (t, 1H), 2.59 (s, 3H). LCMS: m/z 402.2 $[M - H]^-$ |
| 214 | 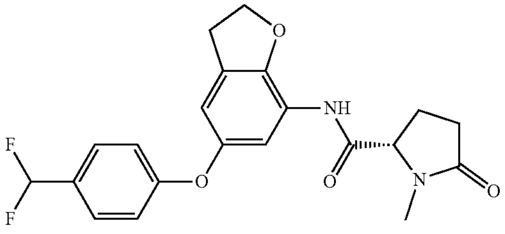 [SMILES: CN1C(=O)CC[C@H]1C(=O)Nc1cc(Oc2ccc(C(F)F)cc2)cc2c1OCC2] Starting materials: 5-(4-(Difluoro-methyl)phenoxy)-2,3-dihydrobenzo-furan-7-amine HCl and (S)-1-Methyl-5-oxopyrrolidine-2-carboxylic acid | Purification method A. $^1$H NMR (400 MHz, Acetonitrile-d3) δ: 8.14 (s, 1H), 7.65 (d, 1H), 7.55 (d, 2H), 7.06 (d, 2H), 6.9 -6.55 (m, 2H), 4.68 (t, 2H), 4.24 (dd, 1H), 3.29 (t, 2H), 2.76 (s, 3H), 2.4 -2.21 (m, 4H). LCMS: m/z 401.2 $[M - H]^-$ |
| 215 | 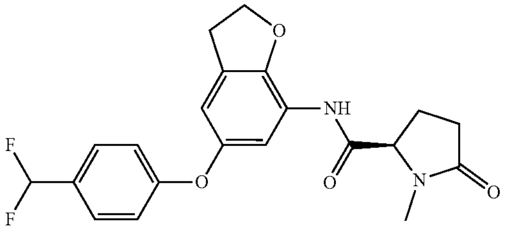 [SMILES: CN1C(=O)CC[C@@H]1C(=O)Nc1cc(Oc2ccc(C(F)F)cc2)cc2c1OCC2] Starting materials: 5-(4-(Difluoro-methyl)phenoxy)-2,3-dihydrobenzo-furan-7-amine HCl and (R)-1-Methyl-5-oxopyrrolidine-2-carboxylic acid | Purification method A. $^1$H NMR (400 MHz, DMSO-d6) δ: 9.91 (s, 1H), 7.54 (m, 3H), 7.23-6.73 (m, 4H), 4.64 (t, 2H), 4.49-4.30 (m, 1H), 3.28-3.18 (m, 3H), 2.63 (s, 3H), 2.35-2.17 (m, 4H). LCMS: m/z 403.0 $[M + H]^+$ |

-continued

| No. | Structure and starting material | Purification method and characterization data |
|---|---|---|
| 216 | 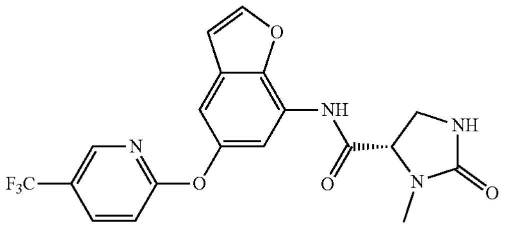 [SMILES: CN1C(=O)NC[C@H]1C(=O)Nc1cc(Oc2ccc(C(F)(F)F)cn2)cc2ccoc12] Starting materials: 5-((5-(Trifluoro-methyl)pyridin-2-yl)oxy)benzofuran-7-amine and (S)-3-Methyl-2-oxo-imidazolidine-4-carboxylic acid | Purification method A. $^1$H NMR (400 MHz, DMSO-d6) δ: 10.49 (s, 1H), 8.55 (s, 1H), 8.23 (dd, 1H), 8.14 (d, 1H), 7.70 (dd,1H), 7.29 (d, 1H), 7.24 (d, 1H), 7.02 (d, 1H), 6.45 (s, 1H), 4.43 (dd, 1H), 3.57 (t, 1H), 3.23 (t, 1H), 2.65 (s, 3H). LCMS: m/z 421.2 [M + H]$^+$ |
| 217 | 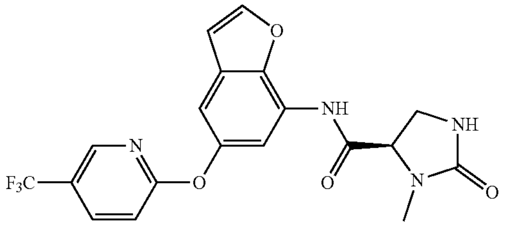 [SMILES: CN1C(=O)NC[C@@H]1C(=O)Nc1cc(Oc2ccc(C(F)(F)F)cn2)cc2ccoc12] Starting materials: 5-((5-(Trifluoro-methyl)pyridin-2-yl)oxy)benzofuran-7-amine and (R)-3-Methyl-2-oxo-imidazolidine-4-carboxylic acid | Purification method A. $^1$H NMR (400 MHz, DMSO-d6) δ: 10.49 (s, 1H), 8.55 (s, 1H), 8.23 (dd, 1H), 8.14 (s, 1H), 7.70 (d, 1H), 7.29 (d, 1H), 7.25 (d, 1H), 7.02 (d, 1H), 6.45 (s, 1H), 5.76 (s, 1H), 4.44 (t, 1H), 3.57 (t, 1H), 3.23 (t, 1H), 2.65 (s, 3H). LCMS: m/z 421.0 [M + H]$^+$ |
| 218 | 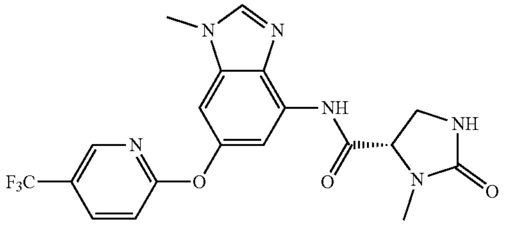 [SMILES: CN1C(=O)NC[C@H]1C(=O)Nc1cc(Oc2ccc(C(F)(F)F)cn2)cc2c1ncn2C] Starting materials: 1-Methyl-6-((5-(trifluoromethyl)pyridin-2-yl)oxy)-1H-benzo[d]imidazol-4-amine and (S)-3-Methyl-2-oxoimidazolidine-4-carboxylic acid | Purification method A. $^1$H NMR (400 MHz, DMSO-d6) δ: 10.27 (s, 1H), 8.56 (s, 1H), 8.31-8.20 (m, 2H), 7.87 (s, 1H), 7.27 (d, 1H), 7.23 (d, 1H), 6.47 (s, 1H), 4.60-4.47 (m, 1H), 3.82 (s, 3H), 3.61-3.52 (m, 1H), 3.44-3.38 (m, 1H). LCMS: m/z 435.2 [M + H]$^+$ |
| 219 | 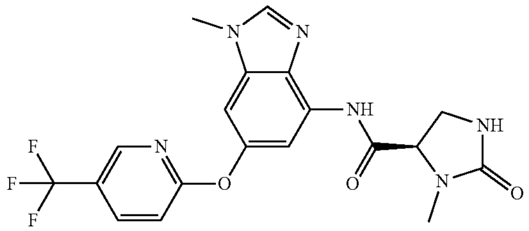 [SMILES: CN1C(=O)NC[C@@H]1C(=O)Nc1cc(Oc2ccc(C(F)(F)F)cn2)cc2c1ncn2C] Starting materials: 1-Methyl-6-((5-(trifluoromethyl)pyridin-2-yl)oxy)-1H-benzo[d]imidazol-4-amine and (R)-3-Methyl-2-oxoimidazolidine-4-carboxylic acid | Purification method A. $^1$H NMR (400 MHz, DMSO-d6) δ: 10.27 (s, 1H), 8.56 (s, 1H), 8.31-8.20 (m, 2H), 7.87 (s, 1H), 7.27 (d, 1H), 7.23 (d, 1H), 6.47 (s, 1H), 4.60-4.47 (m, 1H), 3.82 (s, 3H), 3.61-3.52 (m, 1H), 3.44-3.38 (m, 1H). LCMS: m/z 435.2 [M + H]$^+$ |

-continued

| No. | Structure and starting material | Purification method and characterization data |
|---|---|---|
| 220 | 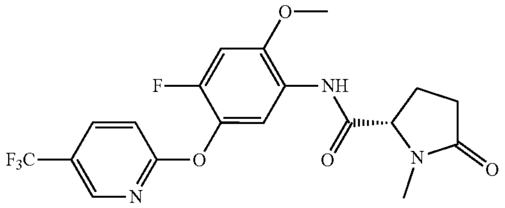 [SMILES: COc1cc(F)c(Oc2ccc(C(F)(F)F)cn2)cc1NC(=O)[C@@H]1CCC(=O)N1C] Starting materials: 4-Fluoro-2-methoxy-5-((5-(trifluoromethyl)-pyridin-2-yl)oxy)aniline and (S)-1-Methyl-5-oxopyrrolidine-2-carboxylic acid | Purification method A. $^1$H NMR (400 MHz, DMSO-$d_6$) δ: 9.68 (s, 1H), 8.55 (s, 1H), 8.26 (dd, 1H), 7.93 (d, 1H), 7.34 (d, 1H), 7.23 (d, 1H), 4.51-4.40 (m, 1H), 3.89 (s, 3H), 2.64 (s, 3H), 2.29-2.14 (m, 3H), 1.97-1.79 (m, 1H). LCMS: m/z 428.0 $[M + H]^+$ |
| 221 | 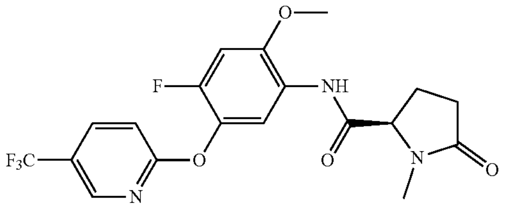 [SMILES: COc1cc(F)c(Oc2ccc(C(F)(F)F)cn2)cc1NC(=O)[C@H]1CCC(=O)N1C] Starting materials: 4-Fluoro-2-methoxy-5-((5-(trifluoromethyl)-pyridin-2-yl)oxy)aniline and (R)-1-Methyl-5-oxopyrrolidine-2-carboxylic acid | Purification method A. $^1$H NMR (400 MHz, DMSO-$d_6$) δ: 9.68 (s, 1H), 8.55 (s, 1H), 8.26 (dd, 1H), 7.93 (d, 1H), 7.34 (d, 1H), 7.23 (d, 1H), 4.48-4.33 (m, 1H), 3.89 (s, 3H), 2.65 (s, 3H), 2.31-2.13 (m, 3H), 1.93-1.78 (m, 1H). LCMS: m/z 428.2 $[M + H]^+$ |
| 222 | 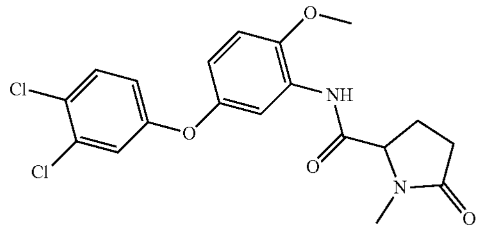 [SMILES: COc1ccc(Oc2ccc(Cl)c(Cl)c2)cc1NC(=O)C1CCC(=O)N1C] Starting material: 5-(3,4-Dichloro-phenoxy)-2-methoxyaniline and 1-Methyl-5-oxopyrrolidine-2-carboxylic acid | Purification method Column chromatography. $^1$H NMR (600 MHz, DMSO-$d_6$) δ: 1.86 – 1.92 (1 H, m), 2.15 – 2.31 (3 H, m), 2.64 (3 H, s), 3.87 (3 H, s), 4.47 (1 H, m), 6.89 (1 H, m), 6.93 (1 H, m), 7.12 (1 H, d), 7.19 (1 H, d), 7.59 (1 H, d), 7.84 (1 H, d), 9.64 (1 H, s). LCMS: m/z 409.0 $[M + H]^+$ |
| 223 | 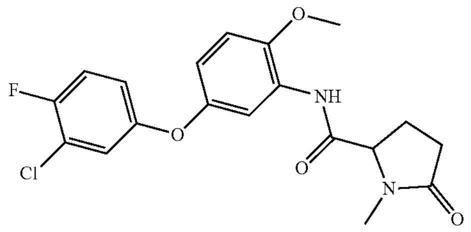 [SMILES: COc1ccc(Oc2ccc(F)c(Cl)c2)cc1NC(=O)C1CCC(=O)N1C] Starting material: 5-(3-Chloro-4-fluorophenoxy)-2-methoxyaniline and 1-Methyl-5-oxopyrrolidine-2-carboxylic acid | Purification method Column chromatography. $^1$H NMR (600 MHz, DMSO-$d_6$) δ: 1.86 – 1.92 (1 H, m), 2.15 – 2.31 (3 H, m), 2.64 (3 H, s), 3.86 (3 H, s), 4.46 (1 H, m), 6.84 (1 H, m), 6.95 (1 H, m), 7.10 (1 H, d), 7.16 (1 H, m), 7.40 (1 H, t), 7.82 (1 H, d), 9.62 (1 H, s). LCMS: m/z 393.0 $[M + H]^+$ |

Example 2. N-(5-(3,4-Difluorophenoxy)-2-(1,3,4-oxadiazol-2-yl)phenyl)-1-methyl-5-oxopyrrolidine-2-carboxamide (Compound 224)

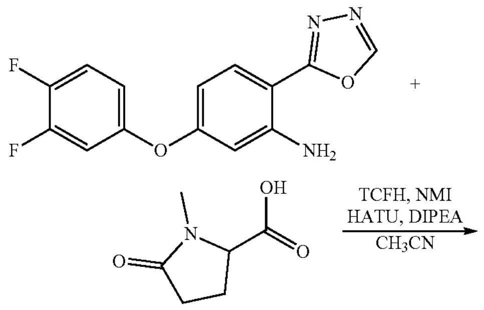

-continued

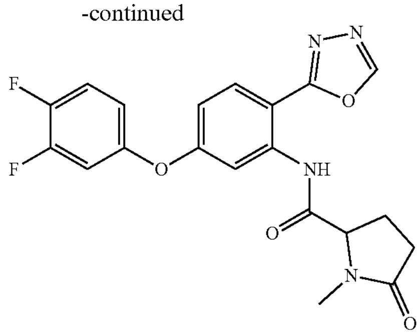

Compound 224

To a solution of 5-(3,4-difluorophenoxy)-2-(1,3,4-oxadiazol-2-yl)aniline (0.122 g, 1 eq., 422 μmol) in acetonitrile (3 mL) was added 1-methyl-5-oxopyrrolidine-2-carboxylic acid (72.5 mg, 1.2 eq., 506 μmol) and DIPEA (218 mg, 294 μL, 4 eq., 1.69 mmol). HATU (321 mg, 2 eq., 844 μmol) was then added and the mixture was stirred overnight at RT. N-(Chloro(dimethylamino)methylene)-N-methylmethanaminium hexafluorophosphate(V) (237 mg, 2 eq., 844 μmol) and 1-methyl-1H-imidazole (208 mg, 202 μL, 6 eq., 2.53 mmol) were added and the mixture was stirred overnight. The mixture was concentrated in vacuum, diluted with EtOAc (10 mL), washed with $NaHSO_4$ (2 mL, 10%), $K_2CO_3$ (2 mL, 10%) and water (2 mL) followed by drying over $Na_2SO_4$. EtOAc was evaporated. The residue was purified by HPLC (2-10 min 0-55% of MeCN, flow rate: 30 mL/min) to afford the title compound (0.0242 g, 58.4 μmol, 13.8%, 100% purity). $^1$H NMR (600 MHz, DMSO-$d_6$) δ: 10.89 (s, 1H), 9.38 (s, 1H), 8.01-7.89 (m, 2H), 7.57-7.50 (m, 1H), 7.45-7.38 (m, 1H), 7.04 (dd, J=8.0, 4.8 Hz, 1H), 6.96 (dd, J=8.8, 2.5 Hz, 1H), 4.26 (dd, J=9.1, 3.9 Hz, 1H), 2.70 (s, 3H), 2.38-2.21 (m, 3H), 2.01-1.93 (m, 1H). LCMS: m/z 415.0 $[M+H]^+$.

The following compounds were prepared according to the procedure described for compound 224. The compound code, structure, starting materials, purification method and characterization data are indicated in the table.

| No | Structure and starting material | Purification method and characterization data |
|---|---|---|
| 225 | 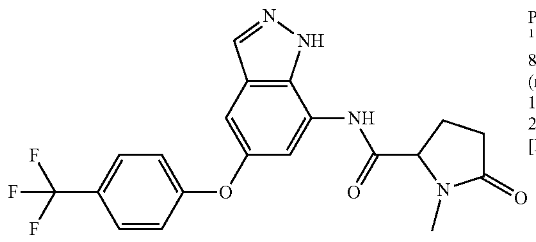 Starting materials: 5-(4-(Trifluoromethyl)phenoxy)-1H-indazol-7-amine and 1-Methyl-5-oxopyrrolidine-2-carboxylic acid | Purification method A. $^1$H NMR (400 MHz, Methanol-d4) δ: 8.10 (s, 1H), 7.64 (d, 2H), 7.43-7.28 (m, 2H), 7.11 (d, 2H), 4.49-4.37 (m, 1H), 2.90 (s, 3H), 2.63-2.34 (m, 3H), 2.29-2.18 (m, 1H). LCMS: m/z 419.0 $[M + H]^+$ |

Example 3. (S)—N-(2-Methoxy-5-(4-(trifluoromethyl)phenoxy)phenyl)-1,3-dimethyl-2-oxoimidazolidine-4-carboxamide (Compound 226)

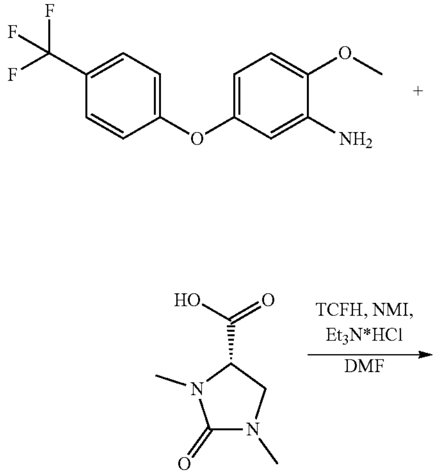

-continued

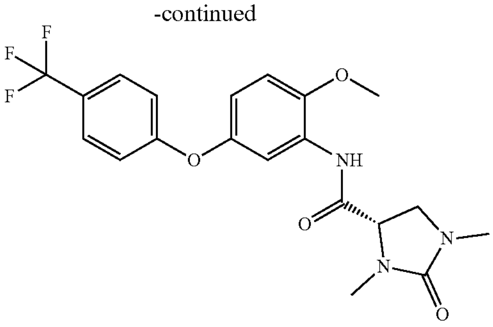

Compound 226

2-Methoxy-5-(4-(trifluoromethyl)phenoxy)aniline (0.07 g, 1 eq., 0.25 mmol), (S)-1,3-dimethyl-2-oxoimidazolidine-4-carboxylic acid (39 mg, 1 eq., 0.25 mmol) and triethylamine hydrochloride (34 mg, 1 eq., 0.25 mmol) were dissolved in DMF (3 mL) followed by stirring for 10 min. Then 1-methyl-1H-imidazole (0.1 g, 99 μL, 5 eq., 1.2 mmol) was added followed by stirring for 10 min. N-(Chloro(dimethyl-amino)methylene)-N-methylmethanaminium hexafluorophosphate(V) (76 mg, 1.1 eq., 0.27 mmol) was then added in a single portion followed by stirring at 20° C. for 10 h. The mixture was filtered and the filtrate was purified by HPLC (Method A) to give the title compound (0.0314 g, 74.2 μmol, 30%, 100% purity). $^1$H NMR (400 MHz, DMSO-$d_6$) δ: 9.57 (s, 1H), 7.88 (t, 1H), 7.71 (d, 2H), 7.15 (d, 1H), 7.08 (d, 2H), 7.00-6.88 (m, 1H), 4.40-4.26 (m, 1H), 3.88 (s, 3H), 3.54 (t, 1H), 3.26-3.16 (m, 1H), 2.64 (d, 6H). LCMS: m/z 424.2 [M+H]$^+$.

The following compounds were prepared according to the procedure described for compound 226. The compound code, structure, starting materials, purification method and characterization data are indicated in the table.

| No | Structure and starting material | Purification method and characterization data |
|---|---|---|
| 227 | 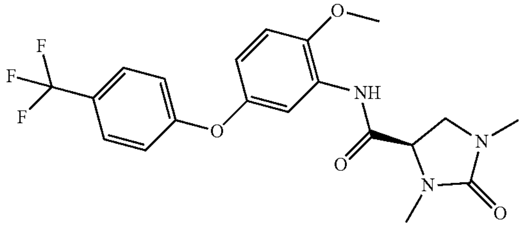 [SMILES: COc1ccc(Oc2ccc(C(F)(F)F)cc2)cc1NC(=O)[C@H]1CN(C)C(=O)N1C] Starting materials: 2-Methoxy-5-(4-(trifluoromethyl)phenoxy)aniline and Lithium (R)-1,3-dimethyl-2-oxoimidazolidine-4-carboxylate | Purification method A. $^1$H NMR (400 MHz, DMSO-d6) δ: 9.58 (s, 1H), 7.88 (d, 1H), 7.71 (d, 2H), 7.15 (d, 1H), 7.08 (d, 2H), 6.93 (dd, 1H), 4.33 (dd, 1H), 3.88 (s, 3H), 3.54 (t, 1H), 3.19 (dd, 1H), 2.64 (d, 6H). LCMS: m/z 424.2 [M + H]$^+$ |

-

Example 4. 4-Hydroxy-N-(2-methoxy-5-(4-(trifluoromethyl)phenoxy)phenyl)-1-methyl-5-oxopyrrolidine-3-carboxamide (Compound 228)

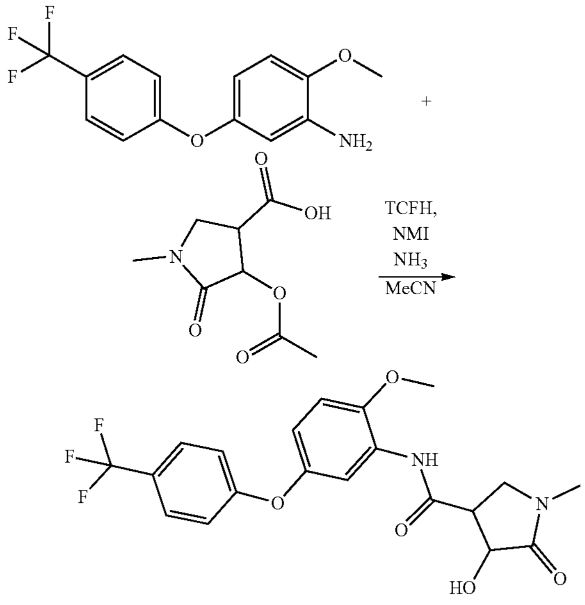

Compound 228

2-Methoxy-5-(4-(trifluoromethyl)phenoxy)aniline (100 mg, 1 eq., 353 μmol), 4-acetoxy-1-methyl-5-oxopyrrolidine-3-carboxylic acid (92.3 mg, 1.3 eq., 459 μmol) and 1-methyl-1H-imidazole (174 mg, 169 μL, 6 eq., 2.12 mmol) were dissolved in acetonitrile (2 mL) followed by stirring the mixture at 22° C. for 10 min. Then N-(chloro(dimethylamino)methylene)-N-methylmethanaminium hexafluorophosphate(V) (198 mg, 2 eq., 706 μmol) was added. The mixture was stirred at 22° C. for 16 h. 4-Acetoxy-1-methyl-5-oxopyrrolidine-3-carboxylic acid (92.3 mg, 1.3 eq., 459 μmol) and N-(chloro(dimethylamino)methylene)-N-methylmethanaminium hexafluoro-phosphate(V) (198 mg, 2 eq., 706 μmol) were added to the mixture followed by stirring at 22° C. for 16 h. The mixture was concentrated and ammonia (60.1 mg, 10 eq., 3.53 mmol) in methanol solution was added. The reaction mass was stirred at 22° C. for 16 h. The solution was purified by reverse phase HPLC (purification method A) to afford the title compound (5 mg, 0.01 mmol, 3%, 95% purity). $^1$H NMR (400 MHz, Methanol-d4) δ: 8.03-8.00 (m, 1H), 7.65-7.57 (m, 2H), 7.10-7.03 (m, 3H), 6.85 (m, 1H), 4.54 (dd, 1H), 3.93 (d, 3H), 3.77-3.67 (m, 1H), 3.58-3.47 (m, 2H), 3.31-3.25 (m, 1H), 2.88 (s, 3H). LCMS: m/z 425.1 $[M+H]^+$.

Example 5. N-(2-Methoxy-5-(4-(trifluoromethyl)phenoxy)phenyl)-5-oxo-1-(5-oxopyrrolidine-2-carbonyl)pyrrolidine-2-carboxamide (Compound 229)

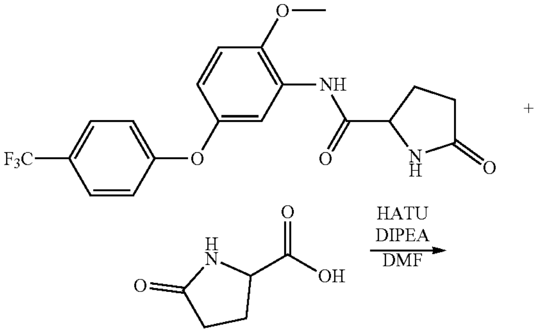

-continued

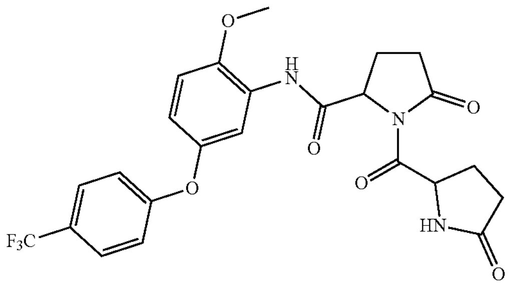

Compound 229

To a solution of N-(2-methoxy-5-(4-(trifluoromethyl)phenoxy)phenyl)-5-oxo-pyrrolidine-2-carboxamide (0.047 g, 1 eq., 0.12 mmol) in DMF (2 mL) was added 5-oxopyrrolidine-2-carboxylic acid (15 mg, 1 eq., 0.12 mmol) and diisopropylethylamine (46 mg, 62 μL, 3 eq., 0.36 mmol). The mixture was stirred at RT for 15 minutes and HATU (68 mg, 1.5 eq., 0.18 mmol) was added in a single portion. The resulting solution was stirred at RT for 10 h. The mixture was concentrated in vacuum, diluted with ethylacetate (10 mL), washed with $NaHSO_4$ (2 mL, 10%), $K_2CO_3$ (2 mL, 10%) and water (2 mL) followed by drying over $Na_2SO_4$. Ethyl acetate was evaporated and the residue was purified by method A to afford the title compound (0.0117 g). $^1$H NMR (400 MHz, DMSO-$d_6$) δ: 9.78 (s, 1H), 7.87 (d, 1H), 7.77 (s, 1H), 7.69 (d, 2H), 7.14 (d, 1H), 7.06 (d, 2H), 6.90 (dd, 1H), 5.16-5.07 (m, 1H), 5.07-5.00 (m, 1H), 3.90 (s, 3H), 2.70-2.56 (m, 1H), 2.46-2.30 (m, 3H), 2.05-1.89 (m, 4H). LCMS: m/z 506.0 $[M+H]^+$.

The following compounds were prepared according to the procedure described for Compound 229. The compound code, structure, starting materials, purification method and characterization data are indicated in the table.

| No | Structure and starting material | Purification method and characterization data |
| --- | --- | --- |
| 230 | 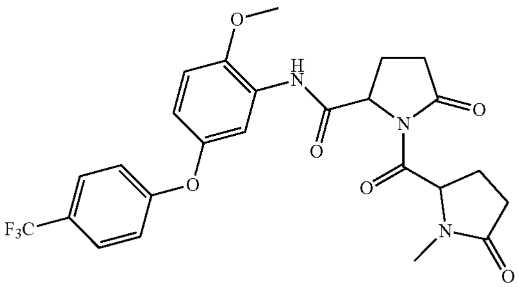 [SMILES: COc1ccc(Oc2ccc(C(F)(F)F)cc2)cc1NC(=O)C1CCC(=O)N1C(=O)C1CCC(=O)N1C] Starting materials: N-(2-Methoxy-5-(4-(trifluoromethyl)phenoxy)-phenyl)-5-oxopyrrolidine-2-carboxamide and 1-Methyl-5-oxopyrrolidine-2-carboxylic acid | Purification method C. $^1$H NMR (400 MHz, Acetonitrile-$d_3$) δ: 8.64 (d, 1H), 8.06-7.97 (m, 1H), 7.67 (d, 2H), 7.12-7.03 (m, 3H), 6.92-6.81 (m, 1H), 5.19 (td, 1H), 4.93 (dd, 1H), 3.95 (d, 3H), 2.78-2.69 (m, 3H), 2.67 (s, 1H), 2.62-2.52 (m, 1H), 2.50-2.38 (m, 2H), 2.20-2.12 (m, 4H). LCMS: m/z 520.2 $[M + H]^+$ |

-continued

| No | Structure and starting material | Purification method and characterization data |
|---|---|---|
| 231 | 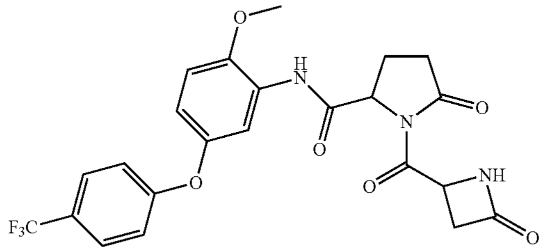 [SMILES: COc1ccc(Oc2ccc(C(F)(F)F)cc2)cc1NC(=O)C1CCC(=O)N1C(=O)C1CC(=O)N1]<br>Starting materials: N-(2-Methoxy-5-(4-(trifluoromethyl)phenoxy)-phenyl)-5-oxopyrrolidine-2-carboxamide and 4-Oxoazetidine-2-carboxylic acid | Purification method A. $^1$H NMR (400 MHz, Acetonitrile-$d_3$) δ: 8.63 (s, 1H), 8.03 (d, 1H), 7.67 (d, 2H), 7.09 (d, 3H), 6.88 (dd, 1H), 6.67-6.60 (m, 1H), 4.98-4.80 (m, 2H), 3.96 (s, 3H), 3.39-3.31 (m, 1H), 2.91-2.80 (m, 1H), 2.77-2.65 (m, 1H), 2.63-2.38 (m, 2H), 1.83-1.78 (m, 1H). LCMS: m/z 493.2 $[M + H]^+$ |
| 232 | 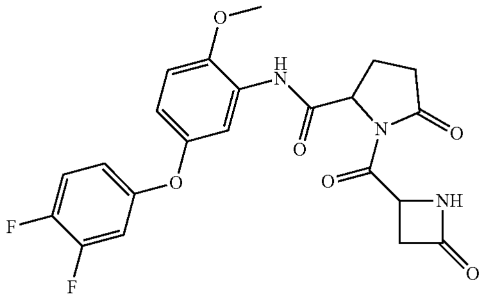 [SMILES: COc1ccc(Oc2ccc(F)c(F)c2)cc1NC(=O)C1CCC(=O)N1C(=O)C1CC(=O)N1]<br>Starting materials: N-(5-(3,4-Di-fluorophenoxy)-2-methoxyphenyl)-5-oxopyrrolidine-2-carboxamide and 4-Oxoazetidine-2-carboxylic acid | Purification method A. $^1$H NMR (400 MHz, Acetonitrile-$d_3$) δ: 8.61 (s, 1H), 7.99 (d, 1H), 7.30-7.18 (m, 1H), 7.05 (d, 1H), 6.98-6.91 (m, 1H), 6.85-6.74 (m, 2H), 6.64 (s, 1H), 4.96-4.85 (m, 2H), 3.94 (s, 3H), 3.43-3.32 (m, 1H), 2.91-2.83 (m, 1H), 2.79-2.63 (m, 1H), 2.58-2.40 (m, 3H). LCMS: m/z 458.0 $[M - H]^-$ |

Example 6. 1-Methyl-5-oxo-N-(7-(3-(trifluoromethyl)phenoxy)-2,3-dihydrobenzo[b][1,4]dioxin-5-yl)pyrrolidine-2-carboxamide (Compound 233)

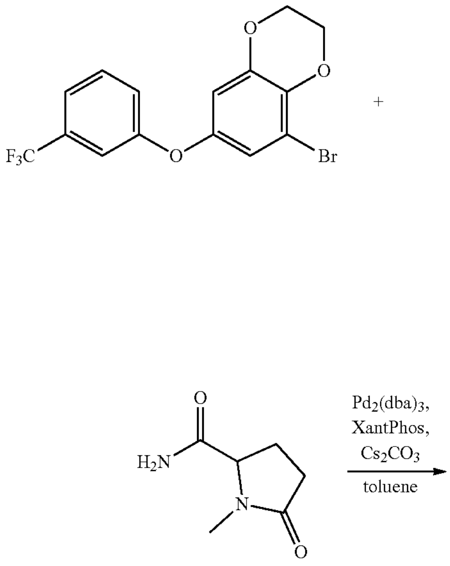

-continued

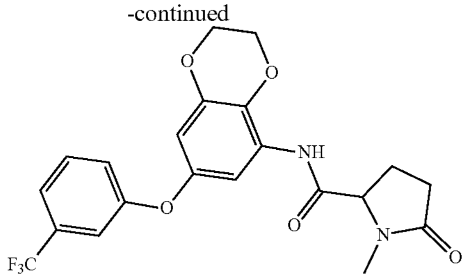

Compound 233

To a mixture of 5-bromo-7-(3-(trifluoromethyl)phenoxy)-2,3-dihydrobenzo[b]-[1,4]dioxine (217.2 mg, 1 eq., 579.0 μmol), 1-methyl-5-oxopyrrolidine-2-carboxamide (123.5 mg, 1.5 eq., 868.5 μmol) and cesium carbonate (565.9 mg, 3 eq., 1.737 mmol) in toluene (4 mL) under argon $Pd_2(dba)_3$ (26.51 mg, 0.05 eq., 28.95 μmol) and 4,5-bis(di-phenylphosphino)-9,9-dimethylxanthene (50.25 mg, 0.15 eq., 86.85 μmol) were added and the mixture was heated at 110° C. for 18 h. After cooling to RT the mixture was concentrated and the residue was purified by method A to afford the title compound (0.0286 g). $^1$H NMR (600 MHz, DMSO-$d_6$) δ: 9.68 (s, 1H), 7.59-7.54 (m, 1H), 7.42 (d, 1H), 7.39 (d, 1H), 7.25-7.19 (m, 2H), 6.47 (d, 1H), 4.44 (dd, 1H), 4.35-4.27 (m, 4H), 2.61 (s, 3H), 2.27-2.12 (m, 3H), 1.89-1.82 (m, 1H). LCMS: m/z 437.0 $[M+H]^+$.

The following compounds were prepared according to the procedure described for Compound 233. The compound code, structure, starting materials, purification method and characterization data are indicated in the table.

| No | Structure and starting material | Purification method and characterization data |
|---|---|---|
| 234 | 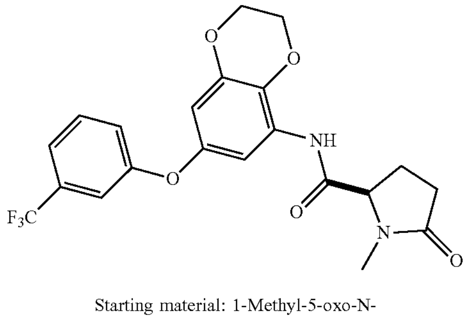<br>Starting material: 1-Methyl-5-oxo-N-(7-(3-(trifluoromethyl)phenoxy)-2,3-dihydrobenzo[b][1,4]dioxin-5-yl)-pyrrolidine-2-carboxamide (racemic) | Purification method A followed by method G. Retention time 10.09 min. $^1$H NMR (600 MHz, DMSO-$d_6$) δ: 9.68 (s, 1H), 7.57 (t, 1H), 7.46-7.34 (m, 2H), 7.25-7.19 (m, 2H), 6.48 (s, 1H), 4.44 (d, 1H), 4.31 (d, 4H), 2.61 (s, 3H), 2.30-2.11 (m, 3H), 1.92-1.80 (m, 1H). LCMS: m/z 437.2 $[M + H]^+$ |
| 235 | 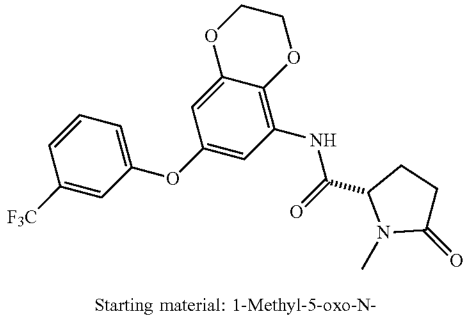<br>Starting material: 1-Methyl-5-oxo-N-(7-(3-(trifluoromethyl)phenoxy)-2,3-dihydrobenzo[b][1,4]dioxin-5-yl)-pyrrolidine-2-carboxamide (racemic) | Purification method A followed by method G. Retention time 27.41 min. $^1$H NMR (600 MHz, DMSO-$d_6$) δ: 9.68 (s, 1H), 7.57 (t, 1H), 7.46-7.34 (m, 2H), 7.25-7.19 (m, 2H), 6.48 (s, 1H), 4.44 (d, 1H), 4.31 (d, 4H), 2.61 (s, 3H), 2.30-2.11 (m, 3H), 1.92-1.80 (m, 1H). LCMS: m/z 437.2 $[M + H]^+$ |
| 236 | 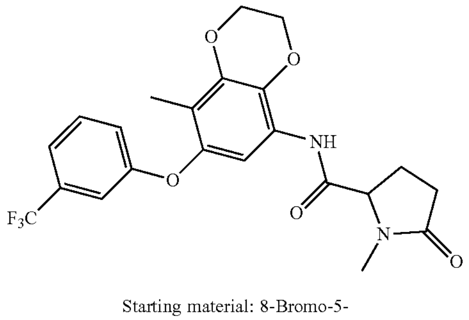<br>Starting material: 8-Bromo-5-methyl-6-(3-(trifluoromethyl)phenoxy)-2,3-dihydrobenzo[b][1,4]dioxine and 1-Methyl-5-oxopyrrolidine-2-carboxamide | Purification method A. $^1$H NMR (400 MHz, DMSO-$d_6$) δ: 9.64 (s, 1H), 7.60-7.53 (m, 1H), 7.39 (d, 1H), 7.34 (s, 1H), 7.15 (d, 1H), 7.09 (dd, 1H), 4.42 (d, 1H), 4.39-4.28 (m, 4H), 2.62 (s, 3H), 2.30-2.13 (m, 3H), 1.93 (d, 3H), 1.91-1.83 (m, 1H). LCMS: m/z 451.4 $[M + H]^+$ |
| 237 | 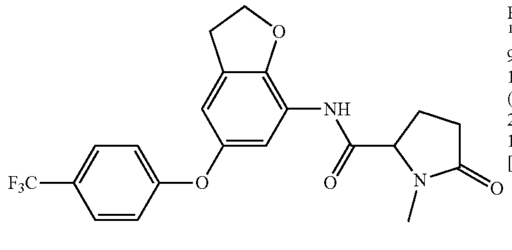<br>Starting material: 7-Bromo-5-(4-(trifluoromethyl)phenoxy)-2,3-dihydrobenzofuran and 1-Methyl-5-oxo-pyrrolidine-2-carboxamide | Purification method A. $^1$H NMR (400 MHz, DMSO-$d_6$) δ: 9.94 (s, 1H), 7.70 (d, 2H), 7.57 (d, 1H), 7.07 (d, 2H), 6.88 (d, 1H), 4.65 (t, 2H), 4.43-4.36 (m, 1H), 3.25 (t, 2H), 2.63 (s, 3H), 2.29-2.15 (m, 3H), 1.93-1.81 (m, 1H). LCMS: m/z 421.2 $[M + H]^+$ |

-continued

| No | Structure and starting material | Purification method and characterization data |
|---|---|---|
| 238 | 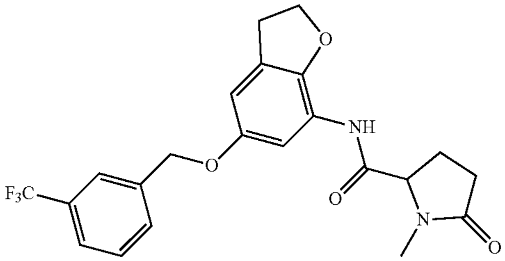 [SMILES: CN1C(=O)CCC1C(=O)Nc1cc(OCc2cccc(C(F)(F)F)c2)cc2c1OCC2] Starting material: 7-Bromo-5-((3-(trifluoromethyl)benzyl)oxy)-2,3-dihydrobenzofuran and 1-Methyl-5-oxopyrrolidine-2-carboxamide | Purification method C. $^1H$ NMR (400 MHz, DMSO-$d_6$) δ: 9.77 (s, 1H), 7.81-7.60 (m, 4H), 7.50-7.45 (m, 1H), 6.79-6.74 (m, 1H), 5.10 (s, 2H), 4.56 (t, 2H), 4.42-4.34 (m, 1H), 3.19 (t, 2H), 2.68-2.65(m, 1H), 2.65 (s, 3H), 2.34-2.18 (m, 3H), 1.91-1.84 (m, 1H). LCMS: m/z 435.0 $[M + H]^+$ |
| 239 | 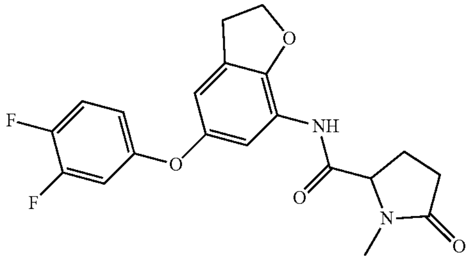 [SMILES: CN1C(=O)CCC1C(=O)Nc1cc(Oc2ccc(F)c(F)c2)cc2c1OCC2] Starting material: 7-Bromo-5-(3,4-difluorophenoxy)-2,3-dihydrobenzofuran and 1-Methyl-5-oxopyrrolidine-2-carboxamide | Purification method A. $^1H$ NMR (400 MHz, Acetonitrile-$d_3$) δ: 8.13 (s, 1H), 7.64 (d, 1H), 7.31-7.20 (m, 1H), 6.96-6.89 (m, 1H), 6.83-6.74 (m, 2H), 4.68 (t, 2H), 4.24 (dd, 1H), 3.28 (t, 2H), 2.44-2.23 (m, 3H). LCMS: m/z 389.2 $[M + H]^+$ |
| 240 | 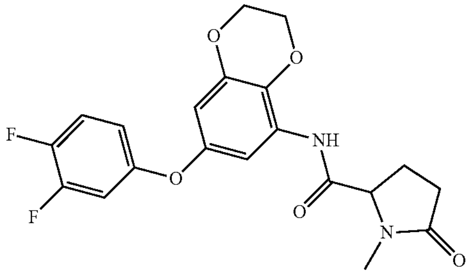 [SMILES: CN1C(=O)CCC1C(=O)Nc1cc(Oc2ccc(F)c(F)c2)cc2c1OCCO2] Starting material: 5-Bromo-7-(3,4-difluorophenoxy)-2,3-dihydrobenzo-[b][1,4]dioxine and 1-Methyl-5-oxo-pyrrolidine-2-carboxamide | Purification method A. $^1H$ NMR (400 MHz, DMSO-$d_6$) δ: 9.67 (s, 1H), 7.48-<br>7.32 (m, 2H), 7.16-7.06 (m, 1H), 6.78 (d, 1H), 6.43 (d, 1H), 4.45 (d, 1H), 4.37-4.26 (m, 4H), 2.64 (d, 3H), 2.31-2.15 (m, 3H), 1.92-1.79 (m, 1H). LCMS: m/z 405.2 $[M + H]^+$ |
| 241 | 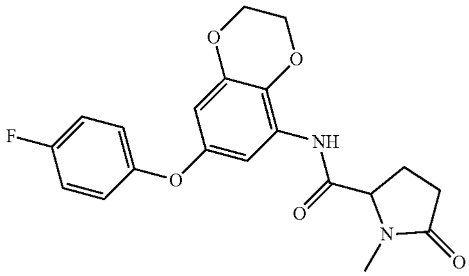 [SMILES: CN1C(=O)CCC1C(=O)Nc1cc(Oc2ccc(F)cc2)cc2c1OCCO2] Starting material: 5-Bromo-7-(4-fluorophenoxy)-2,3-dihydrobenzo-[b][1,4]dioxine and 1-Methyl-5-oxo-pyrrolidine-2-carboxamide | Purification method A. $^1H$ NMR (400 MHz, DMSO-$d_6$) δ: 9.63 (s, 1H), 7.33 (d, 1H), 7.23-7.15 (m, 2H), 7.05-6.93 (m, 2H), 6.35 (d, 1H), 4.48-4.40 (m, 1H), 4.34-4.24 (m, 4H), 2.63 (s, 3H), 2.33-2.12 (m, 3H), 1.94-1.80 (m, 1H). LCMS: m/z 387.2 $[M + H]^+$ |

-continued

| No | Structure and starting material | Purification method and characterization data |
| --- | --- | --- |
| 242 | 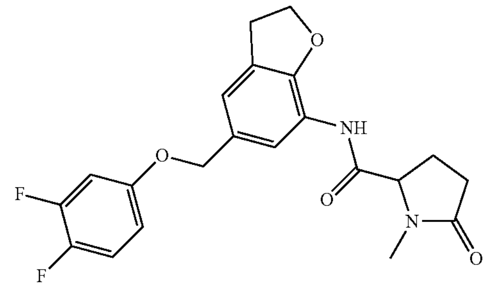 [SMILES: CN1C(=O)CCC1C(=O)Nc1cc(COc2ccc(F)c(F)c2)cc2c1OCC2] Starting material: 7-Bromo-5-((3,4-difluorophenoxy)methyl)-2,3-dihydrobenzofuran and 1-Methyl-5-oxopyrrolidine-2-carboxamide | Purification method A. $^1$H NMR (400 MHz, DMSO-$d_6$) δ: 9.79 (s, 1H), 7.75 (d, 1H), 7.39-7.28 (m, 1H), 7.18-7.06 (m, 2H), 6.85-6.73 (m, 1H), 4.95 (s, 2H), 4.62 (t, 2H), 4.43-4.34 (m, 1H), 3.23 (t, 2H), 2.66 (s, 3H), 2.34-2.17 (m, 3H), 1.95-1.79 (m, 1H). LCMS: m/z 403.0 $[M + H]^+$ |
| 243 | 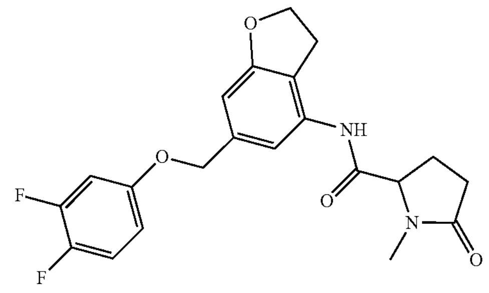 [SMILES: CN1C(=O)CCC1C(=O)Nc1cc(COc2ccc(F)c(F)c2)cc2c1CCO2] Starting material: 6-((3,4-Difluorophenoxy)methyl)-2,3-dihydrobenzofuran-4-yl trifluoromethanesulfonate and 1-methyl-5-oxopyrrolidine-2-carboxamide | Purification method A. $^1$H NMR (500 MHz, DMSO-$d_6$) δ: 9.84 (s, 1H), 7.32 (q, 1H), 7.16 (s, 1H), 7.14-7.05 (m, 1H), 6.79 (d, 1H), 6.64 (s, 1H), 4.99 (s, 2H), 4.52 (t, 2H), 4.33-4.22 (m, 1H), 3.09 (t, 2H), 2.66 (s, 3H), 2.31-2.15 (m, 3H), 1.97-1.81 (m, 1H). LCMS: m/z 403.0 $[M + H]^+$ |
| 244 | 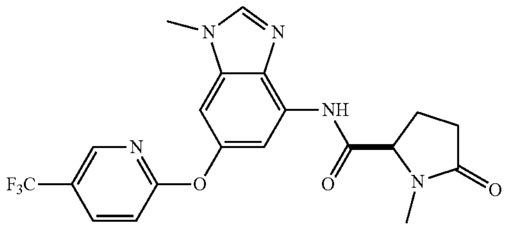 Starting material: 4-Bromo-1-methyl-6-((5-(trifluoromethyl)pyridin-2-yl)oxy)-1H-benzo[d]imidazole and 1-methyl-5-oxopyrrolidine-2-carboxamide | Purification method A followed by method I. Retention time 16.32 min. $^1$H NMR (600 MHz, DMSO-$d_6$) δ: 10.43 (s, 1H), 8.54 (s, 1H), 8.24 (s, 1H), 8.21 (dd, 1H), 7.84 (s, 1H), 7.25 (d, 1H), 7.21 (d, 1H), 4.60 (dd, 1H), 3.80 (s, 3H), 2.65 (s, 3H), 2.31-2.17 (m, 3H), 1.93-1.87 (m, 1H). LCMS: m/z 434.0 $[M + H]^+$ |
| 245 | 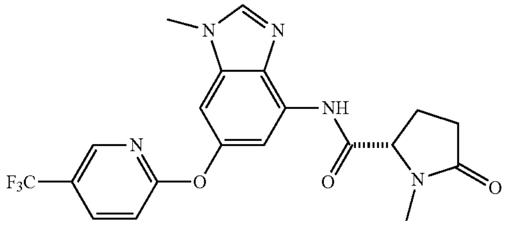 Starting material: 4-Bromo-1-methyl-6-((5-(trifluoromethyl)pyridin-2-yl)oxy)-1H-benzo[d]imidazole and 1-methyl-5-oxopyrrolidine-2-carboxamide | Purification method A followed by method I. Retention time 18.97 min. $^1$H NMR (600 MHz, DMSO-$d_6$) δ: 10.43 (s, 1H), 8.54 (s, 1H), 8.24 (s, 1H), 8.21 (dd, 1H), 7.84 (s, 1H), 7.25 (d, 1H), 7.21 (d, 1H), 4.60 (dd, 1H), 3.80 (s, 3H), 2.65 (s, 3H), 2.31-2.17 (m, 3H), 1.93-1.87 (m, 1H). LCMS: m/z 434.0 $[M + H]^+$ |

Example 7. N-(5-(((3-Fluorophenyl)amino)methyl)-2-methoxyphenyl)-5-oxopyrrolidine-2-carboxamide (Compound 246)

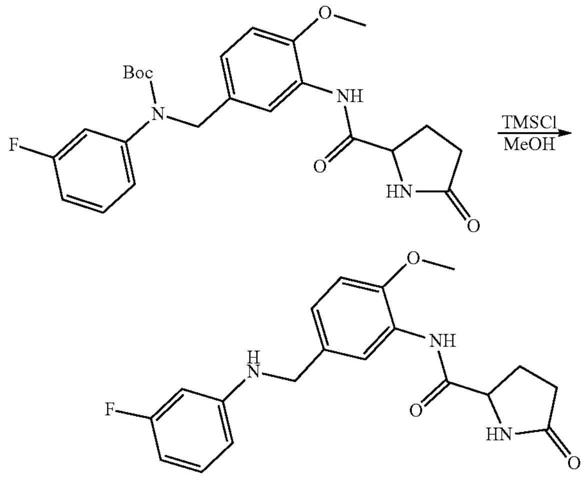

Compound 246

Chlorotrimethylsilane (210 mg, 245 μL, 5 eq., 1.93 mmol) was added slowly to methanol (5 mL) at 0° C. and the mixture was stirred at 0° C. for 30 min. To the obtained solution tert-butyl (3-fluorophenyl)(4-methoxy-3-(5-oxopyrrolidine-2-carboxamido)-benzyl)carbamate (300 mg, 58.89%, 1 eq., 386 μmol) was added and the mixture was stirred at RT for 18 h. The mixture was treated with aqueous $NaHCO_3$ solution (10 mL) and extracted with ethyl acetate (2×20 mL). Combined organic phases were washed with brine (2×15 mL), dried over sodium sulfate, filtered, concentrated and the residue was purified by reverse phase HPLC (water-acetonitrile) to afford the title compound (0.0201 g). $^{1}$H NMR (400 MHz, DMSO-$d_6$) δ: 9.17 (s, 1H), 8.04-7.90 (m, 2H), 7.12-6.96 (m, 3H), 6.58-6.49 (m, 1H), 6.39 (dd, 1H), 6.32-6.18 (m, 2H), 4.34 (dd, 1H), 4.16 (d, 2H), 3.82 (s, 3H), 2.38-2.28 (m, 1H), 2.28-2.02 (m, 2H), 2.03-1.85 (m, 1H). LCMS: m/z 358.2 [M+H]$^+$.

Example 8. N-(5-((4,4-Difluorocyclohexyl)oxy)-2-methoxyphenyl)-1-methyl-5-oxopyrrolidine-2-carboxamide (Compound 247)

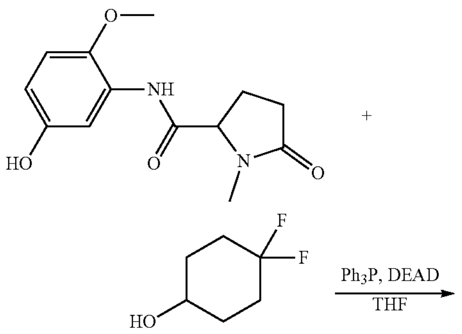

-continued

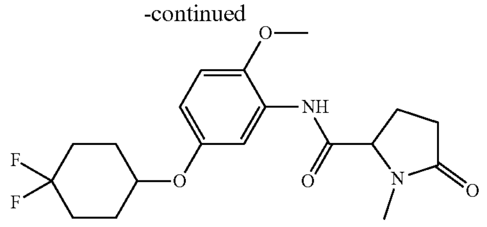

Compound 247

N-(5-hydroxy-2-methoxyphenyl)-1-methyl-5-oxopyrrolidine-2-carboxamide (0.0667 g, 1 eq., 252 μmol), triphenylphosphine (86.1 mg, 1.3 eq., 328 μmol) and DEAD (54.9 mg, 49.5 μL, 1.25 eq., 315 μmol) were dissolved in THF (5.5 mL). The mixture was stirred at RT for 30 min. 4,4-Difluorocyclohexan-1-ol (48.1 mg, 1.4 eq., 353 μmol) was added to the mixture at RT and stirred for 58 h. The mixture was purified by column chromatography to give the title compound (0.0032 g, 7.9 μmol, 3.1%, 95% purity). Purification method C. $^{1}$H NMR (400 MHz, Methanol-$d_4$) δ: 7.75 (d, 1H), 6.97 (d, 1H), 6.77 (dd, 1H), 4.48-4.40 (m, 2H), 3.87 (s, 3H), 2.85 (s, 3H), 2.59-2.47 (m, 1H), 2.47-2.34 (m, 2H), 2.19-2.04 (m, 3H), 1.99-1.84 (m, 6H). LCMS: m/z 383.2 [M+H]$^+$.

Example 9. N-(5-((3,4-Difluorobenzyl)oxy)-2,3-dihydrobenzofuran-7-yl)-1-methyl-5-oxopyrrolidine-2-carboxamide (Compound 248)

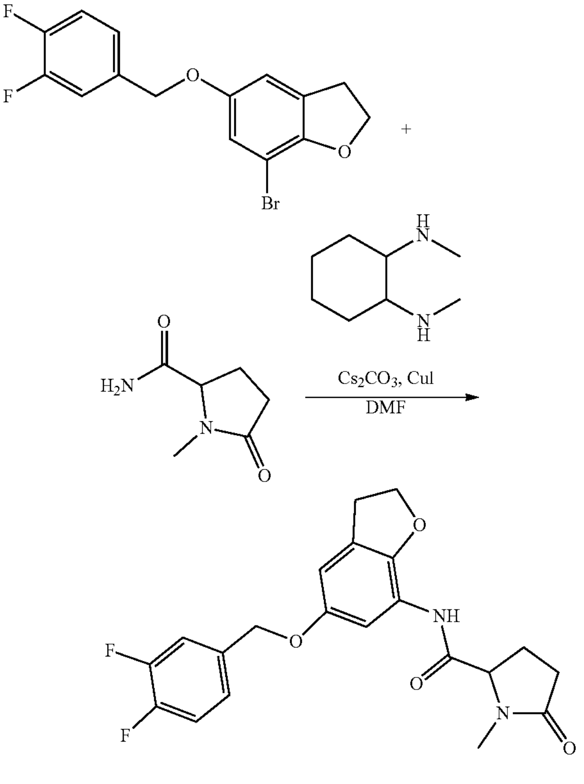

Compound 248

7-Bromo-5-((3,4-difluorobenzyl)oxy)-2,3-dihydrobenzofuran (0.100 g, 1 eq., 293 μmol), 1-methyl-5-oxopyrrolidine- 2-carboxamide (50.0 mg, 1.2 eq., 352 μmol), cesium carbonate (95.5 mg, 1 eq., 293 μmol), copper (I) iodide (16.7 mg, 0.3 eq., 87.9 μmol) and N1,N2-dimethylcyclohexane-1,2-diamine (25.0 mg, 0.6 eq., 176 μmol) were mixed in N,N-dimethylformamide (2 mL). The mixture was heated at 100° C. under argon atmosphere for 12 h. Then N,N-dimethylformamide was evaporated and the residue was diluted with EtOAc (10 mL), washed with water (2×2 mL), dried over $Na_2SO_4$ and concentrated in vacuum. A sample of reaction mixture was analyzed by LCMS. Residue was purified by method A to afford the title compound (0.0035 g). $^1$H NMR (400 MHz, Acetonitrile-$d_3$) δ: 8.03 (s, 1H), 7.59 (d, 1H), 7.46-7.36 (m, 1H), 7.36-7.24 (m, 2H), 6.74 (d, 1H), 5.01 (s, 2H), 4.61 (t, 2H), 4.23 (dd, 1H), 3.24 (t, 2H), 2.78 (s, 3H), 2.45-2.24 (m, 3H). LCMS: m/z 403.0 $[M+H]^+$.

The following compounds were prepared according to the procedure described for Compound 248. The compound number, structure, starting materials, purification method and characterization data are indicated in the table.

| No | Structure and starting material | Purification method and characterization data |
|---|---|---|
| 249 | 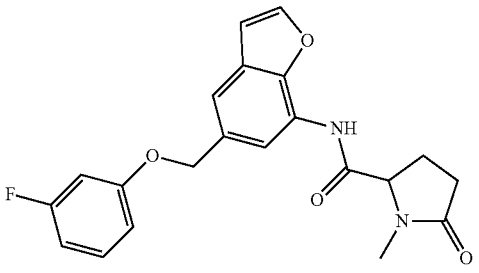 [SMILES: CN1C(=O)CCC1C(=O)Nc1cc(COc2cccc(F)c2)cc2ccoc12] Starting material: 7-Bromo-5-((3-fluorophenoxy)methyl)benzofuran and 1-Methyl-5-oxopyrrolidine-2-carboxamide | Purification method B. $^1$H NMR (400 MHz, DMSO-$d_6$) δ: 10.45 (s, 1H), 8.08 (d, 1H), 7.89 (s, 1H), 7.54 (s, 1H), 7.36-7.26 (m, 1H), 7.06-6.98 (m, 1H), 6.95-6.83 (m, 2H), 6.78 (d, 1H), 5.17 (s, 2H), 4.51-4.42 (m, 1H), 2.71 (s, 3H), 2.38-2.20 (m, 3H), 2.03-1.79 (m, 1H). LCMS: m/z 383.0 $[M + H]^+$ |
| 250 | 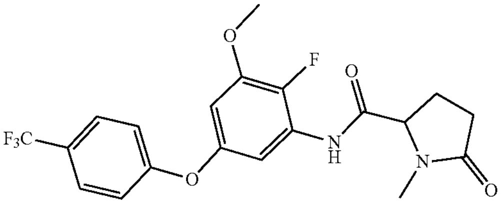 [SMILES: COc1cc(Oc2ccc(C(F)(F)F)cc2)cc(NC(=O)C2CCC(=O)N2C)c1F] Starting material: 2-Fluoro-1-iodo-3-methoxy-5-(4-(trifluoromethyl)-phenoxy)benzene and 1-Methyl-5-oxopyrrolidine-2-carboxamide | Purification method A. $^1$H NMR (400 MHz, DMSO-$d_6$) δ: 9.77 (s, 1H), 7.68 (d, 2H), 7.40-7.30 (m, 1H), 7.01 (d, 3H), 4.11-4.04 (m, 1H), 3.86 (s, 3H), 2.45 (s, 3H), 2.14-2.01 (m, 3H), 1.49-1.40 (m, 1H). LCMS: m/z 427.2 $[M + H]^+$ |
| 251 | 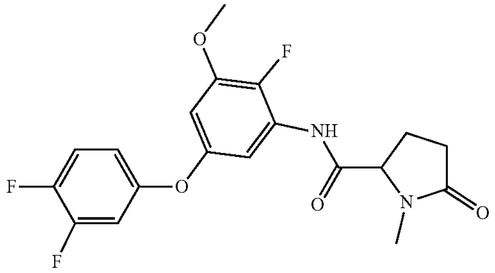 [SMILES: COc1cc(Oc2ccc(F)c(F)c2)cc(NC(=O)C2CCC(=O)N2C)c1F] Starting material: 5-(3,4-Difluoro-phenoxy)-2-fluoro-1-iodo-3-methoxybenzene and 1-Methyl-5-oxopyrrolidine-2-carboxamide | Purification method A. $^1$H NMR (400 MHz, DMSO-$d_6$) δ: 7.51-7.36 (m, 1H), 7.27-7.08 (m, 2H), 6.86 (d, 1H), 6.76 (dd, 1H), 4.44-4.29 (m, 1H), 2.64 (s, 3H), 2.30-2.17 (m, 3H), 1.94-1.82 (m, 1H). LCMS: m/z 395.0 $[M + H]^+$ |

Example 10. N-(2-Methoxy-5-(4-(trifluoromethyl)phenoxy)phenyl)-5-oxotetrahydropyrrolo[2,1-b]thiazole-7a(5H)-carboxamide 1,1-dioxide (Compound 252)

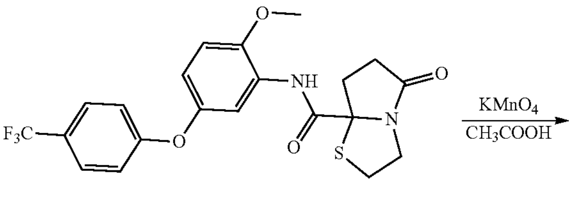

-continued

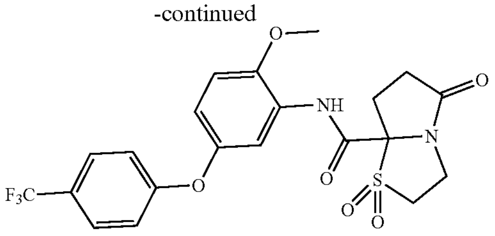

Compound 252

N-(2-Methoxy-5-(4-(trifluoromethyl)phenoxy)phenyl)-5-oxotetrahydropyrrolo-[2,1-b]thiazole-7a(5H)-carboxamide (100 mg, 1 eq., 221 μmol) was dissolved in acetic acid (3 mL) and potassium permanganate (55.9 mg, eq., 354 μmol) was added at RT. The mixture was stirred at RT for 24 h. The mixture was poured into sodium hydrocarbonate saturated solution (30 mL) followed by extraction with ethyl acetate (3x30 mL). Combined organic phases were washed with brine (2x30 mL), dried over sodium sulfate, filtered, concentrated and the residue was purified by purification method A to afford the title compound (0.0079 g). $^{1}H$ NMR (400 MHz, Acetonitrile-$d_3$) δ: 8.77 (s, 1H), 7.99 (d, 1H), 7.70 (d, 2H), 7.15-7.05 (m, 3H), 6.96 (dd, 1H), 4.52-4.38 (m, 1H), 3.95 (s, 3H), 3.73-3.64 (m, 1H), 3.45-3.26 (m, 2H), 2.87-2.66 (m, 3H), 2.57-2.42 (m, 1H). LCMS: m/z 485.2 $[M+H]^+$.

Example 11. N-(3-Methoxy-5-(4-(trifluoromethyl) phenoxy)phenyl)-5-oxopyrro-lidine-2-carboxamide (Compound 253)

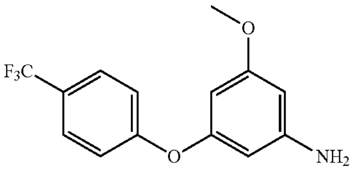

+

-continued

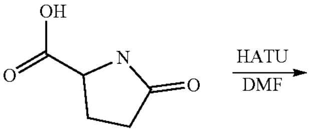

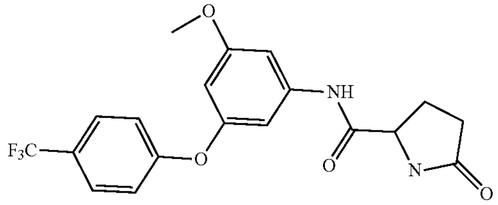

Compound 253

To a solution of 5-oxopyrrolidine-2-carboxylic acid (51.1 mg, 0.40 mmol), 3-methoxy-5-(4-(trifluoromethyl)phenoxy)aniline (112 mg, 0.40 mmol), HATU (226 mg, 0.60 mmol) and dry DMF (2 ml) was added DIPEA (0.34 ml, 2.0 mmol). The mixture was stirred at RT overnight. The reaction mixture was quenched with water (10 ml) followed by extraction with ethyl acetate (2x10 ml). The combined organic layers were washed with water, dried, evaporated and then purified by reverse phase chromatography to yield 0.074 g the title compound. 1H NMR (600 MHz, DMSO-$d_6$) δ: 1.93-2.00 (m, 1H), 2.08-2.22 (m, 2H), 2.28-2.36 (m, 1H), 3.75 (s, 3H), 4.14 (dd, 1H), 6.48 (t, 1H), 6.97 (t, 1H), 7.15-7.21 (m, 3H), 7.76 (d, 2H), 7.86 (s, 1H), 10.14 (s, 1H). LCMS: m/z 395.2 $[M+H]^+$ The following compounds were prepared according to the procedure described for Compound 253. The compound number, structure, starting materials, purification method and characterization data are indicated in the table.

| No | Structure and starting material | Purification method and characterization data |
|---|---|---|
| 254 | 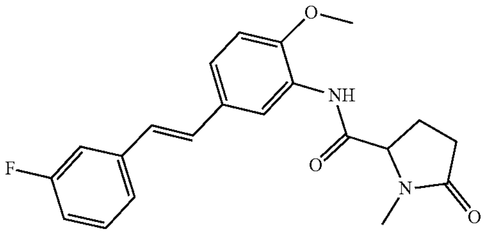 [SMILES: COc1ccc(/C=C/c2cccc(F)c2)cc1NC(=O)C1CCC(=O)N1C] Starting material: 1-Methyl-5-oxopyrrolidine-2-carboxylic acid and (E)-5-(3-Fluorostyryl)-2-methoxyaniline | Purification method A. $^{1}H$ NMR (DMSO-$d_6$, 600 MHz) δ: 9.55 (s, 1H), 8.21 (d, 1H), 7.4-7.5 (m, 4H), 7.28 (d, 1H), 7.0-7.1 (m, 3H), 4.45 (dd, 1H), 3.88 (s, 3H), 2.69 (s, 3H), 2.2-2.4 (m, 3H), 1.9-2.0 (m, 1H). LCMS: m/z 369.3 $[M + H]^+$ |

-continued

| No | Structure and starting material | Purification method and characterization data |
|---|---|---|
| 255 | 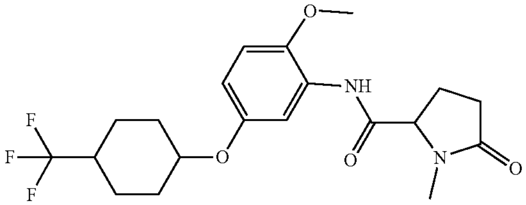 [SMILES: COc1ccc(OC2CCC(C(F)(F)F)CC2)cc1NC(=O)C1CCC(=O)N1C] Starting material: 1-Methyl-5-oxopyrrolidine-2-carboxylic acid and 2-Methoxy-5-((4-(trifluoromethyl)cyclohexyl)oxy)aniline | Purification method A. $^1$H NMR (400 MHz, Chloroform-d) δ: 1.21-1.49 (m, 4H), 1.80 (br s, 1H), 1.98-2.26 (m, 6H), 2.38-2.66 (m, 3H), 2.93 (s, 3H), 3.70-3.93 (m, 3H), 4.01-4.26 (m, 2H), 6.63 (dd, 1H), 6.80 (d, 1H), 8.02-8.10 (m, 2H). LCMS: m/z 414.3 [M + H]$^+$ |
| 256 | 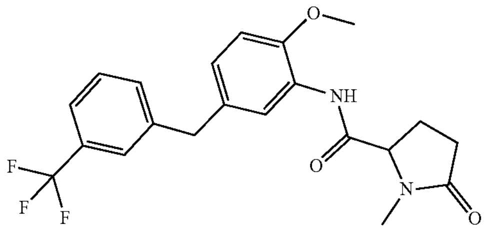 [SMILES: COc1ccc(Cc2cccc(C(F)(F)F)c2)cc1NC(=O)C1CCC(=O)N1C] Starting material: 1-Methyl-5-oxopyrrolidine-2-carboxylic acid and 2-Methoxy-5-(3-(trifluoromethyl)benzyl)aniline | Purification method A. $^1$H NMR (600 MHz, DMSO-d$_6$) δ: 1.85-1.93 (m, 1H), 2.16-2.33 (m, 3H), 2.65 (s, 3H), 3.33 (s, 6H), 3.79-3.85 (m, 3H), 3.96 (s, 2H) 4.39-4.47 (m, 1H), 7.00 (s, 2H), 7.42 (m, 2H), 7.64 (m, 2H), 7.86 (s, 1H), 9.45 (s, 1H). LCMS: m/z 407.2 [M + H]$^+$ |
| 257 | 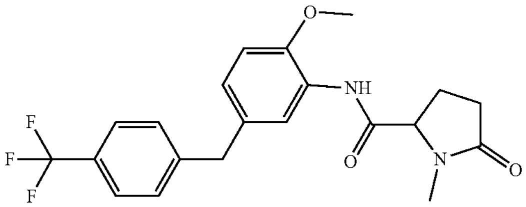 [SMILES: COc1ccc(Cc2ccc(C(F)(F)F)cc2)cc1NC(=O)C1CCC(=O)N1C] Starting material: 1-Methyl-5-oxopyrrolidine-2-carboxylic acid and 2-Methoxy-5-(4-(trifluoromethyl)benzyl)aniline | Purification method A. $^1$H NMR (400 MHz, Chloroform-d) δ: 2.09-2.22 (m, 1H), 2.38-2.64 (m, 3H), 2.93 (s, 3H), 3.79-4.00 (m, 5H), 4.03-4.17 (m, 1H), 6.78-6.92 (m, 2H), 7.34-7.48 (m, 4H), 8.01 (s, 1H), 8.26 (d, 1H). LCMS: m/z 407.3 [M + H]$^+$ |
| 258 | 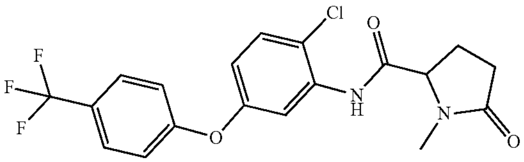 [SMILES: CN1C(=O)CCC1C(=O)Nc1cc(Oc2ccc(C(F)(F)F)cc2)ccc1Cl] Starting material: 1-Methyl-5-oxopyrrolidine-2-carboxylic acid and 2-Chloro-5-(4-(trifluoromethyl)phenoxy)aniline | Purification method A. $^1$H NMR (400 MHz, Chloroform-d) δ: 2.10-2.23 (m, 1H), 2.38-2.66 (m, 3H), 2.98 (s, 3H), 4.09-4.18 (m, 1H), 6.80 (dd, 1H), 7.07 (d, 2H), 7.36-7.42 (m, 1H), 7.60 (d, 2H), 8.03 (s, 1H), 8.19 (d, 1H). LCMS: m/z 413.2 [M + H]$^+$ |
| 259 | 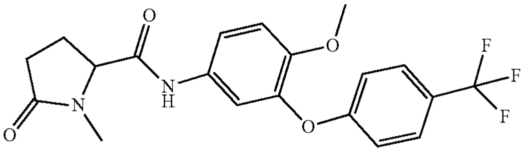 [SMILES: COc1ccc(NC(=O)C2CCC(=O)N2C)cc1Oc1ccc(C(F)(F)F)cc1] Starting material: 1-Methyl-5-oxopyrrolidine-2-carboxylic acid and 4-Methoxy-3-(4-(trifluoromethyl)phenoxy)aniline | Purification method A. $^1$H NMR (400 MHz, Chloroform-d) δ: 2.10-2.17 (m, 1H), 2.37-2.60 (m, 3H), 2.91 (s, 3H), 3.80 (s, 3H), 4.09 (dd, 1H), 6.94-7.03 (m, 3H), 7.36 (d, 1H), 7.40 (dd, 1H), 7.48-7.61 (m, 2H), 7.69 (br s, 1H). LCMS: m/z 409.3 [M + H]$^+$ |

-continued

| No | Structure and starting material | Purification method and characterization data |
|---|---|---|
| 260 | 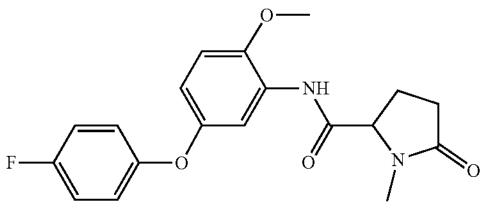 [SMILES: COc1ccc(Oc2ccc(F)cc2)cc1NC(=O)C1CCC(=O)N1C] Starting material: 1-Methyl-5-oxopyrrolidine-2-carboxylic acid and 5-(4-Fluorophenoxy)-2-methoxyaniline | Purification method A. $^1$H NMR (400 MHz, DMSO-$d_6$) δ: 1.82-1.94 (m, 1H), 2.14-2.34 (m, 3H), 2.52-2.69 (m, 3H), 3.80-3.87 (m, 3H), 4.42-4.51 (m, 1H), 6.79 (dd, 1H), 6.92-7.04 (m, 2H), 7.08 (d, 1H), 7.19 (t, 2H), 7.80 (d, 1H), 9.61 (s, 1H). LCMS: m/z 359.2 $[M + H]^+$ |
| 261 | 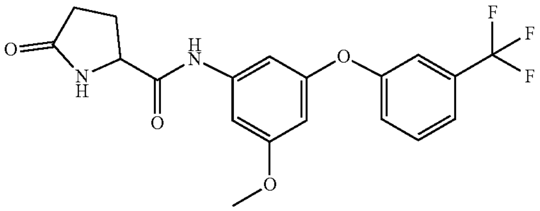 [SMILES: COc1cc(NC(=O)C2CCC(=O)N2)cc(Oc2cccc(C(F)(F)F)c2)c1] Starting material: 5-Oxopyrrolidine-2-carboxylic acid and 3-Methoxy-5-(3-(trifluoromethyl)-phenoxy)aniline | Purification method A. $^1$H NMR (600 MHz, DMSO-$d_6$) δ: 1.93-1.99 (m, 1H), 2.07-2.22 (m, 2H), 2.28-2.35 (m, 1H), 3.74 (s, 3H), 4.13 (dd, 1H), 6.44 (t, 1H), 6.92 (t, 1H), 7.14 (t, 1H), 7.34 (dd, 1H), 7.37 (s, 1H), 7.53 (d, 1H), 7.65 (t, 1H), 7.85 (s, 1H), 10.12 (s, 1H). LCMS: m/z 395.2 $[M + H]^+$ |
| 262 | 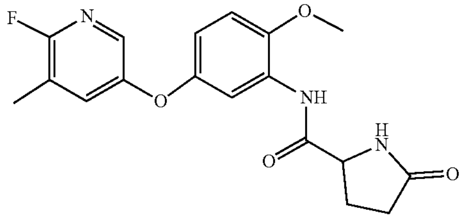 Starting material: 5-Oxopyrrolidine-2-carboxylic acid and 5-((6-Fluoro-5-methylpyridin-3-yl)oxy)-2-methoxyaniline | Purification method A. $^1$H NMR (600 MHz, DMSO-$d_6$) δ: 1.95 (ddt, 1H), 2.07-2.22 (m, 5H), 2.27-2.36 (m, 1H), 3.85 (s, 3H), 4.38 (dd, 1H), 6.82 (dd, 1H), 7.08 (d, 1H), 7.51 (dd, 1H), 7.75 (br s, 1H), 7.87 (d, 1H), 7.92 (s, 1H), 9.32 (s, 1H). LCMS: m/z 374.2 $[M + H]^+$ |
| 263 | 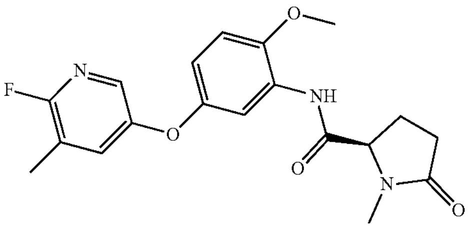 [SMILES: COc1ccc(Oc2cnc(F)c(C)c2)cc1NC(=O)[C@H]1CCC(=O)N1C] Starting material: (2R)-1-Methyl-5-oxopyrrolidine-2-carboxylic acid and 5-((6-Fluoro-5-methylpyridin-3-yl)-oxy)-2-methoxyaniline | Purification method A. 1H NMR (600 MHz, DMSO-d6) 8: 1.85-1.92 (m, 1H), 2.16-2.32 (m, 6H), 2.64 (s, 3H), 3.32 (s, 6H), 3.86 (s, 3H), 4.47 (dd, 1H), 6.83 (dd, 1H), 7.08 (d, 1H), 7.51 (dd, 1H), 7.74 (br s, 1H), 7.84 (d, 1H), 9.61 (s, 1H). LCMS: m/z 374.1 $[M + H]^+$ |

-continued

| No | Structure and starting material | Purification method and characterization data |
| --- | --- | --- |
| 264 | 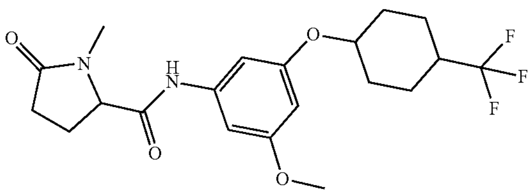 [SMILES: COc1cc(NC(=O)C2CCC(=O)N2C)cc(OC2CCC(C(F)(F)F)CC2)c1] Starting material: 1-Methyl-5-oxopyrrolidine-2-carboxylic acid and 3-Methoxy-5-((4-(trifluoro-methyl)cyclohexyl)oxy)aniline | Purification method A. $^1$H NMR (600 MHz, DMSO-$d_6$) δ: 1.36-1.49 (m, 4H), 1.87-1.95 (m, 3H), 2.08-2.16 (m, 2H), 2.20-2.40 (m, 4H), 2.67 (s, 3H), 3.71 (s, 3H), 4.17-4.28 (m, 2H), 6.27 (t, 1H), 6.87 (d, 2H), 10.13 (s, 1H). LCMS: m/z 415.2 $[M + H]^+$ |
| 265 | 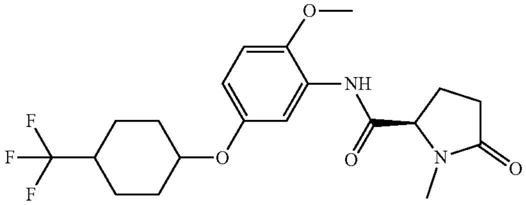 [SMILES: COc1ccc(OC2CCC(C(F)(F)F)CC2)cc1NC(=O)[C@H]1CCC(=O)N1C] Starting material: (2R)-1-Methyl-5-oxopyrrolidine-2-carboxylic acid and 2-Methoxy-5-((4-(trifluoromethyl)-cyclohexyl)oxy)aniline | Purification method A. $^1$H NMR (600 MHz, DMSO-$d_6$) δ: 1.34-1.46 (m, 3H), 1.55-1.69 (m, 2H), 1.86-2.00 (m, 3H), 2.10 (br d, 1H), 2.19-2.37 (m, 4H), 2.67 (s, 3H), 3.79-3.81 (m, 3H), 4.11-4.18 (m, 1H), 4.43-4.50 (m, 1H), 6.72 (dd, 1H), 6.94-6.98 (m, 1H), 7.66 (d, 1H), 9.43-9.49 (m, 1H). LCMS: m/z 415.2 $[M + H]^+$ |
| 266 | 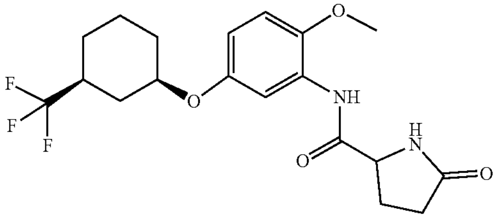 [SMILES: COc1ccc(O[C@@H]2CCC[C@H](C(F)(F)F)C2)cc1NC(=O)C1CCC(=O)N1] Starting material: 5-Oxopyrrolidine-2-carboxylic acid and 2-Methoxy-5-((3-(trifluoro-methyl)cyclohexyl)oxy)aniline | Purification method B. $^1$H NMR (600 MHz, DMSO-$d_6$) δ: 1.16-1.30 (m, 3H), 1.35-1.44 (m, 1H), 1.78-1.86 (m, 2H), 1.93-1.99 (m, 1H), 2.04-2.15 (m, 2H), 2.16-2.24 (m, 2H), 2.29-2.37 (m, 1H), 3.79 (s, 3H), 4.19 (tt, 1H), 4.36 (dd, 1H), 6.70 (dd, 1H), 6.96 (d, 1H), 7.71-7.74 (m, 1H), 7.94 (s, 1H), 9.17 (s, 1H). LCMS: m/z 401.2 $[M + H]^+$ |
| 267 | 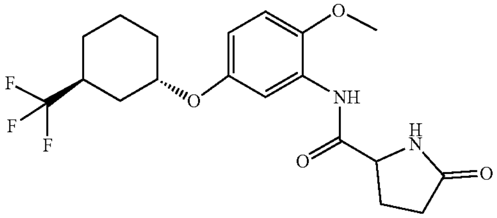 [SMILES: COc1ccc(O[C@H]2CCC[C@H](C(F)(F)F)C2)cc1NC(=O)C1CCC(=O)N1] Starting material: 5-Oxopyrrolidine-2-carboxylic acid and 2-Methoxy-5-((3-(trifluoro-methyl)cyclohexyl)oxy)aniline | Purification method B. $^1$H NMR (600 MHz, DMSO-$d_6$) δ: 1.23-1.36 (m, 1H), 1.43-1.50 (m, 1H), 1.52-1.67 (m, 3H), 1.85-1.90 (m, 2H), 1.94-2.00 (m, 1H), 2.03-2.15 (m, 2H), 2.18-2.24 (m, 1H), 2.29-2.36 (m, 1H), 2.51-2.58 (m, 1H), 3.79 (s, 3H), 4.36 (dd, 1H), 4.62 (br s, 1H), 6.72 (dd, 1H), 6.96 (d, 1H), 7.76 (dd, 1H), 7.94 (s, 1H), 9.19 (s, 1H). LCMS: m/z 401.2 $[M + H]^+$ |

-continued

| No | Structure and starting material | Purification method and characterization data |
|---|---|---|
| 268 | 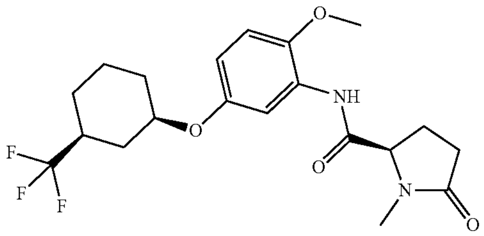 [SMILES: COc1ccc(O[C@@H]2CCC[C@H](C(F)(F)F)C2)cc1NC(=O)[C@H]1CCC(=O)N1C] Starting material: (2R)-1-Methyl-5-oxopyrrolidine-2-carboxylic acid and 2-Methoxy-5-((3-(trifluoromethyl)cyclohexyl)oxy)aniline | Purification method B. $^{1}H$ NMR (600 MHz, DMSO-$d_6$) δ: 1.15-1.29 (m, 3H), 1.35-1.44 (m, 1H), 1.78-1.92 (m, 3H), 2.05 (br d, 1H), 2.16-2.33 (m, 4H), 2.66 (s, 3H), 3.32 (s, 11H), 3.80 (s, 3H), 4.17-4.23 (m, 1H), 4.42-4.46 (m, 1H), 6.72 (dd, 1H), 6.96 (d, 1H), 7.67 (t, 1H), 9.46 (s, 1H). LCMS: m/z 415.2 [M + H]$^+$ |
| 269 | 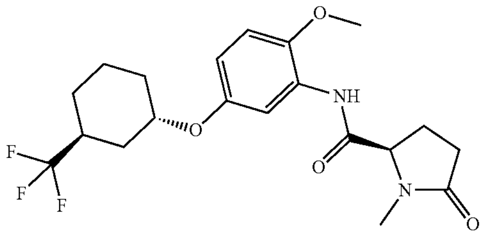 [SMILES: COc1ccc(O[C@H]2CCC[C@H](C(F)(F)F)C2)cc1NC(=O)[C@H]1CCC(=O)N1C] Starting material: (2R)-1-Methyl-5-oxopyrrolidine-2-carboxylic acid and 2-Methoxy-5-((3-(trifluoromethyl)cyclohexyl)oxy)aniline | Purification method B. $^{1}H$ NMR (600 MHz, DMSO-$d_6$) δ: 1.21-1.36 (m, 1H), 1.42-1.50 (m, 1H), 1.53-1.67 (m, 3H), 1.86-1.94 (m, 3H), 2.06 (br d, 1H), 2.18-2.35 (m, 3H), 2.52-2.60 (m, 1H), 2.67 (s, 3H), 3.33 (s, 9H), 3.81 (s, 3H), 4.45 (dd, 1H), 4.63 (br s, 1H), 6.74 (dd, 1H), 6.98 (d, 1H), 7.72 (dd, 1H), 9.49 (s, 1H). LCMS: m/z 415.2 [M + H]$^+$ |
| 270 | 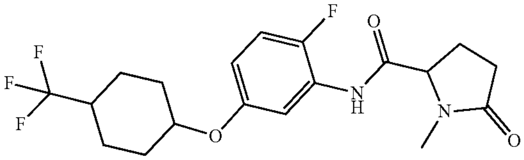 [SMILES: CN1C(=O)CCC1C(=O)Nc1cc(OC2CCC(C(F)(F)F)CC2)ccc1F] Starting material: 1-Methyl-5-oxopyrrolidine-2-carboxylic acid and 2-Fluoro-5-((4-(trifluoromethyl)cyclohexyl)oxy)aniline | Purification method A. $^{1}H$ NMR (600 MHz, DMSO-$d_6$) δ: 1.28-1.48 (m, 4H), 1.88-1.97 (m, 3H), 2.11 (br d, 2H), 2.20-2.39 (m, 4H), 2.67-2.70 (m, 3H) 4.20-4.26 (m, 1H), 4.36-4.41 (m, 1H), 6.77 (dt, 1H), 7.17 (dd, 1H), 7.53 (dd, 1H), 10.03 (s, 1H). LCMS: m/z 403.2 [M + H]$^+$ |
| 271 | 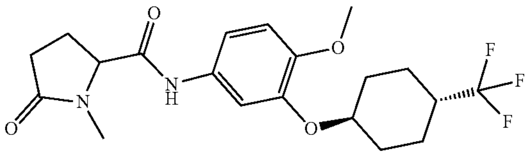 [SMILES: COc1ccc(NC(=O)C2CCC(=O)N2C)cc1O[C@H]1CC[C@H](C(F)(F)F)CC1] Starting material: (2R)-1-Methyl-5-oxopyrrolidine-2-carboxylic acid and 4-Methoxy-3-(((1r,4r)-4-(trifluoromethyl)-cyclohexyl)oxy)aniline | Purification method A. $^{1}H$ NMR (600 MHz, DMSO-$d_6$) δ: 1.34-1.48 (m, 4H), 1.81-2.00 (m, 3H), 2.07-2.16 (m, 2H), 2.19-2.38 (m, 4H), 2.66-2.69 (m, 3H), 3.71 (s, 3H), 4.08-4.21 (m, 2H), 6.92 (d, 1H), 7.16 (dd, 1H), 7.33 (d, 1H), 10.03 (s, 1H). LCMS: m/z 415.2 [M + H]$^+$ |

-continued

| No | Structure and starting material | Purification method and characterization data |
|---|---|---|
| 272 | 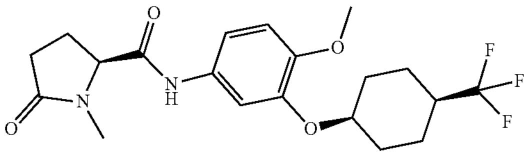 [SMILES: COc1ccc(NC(=O)[C@@H]2CCC(=O)N2C)cc1O[C@H]1CC[C@@H](C(F)(F)F)CC1] Starting material: (2R)-1-Methyl-5-oxopyrrolidine-2-carboxylic acid and 4-Methoxy-3-(((1s,4s)-4-(trifluoromethyl)-cyclohexyl)oxy)aniline | Purification method A. $^{1}$H NMR (600 MHz, DMSO-$d_6$) δ: 1.56-1.71 (m, 7H), 1.77-2.00 (m, 3H), 2.20-2.39 (m, 4H), 2.66 (s, 3H), 3.70-3.80 (m, 3H), 4.16 (dd, 1H), 6.94 (d, 1H), 7.17 (dd, 1H), 7.34 (d, 1H), 10.05 (s, 1H). LCMS: m/z 415.2 $[M + H]^+$ |
| 273 | 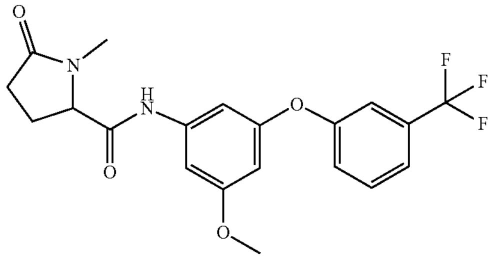 [SMILES: COc1cc(NC(=O)C2CCC(=O)N2C)cc(Oc2cccc(C(F)(F)F)c2)c1] Starting material: 1-Methyl-5-oxopyrrolidine-2-carboxylic acid and 3-Methoxy-5-(3-(trifluoro-methyl)phenoxy)aniline | Purification method A. $^{1}$H NMR (600 MHz, DMSO-$d_6$) δ: 1.87-1.93 (m, 1H), 2.18-2.33 (m, 3H), 2.65 (s, 3H), 3.75 (s, 3H), 4.15-4.20 (m, 1H), 6.45 (t, 1H), 6.90 (t, 1H), 7.16 (t, 1H), 7.34 (dd, 1H), 7.37 (s, 1H), 7.53 (d, 1H), 7.65 (t, 1H), 10.30 (br s, 1H). LCMS: m/z 409.1 $[M + H]^+$ |
| 274 | 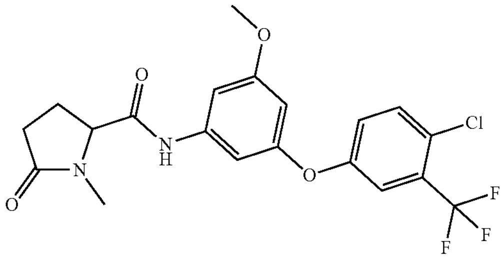 [SMILES: COc1cc(NC(=O)C2CCC(=O)N2C)cc(Oc2ccc(Cl)c(C(F)(F)F)c2)c1] Starting material: 1-Methyl-5-oxopyrrolidine-2-carboxylic acid and 3-(4-Chloro-3-(trifluoro-methyl)phenoxy)-5-methoxy-aniline | Purification method A. $^{1}$H NMR (600 MHz, DMSO-$d_6$) δ: 1.86-1.93 (m, 1H), 2.18-2.30 (m, 3H), 2.65 (s, 3H), 3.74 (s, 3H), 4.17 (dd, 1H), 6.47 (t, 1H), 6.90 (t, 1H), 7.16 (t, 1H), 7.33 (dd, 1H), 7.50 (d, 1H), 7.74 (d, 1H), 10.30 (s, 1H). LCMS: m/z 443.1 $[M + H]^+$ |
| 275 | 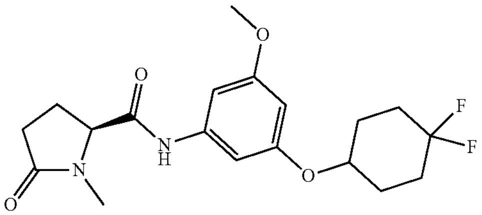 [SMILES: COc1cc(NC(=O)[C@@H]2CCC(=O)N2C)cc(OC2CCC(F)(F)CC2)c1] Starting material: (2R)-1-Methyl-5-oxopyrrolidine-2-carboxylic acid and 3-((4,4-Di-fluorocyclohexyl)oxy)-5-methoxyaniline | Purification method A. $^{1}$H NMR (600 MHz, DMSO-$d_6$) δ: 1.79-1.85 (m, 2H), 1.87-2.07 (m, 7H), 2.18-2.35 (m, 3H), 2.67 (s, 3H), 3.72 (s, 3H), 4.14-4.22 (m, 1H), 6.32 (t, 1H), 6.86 (t, 1H), 6.94 (t, 1H), 10.16 (s, 1H). LCMS: m/z 383.2 $[M + H]^+$ |

-continued

| No | Structure and starting material | Purification method and characterization data |
|---|---|---|
| 276 | 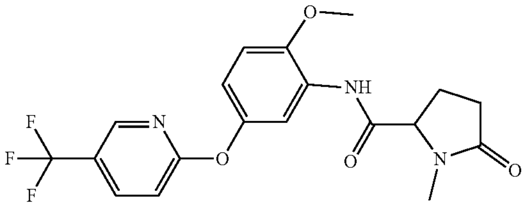 [SMILES: COc1ccc(Oc2ccc(C(F)(F)F)cn2)cc1NC(=O)C1CCC(=O)N1C] Starting material: 1-Methyl-5-oxopyrrolidine-2-carboxylic acid and 2-Methoxy-5-((5-(trifluoro-methyl)pyridin-2-yl)oxy)aniline | Purification method A. $^1$H NMR (600 MHz, DMSO-$d_6$) δ: 1.79-1.86 (m, 1H), 2.09-2.23 (m, 3H), 2.58 (s, 3H), 3.82 (s, 3H), 4.37-4.43 (m, 1H), 6.89 (dd, 1H), 7.05 (d, 1H), 7.13 (d, 1H), 7.81 (d, 1H), 8.14 (dd, 1H), 8.48 (dd, 1H), 9.56 (s, 1H). LCMS: m/z 410.3 [M + H]$^+$ |
| 277 | 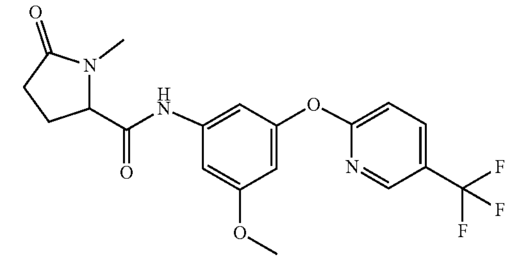 [SMILES: COc1cc(NC(=O)C2CCC(=O)N2C)cc(Oc2ccc(C(F)(F)F)cn2)c1] Starting material: 1-Methyl-5-oxopyrrolidine-2-carboxylic acid and 3-Methoxy-5-((5-(trifluoro-methyl)pyridin-2-yl)oxy)aniline | Purification method A. $^1$H NMR (600 MHz, DMSO-$d_6$) δ: 1.82-1.88 (m, 1H), 2.12-2.25 (m, 3H), 2.59 (s, 3H), 3.67 (s, 3H), 4.10-4.14 (m, 1H), 6.49 (t, 1H), 7.02 (t, 1H), 7.08 (t, 1H), 7.17 (d, 1H), 8.17 (dd, 1H), 8.53 (dd, 1H), 10.26 (s, 1H). LCMS: m/z 410.3 [M + H]$^+$ |
| 278 | 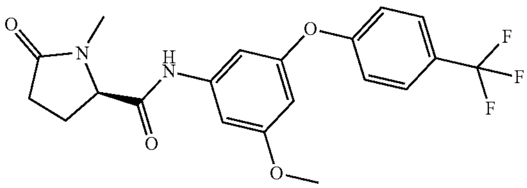 [SMILES: COc1cc(NC(=O)[C@H]2CCC(=O)N2C)cc(Oc2ccc(C(F)(F)F)cc2)c1] Starting material: (2R)-1-Methyl-5-oxopyrrolidine-2-carboxylic acid and 3-Methoxy-5-(4-(trifluoromethyl)phenoxy)-aniline | $^1$H NMR (600 MHz, DMSO-$d_6$) δ: 1.85-1.98 (m, 1H), 2.17-2.33 (m, 3H), 2.65 (s, 3H), 3.70-3.75 (m, 3H), 4.08-4.19 (m, 1H), 6.48 (s, 1H), 6.94 (t, 1H), 7.15-7.20 (m, 3H), 7.75 (d, 2H), 10.30 (s, 1H). LCMS: m/z 409.1 [M + H]$^+$ |
| 279 | 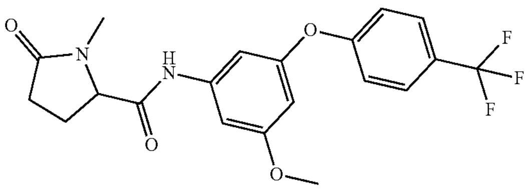 [SMILES: COc1cc(NC(=O)C2CCC(=O)N2C)cc(Oc2ccc(C(F)(F)F)cc2)c1] Starting material: 1-Methyl-5-oxopyrrolidine-2-carboxylic acid and 3-Methoxy-5-(4-(trifluoro-methyl)phenoxy)aniline | Purification method A. $^1$H NMR (600 MHz, DMSO-$d_6$) δ: 1.87-1.93 (m, 1H), 2.18-2.33 (m, 3H), 2.65 (s, 3H), 3.74 (s, 3H), 4.15-4.23 (m, 1H), 6.48 (t, 1H), 6.94 (t, 1H), 7.16-7.21 (m, 3H), 7.75 (d, 2H), 10.30 (s, 1H). LCMS: m/z 409.1 [M + H]$^+$ |

-continued

| No | Structure and starting material | Purification method and characterization data |
|---|---|---|
| 280 | 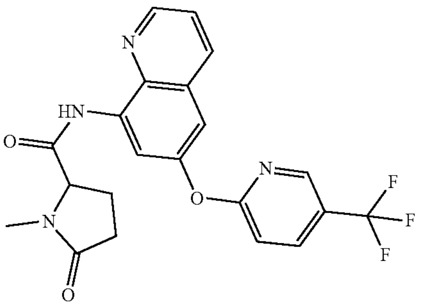 [SMILES: CN1C(=O)CCC1C(=O)Nc1cc(Oc2ccc(C(F)(F)F)cn2)cc2cccnc12] Starting material: 1-Methyl-5-oxopyrrolidine-2-carboxylic acid and 6-((5-(Trifluoromethyl)-pyridin-2-yl)oxy)quinolin-8-amine | Purification method A. $^1H$ NMR (600 MHz, DMSO-$d_6$) δ: 1.86-2.09 (m, 1H), 2.18-2.43 (m, 3H), 2.72 (s, 3H), 4.69-4.72 (m, 1H), 7.55 (s, 1H), 7.62 (s, 1H), 7.68 (dd, 1H), 8.40-8.44 (m, 2H), 8.49 (d, 1H), 8.95 (dd, 1H), 10.60 (s, 1H). LCMS: m/z 431.1 $[M + H]^+$ |
| 281 | 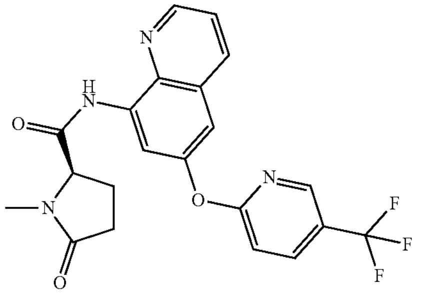 [SMILES: CN1C(=O)CC[C@@H]1C(=O)Nc1cc(Oc2ccc(C(F)(F)F)cn2)cc2cccnc12] Starting material: (2R)-1-Methyl-5-oxopyrrolidine-2-carboxylic acid and 6-((5-(Trifluoromethyl)pyridin-2-yl)oxy)-quinolin-8-amine | Purification method A. $^1H$ NMR (600 MHz, DMSO-$d_6$) δ: 1.86-2.46 (m, 4H), 2.72 (s, 3H), 4.71 (dd, 1H), 7.55 (s, 1H), 7.62 (s, 1H), 7.68 (dd, 1H), 8.40-8.44 (m, 2H), 8.49 (d, 1H), 8.95 (dd, 1H), 10.60 (s, 1H). LCMS: m/z 431.1 $[M + H]^+$ |
| 282 | 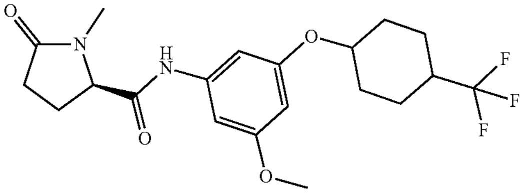 [SMILES: COc1cc(NC(=O)[C@H]2CCC(=O)N2C)cc(OC2CCC(C(F)(F)F)CC2)c1] Starting material: (2R)-1-Methyl-5-oxopyrrolidine-2-carboxylic acid and 3-Methoxy-5-((4-(trifluoromethyl)cyclohexyl)oxy)aniline | Purification method A. $^1H$ NMR (600 MHz, DMSO-$d_6$) δ: 1.36-1.49 (m, 4H), 1.87-1.95 (m, 4H), 2.11-2.40 (m, 5H), 2.67 (s, 3H), 3.71 (s, 3H), 4.14-4.28 (m, 2H), 6.27 (t, 1H), 6.86 (d, 2H), 10.13 (s, 1H). LCMS: m/z 415.2 $[M + H]^+$ |
| 283 | 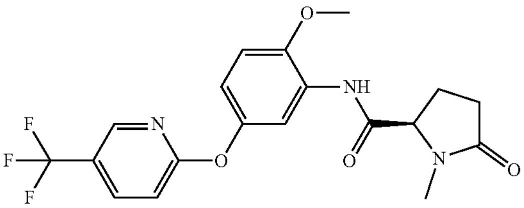 [SMILES: COc1ccc(Oc2ccc(C(F)(F)F)cn2)cc1NC(=O)[C@H]1CCC(=O)N1C] Starting material: (2R)-1-Methyl-5-oxopyrrolidine-2-carboxylic acid and 2-Methoxy-5-((5-(trifluoromethyl)pyridin-2-yl)oxy)aniline | Purification method A. $^1H$ NMR (600 MHz, DMSO-$d_6$) δ: 1.85-1.92 (m, 1H), 2.16-2.35 (m, 3H), 2.65 (s, 3H), 3.89 (s, 3H), 4.44-4.49 (m, 1H), 6.96 (dd, 1H), 7.12 (d, 1H), 7.19 (d, 1H), 7.88 (d, 1H), 8.21 (dd, 1H), 8.54-8.55 (m, 1H), 9.63 (s, 1H). LCMS: m/z 410.2 $[M + H]^+$ |

-continued

| No | Structure and starting material | Purification method and characterization data |
|---|---|---|
| 284 | 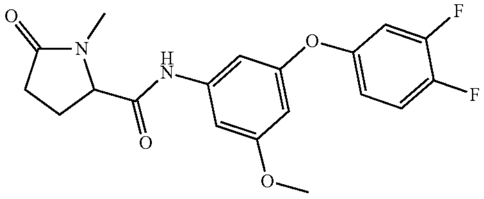 [SMILES: COc1cc(NC(=O)C2CCC(=O)N2C)cc(Oc2ccc(F)c(F)c2)c1]<br>Starting material: 1-Methyl-5-oxopyrrolidine-2-carboxylic acid and 3-(3,4-Difluorophenoxy)-5-methoxyaniline | Purification method A.<br>$^{1}$H NMR (600 MHz, DMSO-$d_6$) δ: 1.84-1.92 (m, 1H), 2.18-2.32 (m, 3H), 2.64 (s, 3H), 3.73 (s, 3H), 4.13-4.19 (m, 1H), 6.38 (t, 1H), 6.85 (t, 1H), 6.91 (dtd, 1H), 7.11 (s, 1H), 7.25 (ddd, 1H), 7.48 (dt, 1H), 10.25 (s, 1H). LCMS: m/z 377.2 $[M + H]^+$ |
| 285 | 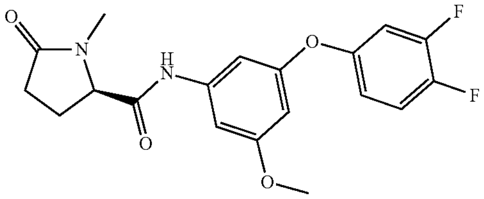 [SMILES: COc1cc(NC(=O)[C@H]2CCC(=O)N2C)cc(Oc2ccc(F)c(F)c2)c1]<br>Starting material: (2R)-1-Methyl-5-oxopyrrolidine-2-carboxylic acid and 3-(3,4-Difluorophenoxy)-5-methoxyaniline | Purification method A.<br>$^{1}$H NMR (600 MHz, DMSO-$d_6$) δ: 1.84-1.97 (m, 1H), 2.16-2.33 (m, 3H), 2.61-2.69 (m, 3H), 3.73 (s, 3H), 4.03-4.19 (m, 1H), 6.38 (t, 1H), 6.85 (t, 1H), 6.91 (d, 1H), 7.11 (s, 1H), 7.25 (ddd, 1H), 7.48 (dt, 1H), 10.25 (s, 1H). LCMS: m/z 377.2 $[M + H]^+$ |
| 286 | 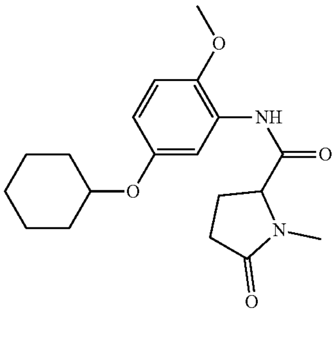 [SMILES: COc1ccc(OC2CCCCC2)cc1NC(=O)C1CCC(=O)N1C]<br>Starting materials: 1-Methyl-5-oxopyrrolidine-2-carboxylic acid and 5-(Cyclohexyloxy)-2-methoxyaniline | Purification method A.<br>$^{1}$H NMR (400 MHz, $CDCl_3$) δ: 8.06 (d, 1H), 8.01 (br s, 1H), 6.78 (d, 1H), 6.63 (dd, 1H), 4.16 (tt, 1H), 4.09 (dd, 1H), 3.83 (s, 3H), 2.93 (s, 3H), 2.65-2.53 (m, 1H), 2.53-2.35 (m, 2H), 2.20-2.12 (m, 1H), 1.95 (m, 2H), 1.77 (m, 2H), 1.57-1.45 (m, 3H), 1.40-1.27 (m, 3H). LCMS: m/z 347.3 $[M + H]^+$ |

-continued

| No | Structure and starting material | Purification method and characterization data |
|---|---|---|
| 287 | 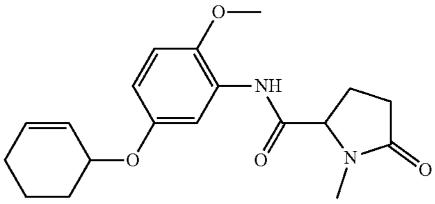 [SMILES: COc1ccc(OC2C=CCCC2)cc1NC(=O)C1CCC(=O)N1C] Starting materials: 5-(Cyclohex-2-en-1-yloxy)-2-methoxyaniline and 1-Methyl-5-oxopyrrolidine-2-carboxylic acid | Purification method A. $^1H$ NMR ($CDCl_3$, 400 MHz) δ: 8.06-8.14 (m, 1H), 8.03 (s, 1H), 6.76-6.81 (m, 1H), 6.61-6.69 (m, 1H), 5.90-6.01 (m, 1H), 5.80-5.90 (m, 1H), 4.72 (br s, 1H), 4.06-4.14 (m, 1H), 3.81-3.88 (m, 3H), 2.93 (s, 3H), 2.51-2.65 (m, 1H), 2.36-2.52 (m, 2H), 1.54-1.66 (m, 1H), 1.54-2.23 (m, 7H). LCMS: m/z 345.240 $(M + H)^+$ |
| 288 | 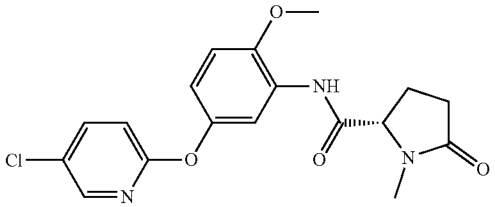 [SMILES: COc1ccc(Oc2ccc(Cl)cn2)cc1NC(=O)[C@@H]1CCC(=O)N1C] Starting materials: 5-((5-Chloropyridin-2-yl)oxy)-2-methoxyaniline and (S)-1-Methyl-5-oxopyrrolidine-2-carboxylic acid | Purification method A. $^1H$ NMR (600 MHz, DMSO-$d_6$) δ: 9.60 (br. s, 1H), 8.18 (dd, 1H), 7.93 (dd, 1H), 7.83 (d, 1H), 7.09 (d, 1H), 7.05 (dd, 1H), 6.90 (dd, 1H), 4.46 (m, 1H), 3.87 (s, 3H), 2.65 (s, 3H), 2.30-2.16 (m, 3H), 1.92-1.86 (m, 1H). LCMS: m/z 376.126 $(M + H)^+$ |
| 289 | 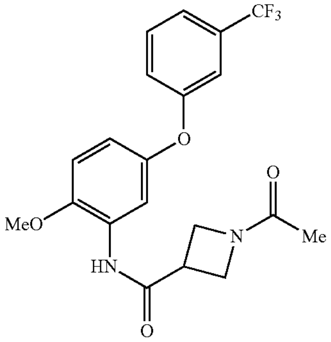 [SMILES: COc1ccc(Oc2cccc(C(F)(F)F)c2)cc1NC(=O)C1CN(C(C)=O)C1] Starting materials: 2-Methoxy-5-(3-(trifluoromethyl)phenoxy)aniline and 1-Acetylazetidine-3-carboxylic acid | Purification method C. $^1H$ NMR ($CDCl_3$, 400 MHz) δ: 8.22 (d, 1H), 7.89 (br s, 1H), 7.40 (app t, 1H), 7.29 (app dt, 1H), 7.16 (m, 1H), 7.12 (m, 1H), 6.88 (d, 1H), 6.77 (dd, 1H), 4.45 (dd, 1H), 4.16-4.32 (m, 3H), 3.91 (s, 3H), 3.45 (tt, 1H), 1.88 (s, 3H). LCMS: m/z 409.159 $(M + H)^+$ |

Example 12. (R)—N-(2-methoxy-5-(4-(trifluoromethoxy)phenoxy)phenyl)-1-methyl-5-oxopyrrolidine-2-carboxamide (Compound 290)

Compound 290

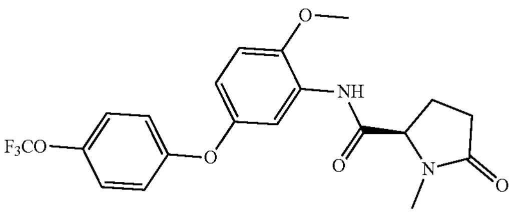

To a mixture of 2-methoxy-5-(4-(trifluoromethoxy)phenoxy)aniline (0.060 g, 0.20 mmol), (2R)-1-methyl-5-oxopyrrolidine-2-carboxylic acid (0.029 g, 0.20 mmol) and HATU (0.114 g, 0.30 mmol) in dry DMF (1.0 ml) was added DIPEA (0.174 ml, 1.00 mmol). The mixture was stirred overnight at RT. The mixture was diluted with EtOAc and washed with water and brine. Organic phase was dried and evaporated. The crude product was purified by reverse phase flash chromatography to afford 0.056 g of the of the title compound. $^1H$ NMR (400 MHz, $CDCl_3$) δ: 8.17 (d, 1H), 8.07 (s, 1H), 7.11-7.18 (m, 2H), 6.91-6.98 (m, 2H), 6.87 (d, 1H), 6.77 (dd, 1H), 4.07-4.14 (m, 1H), 3.90 (s, 3H), 2.94 (s, 3H), 2.37-2.63 (m, 3H), 2.10-2.20 (m, 1H). LCMS: m/z 425.0 $[M+H]^+$ The following compounds were prepared according to the procedure described for Compound 290. The compound number, structure, starting materials, purification method and characterization data are indicated in the table.

| No | Structure and starting material | Characterization data |
|---|---|---|
| 291 | 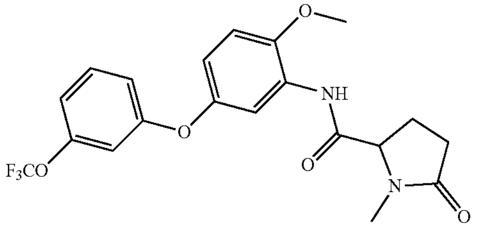 [SMILES: COc1ccc(Oc2cccc(OC(F)(F)F)c2)cc1NC(=O)C1CCC(=O)N1C] Starting material: 2-Methoxy-5-(3-(trifluoromethoxy)-phenoxy)aniline and 1-Methyl-5-oxopyrrolidine-2-carboxylic acid | $^1$H NMR (400 MHz, $CDCl_3$) δ: 8.19 (d, 1H), 8.08 (s, 1H), 7.29 (t, 1H), 6.85-6.92 (m, 3H), 6.77-6.82 (m, 2H), 4.08-4.14 (m, 1H), 3.91 (s, 3H), 2.94 (s, 3H), 2.37-2.63 (m, 3H), 2.11-2.20 (m, 1H). LCMS: m/z 425.1 $[M + H]^+$ |
| 292 | 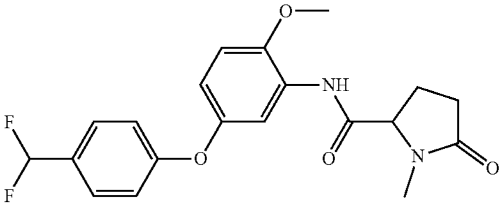 [SMILES: COc1ccc(Oc2ccc(C(F)F)cc2)cc1NC(=O)C1CCC(=O)N1C] Starting material: 5-(4-(Difluoro-methyl)phenoxy)-2-methoxyaniline and 1-Methyl-5-oxopyrrolidine-2-carboxylic acid | $^1$H NMR (400 MHz, $CDCl_3$) δ: 8.18 (d, 1H), 8.07 (s, 1H), 7.40-7.48 (m, 2H), 6.95-7.05 (m, 2H), 6.89 (d, 1H), 6.80 (dd, 1H), 6.61 (t, 1H), 4.07-4.14 (m, 1H), 3.91 (s, 3H), 2.94 (s, 3H), 2.37-2.63 (m, 3H), 2.11-2.20 (m, 1H). LCMS: m/z 391.1 $[M + H]^+$ |
| 293 | 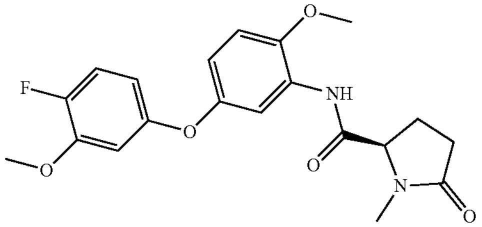 [SMILES: COc1cc(Oc2ccc(OC)c(NC(=O)[C@H]3CCC(=O)N3C)c2)ccc1F] Starting material: 5-(4-Fluoro-3-methoxyphenoxy)-2-methoxyaniline and (2R)-1-Methyl-5-oxopyrrolidine-2-carboxylic acid | $^1$H NMR (400 MHz, $CDCl_3$) δ: 8.13 (d, 1H), 8.05 (s, 1H), 6.98 (dd, 1H), 6.85 (d, 1H), 6.74 (dd, 1H), 6.66 (dd, 1H), 6.39-6.46 (m, 1H), 4.07-4.13 (m, 1H), 3.89 (s, 3H), 3.84 (s, 3H), 2.94 (s, 3H), 2.37-2.63 (m, 3H), 2.10-2.20 (m, 1H). LCMS: m/z 389.1 $[M + H]^+$ |
| 294 | 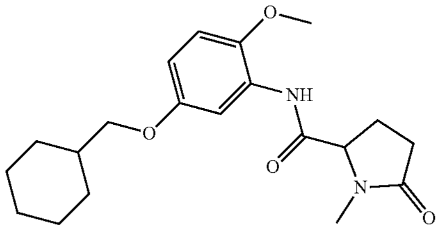 [SMILES: COc1ccc(OCC2CCCCC2)cc1NC(=O)C1CCC(=O)N1C] Starting material: 5-(Cyclohexyl-methoxy)-2-methoxyaniline and 1-Methyl-5-oxopyrrolidine-2-carboxylic acid | $^1$H NMR (400 MHz, $CDCl_3$) δ: 8.05 (d, 1H), 8.03 (s, 1H), 6.80 (d, 1H), 6.61 (dd, 1H), 4.11 (dd, 1H), 3.84 (s, 3H), 3.72 (d, 2H), 2.93 (s, 3H), 2.54-2.66 (m, 1H), 2.36-2.54 (m, 2H), 2.11-2.21 (m, 1H), 1.81-1.91 (m, 2H), 1.63-1.81 (m, 4H), 1.12-1.36 (m, 3H), 0.96-1.10 (m, 2H). LCMS: m/z 361.1 $[M + H]^+$ |

-continued

| No | Structure and starting material | Characterization data |
|---|---|---|
| 295 | 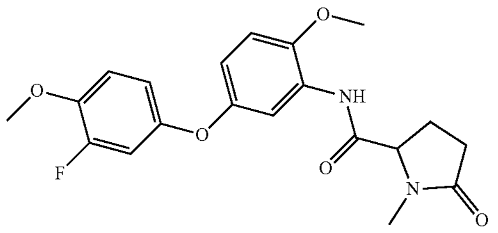 [SMILES: COc1ccc(Oc2ccc(OC)c(NC(=O)C3CCC(=O)N3C)c2)cc1F] Starting material: 5-(3-Fluoro-4-methoxyphenoxy)-2-methoxyaniline and 1-Methyl-5-oxopyrrolidine-2-carboxylic acid | $^1$H NMR (400 MHz, $CDCl_3$) δ: 8.12 (d, 1H), 8.05 (s, 1H), 6.81-6.95 (m, 2H), 6.67-6.79 (m, 3H), 4.06-4.14 (m, 1H), 3.89 (s, 3H), 3.87 (s, 3H), 2.93 (s, 3H), 2.36-2.64 (m, 3H), 2.10-2.21 (m, 1H). LCMS: m/z 389.0 $[M + H]^+$ |
| 296 | 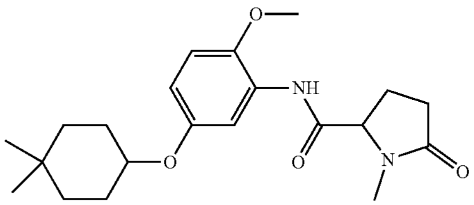 [SMILES: COc1ccc(OC2CCC(C)(C)CC2)cc1NC(=O)C1CCC(=O)N1C] Starting material: 5-((4,4-Dimethyl-cyclohexyl)oxy)-2-methoxyaniline and 1-Methyl-5-oxopyrrolidine-2-carboxylic acid | $^1$H NMR (400 MHz, $CDCl_3$) δ: 8.07 (d, 1H), 8.03 (s, 1H), 6.79 (d, 1H), 6.64 (dd, 1H), 4.06-4.22 (m, 2H), 3.84 (s, 3H), 2.93 (s, 3H), 2.36-2.67 (m, 3H), 2.11-2.23 (m, 1H), 1.78-1.91 (m, 2H), 1.58-1.70 (m, 2H), 1.43-1.57 (m, 2H), 1.18-1.32 (m, 2H), 0.96 (s, 3H), 0.93 (s, 3H). LCMS: m/z 375.4 $[M + H]^+$ |
| 297 | 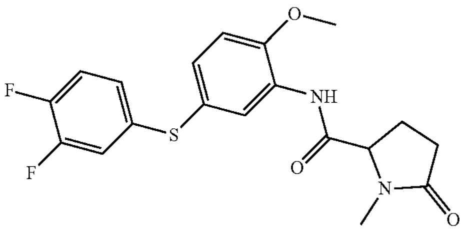 [SMILES: COc1ccc(Sc2ccc(F)c(F)c2)cc1NC(=O)C1CCC(=O)N1C] Starting material: 5-((3,4-Difluoro-phenyl)thio)-2-methoxyaniline and 1-Methyl-5-oxopyrrolidine-2-carboxylic acid | $^1$H NMR (400 MHz, $CDCl_3$) δ: 8.51 (d, 1H), 8.02 (s, 1H), 7.21 (dd, 1H), 6.94-7.10 (m, 3H), 6.90 (d, 1H), 4.08-4.14 (m, 1H), 3.92 (s, 3H), 2.94 (s, 3H), 2.37-2.65 (m, 3H), 2.11-2.20 (m, 1H). LCMS: m/z 393.3 $[M + H]^+$ |
| 298 | 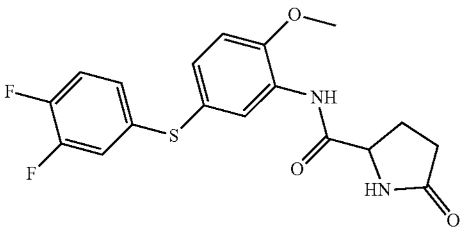 [SMILES: COc1ccc(Sc2ccc(F)c(F)c2)cc1NC(=O)C1CCC(=O)N1] Starting material: 5-((3,4-Difluoro-phenyl)thio)-2-methoxyaniline and 5-Oxopyrrolidine-2-carboxylic acid | $^1$H NMR (400 MHz, $CDCl_3$) δ: 8.51 (d, 1H), 8.30 (s, 1H), 7.20 (dd, 1H), 6.92-7.10 (m, 1H), 6.89 (d, 1H), 6.36 (s, 1H), 4.30 (ddd, 1H), 3.92 (s, 3H), 2.57-2.70 (m, 1H), 2.45-2.57 (m, 1H), 2.22-2.45 (m, 2H). LCMS: m/z 379.2 $[M + H]^+$ |

-continued

| No | Structure and starting material | Characterization data |
|---|---|---|
| 299 | 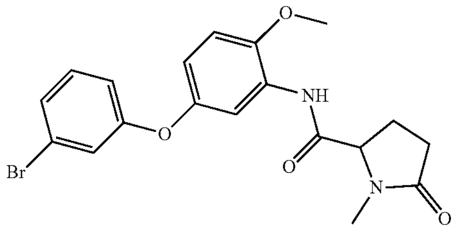 [SMILES: COc1ccc(Oc2cccc(Br)c2)cc1NC(=O)C1CCC(=O)N1C] Starting material: 5-(3-Bromo-phenoxy)-2-methoxyaniline and 1-Methyl-5-oxopyrrolidine-2-carboxylic acid | $^{1}H$ NMR (600 MHz, $CDCl_3$) δ: 8.16 (d, 1H), 8.06 (s, 1H), 7.13-7.18 (m, 2H), 7.04-7.07 (m, 1H), 6.89-6.92 (m, 1H), 6.87 (d, 1H), 6.77 (dd, 1H), 4.10 (dd, 1H), 3.91 (s, 3H), 2.94 (s, 3H), 2.54-2.62 (m, 1H), 2.38-2.52 (m, 2H), 2.12-2.19 (m, 1H). LCMS: m/z 419.2 $[M + H]^+$ |
| 300 | 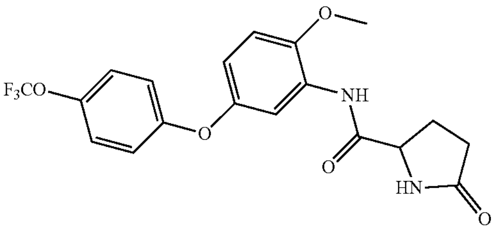 [SMILES: COc1ccc(Oc2ccc(OC(F)(F)F)cc2)cc1NC(=O)C1CCC(=O)N1] Starting material: 2-Methoxy-5-(4-(trifluoromethoxy)-phenoxy)aniline and 5-Oxopyrrolidine-2-carboxylic acid | $^{1}H$ NMR (600 MHz, $CDCl_3$) δ: 8.34 (s, 1H), 8.16 (d, 1H), 7.11-7.16 (m, 2H), 6.91-6.96 (m, 2H), 6.86 (d, 1H), 6.76 (dd, 1H), 6.39 (s, 1H), 4.29 (ddd, 1H), 3.89 (s, 3H), 2.58-2.67 (m, 1H), 2.46-2.54 (m, 1H), 2.34-2.42 (m, 1H), 2.24-2.32 (m, 1H). LCMS: m/z 411.3 $[M + H]^+$ |
| 301 | 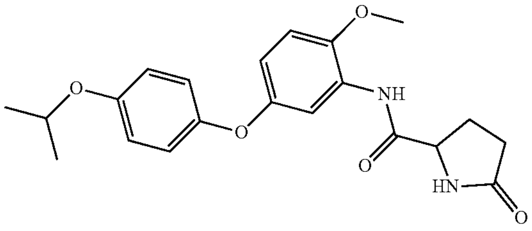 [SMILES: COc1ccc(Oc2ccc(OC(C)C)cc2)cc1NC(=O)C1CCC(=O)N1] Starting material: 5-(4-Isopropoxy-phenoxy)-2-methoxyaniline and 5-Oxopyrrolidine-2-carboxylic acid | $^{1}H$ NMR (400 MHz, $CDCl_3$) δ: 8.30 (s, 1H), 8.11 (d, 1H), 6.87-6.93 (m, 2H), 6.78-6.87 (m, 3H), 6.69 (dd, 1H), 6.22 (s, 1H), 4.46 (sept, 1H), 4.28 (ddd, 1H), 3.87 (s, 3H), 2.56-2.68 (m, 1H), 2.44-2.56 (m, 1H), 2.33-2.44 (m, 1H), 2.22-2.33 (m, 1H), 1.32 (d, 6H). LCMS: m/z 385.2 $[M + H]^+$ |
| 302 | 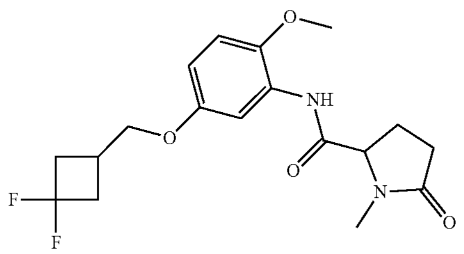 [SMILES: COc1ccc(OCC2CC(F)(F)C2)cc1NC(=O)C1CCC(=O)N1C] Starting material: 5-((3,3-Difluoro-cyclobutyl)methoxy)-2-methoxy-aniline and 1-Methyl-5-oxopyrrolidine-2-carboxylic acid | $^{1}H$ NMR (600 MHz, $CDCl_3$) δ: 8.07 (d, 1H), 8.04 (s, 1H), 6.81 (d, 1H), 6.62 (dd, 1H), 4.09-4.13 (m, 1H), 3.97 (d, 2H), 3.85 (s, 3H), 2.93 (s, 3H), 2.65-2.75 (m, 2H), 2.54-2.63 (m, 2H), 2.38-2.53 (m, 4H), 2.12-2.19 (m, 1H). LCMS: m/z 369.3 $[M + H]^+$ |

-continued

| No | Structure and starting material | Characterization data |
|---|---|---|
| 303 | 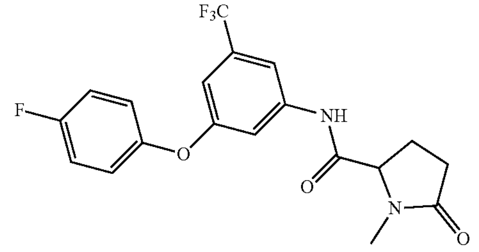 [SMILES: CN1C(=O)CCC1C(=O)Nc1cc(Oc2ccc(F)cc2)cc(C(F)(F)F)c1] Starting material: 5-((3,3-Difluoro-cyclobutyl)methoxy)-2-methoxy-aniline and 1-Methyl-5-oxopyrrolidine-2-carboxylic acid | $^1$H NMR (400 MHz, $CDCl_3$) δ: 9.23 (s, 1H), 7.78-7.85 (m, 1H), 7.48-7.55 (m, 1H), 6.99-7.12 (m, 4H), 6.94-6.99 (m, 1H), 4.16 (dd, 1H), 2.84 (s, 3H), 2.44-2.60 (m, 2H), 2.24-2.39 (m, 1H), 2.09-2.22 (m, 1H). LCMS: m/z 397.5 $[M + H]^+$ |
| 304 | 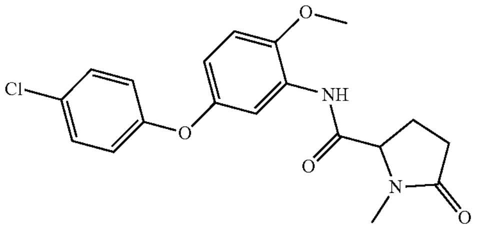 [SMILES: COc1ccc(Oc2ccc(Cl)cc2)cc1NC(=O)C1CCC(=O)N1C] Starting material: 5-(4-Chloro-phenoxy)-2-methoxyaniline and 1-Methyl-5-oxopyrrolidine-2-carboxylic acid | $^1$H NMR (400 MHz, $CDCl_3$) δ: 8.14 (d, 1H), 8.05 (s, 1H), 7.21-7.28 (m, 2H), 6.82-6.92 (m, 3H), 6.75 (dd, 1H), 4.09 (dd, 1H), 3.89 (s, 3H), 2.93 (s, 3H), 2.36-2.65 (m, 3H), 2.09-2.22 (m, 1H). LCMS: m/z 375.0 $[M + H]^+$ |
| 305 | 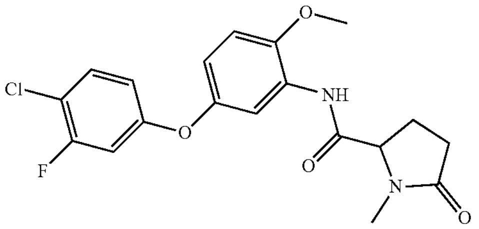 [SMILES: COc1ccc(Oc2ccc(Cl)c(F)c2)cc1NC(=O)C1CCC(=O)N1C] Starting material: 5-(4-Chloro-3-fluorophenoxy)-2-methoxyaniline and 1-Methyl-5-oxopyrrolidine-2-carboxylic acid | $^1$H NMR (400 MHz, $CDCl_3$) δ: 8.17 (d, 1H), 8.07 (s, 1H), 7.22-7.34 (m, 1H), 6.88 (d, 1H), 6.78 (dd, 1H), 6.63-6.75 (m, 2H), 4.04-4.16 (m, 1H), 3.91 (s, 3H), 2.94 (s, 3H), 2.34-2.65 (m, 3H), 2.08-2.22 (m, 1H). LCMS: m/z 393.1 $[M + H]^+$ |
| 306 | 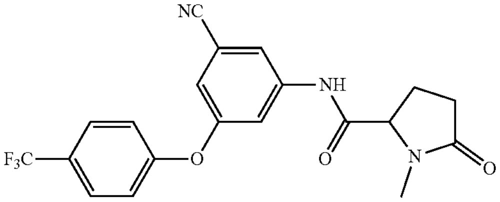 [SMILES: CN1C(=O)CCC1C(=O)Nc1cc(C#N)cc(Oc2ccc(C(F)(F)F)cc2)c1] Starting material: 3-Amino-5-(4-(trifluoromethyl)-phenoxy)benzo-nitrile and 1-Methyl-5-oxopyrrolidine-2-carboxylic acid | $^1$H NMR (400 MHz, $d_6$-DMSO) δ: 10.6 (s, 1H), 7.94 (s, 1H), 7.75-7.86 (m, 2H), 7.53-7.61 (m, 1H), 7.39-7.47 (m, 1H), 7.23-7.34 (m, 2H), 4.15-4.25 (m, 1H), 2.67 (s, 3H), 2.16-2.38 (m, 3H), 1.85-1.99 (m, 1H). LCMS: m/z 404.4 $[M + H]^+$ |

-continued

| No | Structure and starting material | Characterization data |
|---|---|---|
| 307 | 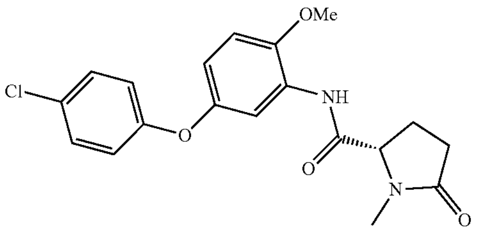 [SMILES: COc1ccc(Oc2ccc(Cl)cc2)cc1NC(=O)[C@@H]1CCC(=O)N1C] Starting material: 5-(4-Chloro-phenoxy)-2-methoxyaniline and (S)-1-Methyl-5-oxopyrrolidine-2-carboxylic acid | $^1$H NMR (400 MHz, $CDCl_3$) δ: 8.14 (d, 1H), 8.05 (s, 1H), 7.21-7.28 (m, 2H), 6.86-6.92 (m, 2H), 6.86 (d, 1H), 6.75 (dd, 1H), 4.09 (dd, 1H), 3.89 (s, 3H), 2.93 (s, 3H), 2.36-2.63 (m, 3H), 2.09-2.19 (m, 1H). LCMS: m/z 375.1 $[M + H]^+$ |
| 308 | 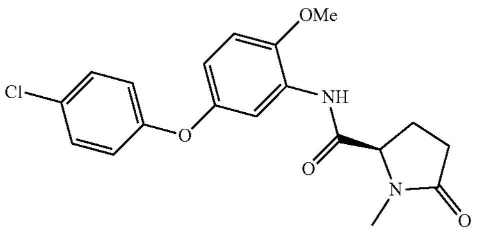 [SMILES: COc1ccc(Oc2ccc(Cl)cc2)cc1NC(=O)[C@H]1CCC(=O)N1C] Starting material: 5-(4-Chloro-phenoxy)-2-methoxyaniline and (R)-1-Methyl-5-oxopyrrolidine-2-carboxylic acid | $^1$H NMR (400 MHz, $CDCl_3$) δ: 8.14 (d, 1H), 8.05 (s, 1H), 7.21-7.28 (m, 2H), 6.86-6.92 (m, 2H), 6.86 (d, 1H), 6.75 (dd, 1H), 4.09 (dd, 1H), 3.89 (s, 3H), 2.93 (s, 3H), 2.36-2.63 (m, 3H), 2.09-2.19 (m, 1H). LCMS: m/z 375.1 $[M + H]^+$ |
| 309 | 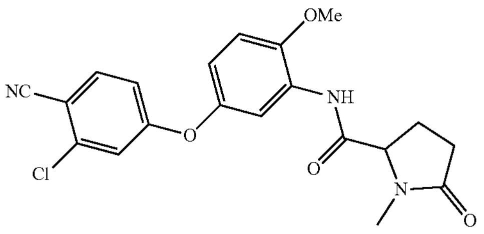 [SMILES: COc1ccc(Oc2ccc(C#N)c(Cl)c2)cc1NC(=O)C1CCC(=O)N1C] Starting material: 4-(3-Amino-4-methoxyphenoxy)-2-chlorobenzo-nitrile and 1-Methyl-5-oxopyrrolidine-2-carboxylic acid | $^1$H NMR (400 MHz, $CDCl_3$) δ: 8.20 (d, 1H), 8.11 (s, 1H), 7.57 (d, 1H), 6.98 (d, 1H), 6.93 (d, 1H), 6.90 (dd, 1H), 6.82 (dd, 1H), 4.12 (dd, 1H), 3.94 (s, 3H), 2.94 (s, 3H), 2.37-2.65 (m, 3H), 2.10-2.21 (m, 1H). LCMS: m/z 400.1 $[M + H]^+$ |
| 310 | 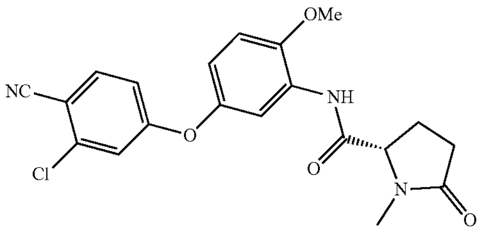 [SMILES: COc1ccc(Oc2ccc(C#N)c(Cl)c2)cc1NC(=O)[C@@H]1CCC(=O)N1C] Starting material: 4-(3-Amino-4-methoxyphenoxy)-2-chlorobenzo-nitrile and (S)-1-Methyl-5-oxopyrrolidine-2-carboxylic acid | $^1$H NMR (400 MHz, $CDCl_3$) δ: 8.20 (d, 1H), 8.11 (s, 1H), 7.57 (d, 1H), 6.98 (d, 1H), 6.93 (d, 1H), 6.90 (dd, 1H), 6.82 (dd, 1H), 4.12 (dd, 1H), 3.94 (s, 3H), 2.94 (s, 3H), 2.37-2.65 (m, 3H), 2.10-2.21 (m, 1H). LCMS: m/z 400.1 $[M + H]^+$ |

-continued

| No | Structure and starting material | Characterization data |
|---|---|---|
| 311 | 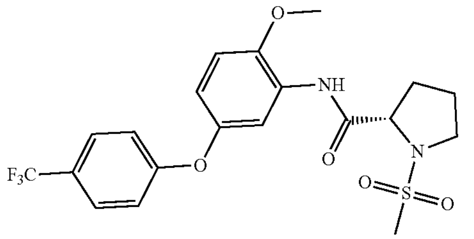 [SMILES: COc1ccc(Oc2ccc(C(F)(F)F)cc2)cc1NC(=O)[C@@H]1CCCN1S(C)(=O)=O] Starting material: 2-Methoxy-5-(4-(trifluoromethyl)-phenoxy)aniline and (Methylsulfonyl)-L-proline | $^1$H NMR (400 MHz, $CDCl_3$) δ: 9.08 (s, 1H), 8.19 (d, 1H), 7.46-7.60 (m, 2H), 6.93-7.06 (m, 2H), 6.87 (d, 1H), 6.78 (dd, 1H), 4.34 (dd, 1H), 3.92 (s, 3H), 3.55-3.66 (m, 1H), 3.38-3.49 (m, 1H), 2.94 (s, 3H), 2.38-2.49 (m, 1H), 2.08-2.22 (m, 1H), 1.94-2.07 (m, 2H). LCMS: m/z 459.6 [M + H]$^+$ |
| 312 | 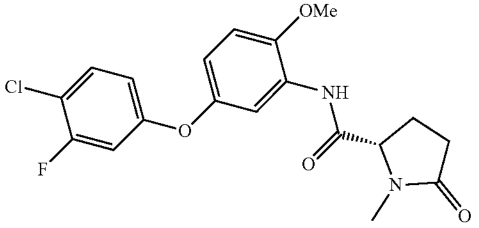 [SMILES: COc1ccc(Oc2ccc(Cl)c(F)c2)cc1NC(=O)[C@@H]1CCC(=O)N1C] Starting material: 5-(4-Chloro-3-fluorophenoxy)-2-methoxyaniline and (S)-1-Methyl-5-oxopyrrolidine-2-carboxylic acid | $^1$H NMR (400 MHz, $CDCl_3$) δ: 8.17 (d, 1H), 8.07 (s, 1H), 7.24-7.32 (m, 1H), 6.88 (d, 1H), 6.78 (dd, 1H), 6.67-6.75 (m, 2H), 4.10 (dd, 1H), 3.91 (s, 3H), 2.94 (s, 3H), 2.36-2.64 (m, 3H), 2.10-2.21 (m, 1H). LCMS: m/z 393.1 [M + H]$^+$ |
| 313 | 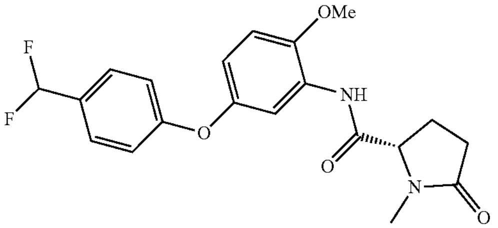 [SMILES: COc1ccc(Oc2ccc(C(F)F)cc2)cc1NC(=O)[C@@H]1CCC(=O)N1C] Starting material: 5-(4-(Difluoro-methyl)phenoxy)-2-methoxyaniline and (S)-1-Methyl-5-oxopyrrolidine-2-carboxylic acid | $^1$H NMR (400 MHz, $CDCl_3$) δ: 8.18 (d, 1H), 8.07 (s, 1H), 7.38-7.48 (m, 2H), 6.94-7.04 (m, 2H), 6.88 (d, 1H), 6.79 (dd, 1H), 6.61 (t, 1H), 4.10 (dd, 1H), 3.91 (s, 3H), 2.93 (s, 3H), 2.36-2.64 (m, 3H), 2.09-2.20 (m, 1H). LCMS: m/z 391.3 [M + H]$^+$ |
| 314 | 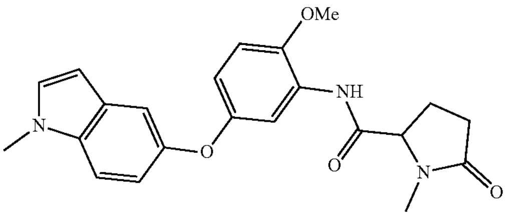 [SMILES: COc1ccc(Oc2ccc3c(ccn3C)c2)cc1NC(=O)C1CCC(=O)N1C] Starting material: 2-Methoxy-5-((1-methyl-1H-indol-5-yl)oxy)aniline and 1-Methyl-5-oxopyrrolidine-2-carboxylic acid | $^1$H NMR (400 MHz, $CDCl_3$) δ: 8.11 (d, 1H), 8.01 (s, 1H), 7.26 (d, 1H), 7.22 (d, 1H), 7.05 (d, 1H), 6.97 (dd, 1H), 6.79 (d, 1H), 6.69 (dd, 1H), 6.39 (d, 1H), 4.03-4.10 (m, 1H), 3.86 (s, 3H), 3.78 (s, 3H), 2.92 (s, 3H), 2.33-2.64 (m, 3H), 2.07-2.19 (m, 1H). LCMS: m/z 394.4 [M + H]$^+$ |

-continued

| No | Structure and starting material | Characterization data |
|---|---|---|
| 315 | 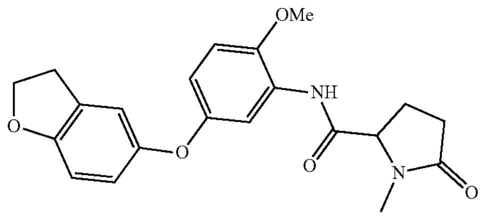 Starting material: 5-((2,3-Dihydro-benzofuran-5-yl)oxy)-2-methoxy-aniline and 1-Methyl-5-oxopyrrolidine-2-carboxylic acid | $^1$H NMR (400 MHz, $CDCl_3$) δ: 8.09 (d, 1H), 8.03 (s, 1H), 6.84-6.89 (m, 1H), 6.81 (d, 1H), 6.75 /dd, 1H), 6.70 (d, 1H), 6.68 (dd, 1H), 4.57 (t, 2H), 4.09 (dd, 1H), 3.87 (s, 3H), 3.18 (t, 2H), 2.93 (s, 3H), 2.35-2.64 (m, 3H), 2.10-2.20 (m, 1H). LCMS: m/z 393.4 $[M + H]^+$ |
| 316 | 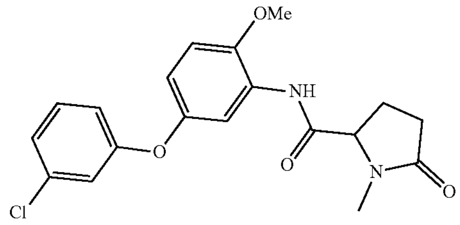 [SMILES: COc1ccc(Oc2cccc(Cl)c2)cc1NC(=O)C1CCC(=O)N1C] Starting material: 5-(3-Chloro-phenoxy)-2-methoxyaniline and 1-Methyl-5-oxopyrrolidine-2-carboxylic acid | $^1$H NMR (400 MHz, $CDCl_3$) δ: 8.16 (d, 1H), 8.07 (s, 1H), 7.21 (t, 1H), 7.01 (d, 1H), 6.82-6.95 (m, 3H), 6.78 (dd, 1H), 4.06-4.15 (m, 1H), 3.91 (s, 3H), 2.94 (s, 3H), 2.35-2.66 (m, 3H), 2.09-2.22 (m, 1H). LCMS: m/z 375.1 $[M + H]^+$ |
| 317 | 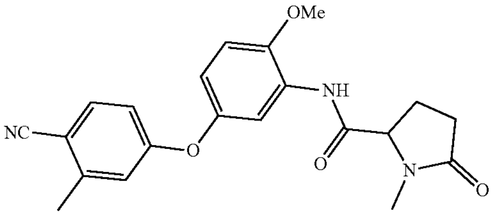 [SMILES: COc1ccc(Oc2ccc(C#N)c(C)c2)cc1NC(=O)C1CCC(=O)N1C] Starting material: 4-(3-Amino-4-methoxyphenoxy)-2-methylbenzo-nitrile and 1-Methyl-5-oxopyrrolidine-2-carboxylic acid | $^1$H NMR (400 MHz, $CDCl_3$) δ: 8.18 (d, 1H), 8.09 (s, 1H), 7.50 (d, 1H), 6.91 (d, 1H), 6.74-6.84 (m, 3H), 4.11 (dd, 1H), 3.92 (s, 3H), 2.94 (s, 3H), 2.48 (s, 3H), 2.37-2.65 (m, 3H), 2.10-2.20 (m, 1H). LCMS: m/z 380.4 $[M + H]^+$ |
| 318 | 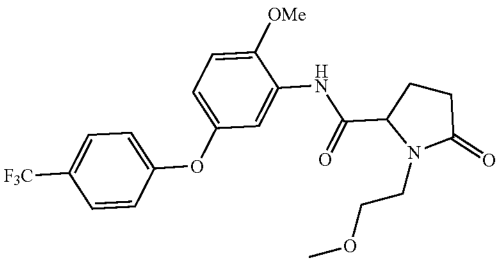 [SMILES: COCCN1C(=O)CCC1C(=O)Nc1cc(Oc2ccc(C(F)(F)F)cc2)ccc1OC] Starting material: 2-Methoxy-5-(4-(trifluoromethyl)-phenoxy)aniline and 1-(2-Methoxyethyl)-5-oxopyrrolidine-2-carboxylic acid | $^1$H NMR (400 MHz, $CDCl_3$) δ: 8.33 (s, 1H), 8.22 (d, 1H), 7.49-7.58 (m, 2H), 6.95-7.03 (m, 2H), 6.90 (d, 1H), 6.79 (dd, 1H), 4.36-4.44 (m, 1H), 3.92 (s, 3H), 3.80-3.89 (m, 1H), 3.49-3.61 (m, 1H), 3.31 (s, 3H), 3.25-3.36 (m, 1H), 2.53-2.67 (m, 1H), 2.29-2.47 (m, 2H), 2.14-2.27 (m, 1H). LCMS: m/z 453.6 $[M + H]^+$ |

-continued

| No | Structure and starting material | Characterization data |
|---|---|---|
| 319 | 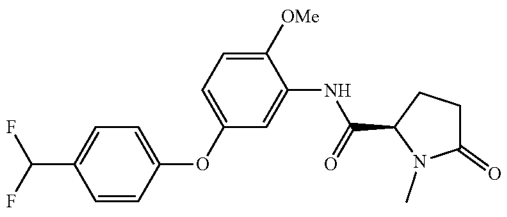 [SMILES: COc1ccc(Oc2ccc(C(F)F)cc2)cc1NC(=O)[C@H]1CCC(=O)N1C] Starting material: 5-(4-(Difluoro-methyl)phenoxy)-2-methoxyaniline and (R)-1-Methyl-5-oxopyrrolidine-2-carboxylic acid | $^{1}H$ NMR (400 MHz, $CDCl_3$) δ: 8.18 (d, 1H), 8.07 (s, 1H), 7.38-7.48 (m, 2H), 6.94-7.04 (m, 2H), 6.88 (d, 1H), 6.79 (dd, 1H), 6.61 (t, 1H), 4.10 (dd, 1H), 3.91 (s, 3H), 2.93 (s, 3H), 2.36-2.64 (m, 3H), 2.09-2.20 (m, 1H). LCMS: m/z 391.3 $[M + H]^+$ |
| 320 | 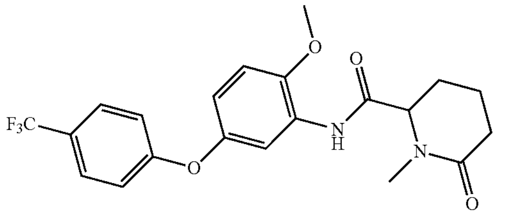 [SMILES: COc1ccc(Oc2ccc(C(F)(F)F)cc2)cc1NC(=O)C1CCCC(=O)N1C] Starting materials: 2-Methoxy-5-(4-(trifluoromethyl)phenoxy)aniline and 1-Methyl-6-oxopiperidine-2-carboxylic acid | $^{1}H$ NMR (400 MHz, $CDCl_3$) δ: 8.24 (br. s, 1H), 8.17 (d, 1H), 7.54 (m, 2H), 7.00 (m, 2H), 6.90 (d, 1H), 6.81 (dd, 1H), 4.04 (dd, 1H), 3.91 (s, 3H), 3.04 (s, 3H), 2.57 (dt, 1H), 2.44 (m, 1H), 2.25 (m, 1H), 2.15-2.06 (m, 1H), 1.86-1.80 (m, 2H). LCMS: m/z 423.5 $[M + H]^+$ |
| 321 | 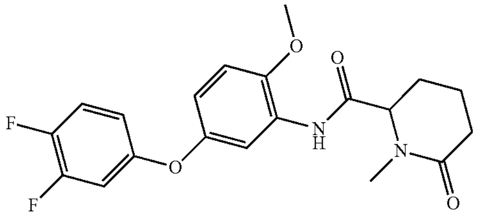 [SMILES: COc1ccc(Oc2ccc(F)c(F)c2)cc1NC(=O)C1CCCC(=O)N1C] Starting materials: 5-(3,4-Difluoro-phenoxy)-2-methoxyaniline and 1-Methyl-6-oxopiperidine-2-carboxylic acid | $^{1}H$ NMR (400 MHz, $CDCl_3$) δ: 8.22 (br. s, 1H), 8.13 (d, 1H), 7.07 (m, 1H), 6.86 (d, 1H), 6.78-6.73 (m, 2H), 6.70-6.66 (m, 1H), 4.04 (dd, 1H), 3.89 (s, 3H), 3.04 (s, 3H), 2.56 (dt, 1H), 2.44 (m, 1H), 2.25 (m, 1H), 2.10 (m, 1H), 1.88-1.80 (m, 2H). LCMS: m/z 391.2 $[M + H]^+$ |
| 322 | 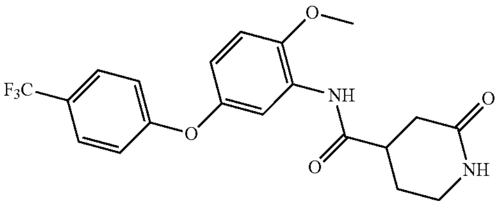 [SMILES: COc1ccc(Oc2ccc(C(F)(F)F)cc2)cc1NC(=O)C1CCNC(=O)C1] Starting materials: 2-Methoxy-5-(4-(trifluoromethyl)phenoxy)aniline and 2-Oxopiperidine-4-carboxylic acid | 1H NMR (600 MHz, CDCl3) 8: 8.22 (d, 1H), 7.89 (br. s, 1H), 7.53 (m, 2H), 6.98 (m, 2H), 6.88 (d, 1H), 6.78 (dd, 1H), 5.88 (br. s, 1H), 3.92 (s, 3H), 3.48 (m, 1H), 3.37 (td, 1H), 2.82 (m, 1H) 2.71-2.61 (m, 2H), 2.15 (m, 1H), 2.02 (m, 1H). LCMS: m/z 409.2 $[M + H]^+$ |
| 323 | 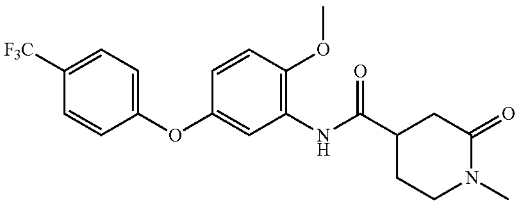 [SMILES: COc1ccc(Oc2ccc(C(F)(F)F)cc2)cc1NC(=O)C1CCN(C)C(=O)C1] Starting materials: 2-Methoxy-5-(4-(trifluoromethyl)phenoxy)aniline and 1-Methyl-2-oxopiperidine-4-carboxylic acid | $^{1}H$ NMR (600 MHz, $CDCl_3$) δ: 8.21 (d, 1H), 7.87 (br. s, 1H), 7.53 (m, 2H), 6.98 (m, 2H), 6.88 (d, 1H), 6.78 (dd, 1H), 3.92 (s, 3H), 3.43-3.34 (m, 2H), 2.97 (s, 3H), 2.80 (m, 1H), 2.70-2.63 (m, 2H), 2.17 (m, 1H), 2.06 (m, 1H). LCMS: m/z 423.3 $[M + H]^+$ |

-continued

| No | Structure and starting material | Characterization data |
|---|---|---|
| 324 | 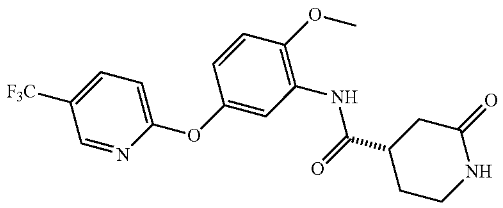 Starting materials: 2-Methoxy-5-((5-(trifluoromethyl)pyridin-2-yl)oxy)-aniline and 2-Oxopiperidine-4-carboxylic acid | Mixture of enantiomers separated with optical HPLC purification. $^1H$ NMR (400 MHz, $CDCl_3$) δ: 8.42 (s, 1H), 8.28 (d, 1H), 7.90 (br. s, 1H), 7.87 (dd, 1H), 7.00 (d, 1H), 6.92 (d, 1H), 6.87 (dd, 1H), 5.87 (s, 1H), 3.92 (s, 3H), 3.48 (m, 1H), 3.37 (td, 1H), 2.82 (m, 1H), 2.73-2.60 (m, 2H), 2.15 (m, 1H), 2.01 (m, 1H). LCMS: m/z 408.602 $(M - H)^-$ $[M + H]^+$ |
| 325 | 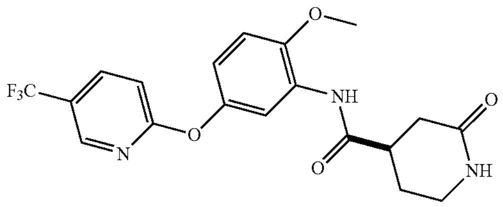 Starting materials: 2-Methoxy-5-((5-(trifluoromethyl)pyridin-2-yl)oxy)-aniline and 2-Oxopiperidine-4-carboxylic acid | Mixture of enantiomers separated with optical HPLC purification. $^1H$ NMR (400 MHz, $CDCl_3$) δ: 8.42 (s, 1H), 8.28 (d, 1H), 7.90 (br. s, 1H), 7.87 (dd, 1H), 7.00 (d, 1H), 6.92 (d, 1H), 6.87 (dd, 1H), 5.86 (s, 1H), 3.92 (s, 3H), 3.48 (m, 1H), 3.37 (td, 1H), 2.82 (m, 1H), 2.73-2.60 (m, 2H), 2.15 (m, 1H), 2.01 (m, 1H). LCMS: m/z 408.532 $(M - H)^-$ |
| 326 | 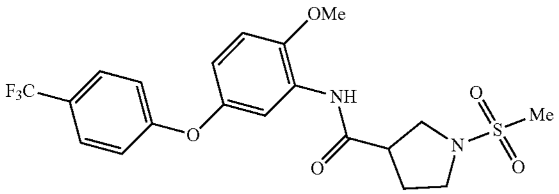 [SMILES: COc1ccc(Oc2ccc(C(F)(F)F)cc2)cc1NC(=O)C1CCN(S(C)(=O)=O)C1] Starting materials: N-(2-Methoxy-5-(4-(trifluoromethyl)phenoxy)-phenyl)pyrrolidine-3-carboxamide and Methanesulfonyl chloride | $^1H$ NMR (600 MHz, $CDCl_3$) δ: 2.24-2.36 (m, 2H), 2.91 (s, 3H), 3.14 (ddd, 1 H), 3.42-3.48 (m, 1H), 3.52 (ddd, 1H), 3.59 (dd, 1H), 3.68 (dd, 1H), 3.93 (s, 3H), 6.78 (dd, 1H), 6.89 (d, 1H), 6.98 (m, 1H), 7.00 (m, 1H), 7.53 (m, 1H), 7.54 (m, 1H), 7.96 (brs, 1H), 8.17 (d, 1H). LCMS: m/z 459.168 $(M + H)^+$ |
| 327 | 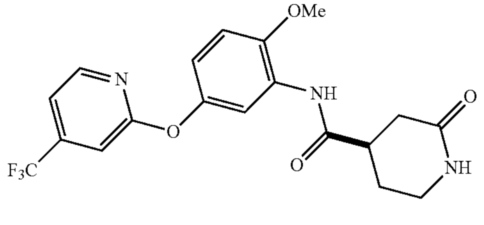 Starting materials: 2-Methoxy-5-((4-(trifluoromethyl)pyridin-2-yl)oxy)-aniline and 2-Oxopiperidine-4-carboxylic acid | Enantiomer obtained with preparative chiral HPLC (methanol, 12 mL/min, column: 10 × 250 mm LuxCell). $^1H$ NMR (600 MHz, DMSO-$d_6$) δ: 9.34 (s, 1H), 8.38 (d, 1H), 7.88 (d, 1H), 7.49 (br. s, 1H), 7.46 (m, 1H), 7.40 (m, 1H), 7.09 (d, 1H) 6.91 (dd, 1H), 3.87 (s, 3H), 3.20-3.06 (m, 3H), 2.27 (d, 2H), 1.93 (m, 1H), 1.68 (m, 1H). LCMS: m/z 410.228 $(M + H)^+$ |

Example 13. N-(2-Fluoro-5-(4-(trifluoromethoxy) phenoxy)phenyl)-1-methyl-S-oxopyrrolidine-2-carboxamide (Compound 328)

Compound 328

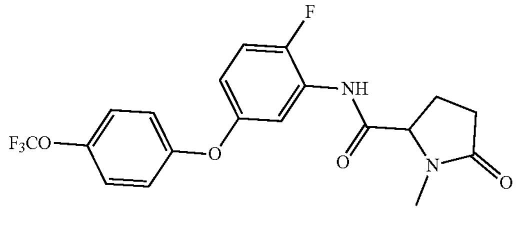

To a mixture of 2-fluoro-5-(4-(trifluoromethoxy)phenoxy)aniline (0.069 g, 0.24 mmol), 1-methyl-5-oxopyrrolidine-2-carboxylic acid (0.034 g, 0.24 mmol) and 1-methylimidazole (0.071 ml, 0.89 mmol) in dry acetonitrile (1.0 ml) was added N,N,N',N'-tetramethylchloroformamidinium-hexafluorophosphate (0.081 g, 0.288 mmol). The mixture was stirred overnight at RT. The mixture was diluted with EtOAc and washed with water and brine. Organic phase was dried and evaporated. Crude product was purified by reverse phase flash chromatography to afford 0.028 g of the title compound. $^1H$ NMR (400 MHz, $CDCl_3$) δ: 8.05 (dd, 1H), 7.81 (s, 1H), 7.14-7.23 (m, 2H), 7.05-7.14 (m, 1H), 6.92-7.03 (m, 2H), 6.71-6.80 (m, 1H), 4.10-4.19 (m, 1H), 2.93 (s, 3H), 2.37-2.64 (m, 3H), 2.10-2.21 (m, 1H). LCMS: m/z 413.0 $[M+H]^+$.

The following compounds were prepared according to the procedure described for Compound 328. The compound number, structure, starting materials and characterization data are indicated in the table.

Example 14. N-(2-Methoxy-5-((4-(trifluoromethyl)-pyridin-2-yl)oxy)phenyl)-1-(2-methoxyacetyl)-5-oxopyrrolidine-2-carboxamide (Compound 331)

Compound 331

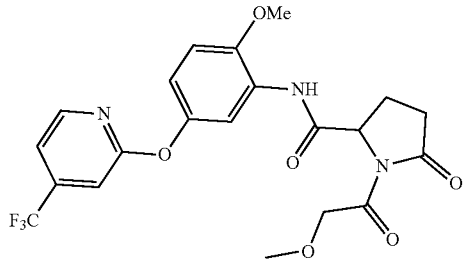

To a mixture of 2-methoxy-5-((4-(trifluoromethyl)pyridin-2-yl)oxy)aniline (0.071 g, 0.25 mmol), 1-(2-methoxyacetyl)-5-oxopyrrolidine-2-carboxylic acid (0.053 g, 0.25 mmol) in EtOAc (0.30 ml) and pyridine (0.15 ml) was added 1-propanephosphonic acid cyclic anhydride, 50 wt-% in EtOAc (0.25 ml, 0.424 mmol). The mixture was stirred at RT overnight. Reaction was quenched with 0.5% HCl-solution and diluted with water and EtOAc. Phases were separated and organic phase was washed with 0.5% HCl-solution, water and brine, dried and evaporated. Crude product was purified by reverse phase flash chromatography to afford the title compound. Yield: 0.046 g. $^1H$ NMR (400 MHz, $CDCl_3$) δ: 8.45 (s, 1H), 8.30 (d, 1H), 8.20 (s, 1H), 7.04-7.22 (m, 2H), 6.82-7.00 (m, 2H), 4.88 (d, 1H), 4.52-4.74 (m, 2H), 3.93 (s, 3H), 3.47 (s, 3H), 2.84-3.03 (m, 1H), 2.47-2.64 (m, 1H), 2.22-2.47 (m, 2H). LCMS: m/z 468.5 $[M+H]^+$

| No | Structure and starting material | Characterization data |
|---|---|---|
| 329 | 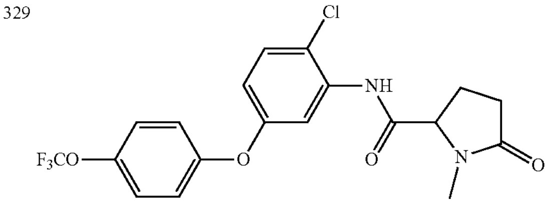<br>Starting material: 2-Chloro-5-(4-(tri-fluoromethoxy)-phenoxy)aniline and 1-Methyl-5-oxopyrrolidine-2-carboxylic acid | $^1H$ NMR (400 MHz, $CDCl_3$) δ: 8.14 (d, 1H), 8.00 (s, 1H), 7.36 (d, 1H), 7.17-7.24 (m, 2H), 6.99-7.06 (m, 2H), 6.75 (dd, 1H), 4.10-4.16 (m, 1H), 2.97 (s, 3H), 2.39-2.65 (m, 3H), 2.12-2.21 (m, 1H). LCMS: m/z 429.2 $[M + H]^+$ |
| 330 | 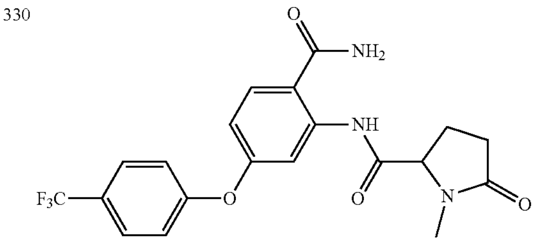<br>Starting materials: 2-Amino-4-(4-(trifluoromethyl)-phenoxy)-benzamide and 1-Methyl-5-oxo-pyrrolidine-2-carboxylic acid | $^1H$ NMR (400 MHz, $CDCl_3$) δ: 12.5 (s, 1H), 8.50 (d, 1H), 7.58-7.74 (m, 3H), 7.44 (br s, 1H), 7.10-7.19 (m, 2H), 6.77 (dd, 1H), 6.66 (br s, 1H), 4.11 (dd, 1H), 2.94 (s, 3H), 2.34-2.66 (m, 3H), 2.09-2.21 (m, 1H). LCMS: m/z 422.1 $[M + H]^+$ |

The following compounds were prepared according to the procedure described for Compound 331. The compound number, structure, starting materials and characterization data are indicated in the table.

| No | Structure and starting material | Characterization data |
|---|---|---|
| 332 | 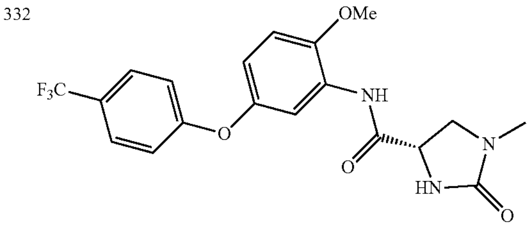<br>Starting materials: 2-Methoxy-5-(4-(trifluoromethyl)phenoxy)aniline and (S)-1-Methyl-2-oxoimidazolidine-4-carboxylic acid | $^1$H NMR (400 MHz, $CDCl_3$) δ: 9.05 (s, 1H), 8.21 (d, 1H), 7.50-7.57 (m, 2H), 6.96-7.02 (m, 2H), 6.88 (d, 1H), 6.80 (dd, 1H), 5.33 (d, 1H), 4.29-4.36 (m, 1H), 3.89 (s, 3H), 3.85-3.92 (m, 1H), 3.53 (dd, 1H), 2.83 (s, 3H). LCMS: m/z 410.2 $[M + H]^+$ |
| 333 | 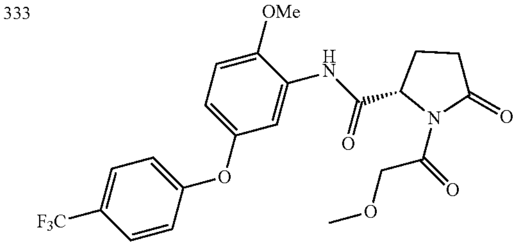<br>Starting materials: 2-Methoxy-5-(4-(trifluoromethyl)-phenoxy)aniline and (S)-1-(2-Methoxyacetyl)-5-oxopyrrolidine-2-carboxylic acid | $^1$H NMR (400 MHz, $CDCl_3$) δ: 8.44 (s, 1H), 8.14 (d, 1H), 7.49-7.56 (m, 2H), 6.94-7.00 (m, 2H), 6.88 (d, 1H), 6.79 (dd, 1H), 4.86 (dd, 1H), 4.57-4.69 (m, 2H), 3.92 (s, 3H), 3.47 (s, 3H), 2.88-3.01 (m, 1H), 2.49-2.59 (m, 1H), 2.25-2.45 (m, 2H). LCMS: m/z 467.5 $[M + H]^+$ |
| 334 | 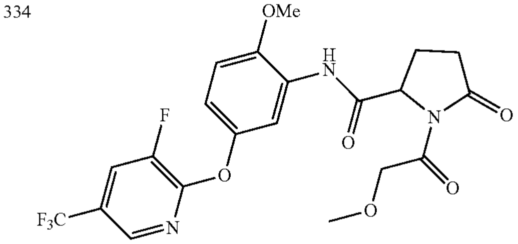<br>Starting materials: 5-((3-Fluoro-5-(tri-fluoromethyl)pyridin-2-yl)oxy)-2-methoxyaniline and 1-(2-Methoxy-acetyl)-5-oxopyrrolidine-2-carboxylic acid | $^1$H NMR (600 MHz, $d_6$-DMSO) δ: 9.80 (s, 1H), 8.38 (dd, 1H), 8.34-8.37 (m, 1H), 7.93 (d, 1H), 7.13 (d, 1H), 7.00 (dd, 1H), 5.09 (dd, 1H), 4.48 (q, 2H), 3.91 (s, 3H), 3.29 (s, 3H), 2.54-2.62 (m, 1H), 2.45-2.52 (m, 1H), 2.31-2.40 (m, 1H), 1.96-2.02 (m, 1H). LCMS: m/z 486.5 $[M + H]^+$ |
| 335 | 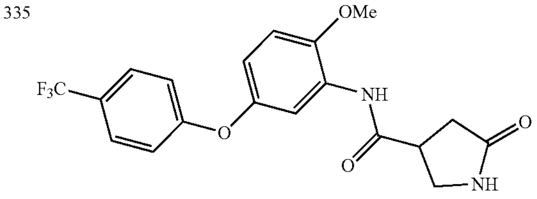<br>Starting materials: 2-Methoxy-5-(4-(trifluoromethyl)-phenoxy)aniline and 5-Oxopyrrolidine-3-carboxylic acid | $^1$H NMR (400 MHz, $CDCl_3$) δ: 8.20 (d, 1H), 7.91 (s, 1H), 7.49-7.57 (m, 2H), 6.95-7.03 (m, 2H), 6.89 (d, 1H), 6.79 (dd, 1H), 6.14 (s, 1H), 3.92 (s, 3H), 3.60-3.76 (m, 2H), 3.38 (quint., 1H), 2.75 (dd, 1H), 2.61 (dd, 1H). LC-MS: m/z 395.2 $[M + H]^+$ |

-continued

| No | Structure and starting material | Characterization data |
|---|---|---|
| 336 | 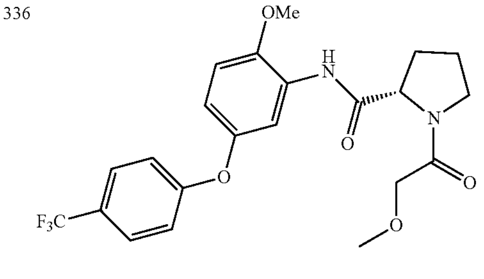 Starting materials: 2-Methoxy-5-(4-(trifluoromethyl)phenoxy)aniline and (2-Methoxyacetyl)-L-proline | $^1$H NMR (400 MHz, $CDCl_3$) δ: 9.26 (s, 1H), 8.16 (d, 1H), 7.48-7.55 (m, 2H), 6.93-7.00 (m, 2H), 6.85 (d, 1H), 6.74 (dd, 1H), 4.78 (dd, 1H), 4.07-4.18 (m, 2H), 3.91 (s, 3H), 3.54-3.63 (m, 1H), 3.48 (s, 3H), 3.42-3.52 (m, 1H), 2.40-2.51 (m, 1H), 2.09-2.24 (m, 1H), 1.83-2.09 (m, 1H). LCMS: m/z 453.6 $[M + H]^+$ |
| 337 | 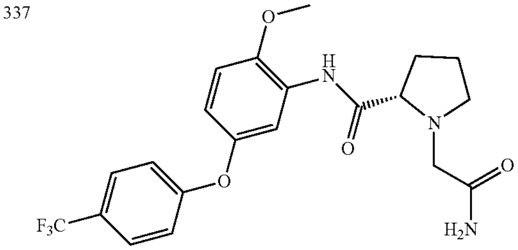 Starting materials: 2-Methoxy-5-(4-(trifluoromethyl)phenoxy)aniline and (2-Amino-2-oxoethyl)-L-proline | $^1$H NMR (400 MHz, $CDCl_3$) δ: 9.46 (s, 1H), 8.23 (d, 1H), 7.49-7.57 (m, 2H), 6.95-7.03 (m, 2H), 6.89 (d, 1H), 6.77 (dd, 1H), 6.58 (bs, 1H), 5.81 (bs, 1H), 3.90 (s, 3H), 3.54 (d, 1H), 3.33-3.43 (m, 2H), 3.19 (d, 1H), 2.49-2.59 (m, 1H), 2.26-2.39 (m, 1H), 1.85-2.07 (m, 3H). LCMS: m/z 438.8 $[M + H]^+$ |
| 338 | 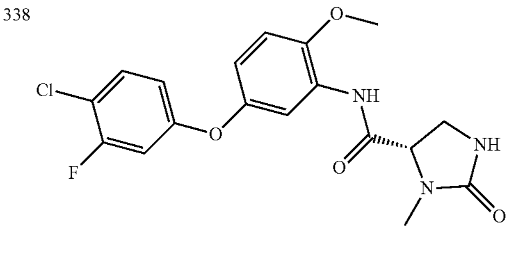 Starting materials: 5-(4-Chloro-3-fluorophenoxy)-2-methoxyaniline and (S)-3-Methyl-2-oxoimidazolidine-4-carboxylic acid | $^1$H NMR (400 MHz, $CDCl_3$) δ: 8.59 (s, 1H), 8.16 (d, 1H), 7.28 (t, 1H), 6.89 (d, 1H), 6.79 (dd, 1H), 6.66-6.76 (m, 2H), 5.15 (s, 1H), 4.13 (dd, 1H), 3.91 (s, 3H), 3.86 (t, 1H), 3.46 (t, 1H), 2.92 (s, 3H). LCMS: m/z 394.2 $[M + H]^+$ |
| 339 | 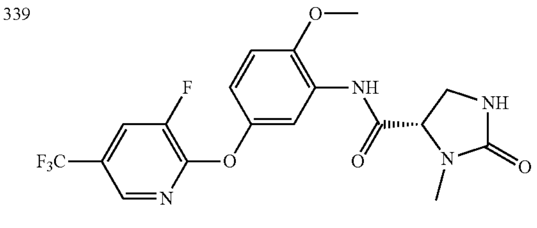 Starting materials: 5-((3-Fluoro-5-(tri-fluoromethyl)pyridin-2-yl)oxy)-2-methoxyaniline and (S)-3-Methyl-2-oxoimidazolidine-4-carboxylic acid | $^1$H NMR (400 MHz, $CDCl_3$) δ: 8.62 (s, 1H), 8.28-8.31 (m, 1H), 8.15-8.19 (m, 1H), 7.67 (dd, 1H), 6.91-6.97 (m, 2H), 4.94 (s, 1H), 4.13 (dd, 1H), 3.93 (s, 3H), 3.85 (t, 1H), 3.41-3.48 (m, 1H), 2.92 (s, 3H). LCMS: m/z 429.4 $[M + H]^+$ |

-continued

| No | Structure and starting material | Characterization data |
|---|---|---|
| 340 | 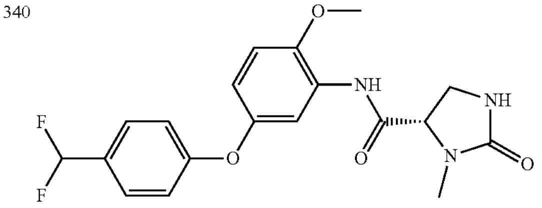<br>Starting materials: 5-(4-(Difluoro-methyl)phenoxy)-2-methoxyaniline and (S)-3-Methyl-2-oxoimidazolidine-4-carboxylic acid | $^1$H NMR (400 MHz, $CDCl_3$) δ: 8.58 (s, 1H), 8.17 (d, 1H), 7.40-7.47 (m, 2H), 6.96-7.03 (m, 2H), 6.89 (d, 1H), 6.80 (dd, 1H), 6.61 (t, 1H), 4.93 (s, 1H), 4.12 (dd, 1H), 3.01 (s, 3H), 3.85 (t, 1H), 3.45 (t, 1H), 2.91 (s, 3H). LCMS: m/z 392.2 $[M + H]^+$ |
| 341 | 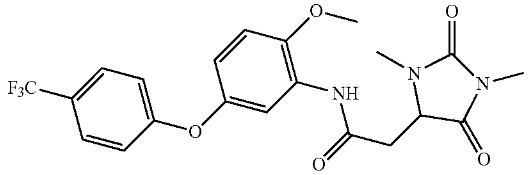 [SMILES: COc1ccc(Oc2ccc(C(F)(F)F)cc2)cc1NC(=O)CC1C(=O)N(C)C(=O)N1C]<br>Starting materials: 2-Methoxy-5-(4-(trifluoromethyl)-phenoxy)aniline and 2-(1,3-Dimethyl-2,5-dioxoimidazo-lidin-4-yl)acetic acid | $^1$H NMR (400 MHz, $CDCl_3$) δ: 8.16 (d, 1H), 7.99 (s, 1H), 7.49-7.58 (m, 2H), 6.94-7.03 (m, 2H), 6.88 (d, 1H), 6.77 (dd, 1H), 4.34 (dd, 1H), 3.91 (s, 3H), 3.06 (dd, 1H), 3.04 (s, 3H), 2.98 (s, 3H), 2.80 (dd, 1H). LCMS: m/z 452.6 $[M + H]^+$ |
| 342 | 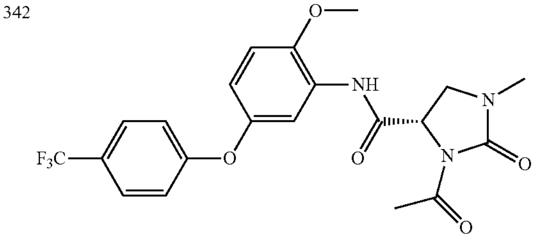<br>Starting materials: 2-Methoxy-5-(4-(trifluoromethyl)-phenoxy)aniline and (S)-3-Acetyl-1-methyl-2-oxoimidazo-lidine-4-carboxylic acid | $^1$H NMR (400 MHz, $CDCl_3$) δ: 9.06 (s, 1H), 8.14 (d, 1H), 7.47-7.58 (m, 2H), 6.93-7.04 (m, 2H), 6.88 (d, 1H), 6.78 (dd, 1H), 4.94 (dd, 1H), 3.92 (s, 3H), 3.87-3.98 (m, 1H), 3.56 (t, 1H), 2.91 (s, 3H), 2.59 (s, 3H). LCMS: m/z 452.5 $[M + H]^+$ |
| 343 | 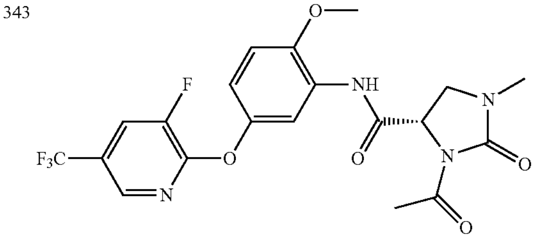<br>Starting materials: 5-((3-Fluoro-5-(tri-fluoromethyl)pyridin-2-yl)oxy)-2-methoxyaniline and (S)-3-Acetyl-1-methyl-2-oxoimidazolidine-4-carboxylic acid | $^1$H NMR (400 MHz, $CDCl_3$) δ: 9.07 (s, 1H), 8.24 (d, 1H), 8.14-8.18 (m, 1H), 7.65 (dd, 1H), 6.88-6.95 (m, 2H), 4.95 (dd, 1H), 3.93 (s, 3H), 3.90-3.95 (m, 1H), 3.56 (t, 1H), 2.91 (s, 3H), 2.58 (s, 3H). LCMS: m/z 471.4 $[M + H]^+$ |
| 344 | 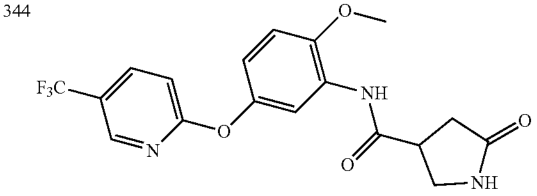<br>Starting materials: 2-Methoxy-5-((5-(trifluoromethyl)pyridin-2-yl)oxy)-aniline and 5-Oxopyrrolidine-3-carboxylic acid | $^1$H NMR (600 MHz, $CDCl_3$) δ: 8.40-8.43 (m, 1H), 8.26 (d, 1H), 7.92 (s, 1H), 7.88 (dd, 1H), 7.00 (d, 1H), 6.92 (d, 1H), 6.88 (dd, 1H), 5.89 (s, 1H), 3.92 (s, 3H), 3.70 (dd, 1H), 3.64 (t, 1H), 3.35-3.42 (m, 1H), 2.75 (dd, 1H), 2.60 (dd, 1H). LCMS: m/z 396.7 $[M + H]^+$ |

-continued

| No | Structure and starting material | Characterization data |
|---|---|---|
| 345 | 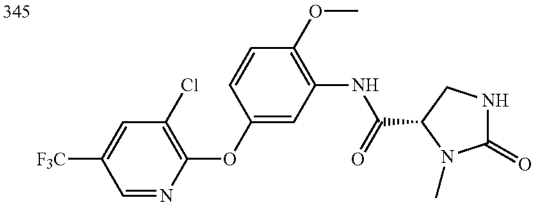<br>Starting materials: 5-((3-Chloro-5-(tri-fluoromethyl)pyridin-2-yl)oxy)-2-methoxyaniline and (S)-3-Methyl-2-oxoimidazolidine-4-carboxylic acid | $^1$H NMR (600 MHz, $CDCl_3$) δ: 8.62 (s, 1H), 8.24-8.29 (m, 2H), 7.97 (d, 1H), 6.95 (d, 1H), 6.92 (dd, 1H), 5.09 (s, 1H), 4.13 (dd, 1H), 3.93 (s, 3H), 3.85 (t, 1H), 3.44 (dd, 1H), 2.92 (s, 3H). LCMS: m/z 445.5 $[M + H]^+$ |
| 346 | 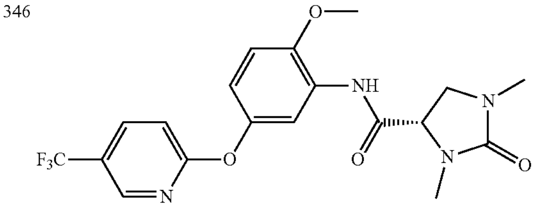<br>Starting materials: 2-Methoxy-5-((5-(trifluoromethyl)pyridin-2-yl)oxy)-aniline and (S)-1,3-Dimethyl-2-oxo-imidazolidine-4-carboxylic acid | $^1$H NMR (600 MHz, $CDCl_3$) δ: 8.67 (s, 1H), 8.40-8.44 (m, 1H), 8.25 (d, 1H), 7.88 (dd, 1H), 7.02 (d, 1H), 6.93 (d, 1H), 6.90 (dd, 1H), 3.96 (dd, 1H), 3.92 (s, 3H), 3.76 (t, 1H), 3.30 (dd, 1H), 2.91 (s, 3H), 2.85 (s, 3H). LCMS: m/z 425.8 $[M + H]^+$ |
| 347 | 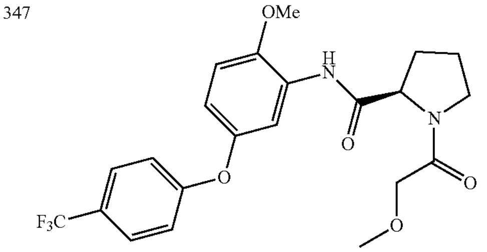<br>Starting materials: 2-Methoxy-5-(4-(trifluoromethyl)phenoxy)aniline and (2-Methoxyacetyl)-D-proline | $^1$H NMR (600 MHz, $d_6$-DMSO) δ: 9.45 (s, 1H), 7.92 (d, 1H), 7.67-7.73 (m, 2H), 7.12 (d, 1H), 7.05-7.09 (m, 2H), 6.87 (dd, 1H), 4.69 (dd, 1H), 4.03-4.10 (m, 2H), 3.87 (s, 3H), 3.41-3.52 (m, 2H), 3.30 (s, 3H), 1.97-2.07 (m, 1H), 1.83-1.97 (m, 3H). LCMS: m/z 453.8 $[M + H]^+$ |
| 348 | 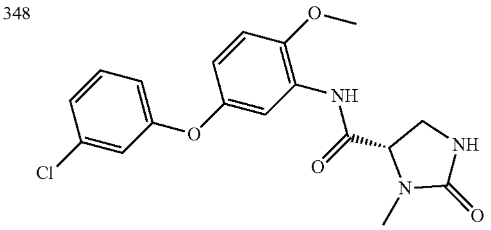<br>Starting materials: 5-(3-Chloro-phenoxy)-2-methoxyaniline and (S)-3-Methyl-2-oxoimidazolidine-4-carboxylic acid | $^1$H NMR (600 MHz, $d_6$-DMSO) δ: 9.47 (s, 1H), 7.85 (d, 1H), 7.37 (t, 1H), 7.14 (ddd, 1H), 7.12 (d, 1H), 6.97 (t, 1H), 6.91 (ddd, 1H), 6.87 (dd, 1H), 6.46 (s, 1H), 4.38 (dd, 1H), 3.87 (s, 3H), 3.53 (t, 1H), 3.17 (ddd, 1H), 2.62 (s, 3H). LCMS: m/z 376.2 $[M + H]^+$ |
| 349 | 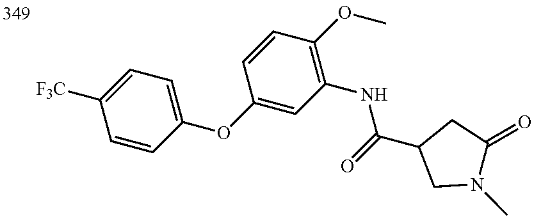<br>Starting materials: 2-Methoxy-5-(4-(trifluoromethyl)-phenoxy)aniline and 1-Methyl-5-oxopyrrolidine-3-carboxylic acid | $^1$H NMR (600 MHz, $d_6$-DMSO) δ: 9.52 (s, 1H), 7.87 (d, 1H), 7.69-7.72 (m, 2H), 7.12 (d, 1H), 7.05-7.09 (m, 2H), 6.90 (d, 1H), 3.88 (s, 3H), 3.50-3.59 (m, 2H), 3.37-3.42 (m, 1H), 2.70 (s, 3H), 2.38-2.44 (m, 1H), 2.45-2.5 (m, 1H). LCMS: m/z 409.5 $[M + H]^+$ |

-continued

| No | Structure and starting material | Characterization data |
|---|---|---|
| 350 | 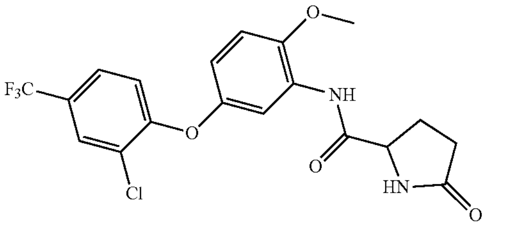 [SMILES: COc1ccc(Oc2ccc(C(F)(F)F)cc2Cl)cc1NC(=O)C1CCC(=O)N1] Starting materials: 5-(2-Chloro-4-(tri-fluoromethyl)phenoxy)-2-methoxy-aniline and 5-Oxopyrrolidine-2-carboxylic acid | $^1$H NMR (600 MHz, $d_6$-DMSO) δ: 9.39 (s, 1H), 8.00 (d, 1H), 7.89-7.93 (m, 2H), 7.65-7.69 (m, 1H), 7.15 (d, 1H), 6.99 (d, 1H), 6.92 (dd, 1H), 4.39 (dd, 1H), 3.88 (s, 3H), 2.28-2.36 (m, 1H), 2.15-2.23 (m, 1H), 2.07-2.14 (m, 1H), 1.92-1.99 (m, 1H). LCMS: m/z 429.1 $[M + H]^+$ |
| 351 | 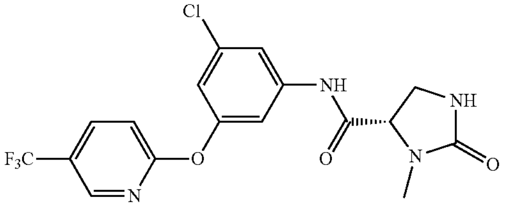 Starting materials: 3-Chloro-5-((5-(trifluoromethyl)pyridin-2-yl)oxy)-aniline and (S)-3-Methyl-2-oxo-imidazolidine-4-carboxylic acid | $^1$H NMR (600 MHz, $d_6$-DMSO) δ: 10.42 (s, 1H), 8.60-8.63 (m, 1H), 8.28 (dd, 1H), 7.68 (t, 1H), 7.45 (t, 1H), 7.32 (d, 1H), 7.12 (d, 1H), 6.49 (s, 1H), 4.18 (dd, 1H), 3.55 (td, 1H), 3.18-3.23 (m, 1H), 2.63 (s, 3H). LCMS: m/z 415.3 $[M + H]^+$ |
| 352 | 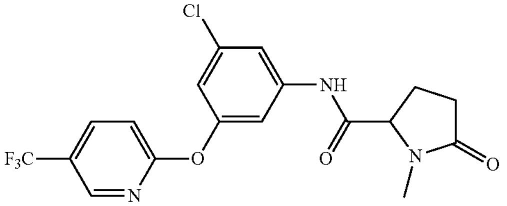 [SMILES: CN1C(=O)CCC1C(=O)Nc1cc(Cl)cc(Oc2ccc(C(F)(F)F)cn2)c1] Starting materials: 3-Chloro-5-((5-(trifluoromethyl)pyridin-2-yl)oxy)-aniline and 1-Methyl-5-oxo-pyrrolidine-2-carboxylic acid | $^1$H NMR (400 MHz, $CDCl_3$) δ: 8.82 (s, 1H), 8.45 (s, 1H), 7.93 (dd, 1H), 7.55-7.62 (m, 2H), 7.06 (d, 1H), 6.95 (s, 1H), 4.14 (dd, 1H), 2.90 (s, 3H), 2.35-2.62 (m, 3H), 2.11-2.23 (m, 1H). LCMS: m/z 414.4 $[M + H]^+$ |
| 353 | 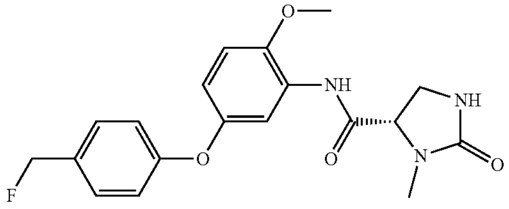 [SMILES: COc1ccc(Oc2ccc(CF)cc2)cc1NC(=O)[C@@H]1CNC(=O)N1C] Starting materials: 5-(4-(Fluoro-methyl)phenoxy)-2-methoxyaniline and (S)-3-Methyl-2-oxoimidazolidine-4-carboxylic acid | $^1$H NMR (400 MHz, $CDCl_3$) δ: 8.57 (s, 1H), 8.15 (d, 1H), 7.28-7.37 (m, 2H), 6.92-7.02 (m, 2H), 6.87 (d, 1H), 6.78 (dd, 1H), 5.32 (d, 2H), 4.86 (s, 1H), 4.12 (dd, 1H), 3.90 (s, 3H), 3.84 (t, 1H), 3.45 (t, 1H), 2.92 (s, 3H). LCMS: m/z 372.4 $[M + H]^+$ |
| 354 | 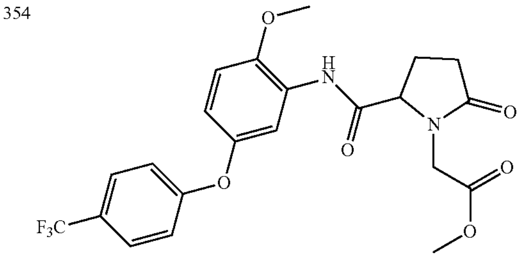 Starting materials: 2-Methoxy-5-(4-(trifluoromethyl)phenoxy)aniline and 1-(2-Methoxy-2-oxoethyl)-5-oxo-pyrrolidine-2-carboxylic acid | $^1$H NMR (400 MHz, $CDCl_3$) δ: 8.20 (s, 1H), 8.15 (d, 1H), 7.50-7.58 (m, 2H), 6.96-7.03 (m, 2H), 6.90 (d, 1H), 6.81 (dd, 1H), 4.62 (d, 1H), 4.41-4.48 (m, 1H), 3.92 (s, 3H), 3.84 (s, 3H), 3.70 (d, 1H), 2.43-2.65 (m, 3H), 2.13-2.25 (m, 1H). LCMS: m/z 467.5 $[M + H]^+$ |

-continued

| No | Structure and starting material | Characterization data |
|---|---|---|
| 355 | 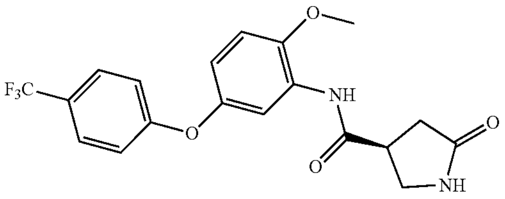 [SMILES: COc1ccc(Oc2ccc(C(F)(F)F)cc2)cc1NC(=O)[C@@H]1CNC(=O)C1] Starting materials: 2-Methoxy-5-(4-(trifluoromethyl)phenoxy)aniline and (S)-5-Oxopyrrolidine-3-carboxylic acid | $^1$H NMR (400 MHz, $CDCl_3$) δ: 8.20 (d, 1H), 7.91 (s, 1H), 7.50-7.57 (m, 2H), 6.95-7.02 (m, 2H), 6.89 (d, 1H), 6.79 (dd, 1H), 6.09 (s, 1H), 3.92 (s, 3H), 3.60-3.75 (m, 2H), 3.33-3.44 (m, 1H), 2.75 (dd, 1H), 2.61 (dd, 1H). LCMS: m/z 395.2 $[M + H]^+$ |
| 356 | 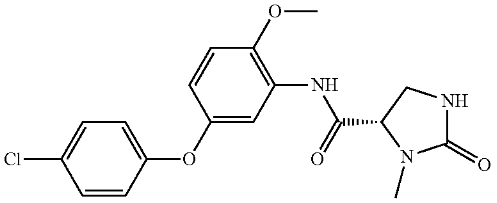 [SMILES: COc1ccc(Oc2ccc(Cl)cc2)cc1NC(=O)[C@@H]1CNC(=O)N1C] Starting materials: 5-(4-Chloro-phenoxy)-2-methoxyaniline and (S)-3-Methyl-2-oxoimidazolidine-4-carboxylic acid | $^1$H NMR (400 MHz, $CDCl_3$) δ: 8.57 (s, 1H), 8.13 (d, 1H), 7.21-7.29 (m, 2H), 6.82-6.94 (m, 3H), 6.76 (dd, 1H), 4.96 (s, 1H), 4.12 (dd, 1H), 3.90 (s, 3H), 3.85 (t, 1H), 3.41-3.48 (m, 1H), 2.92 (s, 3H). LCMS: m/z 376.2 $[M + H]^+$ |
| 357 | 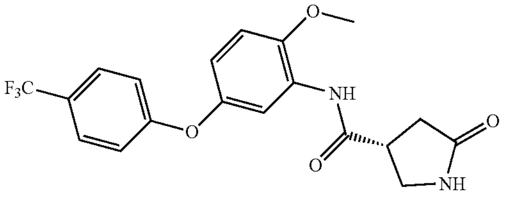 [SMILES: COc1ccc(Oc2ccc(C(F)(F)F)cc2)cc1NC(=O)[C@H]1CNC(=O)C1] Starting materials: 2-Methoxy-5-(4-(trifluoromethyl)phenoxy)aniline and (R)-5-Oxopyrrolidine-3-carboxylic acid | $^1$H NMR (400 MHz, $CDCl_3$) δ: 8.20 (d, 1H), 7.92 (s, 1H), 7.48-7.59 (m, 2H), 6.94-7.05 (m, 2H), 6.89 (d, 1H), 6.79 (dd, 1H), 6.12 (s, 1H), 3.92 (s, 3H), 3.59-3.77 (m, 2H), 3.32-3.45 (m, 1H), 2.75 (dd, 1H), 2.61 (dd, 1H). LCMS: m/z 395.2 $[M + H]^+$ |
| 358 | 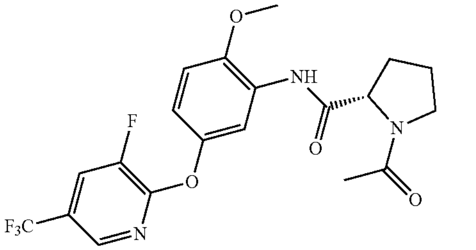 [SMILES: COc1ccc(Oc2ncc(C(F)(F)F)cc2F)cc1NC(=O)[C@@H]1CCCN1C(C)=O] Starting materials: (S)-N-(5-((3-Fluoro-5-(trifluoromethyl)-pyridin-2-yl)oxy)-2-methoxyphenyl)pyrrolidine-2-carboxamide and Acetic acid | $^1$H NMR (400 MHz, $CDCl_3$) δ: 9.51 (s, 1H), 8.27 (d, 1H), 8.13-8.19 (m, 1H), 7.64 (dd, 1H), 6.83-6.96 (m, 2H), 4.73-4.80 (m, 1H), 3.92 (s, 3H), 3.54-3.62 (m, 1H), 3.42-3.51 (m, 1H), 2.45-2.54 (m, 1H), 2.14 (s, 3H), 2.08-2.22 (m, 1H), 1.97-2.07 (m, 1H), 1.81-1.93 (m, 1H). LCMS: m/z 442.6 $[M + H]^+$ |
| 359 | 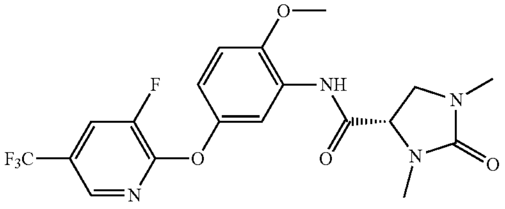 [SMILES: COc1ccc(Oc2ncc(C(F)(F)F)cc2F)cc1NC(=O)[C@@H]1CN(C)C(=O)N1C] Starting materials: 5-((3-Fluoro-5-(tri-fluoromethyl)pyridin-2-yl)oxy)-2-methoxyaniline and (S)-1,3-Dimethyl-2-oxoimidazolidine-4-carboxylic acid | $^1$H NMR (400 MHz, $CDCl_3$) δ: 8.68 (s, 1H), 8.27-8.33 (m, 1H), 8.14-8.19 (m, 1H), 7.67 (dd, 1H), 6.87-6.99 (m, 2H), 3.96 (dd, 1H), 3.92 (s, 3H), 3.76 (t, 1H), 3.30 (dd, 1H), 2.91 (s, 3H), 2.85 (s, 3H). LCMS: m/z 443.3 $[M + H]^+$ |

-continued

| No | Structure and starting material | Characterization data |
|---|---|---|
| 360 | 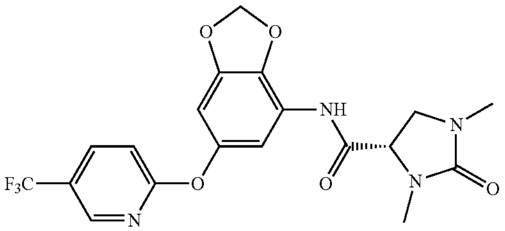 [SMILES: CN1C[C@@H](C(=O)Nc2cc(Oc3ccc(C(F)(F)F)cn3)cc3c2OCO3)N(C)C1=O] Starting materials: 6-((5-(Trifluoro-methyl)pyridin-2-yl)oxy)benzo[d]-[1,3]dioxol-4-amine and (S)-1,3-Di-methyl-2-oxoimidazolidine-4-carboxylic acid | $^1$H NMR (600 MHz, $CDCl_3$) δ: 8.44 (s, 1H), 8.03 (s, 1H), 7.89 (dd, 1H), 7.57 (d, 1H), 7.02 (d, 1H), 6.62 (d, 1H), 6.01-6.08 (m, 2H), 3.96 (dd, 1H), 3.77 (t, 1H), 3.30 (dd, 1H), 2.90 (s, 3H), 2.84 (s, 3H). LCMS: m/z 439.4 $[M + H]^+$ |
| 361 | 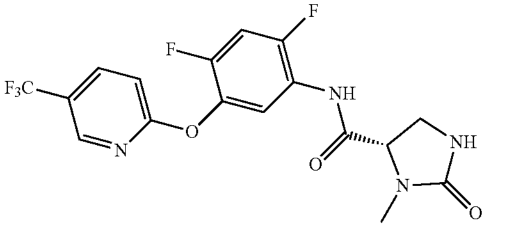 [SMILES: CN1C(=O)NC[C@H]1C(=O)Nc1cc(Oc2ccc(C(F)(F)F)cn2)c(F)cc1F] Starting materials: 2,4-Difluoro-5-((5-(trifluoromethyl)pyridin-2-yl)oxy)-aniline and (S)-3-Methyl-2-oxoimidazolidine-4-carboxylic acid | $^1$H NMR (600 MHz, $CDCl_3$) δ: 8.38 (s, 1H), 8.27 (t, 1H), 8.22 (s, 1H), 7.95 (dd, 1H), 7.13 (d, 1H), 7.06 (t, 1H), 5.11 (s, 1H), 4.15 (dd, 1H), 3.87 (t, 1H), 3.46 (t, 1H), 2.91 (s, 3H). LCMS: m/z 417.4 $[M + H]^+$ |
| 362 | 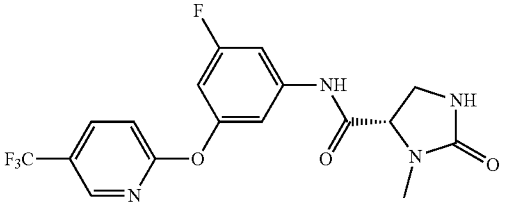 [SMILES: CN1C(=O)NC[C@H]1C(=O)Nc1cc(F)cc(Oc2ccc(C(F)(F)F)cn2)c1] Starting materials: 3-Fluoro-5-((5-(tri-fluoromethyl)pyridin-2-yl)oxy)aniline and (S)-3-Methyl-2-oxoimidazolidine-4-carboxylic acid | $^1$H NMR (600 MHz, $CDCl_3$) δ: 8.93 (s, 1H), 8.45 (s, 1H), 7.94 (dd, 1H), 7.42-7.50 (m, 1H), 7.39 (s, 1H), 7.06 (d, 1H), 6.65-6.73 (m, 1H), 5.12 (s, 1H), 4.14 (dd, 1H), 3.83 (t, 1H), 3.42 (t, 1H), 2.86 (s, 3H). LCMS: m/z 399.4 $[M + H]^+$ |
| 363 | 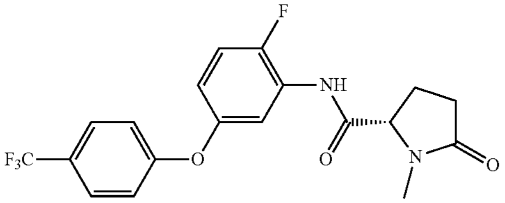 [SMILES: CN1C(=O)CC[C@H]1C(=O)Nc1cc(Oc2ccc(C(F)(F)F)cc2)ccc1F] Starting materials: 2-Fluoro-5-(4-(trifluoromethyl)phenoxy)aniline and (S)-1-Methyl-5-oxopyrrolidine-2-carboxylic acid | $^1$H NMR (600 MHz, $CDCl_3$) δ: 8.10 (d, 1H), 7.77 (s, 1H), 7.55-7.61 (m, 2H), 7.14 (dd, 1H), 7.00-7.06 (m, 2H), 6.80 (ddd, 1H), 4.14 (dd, 1H), 2.93 (s, 3H), 2.54-2.62 (m, 1H), 2.39-2.54 (m, 2H), 2.11-2.19 (m, 1H). LCMS: m/z 397.4 $[M + H]^+$ |

-continued

| No | Structure and starting material | Characterization data |
| --- | --- | --- |
| 364 | 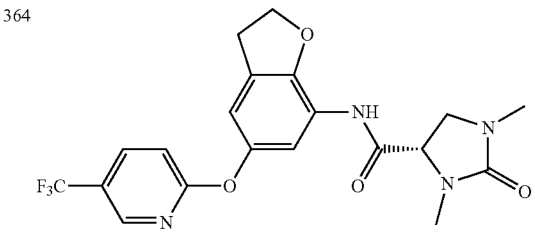<br>Starting materials: 5-((5-(Trifluoro-methyl)pyridin-2-yl)oxy)-2,3-dihydro-benzofuran-7-amine and (S)-1,3-Di-methyl-2-oxoimidazolidine-4-carboxylic acid | $^1$H NMR (400 MHz, $CDCl_3$) δ: 8.40-8.45 (m, 1H), 8.14 (s, 1H), 7.92 (d, 1H), 7.88 (dd, 1H), 7.01 (d, 1H), 6.77-6.83 (m, 1H), 4.61-4.72 (m, 2H), 3.95 (dd, 1H), 3.76 (t, 1H), 3.23-3.34 (m, 3H), 2.90 (s, 3H), 2.84 (s, 3H). LCMS: m/z 437.4 $[M + H]^+$ |
| 365 | 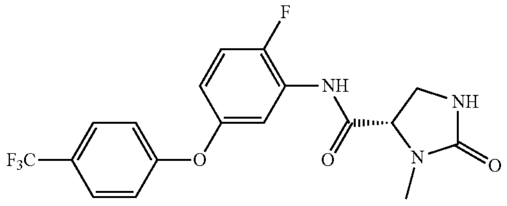 [SMILES: CN1C(=O)NC[C@H]1C(=O)Nc1cc(Oc2ccc(C(F)(F)F)cc2)ccc1F]<br>Starting materials: 3-Fluoro-5-((5-(trifluoromethyl)pyridin-2-yl)oxy)-aniline and (S)-3-Methyl-2-oxoimi-dazolidine-4-carboxylic acid | $^1$H NMR (400 MHz, $CDCl_3$) δ: 8.27 (s, 1H), 8.09 (dd, 1H), 7.53-7.63 (m, 2H), 7.14 (t, 1H), 6.99-7.08 (m, 2H), 6.76-6.86 (m, 1H), 5.08 (s, 1H), 4.15 (dd, 1H), 3.87 (t, 1H), 3.42-3.51 (m, 1H), 2.92 (s, 3H). LCMS: m/z 398.3 $[M + H]^+$ |

Example 15. N-(2-Bromo-5-(3-(trifluoromethyl)phenoxy)phenyl)-1-methyl-5-oxopyrrolidine-2-carboxamide (Compound 366)

Compound 366

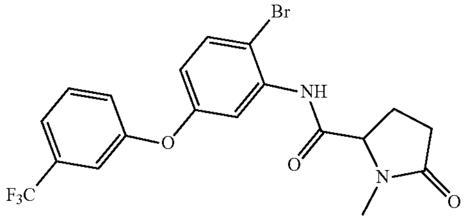

To a cooled (0-5 C) mixture of 1-methyl-5-oxopyrrolidine-2-carboxylic acid (0.067 g, 0.468 mmol) in dry DCM (1.5 ml) was added 1-chloro-N,N,2-trimethyl-1-propenylamine (0.065 ml, 0.488 mmol) and the mixture was stirred at 0-5° C. for 1 h. Then 2-bromo-5-(3-(trifluoromethyl)phenoxy)aniline (0.18 g, 0.390 mmol) dissolved in dry DMF (0.5 ml) and DIPEA (0.34 ml, 1.951 mmol) were added and the mixture was stirred at RT overnight. DCM was evaporated and the mixture diluted with EtOAc. Organic phase was washed with water and brine, dried and evaporated. Crude product was purified by reverse phase flash chromatography to afford the title compound. Yield: 0.019 g. $^1$H NMR (600 MHZ, $d_6$-DMSO) δ: 9.88 (s, 1H), 7.72 (d, 1H), 7.65 (t, 1H), 7.51-7.55 (m, 1H), 7.42 (d, 1H), 7.36-7.39 (m, 1H), 7.34 (dd, 1H), 6.93 (dd, 1H), 4.31-4.38 (m, 1H), 2.70 (s, 3H), 2.17-2.35 (m, 3H), 1.94-2.02 (m, 1H). LCMS: m/z 457.1 $[M+H]^+$.

Example 16. N-(2-Cyano-5-(4-(trifluoromethyl)phenoxy)phenyl)-1-methyl-5-oxopyrrolidine-2-carboxamide (Compound 367)

Compound 367

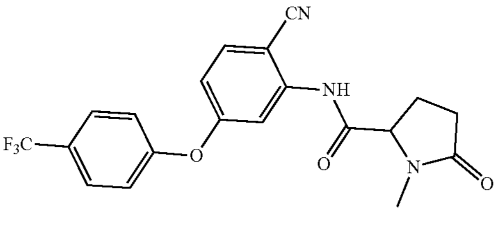

The compound was prepared according to the procedure of the preceding Example starting from 1-methyl-5-oxopyrrolidine-2-carboxylic acid (0.051 g, 0.359 mmol), DCM (1.5 ml), 1-chloro-N,N,2-trimethyl-1-propenylamine (0.057 ml, 0.431 mmol), 2-amino-4-(4-(trifluoromethyl)phenoxy)benzonitrile (0.10 g, 0.359 mmol) and DMF (0.75 ml). Yield: 0.022 g. $^1$H NMR (600 MHz, $d_6$-DMSO) δ: 10.5 (s, 1H), 7.90 (d, 1H), 7.81-7.86 (m, 2H), 7-31-7.37 (m, 2H), 7.30 (d, 1H), 7.08 (dd, 1H), 4.30 (dd, 1H), 2.70 (s, 3H), 2.19-2.36 (m, 3H), 1.94-2.01 (m, 1H). LCMS: m/z 404.4 $[M+H]^+$.

Example 17. N-(2-Fluoro-5-((5-(trifluoromethyl)pyridin-2-yl)oxy)phenyl)-1-methyl-5-oxopyrrolidine-2-carboxamide (Compound 368)

Compound 368

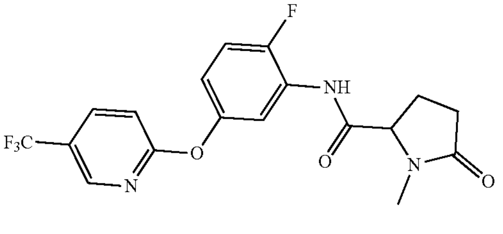

The compound was prepared using the procedure of Intermediate 306 staring from N-(2-fluoro-5-hydroxyphenyl)-1-methyl-5-oxopyrrolidine-2-carboxamide (0.071 g, 0.28 mmol), 2-chloro-5-(trifluoromethyl)pyridine (0.051 g, 0.28 mmol) and $K_2CO_3$ (0.058 g, 0.42 mmol) in dry DMF (1.0 ml). Crude was purified by reverse phase flash chromatography to afford the title compound. Yield: 0.078 g. $^1$H NMR (600 MHz, $CDCl_3$) δ: 8.40-8.43 (m, 1H), 8.21 (dd, 1H), 7.92 (dd, 1H), 7.79 (s, 1H), 7.18 (dd, 1H), 7.05 (d, 1H), 6.91 (dq, 1H), 4.15 8dd, 1H), 2.93 (s, 3H), 2.54-2.62 (m, 1H), 2.39-2.53 (m, 2H), 2.11-2.18 (m, 1H). LCMS: m/z 398.6 $[M+H]^+$.

Example 18. N-(2-Fluoro-5-((5-(trifluoromethyl)pyridin-2-yl)oxy)phenyl)-1-methyl-5-oxopyrrolidine-2-carboxamide (Compound 369)

Compound 369

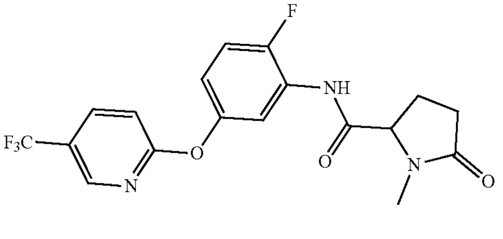

The compound was prepared using the procedure of Intermediate 339 staring from N-(2-fluoro-5-hydroxyphenyl)-1-methyl-5-oxopyrrolidine-2-carboxamide (0.071 g, 0.28 mmol), 2-chloro-5-(trifluoromethyl)pyridine (0.051 g, 0.28 mmol) and $K_2CO_3$ (0.058 g, 0.42 mmol) in dry DMF (1.0 ml). Crude was purified by reverse phase flash chromatography to afford the title compound. Yield: 0.078 g. $^1$H NMR (600 MHz, $CDCl_3$): δ 8.40-8.43 (m, 1H), 8.21 (dd, 1H), 7.92 (dd, 1H), 7.79 (s, 1H), 7.18 (dd, 1H), 7.05 (d, 1H), 6.91 (dq, 1H), 4.15 8dd, 1H), 2.93 (s, 3H), 2.54-2.62 (m, 1H), 2.39-2.53 (m, 2H), 2.11-2.18 (m, 1H). LCMS: m/z 398.6 $[M+H]^+$.

Example 19. (2S,4R)-4-Hydroxy-N-(2-methoxy-5-(4-(trifluoromethyl)phenoxy)phenyl)pyrrolidine-2-carboxamide (Compound 370)

Compound 370

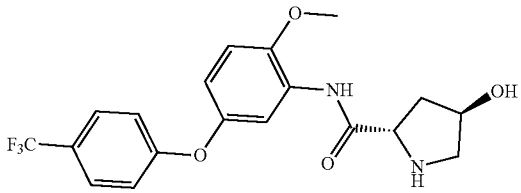

To a mixture of palladium (10 wt-% on carbon, 0.045 g, 0.042 mmol) in methanol (15 ml) was added benzyl (2S,4R)-4-hydroxy-2-((2-methoxy-5-(4-(trifluoro-methyl)phenoxy)phenyl)carbamoyl)pyrrolidine-1-carboxylate (0.111 g, 0.209 mmol) dissolved in methanol (2.0 ml). The mixture was stirred vigorously while ammonium formate (0.132 mg, 2.09 mmol) was added. Stirring was continued at 50° C. until reaction was completed. Cooled mixture was filtered through a short plug of Celite. Celite was washed with methanol. Filtrate was evaporated and re-dissolved in EtOAc. Organic phase was washed with water and brine, dried and evaporated. Crude product was purified by reverse phase flash chromatography to afford the title compound. Yield: 0.041 g. $^1$H NMR (600 MHz, $d_6$-DMSO) δ:10.3 (s, 1H), 8.13 (d, 1H), 7.68-7.73 (m, 2H), 7.13 (d, 1H), 7.05-7.10 (m, 2H), 6.85 (dd, 1H), 4.71 (d, 1H), 4.16-4.20 (m, 1H), 3.89 (s, 3H), 3.87-3.93 (m, 1H), 3.48 (bs, 1H), 2.88 (d, 1H), 2.74 (d, 1H), 1.99-2.06 (m, 1H), 1.72-1.79 (m, 1H). LCMS: m/z 397.6 $[M+H]^+$.

Example 20. (S)-1-Acetyl-N-(2-methoxy-5-(4-(trifluoromethyl)phenoxy)-phenyl)-5-oxopyrrolidine-2-carboxamide (Compound 371)

Compound 371

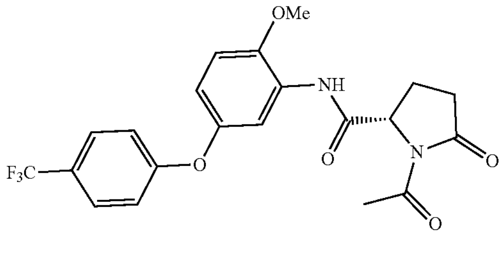

To a cooled (0-5° C.) solution of (S)—N-(2-methoxy-5-(4-(trifluoromethyl)-phenoxy)phenyl)-5-oxopyrrolidine-2-carboxamide (0.086 g, 0.225 mmol) in dry DCM (2.0 ml) was added acetyl chloride (0.018 ml, 0.248 mmol) dissolved in dry DCM (0.25 ml) and triethylamine (0.039 ml, 0.281 mmol) and the mixture was stirred overnight at RT. More acetyl chloride (0.018 ml, 0.248 mmol) and triethylamine (0.039 ml, 0.281 mmol) were added and stirring continued until the reaction was completed. The mixture was diluted with DCM and washed with water, saturated $NaHCO_3$-solution and brine, dried and evaporated. Crude product was purified by reverse phase flash chromatography to afford the title compound. Yield: 0.072 g. $^1$H NMR (400 MHz, $CDCl_3$)

δ: 9.44 (s, 1H), 8.18 (s, 1H), 7.43-7.60 (m, 2H), 6.91-7.07 (m, 2H), 6.86 (d, 1H), 6.74 (d, 1H), 4.75 (d, 1H), 3.91 (s, 3H), 3.59 (t, 1H), 3.47 (dd, 1H), 2.41-2.55 (m, 1H), 2.15 (s, 3H), 1.81-2.22. (m, 3H). LCMS: m/z 423.6 $[M+H]^+$.

Example 21. N-(2-Hydroxy-5-(4-(trifluoromethyl) phenoxy)phenyl)-1-methyl-5-oxopyrrolidine-2-carboxamide (Compound 372)

Compound 372

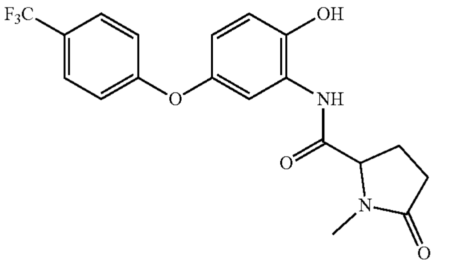

To a solution of Compound 48 (100 mg, 245 μmol) in DCM (5 ml) was added tetrabutyl ammonium iodide (90 mg, 245 μmol) at RT. The solution was cooled to −50° C. Then $BCl_3$ 1 M in heptane (1.469 ml, 1469 μmol) was added dropwise. The mixture was stirred for 10 min at −78° C. and then 1 h 20 min at RT. The mixture was diluted with DCM (10 ml) and poured into ice cold 1 N HCl (5 ml). Phases were separated. The aqueous phase was extracted twice with DCM. The combined organic phases were concentrated under reduced pressure. The crude product was purified by column chromatography to afford the title compound (0.055 g). $^1$H NMR (400 MHz, DMSO) δ: 10.06 (br s 1H), 9.57 (s, 1H), 7.79 (d, 1H), 7.69 (d, 2H), 7.05 (d, 2H), 6.94 (d, 1H), 6.80-6.75 (m, 1H), 4.50-4.42 (m, 1H), 2.65 (s, 3H), 2.31-2.12 (m, 3H), 1.95-1.84 (m, 1H). LCMS: m/z 395.4 $[M+H]^+$ The following compound was prepared according to the procedure described for Compound 372. The compound code, structure, starting materials, purification method and characterization data are indicated in the table.

Example 22. N-(2-Methoxy-5-(4-(trifluoromethyl) phenoxy)phenyl)-1-methyl-6-oxopiperazine-2-carboxamide (Compound 374)

Compound 374

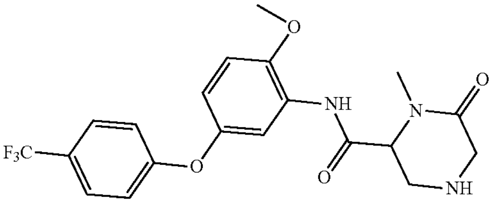

tert-Butyl 3-((2-methoxy-5-(4-(trifluoromethyl)phenoxy) phenyl)carbamoyl)-4-methyl-5-oxopiperazine-1-carboxylate (30.6 mg, 58.5 μmol) was dissolved in HCl (dioxane solution) (2.13 g, 1.43 mL, 10 w-%, 5.85 mmol) and stirred at RT overnight. The mixture was purified by HPLC (Method D) to afford 12.9 mg of the title compound (12.9 mg, 30.5 μmol, 52.1%, 100% purity). $^1$H NMR (400 MHz, DMSO-$d_6$) δ: 9.93 (s, 1H), 7.92 (d, 1H), 7.71 (d, 2H), 7.10 (dd, 3H), 6.91 (dd, 1H), 4.20 (s, 1H), 3.88 (d, 3H), 3.26 (s, 2H), 3.13 (s, 2H), 2.77 (s, 3H). LCMS: m/z 424.2 $[M+H]^+$.

The following compounds were prepared according to the procedure described for Compound 374. The compound code, structure, starting materials, purification method and characterization data are indicated in the table.

| No | Structure and starting material | Purification method and characterization data |
|---|---|---|
| 373 | 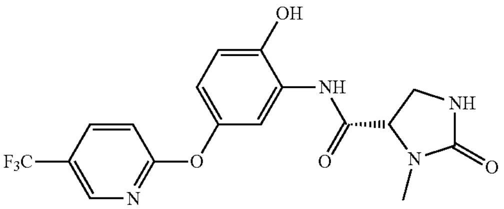<br>Starting materials: (S)-N-(2-methoxy-5-((5-(trifluoromethyl)-pyridin-2-yl)oxy)phenyl)-3-methyl-2-oxoimidazolidine-4-carboxamide | $^1$H NMR (400 MHz, DMSO-d6) δ: 2.64 (3 H, s), 3.14-3.20 (1 H, m), 3.55 (1 H, t), 4.33-4.40 (1 H, m), 6.49 (1 H, br s), 6.78-6.83 (1 H, m), 6.93 (1 H, d), 7.14-7.18 (1 H, m), 7.83 (1 H, d), 8.17-8.21 (1 H, m), 8.53-8.56 (1 H, m), 9.39 (1 H, br s), 10.14 (1 H, br s). LCMS: m/z 397.5 [M + H]+ |

| No | Structure and starting material | Purification method and characterization data |
|---|---|---|
| 375 | 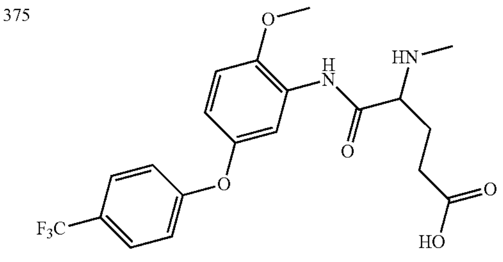 Starting materials: tert-Butyl 4-((tert-butoxycarbonyl)amino)-5-((2-methoxy-5-(4-(trifluoromethyl)-phenoxy)phenyl)amino)-5-oxo-pentanoate | Purification method D. $^1$H NMR (400 MHz, DMSO-d6) δ: 8.11-8.01 (m, 1H), 7.71 (d, 2H), 7.13 (d, 1H), 7.09 (d, 2H), 6.91-6.81 (m, 1H), 3.89 (s, 3H), 3.06-2.99 (m, 1H), 2.35-2.30 (m, 3H), 2.27 (s, 3H), 1.90-1.68 (m, 1H). LCMS: m/z 427.2 [M + H]$^+$ |

Example 23. 1-Methyl-6-oxo-N-(5-(4-(trifluoromethyl)phenoxy)-2,3-dihydro-benzofuran-7-yl)piperazine-2-carboxamide (Compound 376)

Compound 376

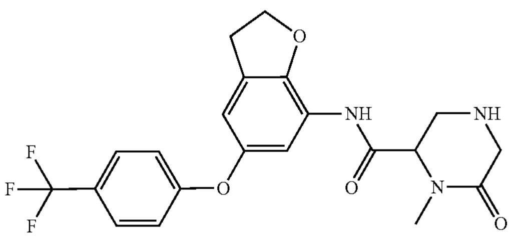

Tert-butyl 4-methyl-3-oxo-5-((5-(4-(trifluoromethyl)phenoxy)-2,3-dihydro-benzofuran-7-yl)carbamoyl)piperazine-1-carboxylate (0.0416 g, 1 eq., 77.7 μmol) was dissolved in methanol (3 mL). TMS-Cl (42.2 mg, 49.3 μL, 5 eq., 388 μmol) was added dropwise. The mixture was stirred at 25° C. for 16 h and then concentrated under reduced pressure. The obtained mixture was subjected to HPLC (purification method D) to give the title compound (0.01 g, 0.02 mmol, 30%, 95% purity). $^1$H NMR (400 MHz, DMSO-d6) δ: 7.70 (d, 2H), 7.60 (s, 1H), 7.07 (d, 2H), 6.86 (s, 1H), 4.65 (t, 2H), 4.20 (t, 1H), 3.29-3.20 (m, 4H), 3.18-3.02 (m, 2H), 2.74 (s, 3H). LCMS: m/z 436.2 [M+H]$^+$.

Example 24. (R)—N-(2-Methoxy-5-(4-(trifluoromethyl)phenoxy)phenyl)-5-oxo-1-(1H-pyrazol-4-yl)pyrrolidine-2-carboxamide (Compound 377)

Compound 377

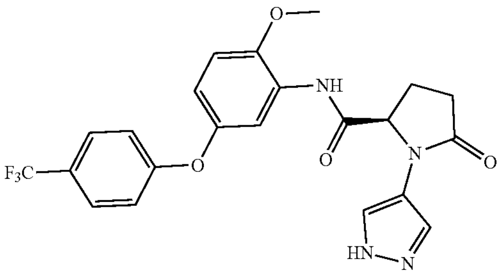

TFA (335 mg, 226 μL, 50 eq., 2.94 mmol) was added to (R)—N-(2-methoxy-5-(4-(trifluoromethyl)phenoxy)phenyl)-1-(1-(4-methoxybenzyl)-1H-pyrazol-4-yl)-5-oxopyrrolidine-2-carboxamide (0.0341 g, 1 eq., 58.7 μmol) followed by refluxing the mixture for 16 h. Then the solvent was evaporated and the residue was purified by HPLC (Method G) to give the title compound (0.0057 g, 12 μmol, 21%, 100% purity). $^1$H NMR (400 MHz, Acetonitrile-d$_3$) δ: 8.62 (s, 1H), 8.01 (d, 1H), 7.79 (s, 2H), 7.66 (d, 2H), 7.07 (dd, 3H), 6.88 (dd, 1H), 4.75 (dd, 1H), 3.92 (s, 3H), 2.66-2.36 (m, 4H), 2.23-2.13 (m, 2H). LCMS: m/z 459.1 [M−H]$^-$.

The following compounds were prepared according to the procedure described for Compound 377. The compound code, structure, starting materials, purification method and characterization data are indicated in the table.

| No | Structure and starting material | Purification method and characterization data |
|---|---|---|
| 378 | 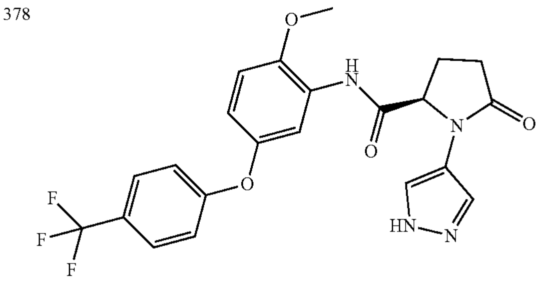 Starting materials: (R)-N-(2-Methoxy-5-(4-(trifluoromethyl)phenoxy)phenyl)-1-(1-(4-methoxybenzyl)-1H-pyrazol-4-yl)-5-oxopyrrolidine-2-carboxamide | Purification method G. $^1$H NMR (500 MHz, Acetonitrile-d3) δ: 8.58 (s, 1H), 7.99 (d, 1H), 7.77 (s, 2H), 7.65 (d, 2H), 7.06 (dd, 3H), 6.86 (dd, 1H), 4.73 (dd, 1H), 3.90 (s, 3H), 2.64-2.33 (m, 4H). LCMS: m/z 461.0 [M + H]$^+$ |

Example 25. 1-(3-Amino-3-oxopropyl)-N-(2-methoxy-5-(4-(trifluoromethyl)-phenoxy)phenyl)-5-oxopyrrolidine-2-carboxamide (Compound 379)

Compound 379

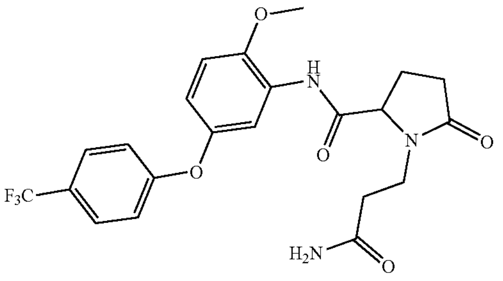

To a solution of 1-(2-cyanoethyl)-N-(2-methoxy-5-(4-(trifluoromethyl)phenoxy)phenyl)-5-oxopyrrolidine-2-carboxamide (158 mg, 1 eq., 353 μmol) in DMSO (2 mL) potassium carbonate (97.6 mg, 2 eq., 706 μmol) followed by hydrogen peroxide (343 mg, 309 μL, 35 w-%, 10 eq., 3.53 mmol) was added. The mixture was stirred at 40° C. for 36 h. Water (20 mL) was added to the residue and the resulted mixture was extracted with ethyl acetate (2×20 mL). Organic layers were combined, washed with brine (20 mL), dried over sodium sulfate, filtered and concentrated. The residue was purified by reverse phase HPLC (purification method B) to afford the title compound (13.4 mg, 28.8 μmol, 8.15%, 100% purity) $^1$H NMR (400 MHz, DMSO-d$_6$) δ: 9.64 (s, 1H), 7.89 (s, 1H), 7.70 (d, 2H), 7.36 (s, 1H), 7.19-7.05 (m, 3H), 6.92 (d, 1H), 6.82 (s, 1H), 4.63-4.55 (m, 1H), 3.88 (s, 3H), 3.64-3.51 (m, 1H), 3.20-2.96 (m, 2H), 2.31-2.12 (m, 4H), 1.96-1.85 (m, 1H). LCMS: m/z 466.2 [M+H]$^+$.

Example 26. (2S,4S)-4-Hydroxy-N-(2-methoxy-5-(4-(trifluoromethyl)phenoxy)phenyl)-1-methyl-5-oxopyrrolidine-2-carboxamide (Compound 380)

Compound 380

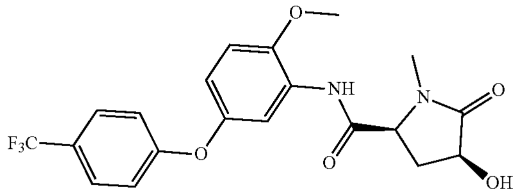

(2S,4S)-4-((tert-Butyldimethylsilyl)oxy)-N-(2-methoxy-5-(4-(trifluoromethyl)-phenoxy)phenyl)-1-methyl-5-oxopyrrolidine-2-carboxamide (0.185 g, 1 eq., 343 μmol) was dissolved in THF (2 mL). Then TBAF (89.8 mg, 343 μL, 1 molar, 1 eq., 343 μmol) was added to the mixture dropwise at 0° C. The resulting mixture was stirred for 20 min and slowly heated to 20° C., stirred at this temperature for 10 h and purified by HPLC (purification method A) to give the title compound (0.0374 g, 88.1 μmol, 25.7%, 100% purity). $^1$H NMR (400 MHz, DMSO-d$_6$) δ: 9.68 (s, 1H), 7.87 (s, 1H), 7.71 (d, 2H), 7.14 (d, 1H), 7.08 (d, 2H), 6.96-6.88 (m, 1H), 4.31 (t, 1H), 4.12 (t, 1H), 3.88 (s, 3H), 2.67 (s, 3H), 2.65-2.57 (m, 1H), 1.74-1.57 (m, 1H). LCMS: m/z 425.0 [M+H]$^+$.

Example 27. 1-Imino-N-(2-methoxy-5-(4-(trifluoromethyl)phenoxy)phenyl)-hexahydro-1λ$^6$-thiopyran-4-carboxamide 1-oxide (Compound 381)

Compound 381

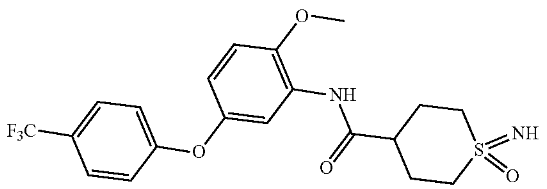

A mixture of N-(2-methoxy-5-(4-(trifluoromethyl)phenoxy)phenyl)tetrahydro-2H-thiopyran-4-carboxamide 1-oxide (250 mg, 1 eq., 585 μmol), phenyl-$\lambda^3$-iodanediyl diacetate (565 mg, 3 eq., 1.75 mmol) and carbamic acid, ammonia salt (183 mg, 4 eq., 2.34 mmol) in methanol (12 mL) was stirred at 22° C. for 12 h. The mixture was concentrated to provide a mixture of a light yellow sludge and an immiscible colorless liquid. The mixture was washed twice with hexane (2×10 mL) by decantation and dried under vacuum. The residue was triturated and stirred in ethyl acetate, filtered, and the collected solid was washed with additional ethyl acetate. The filtrate was concentrated to provide a mixture of cis and trans isomers and purified by HPLC (purification method A) to give the title compound (30.5 mg, 65 μmol, 11%, 95% purity). $^1$H NMR (400 MHz, DMSO-d6) δ: 9.34 (d, 1H), 7.87 (t, 1H), 7.70 (d, 2H), 7.09 (dd, 3H), 6.88 (dd, 1H), 3.87 (s, 3H), 3.70 (s, 0H), 3.48 (s, 1H), 3.16-2.79 (m, 4H), 2.16-1.92 (m, 4H). LCMS: m/z 443.1 $[M+H]^+$.

Example 28. N-(4-Fluoro-2-methoxy-5-(4-(trifluoromethyl)phenoxy)phenyl)-3-methyl-2-oxoimidazolidine-4-carboxamide (Compound 382)

Compound 382

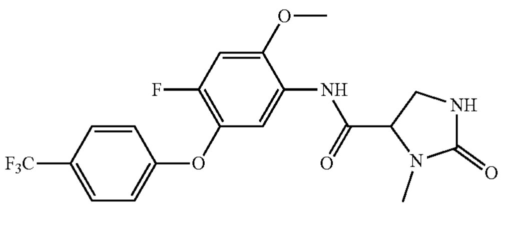

N-(5-(2-Chloro-4-(trifluoromethyl)phenoxy)-4-fluoro-2-methoxyphenyl)-3-methyl-2-oxoimidazolidine-4-carboxamide (0.032 g, 1 eq., 69 μmol) was dissolved in methanol (5 mL). Formic acid, ammonia salt (26 mg, 6 eq., 0.42 mmol) and palladium (7.4 mg, 10 w-%, 0.1 eq., 6.9 μmol) were added. The resulting mixture was stirred at 60° C. for 12 h, cooled to RT and filtered. The filtrate was concentrated under reduced pressure. The residue was dissolved in DMSO (2 mL) and to the obtained solution metal scavenger (SiliaMetS Dimercaptotriazine, 50 mg) was added. The mixture was stirred at RT for 3 h and filtered. The clear filtrate was purified by HPLC (purification method B) to give the title compound (0.0038 g, 8.4 μmol, 12%, 95% purity). $^1$H NMR (400 MHz, DMSO-d6) δ: 9.55 (s, 1H), 7.95 (d, 1H), 7.72 (d, 2H), 7.29 (d, 1H), 7.10 (d, 2H), 6.44 (s, 1H), 4.49-4.26 (m, 1H), 3.89 (s, 3H), 3.52 (t, 1H), 3.16 (t, 1H), 2.61 (s, 3H). LCMS: m/z 428.0 $[M+H]^+$ Example 29. 1,4-Dimethyl-6-oxo-N-(5-(4-(trifluoromethyl)phenoxy)-2,3-dihydrobenzofuran-7-yl) piperazine-2-carboxamide (Compound 383)

Compound 383

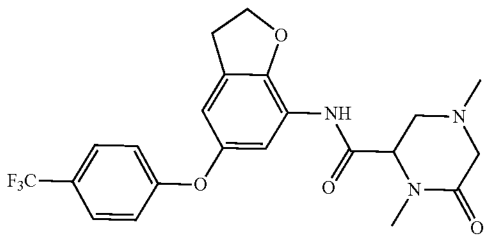

To a solution of 1-methyl-6-oxo-N-(5-(4-(trifluoromethyl)phenoxy)-2,3-di-hydrobenzofuran-7-yl)piperazine-2-carboxamide (0.022 g, 1 eq., 51 μmol) in 1,4-dioxane (2 mL) was added $NaCNBH_4$ (6.4 mg, 2 eq., 0.10 mmol) and water solution of formaldehyde (8.2 mg, 7.5 μL, 37 w-%, 2 eq., 0.10 mmol). Thereafter HOAc (0.01 mL) was added and the mixture was stirred at 25° C. for 12 h and evaporated. The residue was dissolved in DMSO (2 mL) and the metal scavenger (SiliaMetS Dimercaptotriazine, 10 mg) was added. The obtained mixture was stirred at RT for 3 h, filtered and the clear solution was purified by HPLC (purification method A) to afford the title compound (0.0052 g, 11 μmol, 22%, 95% purity). $^1$H NMR (500 MHz, DMSO-d6) δ: 9.97 (s, 1H), 7.68 (d, 2H), 7.57 (s, 1H), 7.05 (d, 2H), 6.84 (s, 1H), 4.63 (t, 2H), 4.20 (t, 1H), 3.23 (t, 2H), 3.12 (d, 1H), 2.93 (dd, 1H), 2.82-2.64 (m, 5H), 2.17 (s, 3H). LCMS: m/z 450.2 $[M+H]^+$ Example 30. N-(5-(4-Amino-2-fluorophenoxy)-2-methoxyphenyl)-1-methyl-5-oxopyrrolidine-2-carboxamide (Compound 384)

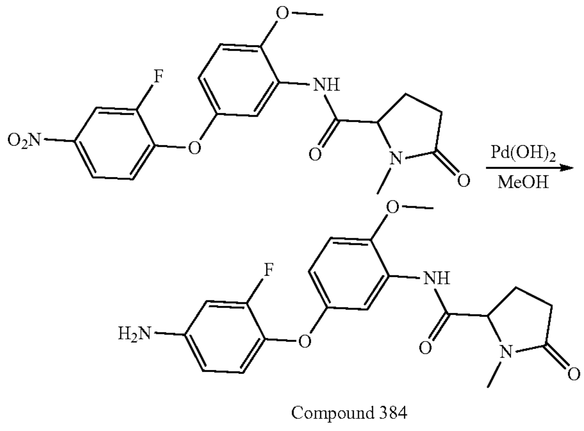

Compound 384

N-(5-(2-Fluoro-4-nitrophenoxy)-2-methoxyphenyl)-1-methyl-5-oxopyrrolidine-2-carboxamide (0.080 g, 1 eq., 0.20 mmol) was dissolved in MeOH and dihydroxy-palladium (28 mg, 10 w-%, 0.1 eq., 20 μmol) was added. The resulting mixture was stirred under hydrogen atmosphere for 16 h, filtered and concentrated to give the title compound (0.065 g, 0.16 mmol, 79%, 90% purity). LCMS: m/z 393.0 $[M+H]^+$ Example 31. N-(5-(4-Chloro-2-fluorophenoxy)-2-methoxyphenyl)-1-methyl-5-oxopyrrolidine-2-carboxamide (Compound 385)

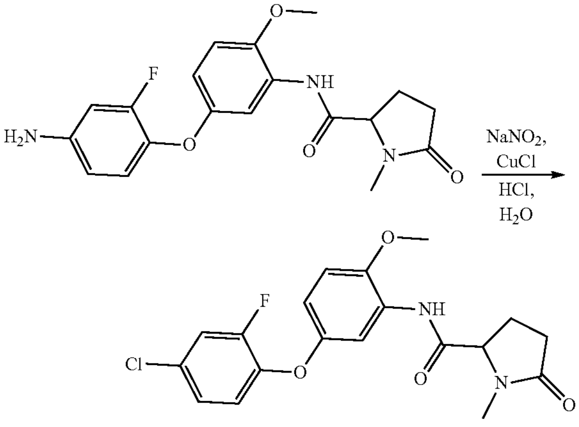

Compound 385

To a solution of N-(5-(4-amino-2-fluorophenoxy)-2-methoxyphenyl)-1-methyl-5-oxopyrrolidine-2-carboxamide (0.056 g, 1 eq., 0.15 mmol) in hydrochloric acid, 22% (0.5 mL) solution of sodium nitrite (12 mg, 1.2 eq., 0.18 mmol) in water (0.1 mL) was added at 0° C. The resulting mixture was stirred at the same temperature for 15 min, then the mixture was poured into solution of copper(I) chloride (21 mg, 1.4 eq., 0.21 mmol) in 37% hydrochloric acid (2 mL) at 0° C. The resulting mixture was stirred at 22° C. for 10 h. The mixture was concentrated under reduced pressure and purified by HPLC (purification method A) to give the title compound (0.0181 g, 46.1 μmol, 31%, 100% purity). $^1$H NMR (400 MHz, DMSO-d6) δ: 9.61 (s, 1H), 7.83 (d, 1H), 7.69-7.53 (m, 1H), 7.26 (d, 1H), 7.06 (t, 2H), 6.88-6.70 (m, 1H), 4.55-4.39 (m, 1H), 3.85 (s, 3H), 2.64 (s, 3H), 2.41-2.11 (m, 3H), 1.95-1.74 (m, 1H). LCMS: m/z 393.0 $[M+H]^+$.

Example 32. N-(5-(3-Acetylphenoxy)-2-methoxy-phenyl)-1-methyl-5-oxopyrro-lidine-2-carboxamide (Compound 386)

a) 1-(4-(4-Methoxy-3-nitrophenoxy)phenyl)ethan-1-one

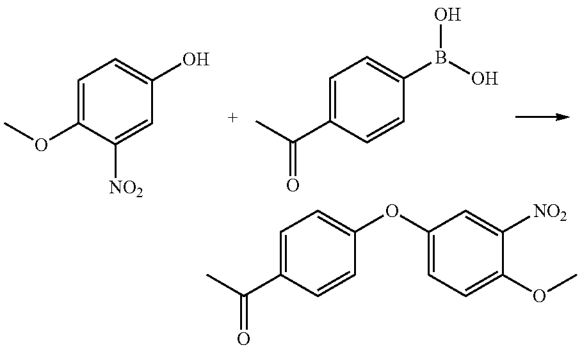

4-Acetylphenylboronic acid (0.33 g, 1.99 mmol), 4-methoxy-3-nitrophenol (0.28 g, 1.66 mmol), $Cu(OAc)_2$ (0.451 mg, 2.48 mmol) and freshly activated powdered 4 Å molecular sieves were added to dry DCM (20 mL). $Et_3N$ (1.15 mL, 8.28 mmol) was then added to the mixture. The mixture was stirred under air atmosphere. Reaction progress was monitored by LCMS. After 24 h, the resulting slurry was filtered through celite and concentrated. The crude product was purified by flash column chromatography (heptane:EtOAc) to yield 0.3 g of the title compound. LCMS: m/z 288.21 $[M+H]^+$.

b) 1-(4-(3-Amino-4-methoxyphenoxy)phenyl)ethan-1-one

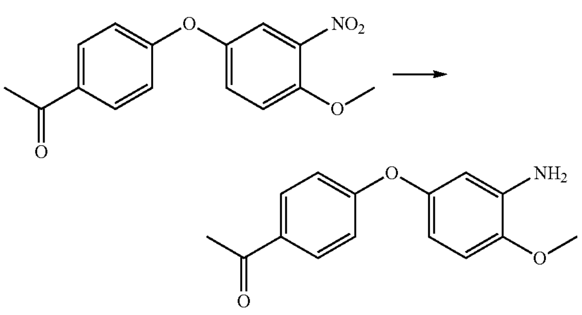

A mixture of 1-(4-(4-methoxy-3-nitrophenoxy)phenyl) ethan-1-one (300 mg, 1.04 mmol), zinc (0.68 g, 10 eq., 10.44 mmol), ammonium chloride (0.56 g, 10 eq. 10.44 mmol) in THF (5 ml), MeOH (3 ml) and water (3 ml) was stirred at RT for 4 h. The mixture was filtered through celite. The filtrate was washed with water (2×30 mL), dried over sodium sulfate, filtered and the solvent was removed under reduced pressure. The residue was purified by flash chromatography to afford (0.19 g) of the title compound. LCMS: m/z 258.65$[M+H]^+$.

c) N-(5-(4-Acetylphenoxy)-2-methoxyphenyl)-1-methyl-5-oxopyrrolidine-2-carboxamide (Compound 386)

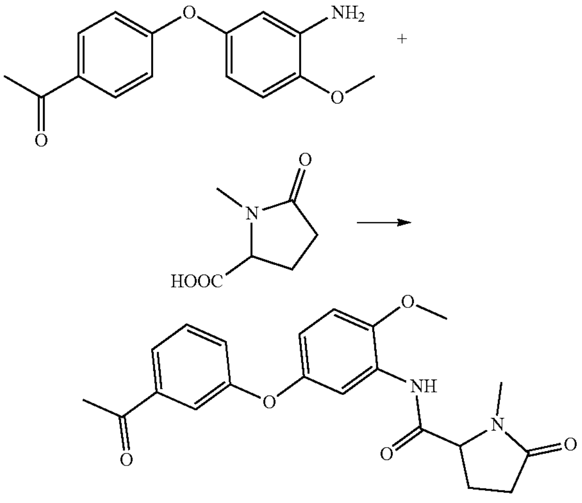

Compound 386

To a solution of 1-methyl-5-oxopyrrolidine-2-carboxylic acid (22.25 mg, 0.15 mmol), 1-(4-(3-amino-4-methoxyphenoxy)phenyl)ethan-1-one (40 mg, 0.16 mmol) and TEA (0.11, 0.78 mmol) in dry DMF (2 ml) at 0° C., was added 1-propanephosphonic acid cyclic anhydride (0.73 ml, 1.24 mmol). The mixture was stirred at RT overnight. The reaction mixture was quenched with water (10 ml) then extracted with ethyl acetate (2×10 ml). The combined organic layers were washed with 2 M $NaHCO_3$, then with water, dried over sodium sulfate, evaporated and then purified by reverse phase chromatography to yield (40.5 mg) of the title compound. $^{1}H$ NMR (600 MHz, DMSO-$d_6$): δ: 1.86-1.92 (m, 1H), 2.16-2.30 (m, 3H), 2.52-2.54 (m, 3H), 2.61-2.65 (m, 3H), 3.89 (s, 3H), 4.47 (dd, 1H), 6.91 (dd, 1H), 6.98-7.01 (m, 2H), 7.14 (d, 1H), 7.87 (d, 1H), 7.94-8.02 (m, 2H), 9.65 (s, 1H). LCMS: m/z 383.28 $[M+H]^+$.

Example 33. N-(5-(3-Acetylphenoxy)-2-methoxyphenyl)-1-methyl-5-oxopyrro-lidine-2-carboxamide (Compound 387)

a) 1-Methoxy-4-nitro-2-(4-(trifluoromethyl)benzyl) benzene

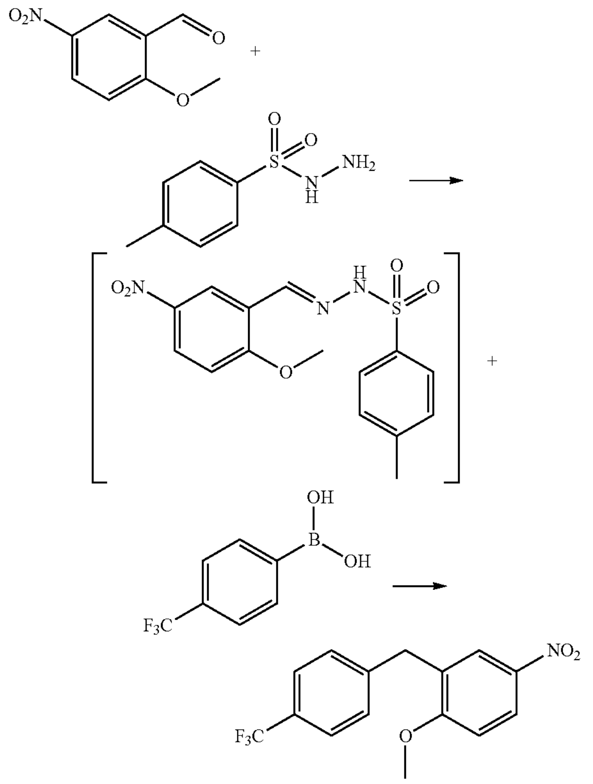

A mixture of 2-methoxy-5-nitro benzaldehyde (0.5 g, 2.8 mmol) and toluene-sulfon hydrazide (0.51 g, 2.8 mmol) in 1,4-dioxane (5 ml) was heated at 60° C. for 90 min. To the crude (E)-N'-(2-methoxy-5-nitrobenzylidene)-4-methylbenzenesulfono-hydrazide was added $K_2CO_3$ (0.53 g, 3.86 mmol) and 4-(trifluoromethyl)phenylboronic acid (0.49 g, 2.6 mmol). The mixture was heated under nitrogen atmosphere at 110° C. for 4 h. After cooling at RT the mixture was quenched with 2 M $NaHCO_3$ (5 ml). The mixture was extracted with ethyl acetate (2×10 ml). The combined organic layers were washed with water, dried, evaporated and then purified by flash chromatography to yield (0.35 g) of the title compound. LCMS: m/z 312.2 $[M+H]^+$.

b) 4-Methoxy-3-(4-(trifluoromethyl)benzyl)aniline

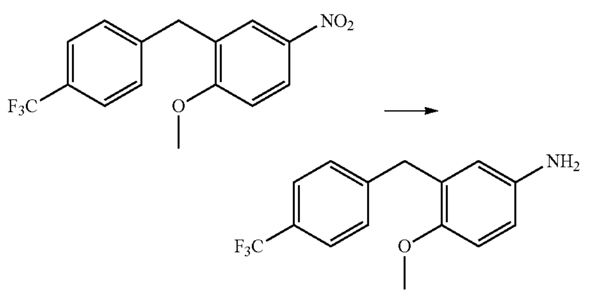

A mixture of 1-methoxy-4-nitro-2-(4-(trifluoromethyl) benzyl)benzene (100 mg, 0.32 mmol), zinc (0.21 g, 10 eq., 3.21 mmol) and ammonium chloride (0.17 g, 10 eq. 3.21 mmol) in THF (10 ml), MeOH (3 ml) and water (3 ml) was stirred at RT for 4 h. The mixture was filtered through celite. The filtrate was washed with water (2×30 mL), dried over sodium sulfate, filtered and the solvent was removed under reduced pressure. The residue was purified by flash chromatography to afford (0.12 g) of the title compound. LCMS: m/z 282.05 $[M+H]^+$.

c) N-(4-Methoxy-3-(4-(trifluoromethyl)benzyl)phenyl)-1-methyl-5-oxo-pyrrolidine-2-carboxamide (Compound 387)

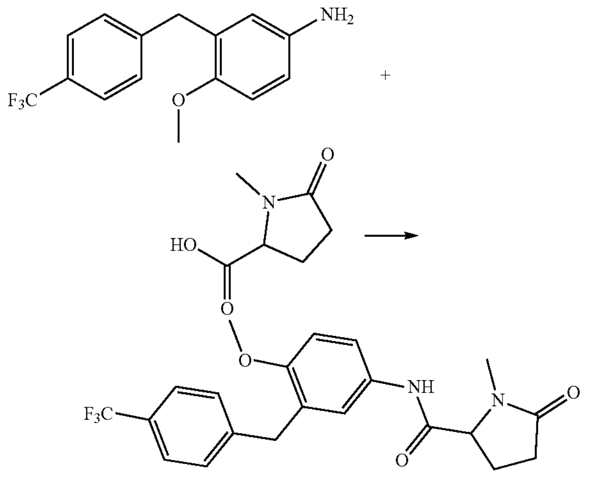

Compound 387

To a solution of 1-methyl-5-oxopyrrolidine-2-carboxylic acid (45.8 mg, 0.32 mmol), 4-methoxy-3-(4-(trifluoromethyl)benzyl)aniline (90 mg, 0.32 mmol) and TEA (0.22, 1.60 mmol) in dry DMF (2 ml) at 0° C. was added 1-propanephosphonic acid cyclic anhydride (1.51 ml, 2.56 mmol). The mixture was stirred at RT overnight. The reaction mixture was quenched with water (10 ml) then extracted with ethyl acetate (2×10 ml). The combined organic layers were washed with 2 M $NaHCO_3$, then with water, dried over sodium sulfate, evaporated and then purified by reverse phase chromatography to yield (5 mg) of the title compound. $^1$H NMR (400 MHz, Chloroform-d) δ: 1.75-2.02 (m, 1H), 2.06-2.22 (m, 1H), 2.31-2.59 (m, 3H), 2.81-2.91 (m, 3H), 3.79-3.93 (m, 3H), 3.96-4.10 (m, 3H), 6.85 (d, 1H), 7.25-7.33 (m, 4H), 7.44-7.57 (m, 3H), 7.84 (br s, 1H). LCMS: m/z 282.05 $[M+H]^+$.

Example 34. N-(2-Methoxy-5-(4-(trifluoromethyl)phenoxy)phenyl)-2-oxo-2,3-dihydrooxazole-4-carboxamide (Compound 388)

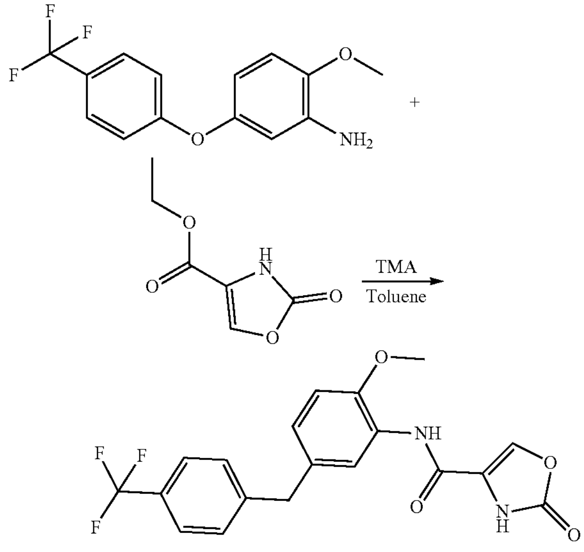

Compound 388

TMA (2 M in Chlorobenzene, 397 µL, 0.794 mmol) was added to a mixture of 2-methoxy-5-(4-(trifluoromethyl)phenoxy)aniline (0.075 g, 0.265 mmol) and ethyl-2-oxo-2,3-dihydrooxazole-4-carboxylate (0.064 g, 0.397 mmol) in toluene (2 ml) followed by heating the mixture at 90° C. for 3 h. The reaction mixture was quenched with ice cold water. The aqueous layer was extracted with EtOAc (2×5 ml). The combined organic layers were evaporated and then purified by reverse phase chromatography to yield 0.029 g of the title compound. $^1$H NMR (400 MHz, DMSO-$d_6$) δ: 3.87 (3H, s), 7.00 (1H, m), 7.11 (2H, d), 7.17 (1H, d), 7.59 (1H, d), 7.72 (2H, d), 7.98 (1H, s), 9.46 (1H, s), 11.44 (1H, br s). LCMS: m/z 395.2 $[M+H]^+$

Example 35. N-(3-(3,4-Difluorophenoxy)-6-methoxy-2-methylphenyl)-1-methyl-5-oxopyrrolidine-2-carboxamide (Compound 389)

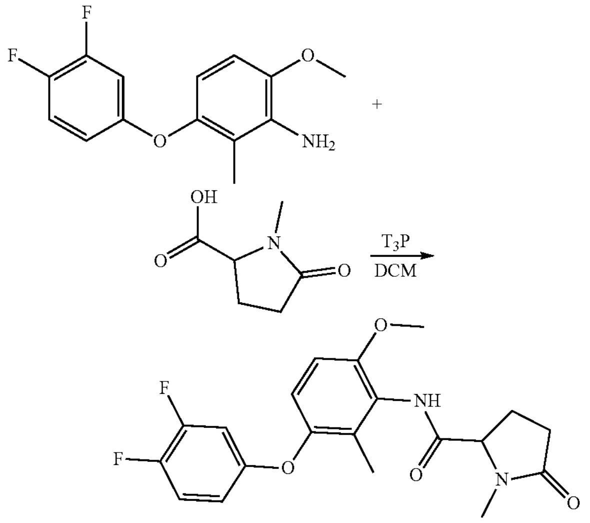

Compound 389

To a solution of 1-methyl-5-oxopyrrolidine-2-carboxylic acid (15 mg, 0.10 mmol), 3-(3,4-difluorophenoxy)-6-methoxy-2-methylaniline (24 mg, 0.09 mmol), $T_3P$ (50% in EtOAc, 80 µl, 0.14 mmol) and DCM (2 ml) was added DIPEA (47 µl, 0.27 mmol). After refluxing for 3 h, additional starting material and reagents were added (1-methyl-5-oxopyrrolidine-2-carboxylic acid 1.15 eq., $T_3P$ 1.5 eq., DIPEA 3.0 eq.) followed by stirring in a closed vessel at 80° C. for 7 h. The reaction mixture was quenched with 2N NaOH (2 ml). The organic layer was separated and the aqueous layer was extracted with EtOAc (1×4 ml). The combined organic layers were evaporated and then purified by reverse phase chromatography to yield 0.016 g of the title compound. $^1$H NMR (400 MHz, DMSO-$d_6$) δ: 1.94 (3H, s), 1.94-2.03 (1H, m), 2.19-2.37 (3H, m), 2.71 (3H, s), 3.79 (3H, s), 4.26-4.33 (1H, m), 6.61 (1H, m), 6.90-7.02 (3H, m), 7.36-7.45 (1H, m), 9.66 (1H, s). LCMS: m/z 391.1 $[M+H]^+$ The following compounds were prepared according to the procedure described for Compound 389. The compound code, structure, starting materials, purification method and characterization data are indicated in the table.

| No | Structure and starting material | Purification method and characterization data |
|---|---|---|
| 390 | 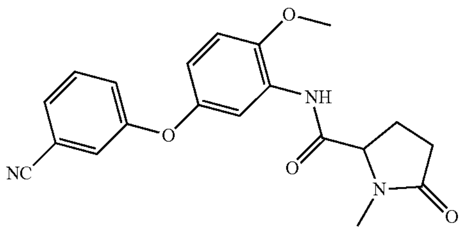 [SMILES: COc1ccc(Oc2cccc(C#N)c2)cc1NC(=O)C1CCC(=O)N1C] Starting materials: 3-(3-Amino-4-methoxyphenoxy)benzonitrile and 1-Methyl-5-oxopyrrolidine-2-carboxylic acid | Purification method Column chromatography. $^1$H NMR (600 MHz, DMSO-$d_6$) δ: 1.86-1.92 (1H, m), 2.15-2.30 (3H, m), 2.64 (3H, s), 3.88 (3H, s), 4.47 (1H, m), 6.88 (1H, m), 7.12 (1H, d), 7.26 (1H, m), 7.38 (1H, m), 7.51-7.57 (2H, m), 7.85 (1H, d), 9.64 (1H, s). LCMS: m/z 366.3 [M + H]$^+$ |

-continued

| No | Structure and starting material | Purification method and characterization data |
|---|---|---|
| 391 | 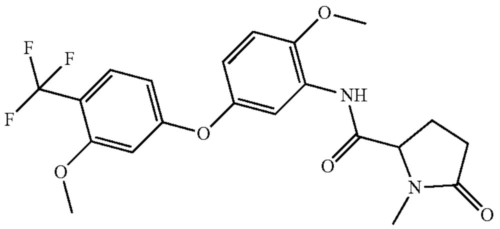 [SMILES: COc1ccc(Oc2ccc(C(F)(F)F)c(OC)c2)cc1NC(=O)C1CCC(=O)N1C] Starting materials: 2-Methoxy-5-(3-methoxy-4-(trifluoromethyl)-phenoxy)aniline and 1-Methyl-5-oxopyrrolidine-2-carboxylic acid | Purification method Column chromatography. $^1$H NMR (400 MHz, DMSO-$d_6$) δ: 1.83-1.96 (1H, m), 2.13-2.34 (3H, m), 2.65 (3H, s), 3.85 (3H, s), 3.88 (3H, s), 4.43-4.50 (1H, m), 6.44 (1H, m), 6.88-6.95 (2H, m), 7.13 (1H, d), 7.54 (1H, d), 7.88 (1H, d), 9.65 (1H, s). LCMS: m/z 439.4 [M + H]+ |
| 392 | 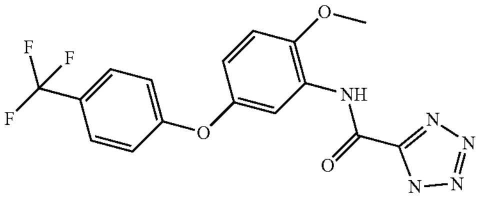 [SMILES: COc1ccc(Oc2ccc(C(F)(F)F)cc2)cc1NC(=O)c1nnn[nH]1] Starting materials: 2-Methoxy-5-(4-(trifluoromethyl)phenoxy)aniline and 1H-Tetrazole-5-carboxylic acid | Purification method Column chromatography. $^1$H NMR (400 MHz, CDCl3) δ: 3.98 (3H, s), 6.86-6.91 (1H, m), 6.96 (1H, d), 7.01 (2H, d), 7.54 (2H, d), 8.22 (1H, d), 9.72 (1H, s. LCMS: m/z 379.9 [M + H]+ |
| 393 | 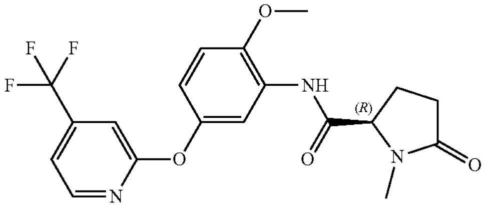 Starting materials: 2-Methoxy-5-((4-(trifluoromethyl)pyridin-2-yl)oxy)-aniline and (2R)-1-Methyl-5-oxo-pyrrolidine-2-carboxylic acid | Purification method Column chromatography. $^1$H NMR (400 MHz, DMSO-$d_6$) δ: 1.83-1.96 (1H, m), 2.11-2.35 (3H, m), 2.65 (3H, s), 3.89 (3H, s), 4.43-4.51 (1H, m), 6.95 (1H, d), 7.12 (1H, d), 7.41 (1H, br s), 7.46 (1H, d), 7.87 (1H, d), 8.38 (1H, d), 9.62 (1H, s). LCMS: m/z 410.4 [M + H]+ |
| 394 | 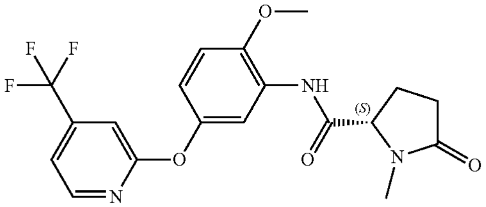 Starting materials: 2-Methoxy-5-((4-(trifluoromethyl)pyridin-2-yl)oxy)-aniline and (S)-1-Methyl-5-oxopyrrolidine-2-carboxylic acid | Purification method Column chromatography. $^1$H NMR (400 MHz, DMSO-$d_6$) δ: 1.83-1.96 (1H, m), 2.11-2.35 (3H, m), 2.65 (3H, s), 3.89 (3H, s), 4.43-4.51 (1H, m), 6.95 (1H, m), 7.12 (1H, d), 7.41 (1H, s), 7.46 (1H, d), 7.87 (1H, d), 8.38 (1H, d), 9.62 (1H, s). LCMS: m/z 410.5 [M + H]+ |
| 395 | 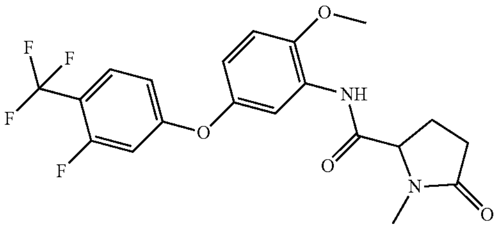 [SMILES: COc1ccc(Oc2ccc(C(F)(F)F)c(F)c2)cc1NC(=O)C1CCC(=O)N1C] Starting material: 5-(3-Fluoro-4-(tri-fluoromethyl)phenoxy)-2-methoxy-aniline and 1-Methyl-5-oxopyrrolidine-2-carboxylic acid | Purification method: Column chromatography. $^1$H NMR (400 MHz, DMSO-$d_6$) δ: 1.85-1.95 (1H, m), 2.14-2.32 (3H, m), 2.65 (3H, s), 3.89 (4H, s), 4.44-4.52 (1H, m), 6.85 (1H, m), 6.97 (1H, m), 7.07 (1H, m), 7.16 (1H, d), 7.74 (1H, t), 7.90 (1H, d), 9.68 (1H, s). LCMS: m/z 427.0 [M + H]+ |

-continued

| No | Structure and starting material | Purification method and characterization data |
|---|---|---|
| 396 | 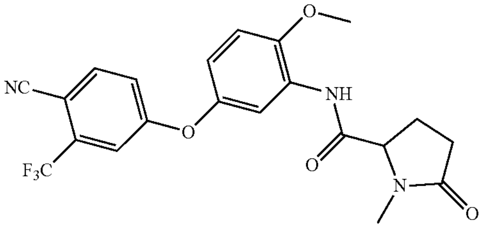 [SMILES: COc1ccc(Oc2ccc(C#N)c(C(F)(F)F)c2)cc1NC(=O)C1CCC(=O)N1C]<br>Starting material: 4-(3-Amino-4-methoxyphenoxy)-2-(trifluoro-methyl)benzonitrile and 1-Methyl-5-oxopyrrolidine-2-carboxylic acid | Purification method: Column chromatography. $^{1}$H NMR (400 MHz, DMSO-$d_6$) δ: 1.83-1.96 (1H, m), 2.14-2.36 (3H, m), 2.65 (3H, s), 3.90 (3H, s), 4.44-4.52 (1H, m), 7.01 (1H, m), 7.18 (1H, d), 7.26 (1H, m), 7.52 (1H, d), 7.92 (1H, d), 8.12 (1H, d), 9.71 (1H, s). LCMS: m/z 434.2 [M + H]+ |
| 397 | 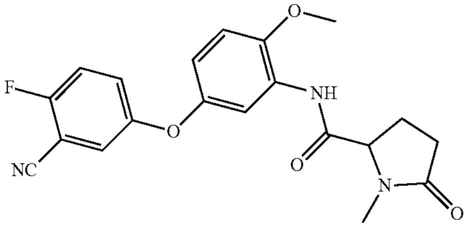 [SMILES: COc1ccc(Oc2ccc(F)c(C#N)c2)cc1NC(=O)C1CCC(=O)N1C]<br>Starting material: 5-(3-Amino-4-methoxyphenoxy)-2-fluorobenzo-nitrile and 1-Methyl-5-oxopyrrolidi-ne-2-carboxylic acid | Purification method: Column chromatography. $^{1}$H NMR (600 MHz, DMSO-$d_6$) δ: 1.86-1.92 (1H, m), 2.15-2.30 (3H, m), 2.64 (3H, s), 3.87 (3H, s), 4.47 (1H, m), 6.85 (1H, m), 7.11 (1H, d), 7.35 (1H, m), 7.50 (1H, d), 7.53 (1H, m), 7.84 (1H, d), 9.64 (1H, s). LCMS: m/z 384.2 [M + H]+ |
| 398 | 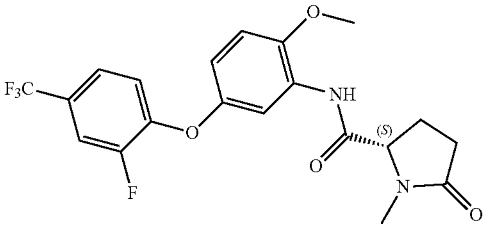<br>Starting materials: 5-(2-Fluoro-4-(trifluoromethyl)phenoxy)-2-methoxyaniline and (S)-1-Methyl-5-oxopyrrolidine-2-carboxylic acid | Purification method: Column chromatography. $^{1}$H NMR (600 MHz, DMSO-$d_6$) δ: 1.86-1.92 (1H, m), 2.16-2.30 (3H, m), 2.64 (3H, s), 3.88 (3H, s), 4.47 (1H, m), 6.93 (1H, m), 7.08 (1H, t), 7.13 (1H, d), 7.54 (1H, d), 7.86 (1H, m), 7.90 (1H, d), 9.66 (1H, s). LCMS: m/z 427.4 [M + H]+ |
| 399 | 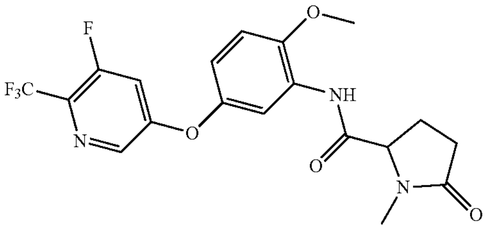 [SMILES: COc1ccc(Oc2cnc(C(F)(F)F)c(F)c2)cc1NC(=O)C1CCC(=O)N1C]<br>Starting material: 5-((5-Fluoro-6-(tri-fluoromethyl)pyridin-3-yl)oxy)-2-methoxyaniline and 1-Methyl-5-oxo-pyrrolidine-2-carboxylic acid | Purification method: Column chromatography. $^{1}$H NMR (400 MHz, DMSO-$d_6$) δ: 1.83-1.95 (1H, m), 2.15-2.34 (3H, m), 2.65 (3H, s), 3.90 (3H, s), 4.45-4.53 (1H, m), 7.03 (1H, m), 7.17 (1H, d), 7.58 (1H, m), 7.96 (1H, d), 8.33 (1H, d), 9.71 (1H, s). LCMS: m/z 428.3 [M + H]+ |
| 400 | 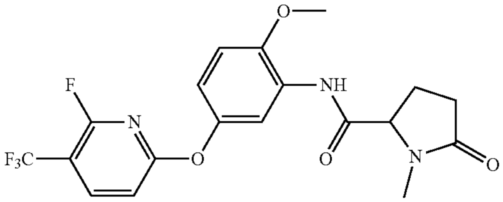 [SMILES: COc1ccc(Oc2ccc(C(F)(F)F)c(F)n2)cc1NC(=O)C1CCC(=O)N1C]<br>Starting material: 5-((6-Fluoro-5-(tri-fluoromethyl)pyridin-2-yl)oxy)-2-methoxyaniline and 1-Methyl-5-oxo-pyrrolidine-2-carboxylic acid | Purification method: Column chromatography. $^{1}$H NMR (400 MHz, DMSO-$d_6$) δ: 1.83-1.97 (1H, m), 2.15-2.33 (3H, m), 2.65 (3H, s), 3.90 (3H, s), 4.41-4.54 (1H, m), 6.98-7.03 (1H, m), 7.06 (1H, d), 7.15 (1H, d), 7.91 (1H, d), 8.36 (1H, t), 9.68 (1H, s). LCMS: m/z 428.4 [M + H]+ |

-continued

| No | Structure and starting material | Purification method and characterization data |
|---|---|---|
| 401 | 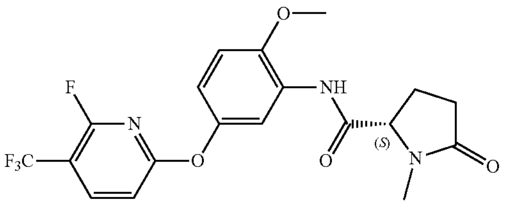 Starting materials: 5-((6-Fluoro-5-(trifluoromethyl)pyridin-2-yl)oxy)-2-methoxyaniline and (S)-1-Methyl-5-oxopyrrolidine-2-carboxylic acid | Purification method: Column chromatography. $^{1}H$ NMR (400 MHz, DMSO-$d_6$) δ: 1.84-1.96 (1H, m), 2.15-2.35 (3H, m), 2.66 (3H, s), 3.90 (3H, s), 4.44-4.53 (1H, m), 6.98-7.04 (1H, m), 7.07 (1H, d), 7.16 (1H, d), 7.92 (1H, d), 8.37 (1H, t), 9.69 (1H, s). LCMS: m/z 428.4 [M + H]+ |
| 402 | 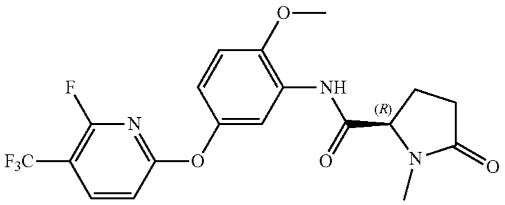 Starting materials: 5-((6-fluoro-5-(trifluoromethyl)pyridin-2-yl)oxy)-2-methoxyaniline, (2R)-1-methyl-5-oxopyrrolidine-2-carboxylic acid | Purification method: Column chromatography. $^{1}H$ NMR (400 MHz, DMSO-$d_6$) δ: 1.83-1.96 (1H, m), 2.14-2.34 (3H, m), 2.65 (3H, s), 3.90 (3H, s), 4.44-4.51 (1H, m), 6.99-7.03 (1H, m), 7.07 (1H, d), 7.15 (1H, d), 7.91 (1H, d), 8.36 (1H, t), 9.68 (1H, s). LCMS: m/z 428.4 [M + H]+ |
| 403 | 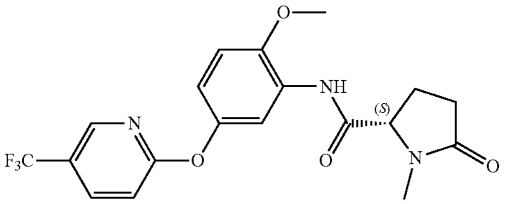 Starting materials: 2-Methoxy-5-((5-(trifluoromethyl)pyridin-2-yl)oxy)-aniline and (S)-1-Methyl-5-oxo-pyrrolidine-2-carboxylic acid | Purification method: Column chromatography. $^{1}H$ NMR (400 MHz, DMSO-$d_6$) δ: 1.82-1.95 (1H, m), 2.13-2.34 (3H, m), 2.65 (3H, s), 3.89 (3H, s), 4.43-4.50 (1H, m), 6.93-6.98 (1H, m), 7.12 (1H, d), 7.19 (1H, d), 7.88 (1H, d), 8.18-8.23 (1H, m), 8.54 (1H, s), 9.63 (1H, s). LCMS: m/z 410.5 [M + H]+ |
| 404 | 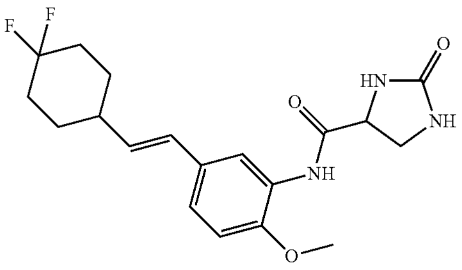 [SMILES: COc1ccc(/C=C/C2CCC(F)(F)CC2)cc1NC(=O)C1CNC(=O)N1] Starting materials: (E)-5-(2-(4,4-di-fluorocyclohexyl)vinyl)-2-methoxy-aniline and 2-Oxoimidazolidine-4-carboxylic acid | Purification method: Column chromatography. $^{1}H$ NMR (400 MHz, DMSO-$d_6$) δ: 1.36-1.50 (2H, m), 1.77-1.97 (4H, m), 1.97-2.09 (2H, m), 2.22-2.34 (1H, m), 3.24-3.31 (1H, m), 3.65 (1H, t), 3.85 (3H, s), 4.30-4.37 (1H, m), 6.02-6.09 (1H, range), 6.35 (1H, d), 6.48 (1H, s), 6.79 (1H, s), 7.01 (1H, d), 7.09-7.16 (1H, m), 8.15 (1H, d), 9.12 (1H, s). LCMS: m/z 380.4 [M + H]+ |

-continued

| No | Structure and starting material | Purification method and characterization data |
|---|---|---|
| 405 | 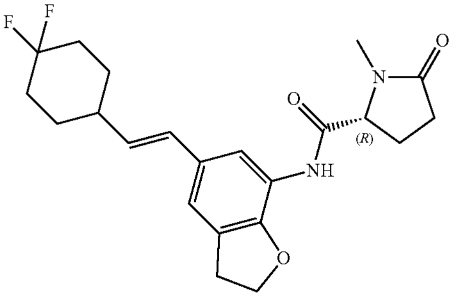<br>Starting materials: (E)-5-(2-(4,4-Di-fluorocyclohexyl)vinyl)-2,3-dihydro-benzofuran-7-amine and (2R)-1-Methyl-5-oxopyrrolidine-2-carboxylic acid | Purification method: Column chromatography. $^1$H NMR (400 MHz, CDCl3) δ: 1.48-1.60 (2H, m), 1.63-1.89 (4H, m), 2.05-2.27 (4H, m), 2.34-2.66 (3H, m), 2.93 (3H, s), 3.24 (2H, t), 4.07-4.13 (1H, m), 4.62 (2H, t), 5.98-6.05 (1H, m), 6.34 (1H, d), 7.01 (1H, s), 7.49 (1H, s), 8.05 (1H, s). LCMS: m/z 405.4 [M + H]+ |
| 406 | 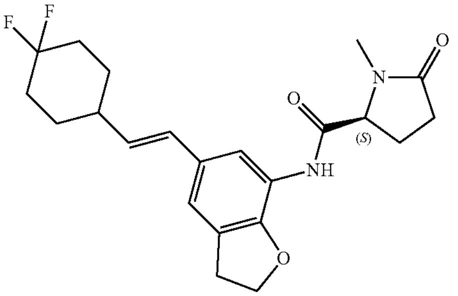<br>Starting materials: (E)-5-(2-(4,4-Difluorocyclohexyl)vinyl)-2,3-di-hydrobenzofuran-7-amine and (S)-1-Methyl-5-oxopyrrolidine-2-carboxylic acid | Purification method: Column chromatography. $^1$H NMR (400 MHz, CDCl3) δ: 1.47-1.60 (2H, m), 1.67-1.89 (4H, m), 2.05-2.26 (4H, m), 2.35-2.53 (2H, m), 2.54-2.66 (1H, m), 2.93 (3H, s), 3.24 (2H, t), 4.08-4.13 (1H, m), 4.62 (2H, t), 5.98-6.05 (1H, m), 6.34 (1H, d), 7.01 (1H, s), 7.49 (1H, s), 8.05 (1H, s). LCMS: m/z 405.4 [M + H]+ |
| 407 | 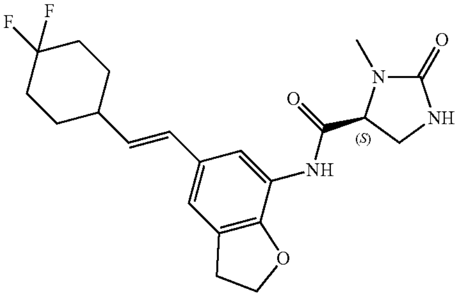<br>Starting materials: (E)-5-(2-(4,4-Difluorocyclohexyl)vinyl)-2,3-di-hydrobenzofuran-7-amine and (S)-3-Methyl-2-oxoimidazolidine-4-carboxylic acid | Purification method: Column chromatography. $^1$H NMR (400 MHz, DMSO-$d_6$) δ: 1.36-1.48 (2H, m), 1.77-1.97 (4H, m), 1.97-2.10 (2H, m), 2.27 (1H, br s), 2.63 (3H, s), 3.12-3.27 (3H, m), 3.52 (1H, br t), 4.31 (1H, br t), 4.59 (2H, br t), 6.00-6.08 (1H, m), 6.32 (1H, br d), 6.42 (1H, br s), 7.11 (1H, br s), 7.66 (1H, br s), 9.62 (1H, br s). LCMS: m/z 406.3 [M + H]+ |
| 408 | 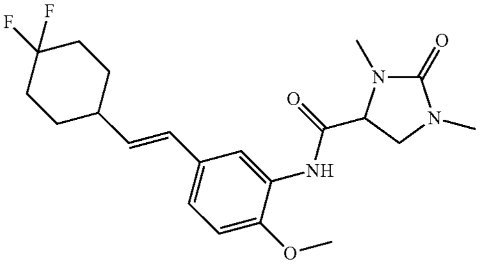<br>Starting materials: (E)-5-(2-(4,4-Difluorocyclohexyl)vinyl)-2-methoxyaniline and 1,3-Dimethyl-2-oxoimidazolidine-4-carboxylic acid | Purification method: Column chromatography. $^1$H NMR (400 MHz, DMSO-$d_6$) δ: 1.37-1.49 (2H, m), 1.78-1.96 (4H, m), 1.98-2.09 (2H, m), 2.22-2.39 (1H, m), 2.66 (3H, s), 2.68 (3H, s), 3.17-3.25 (1H, m), 3.56 (1H, t), 3.83 (3H, s), 4.26-4.33 (1H, m), 6.02-6.10 (1H, m), 6.35 (1H, d), 7.00 (1H, d), 7.11-7.16 (1H, m), 8.02 (1H, d), 9.41 (1H, s). LCMS: m/z 397.5 [M + H]+ |

-continued

| No | Structure and starting material | Purification method and characterization data |
|---|---|---|
| 409 | 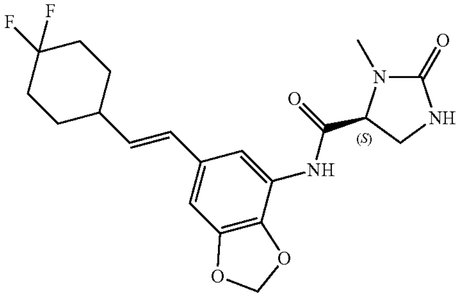 Starting materials: (E)-6-(2-(4,4-difluorocyclohexyl)vinyl)benzo[d][1,3]dioxol-4-amine, (S)-3-methyl-2-oxoimidazolidine-4-carboxylic acid | Purification method: Column chromatography. $^1H$ NMR (400 MHz, DMSO-$d_6$) δ: 1.36-1.48 (2H, m), 1.77-1.96 (4H, m), 1.98-2.08 (2H, m), 2.23-2.32 (1H, m), 2.63 (3H, s), 3.16-3.21 (1H, m), 3.53 (1H, t), 4.25-4.31 (1H, m), 6.04 (2H, s), 6.08-6.15 (1H, m), 6.31 (1H, d), 6.44 (1H, s), 6.91 (1H, d), 7.23 (1H, br d), 9.93 (1H, s). LCMS: m/z 408.3 [M + H]+ |

Example 36. N-(2-Hydroxy-5-(3-methoxy-4-(trifluoromethyl)phenoxy)phenyl)-1-methyl-5-oxopyrrolidine-2-carboxamide (Compound 410)

Compound 410

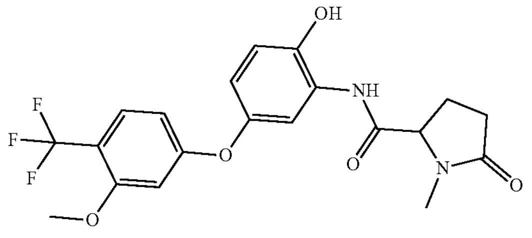

$BCl_3$ (1M in heptane, 798 μL, 0.798 mmol) was added dropwise to a cooled solution of N-(2-methoxy-5-(3-methoxy-4-(trifluoromethyl)phenoxy)phenyl)-1-methyl-5-oxopyrrolidine-2-carboxamide (0.100 g, 0.228 mmol) in DCM (9 ml) at −50° C. followed by stirring at RT for 50 min. The reaction mixture was quenched with 1 N HCl (5 ml). The organic layer was separated and evaporated. The residue was purified by reverse phase chromatography to yield 0.066 g of the title compound. $^1H$ NMR (400 MHz, DMSO-$d_6$) δ: 1.85-1.95 (1H, m), 2.13-2.35 (3H, m), 2.65 (3H, s), 3.84 (3H, s), 4.43-4.50 (1H, m), 6.42 (1H, m), 6.78 (1H, m), 6.86 (1H, d), 6.94 (1H, d), 7.53 (1H, d), 7.79 (1H, d), 9.57 (1H, s), 10.07 (1H, s). LCMS: m/z 425.2 $[M+H]^+$

Example 37. N-(5-(2-Hydroxy-4-(trifluoromethyl)phenoxy)-2-methoxyphenyl)-1-methyl-5-oxopyrrolidine-2-carboxamide (Compound 411)

Compound 411

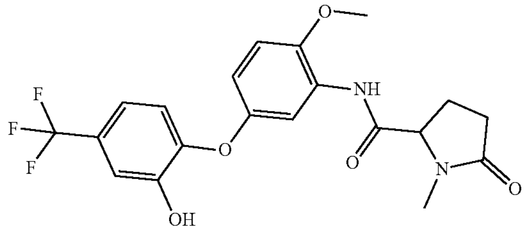

NaH (60% in oil, 0.028 g, 0.704 mmol) was added to a cooled solution of N-(5-(2-fluoro-4-(trifluoromethyl)phenoxy)-2-methoxyphenyl)-1-methyl-5-oxopyrrolidine-2-carboxamide (0.100 g, 0.235 mmol) in DMF (2 ml) at 0° C. followed by stirring for 15 min at RT. Then 2-(Methylsulfonyl)ethanol was added and the mixture was heated at 50° C. for 2.5 h. Additional NaH (60% in oil, 5 eq.) and 2-(Methylsulfonyl)ethanol were then added twice and heated at 80° C. for 5 h and at 100° C. for 5.5 h, respectively. The reaction mixture was quenched with 2 N HCl (2 ml) and extracted with EtOAc (3x3 ml). The organic layer was separated and evaporated. The residue was purified by reverse phase chromatography to yield 0.012 g of the title compound. $^1H$ NMR (600 MHz, DMSO-$d_6$) δ: 1.85-1.92 (1H, m), 2.16-2.31 (3H, m), 2.64 (3H, s), 3.85 (3H, s), 4.46 (1H, m), 6.76 (1H, m), 6.92 (1H, d), 7.07 (1H, d), 7.11 (1H, m), 7.20 (1H, d), 7.80 (1H, d), 9.58 (1H, s), 10.17 (1H, s). LCMS: m/z 425.2 $[M+H]^+$

Example 38. 1-Acetyl-N-(2-methoxy-5-(4-(trifluoromethyl)phenoxy)phenyl)-pyrrolidine-3-carboxamide (Compound 412)

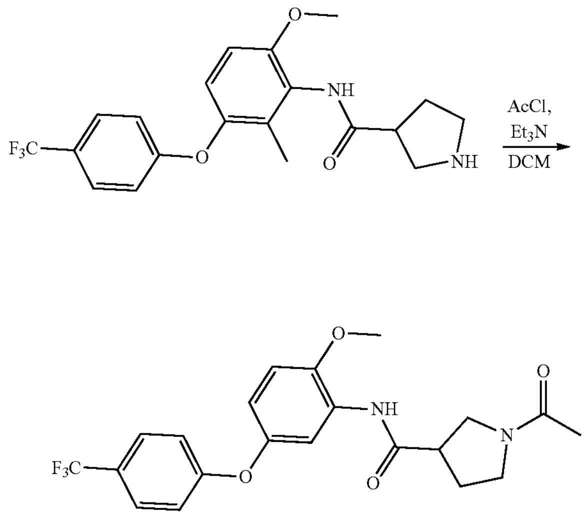

Compound 412

N-(2-Methoxy-5-(4-(trifluoromethyl)phenoxy)phenyl) pyrrolidine-3-carboxamide (74 mg, 1 Eq., 1.321 mmol) and $Et_3N$ (271 μL, 10 eq., 1.945 mmol) were dissolved in DCM (5 mL) under nitrogen. Acetyl chloride was added dropwise at 0° C. and the mixture was stirred and gradually raised to RT. After completion the reaction, the mixture was diluted with EtOAc (20 ml) and washed with brine (2×10 ml). The organic phase was dried over sodium sulfate, filtered and concentrated. The crude residue was purified further with reverse phase chromatography to obtain 36 mg of the title compound. $^1$H NMR (400 MHz, $CDCl_3$ mixture of rotamers in ~1.0:1.2 ratio) δ: 8.19 (m, 1H), 7.93 (br s, 0.45H), 7.88 (br s, 0.52H), 7.57-7.50 (m, 2.1H), 7.02-6.94 (m, 2.1H), 6.90 (m, 1.1H), 6.78 (m, 1H), 3.93 (s, 1.54H), 3.92 (s, 1.72H), 3.91-3.84 (m, 0.59H), 3.81-3.65 (m, 2.7H), 3.55-3.42 (m, 1.12H), 3.16 (m, 0.5H), 3.06 (quin, 0.58H) 2.45-2.34 (m, 0.67H), 2.31-2.16 (m, 1.8H), 2.08 (s, 1.44H), 2.07 (s, 1.63H). LCMS: m/z 423.2 $[M+H]^+$ The following compounds were prepared according to the procedure described for Compound 412. The compound code, structure, starting materials, purification method and characterization data are indicated in the table.

Example 39. 1-Glycyl-N-(2-methoxy-5-(4-(trifluoromethyl)phenoxy)phenyl)-5-oxopyrrolidine-2-carboxamide, HCl (Compound 414)

Compound 414

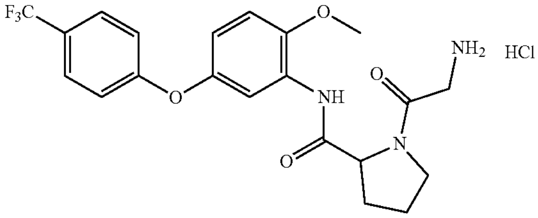

In a Buchner flask benzyl (2-(2-((2-methoxy-5-(4-(trifluoromethyl)phenoxy)-phenyl)carbamoyl)-5-oxopyrrolidin-1-yl)-2-oxoethyl)carbamate (168 mg, 0.287 mmol, 1 eq.) was dissolved in EtOH (10 ml) and palladium (24.4 mg, 0.023 mmol, 0.08 eq.) and HCl (37%, 0.120 ml, 1.435 mmol, 5 eq.) was added. The flask was connected to a $H_2/N_2$/vacuum line and after replacement of air with nitrogen, the mixture was stirred under hydrogen for 2.5 h. The mixture was filtered through a pad of Celite® and washed with a 1:1 mixture of acetonitrile/$H_2O$. The product was frozen at −78° C. and solvents removed on freeze dryer to obtain the title compound. $^1$H NMR (400 MHz, DMSO-d6) δ: 9.91 (s, 1H), 8.17 (br.s, 1H), 7.85 (d, 1H), 7.70 (d, 2H), 7.15 (d, 1H), 7.06 (d, 2H), 6.93 (dd, 1H), 5.15 (m, 1H), 4.20 (d, 1H), 4.17 (d, 1H), 3.91 (s, 3H), 2.71-2.30 (m, 3H), 2.04 (m, 1H). LCMS: m/z 452.598 $[M+H]^+$

| No | Structure and starting material | Purification method and characterization data |
|---|---|---|
| 413 | 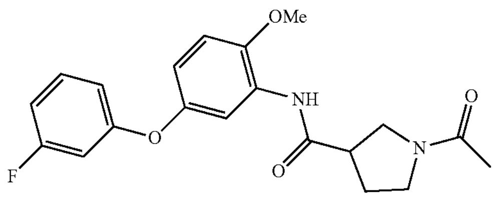 [SMILES: COc1ccc(Oc2cccc(F)c2)cc1NC(=O)C1CCN(C(C)=O)C1] Starting materials: N-(5-(3-fluorophenoxy)-2-methoxyphenyl)pyrrolidine-3-carboxamide and Acetyl chloride | Purification method A. $^1$H NMR ($CDCl_3$, 600 MHz, mixture of rotamers) δ: 8.14 (d, 1H), 7.97 (br s, 1H), 7.22 (dt, 1H), 6.86 (d, 1H), 6.76 (dd, 1H), 6.74-6.69 (m, 2H), 6.60 (dt, 1H), 3.90 (s, 3H), 3.66 (dd, 1H), 3.59 (dd, 1H ), 3.50 (ddd, 2H), 3.43 (m, 1H), 3.21-3.07 (m, 1H), 2.90 (s, 3H), 2.36-2.22 (m, 2H). LCMS: m/z 373.231 $(M + H)^+$ |

Example 40. (S)—N-(2-Methoxy-5-(4-(trifluoromethyl)phenoxy)phenyl)-pyrrolidine-2-carboxamide (Compound 415)

Compound 415

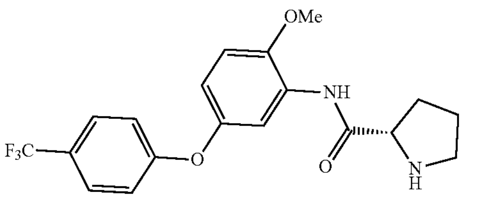

The compound was prepared according to the procedure described for Intermediate 364 starting from tert-butyl (S)-2-((2-methoxy-5-(4-(trifluoromethyl)-phenoxy)phenyl)carbamoyl)-5-oxopyrrolidine-1-carboxylate. The crude end product was treated with saturated $Na_2CO_3$ solution and then extracted with DCM. The organic phase was dried and evaporated to obtain the title compound. $^1H$ NMR (400 MHz, $CDCl_3$) δ: 10.2 (s, 1H), 8.27 (d, 1H), 7.48-7.56 (m, 2H), 6.96-7.03 (m, 2H), 6.87 (d, 1H), 6.74 (dd, 1H), 3.91 (s, 3H), 3.85-3.92 (m, 1H), 2.98-3.15 (m, 2H), 2.14-2.26 (m, 1H), 1.97-2.08 (m, 1H), 1.68-1.85 (m, 2H). LCMS: m/z 381.7 $[M+H]^+$ Example 41. (S)—N-(5-((3-Fluoro-5-(trifluoromethyl)pyridin-2-yl)oxy)-2-methoxyphenyl)pyrrolidine-2-carboxamide (Compound 416)

Compound 416

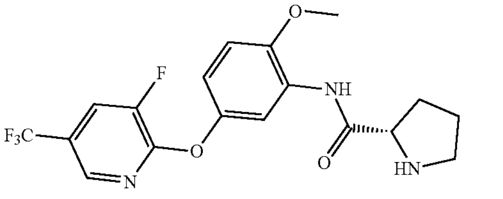

The compound was prepared according to the procedure described for Intermediate 364 starting from tert-butyl (2S)-2-((5-((3-fluoro-5-(trifluoromethyl)-pyridin-2-yl)oxy)-2-methoxyphenyl)carbamoyl)-114-pyrrolidine-1-carboxylate. The crude end product was treated with saturated $Na_2CO_3$ solution and then extracted with DCM. The organic phase was dried and evaporated to obtain the title compound. $^1H$ NMR (400 MHz, $CDCl_3$) δ: 10.2 (s, 1H), 8.37 (d, 1H), 8.14-8.19 (m, 1H), 7.64 (dd, 1H), 6.91 (d, 1H), 6.86 (dd, 1H), 3.92 (s, 3H), 3.86 (dd, 1H), 2.96-3.14 (m, 2H), 2.13 (br, 1H), 2.12-2.24 (m, 1H), 1.96-2.07 (m, 1H), 1.67-1.84 (m, 2H). LCMS: m/z 400.6 $[M+H]^+$ Example 42. (S)—N-(2-Methoxy-5-(4-(trifluoromethyl)phenoxy)phenyl)-N,1-dimethyl-5-oxopyrrolidine-2-carboxamide (Compound 417)

Compound 417

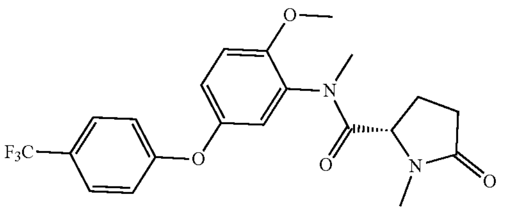

To a cooled (0-5° C.) solution of (S)—N-(2-methoxy-5-(4-(trifluoromethyl)-phenoxy)phenyl)-1-methyl-5-oxopyrrolidine-2-carboxamide (0.204 g, 0.50 mmol) in dry DMF (2.0 mmol) was added sodium hydride, 60 wt-% in oil (0.025 g, 0.625 mmol) followed by stirring the mixture at 0-5° C. for 15 min. Iodomethane (0.062 ml, 1.00 mmol) was added and stirring was continued at RT until reaction was completed. The mixture was diluted with water and extracted with EtOAc. Organic phase was washed with water and brine, dried and evaporated. Crude product was purified by reverse phase flash chromatography to afford the title compound. Yield: 0.152 g. $^1H$ NMR (400 MHz, $CDCl_3$), mixture of rotamers. Chemical shifts for the main rotamer: δ: 7.56-7.64 (m, 2H), 7.07-7.14 (m, 1H), 6.98-7.06 (m, 3H), 6.96 (dd, 1H), 3.93 (dd, 1H), 3.90 (s, 3H), 3.21 (s, 3H), 2.76 (s, 3H), 2.43-2.62 (m, 1H), 2.18-2.31 (m, 1H), 1.77-2.08 (m, 2H). LCMS: m/z 423.4 $[M+H]^+$.

Abbreviations

DCM—Dichloromethane
DEAD—Diethyl azodicarboxylate
DIPEA—N,N-diisopropylethylamine
DMA—Dimethylacetamide
DMAP—4-Dimethylaminopyridine
DMF—N,N-Dimethylformamide
DMSO—Dimethylsulfoxide
ee—Enantiomeric excess
eq.—Molar equivalent
GCMS—Gas chromatography-mass spectrometry
HATU—2-(7-Aza-1H-benzotriazole-1-yl)-1,1,3,3-tetramethyluronium hexafluorophosphate
HPLC—High-performance liquid chromatography
LCMS—Liquid chromatography-mass spectrometry
LiHMDS—Lithium bis(trimethylsilyl)amide
MTBE—Methyl tert-butyl ether
$Pd_2(dba)_3$—Tris(dibenzylideneacetone)dipalladium
$PdCl_2(dppf)$—[1,1'-Bis(diphenylphosphino)ferrocene]dichloropalladium(II)
RT—Room temperature
rt—Retention time
SPhos Pd G2—Chloro(2-dicyclohexylphosphino-2',6'-dimethoxy-1,1'-biphenyl)[2-(2'-amino-1,1'-biphenyl)]palladium(II)
$T_3P$—1-propanephosphonic acid cyclic anhydride
TBAF—Tetra-n-butylammonium fluoride
TEA—Triethylamine
TFA—Trifluoroacetic acid
THF—Tetrahydrofuran
TMA—trimethylaluminium TMS-Cl—Trimethylsilyl chloride XantPhos—4,5-Bis(diphenylphosphino)-9,9-dimethylxanthene

EXPERIMENTS

Experiment 1. TEAD Inhibition

TEAD inhibition was assayed using Hippo Pathway TEAD Reporter—MCF-7 cell line (BPS Bioscience, Catalog #: 60618) which contains firefly luciferase gene under the control of TEAD responsive elements. In the cell line, YAP1 remains in the nucleus inducing constitutive expression of luciferase reporter. Amount of expressed luciferase was detected using ONE-Glo Luciferase Assay System (Promega) and measuring plates with Enspire Multimode Plate Reader (PerkinElmer).

Hippo Pathway TEAD Reporter—MCF-7 cells were plated on white/clear Poly-D-Lysine coated 384 plates (Corning #356660) at the density of 8500 cells/well. Next day test compounds (11 concentrations with 4 replicates) and DMSO control (0.1%) were added to the plate. After 24 h cells were lysed and luciferase activity was measured. The half maximal inhibitory concentration ($IC_{50}$) of the test compounds on YAP-TEAD inhibition was determined.

The compounds of the invention were screened in the above mentioned assay and the $IC_{50}$ values of the compounds are set forth in Table 1 below wherein "A" refers to a group of compounds having $IC_{50}$ value of less than 50 nM, "B" refers to a group of compounds having $IC_{50}$ value in range of 50 to 300 nM and "C" refers to a group of compounds having $IC_{50}$ value in range of 301 nM to 2000 nM.

TABLE 1

| Group | Compound No. |
|---|---|
| A | 1, 21, 22, 23, 28, 33, 45, 47, 48, 59, 66, 67, 68, 69, 70, 75, 76, 81, 87, 88, 91, 92, 93, 97, 99, 100, 101, 102, 103, 105, 107, 109, 110, 114, 117, 118, 119, 128, 129, 130, 131, 133, 134, 136, 139, 141, 143, 149, 150, 151, 152, 153, 154, 156, 157, 159, 162, 163, 164, 165, 166, 167, 168, 170, 171, 175, 176, 177, 178, 179, 180, 182, 184, 185, 186, 187, 189, 192, 196, 206, 208, 209, 210, 213, 214, 215, 216, 217, 222, 223, 226, 227, 229, 230, 231, 234, 237, 239, 240, 248, 253, 255, 264, 265, 276, 278, 279, 282, 283, 290, 292, 294, 296, 297, 298, 299, 300, 304, 305, 307, 308, 312, 313, 316, 317, 318, 319, 320, 322, 335, 338, 339, 340, 345, 348, 349, 351, 352, 355, 356, 361, 362, 363, 365, 375, 377, 382, 385, 391, 395, 398, 399, 400, 401, 402, 403, 405, 406, 407, 409 and 414. |
| B | 8, 10, 11, 17, 18, 19, 24, 25, 27, 29, 30, 32, 34, 36, 37, 39, 42, 43, 49, 52, 53, 55, 56, 57, 60, 62, 63, 71, 73, 74, 77, 78, 80, 82, 83, 86, 89, 90, 94, 95, 96, 98, 104, 108, 111, 112, 115, 116, 125, 126, 127, 135, 138, 140, 144, 147, 148, 155, 160, 161, 169, 172, 173, 174, 194, 197, 198, 200, 207, 211, 212, 218, 232, 233, 235, 238, 241, 242, 244, 245, 247, 249, 254, 256, 257, 258, 259, 260, 261, 263, 266, 267, 268, 269, 270, 271, 273, 274, 275, 277, 281, 284, 285, 286, 288, 291, 293, 295, 309, 310, 315, 321, 325, 328, 331, 334, 336, 337, 342, 346, 350, 357, 359, 360, 364, 368, 369, 371, 376, 379, 379, 380, 381, 383, 396, 404, 408 and 417. |
| C | 2, 3, 4, 5, 6, 7, 9, 12, 13, 14, 15, 16, 20, 26, 31, 35, 38, 40, 41, 44, 46, 50, 51, 54, 58, 61, 64, 65, 72, 79, 84, 85, 106, 113, 120, 121, 122, 123, 124, 132, 137, 142, 145, 146, 181, 183, 188, 190, 191, 193, 199, 201, 202, 203, 205, 224, 225, 228, 236, 243, 246, 251, 252, 262, 272, 287, 289, 301, 302, 303, 306, |

TABLE 1-continued

| Group | Compound No. |
|---|---|
| | 311, 317, 323, 324, 326, 327, 329, 330, 332, 333, 341, 343, 344, 347, 353, 354, 358, 366, 367, 370, 372, 373, 374, 378, 386, 387, 388, 389, 390, 392, 393, 394, 397, 410, 411, 412 and 413. |

The invention claimed is:

1. A compound of formula (I) or a pharmaceutically acceptable salt thereof (I)

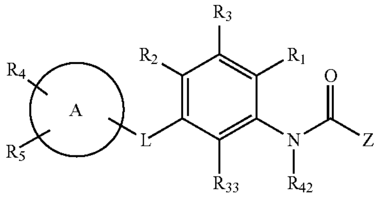

wherein

A is phenyl or pyridyl;

L is —O—;

$R_1$ is $C_{1-7}$ alkoxy;

$R_2$ is hydrogen;

$R_3$ is hydrogen;

$R_4$ is halogen $C_{1-7}$ alkyl;

$R_5$ is hydrogen;

$R_{33}$ and $R_{42}$ are hydrogen;

Z is ring (1a) or (12)

(1a)

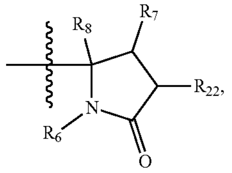

(12)

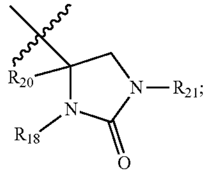

$R_6$ is hydrogen, $C_{1-7}$ alkyl, $C_{3-7}$ cycloalkyl, $C_{3-7}$ cycloalkyl $C_{1-7}$ alkyl, —C(O)—$R_X$, $C_{1-7}$ alkoxy $C_{1-7}$ alkyl, $C_{1-7}$ alkoxycarbonyl $C_{1-7}$ alkyl, —$SO_2C_{1-7}$ alkyl, —$C_{1-7}$ alkyl-C(O)—$NR_{23}R_{24}$, or an optionally substituted 4-6 membered ring having 0-3 heteroatoms as ring atoms independently selected from O, S, and N;

$R_X$ is $C_{1-7}$ alkyl, $C_{3-7}$ cycloalkyl, $C_{1-7}$ alkoxy $C_{1-7}$ alkyl, $C_{1-7}$ alkyl-$NR_{36}R_{37}$, or an optionally substituted 4-6 membered ring having 0-3 heteroatoms as ring atoms independently selected from O, S, and N;

$R_7$, $R_8$, $R_{18}$, $R_{20}$, $R_{21}$, and $R_{22}$ are, independently, hydrogen, $C_{1-7}$ alkyl, $C_{3-7}$ cycloalkyl, hydroxyl, $C_{1-7}$ alkoxy, or $C_{1-7}$ alkylcarbonyl;

$R_{23}$, $R_{24}$, $R_{36}$, and $R_{37}$ are, independently, hydrogen or $C_{1-7}$ alkyl;

wherein optional substitution, in each occurrence, is 1-2 substituents independently selected from $C_{1-7}$ alkyl, halogen, halogen $C_{1-7}$ alkyl, $C_{1-7}$ alkoxy, and oxo.

2. The compound according to claim 1, wherein $R_7$ and $R_8$ are hydrogen.

3. The compound according to claim 1, wherein $R_6$ is hydrogen, $C_{1-7}$ alkyl, or $C_{3-7}$ cycloalkyl.

4. The compound according to claim 1, wherein $R_6$ is —C(O)—$R_X$, wherein $R_X$ is $C_{1-7}$ alkyl or an optionally substituted 4-6 membered ring having 1-3 heteroatoms as ring atoms independently selected from O, S, and N.

5. The compound according to claim 1, wherein $R_{20}$ is hydrogen and $R_{18}$ is $C_{1-7}$ alkyl or $C_{3-7}$ cycloalkyl.

6. The compound according to claim 1, wherein $R_{21}$ is hydrogen or $C_{1-7}$ alkyl.

7. The compound according to claim 1, wherein the compound is N-(2-Methoxy-5-(4-(trifluoromethyl)phenoxy) phenyl)-5-oxopyrrolidine-2-carboxamide or a tautomer or a pharmaceutically acceptable salt thereof.

8. A method for the treatment of cancer comprising administering to a subject in need thereof a therapeutically effective amount of a compound of formula (I) or a pharmaceutically acceptable salt thereof (I)

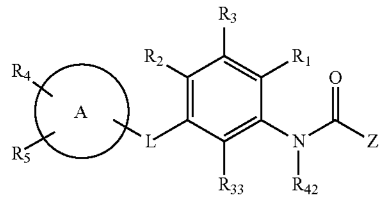

wherein

A is phenyl or pyridyl;

L is —O—;

$R_1$ is $C_{1-7}$ alkoxy;

$R_2$ is hydrogen;

$R_3$ is hydrogen;

$R_4$ is halogen $C_{1-7}$ alkyl;

$R_5$ is hydrogen;

$R_{33}$ and $R_{42}$ are hydrogen;

Z is ring (1a) or (12)

(1a)

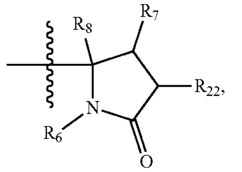

(12)

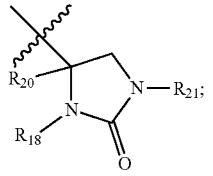

$R_6$ is hydrogen, $C_{1-7}$ alkyl, $C_{3-7}$ cycloalkyl, $C_{3-7}$ cycloalkyl $C_{1-7}$ alkyl, —C(O)—$R_X$, $C_{1-7}$ alkoxy $C_{1-7}$ alkyl, $C_{1-7}$ alkoxycarbonyl $C_{1-7}$ alkyl, —$SO_2C_{1-7}$ alkyl, —$C_{1-7}$ alkyl-C(O)—$NR_{23}R_{24}$ or an optionally substituted 4-6 membered ring having 0-3 heteroatoms as ring atoms independently selected from O, S, and N;

$R_X$ is $C_{1-7}$ alkyl, $C_{3-7}$ cycloalkyl, $C_{1-7}$ alkoxy $C_{1-7}$ alkyl, $C_{1-7}$ alkyl-$NR_{36}R_{37}$, or an optionally substituted 4-6 membered ring having 0-3 heteroatoms as ring atoms independently selected from O, S, and N;

$R_7$, $R_8$, $R_{18}$, $R_{20}$, $R_{21}$, and $R_{22}$ are, independently, hydrogen, $C_{1-7}$ alkyl, $C_{3-7}$ cycloalkyl, hydroxyl, $C_{1-7}$ alkoxy or $C_{1-7}$ alkylcarbonyl;

$R_{23}$, $R_{24}$, $R_{36}$, and $R_{37}$ are, independently, hydrogen, or $C_{1-7}$ alkyl;

wherein optional substitution, in each occurrence, is 1-2 substituents independently selected from $C_{1-7}$ alkyl, halogen, halogen $C_{1-7}$ alkyl, $C_{1-7}$ alkoxy, and oxo.

9. The method according to claim 8, wherein the cancer is mesothelioma, squamous cell carcinoma, a gynaecological cancer, bladder cancer, gastric cancer, liver cancer, lung cancer or colon cancer.

10. A pharmaceutical composition comprising a compound according to claim 1 together with a pharmaceutically acceptable carrier.

11. The compound according to claim 1, wherein the compound is (R)—N-(2-Methoxy-5-(4-(trifluoromethyl) phenoxy)phenyl)-5-oxopyrrolidine-2-carboxamide or a tautomer or a pharmaceutically acceptable salt thereof.

12. The compound according to claim 1, wherein the compound is (S)—N-(2-Methoxy-5-(4-(trifluoromethyl) phenoxy)phenyl)-5-oxopyrrolidine-2-carboxamide or a tautomer or a pharmaceutically acceptable salt thereof.

13. The compound according to claim 1, wherein the compound is 1-Acetyl-N-(2-methoxy-5-(4-(trifluoromethyl) phenoxy)phenyl)-5-oxo-pyrrolidine-2-carboxamide or a tautomer or a pharmaceutically acceptable salt thereof.

14. The compound according to claim 1, wherein the compound is N-(2-Methoxy-5-(4-(trifluoromethyl)phenoxy) phenyl)-1-methyl-5-oxopyrroli-dine-2-carboxamide or a tautomer or a pharmaceutically acceptable salt thereof.

15. The compound according to claim 1, wherein the compound is 1-Ethyl-N-(2-methoxy-5-(4-(trifluoromethyl) phenoxy)phenyl)-5-oxo-pyrrolidine-2-carboxamide or a tautomer or a pharmaceutically acceptable salt thereof.

16. The compound according to claim 1, wherein the compound is (R)—N-(2-Methoxy-5-(4-(trifluoromethyl) phenoxy)phenyl)-1-methyl-5-oxopyrrolidine-2-carboxamide or a tautomer or a pharmaceutically acceptable salt thereof.

17. The compound according to claim 1, wherein the compound is (S)—N-(2-Methoxy-5-(4-(trifluoromethyl) phenoxy)phenyl)-1-methyl-5-oxopyrrolidine-2-carboxamide or a tautomer or a pharmaceutically acceptable salt thereof.

18. The compound according to claim 1, wherein the compound is 1-Isopropyl-N-(2-methoxy-5-(4-(trifluoromethyl)phenoxy)phenyl)-5-oxo-pyrrolidine-2-carboxamide or a tautomer or a pharmaceutically acceptable salt thereof.

19. The compound according to claim 1, wherein the compound is 1-Cyclopropyl-N-(2-methoxy-5-(4-(trifluoromethyl)phenoxy)phenyl)-5-oxopyrrolidine-2-carboxamide or a tautomer or a pharmaceutically acceptable salt thereof.

20. The compound according to claim 1, wherein the compound is N-(2-Methoxy-5-(4-(trifluoromethyl)phenoxy) phenyl)-3-methyl-2-oxo-imidazolidine-4-carboxamide or a tautomer or a pharmaceutically acceptable salt thereof.

21. The compound according to claim 1, wherein the compound is N-(2-Methoxy-5-((5-(trifluoromethyl)pyridin- 2-yl)oxy)phenyl)-3-methyl-2-oxoimidazolidine-4-carboxamide or a tautomer or a pharmaceutically acceptable salt thereof.

22. The compound according to claim 1, wherein the compound is (R)-1-Cyclopropyl-N-(2-methoxy-5-((5-(trifluoromethyl)pyridin-2-yl)oxy)-phenyl)-5-oxopyrrolidine-2-carboxamide or a tautomer or a pharmaceutically acceptable salt thereof.

23. The compound according to claim 1, wherein the compound is(S)-1-Cyclopropyl-N-(2-methoxy-5-((5-(trifluoromethyl)pyridin-2-yl)oxy)-phenyl)-5-oxopyrrolidine-2-carboxamide or a tautomer or a pharmaceutically acceptable salt thereof.

24. The compound according to claim 1, wherein the compound is (S)—N-(2-Methoxy-5-((5-(trifluoromethyl)pyridin-2-yl)oxy)phenyl)-3-methyl-2-oxoimidazolidine-4-carboxamide or a tautomer or a pharmaceutically acceptable salt thereof.

25. The compound according to claim 1, wherein the compound is 3-Cyclopropyl-N-(2-methoxy-5-((5-(trifluoromethyl)pyridin-2-yl)oxy)phenyl)-2-oxoimidazolidine-4-carboxamide or a tautomer or a pharmaceutically acceptable salt thereof.

26. The compound according to claim 1, wherein the compound is (R)-1-(Cyclopropylmethyl)-N-(2-methoxy-5-((5-(trifluoromethyl)pyridin-2-yl)oxy)phenyl)-5-oxopyrrolidine-2-carboxamide or a tautomer or a pharmaceutically acceptable salt thereof.

27. The compound according to claim 1, wherein the compound is(S)-1-(Cyclopropylmethyl)-N-(2-methoxy-5-((5-(trifluoromethyl)pyridin-2-yl)oxy)phenyl)-5-oxopyrrolidine-2-carboxamide or a tautomer or a pharmaceutically acceptable salt thereof.

28. The compound according to claim 1, wherein the compound is (R)—N-(2-methoxy-5-(4-(trifluoromethyl)phenoxy)phenyl)-1,2-dimethyl-5-oxopyrrolidine-2-carboxamide or a tautomer or a pharmaceutically acceptable salt thereof.

29. The compound according to claim 1, wherein the compound is 1-(2-Amino-2-oxoethyl)-N-(2-methoxy-5-(4-(trifluoromethyl) phenoxy)-phenyl)-5-oxopyrrolidine-2-carboxamide or a tautomer or a pharmaceutically acceptable salt thereof.

30. The compound according to claim 1, wherein the compound is N-(2-Methoxy-5-(4-(trifluoromethyl)phenoxy)phenyl)-1,3-dimethyl-2-oxo-imidazolidine-4-carboxamide or a tautomer or a pharmaceutically acceptable salt thereof.

31. The compound according to claim 1, wherein the compound is (S)—N-(2-Methoxy-5-(4-(trifluoromethyl)phenoxy)phenyl)-3-methyl-2-oxoimidazolidine-4-carboxamide or a tautomer or a pharmaceutically acceptable salt thereof.

32. The compound according to claim 1, wherein the compound is (2S)-4-Methoxy-N-(2-methoxy-5-(4-(trifluoromethyl)phenoxy)phenyl)-1-methyl-5-oxopyrrolidine-2-carboxamide or a tautomer or a pharmaceutically acceptable salt thereof.

33. The compound according to claim 1, wherein the compound is N-(5-(4-(Difluoromethyl) phenoxy)-2-methoxyphenyl)-3-methyl-2-oxo-imidazolidine-4-carboxamide or a tautomer or a pharmaceutically acceptable salt thereof.

34. The compound according to claim 1, wherein the compound is (S)—N-(2-Methoxy-5-(4-(trifluoromethyl)phenoxy)phenyl)-1,3-dimethyl-2-oxoimidazolidine-4-carboxamide or a tautomer or a pharmaceutically acceptable salt thereof.

35. The compound according to claim 1, wherein the compound is (R)—N-(2-Methoxy-5-(4-(trifluoromethyl)phenoxy)phenyl)-1,3-dimethyl-2-oxoimidazolidine-4-carboxamide or a tautomer or a pharmaceutically acceptable salt thereof.

36. The compound according to claim 1, wherein the compound is N-(2-Methoxy-5-(4-(trifluoromethyl)phenoxy)phenyl)-5-oxo-1-(5-oxopyrroli-dine-2-carbonyl) pyrrolidine-2-carboxamide or a tautomer or a pharmaceutically acceptable salt thereof.

37. The compound according to claim 1, wherein the compound is N-(2-Methoxy-5-(4-(trifluoromethyl)phenoxy)phenyl)-1-(1-methyl-5-oxo-pyrrolidine-2-carbonyl)-5-oxopyrrolidine-2-carboxamide or a tautomer or a pharmaceutically acceptable salt thereof.

38. The compound according to claim 1, wherein the compound is N-(2-Methoxy-5-(4-(trifluoromethyl)phenoxy)phenyl)-5-oxo-1-(4-oxoazetidine-2-carbonyl) pyrrolidine-2-carboxamide or a tautomer or a pharmaceutically acceptable salt thereof.

39. The compound according to claim 1, wherein the compound is N-(2-methoxy-5-((5-(trifluoromethyl)pyridin-2-yl)oxy)phenyl)-1-methyl-5-oxopyrrolidine-2-carboxamide or a tautomer or a pharmaceutically acceptable salt thereof.

40. The compound according to claim 1, wherein the compound is (R)—N-(2-Methoxy-5-((5-(trifluoromethyl)pyridin-2-yl)oxy)phenyl)-1-methyl-5-oxopyrrolidine-2-carboxamide or a tautomer or a pharmaceutically acceptable salt thereof.

41. The compound according to claim 1, wherein the compound is N-(5-(4-(Difluoromethyl) phenoxy)-2-methoxyphenyl)-1-methyl-5-oxo-pyrrolidine-2-carboxamide or a tautomer or a pharmaceutically acceptable salt thereof.

42. The compound according to claim 1, wherein the compound is (S)—N-(5-(4-(Difluoromethyl) phenoxy)-2-methoxyphenyl)-1-methyl-5-oxo-pyrrolidine-2-carboxamide or a tautomer or a pharmaceutically acceptable salt thereof.

43. The compound according to claim 1, wherein the compound is N-(2-Methoxy-5-(4-(trifluoromethyl)phenoxy)phenyl)-1-(2-methoxyethyl)-5-oxopyrrolidine-2-carboxamide or a tautomer or a pharmaceutically acceptable salt thereof.

44. The compound according to claim 1, wherein the compound is (R)—N-(5-(4-(Difluoromethyl) phenoxy)-2-methoxyphenyl)-1-methyl-5-oxo-pyrrolidine-2-carboxamide or a tautomer or a pharmaceutically acceptable salt thereof.

45. The compound according to claim 1, wherein the compound is (S)—N-(5-(4-(Difluoromethyl) phenoxy)-2-methoxyphenyl)-3-methyl-2-oxo-imidazolidine-4-carboxamide or a tautomer or a pharmaceutically acceptable salt thereof.

46. The compound according to claim 1, wherein the compound is (R)—N-(2-Methoxy-5-(4-(trifluoromethyl)phenoxy)phenyl)-5-oxo-1-(1H-pyrazol-4-yl) pyrrolidine-2-carboxamide or a tautomer or a pharmaceutically acceptable salt thereof.

47. The compound according to claim 1, wherein the compound is (S)—N-(2-Methoxy-5-((5-(trifluoromethyl)pyridin-2-yl)oxy)phenyl)-1-methyl-5-oxopyrrolidine-2-carboxamide or a tautomer or a pharmaceutically acceptable salt thereof.

* * * * *